United States Patent
Graham et al.

(10) Patent No.: US 10,428,044 B2
(45) Date of Patent: *Oct. 1, 2019

(54) 3-AMINO-1,5,6,7-TETRAHYDRO-4H-INDOL-4-ONES

(71) Applicant: Bayer Pharma Aktiengesellschaft, Berlin (DE)

(72) Inventors: Keith Graham, Berlin (DE); Ulrich Klar, Berlin (DE); Hans Briem, Berlin (DE); Marion Hitchcock, Brookline, MA (US); Lars Bärfacker, Düsseldorf (DE); Knut Eis, Berlin (DE); Volker Schulze, Hohen Neuendorf (DE); Gerhard Siemeister, Berlin (DE); Wilhelm Bone, Berlin (DE); Jens Schröder, Berlin (DE); Simon Holton, Berlin (DE); Philip Lienau, Berlin (DE); René Tempel, Berlin (DE); Helmut Sonnenschein, Berlin (DE); Jozsef Bálint, Berlin (DE); Heinz Graubaum, Berlin (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 115 days.

This patent is subject to a terminal disclaimer.

(21) Appl. No.: 15/317,924

(22) PCT Filed: Jun. 17, 2015

(86) PCT No.: PCT/EP2015/063527
§ 371 (c)(1),
(2) Date: Dec. 9, 2016

(87) PCT Pub. No.: WO2015/193339
PCT Pub. Date: Dec. 23, 2015

(65) Prior Publication Data
US 2017/0101391 A1    Apr. 13, 2017

(30) Foreign Application Priority Data

Jun. 17, 2014    (EP) .................................... 14172850

(51) Int. Cl.
| | | |
|---|---|---|
| C07D 401/04 | (2006.01) |
| A61K 31/4439 | (2006.01) |
| C07D 403/04 | (2006.01) |
| A61K 31/506 | (2006.01) |
| C07D 401/14 | (2006.01) |
| A61K 31/444 | (2006.01) |
| C07D 405/14 | (2006.01) |
| C07D 471/04 | (2006.01) |
| A61K 31/437 | (2006.01) |
| A61K 31/501 | (2006.01) |
| A61K 31/4725 | (2006.01) |
| C07D 409/14 | (2006.01) |
| A61K 31/4709 | (2006.01) |
| A61K 31/5377 | (2006.01) |
| C07D 491/056 | (2006.01) |
| A61K 31/436 | (2006.01) |
| C07D 417/14 | (2006.01) |
| C07D 413/14 | (2006.01) |
| A61K 45/06 | (2006.01) |

(52) U.S. Cl.
CPC .......... *C07D 401/04* (2013.01); *A61K 31/436* (2013.01); *A61K 31/437* (2013.01); *A61K 31/444* (2013.01); *A61K 31/4439* (2013.01); *A61K 31/4709* (2013.01); *A61K 31/4725* (2013.01); *A61K 31/501* (2013.01); *A61K 31/506* (2013.01); *A61K 31/5377* (2013.01); *A61K 45/06* (2013.01); *C07D 401/14* (2013.01); *C07D 403/04* (2013.01); *C07D 405/14* (2013.01); *C07D 409/14* (2013.01); *C07D 413/14* (2013.01); *C07D 417/14* (2013.01); *C07D 471/04* (2013.01); *C07D 491/056* (2013.01)

(58) Field of Classification Search
None
See application file for complete search history.

(56) References Cited

FOREIGN PATENT DOCUMENTS

| JP | 2000063354 | 2/2000 |
| WO | WO-199802430 | 1/1998 |
| WO | WO-2011049988 | 4/2011 |

(Continued)

OTHER PUBLICATIONS

Schafer, S., Kolkhof, P. Failure is an option: learning from unsuccessful proof-of-concept trials. Drug Discovery Today. Nov. 2008, 13, 913-916.*

(Continued)

*Primary Examiner* — Po-Chih Chen
(74) *Attorney, Agent, or Firm* — Morrison & Foerster LLP

(57) ABSTRACT

Compounds of formula (I) which are inhibitors of Bub1 kinase, processes for their production and their use as pharmaceuticals.

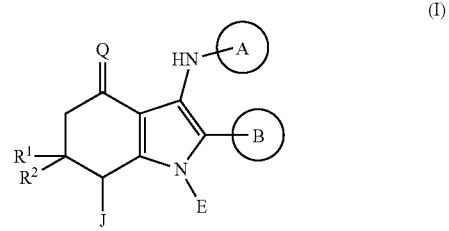

13 Claims, No Drawings
Specification includes a Sequence Listing.

(56) References Cited

FOREIGN PATENT DOCUMENTS

| | | |
|---|---|---|
| WO | WO-2011115804 | 9/2011 |
| WO | WO-2011126903 | 10/2011 |
| WO | WO-2012003405 | 1/2012 |
| WO | WO-2013050438 | 4/2013 |
| WO | WO-2013167698 | 5/2013 |
| WO | WO-2013092512 | 6/2013 |
| WO | WO-2013101830 | 7/2013 |
| WO | WO-2014047111 | 3/2014 |
| WO | WO-2014047325 | 3/2014 |
| WO | WO-2014147144 | 9/2014 |
| WO | WO-2014147203 | 9/2014 |
| WO | WO-2014147204 | 9/2014 |
| WO | WO-2014202583 | 12/2014 |
| WO | WO-2014202584 | 12/2014 |
| WO | WO-2014202586 | 12/2014 |
| WO | WO-2014202588 | 12/2014 |
| WO | WO-2014202590 | 12/2014 |
| WO | WO-2016041925 | 3/2016 |
| WO | WO-2016042080 | 3/2016 |
| WO | WO-2016042081 | 3/2016 |
| WO | WO-2016042084 | 3/2016 |
| WO | WO-2016120196 | 8/2016 |
| WO | WO-2016202755 | 12/2016 |
| WO | WO-2017021348 | 2/2017 |

OTHER PUBLICATIONS

Honig, H., Pullman, W. From bench to clinic and back: Perspective on the 1st IQPC Translational Research conference. Journal of Translational Medicine. Dec. 2004, 2, 44.*
Baron et al., Probing the catalytic functions of Bub1 kinase using the small molecules inhibitors BAY-320 and BAY-524. eLife, 2016, 5, e12187, p. 1-26.*
Jlang et al., Allylic Amination and N-Arylation-Based Domino Reactions Providing Rapid Three-Component Strategies to Fused Pyrroles with Different Substituted Patterns. Journal of Organic Chemistry, 2012, 77, 7497-7505.*
International Search Report dated Aug. 21, 2015 for PCT Application No. PCT/EP2015/063527 filed on Jun. 17, 2015, 3 pages.
PubChem. (2015). Compound Summary for CID 67600641, Chemical Name, "AGN-PC-OHINXA; SCHEMBL8490091; 3-bromo-6,6-dimethyl-2-pyridin-2-yl-5,7-dihydro-1H-indol-4-one," located at<https://pubchem.ncbi.nlin.nih.gov/compound/67600641>, last visited on Jul. 25, 2015, 4 pages.

* cited by examiner

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct

<400> SEQUENCE: 1

Val Leu Leu Pro Lys Lys Ser Phe Ala Glu Pro Gly
1               5                   10

3-AMINO-1,5,6,7-TETRAHYDRO-4H-INDOL-4-ONES

CROSS REFERENCE TO RELATED APPLICATIONS

This application is the national stage of International Application No. PCT/EP2015/063527, filed internationally on Jun. 17, 2015, which claims the benefit of European Application No. 14172850.1, filed Jun. 17, 2014.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052006500SEQLIST.txt, date recorded: Dec. 5, 2016, size: 1 KB).

FIELD OF APPLICATION OF THE INVENTION

The invention relates to substituted tetrahydro-4H-indol-4-one compounds, a process for their production and the use thereof.

BACKGROUND OF THE INVENTION

One of the most fundamental characteristics of cancer cells is their ability to sustain chronic proliferation whereas in normal tissues the entry into and progression through the cell division cycle is tightly controlled to ensure a homeostasis of cell number and maintenance of normal tissue function. Loss of proliferation control was emphasized as one of the six hallmarks of cancer [Hanahan D and Weinberg R A, Cell 100, 57, 2000; Hanahan D and Weinberg R A, Cell 144, 646, 2011].

The eukaryotic cell division cycle (or cell cycle) ensures the duplication of the genome and its distribution to the daughter cells by passing through a coordinated and regulated sequence of events. The cell cycle is divided into four successive phases:
1. The G1 phase represents the time before the DNA replication, in which the cell grows and is sensitive to external stimuli.
2. In the S phase the cell replicates its DNA, and
3. in the G2 phase preparations are made for entry into mitosis.
4. In mitosis (M phase), the duplicated chromosomes get separated supported by a spindle device built from microtubules, and cell division into two daughter cells is completed.

To ensure the extraordinary high fidelity required for an accurate distribution of the chromosomes to the daughter cells, the passage through the cell cycle is strictly regulated and controlled. The enzymes that are necessary for the progression through the cycle must be activated at the correct time and are also turned off again as soon as the corresponding phase is passed. Corresponding control points ("checkpoints") stop or delay the progression through the cell cycle if DNA damage is detected, or the DNA replication or the creation of the spindle device is not yet completed. The mitotic checkpoint (also known as spindle checkpoint or spindle assembly checkpoint) controls the accurate attachment of mircrotubules of the spindle device to the kinetochors (the attachment site for microtubules) of the duplicated chromosomes. The mitotic checkpoint is active as long as unattached kinetochores are present and generates a wait-signal to give the dividing cell the time to ensure that each kinetochore is attached to a spindle pole, and to correct attachment errors. Thus the mitotic checkpoint prevents a mitotic cell from completing cell division with unattached or erroneously attached chromosomes [Suijkerbuijk S J and Kops G J, Biochem. Biophys. Acta 1786, 24, 2008; Musacchio A and Salmon E D, Nat. Rev. Mol. Cell. Biol. 8, 379, 2007]. Once all kinetochores are attached with the mitotic spindle poles in a correct bipolar (amphitelic) fashion, the checkpoint is satisfied and the cell enters anaphase and proceeds through mitosis.

The mitotic checkpoint is established by a complex network of a number of essential proteins, including members of the MAD (mitotic arrest deficient, MAD 1-3) and Bub (Budding uninhibited by benzimidazole, Bub 1-3) families, Mps1 kinase, cdc20, as well as other components [reviewed in Bolanos-Garcia V M and Blundell T L, Trends Biochem. Sci. 36, 141, 2010], many of these being over-expressed in proliferating cells (e.g. cancer cells) and tissues [Yuan B et al., Clin. Cancer Res. 12, 405, 2006]. The major function of an unsatisfied mitotic checkpoint is to keep the anaphase-promoting complex/cyclosome (APC/C) in an inactive state. As soon as the checkpoint gets satisfied the APC/C ubiquitin-ligase targets cyclin B and securin for proteolytic degradation leading to separation of the paired chromosomes and exit from mitosis.

Inactive mutations of the Ser/Thr kinase Bub1 prevented the delay in progression through mitosis upon treatment of cells of the yeast $S.\ cerevisiae$ with microtubule-destabilizing drugs, which led to the identification of Bub1 as a mitotic checkpoint protein [Roberts B T et al., Mol. Cell Biol., 14, 8282, 1994]. A number of recent publications provide evidence that Bub1 plays multiple roles during mitosis which have been reviewed by Elowe [Elowe S, Mol. Cell. Biol. 31, 3085, 2011]. In particular, Bub1 is one of the first mitotic checkpoint proteins that binds to the kinetochores of duplicated chromosomes and probably acts as a scaffolding protein to constitute the mitotic checkpoint complex. Furthermore, via phosphorylation of histone H2A, Bub1 localizes the protein shugoshin to the centromeric region of the chromosomes to prevent premature segregation of the paired chromosomes [Kawashima et al. Science 327, 172, 2010]. In addition, together with a Thr-3 phosphorylated Histone H3 the shugoshin protein functions as a binding site for the chromosomal passenger complex which includes the proteins survivin, borealin, INCENP and Aurora B. The chromosomal passenger complex is seen as a tension sensor within the mitotic checkpoint mechanism, which dissolves erroneously formed microtubule-kinetochor attachments such as syntelic (both sister kinetochors are attached to one spindle pole) or merotelic (one kinetochor is attached to two spindle poles) attachments [Watanabe Y, Cold Spring Harb. Symp. Quant. Biol. 75, 419, 2010]. Recent data suggest that the phosphorylation of histone H2A at Thr 121 by Bub1 kinase is sufficient to localize AuroraB kinase to fulfill the attachment error correction checkpoint [Ricke et al. J. Cell Biol. 199, 931-949, 2012].

Incomplete mitotic checkpoint function has been linked with aneuploidy and tumourigenesis [Weaver B A and Cleveland D W, Cancer Res. 67, 10103, 2007; King R W, Biochim Biophys Acta 1786, 4, 2008]. In contrast, complete inhibition of the mitotic checkpoint has been recognised to result in severe chromosome missegregation and induction of apoptosis in tumour cells [Kops G J et al., Nature Rev. Cancer 5, 773, 2005; Schmidt M and Medema R H, Cell Cycle 5, 159, 2006; Schmidt M and Bastians H, Drug Res. Updates 10, 162, 2007]. Thus, mitotic checkpoint abrogation through pharmacological inhibition of components of the mitotic checkpoint, such as Bub1 kinase, represents a new approach for the treatment of proliferative disorders, including solid tumours such as carcinomas, sarcomas, leukaemias and lymphoid malignancies or other disorders, associated with uncontrolled cellular proliferation.

The present invention relates to chemical compounds that inhibit Bub1 kinase.

Established anti-mitotic drugs such as *vinca* alkaloids, taxanes or epothilones activate the mitotic checkpoint, inducing a mitotic arrest either by stabilising or destabilising microtubule dynamics. This arrest prevents separation of the duplicated chromosomes to form the two daughter cells. Prolonged arrest in mitosis forces a cell either into mitotic exit without cytokinesis (mitotic slippage or adaption) or into mitotic catastrophe leading to cell death [Rieder C L and Maiato H, Dev. Cell 7, 637, 2004]. In contrast, inhibitors of Bub1 prevent the establishment and/or functionality of the mitotic checkpoint and interfere with spindle attachment error correction, which finally results in severe chromosomal missegregation, induction of apoptosis and cell death.

These findings suggest that Bub1 inhibitors should be of therapeutic value for the treatment of proliferative disorders associated with enhanced uncontrolled proliferative cellular processes such as, for example, cancer, inflammation, arthritis, viral diseases, cardiovascular diseases, or fungal diseases in a warm-blooded animal such as man. WO 2013/050438, WO 2013/092512, WO 2013/167698, WO 2014/147203, WO 2014/147204, WO2014202590, WO2014202588, WO2014202584, WO2014202583 WO2015/063003, disclose substituted indazoles, substituted pyrazoles, and substituted cycloalkylpyrazoles, which are Bub1 kinase inhibitors.

JP2000063354 discloses 1,5,6,7-tetrahydro-4H-indol-4-ones which may be used as inhibitors of Endothelin-converting enzyme.

WO98/02430 discloses 1,5,6,7-tetrahydro-4H-indol-4-ones, which may be useful as inhibitors of Interleukin-I and Tumor Necrosis Factor.

Due to the fact that especially cancer disease as being expressed by uncontrolled proliferative cellular processes in tissues of different organs of the human- or animal body still is not considered to be a controlled disease in that sufficient drug therapies already exist, there is a strong need to provide further new therapeutically useful drugs, preferably inhibiting new targets and providing new therapeutic options (e.g. drugs with improved pharmacological properties).

DESCRIPTION OF THE INVENTION

Therefore, inhibitors of Bub1 represent valuable compounds that should complement therapeutic options either as single agents or in combination with other drugs.

In accordance with a first aspect, the invention relates to compounds of formula (I),

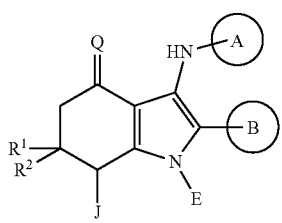

(I)

in which:
R$^1$ represents hydrogen, C$_1$-C$_4$-alkyl, C$_1$-C$_4$-haloalkyl, C$_3$-C$_6$-cycloalkyl, or phenyl,
  wherein said phenyl is optionally substituted, one or more times, independently from each other, with R$^3$,
  wherein said C$_3$-C$_6$-cycloalkyl is optionally substituted, one or more times, independently from each other, with halogen; and
R$^2$ represents hydrogen, C$_1$-C$_4$-alkyl or C$_1$-C$_4$-haloalkyl; or
R$^1$ and R$^2$ together with the carbon atom to which they are attached form a 3- to 7-membered cycloalkyl ring; and
ring A represents a group selected from:

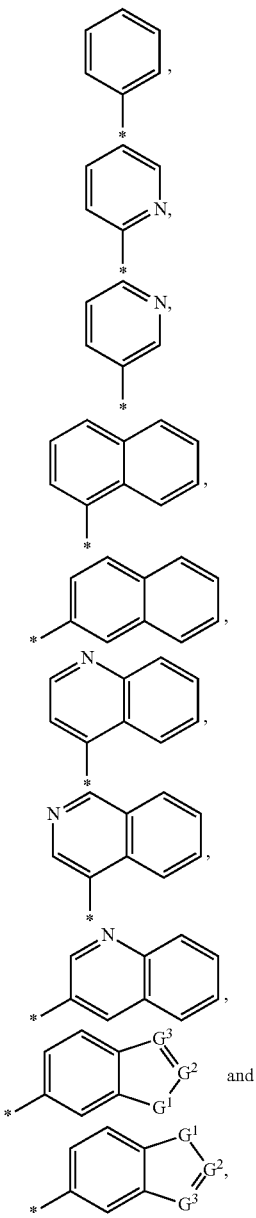

wherein * indicates the point of attachment of said group with the rest of the molecule and said group is optionally substituted, one or more times, independently from each other, with R$^3$; and
G$^1$ represents O, S, or NR$^{21}$, $G^2$, $G^3$ represent, independently from each other, $CR^{21}$ or N;

$R^3$ represents hydrogen, halogen, hydroxy, amino, nitro, cyano, $C_1$-$C_4$-alkyl, $C_3$-$C_6$-cycloalkyl, $C_2$-$C_4$-alkenyl, $C_2$-$C_4$-alkynyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $R^{18}$—O—C(O)—, $R^7R^8N$—C(O)—, $C_1$-$C_4$-alkyl-C(O)—NH—, $R^7R^8N$—, $R^7R^8N$—$SO_2$—, or a group selected from

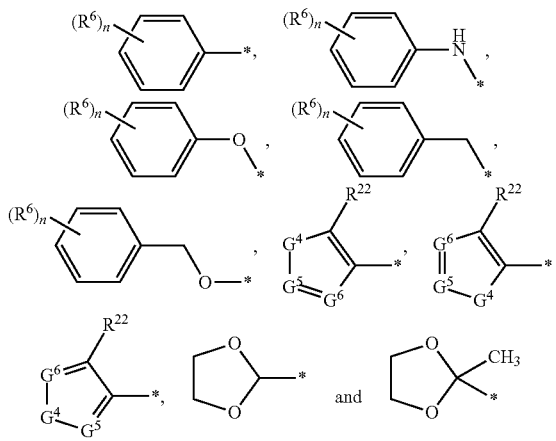

wherein * indicates the point of attachment of said group with the rest of the molecule;
wherein said $C_1$-$C_4$-alkyl, $C_1$-$C_4$-alkoxy, $C_1$-$C_4$-haloalkyl or $C_1$-$C_4$-haloalkoxy groups are optionally substituted with one or two hydroxy groups; and
$G^4$ represents O, S, or $NR^{21}$,
$G^5$, $G^6$ represent, independently from each other, $CR^{21}$ or N;

$R^6$ represents, independently from each other, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl or $C_1$-$C_4$-haloalkoxy; and ring B represents a group selected from:

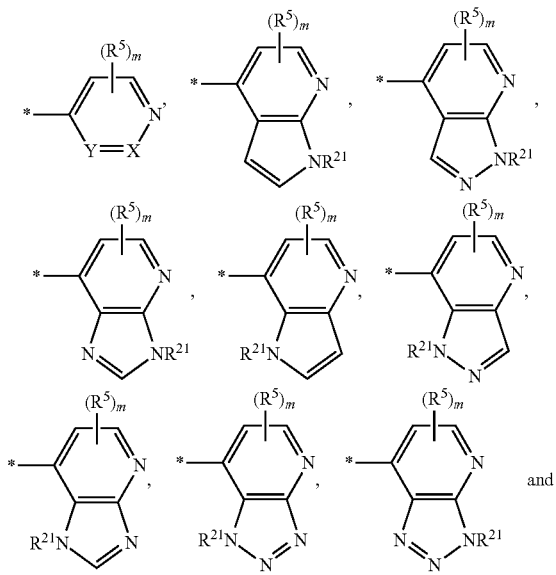

wherein * indicates the point of attachment of said group with the rest of the molecule; and X represents $CR^4$ or N; and Y represents $CR^4$ or N, wherein when one of X and Y represents N, the other represents $CR^4$; and $R^4$ represents, independently from each other, hydrogen, halogen, hydroxy, cyano, $C_1$-$C_4$-alkyl, $C_3$-$C_4$-cycloalkyl, $C_1$-$C_4$-alkoxy, $C_1$-$C_4$-alkyl-S—, $C_1$-$C_4$-alkyl-SO—, $C_1$-$C_4$-alkyl-$SO_2$—, $R^9R^{10}N$—, $R^{11}$—C(O)—($NR^7$)—, ($R^{11}$—C(O)—)($R^{12}$—C(O)—)N—, $R^9R^{10}N$—C(O)—($NR^7$)—, $R^9R^{10}N$—C(S)—($NR^7$)—, $R^{18}$—O—C(O)—($NR^7$)—, $R^9R^{10}N$—$SO_2$— or $C_1$-$C_4$-alkyl-$SO_2$—NH—, wherein said $C_1$-$C_4$-alkyl is optionally substituted, one or more times, independently from each other, with a substituent selected from hydroxy and halogen; and wherein said $C_1$-$C_4$-alkoxy is optionally substituted, one or more times, independently from each other, with a substituent selected from hydroxy, halogen, $C_1$-$C_4$-alkoxy, $C_3$-$C_6$-cycloalkyl and phenyl, wherein said phenyl is optionally substituted, one or more times, independently from each other, with $R^3$; and wherein said $C_3$-$C_4$-cycloalkyl is optionally substituted, one or more times, independently from each other, with halogen;

$R^5$ represents, independently from each other, halogen, hydroxy, amino, nitro, cyano, $C_1$-$C_4$-alkyl, $C_3$-$C_6$-cycloalkyl, $C_1$-$C_4$-alkoxy, $C_1$-$C_4$-haloalkyl, $C_1$-$C_4$-haloalkoxy or phenyl-$C_1$-$C_4$-alkyl, wherein said phenyl group is optionally substituted, one or more times, independently from each other, with a substituent selected from halogen, hydroxy, $C_1$-$C_3$-alkyl, $C_1$-$C_3$-haloalkyl and $C_1$-$C_3$-alkoxy;

wherein said $C_3$-$C_6$-cycloalkyl group is optionally substituted, one or more times, independently from each other, with halogen; and J represents hydrogen or hydroxy; and E represents hydrogen, $C_1$-$C_4$-alkyl, $C_1$-$C_4$-alkoxy-$C_2$-$C_4$-alkyl, $R^{17a}R^{17b}R^{17c}Si$—O—$C_2$-$C_4$-alkyl, $C_1$-$C_4$-alkyl-$SO_2$—$C_1$-$C_4$-alkyl, $R^{18}$—O—C(O)—$C_1$-$C_4$-alkyl, $R^7R^8N$—$C_2$-$C_4$-alkyl, $R^7R^8N$—C(O)—$C_1$-$C_4$-alkyl or phenyl-$C_1$-$C_4$-alkyl, wherein said $C_1$-$C_4$-alkyl is optionally substituted, one or more times, independently from each other, with a substituent selected from hydroxy and halogen; and wherein said phenyl group is optionally substituted, one or more times, independently from each other, with $R^5$;

Q represents O or N—$OR^{16}$;

$R^7$, $R^8$ represent, independently from each other, hydrogen, $C_1$-$C_4$-alkyl or tert-butyl-O—C(O)—; and $R^9$, $R^{10}$ represent, independently from each other, hydrogen, $C_1$-$C_4$-alkyl, $C_3$-$C_6$-cyclo-alkyl-, $C_1$-$C_4$-haloalkyl-, phenyl or heteroaryl, wherein said phenyl or heteroaryl group is optionally substituted, one or more times, independently from each other, with $R^5$; and wherein said $C_1$-$C_4$-alkyl is optionally substituted, one or more times, independently from each other, with a substituent selected from hydroxy, $C_1$-$C_4$-alkoxy, $C_1$-$C_4$-alkyl-S—, $C_3$-$C_6$-cycloalkyl, 4- to 6-membered heterocycloalkyl, phenyl, heteroaryl and $R^{18}$—O—C(O)—, wherein said $C_3$-$C_6$-cycloalkyl or 4- to 6-membered heterocycloalkyl is optionally substituted, one or more times, independently from each other, with a substituent selected from halogen, $C_1$-$C_4$-alkyl and tert-butyl-O—C(O)—, wherein said phenyl or heteroaryl group is optionally substituted, one or more times, independently from each other, with $R^5$; or $R^9$ and $R^{10}$ together with the nitrogen atom to which they are attached form a 3- to 7-membered nitrogen containing heterocyclic ring, optionally containing one additional heteroatom selected from O, NH or S, and which may be optionally substituted, one or more times, independently from each other, with $R^5$; and $R^{11}$, $R^{12}$ represent, independently from each other, $C_1$-$C_4$-alkyl, $C_2$-$C_4$-alkenyl, $C_2$-$C_4$-alkynyl, $C_3$-$C_6$-cycloalkyl, 4- to 6-membered heterocycloalkyl, phenyl, heteroaryl, or $R^{13}$—($C_1$-$C_4$-alkyl)-O—$CH_2$—, wherein said $C_1$-$C_4$-alkyl is optionally substituted, one or more times, independently from each other, with a substituent selected from halogen, hydroxy, cyano, $C_1$-$C_4$-alkoxy,
$R^7R^8N$—, $R^{14}$, $R^{15}$—O—, and phenyl optionally substituted, one or more times, independently from each other, with $R^5$, and wherein said $C_3$-$C_6$-cycloalkyl is optionally substituted, one or more times, independently from each other, with a substituent selected from halogen, cyano, $C_1$-$C_4$-alkyl, $C_1$-$C_4$-haloalkyl and phenyl optionally substituted, one or more times, independently from each other, with $R^5$, and wherein said 4- to 6-membered heterocycloalkyl is optionally substituted, one or more times, independently from each other, with a substituent selected from hydroxy, $C_1$-$C_4$-alkyl, $C_1$-$C_4$-alkoxy, $R^7R^8N$— and $R^{18}$—O—C(O)—, and wherein said phenyl or heteroaryl is optionally substituted, one or more times, independently from each other, with $R^5$;

$R^{13}$ represents branched $C_3$-$C_4$-alkyl, $C_1$-$C_4$-haloalkyl, $C_2$-$C_4$-alkenyl, $C_2$-$C_4$-alkynyl, $C_3$-$C_6$-cycloalkyl, 4- to 6-membered heterocycloalkyl, phenyl or heteroaryl, wherein said phenyl or heteroaryl is optionally substituted, one or more times, independently from each other, with $R^5$;

$R^{14}$ represents $C_1$-$C_4$-alkyl-S—, $C_1$-$C_4$-alkyl-$SO_2$—, $C_3$-$C_6$-cycloalkyl, 4- to 6-membered heterocycloalkyl, phenyl or heteroaryl, wherein said phenyl or heteroaryl is optionally substituted, one or more times, independently from each other, with $R^5$;

$R^{15}$ represents phenyl or heteroaryl, wherein said phenyl or heteroaryl is optionally substituted, one or more times, independently from each other, with $R^5$; and $R^{16}$ represents hydrogen, $C_1$-$C_6$-alkyl, phenyl or $C_1$-$C_4$-alkyl-C(O)—, wherein said phenyl group is optionally substituted, one or more times, independently from each other, with $R^5$;

$R^{17a}$, $R^{17b}$, $R^{17c}$ represent, independently from each other, $C_1$-$C_4$-alkyl;

$R^{18}$ represents hydrogen or $C_1$-$C_6$-alkyl;

$R^{21}$ represents hydrogen, $C_1$-$C_4$-alkyl, $C_1$-$C_4$-haloalkyl, or $C_1$-$C_6$-cycloalkyl optionally substituted, one or more times, independently from each other, with halogen;

$R^{22}$ represents hydrogen, halogen, $C_1$-$C_4$-alkyl, $C_1$-$C_4$-haloalkyl, or $C_1$-$C_6$-cycloalkyl optionally substituted, one or more times, independently from each other, with halogen;

m represents 0, 1 or 2;

n represents 0, 1, 2 or 3;

or an N-oxide, a salt, a tautomer or a stereoisomer of said compound, or a salt of said N-oxide, tautomer or stereoisomer.

In accordance with an embodiment of the first aspect, the invention relates to compounds of formula (Ia),

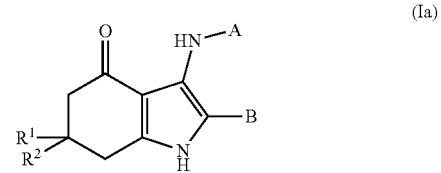

(Ia)

in which:

$R^1$ represents hydrogen, $C_1$-$C_4$-alkyl, $C_1$-$C_4$-haloalkyl or phenyl, wherein said phenyl is optionally substituted, one or more times, independently from each other, with $R^3$; and $R^2$ represents hydrogen, $C_1$-$C_4$-alkyl or $C_1$-$C_4$-haloalkyl; or $R^1$ and $R^2$ together with the carbon atom to which they are attached form a 3- to 7-membered cycloalkyl ring; and A represents a group selected from:

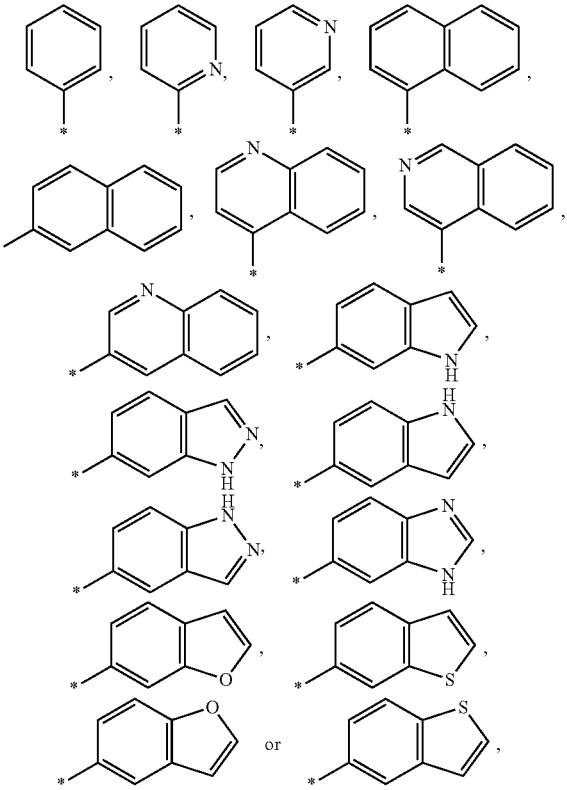

wherein * indicates the point of attachment of said group with the rest of the molecule and said group is optionally substituted, one or more times, independently from each other, with $R^3$; and $R^3$ represents hydrogen, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $C_1$-$C_4$-alkyl-O—C(O)—, $R^7R^8N$—C(O)—, $C_1$-$C_4$-alkyl-C(O)—NH—, or a group

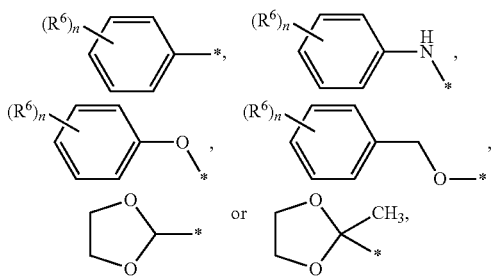

wherein said $C_1$-$C_4$-alkyl, $C_1$-$C_4$-alkoxy, $C_1$-$C_4$-haloalkyl or $C_1$-$C_4$-haloalkoxy groups are optionally substituted with hydroxy; and $R^6$ represents, independently from each other, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl or $C_1$-$C_4$-haloalkoxy; and B represents a group selected from:

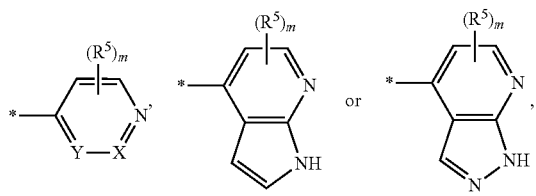

wherein * indicates the point of attachment of said group with the rest of the molecule; and X represents $CR^4$ or N; and Y represents $CR^4$ or N,
  wherein when one of X and Y represents N, the other represents $CR^4$; and $R^4$ represents, independently from each other, hydrogen, halogen, hydroxy, cyano, $C_1$-$C_4$-alkyl, $C_1$-$C_4$-alkoxy, $R^9R^{10}N$—, $R^{11}$—C(O)—NH—, $(R^{11}$—C(O)—)($R^{12}$—C(O)—)N— or $C_1$-$C_4$-alkyl-SO$_2$—NH—; and $R^5$ represents, independently from each other, halogen, hydroxy, amino, nitro, cyano, $C_1$-$C_4$-alkyl or $C_1$-$C_4$-alkoxy; and $R^7$, $R^8$ represent, independently from each other, hydrogen or $C_1$-$C_4$-alkyl; and $R^9$, $R^{10}$ represent, independently from each other, hydrogen, $C_1$-$C_4$-alkyl, $C_3$-$C_6$-cycloalkyl-, $C_1$-$C_4$-haloalkyl- or phenyl, wherein said phenyl group is optionally substituted with $R^5$; or $R^9$ and $R^{10}$ together with the nitrogen atom to which they are attached form a 3- to 7-membered nitrogen containing heterocyclic ring, optionally containing one additional heteroatom selected from O, NH or S, and which may be optionally substituted, one or more times, independently from each other, with $R^5$; and $R^{11}$, $R^{12}$ represent, independently from each other, $C_1$-$C_4$-alkyl, $C_3$-$C_6$-cycloalkyl- or $C_1$-$C_4$-haloalkyl-;

n represents 0, 1, 2 or 3; and m represents 0, 1 or 2;

or an N-oxide, a salt, a tautomer or a stereoisomer of said compound, or a salt of said N-oxide, tautomer or stereoisomer.

In a second aspect, the invention relates to compounds of formula (I) as described supra, wherein:

$R^1$ represents hydrogen, $C_1$-$C_4$-alkyl, $C_1$-$C_4$-haloalkyl or phenyl, wherein said phenyl is optionally substituted, one or more times, independently from each other, with $R^3$; and $R^2$ represents hydrogen, $C_1$-$C_4$-alkyl or $C_1$-$C_4$-haloalkyl; or $R^1$ and $R^2$ together with the carbon atom to which they are attached form a 3- to 7-membered cycloalkyl ring; and ring A represents a group selected from:

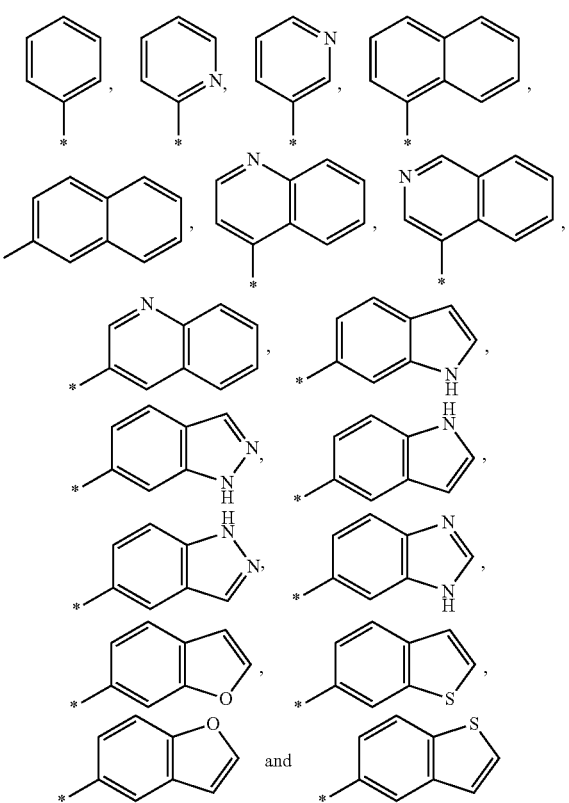

wherein * indicates the point of attachment of said group with the rest of the molecule and said group is optionally substituted, one or more times, independently from each other, with $R^3$; and $R^3$ represents hydrogen, halogen, hydroxy, amino, nitro, cyano, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $R^{18}$—O—C(O)—, $R^7R^8N$—C(O)—, $C_1$-$C_4$-alkyl-C(O)—NH—, $R^7R^8N$—, $R^7R^8N$—SO$_2$—, or a group selected from

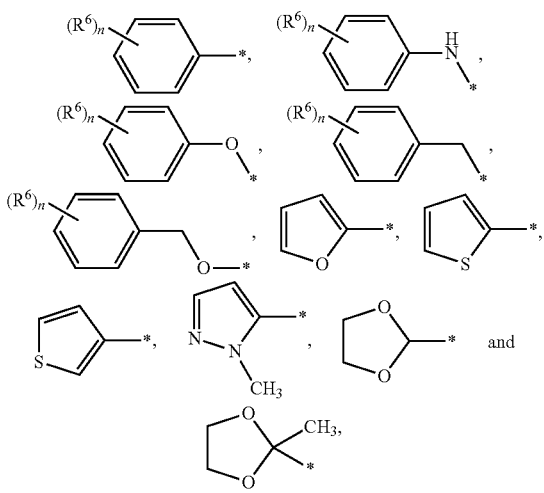

wherein * indicates the point of attachment of said group with the rest of the molecule;
wherein said $C_1$-$C_4$-alkyl, $C_1$-$C_4$-alkoxy, $C_1$-$C_4$-haloalkyl or $C_1$-$C_4$-haloalkoxy groups are optionally substituted with one or two hydroxy groups; and
$R^6$ represents, independently from each other, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl or $C_1$-$C_4$-haloalkoxy; and
ring B represents a group selected from:

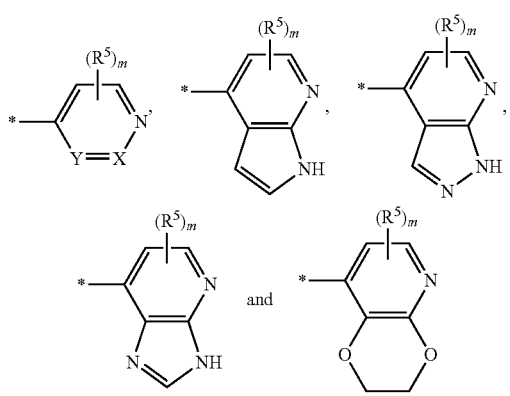

wherein * indicates the point of attachment of said group with the rest of the molecule; and
X represents $CR^4$ or N; and
Y represents $CR^4$ or N,
  wherein when one of X and Y represents N, the other represents $CR^4$; and
$R^4$ represents, independently from each other, hydrogen, halogen, hydroxy, cyano, $C_1$-$C_4$-alkyl, $C_1$-$C_4$-alkoxy, $C_1$-$C_4$-alkyl-S—, $C_1$-$C_4$-alkyl-SO—, $C_1$-$C_4$-alkyl-SO_2—, $R^9R^{10}N—$, $R^{11}—C(O)—(NR^7)—$, $(R^{11}—C(O)—)(R^{12}—C(O)—)N—$, $R^9R^{10}N—C(O)—(NR^7)—$, $R^9R^{10}N—C(S)—(NR^7)—$, $R^{18}—O—C(O)—(NR^7)—$, $R^9R^{10}N—SO_2—$ or $C_1$-$C_4$-alkyl-SO_2—NH—,
  wherein said $C_1$-$C_4$-alkyl is optionally substituted, one or more times, independently from each other, with a substituent selected from hydroxy and halogen; and
  wherein said $C_1$-$C_4$-alkoxy is optionally substituted, one or more times, independently from each other, with a substituent selected from hydroxy, halogen, $C_1$-$C_4$-alkoxy, $C_3$-$C_6$-cycloalkyl and phenyl, wherein said phenyl is optionally substituted, one or more times, independently from each other, with $R^3$; and
$R^5$ represents, independently from each other, halogen, hydroxy, amino, nitro, cyano, $C_1$-$C_4$-alkyl, $C_1$-$C_4$-alkoxy, $C_1$-$C_4$-haloalkyl, $C_1$-$C_4$-haloalkoxy or phenyl-$C_1$-$C_4$-alkyl,
  wherein said phenyl group is optionally substituted, one or more times, independently from each other, with a substituent selected from halogen, hydroxy, $C_1$-$C_3$-alkyl, $C_1$-$C_3$-haloalkyl and $C_1$-$C_3$-alkoxy; and
J represents hydrogen or hydroxy; and
E represents hydrogen, $C_1$-$C_4$-alkyl, $C_1$-$C_4$-alkoxy-$C_2$-$C_4$-alkyl, $R^{17a}R^{17b}R^{17c}Si—O—C_2$-$C_4$-alkyl, $C_1$-$C_4$-alkyl-SO_2—$C_1$-$C_4$-alkyl, $R^{18}—O—C(O)—C_1$-$C_4$-alkyl, $R^7R^8N—C_2$-$C_4$-alkyl, $R^7R^8N—C(O)—C_1$-$C_4$-alkyl or phenyl-$C_1$-$C_4$-alkyl,
  wherein said $C_1$-$C_4$-alkyl is optionally substituted, one or more times, independently from each other, with a substituent selected from hydroxy and halogen; and
  wherein said phenyl group is optionally substituted, one or more times, independently from each other, with $R^5$;
Q represents O or N—$OR^{16}$;
$R^7$, $R^8$ represent, independently from each other, hydrogen, $C_1$-$C_4$-alkyl or
tert-butyl-O—C(O)—;
and
$R^9$, $R^{10}$ represent, independently from each other, hydrogen, $C_1$-$C_4$-alkyl, $C_3$-$C_6$-cyclo-alkyl-, $C_1$-$C_4$-haloalkyl-, phenyl or heteroaryl,
  wherein said phenyl or heteroaryl group is optionally substituted, one or more times, independently from each other, with $R^5$; and
  wherein said $C_1$-$C_4$-alkyl is optionally substituted, one or more times, independently from each other, with hydroxy, $C_1$-$C_4$-alkoxy, $C_1$-$C_4$-alkyl-S—, $C_3$-$C_6$-cycloalkyl, 4- to 6-membered heterocycloalkyl, phenyl, heteroaryl or $R^{18}—O—C(O)—$,
    wherein said $C_3$-$C_6$-cycloalkyl or 4- to 6-membered heterocycloalkyl is optionally substituted, one or more times, independently from each other, with a substituent selected from halogen, $C_1$-$C_4$-alkyl and tert-butyl-O—C(O)—,
    wherein said phenyl or heteroaryl group is optionally substituted, one or more times, independently from each other, with $R^5$; or
$R^9$ and $R^{10}$ together with the nitrogen atom to which they are attached form a 3- to 7-membered nitrogen containing heterocyclic ring, optionally containing one additional heteroatom selected from O, NH or S, and which may be optionally substituted, one or more times, independently from each other, with $R^5$; and
$R^{11}$, $R^{12}$ represent, independently from each other, $C_1$-$C_4$-alkyl, $C_2$-$C_4$-alkenyl, $C_2$-$C_4$-alkynyl, $C_3$-$C_6$-cycloalkyl, 4- to 6-membered heterocycloalkyl, phenyl, heteroaryl, or $R^{13}—(C_1$-$C_4$-alkyl)-O—CH_2—$,
  wherein said $C_1$-$C_4$-alkyl is optionally substituted, one or more times, independently from each other, with a substituent selected from halogen, hydroxy, cyano, $C_1$-$C_4$-alkoxy, $R^7R^8N—$, $R^{14}$, $R^{15}—O—$, and phenyl optionally substituted, one or more times, independently from each other, with $R^5$, and wherein said $C_3$-$C_6$-cycloalkyl is optionally substituted, one or more times, independently from each other, with a substituent selected from halogen, cyano, $C_1$-$C_4$-alkyl, $C_1$-$C_4$-haloalkyl and phenyl optionally substituted, one or more times, independently from each other, with $R^5$, and wherein said 4- to 6-membered heterocycloalkyl is optionally substituted, one or more times, independently from each other, with a substituent selected from hydroxy, $C_1$-$C_4$-alkyl, $C_1$-$C_4$-alkoxy, $R^7R^8N$— and $R^{18}$—O—C(O)—, and wherein said phenyl or heteroaryl is optionally substituted, one or more times, independently from each other, with $R^5$;

$R^{13}$ represents branched $C_3$-$C_4$-alkyl, $C_1$-$C_4$-haloalkyl, $C_2$-$C_4$-alkenyl, $C_2$-$C_4$-alkynyl, $C_3$-$C_6$-cycloalkyl, 4- to 6-membered heterocycloalkyl, phenyl or heteroaryl, wherein said phenyl or heteroaryl is optionally substituted, one or more times, independently from each other, with $R^5$;

$R^{14}$ represents $C_1$-$C_4$-alkyl-S—, $C_1$-$C_4$-alkyl-$SO_2$—, $C_3$-$C_6$-cycloalkyl, 4- to 6-membered heterocycloalkyl, phenyl or heteroaryl, wherein said phenyl or heteroaryl is optionally substituted, one or more times, independently from each other, with $R^5$;

$R^{15}$ represents phenyl or heteroaryl, wherein said phenyl or heteroaryl is optionally substituted, one or more times, independently from each other, with $R^5$; and $R^{16}$ represents hydrogen, $C_1$-$C_6$-alkyl, phenyl or $C_1$-$C_4$-alkyl-C(O)—, wherein said phenyl group is optionally substituted, one or more times, independently from each other, with $R^5$;

$R^{17a}$, $R^{17b}$, $R^{17c}$ represent, independently from each other, $C_1$-$C_4$-alkyl;

$R^{18}$ represents hydrogen or $C_1$-$C_6$-alkyl;

m represents 0, 1 or 2;

n represents 0, 1, 2 or 3; and or an N-oxide, a salt, a tautomer or a stereoisomer of said compound, or a salt of said N-oxide, tautomer or stereoisomer.

In accordance with an embodiment of the second aspect, the invention relates to compounds of formula (Ia) as described supra, wherein $R^1$ represents hydrogen, $C_1$-$C_4$-alkyl, $C_1$-$C_2$-haloalkyl or phenyl, wherein said phenyl is optionally substituted, one or more times, independently from each other, with halogen, hydroxy, amino, nitro, cyano, $C_1$-$C_2$-alkyl, $C_1$-$C_2$-alkoxy, $C_1$-$C_2$-alkoxy-$C_1$-$C_2$-alkyl-, $C_1$-$C_2$-haloalkyl, $C_1$-$C_2$-haloalkoxy, $C_1$-$C_2$-alkyl-C(O)—, $C_1$-$C_2$-alkyl-O—C(O)—, $R^7R^8N$—C(O)— or $C_1$-$C_4$-alkyl-C(O)—NH—, wherein said $C_1$-$C_2$-alkyl, $C_1$-$C_2$-alkoxy, $C_1$-$C_2$-haloalkyl or $C_1$-$C_2$-haloalkoxy groups are optionally substituted with hydroxy; and $R^2$ represents hydrogen, $C_1$-$C_4$-alkyl or $C_1$-$C_2$-haloalkyl; or $R^1$ and $R^2$ together with the carbon atom to which they are attached form a 3- to 6-membered cycloalkyl ring; and A represents a group selected from:

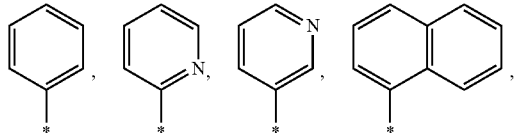

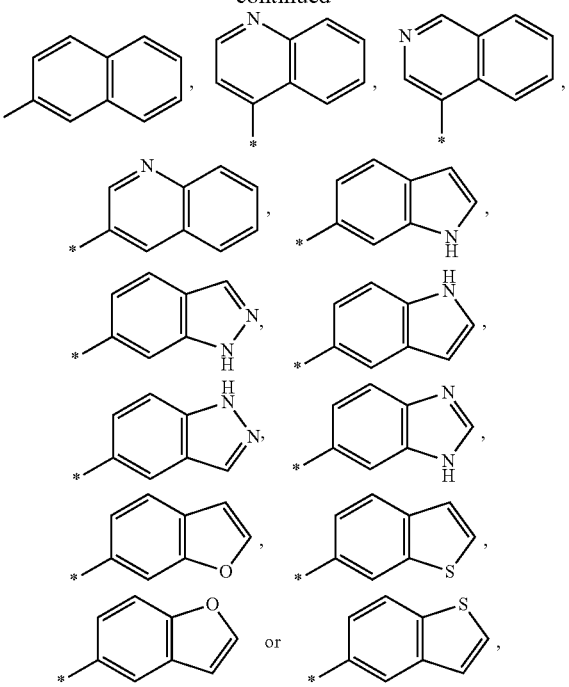

wherein * indicates the point of attachment of said group with the rest of the molecule and said group is optionally substituted, one or more times, independently from each other, with $R^3$; and $R^3$ represents hydrogen, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $C_1$-$C_4$-alkyl-O—C(O)—, $R^7R^8N$—C(O)—, $C_1$-$C_4$-alkyl-C(O)—NH—, or a group

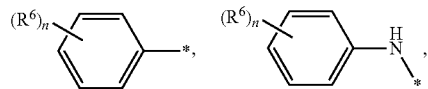

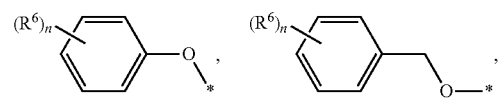

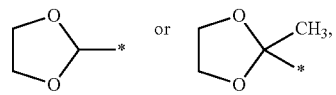

wherein said $C_1$-$C_4$-alkyl, $C_1$-$C_4$-alkoxy, $C_1$-$C_4$-haloalkyl or $C_1$-$C_4$-haloalkoxy groups are optionally substituted with hydroxy; and $R^6$ represents, independently from each other, halogen, hydroxy, amino, nitro, cyano, $C_1$-$C_2$-alkyl, $C_1$-$C_2$-alkoxy, $C_1$-$C_2$-alkoxy-$C_1$-$C_2$-alkyl-, $C_1$-$C_2$-haloalkyl or $C_1$-$C_2$-haloalkoxy; and B represents a group selected from:

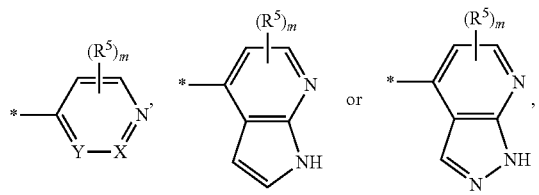

wherein * indicates the point of attachment of said group with the rest of the molecule; and X represents $CR^4$ or N; and
Y represents $CR^4$ or N,
  wherein when one of X and Y represents N, the other represents $CR^4$; and
$R^4$ represents, independently from each other, hydrogen, halogen, hydroxy, cyano, $C_1$-$C_4$-alkyl, $C_1$-$C_4$-alkoxy, $R^9R^{10}N$—, $R^{11}$—C(O)—NH—, ($R^{11}$—C(O)—)($R^{12}$—C(O)—)N— or $C_1$-$C_4$-alkyl-$SO_2$—NH—; and
$R^5$ represents, independently from each other, halogen, hydroxy, amino, nitro, cyano, $C_1$-$C_2$-alkyl or $C_1$-$C_2$-alkoxy; and
$R^7$, $R^8$ represent, independently from each other, hydrogen or $C_1$-$C_4$-alkyl; and
$R^9$, $R^{10}$ represent, independently from each other, hydrogen, $C_1$-$C_4$-alkyl or phenyl, wherein said phenyl group is optionally substituted, one or more times, independently from each other, with $R^5$; or
$R^9$ and $R^{10}$ together with the nitrogen atom to which they are attached form a 4- to 6-membered nitrogen containing heterocyclic ring, optionally containing at least one additional heteroatom selected from O, NH or S, and which may be optionally substituted, one or more times, independently from each other, with $R^5$; and
$R^{11}$, $R^{12}$ represent, independently from each other, $C_1$-$C_4$-alkyl, $C_3$-$C_6$-cycloalkyl- or $C_1$-$C_4$-haloalkyl-;
n represents 0, 1, 2 or 3; and
m represents 0, 1 or 2;
or an N-oxide, a salt, a tautomer or a stereoisomer of said compound, or a salt of said N-oxide, tautomer or stereoisomer.

In a third aspect, the invention relates to compounds of formula (I) as described supra, wherein
$R^1$ represents hydrogen, $C_1$-$C_4$-alkyl, $C_1$-$C_2$-haloalkyl or phenyl, wherein said phenyl is optionally substituted, one or more times, independently from each other, with $R^3$; and
$R^2$ represents hydrogen, $C_1$-$C_2$-alkyl or $C_1$-$C_2$-haloalkyl; or
$R^1$ and $R^2$ together with the carbon atom to which they are attached form a 3- to 7-membered cycloalkyl ring; and
A represents a group selected from:

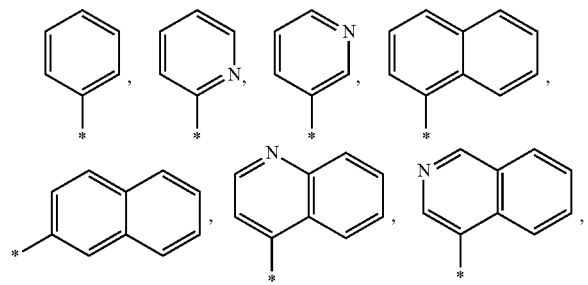

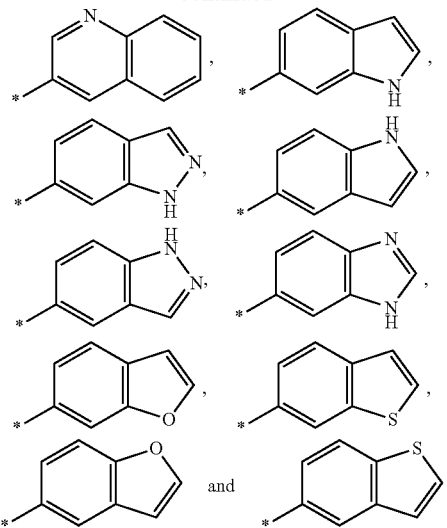

wherein * indicates the point of attachment of said group with the rest of the molecule and said group is optionally substituted, one or more times, independently from each other, with $R^3$; and $R^3$ represents hydrogen, halogen, hydroxy, amino, nitro, cyano, $C_1$-$C_4$-alkyl, $C_2$-$C_4$-alkynyl, $C_1$-$C_4$-alkoxy, $C_1$-$C_2$-alkoxy-$C_1$-$C_2$-alkyl-, $C_1$-$C_2$-haloalkyl, $C_1$-$C_2$-haloalkoxy, $C_1$-$C_2$-alkyl-C(O)—, $R^{18}$—O—C(O)—, $R^7R^8N$—C(O)—, $C_1$-$C_3$-alkyl-C(O)—NH—, $R^7R^8N$—, $R^7R^8N$—$SO_2$—,
or a group selected from

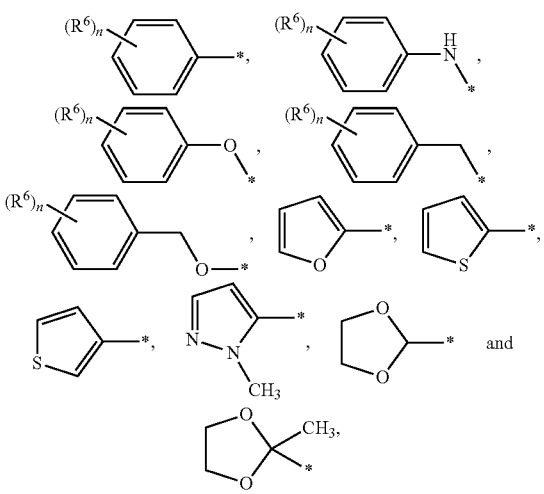

wherein * indicates the point of attachment of said group with the rest of the molecule;
wherein said $C_1$-$C_4$-alkyl, $C_1$-$C_4$-alkoxy, $C_1$-$C_2$-haloalkyl or $C_1$-$C_2$-haloalkoxy groups are optionally substituted with one or two hydroxy groups; and
$R^6$ represents, independently from each other, halogen, hydroxy, amino, nitro, cyano, $C_1$-$C_2$-alkyl, $C_1$-$C_2$-alkoxy, $C_1$-$C_2$-alkoxy-$C_1$-$C_2$-alkyl-, $C_1$-$C_2$-haloalkyl or $C_1$-$C_2$-haloalkoxy; and B represents a group selected from:

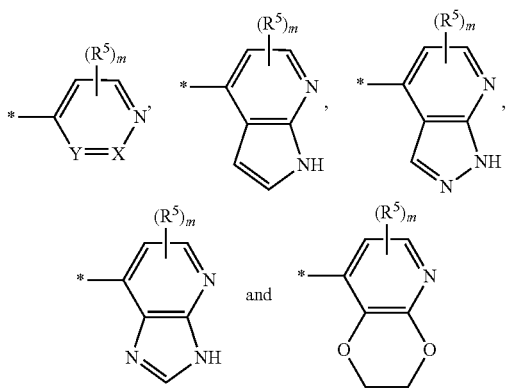

wherein * indicates the point of attachment of said group with the rest of the molecule; and
X represents $CR^4$ or N; and
Y represents $CR^4$ or N,
wherein when one of X and Y represents N, the other represents $CR^4$; and
$R^4$ represents, independently from each other, hydrogen, halogen, hydroxy, cyano, $C_1$-$C_3$-alkyl, $C_1$-$C_4$-alkoxy, $C_1$-$C_2$-alkyl-S—, $C_1$-$C_2$-alkyl-SO—, $C_1$-$C_2$-alkyl-$SO_2$—, $R^9R^{10}N$—, $R^{11}$—C(O)—($NR^7$)—, ($R^{11}$—C(O)—)($R^{12}$—C(O)—)N—, $R^9R^{10}N$—C(O)—($NR^7$)—, $R^9R^{10}N$—C(S)—($NR^7$)—, $R^{18}$—O—C(O)—($NR^7$)—, $R^9R^{10}N$—$SO_2$— or $C_1$-$C_2$-alkyl-$SO_2$—NH—,
wherein said $C_1$-$C_3$-alkyl is optionally substituted, one or more times, independently from each other, with a substituent selected from hydroxy and halogen; and
wherein said $C_1$-$C_4$-alkoxy is optionally substituted, one or more times, independently from each other, with hydroxy, halogen, $C_1$-$C_4$-alkoxy, $C_3$-$C_6$-cycloalkyl or phenyl, wherein said phenyl is optionally substituted, one or more times, independently from each other, with $R^3$; and
$R^5$ represents, independently from each other, halogen, hydroxy, amino, nitro, cyano, $C_1$-$C_4$-alkyl, $C_1$-$C_3$-alkoxy, $C_1$-$C_3$-haloalkyl, $C_1$-$C_3$-haloalkoxy or phenyl-$C_1$-$C_4$-alkyl,
wherein said phenyl group is optionally substituted, one or more times, independently from each other, with $C_1$-$C_2$-alkoxy; and
J represents hydrogen or hydroxy; and
E represents hydrogen, $C_1$-$C_4$-alkyl, $R^{17a}R^{17b}R^{17c}Si$—O—$C_2$-alkyl, $R^{18}$—O—C(O)—$C_1$-$C_2$-alkyl, $R^7R^8N$—C(O)—$C_1$-$C_2$-alkyl or phenyl-$C_1$-$C_2$-alkyl,
wherein said $C_1$-$C_4$-alkyl is optionally substituted, one or more times, independently from each other, with a substituent selected from hydroxy and halogen; and
wherein said phenyl group is optionally substituted, one or more times, independently from each other, with $R^5$;
Q represents O or N—$OR^{16}$;
$R^7$, $R^8$ represent, independently from each other, hydrogen, $C_1$-$C_4$-alkyl or
tert-butyl-O—C(O)—;
and
$R^9$, $R^{10}$ represent, independently from each other, hydrogen, $C_1$-$C_4$-alkyl, $C_3$-$C_6$-cyclo-alkyl-, $C_1$-$C_4$-haloalkyl-, phenyl or heteroaryl,
wherein said phenyl or heteroaryl group is optionally substituted, one or more times, independently from each other, with $R^5$; and wherein said $C_1$-$C_4$-alkyl is optionally substituted, one or more times, independently from each other, with a substituent selected from hydroxy, $C_1$-$C_2$-alkoxy, $C_1$-$C_2$-alkyl-S—, $C_3$-$C_6$-cycloalkyl, 4- to 6-membered heterocycloalkyl, phenyl, heteroaryl and $R^{18}$—O—C(O)—,
wherein said 4- to 6-membered heterocycloalkyl is optionally substituted, one or more times, independently from each other, with a substituent selected from $C_1$-$C_2$-alkyl and tert-butyl-O—C(O)—,
wherein said phenyl or heteroaryl group is optionally substituted, one or more times, independently from each other, with $R^5$; or
$R^9$ and $R^{10}$ together with the nitrogen atom to which they are attached form a 3- to 7-membered nitrogen containing heterocyclic ring, optionally containing one additional heteroatom selected from O, and NH, and which may be optionally substituted, one or more times, independently from each other, with $R^5$; and
$R^{11}$, $R^{12}$ represent, independently from each other, $C_1$-$C_4$-alkyl, $C_3$-$C_6$-cycloalkyl, 4- to 6-membered heterocycloalkyl, phenyl, heteroaryl, $R^{13}$—$(CH_2)_o$—O—$CH_2$—, $R^{14}$—$(CH_2)_o$—, or $R^{15}$—O—$(CH_2)_o$—,
wherein said $C_1$-$C_4$-alkyl is optionally substituted, one or more times, independently from each other, with a substituent selected from halogen, hydroxy, cyano, $C_1$-$C_4$-alkoxy, $R^7R^8N$—, and phenyl optionally substituted, one or more times, independently from each other, with $R^5$, and
wherein said $C_3$-$C_6$-cycloalkyl is optionally substituted, one or more times, independently from each other, with a substituent selected from halogen, cyano, $C_1$-$C_2$-alkyl, $C_1$-$C_2$-haloalkyl and phenyl optionally substituted, one or more times, independently from each other, with $R^5$, and
wherein said 4- to 6-membered heterocycloalkyl is optionally substituted, one or more times, independently from each other, with a substituent selected from hydroxy, $C_1$-$C_2$-alkyl, $C_1$-$C_2$-alkoxy, $R^7R^8N$— and $R^{18}$—O—C(O)—, and
wherein said phenyl or heteroaryl is optionally substituted, one or more times, independently from each other, with $R^5$;
$R^{13}$ represents branched $C_3$-$C_4$-alkyl, $C_1$-$C_2$-haloalkyl, $C_2$-$C_3$-alkenyl, $C_2$-$C_3$-alkynyl, $C_3$-$C_6$-cycloalkyl, 4- to 6-membered heterocycloalkyl, phenyl or heteroaryl,
wherein said phenyl or heteroaryl is optionally substituted, one or more times, independently from each other, with $R^5$;
$R^{14}$ represents $C_1$-$C_2$-alkyl-S—, $C_1$-$C_2$-alkyl-$SO_2$—, $C_3$-$C_6$-cycloalkyl, 4- to 6-membered heterocycloalkyl, phenyl or heteroaryl,
wherein said phenyl or heteroaryl is optionally substituted, one or more times, independently from each other, with $R^5$;
$R^{15}$ represents phenyl or heteroaryl,
wherein said phenyl or heteroaryl is optionally substituted, one or more times, independently from each other, with $R^5$; and
$R^{16}$ represents hydrogen, $C_1$-$C_2$-alkyl, or $C_1$-$C_2$-alkyl-C(O)—,
$R^{17a}$, $R^{17b}$, $R^{17c}$ represent, independently from each other, $C_1$-$C_4$-alkyl;
$R^{18}$ represents hydrogen or $C_1$-$C_4$-alkyl;
m represents 0, 1 or 2;
n represents 0, 1, or 2; and
o represents 1, 2, 3 or 4;

or an N-oxide, a salt, a tautomer or a stereoisomer of said compound, or a salt of said N-oxide, tautomer or stereoisomer.

In accordance with an embodiment of the third aspect, the invention relates to compounds of formula (Ia) as described supra, wherein $R^1$ represents hydrogen, $C_1$-$C_4$-alkyl, $C_1$-$C_2$-haloalkyl or phenyl, wherein said phenyl is optionally substituted, one or more times, independently from each other, with halogen, hydroxy, amino, nitro, cyano, $C_1$-$C_2$-alkyl, $C_1$-$C_2$-alkoxy, $C_1$-$C_2$-alkoxy-$C_1$-$C_2$-alkyl-, $C_1$-$C_2$-haloalkyl, $C_1$-$C_2$-haloalkoxy, wherein said $C_1$-$C_2$-alkyl, $C_1$-$C_2$-alkoxy, $C_1$-$C_2$-haloalkyl or $C_1$-$C_2$-haloalkoxy groups are optionally substituted with hydroxy; and $R^2$ represents hydrogen, $C_1$-$C_4$-alkyl or $C_1$-$C_2$-haloalkyl; or $R^1$ and $R^2$ together with the carbon atom to which they are attached form a 3- to 4-membered cycloalkyl ring; and A represents a group selected from:

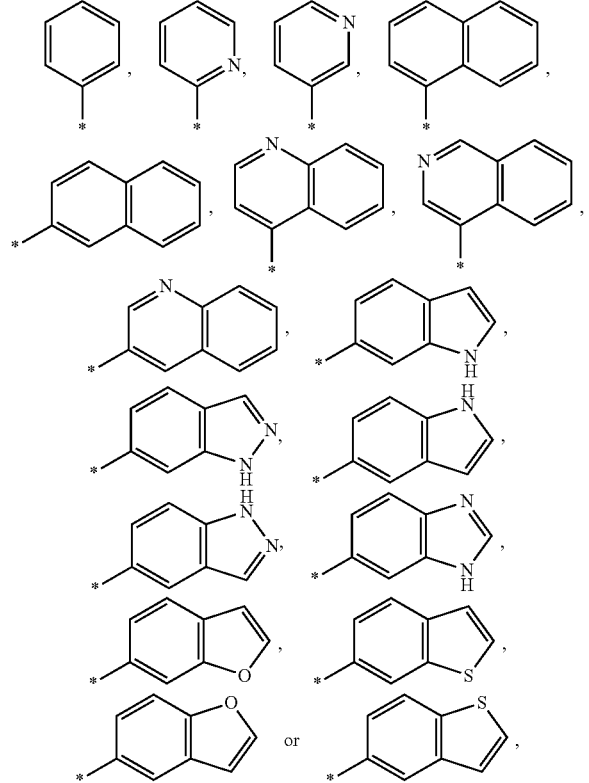

wherein * indicates the point of attachment of said group with the rest of the molecule and said group

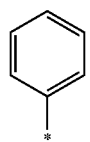 [SMILES: *c1ccccc1]

is optionally substituted, one or more times, independently from each other, with $R^3$; and $R^3$ represents hydrogen, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $C_1$-$C_4$-alkyl-O—C(O)—, $R^7R^8N$—C(O)—, $C_1$-$C_4$-alkyl-C(O)—NH—, or a group

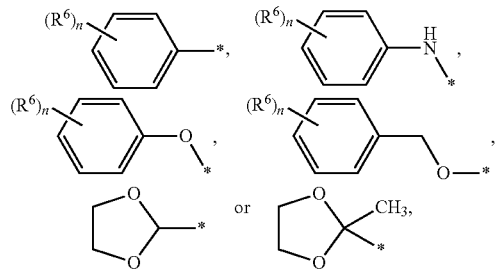

wherein said $C_1$-$C_4$-alkyl, $C_1$-$C_4$-alkoxy, $C_1$-$C_4$-haloalkyl or $C_1$-$C_4$-haloalkoxy groups are optionally substituted with hydroxy; and $R^6$ represents, independently from each other, halogen, hydroxy, amino, nitro, cyano, $C_1$-$C_2$-alkyl, $C_1$-$C_2$-alkoxy, $C_1$-$C_2$-alkoxy-$C_1$-$C_2$-alkyl-, $C_1$-$C_2$-haloalkyl or $C_1$-$C_2$-haloalkoxy; and B represents a group selected from:

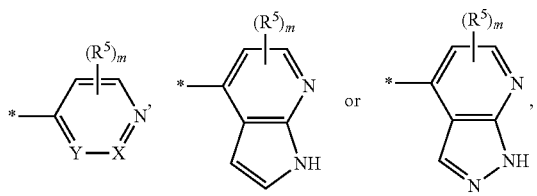

wherein * indicates the point of attachment of said group with the rest of the molecule; and X represents $CR^4$ or N; and Y represents $CR^4$ or N, wherein when one of X and Y represents N, the other represents $CR^4$; and $R^4$ represents, independently from each other, hydrogen, halogen, hydroxy, cyano, $C_1$-$C_2$-alkyl, $C_1$-$C_2$-alkoxy, $R^9R^{10}N$—, $R^{11}$—C(O)—NH—, $(R^{11}$—C(O)—)($R^{12}$—C(O)—)N— or $C_1$-$C_4$-alkyl-$SO_2$—NH—; and $R^5$ represents, independently from each other, halogen, hydroxy, amino, nitro, cyano, $C_1$-$C_2$-alkyl or $C_1$-$C_2$-alkoxy; and $R^7$, $R^8$ represent, independently from each other, hydrogen or $C_1$-$C_2$-alkyl; and $R^9$, $R^{10}$ represent, independently from each other, hydrogen, $C_1$-$C_2$-alkyl or phenyl, wherein said phenyl group is optionally substituted, one or more times, independently from each other, with $R^5$; or $R^9$ and $R^{10}$ together with the nitrogen atom to which they are attached form a 5- to 6-membered nitrogen containing heterocyclic ring, optionally containing at least one additional heteroatom selected from O, and which may be optionally substituted, one or more times, independently from each other, with $R^5$; and $R^{11}$, $R^{12}$ represent, independently from each other, $C_1$-$C_4$-alkyl, $C_3$-$C_6$-cycloalkyl- or $C_1$-$C_2$-haloalkyl-;

n represents 0, 1, 2 or 3; and m represents 0, 1 or 2;

or an N-oxide, a salt, a tautomer or a stereoisomer of said compound, or a salt of said N-oxide, tautomer or stereoisomer.

In a fourth aspect the invention relates to compounds of formula (I) as described supra, wherein:

$R^1$ represents hydrogen, $C_1$-$C_4$-alkyl, $C_1$-$C_2$-haloalkyl or phenyl, wherein said phenyl is optionally substituted, one or more times, independently from each other, with $R^3$; and $R^2$ represents hydrogen, or $C_1$-$C_2$-alkyl; or $R^1$ and $R^2$ together with the carbon atom to which they are attached form a 3- to 6-membered cycloalkyl ring; and ring A represents a group selected from:

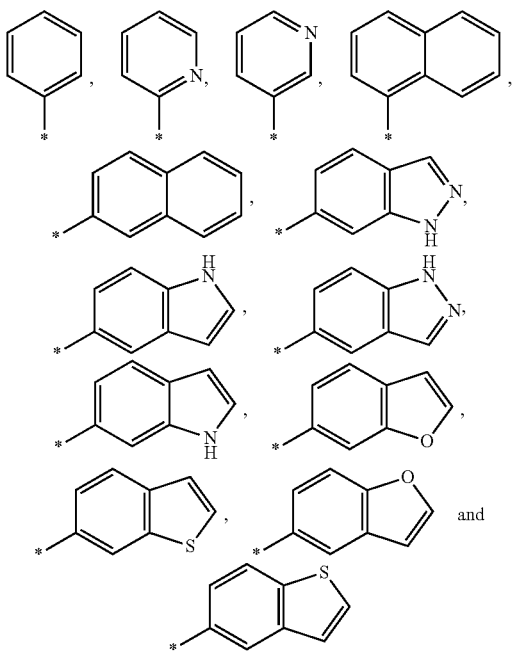

wherein * indicates the point of attachment of said group with the rest of the molecule and said group is optionally substituted, one or more times, independently from each other, with $R^3$; and $R^3$ represents hydrogen, halogen, hydroxy, amino, nitro, cyano, $C_1$-$C_4$-alkyl, $C_2$-alkynyl, $C_1$-$C_3$-alkoxy, $C_1$-alkoxy-$C_2$-alkyl-, $C_1$-$C_2$-haloalkyl, $C_1$-$C_2$-haloalkoxy, $C_1$-$C_2$-alkyl-C(O)—, $R^{18}$—O—C(O)—, $R^7R^8$N—C(O)—, $C_1$-$C_3$-alkyl-C(O)—NH—, or a group selected from

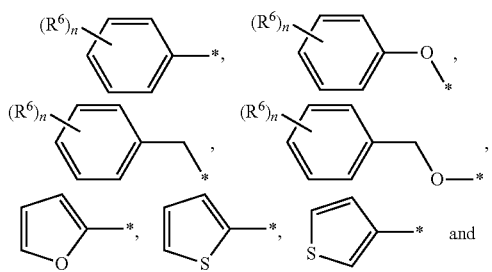

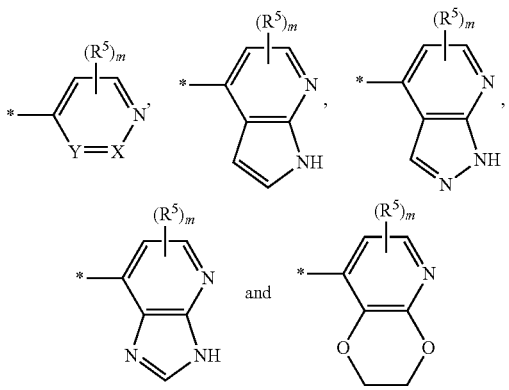

wherein * indicates the point of attachment of said group with the rest of the molecule;

wherein said $C_1$-$C_4$-alkyl, $C_1$-$C_3$-alkoxy, $C_1$-$C_2$-haloalkyl or $C_1$-$C_2$-haloalkoxy groups are optionally substituted with one or two hydroxy groups; and $R^6$ represents $C_1$-alkoxy; and ring B represents a group selected from:

wherein * indicates the point of attachment of said group with the rest of the molecule; and X represents $CR^4$ or N; and Y represents $CR^4$ or N,
wherein when one of X and Y represents N, the other represents $CR^4$; and $R^4$ represents, independently from each other, hydrogen, halogen, hydroxy, cyano, $C_1$-$C_2$-alkyl, $C_1$-$C_4$-alkoxy, $C_1$-$C_2$-alkyl-S—, $R^9R^{10}$N—, $R^{11}$—C(O)—(NH)—, $(R^{11}$—C(O)—)($R^{12}$—C(O)—)N—, $R^9R^{10}$N—C(O)—$(NR^7)$—, $R^9R^{10}$N—C(S)—$(NR^7)$—, $R^{18}$—O—C(O)—$(NR^7)$—, $R^9R^{10}$N—SO$_2$— or $C_1$-$C_2$-alkyl-SO$_2$—NH—,
wherein said $C_1$-$C_2$-alkyl is optionally substituted, one time with hydroxy and/or one, two or three times, independently from each other, with halogen; and
wherein said $C_1$-$C_4$-alkoxy is optionally substituted, one or more times, independently from each other, with a substituent selected from hydroxy, halogen, $C_1$-$C_2$-alkoxy, and $C_3$-$C_4$-cycloalkyl; and $R^5$ represents, independently from each other, halogen, amino, $C_1$-$C_4$-alkyl, $C_1$-$C_2$-alkoxy, or phenyl-$C_1$-$C_2$-alkyl,
wherein said phenyl group is optionally substituted, one or more times, with $C_1$-alkoxy; and J represents hydrogen or hydroxy; and E represents hydrogen, $C_1$-$C_4$-alkyl, $R^{18}$—O—C(O)—$C_1$-$C_2$-alkyl, or $R^7R^8$N—C(O)—$C_1$-$C_2$-alkyl,
wherein said $C_1$-$C_4$-alkyl is optionally substituted, one or more times, independently from each other, with a substituent selected from hydroxy and halogen;

Q represents O or N—$OR^{16}$;

$R^7$, $R^8$ represent, independently from each other, hydrogen, $C_1$-$C_2$-alkyl or
tert-butyl-O—C(O)—;

and

R$^9$, R$^{10}$ represent, independently from each other, hydrogen, C$_1$-C$_4$-alkyl, C$_3$-C$_6$-cyclo-alkyl-, C$_1$-C$_4$-haloalkyl-, phenyl or heteroaryl,
  wherein said phenyl or heteroaryl group is optionally substituted, one or more times, independently from each other, with R$^5$; and
  wherein said C$_1$-C$_4$-alkyl is optionally substituted, one or more times, independently from each other, with a substituent selected from hydroxy, C$_1$-alkoxy, C$_1$-alkyl-S—, C$_3$-C$_6$-cycloalkyl, 4- to 6-membered heterocycloalkyl, phenyl, heteroaryl and R$^{18}$—O—C(O)—,
    wherein said 4- to 6-membered heterocycloalkyl is optionally substituted, one time with tert-butyl-O—C(O)—,
    wherein said phenyl or heteroaryl group is optionally substituted, one or more times, independently from each other, with R$^5$;

and

R$^{11}$, R$^{12}$ represent, independently from each other, C$_1$-C$_4$-alkyl, C$_3$-C$_6$-cycloalkyl, 4- to 6-membered heterocycloalkyl, phenyl, heteroaryl, R$^{13}$—(CH$_2$)$_o$—O—CH$_2$—, R$^{14}$—(CH$_2$)$_o$—, or R$^{15}$—O—(CH$_2$)$_o$—,
  wherein said C$_1$-C$_4$-alkyl is optionally substituted, one or more times, independently from each other, with a substituent selected from halogen, hydroxy, cyano, C$_1$-C$_4$-alkoxy, R$^7$R$^8$N—, and phenyl optionally substituted, one or more times, independently from each other, with R$^5$, and
  wherein said C$_3$-C$_6$-cycloalkyl is optionally substituted, one or two times, independently from each other, with a substituent selected from halogen, cyano, C$_1$-C$_2$-alkyl, C$_1$-C$_2$-haloalkyl and phenyl optionally substituted, one or more times, independently from each other, with R$^5$, and
  wherein said 4- to 6-membered heterocycloalkyl is optionally substituted, one or more times, independently from each other, with a substituent selected from C$_1$-C$_2$-alkyl, and R$^{18}$—O—C(O)—, and
  wherein said phenyl or heteroaryl is optionally substituted, one or more times, independently from each other, with R$^5$;

R$^{13}$ represents branched C$_3$-C$_4$-alkyl, C$_1$-C$_2$-haloalkyl, C$_2$-C$_3$-alkenyl, C$_2$-C$_3$-alkynyl, 4- to 6-membered heterocycloalkyl, phenyl or heteroaryl,
  wherein said phenyl or heteroaryl is optionally substituted, one or more times, independently from each other, with R$^5$;

R$^{14}$ represents C$_1$-C$_2$-alkyl-S—, C$_1$-C$_2$-alkyl-SO$_2$—, C$_3$-C$_6$-cycloalkyl, 4- to 6-membered heterocycloalkyl, phenyl or heteroaryl,
  wherein said phenyl or heteroaryl is optionally substituted, one or more times, independently from each other, with R$^5$;

R$^{15}$ represents phenyl or heteroaryl,
  wherein said phenyl or heteroaryl is optionally substituted, one or more times, independently from each other, with R$^5$; and R$^{16}$ represents hydrogen, or C$_1$-C$_2$-alkyl-C(O)—;

R$^{18}$ represents hydrogen or C$_1$-C$_4$-alkyl;

m represents 0, 1 or 2;

n represents 0, or 1; and o represents 1, 2, 3 or 4;

or an N-oxide, a salt, a tautomer or a stereoisomer of said compound, or a salt of said N-oxide, tautomer or stereoisomer.

In accordance with an embodiment of the fourth aspect the invention relates to compounds of formula (Ia) as described supra,
  wherein
  R$^1$ represents hydrogen, methyl, ethyl, isopropyl, isobutyl, —CF$_3$ or phenyl; and
  R$^2$ represents hydrogen, methyl, ethyl, isopropyl, isobutyl or —CF$_3$; or
  R$^1$ and R$^2$ together with the carbon atom to which they are attached form a 3- or 4-membered cycloalkyl ring; and
  A represents a group

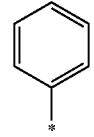

wherein * indicates the point of attachment of said group with the rest of the molecule and said group is optionally substituted, one or more times, independently from each other, with R$^3$; and R$^3$ represents hydrogen, F, Cl, Br, hydroxy, amino, nitro, cyano, methyl, ethyl, isopropyl, t-butyl, CH$_3$O—, CH$_3$CH$_2$O—, CH$_3$CH$_2$CH$_2$O—, (CH$_3$)$_2$CH—O—, CH$_2$(OH)—CH$_2$—O—, CF$_3$O—, —CH$_2$(OH), —CH(OH)CH$_2$CH$_3$, —CH(OH)CF$_3$, —CH(CH$_3$)—O—CH$_3$, —CH(OH)—CH$_3$, —C(O)CH$_3$, —CF$_3$, CH$_3$—C(O)—NH—, CH$_3$CH$_2$—C(O)—NH—, CH$_3$CH$_2$CH$_2$—C(O)—NH—, (CH$_3$)$_2$CH—C(O)—NH—, CH$_3$—NH—C(O)—, CH$_3$CH$_2$—NH—C(O)—, NH$_2$—C(O)—, —OCHF$_2$, (CH$_3$)$_3$C—O—C(O)—, or a group

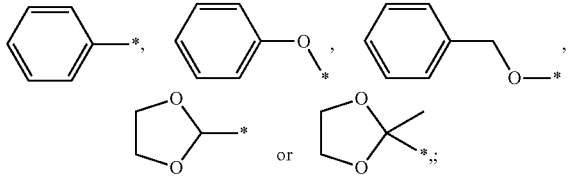

and

B represents a group selected from:

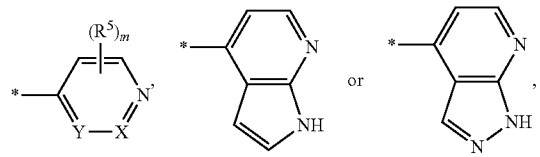

wherein * indicates the point of attachment of said group with the rest of the molecule; and X represents CR$^4$ or N; and Y represents CR$^4$ or N,
  wherein when one of X and Y represents N, the other represents CR$^4$; and R$^4$ represents, independently from each other, hydrogen, F, Cl, Br, cyano, methyl, —OCH$_3$, amino, —NHCH$_3$, —NH—C(O)—CH$_3$, —NH—C(O)—CHF$_2$, —NH—C(O)—CH$_2$CH$_3$, —NH—C(O)—CH(CH$_3$)$_2$, —NH—C(O)-cyclopropyl, —N(—C(O)—CH$_3$)$_2$, —N(—C(O)-cyclopropyl)$_2$, —NH—S(O)$_2$—CH$_3$,

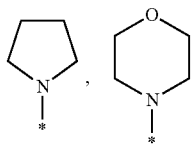

or phenyl-NH—, wherein said phenyl group is optionally substituted, one or more times, independently from each other, with $R^5$.

wherein * indicates the point of attachment of said group with the rest of the molecule; and $R^5$ represents F; and m represents 0 or 1;

or an N-oxide, a salt, a tautomer or a stereoisomer of said compound, or a salt of said N-oxide, tautomer or stereoisomer.

In accordance with a fifth aspect, the invention relates to compounds of formula (I) as described supra, wherein:

$R^1$ represents hydrogen, $C_1$-$C_3$-alkyl, $C_1$-$C_2$-haloalkyl or phenyl, wherein said phenyl is optionally substituted, one or more times, independently from each other, with $R^3$; and $R^2$ represents hydrogen, or $C_1$-$C_2$-alkyl; or $R^1$ and $R^2$ together with the carbon atom to which they are attached form a 3- to 4-membered cycloalkyl ring; and ring A represents a group selected from:

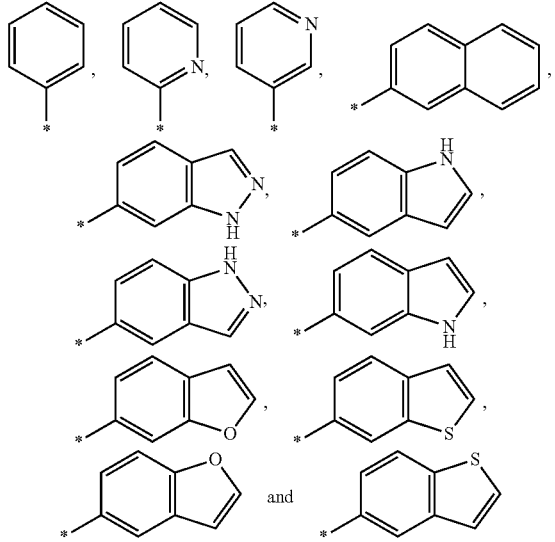

wherein * indicates the point of attachment of said group with the rest of the molecule and said group is optionally substituted, one or more times, independently from each other, with $R^3$; and $R^3$ represents hydrogen, halogen, hydroxy, nitro, cyano, $C_1$-$C_3$-alkyl, $C_1$-$C_3$-alkoxy, $C_1$-haloalkyl, $C_1$-haloalkoxy, $C_1$-$C_2$-alkyl-C(O)—, $R^{18}$—O—C(O)—, $R^7R^8N$—C(O)—, or a group selected from

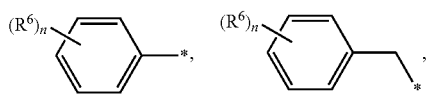

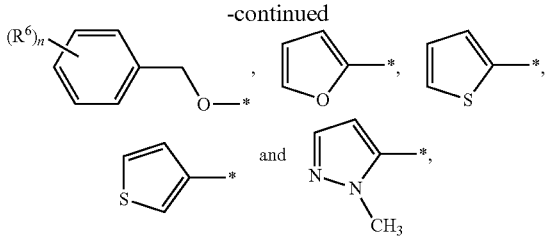

wherein * indicates the point of attachment of said group with the rest of the molecule;

wherein said $C_1$-$C_3$-alkyl, $C_1$-$C_3$-alkoxy, $C_1$-haloalkyl or $C_1$-haloalkoxy groups are optionally substituted with one hydroxy group; and $R^6$ represents $C_1$-alkoxy; and ring B represents a group selected from:

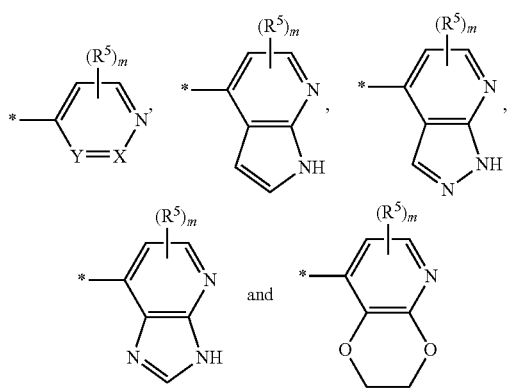

wherein * indicates the point of attachment of said group with the rest of the molecule; and X represents $CR^4$ or N; and Y represents $CR^4$ or N, wherein when one of X and Y represents N, the other represents $CR^4$; and $R^4$ represents, independently from each other, hydrogen, halogen, hydroxy, cyano, $C_1$-alkyl, $C_1$-$C_3$-alkoxy, $C_1$-alkyl-S—, $R^9R^{10}N$—, $R^{11}$—C(O)—(NH)—, $(R^{11}$—C(O)—)($R^{12}$—C(O)—)N—, $R^9R^{10}N$—C(O)—(NR$^7$)—, $R^9R^{10}N$—C(S)—(NR$^7$)—, or $R^{18}$—O—C(O)—(NR$^7$)—, wherein said $C_1$-alkyl is optionally substituted, one, two or three times, independently from each other, with halogen; and wherein said $C_1$-$C_3$-alkoxy is optionally substituted, one or more times, independently from each other, with a substituent selected from hydroxy, halogen, $C_1$-$C_2$-alkoxy, and $C_3$-$C_4$-cycloalkyl; and $R^5$ represents, independently from each other, halogen, amino, $C_1$-$C_4$-alkyl, $C_1$-alkoxy, or phenyl-$C_1$-alkyl, wherein said phenyl group is optionally substituted one time, with $C_1$-alkoxy; and J represents hydrogen or hydroxy; and E represents hydrogen, $C_1$-$C_3$-alkyl, $R^{18}$—O—C(O)—$C_1$-$C_2$-alkyl, or $R^7R^8N$—C(O)—$C_1$-$C_2$-alkyl, wherein said $C_1$-$C_3$-alkyl is optionally substituted, one or more times, independently from each other, with a substituent selected from hydroxy and halogen;

Q represents O or N—OR$^{16}$;
R$^7$, R$^8$ represent, independently from each other, hydrogen, C$_1$-alkyl or
tert-butyl-O—C(O)—;
and
R$^9$, R$^{10}$ represent, independently from each other, hydrogen, C$_1$-C$_4$-alkyl, C$_3$-C$_4$-cyclo-alkyl-, C$_1$-C$_3$-haloalkyl-, phenyl or heteroaryl,
  wherein said phenyl or heteroaryl group is optionally substituted, one or more times, independently from each other, with R$^5$; and
    wherein said C$_1$-C$_4$-alkyl is optionally substituted, one or more times, independently from each other, with a substituent selected from hydroxy, C$_1$-alkoxy, C$_1$-alkyl-S—, C$_3$-cycloalkyl, heteroaryl and R$^{18}$—O—C(O)—; and
R$^{11}$, R$^{12}$ represent, independently from each other, C$_1$-C$_4$-alkyl, C$_3$-C$_4$-cycloalkyl, 4- to 6-membered heterocycloalkyl, phenyl, heteroaryl, R$^{13}$—(CH$_2$)$_o$—O—CH$_2$—, R$^{14}$—(CH$_2$)$_o$—, or R$^{15}$—O—(CH$_2$)$_o$—,
  wherein said C$_1$-C$_4$-alkyl is optionally substituted, one or more times, independently from each other, with a substituent selected from halogen, hydroxy, cyano, C$_1$-C$_4$-alkoxy, R$^7$R$^8$N—, and phenyl optionally substituted, one or more times, independently from each other, with R$^5$, and
  wherein said C$_3$-C$_4$-cycloalkyl is optionally substituted, one or two times, independently from each other, with halogen, cyano, C$_1$-alkyl, C$_1$-haloalkyl or phenyl optionally substituted, one or more times, independently from each other, with R$^5$, and
  wherein said 4- to 6-membered heterocycloalkyl is optionally substituted, one or more times, independently from each other, with a substituent selected from C$_1$-alkyl, and R$^{18}$—O—C(O)—, and
  wherein said phenyl or heteroaryl is optionally substituted, one or two times, independently from each other, with R$^5$;
R$^{13}$ represents branched C$_3$-alkyl, C$_1$-C$_2$-haloalkyl, C$_2$-alkenyl, C$_2$-alkynyl, 4- to 6-membered heterocycloalkyl, phenyl or heteroaryl,
  wherein said phenyl or heteroaryl is optionally substituted, one or two times, independently from each other, with R$^5$;
R$^{14}$ represents C$_1$-alkyl-S—, C$_1$-alkyl-SO$_2$—, C$_3$-C$_4$-cycloalkyl, 4- to 6-membered heterocycloalkyl, phenyl or heteroaryl,
  wherein said phenyl or heteroaryl is optionally substituted, one or two times, independently from each other, with R$^5$;
R$^{15}$ represents phenyl or heteroaryl,
  wherein said phenyl or heteroaryl is optionally substituted, one or more times, independently from each other, with R$^5$; and
R$^{16}$ represents hydrogen, or C$_1$-alkyl-C(O)—;
R$^{18}$ represents hydrogen or C$_1$-C$_4$-alkyl;
m represents 0, 1 or 2;
n represents 0, or 1; and
o represents 1, 2, 3 or 4;
or an N-oxide, a salt, a tautomer or a stereoisomer of said compound, or a salt of said N-oxide, tautomer or stereoisomer.

In accordance with an embodiment of the fifth aspect, the invention relates to compounds of formula (Ia) as described supra,
wherein
R$^1$ represents methyl; and
R$^2$ represents methyl; and
A represents a group selected from:

wherein * indicates the point of attachment of said group with the rest of the molecule; and
B represents a group selected from:

wherein * indicates the point of attachment of said group with the rest of the molecule; and
X represents CR$^4$; and
Y represents CR$^4$; and
R$^4$ represents hydrogen;
or an N-oxide, a salt, a tautomer or a stereoisomer of said compound, or a salt of said N-oxide, tautomer or stereoisomer.

In accordance with a sixth aspect, the invention relates to compounds of formula (I) as described supra, wherein:
R$^1$ represents hydrogen, C$_1$-C$_3$-alkyl, C$_1$-alkyl substituted one time with chlorine, C$_1$-alkyl substituted one, two or three times with fluorine, or phenyl, wherein said phenyl is optionally substituted, one or more times, independently from each other, with R$^3$; and
R$^2$ represents hydrogen, or C$_1$-alkyl; or
R$^1$ and R$^2$ together with the carbon atom to which they are attached form a 3- to 4-membered cycloalkyl ring; and
ring A represents a group selected from:

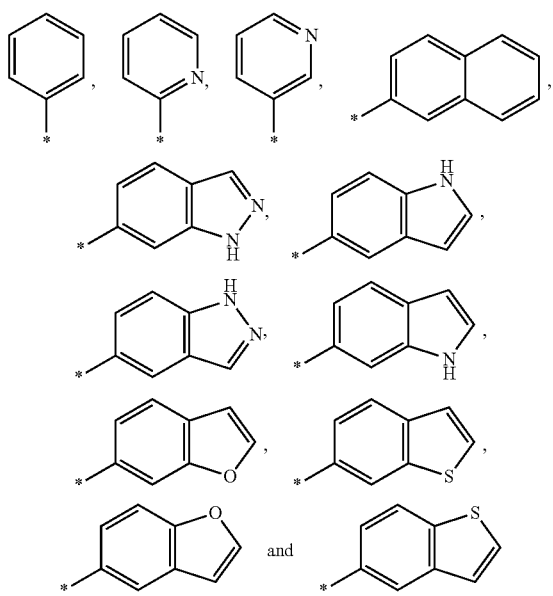

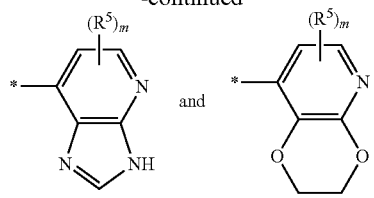

wherein * indicates the point of attachment of said group with the rest of the molecule and said group is optionally substituted, one or more times, independently from each other, with $R^3$; and $R^3$ represents hydrogen, fluorine, chlorine, bromine, hydroxy, nitro, cyano, $C_1$-$C_3$-alkyl, $C_1$-$C_3$-alkoxy, —$CF_3$, —$OCF_3$, —$OCHF_2$, $C_1$-alkyl-C(O)—, $R^{18}$—O—C(O)—, $R^7R^8N$—C(O)—, or a group selected from

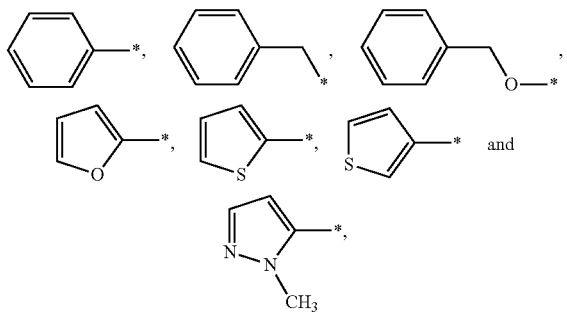

wherein * indicates the point of attachment of said group with the rest of the molecule;

wherein said $C_1$-$C_3$-alkyl, group is optionally substituted with one hydroxy group; and ring B represents a group selected from:

wherein * indicates the point of attachment of said group with the rest of the molecule; and X represents $CR^4$; and Y represents $CR^4$ or N, wherein when one of X and Y represents N, the other represents $CR^4$; and $R^4$ represents, independently from each other, hydrogen, halogen, hydroxy, cyano, $C_1$-alkyl, $C_1$-$C_3$-alkoxy, $C_1$-alkyl-S—, $R^9R^{10}N$—, $R^{11}$—C(O)—(NH)—, ($R^{11}$—C(O)—)($R^{12}$—C(O)—)N—, $R^9R^{10}N$—C(O)—($NR^7$)—, $R^9R^{10}N$—C(S)—($NR^7$)—, or $R^{18}$—O—C(O)—($NR^7$)—, wherein said $C_1$-alkyl is optionally substituted, one or two times, with fluorine; and wherein said $C_1$-$C_3$-alkoxy is optionally substituted, one or more times, independently from each other, with a substituent selected from hydroxy, fluorine, $C_1$-alkoxy, and $C_3$-cycloalkyl; and $R^5$ represents, independently from each other, fluorine, chlorine, amino, $C_1$-$C_4$-alkyl, $C_1$-alkoxy, or phenyl-$C_1$-alkyl, wherein said phenyl group is optionally substituted one time with $C_1$-alkoxy; and J represents hydrogen or hydroxy; and E represents hydrogen, $C_1$-$C_3$-alkyl, or $R^7R^8N$—C(O)—$C_1$-$C_2$-alkyl, wherein said $C_1$-$C_3$-alkyl is optionally substituted one time with hydroxy and/or optionally substituted one, two or three times with fluorine;

Q represents O or N—$OR^{16}$;

$R^7$, $R^8$ represent, independently from each other, hydrogen, $C_1$-alkyl or tert-butyl-O—C(O)—;

and $R^9$, $R^{10}$ represent, independently from each other, hydrogen, $C_1$-$C_3$-alkyl, $C_3$-$C_4$-cyclo-alkyl-, $C_1$-$C_3$-haloalkyl-, or heteroaryl, wherein said heteroaryl group is optionally substituted, one time with $R^5$; and wherein said $C_1$-$C_3$-alkyl is optionally substituted, one or more times, independently from each other, with a substituent selected from hydroxy, $C_1$-alkoxy, $C_1$-alkyl-S—, $C_3$-cycloalkyl, and heteroaryl; and $R^{11}$, $R^{12}$ represent, independently from each other, $C_1$-$C_4$-alkyl, $C_3$-$C_4$-cycloalkyl, 4- to 5-membered heterocycloalkyl, phenyl, heteroaryl, $R^{13}$—$(CH_2)_o$—O—$CH_2$—, $R^{14}$—$(CH_2)_o$—, or $R^{15}$—O—$(CH_2)_o$—, wherein said $C_1$-$C_4$-alkyl is optionally substituted, one or more times, independently from each other, with a substituent selected from halogen, hydroxy, cyano, $C_1$-$C_4$-alkoxy, $R^7R^8N$—, and phenyl optionally substituted, one or more times, independently from each other, with $R^5$, and wherein said $C_3$-$C_4$-cycloalkyl is optionally substituted, one or two times, independently from each other, with a substituent selected from fluorine, cyano, $C_1$-alkyl, —$CF_3$ and phenyl, and wherein said 4- to 6-membered heterocycloalkyl is optionally substituted, one or more times, independently from each other, with $C_1$-alkyl, or $R^{18}$—O—C(O)—, wherein said phenyl or heteroaryl is optionally substituted, one or two times, independently from each other, with $R^5$;

$R^{13}$ represents branched $C_3$-alkyl, $C_1$-$C_2$-haloalkyl, $C_2$-alkenyl, $C_2$-alkynyl, 6-membered heterocycloalkyl, phenyl or heteroaryl, wherein said phenyl or heteroaryl is optionally substituted, one time, with $R^5$;

$R^{14}$ represents $C_1$-alkyl-S—, $C_1$-alkyl-SO$_2$—, $C_3$-cycloalkyl, 5-membered heterocycloalkyl, phenyl or heteroaryl, wherein said phenyl or heteroaryl is optionally substituted, one time, with $R^5$;

$R^{15}$ represents phenyl or heteroaryl; and $R^{16}$ represents hydrogen, or $C_1$-alkyl-C(O)—;

$R^{18}$ represents hydrogen or $C_1$-$C_4$-alkyl;

m represents 0, or 1;

o represents 1, 2, 3 or 4;

or an N-oxide, a salt, a tautomer or a stereoisomer of said compound, or a salt of said N-oxide, tautomer or stereoisomer.

In a further aspect of the invention compounds of formula (I) as described above are selected from the group consisting of:

6,6-dimethyl-3-(phenylamino)-2-(pyridin-4-yl)-1,5,6,7-tetrahydro-4H-indol-4-one 2-(3-chloropyridin-4-yl)-6,6-dimethyl-3-(phenylamino)-1,5,6,7-tetrahydro-4H-indol-4-one 6,6-dimethyl-3-[(3-methylphenyl)amino]-2-(pyridin-4-yl)-1,5,6,7-tetrahydro-4H-indol-4-one 3-[(3-chlorophenyl)amino]-6,6-dimethyl-2-(pyridin-4-yl)-1,5,6,7-tetrahydro-4H-indol-4-one 6,6-dimethyl-3-(phenylamino)-2-(pyrimidin-4-yl)-1,5,6,7-tetrahydro-4H-indol-4-one 3-[(3-fluorophenyl)amino]-6,6-dimethyl-2-(pyridin-4-yl)-1,5,6,7-tetrahydro-4H-indol-4-one (6S)-3-(phenylamino)-6-(propan-2-yl)-2-(pyridin-4-yl)-1,5,6,7-tetrahydro-4H-indol-4-one 6-phenyl-3-(phenylamino)-2-(pyridin-4-yl)-1,5,6,7-tetrahydro-4H-indol-4-one 3-(phenylamino)-2-(pyridin-4-yl)-1,5,6,7-tetrahydro-4H-indol-4-one 3-[(4-chlorophenyl)amino]-6,6-dimethyl-2-(pyridin-4-yl)-1,5,6,7-tetrahydro-4H-indol-4-one 3-[(4-fluorophenyl)amino]-6,6-dimethyl-2-(pyridin-4-yl)-1,5,6,7-tetrahydro-4H-indol-4-one 3-[(3-bromophenyl)amino]-6,6-dimethyl-2-(pyridin-4-yl)-1,5,6,7-tetrahydro-4H-indol-4-one 3'-(phenylamino)-2'-(pyridin-4-yl)-1',7'-dihydrospiro[cyclobutane-1,6'-indol]-4'(5'H)-one 3-[(3-fluoro-5-methylphenyl)amino]-6,6-dimethyl-2-(pyridin-4-yl)-1,5,6,7-tetrahydro-4H-indol-4-one 3-[(3-ethylphenyl)amino]-6,6-dimethyl-2-(pyridin-4-yl)-1,5,6,7-tetrahydro-4H-indol-4-one 6,6-dimethyl-3-[(3-nitrophenyl)amino]-2-(pyridin-4-yl)-1,5,6,7-tetrahydro-4H-indol-4-one (6R)-3-(phenylamino)-6-(propan-2-yl)-2-(pyridin-4-yl)-1,5,6,7-tetrahydro-4H-indol-4-one (6S)-3-(phenylamino)-6-(propan-2-yl)-2-(pyridin-4-yl)-1,5,6,7-tetrahydro-4H-indol-4-one 3-[(3-chloro-5-fluorophenyl)amino]-6,6-dimethyl-2-(pyridin-4-yl)-1,5,6,7-tetrahydro-4H-indol-4-one 3-(phenylamino)-2-(pyridin-4-yl)-6-(trifluoromethyl)-1,5,6,7-tetrahydro-4H-indol-4-one 3-[(3,4-difluorophenyl)amino]-6,6-dimethyl-2-(pyridin-4-yl)-1,5,6,7-tetrahydro-4H-indol-4-one 6-methyl-3-(phenylamino)-2-(pyridin-4-yl)-1,5,6,7-tetrahydro-4H-indol-4-one 3-[(3-fluorophenyl)amino]-2-(2-fluoropyridin-4-yl)-6,6-dimethyl-1,5,6,7-tetrahydro-4H-indol-4-one 6,6-dimethyl-2-(pyridin-4-yl)-3-(pyridin-2-ylamino)-1,5,6,7-tetrahydro-4H-indol-4-one 3-(1-benzofuran-6-ylamino)-6,6-dimethyl-2-(pyridin-4-yl)-1,5,6,7-tetrahydro-4H-indol-4-one 6,6-dimethyl-3-(phenylamino)-2-(1H-pyrrolo[2,3-b]pyridin-4-yl)-1,5,6,7-tetrahydro-4H-indol-4-one 6-ethyl-3-(phenylamino)-2-(pyridin-4-yl)-1,5,6,7-tetrahydro-4H-indol-4-one 6-(2-methylpropyl)-3-(phenylamino)-2-(pyridin-4-yl)-1,5,6,7-tetrahydro-4H-indol-4-one 2-(3-fluoropyridin-4-yl)-6,6-dimethyl-3-(phenylamino)-1,5,6,7-tetrahydro-4H-indol-4-one 3-[(3,5-difluorophenyl)amino]-6,6-dimethyl-2-(pyridin-4-yl)-1,5,6,7-tetrahydro-4H-indol-4-one 6,6-dimethyl-2-(pyridin-4-yl)-3-[(3,4,5-trifluorophenyl)amino]-1,5,6,7-tetrahydro-4H-indol-4-one 2-(2-chloropyridin-4-yl)-3-(phenylamino)-1,5,6,7-tetrahydro-4H-indol-4-one 6,6-dimethyl-3-(phenylamino)-2-(1H-pyrazolo[3,4-b]pyridin-4-yl)-1,5,6,7-tetrahydro-4H-indol-4-one N-4-[6,6-dimethyl-4-oxo-3-(phenylamino)-4,5,6,7-tetrahydro-1H-indol-2-yl]pyridin-2-ylpropanamide N-4-[6,6-dimethyl-4-oxo-3-(phenylamino)-4,5,6,7-tetrahydro-1H-indol-2-yl]pyridin-2-ylacetamide 3'-(phenylamino)-2'-(pyridin-4-yl)-1',7'-dihydrospiro[cyclopropane-1,6'-indol]-4'(5'H)-one N-4-[6,6-dimethyl-4-oxo-3-(phenylamino)-4,5,6,7-tetrahydro-1H-indol-2-yl]pyridin-2-ylcyclopropanecarboxamide N-4-[4-oxo-3-(phenylamino)-4,5,6,7-tetrahydro-1H-indol-2-yl]pyridin-2-ylacetamide N-(4-3-[(3-fluorophenyl)amino]-4-oxo-4,5,6,7-tetrahydro-1H-indol-2-ylpyridin-2-yl)acetamide 3-[(3-fluorophenyl)amino]-2-(pyridin-4-yl)-1,5,6,7-tetrahydro-4H-indol-4-one 3-[(4-fluorophenyl)amino]-2-(pyridin-4-yl)-1,5,6,7-tetrahydro-4H-indol-4-one 3-[(3-fluorophenyl)amino]-2-(pyridin-4-yl)-6-(trifluoromethyl)-1,5,6,7-tetrahydro-4H-indol-4-one 2-(2-fluoropyridin-4-yl)-3-(phenylamino)-1,5,6,7-tetrahydro-4H-indol-4-one 3-(biphenyl-3-ylamino)-6,6-dimethyl-2-(pyridin-4-yl)-1,5,6,7-tetrahydro-4H-indol-4-one 4-[6,6-dimethyl-4-oxo-3-(phenylamino)-4,5,6,7-tetrahydro-1H-indol-2-yl]pyridine-2-carbonitrile N-(4-{3-[(3-fluorophenyl)amino]-4-oxo-4,5,6,7-tetrahydro-1H-indol-2-yl}pyridin-2-yl)cyclopropanecarboxamide N-4-[4-oxo-3-(phenylamino)-4,5,6,7-tetrahydro-1H-indol-2-yl]pyridin-2-ylcyclopropanecarboxamide 2-(2-aminopyridin-4-yl)-3-(phenylamino)-6-(propan-2-yl)-1,5,6,7-tetrahydro-4H-indol-4-one 2-(2-aminopyridin-4-yl)-3-[(3-fluorophenyl)amino]-6-(propan-2-yl)-1,5,6,7-tetrahydro-4H-indol-4-one 6,6-dimethyl-2-(pyridin-4-yl)-3-[3-(trifluoromethyl)phenyl]amino-1,5,6,7-tetrahydro-4H-indol-4-one 3-[(3-methoxyphenyl)amino]-6,6-dimethyl-2-(pyridin-4-yl)-1,5,6,7-tetrahydro-4H-indol-4-one 6,6-dimethyl-3-[(2-methylphenyl)amino]-2-(pyridin-4-yl)-1,5,6,7-tetrahydro-4H-indol-4-one 6,6-dimethyl-3-[(4-methylphenyl)amino]-2-(pyridin-4-yl)-1,5,6,7-tetrahydro-4H-indol-4-one
6,6-dimethyl-3-(phenylamino)-2-(pyridazin-4-yl)-1,5,6,7-tetrahydro-4H-indol-4-one
3-[(2,3-dimethoxyphenyl)amino]-6,6-dimethyl-2-(pyridin-4-yl)-1,5,6,7-tetrahydro-4H-indol-4-one
3-[(3,4-dimethoxyphenyl)amino]-6,6-dimethyl-2-(pyridin-4-yl)-1,5,6,7-tetrahydro-4H-indol-4-one
3-[(4-methoxyphenyl)amino]-6,6-dimethyl-2-(pyridin-4-yl)-1,5,6,7-tetrahydro-4H-indol-4-one
3-[(2-fluorophenyl)amino]-6,6-dimethyl-2-(pyridin-4-yl)-1,5,6,7-tetrahydro-4H-indol-4-one
3-[(2-chlorophenyl)amino]-6,6-dimethyl-2-(pyridin-4-yl)-1,5,6,7-tetrahydro-4H-indol-4-one
3-[(2,4-dimethoxyphenyl)amino]-6,6-dimethyl-2-(pyridin-4-yl)-1,5,6,7-tetrahydro-4H-indol-4-one
6,6-dimethyl-2-(pyridin-4-yl)-3-(pyridin-3-ylamino)-1,5,6,7-tetrahydro-4H-indol-4-one
3-(isoquinolin-4-ylamino)-6,6-dimethyl-2-(pyridin-4-yl)-1,5,6,7-tetrahydro-4H-indol-4-one
3-[(3-aminophenyl)amino]-6,6-dimethyl-2-(pyridin-4-yl)-1,5,6,7-tetrahydro-4H-indol-4-one
6,6-dimethyl-2-(pyridin-4-yl)-3-(quinolin-3-ylamino)-1,5,6,7-tetrahydro-4H-indol-4-one
3-(1-benzofuran-5-ylamino)-6,6-dimethyl-2-(pyridin-4-yl)-1,5,6,7-tetrahydro-4H-indol-4-one
3-(1H-indol-6-ylamino)-6,6-dimethyl-2-(pyridin-4-yl)-1,5,6,7-tetrahydro-4H-indol-4-one
3-(1-benzothiophen-5-ylamino)-6,6-dimethyl-2-(pyridin-4-yl)-1,5,6,7-tetrahydro-4H-indol-4-one
3-(1H-indol-5-ylamino)-6,6-dimethyl-2-(pyridin-4-yl)-1,5,6,7-tetrahydro-4H-indol-4-one
3-[(2-bromophenyl)amino]-6,6-dimethyl-2-(pyridin-4-yl)-1,5,6,7-tetrahydro-4H-indol-4-one
3-[(4-bromophenyl)amino]-6,6-dimethyl-2-(pyridin-4-yl)-1,5,6,7-tetrahydro-4H-indol-4-one
3-(1H-benzimidazol-6-ylamino)-6,6-dimethyl-2-(pyridin-4-yl)-1,5,6,7-tetrahydro-4H-indol-4-one
3-(1H-indazol-6-ylamino)-6,6-dimethyl-2-(pyridin-4-yl)-1,5,6,7-tetrahydro-4H-indol-4-one
6,6-dimethyl-2-(pyridin-4-yl)-3-(quinolin-4-ylamino)-1,5,6,7-tetrahydro-4H-indol-4-one
3-[(2,5-dimethoxyphenyl)amino]-6,6-dimethyl-2-(pyridin-4-yl)-1,5,6,7-tetrahydro-4H-indol-4-one
3-[(3,5-dichlorophenyl)amino]-6,6-dimethyl-2-(pyridin-4-yl)-1,5,6,7-tetrahydro-4H-indol-4-one
3-[(2,5-dichlorophenyl)amino]-6,6-dimethyl-2-(pyridin-4-yl)-1,5,6,7-tetrahydro-4H-indol-4-one
3-[6,6-dimethyl-4-oxo-2-(pyridin-4-yl)-4,5,6,7-tetrahydro-1H-indol-3-yl]aminobenzonitrile
3-[3-(benzyloxy)phenyl]amino-6,6-dimethyl-2-(pyridin-4-yl)-1,5,6,7-tetrahydro-4H-indol-4-one
3-[(4-fluoro-3-methylphenyl)amino]-6,6-dimethyl-2-(pyridin-4-yl)-1,5,6,7-tetrahydro-4H-indol-4-one
3-[(2-fluoro-5-methylphenyl)amino]-6,6-dimethyl-2-(pyridin-4-yl)-1,5,6,7-tetrahydro-4H-indol-4-one
3-[(4-ethylphenyl)amino]-6,6-dimethyl-2-(pyridin-4-yl)-1,5,6,7-tetrahydro-4H-indol-4-one
3-[(2-ethylphenyl)amino]-6,6-dimethyl-2-(pyridin-4-yl)-1,5,6,7-tetrahydro-4H-indol-4-one
6,6-dimethyl-3-[3-(propan-2-yl)phenyl]amino-2-(pyridin-4-yl)-1,5,6,7-tetrahydro-4H-indol-4-one
6,6-dimethyl-3-[4-(propan-2-yl)phenyl]amino-2-(pyridin-4-yl)-1,5,6,7-tetrahydro-4H-indol-4-one
3-[(5-chloro-2-fluorophenyl)amino]-6,6-dimethyl-2-(pyridin-4-yl)-1,5,6,7-tetrahydro-4H-indol-4-one
6,6-dimethyl-3-[2-(propan-2-yl)phenyl]amino-2-(pyridin-4-yl)-1,5,6,7-tetrahydro-4H-indol-4-one
3-[(3-hydroxyphenyl)amino]-6,6-dimethyl-2-(pyridin-4-yl)-1,5,6,7-tetrahydro-4H-indol-4-one
6,6-dimethyl-3-[(4-nitrophenyl)amino]-2-(pyridin-4-yl)-1,5,6,7-tetrahydro-4H-indol-4-one
3-[(3-chloro-2-methylphenyl)amino]-6,6-dimethyl-2-(pyridin-4-yl)-1,5,6,7-tetrahydro-4H-indol-4-one
3-[(3-chloro-4-methylphenyl)amino]-6,6-dimethyl-2-(pyridin-4-yl)-1,5,6,7-tetrahydro-4H-indol-4-one
3-[(5-chloro-2-methylphenyl)amino]-6,6-dimethyl-2-(pyridin-4-yl)-1,5,6,7-tetrahydro-4H-indol-4-one
3-[(3-chloro-2-fluorophenyl)amino]-6,6-dimethyl-2-(pyridin-4-yl)-1,5,6,7-tetrahydro-4H-indol-4-one
3-[(3-chloro-4-fluorophenyl)amino]-6,6-dimethyl-2-(pyridin-4-yl)-1,5,6,7-tetrahydro-4H-indol-4-one
3-[(2-fluoro-3-methylphenyl)amino]-6,6-dimethyl-2-(pyridin-4-yl)-1,5,6,7-tetrahydro-4H-indol-4-one
N-(3-[6,6-dimethyl-4-oxo-2-(pyridin-4-yl)-4,5,6,7-tetrahydro-1H-indol-3-yl]aminophenyl)-2-methylpropanamide
N-(3-[6,6-dimethyl-4-oxo-2-(pyridin-4-yl)-4,5,6,7-tetrahydro-1H-indol-3-yl]aminophenyl)propanamide
3-[6,6-dimethyl-4-oxo-2-(pyridin-4-yl)-4,5,6,7-tetrahydro-1H-indol-3-yl]amino-N-methylbenzamide
3-(1H-indazol-5-ylamino)-6,6-dimethyl-2-(pyridin-4-yl)-1,5,6,7-tetrahydro-4H-indol-4-one
3-[6,6-dimethyl-4-oxo-2-(pyridin-4-yl)-4,5,6,7-tetrahydro-1H-indol-3-yl]aminobenzamide
N-(3-[6,6-dimethyl-4-oxo-2-(pyridin-4-yl)-4,5,6,7-tetrahydro-1H-indol-3-yl]aminophenyl)butanamide
2-(2-chloropyridin-4-yl)-6,6-dimethyl-3-(phenylamino)-1,5,6,7-tetrahydro-4H-indol-4-one
3-[(3-ethoxyphenyl)amino]-6,6-dimethyl-2-(pyridin-4-yl)-1,5,6,7-tetrahydro-4H-indol-4-one
6,6-dimethyl-3-[3-(propan-2-yloxy)phenyl]amino-2-(pyridin-4-yl)-1,5,6,7-tetrahydro-4H-indol-4-one
3-[3-(2-hydroxyethoxy)phenyl]amino-6,6-dimethyl-2-(pyridin-4-yl)-1,5,6,7-tetrahydro-4H-indol-4-one
6,6-dimethyl-2-(pyridin-4-yl)-3-[3-(trifluoromethoxy)phenyl]amino-1,5,6,7-tetrahydro-4H-indol-4-one
6,6-dimethyl-3-[(3-propoxyphenyl)amino]-2-(pyridin-4-yl)-1,5,6,7-tetrahydro-4H-indol-4-one
N-(3-[6,6-dimethyl-4-oxo-2-(pyridin-4-yl)-4,5,6,7-tetrahydro-1H-indol-3-yl]aminophenyl)acetamide
3-[(4-fluoro-3-methoxyphenyl)amino]-6,6-dimethyl-2-(pyridin-4-yl)-1,5,6,7-tetrahydro-4H-indol-4-one
3-[4-fluoro-3-(hydroxymethyl)phenyl]amino-6,6-dimethyl-2-(pyridin-4-yl)-1,5,6,7-tetrahydro-4H-indol-4-one
3-[3-(1-hydroxyethyl)phenyl]amino-6,6-dimethyl-2-(pyridin-4-yl)-1,5,6,7-tetrahydro-4H-indol-4-one
3-[(3-acetylphenyl)amino]-6,6-dimethyl-2-(pyridin-4-yl)-1,5,6,7-tetrahydro-4H-indol-4-one
3-[(3-tert-butylphenyl)amino]-6,6-dimethyl-2-(pyridin-4-yl)-1,5,6,7-tetrahydro-4H-indol-4-one
3-[6,6-dimethyl-4-oxo-2-(pyridin-4-yl)-4,5,6,7-tetrahydro-1H-indol-3-yl]amino-N,N-dimethylbenzamide
3-[3-(difluoromethoxy)phenyl]amino-6,6-dimethyl-2-(pyridin-4-yl)-1,5,6,7-tetrahydro-4H-indol-4-one
tert-butyl 3-[6,6-dimethyl-4-oxo-2-(pyridin-4-yl)-4,5,6,7-tetrahydro-1H-indol-3-yl]aminobenzoate
3-[3-(1,3-dioxolan-2-yl)phenyl]amino-6,6-dimethyl-2-(pyridin-4-yl)-1,5,6,7-tetrahydro-4H-indol-4-one
3-[(4-fluoro-2-methoxyphenyl)amino]-6,6-dimethyl-2-(pyridin-4-yl)-1,5,6,7-tetrahydro-4H-indol-4-one
2-(2-aminopyridin-4-yl)-6,6-dimethyl-3-(phenylamino)-1,5,6,7-tetrahydro-4H-indol-4-one 3-[(3-fluorophenyl)amino]-2-{2-[(3-fluorophenyl)amino]pyridin-4-yl}-6,6-dimethyl-1,5,6,7-tetrahydro-4H-indol-4-one 3-[(2-methoxyphenyl)amino]-6,6-dimethyl-2-(pyridin-4-yl)-1,5,6,7-tetrahydro-4H-indol-4-one 3-[(2-ethoxy-4-fluorophenyl)amino]-6,6-dimethyl-2-(pyridin-4-yl)-1,5,6,7-tetrahydro-4H-indol-4-one 6,6-dimethyl-3-(phenylamino)-2-[2-(pyrrolidin-1-yl)pyridin-4-yl]-1,5,6,7-tetrahydro-4H-indol-4-one 6,6-dimethyl-2-[2-(morpholin-4-yl)pyridin-4-yl]-3-(phenylamino)-1,5,6,7-tetrahydro-4H-indol-4-one 3-[(2-ethoxyphenyl)amino]-6,6-dimethyl-2-(pyridin-4-yl)-1,5,6,7-tetrahydro-4H-indol-4-one 3-[4-fluoro-3-(trifluoromethyl)phenyl]amino-6,6-dimethyl-2-(pyridin-4-yl)-1,5,6,7-tetrahydro-4H-indol-4-one 3-(1-benzothiophen-6-ylamino)-6,6-dimethyl-2-(pyridin-4-yl)-1,5,6,7-tetrahydro-4H-indol-4-one 6,6-dimethyl-2-(3-methylpyridin-4-yl)-3-(phenylamino)-1,5,6,7-tetrahydro-4H-indol-4-one N-4-[6,6-dimethyl-4-oxo-3-(phenylamino)-4,5,6,7-tetrahydro-1H-indol-2-yl]pyridin-2-yl-2-methylpropanamide N-acetyl-N-4-[6,6-dimethyl-4-oxo-3-(phenylamino)-4,5,6,7-tetrahydro-1H-indol-2-yl]pyridin-2-ylacetamide 3-[(3,4-difluorophenyl)amino]-2-(pyridin-4-yl)-1,5,6,7-tetrahydro-4H-indol-4-one 2-(3,5-difluoropyridin-4-yl)-6,6-dimethyl-3-(phenylamino)-1,5,6,7-tetrahydro-4H-indol-4-one 2-(3,5-difluoropyridin-4-yl)-3-[(3-fluorophenyl)amino]-1,5,6,7-tetrahydro-4H-indol-4-one 2-(2-bromopyridin-4-yl)-6,6-dimethyl-3-(phenylamino)-1,5,6,7-tetrahydro-4H-indol-4-one 2-(2-aminopyridin-4-yl)-3-[(3-fluorophenyl)amino]-1,5,6,7-tetrahydro-4H-indol-4-one 2-(2-aminopyridin-4-yl)-3-(phenylamino)-1,5,6,7-tetrahydro-4H-indol-4-one 6,6-dimethyl-3-(phenylamino)-2-[2-(trifluoromethyl)pyridin-4-yl]-1,5,6,7-tetrahydro-4H-indol-4-one 2-(3-chloropyridin-4-yl)-3-[(4-fluorophenyl)amino]-1,5,6,7-tetrahydro-4H-indol-4-one 2-(2-methylpyridin-4-yl)-3-(phenylamino)-1,5,6,7-tetrahydro-4H-indol-4-one 3-[6,6-dimethyl-4-oxo-2-(pyridin-4-yl)-4,5,6,7-tetrahydro-1H-indol-3-yl]amino-N-ethylbenzamide 6,6-dimethyl-2-[2-(methylamino)pyridin-4-yl]-3-(phenylamino)-1,5,6,7-tetrahydro-4H-indol-4-one 2-[6,6-dimethyl-4-oxo-2-(pyridin-4-yl)-4,5,6,7-tetrahydro-1H-indol-3-yl]aminobenzonitrile 5-[6,6-dimethyl-4-oxo-2-(pyridin-4-yl)-4,5,6,7-tetrahydro-1H-indol-3-yl]amino-2-fluorobenzonitrile 3-[4-fluoro-3-(trifluoromethoxy)phenyl]amino-6,6-dimethyl-2-(pyridin-4-yl)-1,5,6,7-tetrahydro-4H-indol-4-one 6,6-dimethyl-2-(2-methylpyridin-4-yl)-3-(phenylamino)-1,5,6,7-tetrahydro-4H-indol-4-one 2-(2-methoxypyridin-4-yl)-3-(phenylamino)-1,5,6,7-tetrahydro-4H-indol-4-one 3-[6,6-dimethyl-4-oxo-2-(pyridin-4-yl)-4,5,6,7-tetrahydro-1H-indol-3-yl]aminobenzoic acid 2-(2-bromopyridin-4-yl)-3-(phenylamino)-1,5,6,7-tetrahydro-4H-indol-4-one 6,6-dimethyl-3-[3-(2-methyl-1,3-dioxolan-2-yl)phenyl]amino-2-(pyridin-4-yl)-1,5,6,7-tetrahydro-4H-indol-4-one 3-[3-(1-hydroxypropyl)phenyl]amino-6,6-dimethyl-2-(pyridin-4-yl)-1,5,6,7-tetrahydro-4H-indol-4-one 6,6-dimethyl-2-(pyridin-4-yl)-3-[3-(2,2,2-trifluoro-1-hydroxyethyl)phenyl]amino-1,5,6,7-tetrahydro-4H-indol-4-one 3-[3-(1-methoxyethyl)phenyl]amino-6,6-dimethyl-2-(pyridin-4-yl)-1,5,6,7-tetrahydro-4H-indol-4-one 6,6-dimethyl-3-(naphthalen-1-ylamino)-2-(pyridin-4-yl)-1,5,6,7-tetrahydro-4H-indol-4-one 6,6-dimethyl-3-(naphthalen-2-ylamino)-2-(pyridin-4-yl)-1,5,6,7-tetrahydro-4H-indol-4-one 6,6-dimethyl-3-[(2-phenoxyphenyl)amino]-2-(pyridin-4-yl)-1,5,6,7-tetrahydro-4H-indol-4-one 3-(biphenyl-2-ylamino)-6,6-dimethyl-2-(pyridin-4-yl)-1,5,6,7-tetrahydro-4H-indol-4-one 6,6-dimethyl-2-(1-oxidopyridin-4-yl)-3-(phenylamino)-1,5,6,7-tetrahydro-4H-indol-4-one N-(cyclopropylcarbonyl)-N-(4-{3-[(3-fluorophenyl)amino]-4-oxo-4,5,6,7-tetrahydro-1H-indol-2-yl}pyridin-2-yl)cyclopropanecarboxamide N-(cyclopropylcarbonyl)-N-4-[4-oxo-3-(phenylamino)-4,5,6,7-tetrahydro-1H-indol-2-yl]pyridin-2-ylcyclopropanecarboxamide 2-[2-(dimethylamino)pyridin-4-yl]-6,6-dimethyl-3-(phenylamino)-1,5,6,7-tetrahydro-4H-indol-4-one N-4-[6,6-dimethyl-4-oxo-3-(phenylamino)-4,5,6,7-tetrahydro-1H-indol-2-yl]pyridin-2-ylmethanesulfonamide N-4-[6,6-dimethyl-4-oxo-3-(phenylamino)-4,5,6,7-tetrahydro-1H-indol-2-yl]pyridin-2-yl-2,2-difluoroacetamide 2-(2-aminopyridin-4-yl)-3-[(4-fluorophenyl)amino]-6-(propan-2-yl)-1,5,6,7-tetrahydro-4H-indol-4-one N-4-[4-oxo-3-(phenylamino)-4,5,6,7-tetrahydro-1H-indol-2-yl]pyridin-2-ylmethanesulfonamide 1-methyl-3-(phenylamino)-2-(pyridin-4-yl)-1,5,6,7-tetrahydro-4H-indol-4-one 1-ethyl-3-(phenylamino)-2-(pyridin-4-yl)-1,5,6,7-tetrahydro-4H-indol-4-one 3-(phenylamino)-1-propyl-2-(pyridin-4-yl)-1,5,6,7-tetrahydro-4H-indol-4-one methyl 3-[4-oxo-3-(phenylamino)-2-(pyridin-4-yl)-4,5,6,7-tetrahydro-1H-indol-1-yl]propanoate 3-[4-oxo-3-(phenylamino)-2-(pyridin-4-yl)-4,5,6,7-tetrahydro-1H-indol-1-yl]propanoic acid 3-[4-oxo-3-(phenylamino)-2-(pyridin-4-yl)-4,5,6,7-tetrahydro-1H-indol-1-yl]propanamide 1-(3-hydroxypropyl)-3-(phenylamino)-2-(pyridin-4-yl)-1,5,6,7-tetrahydro-4H-indol-4-one 1-[2-(methylsulfonyl)ethyl]-3-(phenylamino)-2-(pyridin-4-yl)-1,5,6,7-tetrahydro-4H-indol-4-one 2-(3-chloropyridin-4-yl)-1-ethyl-3-(phenylamino)-1,5,6,7-tetrahydro-4H-indol-4-one 1,6-dimethyl-3-(phenylamino)-2-(pyridin-4-yl)-1,5,6,7-tetrahydro-4H-indol-4-one 1,6,6-trimethyl-3-(phenylamino)-2-(pyridin-4-yl)-1,5,6,7-tetrahydro-4H-indol-4-one 6,6-dimethyl-3-(phenylamino)-2-(pyridin-4-yl)-1-(2,2,2-trifluoroethyl)-1,5,6,7-tetrahydro-4H-indol-4-one 1-ethyl-6,6-dimethyl-3-(phenylamino)-2-(pyridin-4-yl)-1,5,6,7-tetrahydro-4H-indol-4-one 6,6-dimethyl-3-(phenylamino)-1-propyl-2-(pyridin-4-yl)-1,5,6,7-tetrahydro-4H-indol-4-one 1-(2-[tert-butyl(dimethyl)silyl]oxyethyl)-6,6-dimethyl-3-(phenylamino)-2-(pyridin-4-yl)-1,5,6,7-tetrahydro-4H-indol-4-one 1-(2-hydroxyethyl)-6,6-dimethyl-3-(phenylamino)-2-(pyridin-4-yl)-1,5,6,7-tetrahydro-4H-indol-4-one 4-[1-(2-amino-2-oxoethyl)-6,6-dimethyl-4-oxo-3-(phenylamino)-4,5,6,7-tetrahydro-1H-indol-2-yl]pyridinium formate 1-benzyl-6,6-dimethyl-3-(phenylamino)-2-(pyridin-4-yl)-1,5,6,7-tetrahydro-4H-indol-4-one N-4-[1-ethyl-6,6-dimethyl-4-oxo-3-(phenylamino)-4,5,6,7-tetrahydro-1H-indol-2-yl]pyridin-2-ylacetamide
1-(2,2-difluoroethyl)-6,6-dimethyl-3-(phenylamino)-2-(pyridin-4-yl)-1,5,6,7-tetrahydro-4H-indol-4-one
4-(hydroxyimino)-6,6-dimethyl-N-phenyl-2-(pyridin-4-yl)-4,5,6,7-tetrahydro-1H-indol-3-amine
1-([6,6-dimethyl-3-(phenylamino)-2-(pyridin-4-yl)-1,5,6,7-tetrahydro-4H-indol-4-ylidene]aminooxy)ethanone
2-(3-bromopyridin-4-yl)-3-(phenylamino)-1,5,6,7-tetrahydro-4H-indol-4-one
4-[4-oxo-3-(phenylamino)-4,5,6,7-tetrahydro-1H-indol-2-yl]pyridine-3-carbonitrile
4-{3-[(3-fluorophenyl)amino]-6,6-dimethyl-4-oxo-4,5,6,7-tetrahydro-1H-indol-2-yl}pyridine-3-carbonitrile
2-(3-bromopyridin-4-yl)-6,6-dimethyl-3-(phenylamino)-1,5,6,7-tetrahydro-4H-indol-4-one
6,6-dimethyl-2-[2-(methylsulfanyl)pyridin-4-yl]-3-(phenylamino)-1,5,6,7-tetrahydro-4H-indol-4-one
6,6-dimethyl-2-[3-(methylsulfanyl)pyridin-4-yl]-3-(phenylamino)-1,5,6,7-tetrahydro-4H-indol-4-one
4-[6,6-dimethyl-4-oxo-3-(phenylamino)-4,5,6,7-tetrahydro-1H-indol-2-yl]pyridin-3-yl(methyl)sulfoniumolate
2-(2-aminopyridin-4-yl)-3-[(3-bromophenyl)amino]-6,6-dimethyl-1,5,6,7-tetrahydro-4H-indol-4-one
2-{2-[(1-benzyl-1H-pyrazol-4-yl)amino]pyridin-4-yl}-6,6-dimethyl-3-(phenylamino)-1,5,6,7-tetrahydro-4H-indol-4-one
6,6-dimethyl-2-{2-[(1-methyl-1H-pyrazol-4-yl)amino]pyridin-4-yl}-3-(phenylamino)-1,5,6,7-tetrahydro-4H-indol-4-one
2'-(2-aminopyridin-4-yl)-3'-(phenylamino)-1',7'-dihydrospiro[cyclopropane-1,6'-indol]-4'(5'H)-one
2'-(2-fluoropyridin-4-yl)-3'-(phenylamino)-1',7'-dihydrospiro[cyclopropane-1,6'-indol]-4'(5'H)-one
2'-(3-fluoropyridin-4-yl)-3'-(phenylamino)-1',7'-dihydrospiro[cyclopropane-1,6'-indol]-4'(5'H)-one
2-(2,6-dimethylpyridin-4-yl)-6,6-dimethyl-3-(phenylamino)-1,5,6,7-tetrahydro-4H-indol-4-one
2-(2,3-dihydro[1,4]dioxino[2,3-b]pyridin-8-yl)-6,6-dimethyl-3-(phenylamino)-1,5,6,7-tetrahydro-4H-indol-4-one
2-(2-aminopyridin-4-yl)-3-[(4-fluorophenyl)amino]-1,5,6,7-tetrahydro-4H-indol-4-one
2-(2-aminopyridin-4-yl)-3-[(3,4-difluorophenyl)amino]-1,5,6,7-tetrahydro-4H-indol-4-one
2-(2-fluoropyridin-4-yl)-6,6-dimethyl-3-(phenylamino)-1,5,6,7-tetrahydro-4H-indol-4-one
2-(2,3-dichloropyridin-4-yl)-6,6-dimethyl-3-(phenylamino)-1,5,6,7-tetrahydro-4H-indol-4-one
2-(2,5-dichloropyridin-4-yl)-6,6-dimethyl-3-(phenylamino)-1,5,6,7-tetrahydro-4H-indol-4-one
2-(2,6-dichloropyridin-4-yl)-6,6-dimethyl-3-(phenylamino)-1,5,6,7-tetrahydro-4H-indol-4-one
2-(2,6-dichloropyridin-4-yl)-3-(phenylamino)-1,5,6,7-tetrahydro-4H-indol-4-one
2-(2,5-difluoropyridin-4-yl)-3-(phenylamino)-1,5,6,7-tetrahydro-4H-indol-4-one
2-(2-chloro-3-fluoropyridin-4-yl)-6,6-dimethyl-3-(phenylamino)-1,5,6,7-tetrahydro-4H-indol-4-one
2-(2-chloro-5-fluoropyridin-4-yl)-6,6-dimethyl-3-(phenylamino)-1,5,6,7-tetrahydro-4H-indol-4-one
2-(3H-imidazo[4,5-b]pyridin-7-yl)-6,6-dimethyl-3-(phenylamino)-1,5,6,7-tetrahydro-4H-indol-4-one
2-(2-aminopyridin-4-yl)-3-[(3,4-difluorophenyl)amino]-6-(propan-2-yl)-1,5,6,7-tetrahydro-4H-indol-4-one
2-(2-aminopyrimidin-4-yl)-6,6-dimethyl-3-(phenylamino)-1,5,6,7-tetrahydro-4H-indol-4-one
2-(6-aminopyrimidin-4-yl)-6,6-dimethyl-3-(phenylamino)-1,5,6,7-tetrahydro-4H-indol-4-one
N-4-[4-oxo-3-(phenylamino)-4,5,6,7-tetrahydro-1H-indol-2-yl]pyridin-2-ylpropanamide
N-4-[4-oxo-3-(phenylamino)-4,5,6,7-tetrahydro-1H-indol-2-yl]pyridin-2-ylbutanamide
2,2-dimethyl-N-4-[4-oxo-3-(phenylamino)-4,5,6,7-tetrahydro-1H-indol-2-yl]pyridin-2-ylpropanamide
1-methyl-N-4-[4-oxo-3-(phenylamino)-4,5,6,7-tetrahydro-1H-indol-2-yl]pyridin-2-ylcyclopropanecarboxamide
N-4-[4-oxo-3-(phenylamino)-4,5,6,7-tetrahydro-1H-indol-2-yl]pyridin-2-ylcyclobutanecarboxamide
2-methyl-N-4-[4-oxo-3-(phenylamino)-4,5,6,7-tetrahydro-1H-indol-2-yl]pyridin-2-ylpropanamide
2-cyclopropyl-N-4-[4-oxo-3-(phenylamino)-4,5,6,7-tetrahydro-1H-indol-2-yl]pyridin-2-ylacetamide
2,2-dimethyl-N-4-[4-oxo-3-(phenylamino)-4,5,6,7-tetrahydro-1H-indol-2-yl]pyridin-2-ylcyclopropanecarboxamide
N-4-[4-oxo-3-(phenylamino)-4,5,6,7-tetrahydro-1H-indol-2-yl]pyridin-2-yl-2-phenylacetamide
N-4-[4-oxo-3-(phenylamino)-4,5,6,7-tetrahydro-1H-indol-2-yl]pyridin-2-ylbut-3-ynamide
N-4-[4-oxo-3-(phenylamino)-4,5,6,7-tetrahydro-1H-indol-2-yl]pyridin-2-yl-3-phenylpropanamide
N-4-[4-oxo-3-(phenylamino)-4,5,6,7-tetrahydro-1H-indol-2-yl]pyridin-2-yl-4-phenylbutanamide
2-methyl-N-4-[4-oxo-3-(phenylamino)-4,5,6,7-tetrahydro-1H-indol-2-yl]pyridin-2-ylcyclopropanecarboxamide
N-4-[4-oxo-3-(phenylamino)-4,5,6,7-tetrahydro-1H-indol-2-yl]pyridin-2-ylbenzamide
rel-(1S,2S)—N-4-[4-oxo-3-(phenylamino)-4,5,6,7-tetrahydro-1H-indol-2-yl]pyridin-2-yl-2-phenylcyclopropanecarboxamide
N-4-[6,6-dimethyl-4-oxo-3-(phenylamino)-4,5,6,7-tetrahydro-1H-indol-2-yl]pyridin-2-yl-N-methylacetamide
2-fluoro-N-4-[4-oxo-3-(phenylamino)-4,5,6,7-tetrahydro-1H-indol-2-yl]pyridin-2-ylpropanamide
2-fluoro-2-methyl-N-4-[4-oxo-3-(phenylamino)-4,5,6,7-tetrahydro-1H-indol-2-yl]pyridin-2-ylpropanamide
3-hydroxy-2,2-dimethyl-N-4-[4-oxo-3-(phenylamino)-4,5,6,7-tetrahydro-1H-indol-2-yl]pyridin-2-ylpropanamide
2-(methylsulfanyl)-N-4-[4-oxo-3-(phenylamino)-4,5,6,7-tetrahydro-1H-indol-2-yl]pyridin-2-ylacetamide
2-cyano-2-methyl-N-4-[4-oxo-3-(phenylamino)-4,5,6,7-tetrahydro-1H-indol-2-yl]pyridin-2-ylpropanamide
1-cyano-N-4-[4-oxo-3-(phenylamino)-4,5,6,7-tetrahydro-1H-indol-2-yl]pyridin-2-ylcyclopropanecarboxamide
3,3,3-trifluoro-2-methyl-N-4-[4-oxo-3-(phenylamino)-4,5,6,7-tetrahydro-1H-indol-2-yl]pyridin-2-ylpropanamide
2-(methylsulfonyl)-N-4-[4-oxo-3-(phenylamino)-4,5,6,7-tetrahydro-1H-indol-2-yl]pyridin-2-ylacetamide
rel-(1R,2S)-2-fluoro-N-4-[4-oxo-3-(phenylamino)-4,5,6,7-tetrahydro-1H-indol-2-yl]pyridin-2-ylcyclopropanecarboxamide
(1S,2R)-2-fluoro-N-4-[4-oxo-3-(phenylamino)-4,5,6,7-tetrahydro-1H-indol-2-yl]pyridin-2-ylcyclopropanecarboxamide
(1R,2S)-2-fluoro-N-4-[4-oxo-3-(phenylamino)-4,5,6,7-tetrahydro-1H-indol-2-yl]pyridin-2-ylcyclopropanecarboxamide
rel-(1S,2S)-2-fluoro-N-4-[4-oxo-3-(phenylamino)-4,5,6,7-tetrahydro-1H-indol-2-yl]pyridin-2-ylcyclopropanecarboxamide
(1R,2R)-2-fluoro-N-4-[4-oxo-3-(phenylamino)-4,5,6,7-tetrahydro-1H-indol-2-yl]pyridin-2-ylcyclopropanecarboxamide rel-(1S,2R)—N-4-[6,6-dimethyl-4-oxo-3-(phenylamino)-4,5,6,7-tetrahydro-1H-indol-2-yl]pyridin-2-yl-2-fluorocyclopropanecarboxamide
(1S,2R)—N-[4-(3-anilino-6,6-dimethyl-4-oxo-4,5,6,7-tetrahydro-1H-indol-2-yl)pyridin-2-yl]-2-fluorocyclopropanecarboxamide
(1R,2S)—N-[4-(3-anilino-6,6-dimethyl-4-oxo-4,5,6,7-tetrahydro-1H-indol-2-yl)pyridin-2-yl]-2-fluorocyclopropanecarboxamide
rel-(1R,2R)—N-4-[6,6-dimethyl-4-oxo-3-(phenylamino)-4,5,6,7-tetrahydro-1H-indol-2-yl]pyridin-2-yl-2-fluorocyclopropanecarboxamide
(1S,2S)—N-[4-(3-anilino-6,6-dimethyl-4-oxo-4,5,6,7-tetrahydro-1H-indol-2-yl)pyridin-2-yl]-2-fluorocyclopropanecarboxamide
(1R,2R)—N-4-[6,6-dimethyl-4-oxo-3-(phenylamino)-4,5,6,7-tetrahydro-1H-indol-2-yl]pyridin-2-yl-2-fluorocyclopropanecarboxamide
2,2-difluoro-N-4-[4-oxo-3-(phenylamino)-4,5,6,7-tetrahydro-1H-indol-2-yl]pyridin-2-ylcyclopropanecarboxamide
1-fluoro-N-4-[4-oxo-3-(phenylamino)-4,5,6,7-tetrahydro-1H-indol-2-yl]pyridin-2-ylcyclopropanecarboxamide
rel-(1S,2R)—N-4-[4-oxo-3-(phenylamino)-4,5,6,7-tetrahydro-1H-indol-2-yl]pyridin-2-yl-2-(trifluoromethyl)cyclopropanecarboxamide
3-fluoro-2,2-dimethyl-N-4-[4-oxo-3-(phenylamino)-4,5,6,7-tetrahydro-1H-indol-2-yl]pyridin-2-ylpropanamide
2-fluoro-N-4-[4-oxo-3-(phenylamino)-4,5,6,7-tetrahydro-1H-indol-2-yl]pyridin-2-ylbenzamide
3-fluoro-N-4-[4-oxo-3-(phenylamino)-4,5,6,7-tetrahydro-1H-indol-2-yl]pyridin-2-ylbenzamide
4-fluoro-N-4-[4-oxo-3-(phenylamino)-4,5,6,7-tetrahydro-1H-indol-2-yl]pyridin-2-ylbenzamide
N-4-[6,6-dimethyl-4-oxo-3-(phenylamino)-4,5,6,7-tetrahydro-1H-indol-2-yl]pyridin-2-yl-4-fluorobenzamide
N-4-[4-oxo-3-(phenylamino)-4,5,6,7-tetrahydro-1H-indol-2-yl]pyridin-2-ylpyridine-4-carboxamide
N-4-[4-oxo-3-(phenylamino)-4,5,6,7-tetrahydro-1H-indol-2-yl]pyridin-2-ylpyridine-2-carboxamide
N-4-[4-oxo-3-(phenylamino)-4,5,6,7-tetrahydro-1H-indol-2-yl]pyridin-2-yl-1,3-thiazole-2-carboxamide
N-4-[4-oxo-3-(phenylamino)-4,5,6,7-tetrahydro-1H-indol-2-yl]pyridin-2-yl-1,3-thiazole-4-carboxamide
N-4-[6,6-dimethyl-4-oxo-3-(phenylamino)-4,5,6,7-tetrahydro-1H-indol-2-yl]pyridin-2-yl-1,3-thiazole-4-carboxamide
N-4-[4-oxo-3-(phenylamino)-4,5,6,7-tetrahydro-1H-indol-2-yl]pyridin-2-yl-1,3-thiazole-5-carboxamide
N-4-[4-oxo-3-(phenylamino)-4,5,6,7-tetrahydro-1H-indol-2-yl]pyridin-2-yl-1H-imidazole-2-carboxamide
N-4-[4-oxo-3-(phenylamino)-4,5,6,7-tetrahydro-1H-indol-2-yl]pyridin-2-yl-1H-pyrazole-5-carboxamide
N-4-[4-oxo-3-(phenylamino)-4,5,6,7-tetrahydro-1H-indol-2-yl]pyridin-2-yl-1,2-thiazole-3-carboxamide
N-4-[4-oxo-3-(phenylamino)-4,5,6,7-tetrahydro-1H-indol-2-yl]pyridin-2-yl-1,2-thiazole-4-carboxamide
N-4-[4-oxo-3-(phenylamino)-4,5,6,7-tetrahydro-1H-indol-2-yl]pyridin-2-yl-1,3-oxazole-4-carboxamide
N-4-[4-oxo-3-(phenylamino)-4,5,6,7-tetrahydro-1H-indol-2-yl]pyridin-2-ylpyridine-3-carboxamide
N-4-[4-oxo-3-(phenylamino)-4,5,6,7-tetrahydro-1H-indol-2-yl]pyridin-2-yl-1,2-thiazole-5-carboxamide
N-4-[4-oxo-3-(phenylamino)-4,5,6,7-tetrahydro-1H-indol-2-yl]pyridin-2-yl-1H-1,2,3-triazole-5-carboxamide
N-4-[4-oxo-3-(phenylamino)-4,5,6,7-tetrahydro-1H-indol-2-yl]pyridin-2-yl-1,3-oxazole-5-carboxamide
N-4-[4-oxo-3-(phenylamino)-4,5,6,7-tetrahydro-1H-indol-2-yl]pyridin-2-yl-1H-tetrazole-5-carboxamide
N-4-[4-oxo-3-(phenylamino)-4,5,6,7-tetrahydro-1H-indol-2-yl]pyridin-2-yl-2-(1H-pyrrol-2-yl)acetamide
N-4-[4-oxo-3-(phenylamino)-4,5,6,7-tetrahydro-1H-indol-2-yl]pyridin-2-yl-2-(1,3-thiazol-2-yl)acetamide
N-4-[4-oxo-3-(phenylamino)-4,5,6,7-tetrahydro-1H-indol-2-yl]pyridin-2-yl-2-(1H-pyrrol-3-yl)acetamide
N-4-[4-oxo-3-(phenylamino)-4,5,6,7-tetrahydro-1H-indol-2-yl]pyridin-2-yl-2-(1,3-thiazol-4-yl)acetamide
2-(furan-2-yl)-N-4-[4-oxo-3-(phenylamino)-4,5,6,7-tetrahydro-1H-indol-2-yl]pyridin-2-ylacetamide
2-(3-methyl-1,2-oxazol-5-yl)-N-4-[4-oxo-3-(phenylamino)-4,5,6,7-tetrahydro-1H-indol-2-yl]pyridin-2-ylacetamide
N-4-[4-oxo-3-(phenylamino)-4,5,6,7-tetrahydro-1H-indol-2-yl]pyridin-2-yl-2-(thiophen-2-yl)acetamide
N-4-[4-oxo-3-(phenylamino)-4,5,6,7-tetrahydro-1H-indol-2-yl]pyridin-2-yl-2-(thiophen-3-yl)acetamide
2-(1-methyl-1H-pyrazol-5-yl)-N-4-[4-oxo-3-(phenylamino)-4,5,6,7-tetrahydro-1H-indol-2-yl]pyridin-2-ylacetamide
N-4-[4'-oxo-3'-(phenylamino)-1',4',5',7'-tetrahydrospiro[cyclopropane-1,6'-indol]-2'-yl]pyridin-2-ylacetamide
N-4-[4'-oxo-3'-(phenylamino)-1',4',5',7'-tetrahydrospiro[cyclopropane-1,6'-indol]-2'-yl]pyridin-2-ylcyclopropanecarboxamide
tert-butyl 3-(4-[4-oxo-3-(phenylamino)-4,5,6,7-tetrahydro-1H-indol-2-yl]pyridin-2-ylcarbamoyl)azetidine-1-carboxylate
N-4-[4-oxo-3-(phenylamino)-4,5,6,7-tetrahydro-1H-indol-2-yl]pyridin-2-ylazetidine-3-carboxamide
tert-butyl methyl[2-oxo-2-(4-[4-oxo-3-(phenylamino)-4,5,6,7-tetrahydro-1H-indol-2-yl]pyridin-2-ylamino)ethyl]carbamate
N-[4-(3-anilino-4-oxo-4,5,6,7-tetrahydro-1H-indol-2-yl)pyridin-2-yl]-N$^2$-methylglycinamide
tert-butyl methyl[3-oxo-3-(4-[4-oxo-3-(phenylamino)-4,5,6,7-tetrahydro-1H-indol-2-yl]pyridin-2-ylamino)propyl]carbamate
N-[4-(3-anilino-4-oxo-4,5,6,7-tetrahydro-1H-indol-2-yl)pyridin-2-yl]-N$^3$-methyl-beta-alaninamide
tert-butyl methyl[(2R)-1-oxo-1-(4-[4-oxo-3-(phenylamino)-4,5,6,7-tetrahydro-1H-indol-2-yl]pyridin-2-ylamino)propan-2-yl]carbamate
N-[4-(3-anilino-4-oxo-4,5,6,7-tetrahydro-1H-indol-2-yl)pyridin-2-yl]-N$^2$-methyl-D-alaninamide
tert-butyl methyl[(2S)-1-oxo-1-(4-[4-oxo-3-(phenylamino)-4,5,6,7-tetrahydro-1H-indol-2-yl]pyridin-2-ylamino)propan-2-yl]carbamate
N-[4-(3-anilino-4-oxo-4,5,6,7-tetrahydro-1H-indol-2-yl)pyridin-2-yl]-N$^2$-methyl-L-alaninamide
N-[4-(3-anilino-4-oxo-4,5,6,7-tetrahydro-1H-indol-2-yl)pyridin-2-yl]-N$^2$,N$^2$-dimethyl-D-alaninamide
N-[4-(3-anilino-4-oxo-4,5,6,7-tetrahydro-1H-indol-2-yl)pyridin-2-yl]-N$^2$,2-dimethylalaninamide
N-[4-(3-anilino-4-oxo-4,5,6,7-tetrahydro-1H-indol-2-yl)pyridin-2-yl]-N$^2$,N$^2$-dimethylglycinamide
N-4-[4-oxo-3-(phenylamino)-4,5,6,7-tetrahydro-1H-indol-2-yl]pyridin-2-yl-2-(pyrrolidin-1-yl)acetamide
1-methyl-N-4-[4-oxo-3-(phenylamino)-4,5,6,7-tetrahydro-1H-indol-2-yl]pyridin-2-yl-D-prolinamide
1-methyl-5-oxo-N-4-[4-oxo-3-(phenylamino)-4,5,6,7-tetrahydro-1H-indol-2-yl]pyridin-2-yl-D-prolinamide
5-oxo-N-4-[4-oxo-3-(phenylamino)-4,5,6,7-tetrahydro-1H-indol-2-yl]pyridin-2-yl-D-prolinamide
methyl (4-{3-[(3-fluorophenyl)amino]-4-oxo-4,5,6,7-tetrahydro-1H-indol-2-yl}pyridin-2-yl)carbamate N-(4-{3-[(4-fluorophenyl)amino]-4-oxo-4,5,6,7-tetrahydro-1H-indol-2-yl}pyridin-2-yl)acetamide
N-(4-{3-[(4-fluorophenyl)amino]-4-oxo-4,5,6,7-tetrahydro-1H-indol-2-yl}pyridin-2-yl)cyclopropanecarboxamide
N-(4-{3-[(3,4-difluorophenyl)amino]-4-oxo-4,5,6,7-tetrahydro-1H-indol-2-yl}pyridin-2-yl)acetamide
N-(4-{3-[(3,4-difluorophenyl)amino]-4-oxo-4,5,6,7-tetrahydro-1H-indol-2-yl}pyridin-2-yl)cyclopropanecarboxamide
N-4-[4-oxo-3-(phenylamino)-6-(propan-2-yl)-4,5,6,7-tetrahydro-1H-indol-2-yl]pyridin-2-ylacetamide
N-4-[4-oxo-3-(phenylamino)-6-(propan-2-yl)-4,5,6,7-tetrahydro-1H-indol-2-yl]pyridin-2-ylcyclopropanecarboxamide
N-4-[3-[(3-fluorophenyl)amino]-4-oxo-6-(propan-2-yl)-4,5,6,7-tetrahydro-1H-indol-2-yl]pyridin-2-ylacetamide
N-4-[3-[(3-fluorophenyl)amino]-4-oxo-6-(propan-2-yl)-4,5,6,7-tetrahydro-1H-indol-2-yl]pyridin-2-ylcyclopropanecarboxamide
N-4-[3-[(4-fluorophenyl)amino]-4-oxo-6-(propan-2-yl)-4,5,6,7-tetrahydro-1H-indol-2-yl]pyridin-2-ylacetamide
N-4-[3-[(4-fluorophenyl)amino]-4-oxo-6-(propan-2-yl)-4,5,6,7-tetrahydro-1H-indol-2-yl]pyridin-2-ylcyclopropanecarboxamide
N-4-[3-[(3,4-difluorophenyl)amino]-4-oxo-6-(propan-2-yl)-4,5,6,7-tetrahydro-1H-indol-2-yl]pyridin-2-ylacetamide
N-4-[3-[(3,4-difluorophenyl)amino]-4-oxo-6-(propan-2-yl)-4,5,6,7-tetrahydro-1H-indol-2-yl]pyridin-2-ylcyclopropanecarboxamide
2-methoxy-N-4-[4-oxo-3-(phenylamino)-4,5,6,7-tetrahydro-1H-indol-2-yl]pyridin-2-ylacetamide
2-methoxy-2-methyl-N-4-[4-oxo-3-(phenylamino)-4,5,6,7-tetrahydro-1H-indol-2-yl]pyridin-2-ylpropanamide
2-hydroxy-2-methyl-N-4-[4-oxo-3-(phenylamino)-4,5,6,7-tetrahydro-1H-indol-2-yl]pyridin-2-ylpropanamide
2-ethoxy-2-methyl-N-4-[4-oxo-3-(phenylamino)-4,5,6,7-tetrahydro-1H-indol-2-yl]pyridin-2-ylpropanamide
2-methoxy-N-4-[4-oxo-3-(phenylamino)-4,5,6,7-tetrahydro-1H-indol-2-yl]pyridin-2-ylpropanamide
N-4-[4-oxo-3-(phenylamino)-4,5,6,7-tetrahydro-1H-indol-2-yl]pyridin-2-yl-2-propoxyacetamide
2-(2-methylpropoxy)-N-4-[4-oxo-3-(phenylamino)-4,5,6,7-tetrahydro-1H-indol-2-yl]pyridin-2-ylacetamide
N-4-[4-oxo-3-(phenylamino)-4,5,6,7-tetrahydro-1H-indol-2-yl]pyridin-2-yl-2-(2,2,3,3-tetrafluoropropoxy)acetamide
2-butoxy-N-4-[4-oxo-3-(phenylamino)-4,5,6,7-tetrahydro-1H-indol-2-yl]pyridin-2-ylacetamide
2-ethoxy-N-4-[4-oxo-3-(phenylamino)-4,5,6,7-tetrahydro-1H-indol-2-yl]pyridin-2-ylacetamide
N-4-[4-oxo-3-(phenylamino)-4,5,6,7-tetrahydro-1H-indol-2-yl]pyridin-2-yl-2-(prop-2-en-1-yloxy)acetamide
N-4-[4-oxo-3-(phenylamino)-4,5,6,7-tetrahydro-1H-indol-2-yl]pyridin-2-yl-2-(prop-2-yn-1-yloxy)acetamide
N-4-[4-oxo-3-(phenylamino)-4,5,6,7-tetrahydro-1H-indol-2-yl]pyridin-2-yl-2-phenoxyacetamide
2-(3-fluorophenoxy)-N-4-[4-oxo-3-(phenylamino)-4,5,6,7-tetrahydro-1H-indol-2-yl]pyridin-2-ylacetamide
2-(2-fluorophenoxy)-N-4-[4-oxo-3-(phenylamino)-4,5,6,7-tetrahydro-1H-indol-2-yl]pyridin-2-ylacetamide
2-(benzyloxy)-N-4-[4-oxo-3-(phenylamino)-4,5,6,7-tetrahydro-1H-indol-2-yl]pyridin-2-ylacetamide
2-[(4-fluorobenzyl)oxy]-N-4-[4-oxo-3-(phenylamino)-4,5,6,7-tetrahydro-1H-indol-2-yl]pyridin-2-ylacetamide
2-[(4-methoxybenzyl)oxy]-N-4-[4-oxo-3-(phenylamino)-4,5,6,7-tetrahydro-1H-indol-2-yl]pyridin-2-ylacetamide
N-4-[4-oxo-3-(phenylamino)-4,5,6,7-tetrahydro-1H-indol-2-yl]pyridin-2-yl-2-[tetrahydro-2H-pyran-2-ylmethoxy]acetamide
N-4-[4-oxo-3-(phenylamino)-4,5,6,7-tetrahydro-1H-indol-2-yl]pyridin-2-yl-2-(thiophen-3-yloxy)acetamide
2-[(2-chlorothiophen-3-yl)oxy]-N-4-[4-oxo-3-(phenylamino)-4,5,6,7-tetrahydro-1H-indol-2-yl]pyridin-2-ylacetamide
2-[(5-methyl-1,2-oxazol-3-yl)oxy]-N-4-[4-oxo-3-(phenylamino)-4,5,6,7-tetrahydro-1H-indol-2-yl]pyridin-2-ylacetamide
N-4-[4-oxo-3-(phenylamino)-4,5,6,7-tetrahydro-1H-indol-2-yl]pyridin-2-yl-2-(pyridin-2-yloxy)acetamide
2-(1,2-oxazol-3-yloxy)-N-4-[4-oxo-3-(phenylamino)-4,5,6,7-tetrahydro-1H-indol-2-yl]pyridin-2-ylacetamide
2-[(3-methyl-1,2,4-oxadiazol-5-yl)methoxy]-N-4-[4-oxo-3-(phenylamino)-4,5,6,7-tetrahydro-1H-indol-2-yl]pyridin-2-ylacetamide
2-[(3-methyl-1,2-oxazol-5-yl)methoxy]-N-4-[4-oxo-3-(phenylamino)-4,5,6,7-tetrahydro-1H-indol-2-yl]pyridin-2-ylacetamide
2-[(1-methyl-1H-pyrazol-5-yl)methoxy]-N-4-[4-oxo-3-(phenylamino)-4,5,6,7-tetrahydro-1H-indol-2-yl]pyridin-2-ylacetamide
2-(furan-2-ylmethoxy)-N-4-[4-oxo-3-(phenylamino)-4,5,6,7-tetrahydro-1H-indol-2-yl]pyridin-2-ylacetamide
2-[(5-methyl-1,3,4-oxadiazol-2-yl)methoxy]-N-4-[4-oxo-3-(phenylamino)-4,5,6,7-tetrahydro-1H-indol-2-yl]pyridin-2-ylacetamide
2-[(5-methyl-1,2-oxazol-3-yl)methoxy]-N-4-[4-oxo-3-(phenylamino)-4,5,6,7-tetrahydro-1H-indol-2-yl]pyridin-2-ylacetamide
2-[(5-methyl-1,3-oxazol-2-yl)methoxy]-N-4-[4-oxo-3-(phenylamino)-4,5,6,7-tetrahydro-1H-indol-2-yl]pyridin-2-ylacetamide
2-[(5-methyl-1,3,4-thiadiazol-2-yl)methoxy]-N-4-[4-oxo-3-(phenylamino)-4,5,6,7-tetrahydro-1H-indol-2-yl]pyridin-2-ylacetamide
N-6-[6,6-dimethyl-4-oxo-3-(phenylamino)-4,5,6,7-tetrahydro-1H-indol-2-yl]pyrimidin-4-ylacetamide
2-[2-(methylamino)pyridin-4-yl]-3-(phenylamino)-1,5,6,7-tetrahydro-4H-indol-4-one
2-[2-(cyclobutylamino)pyridin-4-yl]-6,6-dimethyl-3-(phenylamino)-1,5,6,7-tetrahydro-4H-indol-4-one
2-[2-(azetidin-1-yl)pyridin-4-yl]-6,6-dimethyl-3-(phenylamino)-1,5,6,7-tetrahydro-4H-indol-4-one
6,6-dimethyl-3-(phenylamino)-2-{2-[(2,2,2-trifluoroethyl)amino]pyridin-4-yl}-1,5,6,7-tetrahydro-4H-indol-4-one
6,6-dimethyl-3-(phenylamino)-2-{2-[(3,3,3-trifluoropropyl)amino]pyridin-4-yl}-1,5,6,7-tetrahydro-4H-indol-4-one
2-(2-[1,1-difluoropropan-2-yl]aminopyridin-4-yl)-6,6-dimethyl-3-(phenylamino)-1,5,6,7-tetrahydro-4H-indol-4-one
3-(phenylamino)-2-[2-(propan-2-ylamino)pyridin-4-yl]-1,5,6,7-tetrahydro-4H-indol-4-one
3-(phenylamino)-2-{2-[(3,3,3-trifluoropropyl)amino]pyridin-4-yl}-1,5,6,7-tetrahydro-4H-indol-4-one
2-[2-(benzylamino)pyridin-4-yl]-3-(phenylamino)-1,5,6,7-tetrahydro-4H-indol-4-one
3-(phenylamino)-2-{2-[(pyridin-4-ylmethyl)amino]pyridin-4-yl}-1,5,6,7-tetrahydro-4H-indol-4-one
2-{2-[(cyclopropylmethyl)amino]pyridin-4-yl}-3-(phenylamino)-1,5,6,7-tetrahydro-4H-indol-4-one
N-4-[4-oxo-3-(phenylamino)-4,5,6,7-tetrahydro-1H-indol-2-yl]pyridin-2-ylglycine 2-[2-([(4S)-2,2-dimethyl-1,3-dioxolan-4-yl]methylamino)pyridin-4-yl]-3-(phenylamino)-1,5,6,7-tetrahydro-4H-indol-4-one
2-(2-[(2S)-2,3-dihydroxypropyl]aminopyridin-4-yl)-3-(phenylamino)-1,5,6,7-tetrahydro-4H-indol-4-one
3-(phenylamino)-2-{2-[(pyridin-3-ylmethyl)amino]pyridin-4-yl}-1,5,6,7-tetrahydro-4H-indol-4-one
tert-butyl 3-[(4-[4-oxo-3-(phenylamino)-4,5,6,7-tetrahydro-1H-indol-2-yl]pyridin-2-ylamino)methyl]azetidine-1-carboxylate
2-{2-[(1-methyl-1H-tetrazol-5-yl)amino]pyridin-4-yl}-3-(phenylamino)-1,5,6,7-tetrahydro-4H-indol-4-one
2-{2-[(3-fluorophenyl)amino]pyridin-4-yl}-3-(phenylamino)-1,5,6,7-tetrahydro-4H-indol-4-one
3-(phenylamino)-2-[3-(propan-2-ylamino)pyridin-4-yl]-1,5,6,7-tetrahydro-4H-indol-4-one
1-ethyl-3-{4-[4-oxo-3-(phenylamino)-4,5,6,7-tetrahydro-1H-indol-2-yl]pyridin-2-yl}urea
1-{4-[4-oxo-3-(phenylamino)-4,5,6,7-tetrahydro-1H-indol-2-yl]pyridin-2-yl}-3-propan-2-ylurea
1-cyclopropyl-3-{4-[4-oxo-3-(phenylamino)-4,5,6,7-tetrahydro-1H-indol-2-yl]pyridin-2-yl}urea
1-tert-butyl-3-{4-[4-oxo-3-(phenylamino)-4,5,6,7-tetrahydro-1H-indol-2-yl]pyridin-2-yl}urea
1-(2-methylpropyl)-3-{4-[4-oxo-3-(phenylamino)-4,5,6,7-tetrahydro-1H-indol-2-yl]pyridin-2-yl}urea
1-{4-[4-oxo-3-(phenylamino)-4,5,6,7-tetrahydro-1H-indol-2-yl]pyridin-2-yl}-3-(2,2,2-trifluoroethyl)urea
1-(2-methoxyethyl)-3-{4-[4-oxo-3-(phenylamino)-4,5,6,7-tetrahydro-1H-indol-2-yl]pyridin-2-yl}urea
1-(furan-2-ylmethyl)-3-{4-[4-oxo-3-(phenylamino)-4,5,6,7-tetrahydro-1H-indol-2-yl]pyridin-2-yl}urea
1-{4-[4-oxo-3-(phenylamino)-4,5,6,7-tetrahydro-1H-indol-2-yl]pyridin-2-yl}-3-pyridin-4-ylurea
1-{4-[4-oxo-3-(phenylamino)-4,5,6,7-tetrahydro-1H-indol-2-yl]pyridin-2-yl}-3-pyridin-2-ylurea
1-(2,2-difluoroethyl)-3-{4-[4-oxo-3-(phenylamino)-4,5,6,7-tetrahydro-1H-indol-2-yl]pyridin-2-yl}urea
1-(2-chloroethyl)-3-{4-[4-oxo-3-(phenylamino)-4,5,6,7-tetrahydro-1H-indol-2-yl]pyridin-2-yl}urea
1-[2-(methylsulfanyl)ethyl]-3-{4-[4-oxo-3-(phenylamino)-4,5,6,7-tetrahydro-1H-indol-2-yl]pyridin-2-yl}urea
1-(1-methyl-1H-pyrazol-4-yl)-3-{4-[4-oxo-3-(phenylamino)-4,5,6,7-tetrahydro-1H-indol-2-yl]pyridin-2-yl}urea
1-{4-[6,6-dimethyl-4-oxo-3-(phenylamino)-4,5,6,7-tetrahydro-1H-indol-2-yl]pyridin-2-yl}-3-(1-methyl-1H-pyrazol-4-yl)urea
1-methyl-3-{4-[4-oxo-3-(phenylamino)-4,5,6,7-tetrahydro-1H-indol-2-yl]pyridin-2-yl}thiourea
1-ethyl-3-{4-[4-oxo-3-(phenylamino)-4,5,6,7-tetrahydro-1H-indol-2-yl]pyridin-2-yl}thiourea
1-{4-[4-oxo-3-(phenylamino)-4,5,6,7-tetrahydro-1H-indol-2-yl]pyridin-2-yl}-3-(2,2,2-trifluoroethyl)thiourea
1-cyclopropyl-3-{4-[4-oxo-3-(phenylamino)-4,5,6,7-tetrahydro-1H-indol-2-yl]pyridin-2-yl}thiourea
1-tert-butyl-3-{4-[4-oxo-3-(phenylamino)-4,5,6,7-tetrahydro-1H-indol-2-yl]pyridin-2-yl}thiourea
1-cyclopentyl-3-{4-[4-oxo-3-(phenylamino)-4,5,6,7-tetrahydro-1H-indol-2-yl]pyridin-2-yl}thiourea
1-(cyclopropylmethyl)-3-{4-[4-oxo-3-(phenylamino)-4,5,6,7-tetrahydro-1H-indol-2-yl]pyridin-2-yl}thiourea
1-{4-[4-oxo-3-(phenylamino)-4,5,6,7-tetrahydro-1H-indol-2-yl]pyridin-2-yl}-3-propylthiourea
2-[2-(difluoromethyl)pyridin-4-yl]-6,6-dimethyl-3-(phenylamino)-1,5,6,7-tetrahydro-4H-indol-4-one
2-[2-(difluoromethyl)pyridin-4-yl]-3-(phenylamino)-1,5,6,7-tetrahydro-4H-indol-4-one
2-[2-(difluoromethyl)pyridin-4-yl]-3-[(3-fluorophenyl)amino]-6,6-dimethyl-1,5,6,7-tetrahydro-4H-indol-4-one
2-(3-methoxypyridin-4-yl)-6,6-dimethyl-3-(phenylamino)-1,5,6,7-tetrahydro-4H-indol-4-one
2-(3-ethoxypyridin-4-yl)-6,6-dimethyl-3-(phenylamino)-1,5,6,7-tetrahydro-4H-indol-4-one
6,6-dimethyl-3-(phenylamino)-2-(3-propoxypyridin-4-yl)-1,5,6,7-tetrahydro-4H-indol-4-one
6,6-dimethyl-3-(phenylamino)-2-[3-(propan-2-yloxy)pyridin-4-yl]-1,5,6,7-tetrahydro-4H-indol-4-one
2-(3-tert-butoxypyridin-4-yl)-6,6-dimethyl-3-(phenylamino)-1,5,6,7-tetrahydro-4H-indol-4-one
2-[3-(2,2-difluoroethoxy)pyridin-4-yl]-6,6-dimethyl-3-(phenylamino)-1,5,6,7-tetrahydro-4H-indol-4-one
2-[3-(2-hydroxyethoxy)pyridin-4-yl]-6,6-dimethyl-3-(phenylamino)-1,5,6,7-tetrahydro-4H-indol-4-one
2-[3-(2-methoxyethoxy)pyridin-4-yl]-6,6-dimethyl-3-(phenylamino)-1,5,6,7-tetrahydro-4H-indol-4-one
2-[3-(cyclopropylmethoxy)pyridin-4-yl]-6,6-dimethyl-3-(phenylamino)-1,5,6,7-tetrahydro-4H-indol-4-one
6,6-dimethyl-3-(phenylamino)-2-[3-(2,2,2-trifluoroethoxy)pyridin-4-yl]-1,5,6,7-tetrahydro-4H-indol-4-one
2-(3-methoxypyridin-4-yl)-3-(phenylamino)-1,5,6,7-tetrahydro-4H-indol-4-one
3-(biphenyl-4-ylamino)-6,6-dimethyl-2-(pyridin-4-yl)-1,5,6,7-tetrahydro-4H-indol-4-one
3-[(3-benzylphenyl)amino]-6,6-dimethyl-2-(pyridin-4-yl)-1,5,6,7-tetrahydro-4H-indol-4-one
3-[(2-benzylphenyl)amino]-6,6-dimethyl-2-(pyridin-4-yl)-1,5,6,7-tetrahydro-4H-indol-4-one
6,6-dimethyl-3-[3-(1-methyl-1H-pyrazol-5-yl)phenyl]amino-2-(pyridin-4-yl)-1,5,6,7-tetrahydro-4H-indol-4-one
6,6-dimethyl-2-(pyridin-4-yl)-3-[3-(thiophen-3-yl)phenyl]amino-1,5,6,7-tetrahydro-4H-indol-4-one
3-[3-(furan-2-yl)phenyl]amino-6,6-dimethyl-2-(pyridin-4-yl)-1,5,6,7-tetrahydro-4H-indol-4-one
6,6-dimethyl-2-(pyridin-4-yl)-3-[3-(thiophen-2-yl)phenyl]amino-1,5,6,7-tetrahydro-4H-indol-4-one
6,6-dimethyl-3-[(3-phenoxyphenyl)amino]-2-(pyridin-4-yl)-1,5,6,7-tetrahydro-4H-indol-4-one
6,6-dimethyl-3-[(4-phenylpyridin-2-yl)amino]-2-(pyridin-4-yl)-1,5,6,7-tetrahydro-4H-indol-4-one
6,6-dimethyl-3-[(6-phenylpyridin-2-yl)amino]-2-(pyridin-4-yl)-1,5,6,7-tetrahydro-4H-indol-4-one
3-[2-(hydroxymethyl)phenyl]amino-6,6-dimethyl-2-(pyridin-4-yl)-1,5,6,7-tetrahydro-4H-indol-4-one
3-[2-(2-hydroxyethyl)phenyl]amino-6,6-dimethyl-2-(pyridin-4-yl)-1,5,6,7-tetrahydro-4H-indol-4-one
3-[(3-ethynylphenyl)amino]-6,6-dimethyl-2-(pyridin-4-yl)-1,5,6,7-tetrahydro-4H-indol-4-one
2-[6,6-dimethyl-4-oxo-2-(pyridin-4-yl)-4,5,6,7-tetrahydro-1H-indol-3-yl]aminobenzamide
methyl 3-[6,6-dimethyl-4-oxo-2-(pyridin-4-yl)-4,5,6,7-tetrahydro-1H-indol-3-yl]aminothiophene-2-carboxylate
3-[6,6-dimethyl-4-oxo-2-(pyridin-4-yl)-4,5,6,7-tetrahydro-1H-indol-3-yl]aminothiophene-2-carboxylic acid
4-[6,6-dimethyl-4-oxo-2-(pyridin-4-yl)-4,5,6,7-tetrahydro-1H-indol-3-yl]aminobenzenesulfonamide
4-[6,6-dimethyl-4-oxo-2-(pyridin-4-yl)-4,5,6,7-tetrahydro-1H-indol-3-yl]aminobenzonitrile
3-[4-(dimethylamino)phenyl]amino-6,6-dimethyl-2-(pyridin-4-yl)-1,5,6,7-tetrahydro-4H-indol-4-one
2-(3-chloropyridin-4-yl)-3-[(3-fluorophenyl)amino]-6-(trifluoromethyl)-1,5,6,7-tetrahydro-4H-indol-4-one 2-[2-(hydroxymethyl)pyridin-4-yl]-6,6-dimethyl-3-(phenylamino)-1,5,6,7-tetrahydro-4H-indol-4-one
6,6-dimethyl-3-(phenylamino)-2-[3-(trifluoromethyl)pyridin-4-yl]-1,5,6,7-tetrahydro-4H-indol-4-one
4-[6,6-dimethyl-4-oxo-3-(phenylamino)-4,5,6,7-tetrahydro-1H-indol-2-yl]pyridine-2-sulfonamide
(6R)-3-(phenylamino)-2-(pyridin-4-yl)-6-(trifluoromethyl)-1,5,6,7-tetrahydro-4H-indol-4-one
(6S)-3-(phenylamino)-2-(pyridin-4-yl)-6-(trifluoromethyl)-1,5,6,7-tetrahydro-4H-indol-4-one
6-(fluoromethyl)-3-(phenylamino)-2-(pyridin-4-yl)-1,5,6,7-tetrahydro-4H-indol-4-one
6-(chloromethyl)-3-(phenylamino)-2-(pyridin-4-yl)-1,5,6,7-tetrahydro-4H-indol-4-one
N-4-[6-(chloromethyl)-4-oxo-3-(phenylamino)-4,5,6,7-tetrahydro-1H-indol-2-yl]pyridin-2-ylacetamide
7-hydroxy-6,6-dimethyl-3-(phenylamino)-2-(pyridin-4-yl)-1,5,6,7-tetrahydro-4H-indol-4-one
7-hydroxy-3-(phenylamino)-2-(pyridin-4-yl)-1,5,6,7-tetrahydro-4H-indol-4-one
1-methyl-N-4-[4-oxo-3-(phenylamino)-4,5,6,7-tetrahydro-1H-indol-2-yl]pyridin-2-yl-1H-pyrazole-4-carboxamide
1-tert-butyl-N-4-[4-oxo-3-(phenylamino)-4,5,6,7-tetrahydro-1H-indol-2-yl]pyridin-2-yl-1H-pyrazole-4-carboxamide
1-benzyl-N-4-[4-oxo-3-(phenylamino)-4,5,6,7-tetrahydro-1H-indol-2-yl]pyridin-2-yl-1H-pyrazole-4-carboxamide
1-(4-methoxybenzyl)-N-4-[4-oxo-3-(phenylamino)-4,5,6,7-tetrahydro-1H-indol-2-yl]pyridin-2-yl-1H-pyrazole-4-carboxamide
3,4-difluoro-N-4-[4-oxo-3-(phenylamino)-4,5,6,7-tetrahydro-1H-indol-2-yl]pyridin-2-ylbenzamide
3,5-difluoro-N-4-[4-oxo-3-(phenylamino)-4,5,6,7-tetrahydro-1H-indol-2-yl]pyridin-2-ylbenzamide
4-fluoro-3-methoxy-N-4-[4-oxo-3-(phenylamino)-4,5,6,7-tetrahydro-1H-indol-2-yl]pyridin-2-ylbenzamide
1-methyl-N-4-[4-oxo-3-(phenylamino)-4,5,6,7-tetrahydro-1H-indol-2-yl]pyridin-2-yl-1H-pyrazole-3-carboxamide
2-[3-(cyclopropylmethoxy)pyridin-4-yl]-3-(phenylamino)-1,5,6,7-tetrahydro-4H-indol-4-one
3-(phenylamino)-2-(3-propoxypyridin-4-yl)-1,5,6,7-tetrahydro-4H-indol-4-one
2-[3-(2,2-difluoroethoxy)pyridin-4-yl]-3-(phenylamino)-1,5,6,7-tetrahydro-4H-indol-4-one
3-(phenylamino)-2-[3-(2,2,2-trifluoroethoxy)pyridin-4-yl]-1,5,6,7-tetrahydro-4H-indol-4-one
2-[3-(2-hydroxyethoxy)pyridin-4-yl]-3-(phenylamino)-1,5,6,7-tetrahydro-4H-indol-4-one
(4S)-2,2-dimethyl-N-4-[4-oxo-3-(phenylamino)-4,5,6,7-tetrahydro-1H-indol-2-yl]pyridin-2-yl-1,3-dioxolane-4-carboxamide
N-4-[6-(fluoromethyl)-4-oxo-3-(phenylamino)-4,5,6,7-tetrahydro-1H-indol-2-yl]pyridin-2-ylacetamide
N-[4-(3-anilino-4-oxo-4,5,6,7-tetrahydro-1H-indol-2-yl)pyridin-2-yl]-2-(4-fluorophenoxy)acetamide
N-[4-(3-anilino-4-oxo-4,5,6,7-tetrahydro-1H-indol-2-yl)pyridin-2-yl]-2-(1-methyl-1H-imidazol-2-yl)acetamide
3-anilino-2-(3-hydroxypyridin-4-yl)-6,6-dimethyl-1,5,6,7-tetrahydro-4H-indol-4-one
N-4-[6,6-dimethyl-4-oxo-3-(phenylamino)-4,5,6,7-tetrahydro-1H-indol-2-yl]pyridin-2-yl-1H-pyrazole-3-carboxamide
rel-(1R,2S)-2-fluoro-N-4-[4'-oxo-3'-(phenylamino)-1',4',5',7'-tetrahydrospiro[cyclopropane-1,6'-indol]-2'-yl]pyridin-2-ylcyclopropanecarboxamide
N-4-[6,6-dimethyl-4-oxo-3-(phenylamino)-4,5,6,7-tetrahydro-1H-indol-2-yl]pyridin-2-yl-3,5-difluorobenzamide
2-[2-(benzyloxy)pyridin-4-yl]-6,6-dimethyl-3-(phenylamino)-1,5,6,7-tetrahydro-4H-indol-4-one
2-(2-hydroxypyridin-4-yl)-6,6-dimethyl-3-(phenylamino)-1,5,6,7-tetrahydro-4H-indol-4-one
N-4-[4'-oxo-3'-(phenylamino)-1',4',5',7'-tetrahydrospiro[cyclopropane-1,6'-indol]-2'-yl]pyridin-2-yl-1,3-oxazole-4-carboxamide
4-(methoxyimino)-6,6-dimethyl-N-phenyl-2-(pyridin-4-yl)-4,5,6,7-tetrahydro-1H-indol-3-amine
1-tert-butyl-N-4-[6,6-dimethyl-4-oxo-3-(phenylamino)-4,5,6,7-tetrahydro-1H-indol-2-yl]pyridin-2-yl-1H-pyrazole-4-carboxamide
N-4-[6,6-dimethyl-4-oxo-3-(phenylamino)-4,5,6,7-tetrahydro-1H-indol-2-yl]pyridin-2-yl-3,4-difluorobenzamide
N-4-[6,6-dimethyl-4-oxo-3-(phenylamino)-4,5,6,7-tetrahydro-1H-indol-2-yl]pyridin-2-yl-4-fluoro-3-methoxybenzamide
N-4-[6,6-dimethyl-4-oxo-3-(phenylamino)-4,5,6,7-tetrahydro-1H-indol-2-yl]pyridin-2-yl-2-fluoro-2-methylpropanamide
2-(benzyloxy)-N-4-[6,6-dimethyl-4-oxo-3-(phenylamino)-4,5,6,7-tetrahydro-1H-indol-2-yl]pyridin-2-ylacetamide
N-4-[6,6-dimethyl-4-oxo-3-(phenylamino)-4,5,6,7-tetrahydro-1H-indol-2-yl]pyridin-2-yl-2,2-difluorocyclopropanecarboxamide
1-benzyl-N-4-[6,6-dimethyl-4-oxo-3-(phenylamino)-4,5,6,7-tetrahydro-1H-indol-2-yl]pyridin-2-yl-1H-pyrazole-4-carboxamide
N-4-[6,6-dimethyl-4-oxo-3-(phenylamino)-4,5,6,7-tetrahydro-1H-indol-2-yl]pyridin-2-yl-1-(4-methoxybenzyl)-1H-pyrazole-4-carboxamide
N-4-[6,6-dimethyl-4-oxo-3-(phenylamino)-4,5,6,7-tetrahydro-1H-indol-2-yl]pyridin-2-yl-1,3-thiazole-5-carboxamide
3-[2-(hydroxymethyl)-5-methylphenyl]amino-6,6-dimethyl-2-(pyridin-4-yl)-1,5,6,7-tetrahydro-4H-indol-4-one
3-[2-(hydroxymethyl)-4-methylphenyl]amino-6,6-dimethyl-2-(pyridin-4-yl)-1,5,6,7-tetrahydro-4H-indol-4-one
3-[2-(hydroxymethyl)-3-methylphenyl]amino-6,6-dimethyl-2-(pyridin-4-yl)-1,5,6,7-tetrahydro-4H-indol-4-one
3-(phenylamino)-2-{2-[(4-phenylbutyl)amino]pyridin-4-yl}-1,5,6,7-tetrahydro-4H-indol-4-one
3-[4-fluoro-2-(hydroxymethyl)phenyl]amino-6,6-dimethyl-2-(pyridin-4-yl)-1,5,6,7-tetrahydro-4H-indol-4-one
3-[3-fluoro-2-(hydroxymethyl)phenyl]amino-6,6-dimethyl-2-(pyridin-4-yl)-1,5,6,7-tetrahydro-4H-indol-4-one
3-[5-fluoro-2-(hydroxymethyl)phenyl]amino-6,6-dimethyl-2-(pyridin-4-yl)-1,5,6,7-tetrahydro-4H-indol-4-one
3-[2-(2-hydroxypropan-2-yl)phenyl]amino-6,6-dimethyl-2-(pyridin-4-yl)-1,5,6,7-tetrahydro-4H-indol-4-one
3-(phenylamino)-2-{2-[(2-phenylethyl)amino]pyridin-4-yl}-1,5,6,7-tetrahydro-4H-indol-4-one
3-(phenylamino)-2-{2-[(3-phenylpropyl)amino]pyridin-4-yl}-1,5,6,7-tetrahydro-4H-indol-4-one
4-(ethoxyimino)-6,6-dimethyl-N-phenyl-2-(pyridin-4-yl)-4,5,6,7-tetrahydro-1H-indol-3-amine
N-4-[4-oxo-3-(phenylamino)-4,5,6,7-tetrahydro-1H-indol-2-yl]pyridin-2-yl-2-(pyridin-3-ylmethoxy)acetamide
2-[(1-methyl-1H-imidazol-2-yl)methoxy]-N-4-[4-oxo-3-(phenylamino)-4,5,6,7-tetrahydro-1H-indol-2-yl]pyridin-2-ylacetamide
2-[(1-methyl-1H-1,2,4-triazol-5-yl)methoxy]-N-4-[4-oxo-3-(phenylamino)-4,5,6,7-tetrahydro-1H-indol-2-yl]pyridin-2-ylacetamide
N-4-[4-oxo-3-(phenylamino)-4,5,6,7-tetrahydro-1H-indol-2-yl]pyridin-2-yl-2-(pyridin-2-ylmethoxy)acetamide 2-[(4-methyl-1,3-thiazol-5-yl)methoxy]-N-4-[4-oxo-3-(phenylamino)-4,5,6,7-tetrahydro-1H-indol-2-yl]pyridin-2-ylacetamide 6,6-dimethyl-3-(phenylamino)-2-{2-[(3-phenylpropyl)amino]pyridin-4-yl}-1,5,6,7-tetrahydro-4H-indol-4-one 6,6-dimethyl-3-(phenylamino)-2-{2-[(2-phenylethyl)amino]pyridin-4-yl}-1,5,6,7-tetrahydro-4H-indol-4-one 2-{2-[(4-fluorobenzyl)amino]pyridin-4-yl}-3-(phenylamino)-1,5,6,7-tetrahydro-4H-indol-4-one 3-(phenylamino)-2-{2-[(1,3-thiazol-5-ylmethyl)amino]pyridin-4-yl}-1,5,6,7-tetrahydro-4H-indol-4-one 3-(phenylamino)-2-{2-[(1,3-thiazol-4-ylmethyl)amino]pyridin-4-yl}-1,5,6,7-tetrahydro-4H-indol-4-one N-4-[4-oxo-3-(phenylamino)-4,5,6,7-tetrahydro-1H-indol-2-yl]pyridin-2-yl-2-(2,2,2-trifluoroethoxy)acetamide 2-(pyridin-4-yl)-3-(pyridin-2-ylamino)-1,5,6,7-tetrahydro-4H-indol-4-one N-4-[6,6-dimethyl-4-oxo-3-(phenylamino)-4,5,6,7-tetrahydro-1H-indol-2-yl]pyridin-2-yl-1-methyl-1H-pyrazole-3-carboxamide N-4-[6,6-dimethyl-4-oxo-3-(phenylamino)-4,5,6,7-tetrahydro-1H-indol-2-yl]pyridin-2-yl-1,3-thiazole-2-carboxamide N-4-[6,6-dimethyl-4-oxo-3-(phenylamino)-4,5,6,7-tetrahydro-1H-indol-2-yl]pyridin-2-yl-1-methyl-1H-pyrazole-4-carboxamide 6,6-dimethyl-3-(phenylamino)-2-{2-[(4-phenylbutyl)amino]pyridin-4-yl}-1,5,6,7-tetrahydro-4H-indol-4-one 6,6-dimethyl-3-(phenylamino)-2-{2-[(1,3-thiazol-5-ylmethyl)amino]pyridin-4-yl}-1,5,6,7-tetrahydro-4H-indol-4-one 2-{2-[(cyclopropylmethyl)amino]pyridin-4-yl}-6,6-dimethyl-3-(phenylamino)-1,5,6,7-tetrahydro-4H-indol-4-one 3-[4-(hydroxymethyl)pyridin-3-yl]amino-6,6-dimethyl-2-(pyridin-4-yl)-1,5,6,7-tetrahydro-4H-indol-4-one 3-[3-(hydroxymethyl)pyridin-2-yl]amino-6,6-dimethyl-2-(pyridin-4-yl)-1,5,6,7-tetrahydro-4H-indol-4-one 3-[(4-benzylphenyl)amino]-6,6-dimethyl-2-(pyridin-4-yl)-1,5,6,7-tetrahydro-4H-indol-4-one 6,6-dimethyl-3-[(4-phenoxyphenyl)amino]-2-(pyridin-4-yl)-1,5,6,7-tetrahydro-4H-indol-4-one, or an N-oxide, a salt, a tautomer or a stereoisomer of said compound, or a salt of said N-oxide, tautomer or stereoisomer.

In a further aspect of the invention compounds of formula (I) or (Ia) as described above are selected from the group consisting of:

6,6-dimethyl-3-(phenylamino)-2-(pyridin-4-yl)-1,5,6,7-tetrahydro-4H-indol-4-one 2-(3-chloropyridin-4-yl)-6,6-dimethyl-3-(phenylamino)-1,5,6,7-tetrahydro-4H-indol-4-one 6,6-dimethyl-3-[(3-methylphenyl)amino]-2-(pyridin-4-yl)-1,5,6,7-tetrahydro-4H-indol-4-one 3-[(3-chlorophenyl)amino]-6,6-dimethyl-2-(pyridin-4-yl)-1,5,6,7-tetrahydro-4H-indol-4-one 6,6-dimethyl-3-(phenylamino)-2-(pyrimidin-4-yl)-1,5,6,7-tetrahydro-4H-indol-4-one 3-[(3-fluorophenyl)amino]-6,6-dimethyl-2-(pyridin-4-yl)-1,5,6,7-tetrahydro-4H-indol-4-one 3-(phenylamino)-6-(propan-2-yl)-2-(pyridin-4-yl)-1,5,6,7-tetrahydro-4H-indol-4-one 6-phenyl-3-(phenylamino)-2-(pyridin-4-yl)-1,5,6,7-tetrahydro-4H-indol-4-one 3-(phenylamino)-2-(pyridin-4-yl)-1,5,6,7-tetrahydro-4H-indol-4-one 3-[(4-chlorophenyl)amino]-6,6-dimethyl-2-(pyridin-4-yl)-1,5,6,7-tetrahydro-4H-indol-4-one 3-[(4-fluorophenyl)amino]-6,6-dimethyl-2-(pyridin-4-yl)-1,5,6,7-tetrahydro-4H-indol-4-one 3-[(3-bromophenyl)amino]-6,6-dimethyl-2-(pyridin-4-yl)-1,5,6,7-tetrahydro-4H-indol-4-one 3'-(phenylamino)-2'-(pyridin-4-yl)-1',7'-dihydrospiro[cyclobutane-1,6'-indol]-4'(5'H)-one 3-[(3-fluoro-5-methylphenyl)amino]-6,6-dimethyl-2-(pyridin-4-yl)-1,5,6,7-tetrahydro-4H-indol-4-one 3-[(3-ethylphenyl)amino]-6,6-dimethyl-2-(pyridin-4-yl)-1,5,6,7-tetrahydro-4H-indol-4-one 6,6-dimethyl-3-[(3-nitrophenyl)amino]-2-(pyridin-4-yl)-1,5,6,7-tetrahydro-4H-indol-4-one 3-(phenylamino)-6-(propan-2-yl)-2-(pyridin-4-yl)-1,5,6,7-tetrahydro-4H-indol-4-one 3-(phenylamino)-6-(propan-2-yl)-2-(pyridin-4-yl)-1,5,6,7-tetrahydro-4H-indol-4-one 3-[(3-chloro-5-fluorophenyl)amino]-6,6-dimethyl-2-(pyridin-4-yl)-1,5,6,7-tetrahydro-4H-indol-4-one 3-(phenylamino)-2-(pyridin-4-yl)-6-(trifluoromethyl)-1,5,6,7-tetrahydro-4H-indol-4-one 3-[(3,4-difluorophenyl)amino]-6,6-dimethyl-2-(pyridin-4-yl)-1,5,6,7-tetrahydro-4H-indol-4-one 6-methyl-3-(phenylamino)-2-(pyridin-4-yl)-1,5,6,7-tetrahydro-4H-indol-4-one 3-[(3-fluorophenyl)amino]-2-(2-fluoropyridin-4-yl)-6,6-dimethyl-1,5,6,7-tetrahydro-4H-indol-4-one 6,6-dimethyl-2-(pyridin-4-yl)-3-(pyridin-2-ylamino)-1,5,6,7-tetrahydro-4H-indol-4-one 3-(1-benzofuran-6-ylamino)-6,6-dimethyl-2-(pyridin-4-yl)-1,5,6,7-tetrahydro-4H-indol-4-one 6,6-dimethyl-3-(phenylamino)-2-(1H-pyrrolo[2,3-b]pyridin-4-yl)-1,5,6,7-tetrahydro-4H-indol-4-one 6-ethyl-3-(phenylamino)-2-(pyridin-4-yl)-1,5,6,7-tetrahydro-4H-indol-4-one 6-(2-methylpropyl)-3-(phenylamino)-2-(pyridin-4-yl)-1,5,6,7-tetrahydro-4H-indol-4-one 2-(3-fluoropyridin-4-yl)-6,6-dimethyl-3-(phenylamino)-1,5,6,7-tetrahydro-4H-indol-4-one 3-[(3,5-difluorophenyl)amino]-6,6-dimethyl-2-(pyridin-4-yl)-1,5,6,7-tetrahydro-4H-indol-4-one 6,6-dimethyl-2-(pyridin-4-yl)-3-[(3,4,5-trifluorophenyl)amino]-1,5,6,7-tetrahydro-4H-indol-4-one 2-(3-chloropyridin-4-yl)-3-(phenylamino)-1,5,6,7-tetrahydro-4H-indol-4-one 6,6-dimethyl-3-(phenylamino)-2-(1H-pyrazolo[3,4-b]pyridin-4-yl)-1,5,6,7-tetrahydro-4H-indol-4-one N-{4-[6,6-dimethyl-4-oxo-3-(phenylamino)-4,5,6,7-tetrahydro-1H-indol-2-yl]pyridin-2-yl}propanamide N-{4-[6,6-dimethyl-4-oxo-3-(phenylamino)-4,5,6,7-tetrahydro-1H-indol-2-yl]pyridin-2-yl}acetamide 3'-(phenylamino)-2'-(pyridin-4-yl)-1',7'-dihydrospiro[cyclopropane-1,6'-indol]-4'(5'H)-one N-{4-[6,6-dimethyl-4-oxo-3-(phenylamino)-4,5,6,7-tetrahydro-1H-indol-2-yl]pyridin-2-yl}cyclopropanecarboxamide N-{4-[4-oxo-3-(phenylamino)-4,5,6,7-tetrahydro-1H-indol-2-yl]pyridin-2-yl}acetamide N-(4-{3-[(3-fluorophenyl)amino]-4-oxo-4,5,6,7-tetrahydro-1H-indol-2-yl}pyridin-2-yl)acetamide 3-[(3-fluorophenyl)amino]-2-(pyridin-4-yl)-1,5,6,7-tetrahydro-4H-indol-4-one 3-[(4-fluorophenyl)amino]-2-(pyridin-4-yl)-1,5,6,7-tetrahydro-4H-indol-4-one 3-[(3-fluorophenyl)amino]-2-(pyridin-4-yl)-6-(trifluoromethyl)-1,5,6,7-tetrahydro-4H-indol-4-one 2-(2-fluoropyridin-4-yl)-3-(phenylamino)-1,5,6,7-tetra-hydro-4H-indol-4-one 3-(biphenyl-3-ylamino)-6,6-dimethyl-2-(pyridin-4-yl)-1,5,6,7-tetrahydro-4H-indol-4-one 4-[6,6-dimethyl-4-oxo-3-(phenylamino)-4,5,6,7-tetrahydro-1H-indol-2-yl]pyridine-2-carbonitrile N-(4-{3-[(3-fluorophenyl)amino]-4-oxo-4,5,6,7-tetrahydro-1H-indol-2-yl}pyridin-2-yl)cyclopropanecarboxamide N-{4-[4-oxo-3-(phenylamino)-4,5,6,7-tetrahydro-1H-indol-2-yl]pyridin-2-yl}cyclopropanecarboxamide 2-(2-aminopyridin-4-yl)-3-(phenylamino)-6-(propan-2-yl)-1,5,6,7-tetrahydro-4H-indol-4-one 2-(2-aminopyridin-4-yl)-3-[(3-fluorophenyl)amino]-6-(propan-2-yl)-1,5,6,7-tetrahydro-4H-indol-4-one 6,6-dimethyl-2-(pyridin-4-yl)-3-{[3-(trifluoromethyl)phenyl]amino}-1,5,6,7-tetrahydro-4H-indol-4-one 3-[(3-methoxyphenyl)amino]-6,6-dimethyl-2-(pyridin-4-yl)-1,5,6,7-tetrahydro-4H-indol-4-one 6,6-dimethyl-3-[(2-methylphenyl)amino]-2-(pyridin-4-yl)-1,5,6,7-tetrahydro-4H-indol-4-one 6,6-dimethyl-3-[(4-methylphenyl)amino]-2-(pyridin-4-yl)-1,5,6,7-tetrahydro-4H-indol-4-one 6,6-dimethyl-3-(phenylamino)-2-(pyridazin-4-yl)-1,5,6,7-tetrahydro-4H-indol-4-one 3-[(2,3-dimethoxyphenyl)amino]-6,6-dimethyl-2-(pyridin-4-yl)-1,5,6,7-tetrahydro-4H-indol-4-one 3-[(3,4-dimethoxyphenyl)amino]-6,6-dimethyl-2-(pyridin-4-yl)-1,5,6,7-tetrahydro-4H-indol-4-one 3-[(4-methoxyphenyl)amino]-6,6-dimethyl-2-(pyridin-4-yl)-1,5,6,7-tetrahydro-4H-indol-4-one 3-[(2-fluorophenyl)amino]-6,6-dimethyl-2-(pyridin-4-yl)-1,5,6,7-tetrahydro-4H-indol-4-one 3-[(2-chlorophenyl)amino]-6,6-dimethyl-2-(pyridin-4-yl)-1,5,6,7-tetrahydro-4H-indol-4-one 3-[(2,4-dimethoxyphenyl)amino]-6,6-dimethyl-2-(pyridin-4-yl)-1,5,6,7-tetrahydro-4H-indol-4-one 6,6-dimethyl-2-(pyridin-4-yl)-3-(pyridin-3-ylamino)-1,5,6,7-tetrahydro-4H-indol-4-one 3-(isoquinolin-4-ylamino)-6,6-dimethyl-2-(pyridin-4-yl)-1,5,6,7-tetrahydro-4H-indol-4-one 3-[(3-aminophenyl)amino]-6,6-dimethyl-2-(pyridin-4-yl)-1,5,6,7-tetrahydro-4H-indol-4-one 6,6-dimethyl-2-(pyridin-4-yl)-3-(quinolin-3-ylamino)-1,5,6,7-tetrahydro-4H-indol-4-one 3-(1-benzofuran-5-ylamino)-6,6-dimethyl-2-(pyridin-4-yl)-1,5,6,7-tetrahydro-4H-indol-4-one 3-(1H-indol-6-ylamino)-6,6-dimethyl-2-(pyridin-4-yl)-1,5,6,7-tetrahydro-4H-indol-4-one 3-(1-benzothiophen-5-ylamino)-6,6-dimethyl-2-(pyridin-4-yl)-1,5,6,7-tetrahydro-4H-indol-4-one 3-(1H-indol-5-ylamino)-6,6-dimethyl-2-(pyridin-4-yl)-1,5,6,7-tetrahydro-4H-indol-4-one 3-[(2-bromophenyl)amino]-6,6-dimethyl-2-(pyridin-4-yl)-1,5,6,7-tetrahydro-4H-indol-4-one 3-[(4-bromophenyl)amino]-6,6-dimethyl-2-(pyridin-4-yl)-1,5,6,7-tetrahydro-4H-indol-4-one 3-(1H-benzimidazol-6-ylamino)-6,6-dimethyl-2-(pyridin-4-yl)-1,5,6,7-tetrahydro-4H-indol-4-one 3-(1H-indazol-6-ylamino)-6,6-dimethyl-2-(pyridin-4-yl)-1,5,6,7-tetrahydro-4H-indol-4-one 6,6-dimethyl-2-(pyridin-4-yl)-3-(quinolin-4-ylamino)-1,5,6,7-tetrahydro-4H-indol-4-one 3-[(2,5-dimethoxyphenyl)amino]-6,6-dimethyl-2-(pyridin-4-yl)-1,5,6,7-tetrahydro-4H-indol-4-one 3-[(3,5-dichlorophenyl)amino]-6,6-dimethyl-2-(pyridin-4-yl)-1,5,6,7-tetrahydro-4H-indol-4-one 3-[(2,5-dichlorophenyl)amino]-6,6-dimethyl-2-(pyridin-4-yl)-1,5,6,7-tetrahydro-4H-indol-4-one 3-{[6,6-dimethyl-4-oxo-2-(pyridin-4-yl)-4,5,6,7-tetrahydro-1H-indol-3-yl]amino}benzonitrile 3-{[3-(benzyloxy)phenyl]amino}-6,6-dimethyl-2-(pyridin-4-yl)-1,5,6,7-tetrahydro-4H-indol-4-one 3-[(4-fluoro-3-methylphenyl)amino]-6,6-dimethyl-2-(pyridin-4-yl)-1,5,6,7-tetrahydro-4H-indol-4-one 3-[(2-fluoro-5-methylphenyl)amino]-6,6-dimethyl-2-(pyridin-4-yl)-1,5,6,7-tetrahydro-4H-indol-4-one 3-[(4-ethylphenyl)amino]-6,6-dimethyl-2-(pyridin-4-yl)-1,5,6,7-tetrahydro-4H-indol-4-one 3-[(2-ethylphenyl)amino]-6,6-dimethyl-2-(pyridin-4-yl)-1,5,6,7-tetrahydro-4H-indol-4-one 6,6-dimethyl-3-{[3-(propan-2-yl)phenyl]amino}-2-(pyridin-4-yl)-1,5,6,7-tetrahydro-4H-indol-4-one 6,6-dimethyl-3-{[4-(propan-2-yl)phenyl]amino}-2-(pyridin-4-yl)-1,5,6,7-tetrahydro-4H-indol-4-one 3-[(5-chloro-2-fluorophenyl)amino]-6,6-dimethyl-2-(pyridin-4-yl)-1,5,6,7-tetrahydro-4H-indol-4-one 6,6-dimethyl-3-{[2-(propan-2-yl)phenyl]amino}-2-(pyridin-4-yl)-1,5,6,7-tetrahydro-4H-indol-4-one 3-[(3-hydroxyphenyl)amino]-6,6-dimethyl-2-(pyridin-4-yl)-1,5,6,7-tetrahydro-4H-indol-4-one 6,6-dimethyl-3-[(4-nitrophenyl)amino]-2-(pyridin-4-yl)-1,5,6,7-tetrahydro-4H-indol-4-one 3-[(3-chloro-2-methylphenyl)amino]-6,6-dimethyl-2-(pyridin-4-yl)-1,5,6,7-tetrahydro-4H-indol-4-one 3-[(3-chloro-4-methylphenyl)amino]-6,6-dimethyl-2-(pyridin-4-yl)-1,5,6,7-tetrahydro-4H-indol-4-one 3-[(5-chloro-2-methylphenyl)amino]-6,6-dimethyl-2-(pyridin-4-yl)-1,5,6,7-tetrahydro-4H-indol-4-one 3-[(3-chloro-2-fluorophenyl)amino]-6,6-dimethyl-2-(pyridin-4-yl)-1,5,6,7-tetrahydro-4H-indol-4-one 3-[(3-chloro-4-fluorophenyl)amino]-6,6-dimethyl-2-(pyridin-4-yl)-1,5,6,7-tetrahydro-4H-indol-4-one 3-[(2-fluoro-3-methylphenyl)amino]-6,6-dimethyl-2-(pyridin-4-yl)-1,5,6,7-tetrahydro-4H-indol-4-one N-(3-{[6,6-dimethyl-4-oxo-2-(pyridin-4-yl)-4,5,6,7-tetrahydro-1H-indol-3-yl]amino}phenyl)-2-methylpropanamide N-(3-{[6,6-dimethyl-4-oxo-2-(pyridin-4-yl)-4,5,6,7-tetrahydro-1H-indol-3-yl]amino}phenyl)propanamide 3-{[6,6-dimethyl-4-oxo-2-(pyridin-4-yl)-4,5,6,7-tetrahydro-1H-indol-3-yl]amino}-N-methylbenzamide 3-(1H-indazol-5-ylamino)-6,6-dimethyl-2-(pyridin-4-yl)-1,5,6,7-tetrahydro-4H-indol-4-one 3-{[6,6-dimethyl-4-oxo-2-(pyridin-4-yl)-4,5,6,7-tetrahydro-1H-indol-3-yl]amino}benzamide N-(3-{[6,6-dimethyl-4-oxo-2-(pyridin-4-yl)-4,5,6,7-tetrahydro-1H-indol-3-yl]amino}phenyl)butanamide 2-(2-chloropyridin-4-yl)-6,6-dimethyl-3-(phenylamino)-1,5,6,7-tetrahydro-4H-indol-4-one 3-[(3-ethoxyphenyl)amino]-6,6-dimethyl-2-(pyridin-4-yl)-1,5,6,7-tetrahydro-4H-indol-4-one 6,6-dimethyl-3-{[3-(propan-2-yloxy)phenyl]amino}-2-(pyridin-4-yl)-1,5,6,7-tetrahydro-4H-indol-4-one 3-{[3-(2-hydroxyethoxy)phenyl]amino}-6,6-dimethyl-2-(pyridin-4-yl)-1,5,6,7-tetrahydro-4H-indol-4-one 6,6-dimethyl-2-(pyridin-4-yl)-3-{[3-(trifluoromethoxy)phenyl]amino}-1,5,6,7-tetrahydro-4H-indol-4-one 6,6-dimethyl-3-[(3-propoxyphenyl)amino]-2-(pyridin-4-yl)-1,5,6,7-tetrahydro-4H-indol-4-one N-(3-{[6,6-dimethyl-4-oxo-2-(pyridin-4-yl)-4,5,6,7-tetrahydro-1H-indol-3-yl]amino}phenyl)acetamide 3-[(4-fluoro-3-methoxyphenyl)amino]-6,6-dimethyl-2-(pyridin-4-yl)-1,5,6,7-tetrahydro-4H-indol-4-one 3-{[4-fluoro-3-(hydroxymethyl)phenyl]amino}-6,6-dimethyl-2-(pyridin-4-yl)-1,5,6,7-tetrahydro-4H-indol-4-one
3-{[3-(1-hydroxyethyl)phenyl]amino}-6,6-dimethyl-2-(pyridin-4-yl)-1,5,6,7-tetrahydro-4H-indol-4-one
3-[(3-acetylphenyl)amino]-6,6-dimethyl-2-(pyridin-4-yl)-1,5,6,7-tetrahydro-4H-indol-4-one
3-[(3-tert-butylphenyl)amino]-6,6-dimethyl-2-(pyridin-4-yl)-1,5,6,7-tetrahydro-4H-indol-4-one
3-{[3-(difluoromethoxy)phenyl]amino}-6,6-dimethyl-2-(pyridin-4-yl)-1,5,6,7-tetrahydro-4H-indol-4-one
tert-butyl 3-{[6,6-dimethyl-4-oxo-2-(pyridin-4-yl)-4,5,6,7-tetrahydro-1H-indol-3-yl]amino}benzoate
3-{[3-(1,3-dioxolan-2-yl)phenyl]amino}-6,6-dimethyl-2-(pyridin-4-yl)-1,5,6,7-tetrahydro-4H-indol-4-one
3-[(4-fluoro-2-methoxyphenyl)amino]-6,6-dimethyl-2-(pyridin-4-yl)-1,5,6,7-tetrahydro-4H-indol-4-one
2-(2-aminopyridin-4-yl)-6,6-dimethyl-3-(phenylamino)-1,5,6,7-tetrahydro-4H-indol-4-one
3-[(3-fluorophenyl)amino]-2-{2-[(3-fluorophenyl)amino]pyridin-4-yl}-6,6-dimethyl-1,5,6,7-tetrahydro-4H-indol-4-one
3-[(2-methoxyphenyl)amino]-6,6-dimethyl-2-(pyridin-4-yl)-1,5,6,7-tetrahydro-4H-indol-4-one
3-[(2-ethoxy-4-fluorophenyl)amino]-6,6-dimethyl-2-(pyridin-4-yl)-1,5,6,7-tetrahydro-4H-indol-4-one
6,6-dimethyl-3-(phenylamino)-2-[2-(pyrrolidin-1-yl)pyridin-4-yl]-1,5,6,7-tetrahydro-4H-indol-4-one
6,6-dimethyl-2-[2-(morpholin-4-yl)pyridin-4-yl]-3-(phenylamino)-1,5,6,7-tetrahydro-4H-indol-4-one
3-[(2-ethoxyphenyl)amino]-6,6-dimethyl-2-(pyridin-4-yl)-1,5,6,7-tetrahydro-4H-indol-4-one
3-{[4-fluoro-3-(trifluoromethyl)phenyl]amino}-6,6-dimethyl-2-(pyridin-4-yl)-1,5,6,7-tetrahydro-4H-indol-4-one
3-(1-benzothiophen-6-ylamino)-6,6-dimethyl-2-(pyridin-4-yl)-1,5,6,7-tetrahydro-4H-indol-4-one
6,6-dimethyl-2-(3-methylpyridin-4-yl)-3-(phenylamino)-1,5,6,7-tetrahydro-4H-indol-4-one
N-{4-[6,6-dimethyl-4-oxo-3-(phenylamino)-4,5,6,7-tetrahydro-1H-indol-2-yl]pyridin-2-yl}-2-methylpropanamide
N-acetyl-N-{4-[6,6-dimethyl-4-oxo-3-(phenylamino)-4,5,6,7-tetrahydro-1H-indol-2-yl]pyridin-2-yl}acetamide
3-[(3,4-difluorophenyl)amino]-2-(pyridin-4-yl)-1,5,6,7-tetrahydro-4H-indol-4-one
2-(3,5-difluoropyridin-4-yl)-6,6-dimethyl-3-(phenylamino)-1,5,6,7-tetrahydro-4H-indol-4-one
2-(3,5-difluoropyridin-4-yl)-3-[(3-fluorophenyl)amino]-1,5,6,7-tetrahydro-4H-indol-4-one
2-(2-bromopyridin-4-yl)-6,6-dimethyl-3-(phenylamino)-1,5,6,7-tetrahydro-4H-indol-4-one
2-(2-aminopyridin-4-yl)-3-[(3-fluorophenyl)amino]-1,5,6,7-tetrahydro-4H-indol-4-one
2-(2-aminopyridin-4-yl)-3-(phenylamino)-1,5,6,7-tetrahydro-4H-indol-4-one
2-(3-chloropyridin-4-yl)-3-[(4-fluorophenyl)amino]-1,5,6,7-tetrahydro-4H-indol-4-one
2-(2-methylpyridin-4-yl)-3-(phenylamino)-1,5,6,7-tetrahydro-4H-indol-4-one
3-{[6,6-dimethyl-4-oxo-2-(pyridin-4-yl)-4,5,6,7-tetrahydro-1H-indol-3-yl]amino}-N-ethylbenzamide
6,6-dimethyl-2-[2-(methylamino)pyridin-4-yl]-3-(phenylamino)-1,5,6,7-tetrahydro-4H-indol-4-one
2-{[6,6-dimethyl-4-oxo-2-(pyridin-4-yl)-4,5,6,7-tetrahydro-1H-indol-3-yl]amino}benzonitrile
5-{[6,6-dimethyl-4-oxo-2-(pyridin-4-yl)-4,5,6,7-tetrahydro-1H-indol-3-yl]amino}-2-fluorobenzonitrile
3-{[4-fluoro-3-(trifluoromethoxy)phenyl]amino}-6,6-dimethyl-2-(pyridin-4-yl)-1,5,6,7-tetrahydro-4H-indol-4-one
6,6-dimethyl-2-(2-methylpyridin-4-yl)-3-(phenylamino)-1,5,6,7-tetrahydro-4H-indol-4-one
2-(2-methoxypyridin-4-yl)-3-(phenylamino)-1,5,6,7-tetrahydro-4H-indol-4-one
2-(2-bromopyridin-4-yl)-3-(phenylamino)-1,5,6,7-tetrahydro-4H-indol-4-one
6,6-dimethyl-3-{[3-(2-methyl-1,3-dioxolan-2-yl)phenyl]amino}-2-(pyridin-4-yl)-1,5,6,7-tetrahydro-4H-indol-4-one
3-{[3-(1-hydroxypropyl)phenyl]amino}-6,6-dimethyl-2-(pyridin-4-yl)-1,5,6,7-tetrahydro-4H-indol-4-one
6,6-dimethyl-2-(pyridin-4-yl)-3-{[3-(2,2,2-trifluoro-1-hydroxyethyl)phenyl]amino}-1,5,6,7-tetrahydro-4H-indol-4-one
3-{[3-(1-methoxyethyl)phenyl]amino}-6,6-dimethyl-2-(pyridin-4-yl)-1,5,6,7-tetrahydro-4H-indol-4-one
6,6-dimethyl-3-(naphthalen-1-ylamino)-2-(pyridin-4-yl)-1,5,6,7-tetrahydro-4H-indol-4-one
6,6-dimethyl-3-(naphthalen-2-ylamino)-2-(pyridin-4-yl)-1,5,6,7-tetrahydro-4H-indol-4-one
6,6-dimethyl-3-[(2-phenoxyphenyl)amino]-2-(pyridin-4-yl)-1,5,6,7-tetrahydro-4H-indol-4-one
3-(biphenyl-2-ylamino)-6,6-dimethyl-2-(pyridin-4-yl)-1,5,6,7-tetrahydro-4H-indol-4-one
N-(cyclopropylcarbonyl)-N-(4-{3-[(3-fluorophenyl)amino]-4-oxo-4,5,6,7-tetrahydro-1H-indol-2-yl}pyridin-2-yl)cyclopropanecarboxamide
N-(cyclopropylcarbonyl)-N-{4-[4-oxo-3-(phenylamino)-4,5,6,7-tetrahydro-1H-indol-2-yl]pyridin-2-yl}cyclopropanecarboxamide
N-{4-[6,6-dimethyl-4-oxo-3-(phenylamino)-4,5,6,7-tetrahydro-1H-indol-2-yl]pyridin-2-yl}methanesulfonamide
N-{4-[6,6-dimethyl-4-oxo-3-(phenylamino)-4,5,6,7-tetrahydro-1H-indol-2-yl]pyridin-2-yl}-2,2-difluoroacetamide
2-(2-aminopyridin-4-yl)-3-[(4-fluorophenyl)amino]-6-(propan-2-yl)-1,5,6,7-tetrahydro-4H-indol-4-one
N-{4-[4-oxo-3-(phenylamino)-4,5,6,7-tetrahydro-1H-indol-2-yl]pyridin-2-yl}methanesulfonamide,
or an N-oxide, a salt, a tautomer or a stereoisomer of said compound, or a salt of said N-oxide, tautomer or stereoisomer.

In one aspect of the invention compounds of formula (I) or (Ia) as described above are selected from the group consisting of:
6,6-dimethyl-3-(phenylamino)-2-(pyridin-4-yl)-1,5,6,7-tetrahydro-4H-indol-4-one
2-(3-chloropyridin-4-yl)-6,6-dimethyl-3-(phenylamino)-1,5,6,7-tetrahydro-4H-indol-4-one
6,6-dimethyl-3-[(3-methylphenyl)amino]-2-(pyridin-4-yl)-1,5,6,7-tetrahydro-4H-indol-4-one
3-[(3-chlorophenyl)amino]-6,6-dimethyl-2-(pyridin-4-yl)-1,5,6,7-tetrahydro-4H-indol-4-one
6,6-dimethyl-3-(phenylamino)-2-(pyrimidin-4-yl)-1,5,6,7-tetrahydro-4H-indol-4-one
3-[(3-fluorophenyl)amino]-6,6-dimethyl-2-(pyridin-4-yl)-1,5,6,7-tetrahydro-4H-indol-4-one
3-(phenylamino)-6-(propan-2-yl)-2-(pyridin-4-yl)-1,5,6,7-tetrahydro-4H-indol-4-one
6-phenyl-3-(phenylamino)-2-(pyridin-4-yl)-1,5,6,7-tetrahydro-4H-indol-4-one
3-(phenylamino)-2-(pyridin-4-yl)-1,5,6,7-tetrahydro-4H-indol-4-one
3-[(4-chlorophenyl)amino]-6,6-dimethyl-2-(pyridin-4-yl)-1,5,6,7-tetrahydro-4H-indol-4-one 3-[(4-fluorophenyl)amino]-6,6-dimethyl-2-(pyridin-4-yl)-1,5,6,7-tetrahydro-4H-indol-4-one
3-[(3-bromophenyl)amino]-6,6-dimethyl-2-(pyridin-4-yl)-1,5,6,7-tetrahydro-4H-indol-4-one
3'-(phenylamino)-2'-(pyridin-4-yl)-1',7'-dihydrospiro[cyclobutane-1,6'-indol]-4'(5'H)-one
3-[(3-fluoro-5-methylphenyl)amino]-6,6-dimethyl-2-(pyridin-4-yl)-1,5,6,7-tetrahydro-4H-indol-4-one
3-[(3-ethylphenyl)amino]-6,6-dimethyl-2-(pyridin-4-yl)-1,5,6,7-tetrahydro-4H-indol-4-one
6,6-dimethyl-3-[(3-nitrophenyl)amino]-2-(pyridin-4-yl)-1,5,6,7-tetrahydro-4H-indol-4-one
3-(phenylamino)-6-(propan-2-yl)-2-(pyridin-4-yl)-1,5,6,7-tetrahydro-4H-indol-4-one
3-(phenylamino)-6-(propan-2-yl)-2-(pyridin-4-yl)-1,5,6,7-tetrahydro-4H-indol-4-one
3-[(3-chloro-5-fluorophenyl)amino]-6,6-dimethyl-2-(pyridin-4-yl)-1,5,6,7-tetrahydro-4H-indol-4-one
3-(phenylamino)-2-(pyridin-4-yl)-6-(trifluoromethyl)-1,5,6,7-tetrahydro-4H-indol-4-one
3-[(3,4-difluorophenyl)amino]-6,6-dimethyl-2-(pyridin-4-yl)-1,5,6,7-tetrahydro-4H-indol-4-one
6-methyl-3-(phenylamino)-2-(pyridin-4-yl)-1,5,6,7-tetrahydro-4H-indol-4-one
3-[(3-fluorophenyl)amino]-2-(2-fluoropyridin-4-yl)-6,6-dimethyl-1,5,6,7-tetrahydro-4H-indol-4-one
6,6-dimethyl-3-(phenylamino)-2-(1H-pyrrolo[2,3-b]pyridin-4-yl)-1,5,6,7-tetrahydro-4H-indol-4-one
6-ethyl-3-(phenylamino)-2-(pyridin-4-yl)-1,5,6,7-tetrahydro-4H-indol-4-one
6-(2-methylpropyl)-3-(phenylamino)-2-(pyridin-4-yl)-1,5,6,7-tetrahydro-4H-indol-4-one
2-(3-fluoropyridin-4-yl)-6,6-dimethyl-3-(phenylamino)-1,5,6,7-tetrahydro-4H-indol-4-one
3-[(3,5-difluorophenyl)amino]-6,6-dimethyl-2-(pyridin-4-yl)-1,5,6,7-tetrahydro-4H-indol-4-one
6,6-dimethyl-2-(pyridin-4-yl)-3-[(3,4,5-trifluorophenyl)amino]-1,5,6,7-tetrahydro-4H-indol-4-one
2-(3-chloropyridin-4-yl)-3-(phenylamino)-1,5,6,7-tetrahydro-4H-indol-4-one
6,6-dimethyl-3-(phenylamino)-2-(1H-pyrazolo[3,4-b]pyridin-4-yl)-1,5,6,7-tetrahydro-4H-indol-4-one
N-{4-[6,6-dimethyl-4-oxo-3-(phenylamino)-4,5,6,7-tetrahydro-1H-indol-2-yl]pyridin-2-yl}propanamide
N-{4-[6,6-dimethyl-4-oxo-3-(phenylamino)-4,5,6,7-tetrahydro-1H-indol-2-yl]pyridin-2-yl}acetamide
3'-(phenylamino)-2'-(pyridin-4-yl)-1',7'-dihydrospiro[cyclopropane-1,6'-indol]-4'(5'H)-one
N-{4-[6,6-dimethyl-4-oxo-3-(phenylamino)-4,5,6,7-tetrahydro-1H-indol-2-yl]pyridin-2-yl}cyclopropanecarboxamide
N-{4-[4-oxo-3-(phenylamino)-4,5,6,7-tetrahydro-1H-indol-2-yl]pyridin-2-yl}acetamide
N-(4-{3-[(3-fluorophenyl)amino]-4-oxo-4,5,6,7-tetrahydro-1H-indol-2-yl}pyridin-2-yl)acetamide
3-[(3-fluorophenyl)amino]-2-(pyridin-4-yl)-1,5,6,7-tetrahydro-4H-indol-4-one
3-[(4-fluorophenyl)amino]-2-(pyridin-4-yl)-1,5,6,7-tetrahydro-4H-indol-4-one
3-[(3-fluorophenyl)amino]-2-(pyridin-4-yl)-6-(trifluoromethyl)-1,5,6,7-tetrahydro-4H-indol-4-one
2-(2-fluoropyridin-4-yl)-3-(phenylamino)-1,5,6,7-tetrahydro-4H-indol-4-one
3-(biphenyl-3-ylamino)-6,6-dimethyl-2-(pyridin-4-yl)-1,5,6,7-tetrahydro-4H-indol-4-one
4-[6,6-dimethyl-4-oxo-3-(phenylamino)-4,5,6,7-tetrahydro-1H-indol-2-yl]pyridine-2-carbonitrile
N-(4-{3-[(3-fluorophenyl)amino]-4-oxo-4,5,6,7-tetrahydro-1H-indol-2-yl}pyridin-2-yl)cyclopropanecarboxamide
N-{4-[4-oxo-3-(phenylamino)-4,5,6,7-tetrahydro-1H-indol-2-yl]pyridin-2-yl}cyclopropanecarboxamide
2-(2-aminopyridin-4-yl)-3-(phenylamino)-6-(propan-2-yl)-1,5,6,7-tetrahydro-4H-indol-4-one
2-(2-aminopyridin-4-yl)-3-[(3-fluorophenyl)amino]-6-(propan-2-yl)-1,5,6,7-tetrahydro-4H-indol-4-one
6,6-dimethyl-2-(pyridin-4-yl)-3-{[3-(trifluoromethyl)phenyl]amino}-1,5,6,7-tetrahydro-4H-indol-4-one
3-[(3-methoxyphenyl)amino]-6,6-dimethyl-2-(pyridin-4-yl)-1,5,6,7-tetrahydro-4H-indol-4-one
6,6-dimethyl-3-[(2-methylphenyl)amino]-2-(pyridin-4-yl)-1,5,6,7-tetrahydro-4H-indol-4-one
6,6-dimethyl-3-[(4-methylphenyl)amino]-2-(pyridin-4-yl)-1,5,6,7-tetrahydro-4H-indol-4-one
6,6-dimethyl-3-(phenylamino)-2-(pyridazin-4-yl)-1,5,6,7-tetrahydro-4H-indol-4-one
3-[(2,3-dimethoxyphenyl)amino]-6,6-dimethyl-2-(pyridin-4-yl)-1,5,6,7-tetrahydro-4H-indol-4-one
3-[(3,4-dimethoxyphenyl)amino]-6,6-dimethyl-2-(pyridin-4-yl)-1,5,6,7-tetrahydro-4H-indol-4-one
3-[(4-methoxyphenyl)amino]-6,6-dimethyl-2-(pyridin-4-yl)-1,5,6,7-tetrahydro-4H-indol-4-one
3-[(2-fluorophenyl)amino]-6,6-dimethyl-2-(pyridin-4-yl)-1,5,6,7-tetrahydro-4H-indol-4-one
3-[(2-chlorophenyl)amino]-6,6-dimethyl-2-(pyridin-4-yl)-1,5,6,7-tetrahydro-4H-indol-4-one
3-[(2,4-dimethoxyphenyl)amino]-6,6-dimethyl-2-(pyridin-4-yl)-1,5,6,7-tetrahydro-4H-indol-4-one
3-[(3-aminophenyl)amino]-6,6-dimethyl-2-(pyridin-4-yl)-1,5,6,7-tetrahydro-4H-indol-4-one
3-[(2-bromophenyl)amino]-6,6-dimethyl-2-(pyridin-4-yl)-1,5,6,7-tetrahydro-4H-indol-4-one
3-[(4-bromophenyl)amino]-6,6-dimethyl-2-(pyridin-4-yl)-1,5,6,7-tetrahydro-4H-indol-4-one
3-[(2,5-dimethoxyphenyl)amino]-6,6-dimethyl-2-(pyridin-4-yl)-1,5,6,7-tetrahydro-4H-indol-4-one
3-[(3,5-dichlorophenyl)amino]-6,6-dimethyl-2-(pyridin-4-yl)-1,5,6,7-tetrahydro-4H-indol-4-one
3-[(2,5-dichlorophenyl)amino]-6,6-dimethyl-2-(pyridin-4-yl)-1,5,6,7-tetrahydro-4H-indol-4-one
3-{[6,6-dimethyl-4-oxo-2-(pyridin-4-yl)-4,5,6,7-tetrahydro-1H-indol-3-yl]amino}benzonitrile
3-{[3-(benzyloxy)phenyl]amino}-6,6-dimethyl-2-(pyridin-4-yl)-1,5,6,7-tetrahydro-4H-indol-4-one
3-[(4-fluoro-3-methylphenyl)amino]-6,6-dimethyl-2-(pyridin-4-yl)-1,5,6,7-tetrahydro-4H-indol-4-one
3-[(2-fluoro-5-methylphenyl)amino]-6,6-dimethyl-2-(pyridin-4-yl)-1,5,6,7-tetrahydro-4H-indol-4-one
3-[(4-ethylphenyl)amino]-6,6-dimethyl-2-(pyridin-4-yl)-1,5,6,7-tetrahydro-4H-indol-4-one
3-[(2-ethylphenyl)amino]-6,6-dimethyl-2-(pyridin-4-yl)-1,5,6,7-tetrahydro-4H-indol-4-one
6,6-dimethyl-3-{[3-(propan-2-yl)phenyl]amino}-2-(pyridin-4-yl)-1,5,6,7-tetrahydro-4H-indol-4-one
6,6-dimethyl-3-{[4-(propan-2-yl)phenyl]amino}-2-(pyridin-4-yl)-1,5,6,7-tetrahydro-4H-indol-4-one
3-[(5-chloro-2-fluorophenyl)amino]-6,6-dimethyl-2-(pyridin-4-yl)-1,5,6,7-tetrahydro-4H-indol-4-one
6,6-dimethyl-3-{[2-(propan-2-yl)phenyl]amino}-2-(pyridin-4-yl)-1,5,6,7-tetrahydro-4H-indol-4-one
3-[(3-hydroxyphenyl)amino]-6,6-dimethyl-2-(pyridin-4-yl)-1,5,6,7-tetrahydro-4H-indol-4-one
6,6-dimethyl-3-[(4-nitrophenyl)amino]-2-(pyridin-4-yl)-1,5,6,7-tetrahydro-4H-indol-4-one 3-[(3-chloro-2-methylphenyl)amino]-6,6-dimethyl-2-(pyridin-4-yl)-1,5,6,7-tetrahydro-4H-indol-4-one
3-[(3-chloro-4-methylphenyl)amino]-6,6-dimethyl-2-(pyridin-4-yl)-1,5,6,7-tetrahydro-4H-indol-4-one
3-[(5-chloro-2-methylphenyl)amino]-6,6-dimethyl-2-(pyridin-4-yl)-1,5,6,7-tetrahydro-4H-indol-4-one
3-[(3-chloro-2-fluorophenyl)amino]-6,6-dimethyl-2-(pyridin-4-yl)-1,5,6,7-tetrahydro-4H-indol-4-one
3-[(3-chloro-4-fluorophenyl)amino]-6,6-dimethyl-2-(pyridin-4-yl)-1,5,6,7-tetrahydro-4H-indol-4-one
3-[(2-fluoro-3-methylphenyl)amino]-6,6-dimethyl-2-(pyridin-4-yl)-1,5,6,7-tetrahydro-4H-indol-4-one
N-(3-{[6,6-dimethyl-4-oxo-2-(pyridin-4-yl)-4,5,6,7-tetrahydro-1H-indol-3-yl]amino}phenyl)-2-methylpropanamide
N-(3-{[6,6-dimethyl-4-oxo-2-(pyridin-4-yl)-4,5,6,7-tetrahydro-1H-indol-3-yl]amino}phenyl)propanamide
3-{[6,6-dimethyl-4-oxo-2-(pyridin-4-yl)-4,5,6,7-tetrahydro-1H-indol-3-yl]amino}-N-methylbenzamide
3-{[6,6-dimethyl-4-oxo-2-(pyridin-4-yl)-4,5,6,7-tetrahydro-1H-indol-3-yl]amino}benzamide
N-(3-{[6,6-dimethyl-4-oxo-2-(pyridin-4-yl)-4,5,6,7-tetrahydro-1H-indol-3-yl]amino}phenyl)butanamide
2-(2-chloropyridin-4-yl)-6,6-dimethyl-3-(phenylamino)-1,5,6,7-tetrahydro-4H-indol-4-one
3-[(3-ethoxyphenyl)amino]-6,6-dimethyl-2-(pyridin-4-yl)-1,5,6,7-tetrahydro-4H-indol-4-one
6,6-dimethyl-3-{[3-(propan-2-yloxy)phenyl]amino}-2-(pyridin-4-yl)-1,5,6,7-tetrahydro-4H-indol-4-one
3-{[3-(2-hydroxyethoxy)phenyl]amino}-6,6-dimethyl-2-(pyridin-4-yl)-1,5,6,7-tetrahydro-4H-indol-4-one
6,6-dimethyl-2-(pyridin-4-yl)-3-{[3-(trifluoromethoxy)phenyl]amino}-1,5,6,7-tetrahydro-4H-indol-4-one
6,6-dimethyl-3-[(3-propoxyphenyl)amino]-2-(pyridin-4-yl)-1,5,6,7-tetrahydro-4H-indol-4-one
N-(3-{[6,6-dimethyl-4-oxo-2-(pyridin-4-yl)-4,5,6,7-tetrahydro-1H-indol-3-yl]amino}phenyl)acetamide
3-[(4-fluoro-3-methoxyphenyl)amino]-6,6-dimethyl-2-(pyridin-4-yl)-1,5,6,7-tetrahydro-4H-indol-4-one
3-{[4-fluoro-3-(hydroxymethyl)phenyl]amino}-6,6-dimethyl-2-(pyridin-4-yl)-1,5,6,7-tetrahydro-4H-indol-4-one
3-{[3-(1-hydroxyethyl)phenyl]amino}-6,6-dimethyl-2-(pyridin-4-yl)-1,5,6,7-tetrahydro-4H-indol-4-one
3-[(3-acetylphenyl)amino]-6,6-dimethyl-2-(pyridin-4-yl)-1,5,6,7-tetrahydro-4H-indol-4-one
3-[(3-tert-butylphenyl)amino]-6,6-dimethyl-2-(pyridin-4-yl)-1,5,6,7-tetrahydro-4H-indol-4-one
3-{[3-(difluoromethoxy)phenyl]amino}-6,6-dimethyl-2-(pyridin-4-yl)-1,5,6,7-tetrahydro-4H-indol-4-one
tert-butyl 3-{[6,6-dimethyl-4-oxo-2-(pyridin-4-yl)-4,5,6,7-tetrahydro-1H-indol-3-yl]amino}benzoate
3-{[3-(1,3-dioxolan-2-yl)phenyl]amino}-6,6-dimethyl-2-(pyridin-4-yl)-1,5,6,7-tetrahydro-4H-indol-4-one
3-[(4-fluoro-2-methoxyphenyl)amino]-6,6-dimethyl-2-(pyridin-4-yl)-1,5,6,7-tetrahydro-4H-indol-4-one
2-(2-aminopyridin-4-yl)-6,6-dimethyl-3-(phenylamino)-1,5,6,7-tetrahydro-4H-indol-4-one
3-[(3-fluorophenyl)amino]-2-{2-[(3-fluorophenyl)amino]pyridin-4-yl}-6,6-dimethyl-1,5,6,7-tetrahydro-4H-indol-4-one
3-[(2-methoxyphenyl)amino]-6,6-dimethyl-2-(pyridin-4-yl)-1,5,6,7-tetrahydro-4H-indol-4-one
3-[(2-ethoxy-4-fluorophenyl)amino]-6,6-dimethyl-2-(pyridin-4-yl)-1,5,6,7-tetrahydro-4H-indol-4-one
6,6-dimethyl-3-(phenylamino)-2-[2-(pyrrolidin-1-yl)pyridin-4-yl]-1,5,6,7-tetrahydro-4H-indol-4-one
6,6-dimethyl-2-[2-(morpholin-4-yl)pyridin-4-yl]-3-(phenylamino)-1,5,6,7-tetrahydro-4H-indol-4-one
3-[(2-ethoxyphenyl)amino]-6,6-dimethyl-2-(pyridin-4-yl)-1,5,6,7-tetrahydro-4H-indol-4-one
3-{[4-fluoro-3-(trifluoromethyl)phenyl]amino}-6,6-dimethyl-2-(pyridin-4-yl)-1,5,6,7-tetrahydro-4H-indol-4-one
6,6-dimethyl-2-(3-methylpyridin-4-yl)-3-(phenylamino)-1,5,6,7-tetrahydro-4H-indol-4-one
N-{4-[6,6-dimethyl-4-oxo-3-(phenylamino)-4,5,6,7-tetrahydro-1H-indol-2-yl]pyridin-2-yl}-2-methylpropanamide
N-acetyl-N-{4-[6,6-dimethyl-4-oxo-3-(phenylamino)-4,5,6,7-tetrahydro-1H-indol-2-yl]pyridin-2-yl}acetamide
3-[(3,4-difluorophenyl)amino]-2-(pyridin-4-yl)-1,5,6,7-tetrahydro-4H-indol-4-one
2-(3,5-difluoropyridin-4-yl)-6,6-dimethyl-3-(phenylamino)-1,5,6,7-tetrahydro-4H-indol-4-one
2-(3,5-difluoropyridin-4-yl)-3-[(3-fluorophenyl)amino]-1,5,6,7-tetrahydro-4H-indol-4-one
2-(2-bromopyridin-4-yl)-6,6-dimethyl-3-(phenylamino)-1,5,6,7-tetrahydro-4H-indol-4-one
2-(2-aminopyridin-4-yl)-3-[(3-fluorophenyl)amino]-1,5,6,7-tetrahydro-4H-indol-4-one
2-(2-aminopyridin-4-yl)-3-(phenylamino)-1,5,6,7-tetrahydro-4H-indol-4-one
2-(3-chloropyridin-4-yl)-3-[(4-fluorophenyl)amino]-1,5,6,7-tetrahydro-4H-indol-4-one
2-(2-methylpyridin-4-yl)-3-(phenylamino)-1,5,6,7-tetrahydro-4H-indol-4-one
3-{[6,6-dimethyl-4-oxo-2-(pyridin-4-yl)-4,5,6,7-tetrahydro-1H-indol-3-yl]amino}-N-ethylbenzamide
6,6-dimethyl-2-[2-(methylamino)pyridin-4-yl]-3-(phenylamino)-1,5,6,7-tetrahydro-4H-indol-4-one
2-{[6,6-dimethyl-4-oxo-2-(pyridin-4-yl)-4,5,6,7-tetrahydro-1H-indol-3-yl]amino}benzonitrile
5-{[6,6-dimethyl-4-oxo-2-(pyridin-4-yl)-4,5,6,7-tetrahydro-1H-indol-3-yl]amino}-2-fluorobenzonitrile
3-{[4-fluoro-3-(trifluoromethoxy)phenyl]amino}-6,6-dimethyl-2-(pyridin-4-yl)-1,5,6,7-tetrahydro-4H-indol-4-one
6,6-dimethyl-2-(2-methylpyridin-4-yl)-3-(phenylamino)-1,5,6,7-tetrahydro-4H-indol-4-one
2-(2-methoxypyridin-4-yl)-3-(phenylamino)-1,5,6,7-tetrahydro-4H-indol-4-one
2-(2-bromopyridin-4-yl)-3-(phenylamino)-1,5,6,7-tetrahydro-4H-indol-4-one
6,6-dimethyl-3-{[3-(2-methyl-1,3-dioxolan-2-yl)phenyl]amino}-2-(pyridin-4-yl)-1,5,6,7-tetrahydro-4H-indol-4-one
3-{[3-(1-hydroxypropyl)phenyl]amino}-6,6-dimethyl-2-(pyridin-4-yl)-1,5,6,7-tetrahydro-4H-indol-4-one
6,6-dimethyl-2-(pyridin-4-yl)-3-{[3-(2,2,2-trifluoro-1-hydroxyethyl)phenyl]amino}-1,5,6,7-tetrahydro-4H-indol-4-one
3-{[3-(1-methoxyethyl)phenyl]amino}-6,6-dimethyl-2-(pyridin-4-yl)-1,5,6,7-tetrahydro-4H-indol-4-one
6,6-dimethyl-3-[(2-phenoxyphenyl)amino]-2-(pyridin-4-yl)-1,5,6,7-tetrahydro-4H-indol-4-one
3-(biphenyl-2-ylamino)-6,6-dimethyl-2-(pyridin-4-yl)-1,5,6,7-tetrahydro-4H-indol-4-one
N-(cyclopropylcarbonyl)-N-(4-{3-[(3-fluorophenyl)amino]-4-oxo-4,5,6,7-tetrahydro-1H-indol-2-yl}pyridin-2-yl)cyclopropanecarboxamide
N-(cyclopropylcarbonyl)-N-{4-[4-oxo-3-(phenylamino)-4,5,6,7-tetrahydro-1H-indol-2-yl]pyridin-2-yl}cyclopropanecarboxamide
N-{4-[6,6-dimethyl-4-oxo-3-(phenylamino)-4,5,6,7-tetrahydro-1H-indol-2-yl]pyridin-2-yl}methanesulfonamide N-{4-[6,6-dimethyl-4-oxo-3-(phenylamino)-4,5,6,7-tetrahydro-1H-indol-2-yl]pyridin-2-yl}-2,2-difluoroacetamide 2-(2-aminopyridin-4-yl)-3-[(4-fluorophenyl)amino]-6-(propan-2-yl)-1,5,6,7-tetrahydro-4H-indol-4-one N-{4-[4-oxo-3-(phenylamino)-4,5,6,7-tetrahydro-1H-indol-2-yl]pyridin-2-yl}methanesulfonamide, or an N-oxide, a salt, a tautomer or a stereoisomer of said compound, or a salt of said N-oxide, tautomer or stereoisomer.

In one aspect of the invention compounds of formula (I) or (Ia) as described above are selected from the group consisting of:

6,6-dimethyl-2-(pyridin-4-yl)-3-(pyridin-2-ylamino)-1,5,6,7-tetrahydro-4H-indol-4-one 3-(1-benzofuran-6-ylamino)-6,6-dimethyl-2-(pyridin-4-yl)-1,5,6,7-tetrahydro-4H-indol-4-one 6,6-dimethyl-2-(pyridin-4-yl)-3-(pyridin-3-ylamino)-1,5,6,7-tetrahydro-4H-indol-4-one 3-(isoquinolin-4-ylamino)-6,6-dimethyl-2-(pyridin-4-yl)-1,5,6,7-tetrahydro-4H-indol-4-one 6,6-dimethyl-2-(pyridin-4-yl)-3-(quinolin-3-ylamino)-1,5,6,7-tetrahydro-4H-indol-4-one 3-(1-benzofuran-5-ylamino)-6,6-dimethyl-2-(pyridin-4-yl)-1,5,6,7-tetrahydro-4H-indol-4-one 3-(1H-indol-6-ylamino)-6,6-dimethyl-2-(pyridin-4-yl)-1,5,6,7-tetrahydro-4H-indol-4-one 3-(1-benzothiophen-5-ylamino)-6,6-dimethyl-2-(pyridin-4-yl)-1,5,6,7-tetrahydro-4H-indol-4-one 3-(1H-indol-5-ylamino)-6,6-dimethyl-2-(pyridin-4-yl)-1,5,6,7-tetrahydro-4H-indol-4-one 3-(1H-benzimidazol-6-ylamino)-6,6-dimethyl-2-(pyridin-4-yl)-1,5,6,7-tetrahydro-4H-indol-4-one 3-(1H-indazol-6-ylamino)-6,6-dimethyl-2-(pyridin-4-yl)-1,5,6,7-tetrahydro-4H-indol-4-one 6,6-dimethyl-2-(pyridin-4-yl)-3-(quinolin-4-ylamino)-1,5,6,7-tetrahydro-4H-indol-4-one 3-(1H-indazol-5-ylamino)-6,6-dimethyl-2-(pyridin-4-yl)-1,5,6,7-tetrahydro-4H-indol-4-one 3-(1-benzothiophen-6-ylamino)-6,6-dimethyl-2-(pyridin-4-yl)-1,5,6,7-tetrahydro-4H-indol-4-one 6,6-dimethyl-3-(naphthalen-1-ylamino)-2-(pyridin-4-yl)-1,5,6,7-tetrahydro-4H-indol-4-one 6,6-dimethyl-3-(naphthalen-2-ylamino)-2-(pyridin-4-yl)-1,5,6,7-tetrahydro-4H-indol-4-one or an N-oxide, a salt, a tautomer or a stereoisomer of said compound, or a salt of said N-oxide, tautomer or stereoisomer.

Another aspect of the invention is a compound of formula (II):

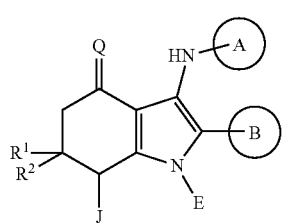

in which ring A, $R^1$, $R^2$, $R^3$, $R^6$, n, o, $R^4$, $R^7$, $R^8$, $R^9$, $R^{10}$, $R^{11}$, $R^{12}$, $R^{13}$, $R^{14}$, $R^{15}$, $R^{16}$, $R^{17a}$, $R^{17b}$, $R^{17c}$, $R^{18}$, Q, J and E are as defined in the aspects and/or embodiments of the invention described herein, and ring B represents a group selected from:

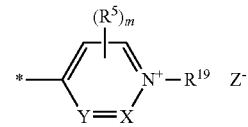

wherein * indicates the point of attachment of said group with the rest of the molecule;

Y, X, m and $R^5$ are as defined in the aspects and/or embodiments of the invention described herein, and $R^{19}$ represents $C_1$-$C_4$-alkyl optionally substituted, one or more times, independently from each other, with a substituent selected from halogen, hydroxyl, cyano, $C_1$-$C_4$-alkoxy and $R^{18}$—O—C(O)—, $Z^-$ represents a physiologically acceptable anion;

or an N-oxide, a salt, a tautomer or a stereoisomer of said compound, or a salt of said N-oxide, tautomer or stereoisomer.

In an embodiment, the invention relates to compounds of formula (II), wherein:

ring B represents a group selected from:

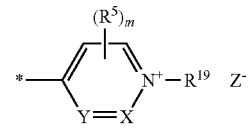

wherein * indicates the point of attachment of said group with the rest of the molecule;

$R^{19}$ represents $C_1$-$C_4$-alkyl optionally substituted, one or more times, independently from each other, with a substituent selected from halogen, hydroxyl, cyano, $C_1$-$C_4$-alkoxy and $R^{18}$—O—C(O)—, $Z^-$ represents a physiologically acceptable anion; and ring A, $R^1$, $R^2$, $R^3$, $R^6$, n, o, $R^4$, $R^7$, $R^8$, $R^9$, $R^{10}$, $R^{11}$, $R^{12}$, $R^{13}$, $R^{14}$, $R^{15}$, $R^{16}$, $R^{17a}$, $R^{17b}$, $R^{17c}$, $R^{18}$, Q, J, E, Y, X, m and $R^5$ are as defined in the aspects one, two, three, four or five as defined supra, or an N-oxide, a salt, a tautomer or a stereoisomer of said compound, or a salt of said N-oxide, tautomer or stereoisomer.

In an embodiment, the invention relates to compounds of formula (II), wherein $Z^-$ represents $Br^-$, $I^-$ or $CF_3SO_3^-$.

In an embodiment, the invention relates to compounds of formula (II), wherein $R^{19}$ represents $C_1$-$C_4$-alkyl optionally substituted, one or more times, independently from each other, with a substituent selected from halogen, hydroxyl, and $R^{18}$—O—C(O)—.

In an embodiment, the invention relates to compounds of formula (II), wherein ring A represents phenyl, $R^3$ is hydrogen, $R^1$ and $R^2$ represent, independently of each other, $C_1$-$C_2$-alkyl, Q represents O, J represents hydrogen, Y and X represent CH, m is 0, $R^{19}$ represents $C_1$-$C_3$-alkyl optionally substituted, one or more times, independently from each other, with halogen, preferably fluorine, and hydroxyl, Z⁻ represents Br⁻, I⁻ or CF₃SO₃⁻;

or an N-oxide, a salt, a tautomer or a stereoisomer of said compound, or a salt of said N-oxide, tautomer or stereoisomer.

In one aspect of the invention compounds of formula (II) as described above are selected from the group consisting of:

4-[6,6-dimethyl-4-oxo-3-(phenylamino)-4,5,6,7-tetrahydro-1H-indol-2-yl]-1-(propan-2-yl)pyridinium iodide 4-[6,6-dimethyl-4-oxo-3-(phenylamino)-4,5,6,7-tetrahydro-1H-indol-2-yl]-1-(2,2,2-trifluoroethyl)pyridinium trifluoromethanesulfonate 4-[6,6-dimethyl-4-oxo-3-(phenylamino)-4,5,6,7-tetrahydro-1H-indol-2-yl]-1-(3-hydroxypropyl)pyridinium iodide 1-(2,2-difluoroethyl)-4-[6,6-dimethyl-4-oxo-3-(phenylamino)-4,5,6,7-tetrahydro-1H-indol-2-yl]pyridinium [dihydroxy(trifluoromethyl)-λ⁴-sulfanyl]oxidanide 4-[6,6-dimethyl-4-oxo-3-(phenylamino)-4,5,6,7-tetrahydro-1H-indol-2-yl]-1-(2-methoxy-2-oxoethyl)pyridinium bromide, or an N-oxide, a salt, a tautomer or a stereoisomer of said compound, or a salt of said N-oxide, tautomer or stereoisomer.

One aspect of the invention are compounds of formula (I) as described in the examples, as characterized by their names in the title, as claimed in claim 7 or 9, and their structures as well as the subcombinations of all residues specifically disclosed in the compounds of the examples.

Another aspect of the present invention are the intermediates as used for their synthesis.

One special aspect of the invention is intermediate (1-2),

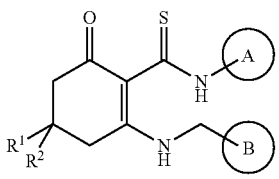

1-2 whereby R¹, R², A, B have the meaning according to any of claims 1 to 6 or as defined in the aspects and embodiments described herein.

One special aspect of the invention is intermediate (1-6),

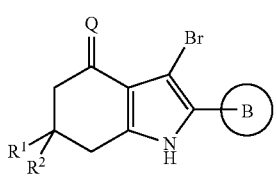

1-6 whereby R¹, R², B have the meaning according to any of claims 1 to 6 or as defined in the aspects and embodiments herein.

Another aspect of the invention relates to the use of any of the intermediates described herein for preparing a compound of formula (I) as defined herein or an N-oxide, a salt, a tautomer or a stereoisomer of said compound, or a salt of said N-oxide, tautomer or stereoisomer.

Another aspect of the present invention is a method of preparing a compound of general formula (I) according as defined herein, said method comprising the step of allowing an intermediate compound of general formula (1-2):

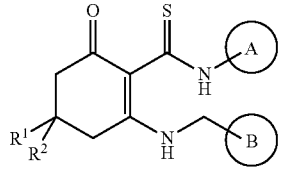

1-2 in which R¹, R², ring A and ring B are as defined herein for the compound of formula (I), with a base and/or oxidizing reagent, preferably an oxidizing agent, such as, for example hydrogen peroxide, thereby giving a compound of general formula (I):

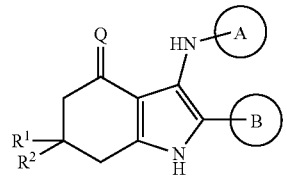

(I)

in which R¹, R², ring A and ring B are as defined herein for the compound of formula (I).

Another aspect of the present invention is a method of preparing a compound of general formula (I) according as defined herein, said method comprising the step of allowing an intermediate compound of general formula (1-6):

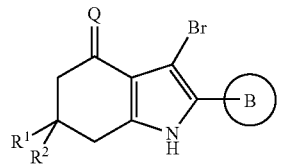

1-6 in which R¹, R², and ring B are as defined herein for the compound of formula (I), with an amine of formula

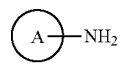

in which ring A is as defined herein for the compound of formula (I), thereby giving a compound of general formula (I):

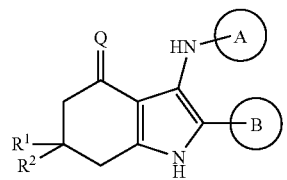

(I)

in which R¹, R², ring A and ring B are as defined herein for the compound of formula (I).

Another aspect of the present invention is a method of preparing a compound of general formula (II) according as defined herein, said method comprising the step of allowing an a compound of general formula (I):

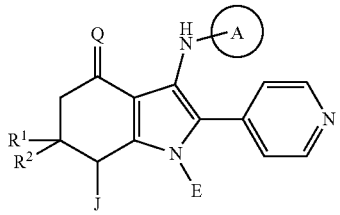

I in which R¹, R², J, E, Q, ring A and ring B are as defined herein for the compound of formula (I),
with an alkylating reagent which contains a suitable leaving group, such as, for example, F, Cl, Br, I or aryl sulfonate, such as, for example para-toluene sulfonate, or alkyl sulfonate, such as, for example methane sulfonate or trifluoromethane sulfonate,
thereby giving a compound of general formula (II):

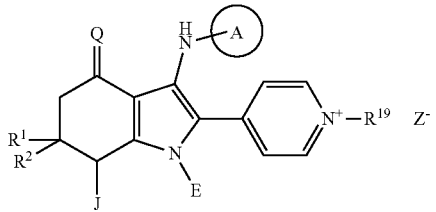

II in which R¹, R², E, J, Q, R¹⁹, Z⁻, and ring A are as defined herein for the compound of formula (II).

In a further embodiment of the above-mentioned aspects, the invention relates to compounds of formula (I), wherein:
R¹ represents hydrogen, $C_1$-$C_4$-alkyl, $C_1$-$C_4$-haloalkyl or phenyl, wherein said phenyl is optionally substituted, one or more times, independently from each other, with R³; and
R² represents hydrogen, $C_1$-$C_4$-alkyl or $C_1$-$C_4$-haloalkyl; or
R¹ and R² together with the carbon atom to which they are attached form a 3- to 7-membered cycloalkyl ring; and
ring A represents a group selected from:

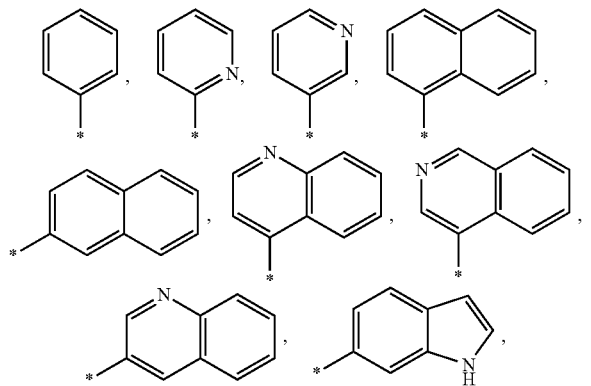

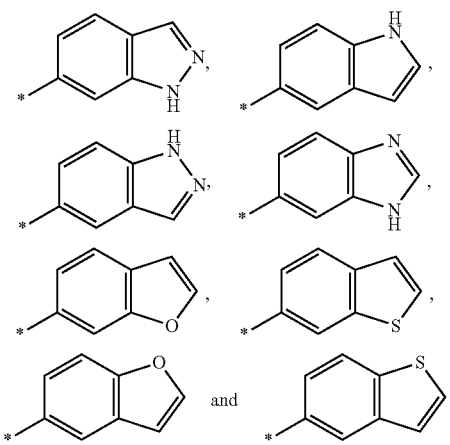

wherein * indicates the point of attachment of said group with the rest of the molecule and said group is optionally substituted, one or more times, independently from each other, with R³; and R³ represents hydrogen, halogen, hydroxy, amino, nitro, cyano, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, R¹⁸—O—C(O)—, R⁷R⁸N—C(O)—, $C_1$-$C_4$-alkyl-C(O)—NH—, R⁷R⁸N—, R⁷R⁸N—SO₂—, or a group selected from

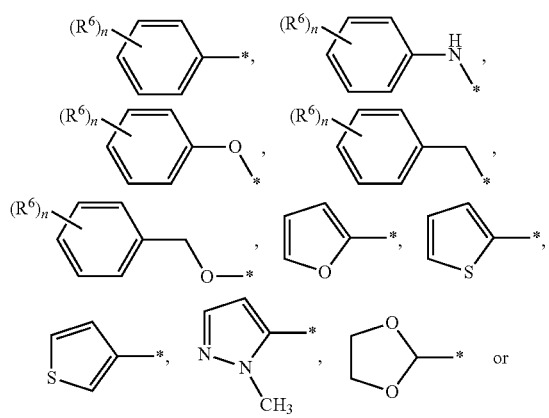

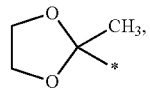

wherein * indicates the point of attachment of said group with the rest of the molecule;

wherein said $C_1$-$C_4$-alkyl, $C_1$-$C_4$-alkoxy, $C_1$-$C_4$-haloalkyl or $C_1$-$C_4$-haloalkoxy groups are optionally substituted with one or two hydroxy groups; and R⁶ represents, independently from each other, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl or $C_1$-$C_4$-haloalkoxy; and ring B represents a group selected from:

wherein * indicates the point of attachment of said group with the rest of the molecule; and X represents $CR^4$ or N; and
Y represents $CR^4$ or N,
  wherein when one of X and Y represents N, the other represents $CR^4$; and
$R^4$ represents, independently from each other, hydrogen, halogen, hydroxy, cyano, $C_1$-$C_4$-alkyl, $C_1$-$C_4$-alkoxy, $C_1$-$C_4$-alkyl-S—, $C_1$-$C_4$-alkyl-SO—, $C_1$-$C_4$-alkyl-SO$_2$—, $R^9R^{10}$N—, $R^{11}$—C(O)—(NR$^7$)—, ($R^{11}$—C(O)—)($R^{12}$—C(O)—)N—, $R^9R^{10}$N—C(O)—(NR$^7$)—, $R^9R^{10}$N—C(S)—(NR$^7$)—, $R^{18}$—O—C(O)—(NR$^7$)—, $R^9R^{10}$N—SO$_2$— or $C_1$-$C_4$-alkyl-SO$_2$—NH—,
  wherein said $C_1$-$C_4$-alkyl is optionally substituted, one or more times, independently from each other, with a substituent selected from hydroxy and halogen; and
  wherein said $C_1$-$C_4$-alkoxy is optionally substituted, one or more times, independently from each other, with a substituent selected from hydroxy, halogen, $C_1$-$C_4$-alkoxy, $C_3$-$C_6$-cycloalkyl and phenyl, wherein said phenyl is optionally substituted, one or more times, independently from each other, with $R^3$; and
$R^5$ represents, independently from each other, halogen, hydroxy, amino, nitro, cyano, $C_1$-$C_4$-alkyl, $C_1$-$C_4$-alkoxy, $C_1$-$C_4$-haloalkyl, $C_1$-$C_4$-haloalkoxy or phenyl-$C_1$-$C_4$-alkyl,
  wherein said phenyl group is optionally substituted, one or more times, independently from each other, with a substituent selected from halogen, hydroxy, $C_1$-$C_3$-alkyl, $C_1$-$C_3$-haloalkyl and $C_1$-$C_3$-alkoxy; and
J represents hydrogen or hydroxy; and
E represents hydrogen, $C_1$-$C_4$-alkyl, $C_1$-$C_4$-alkoxy-$C_2$-$C_4$-alkyl, $R^{17a}R^{17b}R^{17c}$Si—O—$C_2$-$C_4$-alkyl, $C_1$-$C_4$-alkyl-SO$_2$—$C_1$-$C_4$-alkyl, $R^{18}$—O—C(O)—$C_1$-$C_4$-alkyl, $R^7R^8$N—$C_2$-$C_4$-alkyl, $R^7R^8$N—C(O)—$C_1$-$C_4$-alkyl or phenyl-$C_1$-$C_4$-alkyl,
  wherein said $C_1$-$C_4$-alkyl is optionally substituted, one or more times, independently from each other, with a substituent selected from hydroxy and halogen; and
  wherein said phenyl group is optionally substituted, one or more times, independently from each other, with $R^5$;
Q represents O or N—OR$^{16}$;
$R^7$, $R^8$ represent, independently from each other, hydrogen, $C_1$-$C_4$-alkyl or tert-butyl-O—C(O)—;
and
$R^9$, $R^{10}$ represent, independently from each other, hydrogen, $C_1$-$C_4$-alkyl, $C_3$-$C_6$-cyclo-alkyl-, $C_1$-$C_4$-haloalkyl-, phenyl or heteroaryl,
  wherein said phenyl or heteroaryl group is optionally substituted, one or more times, independently from each other, with $R^5$; and
  wherein said $C_1$-$C_4$-alkyl is optionally substituted, one or more times, independently from each other, with a substituent selected from hydroxy, $C_1$-$C_4$-alkoxy, $C_1$-$C_4$-alkyl-S—, $C_3$-$C_6$-cycloalkyl, 4- to 6-membered heterocycloalkyl, phenyl, heteroaryl and $R^{18}$—O—C(O)—,
    wherein said $C_3$-$C_6$-cycloalkyl or 4- to 6-membered heterocycloalkyl is optionally substituted, one or more times, independently from each other, with a substituent selected from halogen, $C_1$-$C_4$-alkyl and tert-butyl-O—C(O)—,
    wherein said phenyl or heteroaryl group is optionally substituted, one or more times, independently from each other, with $R^5$; or
$R^9$ and $R^{10}$ together with the nitrogen atom to which they are attached form a 3- to 7-membered nitrogen containing heterocyclic ring, optionally containing one additional heteroatom selected from O, NH or S, and which may be optionally substituted, one or more times, independently from each other, with $R^5$; and
$R^{11}$, $R^{12}$ represent, independently from each other, $C_1$-$C_4$-alkyl, $C_2$-$C_4$-alkenyl, $C_2$-$C_4$-alkynyl, $C_3$-$C_6$-cycloalkyl, 4- to 6-membered heterocycloalkyl, phenyl, heteroaryl, or $R^{13}$—($C_1$-$C_4$-alkyl)-O—CH$_2$—,
  wherein said $C_1$-$C_4$-alkyl is optionally substituted, one or more times, independently from each other, with a substituent selected from halogen, hydroxy, cyano, $C_1$-$C_4$-alkoxy, $R^7R^8$N—, $R^{14}$, $R^{15}$—O—, and phenyl optionally substituted, one or more times, independently from each other, with $R^5$, and
  wherein said $C_3$-$C_6$-cycloalkyl is optionally substituted, one or more times, independently from each other, with a substituent selected from halogen, cyano, $C_1$-$C_4$-alkyl, $C_1$-$C_4$-haloalkyl and phenyl optionally substituted, one or more times, independently from each other, with $R^5$, and
  wherein said 4- to 6-membered heterocycloalkyl is optionally substituted, one or more times, independently from each other, with a substituent selected from hydroxy, $C_1$-$C_4$-alkyl, $C_1$-$C_4$-alkoxy, $R^7R^8$N— and $R^{18}$—O—C(O)—, and
  wherein said phenyl or heteroaryl is optionally substituted, one or more times, independently from each other, with $R^5$;
$R^{13}$ represents branched $C_3$-$C_4$-alkyl, $C_1$-$C_4$-haloalkyl, $C_2$-$C_4$-alkenyl, $C_2$-$C_4$-alkynyl, $C_3$-$C_6$-cycloalkyl, 4- to 6-membered heterocycloalkyl, phenyl or heteroaryl, wherein said phenyl or heteroaryl is optionally substituted, one or more times, independently from each other, with $R^5$;

$R^{14}$ represents $C_1$-$C_4$-alkyl-S—, $C_1$-$C_4$-alkyl-SO$_2$—, $C_3$-$C_6$-cycloalkyl, 4- to 6-membered heterocycloalkyl, phenyl or heteroaryl,
wherein said phenyl or heteroaryl is optionally substituted, one or more times, independently from each other, with $R^5$;

$R^{15}$ represents phenyl or heteroaryl,
wherein said phenyl or heteroaryl is optionally substituted, one or more times, independently from each other, with $R^5$; and $R^{16}$ represents hydrogen, $C_1$-$C_6$-alkyl, phenyl or $C_1$-$C_4$-alkyl-C(O)—,
wherein said phenyl group is optionally substituted, one or more times, independently from each other, with $R^5$;

$R^{17a}$, $R^{17b}$, $R^{17c}$ represent, independently from each other, $C_1$-$C_4$-alkyl;

$R^{18}$ represents hydrogen or $C_1$-$C_6$-alkyl;

m represents 0, 1 or 2;

n represents 0, 1, 2 or 3; and or an N-oxide, a salt, a tautomer or a stereoisomer of said compound, or a salt of said N-oxide, tautomer or stereoisomer.

In a further embodiment of the above-mentioned aspects, the invention relates to compounds of formula (Ia), wherein $R^1$ represents hydrogen, $C_1$-$C_4$-alkyl, $C_1$-$C_4$-haloalkyl or phenyl; and $R^2$ represents hydrogen, $C_1$-$C_4$-alkyl or $C_1$-$C_4$-haloalkyl; or $R^1$ and $R^2$ together with the carbon atom to which they are attached form a 3-7-membered cycloalkyl ring; and A represents a group:

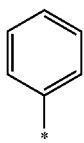

wherein * indicates the point of attachment of said group with the rest of the molecule and said group is optionally substituted, one or more times, independently from each other, with $R^3$; and $R^3$ represents hydrogen, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $C_1$-$C_4$-alkyl-O—C(O)—, $R^7R^8N$—C(O)—, $C_1$-$C_4$-alkyl-C(O)—NH—, or a group

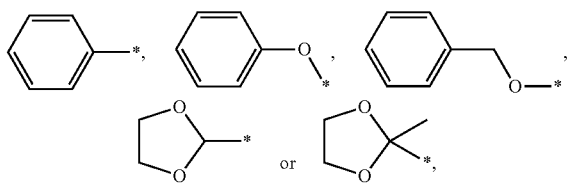

wherein said $C_1$-$C_4$-alkyl, $C_1$-$C_4$-alkoxy, $C_1$-$C_4$-haloalkyl or $C_1$-$C_4$-haloalkoxy groups are optionally substituted with hydroxy; and B represents a group selected from:

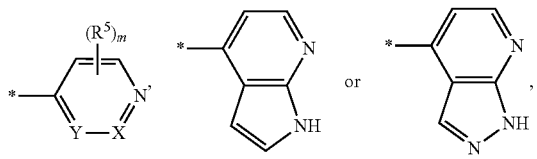

wherein * indicates the point of attachment of said group with the rest of the molecule; and X represents $CR^4$ or N; and Y represents $CR^4$ or N,
wherein when one of X and Y represents N, the other represents $CR^4$; and $R^4$ represents, independently from each other, hydrogen, halogen, hydroxy, cyano, $C_1$-$C_4$-alkyl, $C_1$-$C_4$-alkoxy, $R^9R^{10}N$—, $R^{11}$—C(O)—NH—, $(R^{11}$—C(O)—)($R^{12}$—C(O)—)N— or $C_1$-$C_4$-alkyl-SO$_2$—NH—; and $R^5$ represents, independently from each other, halogen; and $R^7$, $R^8$ represent, independently from each other, hydrogen or $C_1$-$C_4$-alkyl; and $R^9$, $R^{10}$ represent, independently from each other, hydrogen, $C_1$-$C_4$-alkyl or phenyl, wherein said phenyl group is optionally substituted, one or more times, independently from each other, with $R^5$; or $R^9$ and $R^{10}$ together with the nitrogen atom to which they are attached form a 3- to 7-membered nitrogen containing heterocyclic ring, optionally containing at least one additional heteroatom selected from O; and $R^{11}$, $R^{12}$ represent, independently from each other, $C_1$-$C_4$-alkyl, $C_3$-$C_6$-cycloalkyl- or $C_1$-$C_4$-haloalkyl-; and m represents 0 or 1;

or an N-oxide, a salt, a tautomer or a stereoisomer of said compound, or a salt of said N-oxide, tautomer or stereoisomer.

In a further embodiment of the above-mentioned aspects, the invention relates to compounds of formula (I), wherein Q represents O or N—$OR^{16}$.

In a further embodiment of the above-mentioned aspects, the invention relates to compounds of formula (I), wherein Q represents O.

In a further embodiment of the above-mentioned aspects, the invention relates to compounds of formula (I), wherein Q represents N—$OR^{16}$.

In a further embodiment of the above-mentioned aspects, the invention relates to compounds of formula (I) or (Ia), wherein:

$R^1$ represents hydrogen, $C_1$-$C_4$-alkyl, $C_1$-$C_4$-haloalkyl, $C_3$-$C_6$-cycloalkyl, or phenyl,
wherein said phenyl is optionally substituted, one or more times, independently from each other, with $R^3$,
wherein said $C_3$-$C_6$-cycloalkyl is optionally substituted, one or more times, independently from each other, with halogen.

In a further embodiment of the above-mentioned aspects, the invention relates to compounds of formula (I) or (Ia), wherein:

$R^1$ represents hydrogen, $C_1$-$C_4$-alkyl, $C_1$-$C_4$-haloalkyl, $C_3$-$C_6$-cycloalkyl, or phenyl,
wherein said phenyl is optionally substituted, one or more times, independently from each other, with $R^3$,
wherein said $C_3$-$C_6$-cycloalkyl is optionally substituted, one or more times, independently from each other, with halogen; and $R^2$ represents hydrogen, $C_1$-$C_4$-alkyl or $C_1$-$C_4$-haloalkyl.

In a further embodiment of the above-mentioned aspects, the invention relates to compounds of formula (I) or (Ia), wherein $R^1$ represents hydrogen and
$R^2$ represents hydrogen.

In a further embodiment of the above-mentioned aspects, the invention relates to compounds of formula (I) or (Ia), wherein $R^1$ represents methyl and
$R^2$ represents methyl.

In a further embodiment of the above-mentioned aspects, the invention relates to compounds of formula (I) or (Ia), wherein $R^1$ represents hydrogen, $C_1$-$C_4$-alkyl, $C_1$-$C_4$-haloalkyl or phenyl, wherein said phenyl is optionally substituted, one or more times, independently from each other, with $R^3$; and
$R^2$ represents hydrogen, or $C_1$-$C_2$-alkyl.

In a further embodiment of the above-mentioned aspects, the invention relates to compounds of formula (I) or (Ia), wherein $R^1$ represents hydrogen, $C_1$-$C_4$-alkyl, $C_1$-$C_2$-haloalkyl or phenyl, wherein said phenyl is optionally substituted, one or more times, independently from each other, with $R^3$; and
$R^2$ represents hydrogen, $C_1$-$C_2$-alkyl or $C_1$-$C_2$-haloalkyl.

In a further embodiment of the above-mentioned aspects, the invention relates to compounds of formula (I) or (Ia), wherein $R^1$ represents hydrogen, $C_1$-$C_3$-alkyl, $C_1$-alkyl substituted one time with chlorine, $C_1$-alkyl substituted one, two or three times with fluorine, or phenyl, wherein said phenyl is optionally substituted, one or more times, independently from each other, with $R^3$; and
$R^2$ represents hydrogen, or $C_1$-alkyl.

In a further embodiment of the above-mentioned aspects, the invention relates to compounds of formula (I) or (Ia), wherein $R^1$ represents hydrogen, $C_1$-$C_4$-alkyl, $C_1$-$C_4$-haloalkyl or phenyl, wherein said phenyl is optionally substituted, one or more times, independently from each other, with $R^3$.

In a further embodiment of the above-mentioned aspects, the invention relates to compounds of formula (I) or (Ia), wherein $R^1$ represents hydrogen, methyl, ethyl, isopropyl, isobutyl, —$CF_3$ or phenyl.

In a further embodiment of the above-mentioned aspects, the invention relates to compounds of formula (I) or (Ia), wherein $R^2$ represents hydrogen, $C_1$-$C_4$-alkyl or $C_1$-$C_4$-haloalkyl.

In a further embodiment of the above-mentioned aspects, the invention relates to compounds of formula (I) or (Ia), wherein $R^2$ represents hydrogen, methyl, ethyl, isopropyl, isobutyl or —$CF_3$, preferably hydrogen, methyl or ethyl.

In a further embodiment of the above-mentioned aspects, the invention relates to compounds of formula (I) or (Ia), wherein $R^1$ and $R^2$ together with the carbon atom to which they are attached form a 3- to 7-membered cycloalkyl ring, preferably a 3- to 6-membered cycloalkyl ring, more preferably a a 3- to 4-membered cycloalkyl ring.

In a further embodiment of the above-mentioned aspects, the invention relates to compounds of formula (I) or (Ia), wherein:

ring A represents a group selected from:

wherein * indicates the point of attachment of said group with the rest of the molecule and said group is optionally substituted, one or more times, independently from each other, with $R^3$; and $G^1$ represents O, S, or $NR^{21}$, $G^2$, $G^3$ represent, independently from each other, $CR^{21}$ or N.

In a further embodiment of the above-mentioned aspects, the invention relates to compounds of formula (I) or (Ia), wherein:

ring A represents a group selected from:

wherein * indicates the point of attachment of said group with the rest of the molecule and said group is optionally substituted, one or more times, independently from each other, with $R^3$; and $G^1$ represents O, S, or $NR^{21}$, one of $G^2$ and $G^3$ represents N and the other $CR^{21}$.

In a further embodiment of the above-mentioned aspects, the invention relates to compounds of formula (I) or (Ia), wherein:

ring A represents a group selected from:

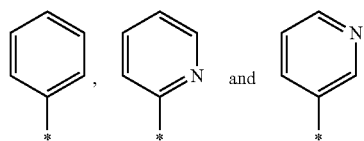

wherein * indicates the point of attachment of said group with the rest of the molecule and said group is optionally substituted, one or more times, independently from each other, with R³.

In a further embodiment of the above-mentioned aspects, the invention relates to compounds of formula (I) or (Ia), wherein ring A represents a group selected from:

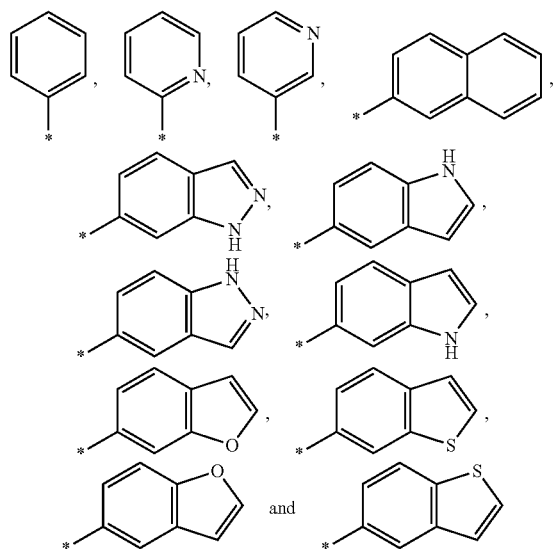

wherein * indicates the point of attachment of said group with the rest of the molecule and said group is optionally substituted, one or more times, independently from each other, with R³.

In a further embodiment of the above-mentioned aspects, the invention relates to compounds of formula (I) or (Ia), wherein ring A represents a group selected from:

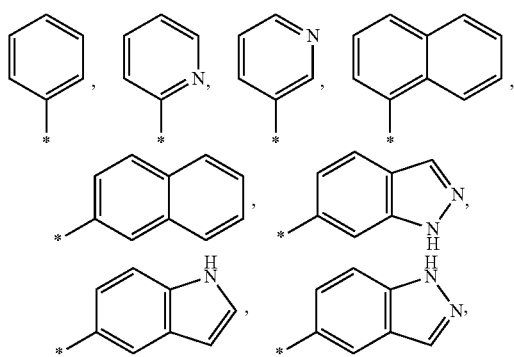

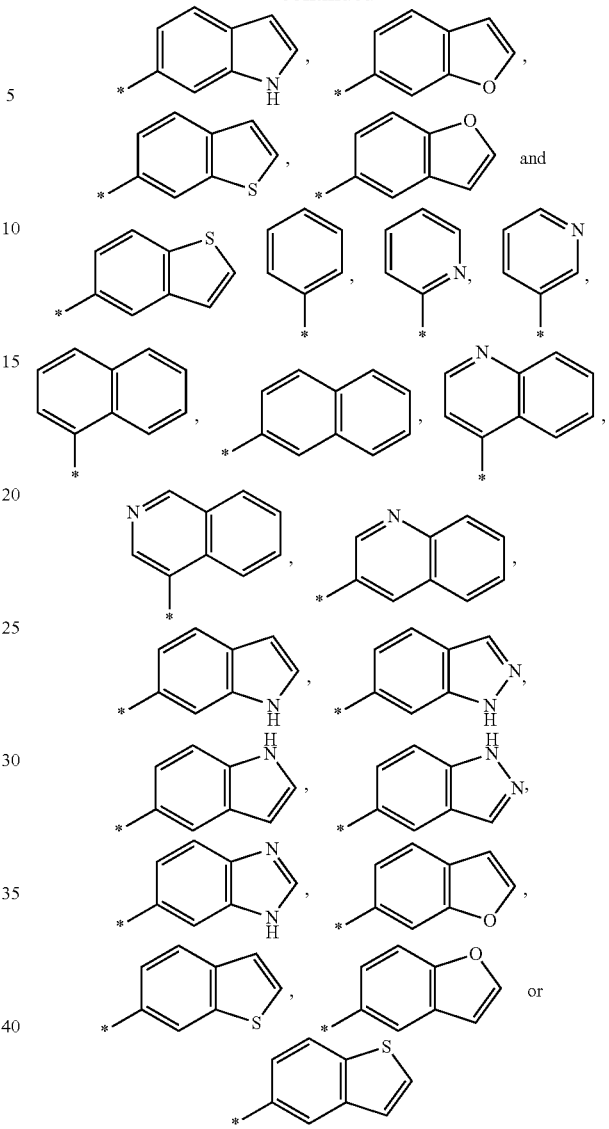

wherein * indicates the point of attachment of said group with the rest of the molecule and said group is optionally substituted, one or more times, independently from each other, with R³.

In a further embodiment of the above-mentioned aspects, the invention relates to compounds of formula (I) or (Ia), wherein A represents a group:

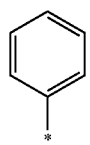

wherein * indicates the point of attachment of said group with the rest of the molecule and said group is optionally substituted, one or more times, independently from each other, with R³.

In a further embodiment of the above-mentioned aspects, the invention relates to compounds of formula (I) or (Ia), wherein A represents a group:

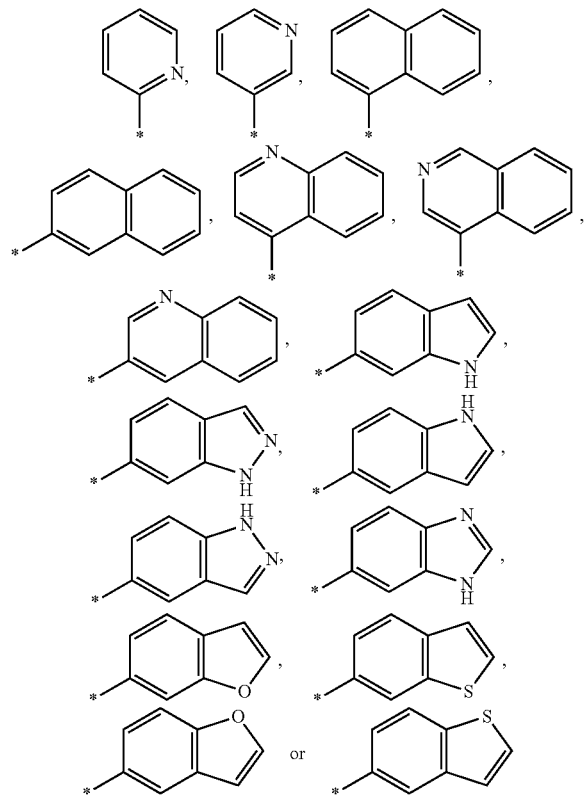

wherein * indicates the point of attachment of said group with the rest of the molecule and said group is optionally substituted, one or more times, independently from each other, with $R^3$.

In a further embodiment of the above-mentioned aspects, the invention relates to compounds of formula (I) or (Ia), wherein:

$R^3$ represents hydrogen, halogen, hydroxy, amino, nitro, cyano, $C_1$-$C_4$-alkyl, $C_3$-$C_6$-cycloalkyl, $C_2$-$C_4$-alkenyl, $C_2$-$C_4$-alkynyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $R^{18}$—O—C(O)—, $R^7R^8N$—C(O)—, $C_1$-$C_4$-alkyl-C(O)—NH—, $R^7R^8N$—, $R^7R^8N$—$SO_2$—, or a group selected from

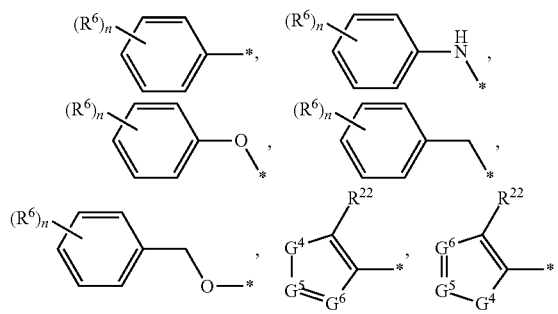

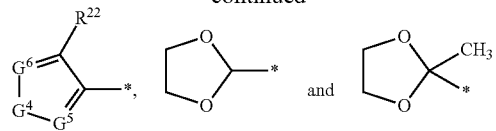

wherein * indicates the point of attachment of said group with the rest of the molecule;
wherein said $C_1$-$C_4$-alkyl, $C_1$-$C_4$-alkoxy, $C_1$-$C_4$-haloalkyl or $C_1$-$C_4$-haloalkoxy groups are optionally substituted with one or two hydroxy groups; and
$G^4$ represents O, S, or $NR^{21}$,
$G^5$, $G^6$ represent, independently from each other, $CR^{21}$ or N.

In a further embodiment of the above-mentioned aspects, the invention relates to compounds of formula (I) or (Ia), wherein:

$R^3$ represents hydrogen, halogen, hydroxy, amino, nitro, cyano, $C_1$-$C_4$-alkyl, $C_3$-$C_6$-cycloalkyl, $C_2$-$C_4$-alkenyl, $C_2$-$C_4$-alkynyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $R^{18}$—O—C(O)—, $R^7R^8N$—C(O)—, $C_1$-$C_4$-alkyl-C(O)—NH—, $R^7R^8N$—, $R^7R^8N$—$SO_2$—, or a group selected from

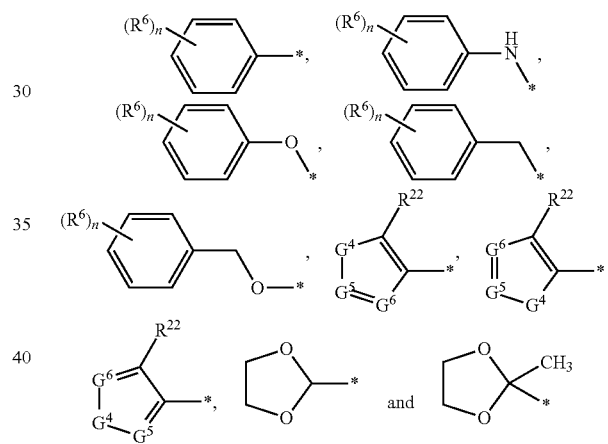

wherein * indicates the point of attachment of said group with the rest of the molecule;
wherein said $C_1$-$C_4$-alkyl, $C_1$-$C_4$-alkoxy, $C_1$-$C_4$-haloalkyl or $C_1$-$C_4$-haloalkoxy groups are optionally substituted with one or two hydroxy groups; and
$G^4$ represents O, S, or $NR^{21}$,
one of $G^5$ and $G^6$ represents N and the other $CR^{21}$.

In a further embodiment of the above-mentioned aspects, the invention relates to compounds of formula (I) or (Ia), wherein:

$R^3$ represents hydrogen, halogen, hydroxy, amino, nitro, cyano, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $R^{18}$—O—C(O)—, $R^7R^8N$—C(O)—, $C_1$-$C_4$-alkyl-C(O)—NH—, $R^7R^8N$—, $R^7R^8N$—$SO_2$—, or a group selected from

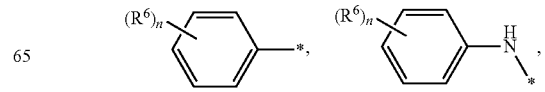

-continued

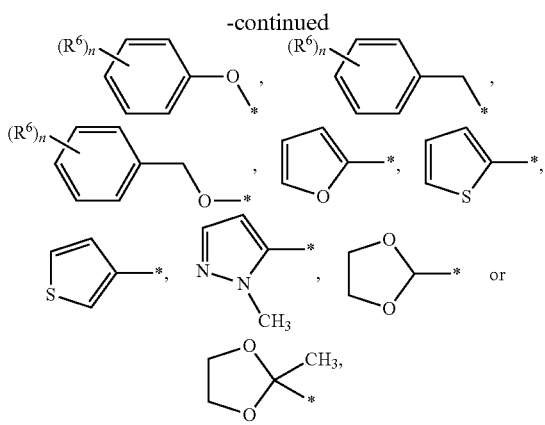

wherein * indicates the point of attachment of said group with the rest of the molecule;
wherein said $C_1$-$C_4$-alkyl, $C_1$-$C_4$-alkoxy, $C_1$-$C_4$-haloalkyl or $C_1$-$C_4$-haloalkoxy groups are optionally substituted with one or two hydroxy groups.

In a further embodiment of the above-mentioned aspects, the invention relates to compounds of formula (I) or (Ia), wherein
$R^3$ represents hydrogen, halogen, hydroxy, amino, nitro, cyano, $C_1$-$C_4$-alkyl, $C_2$-$C_4$-alkynyl, $C_1$-$C_4$-alkoxy, $C_1$-$C_2$-alkoxy-$C_1$-$C_2$-alkyl-, $C_1$-$C_2$-haloalkyl, $C_1$-$C_2$-haloalkoxy, $C_1$-$C_2$-alkyl-C(O)—, $R^{18}$—O—C(O)—, $R^7R^8N$—C(O)—, $C_1$-$C_3$-alkyl-C(O)—NH—, $R^7R^8N$—, $R^7R^8N$—SO_2—, or a group selected from

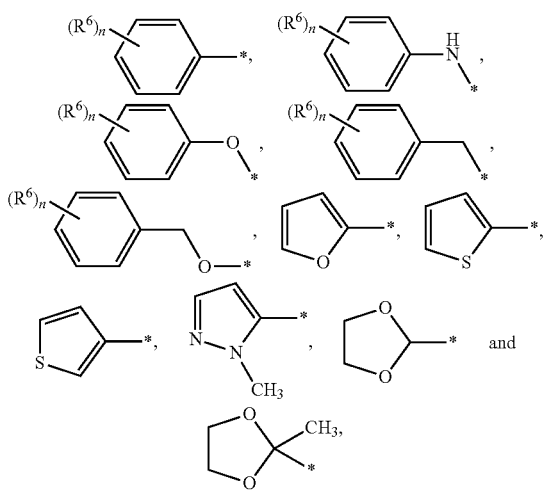

wherein * indicates the point of attachment of said group with the rest of the molecule;
wherein said $C_1$-$C_4$-alkyl, $C_1$-$C_4$-alkoxy, $C_1$-$C_2$-haloalkyl or $C_1$-$C_2$-haloalkoxy groups are optionally substituted with one or two hydroxy groups.

In a further embodiment of the above-mentioned aspects, the invention relates to compounds of formula (I) or (Ia), wherein
$R^3$ represents hydrogen, halogen, hydroxy, amino, nitro, cyano, $C_1$-$C_4$-alkyl, $C_2$-alkynyl, $C_1$-$C_3$-alkoxy, $C_1$-alkoxy-$C_2$-alkyl-, $C_1$-$C_2$-haloalkyl, $C_1$-$C_2$-haloalkoxy, $C_1$-$C_2$-alkyl-C(O)—, $R^{18}$—O—C(O)—, $R^7R^8N$—C(O)—, $C_1$-$C_3$-alkyl-C(O)—NH—, or a group selected from

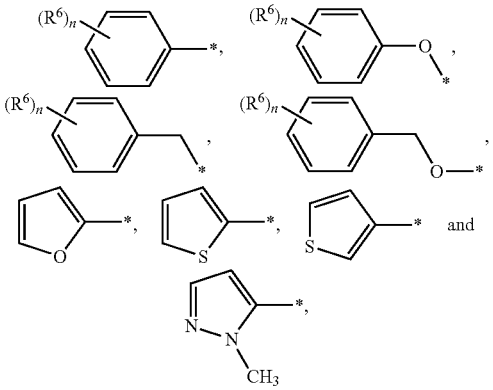

wherein * indicates the point of attachment of said group with the rest of the molecule;
wherein said $C_1$-$C_4$-alkyl, $C_1$-$C_3$-alkoxy, $C_1$-$C_2$-haloalkyl or $C_1$-$C_2$-haloalkoxy groups are optionally substituted with one or two hydroxy groups.

In a further embodiment of the above-mentioned aspects, the invention relates to compounds of formula (I) or (Ia), wherein
$R^3$ represents hydrogen, halogen, hydroxy, nitro, cyano, $C_1$-$C_3$-alkyl, $C_1$-$C_3$-alkoxy, $C_1$-haloalkyl, $C_1$-haloalkoxy, $C_1$-$C_2$-alkyl-C(O)—, $R^{18}$—O—C(O)—, $R^7R^8N$—C(O)—, or a group selected from

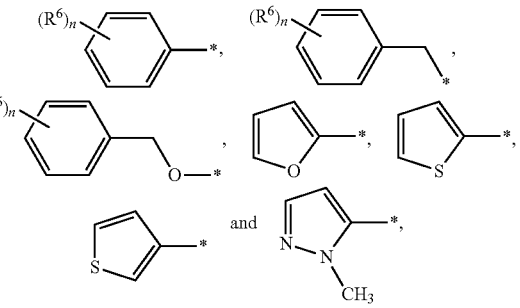

wherein * indicates the point of attachment of said group with the rest of the molecule;
wherein said $C_1$-$C_3$-alkyl, $C_1$-$C_3$-alkoxy, $C_1$-haloalkyl or $C_1$-haloalkoxy groups are optionally substituted with one hydroxy group.

In a further embodiment of the above-mentioned aspects, the invention relates to compounds of formula (I) or (Ia), wherein
$R^3$ represents hydrogen, fluorine, chlorine, bromine, hydroxy, nitro, cyano, $C_1$-$C_3$-alkyl, $C_1$-$C_3$-alkoxy, —CF$_3$, —OCF$_3$, —OCHF$_2$, $C_1$-alkyl-C(O)—, $R^{18}$—O—C(O)—, $R^7R^8N$—C(O)—,
or a group selected from

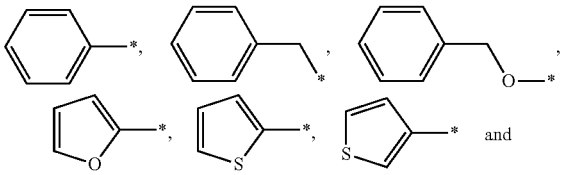

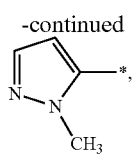

wherein * indicates the point of attachment of said group with the rest of the molecule;

wherein said $C_1$-$C_3$-alkyl, group is optionally substituted with one hydroxy group.

In a further embodiment of the above-mentioned aspects, the invention relates to compounds of formula (I) or (Ia), wherein $R^3$ represents hydrogen, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $C_1$-$C_4$-alkyl-O—C(O)—, $R^7R^8N$—C(O)—, $C_1$-$C_4$-alkyl-C(O)—NH—, or a group

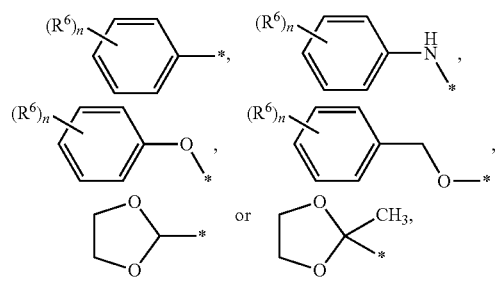

wherein * indicates the point of attachment of said group with the rest of the molecule, wherein said $C_1$-$C_4$-alkyl, $C_1$-$C_4$-alkoxy, $C_1$-$C_4$-haloalkyl or $C_1$-$C_4$-haloalkoxy groups are optionally substituted with hydroxyl.

In a further embodiment of the above-mentioned aspects, the invention relates to compounds of formula (I) or (Ia), wherein $R^3$ represents hydrogen, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $C_1$-$C_4$-alkyl-O—C(O)—, $R^7R^8N$—C(O)—, $C_1$-$C_4$-alkyl-C(O)—NH—, or a group

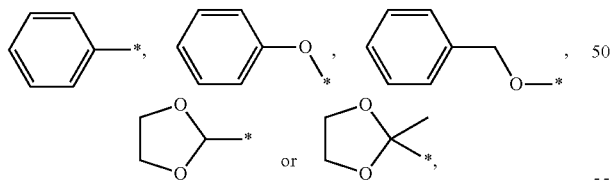

wherein * indicates the point of attachment of said group with the rest of the molecule, wherein said $C_1$-$C_4$-alkyl, $C_1$-$C_4$-alkoxy, $C_1$-$C_4$-haloalkyl or $C_1$-$C_4$-haloalkoxy groups are optionally substituted with hydroxyl.

In a further embodiment of the above-mentioned aspects, the invention relates to compounds of formula (I) or (Ia), wherein $R^3$ represents hydrogen, F, Cl, Br, hydroxy, amino, nitro, cyano, methyl, ethyl, isopropyl, t-butyl, $CH_3O$—, $CH_3CH_2O$—, $CH_3CH_2CH_2O$—, $(CH_3)_2CH$—O—, $CH_2$(OH)—$CH_2$—O—, $CF_3O$—, —$CH_2(OH)$, —$CH(OH)CH_2CH_3$, —$CH(OH)CF_3$, —$CH(CH_3)$—O—$CH_3$, —$CH(OH)$—$CH_3$, —$C(O)CH_3$, —$CF_3$, $CH_3$—C(O)—NH—, $CH_3CH_2$—C(O)—NH—, $CH_3CH_2CH_2$—C(O)—NH—, $(CH_3)_2CH$—C(O)—NH—, $CH_3$—NH—C(O)—, $CH_3CH_2$—NH—C(O)—, $NH_2$—C(O)—, —$OCHF_2$, $(CH_3)_3C$—O—C(O)—, or a group

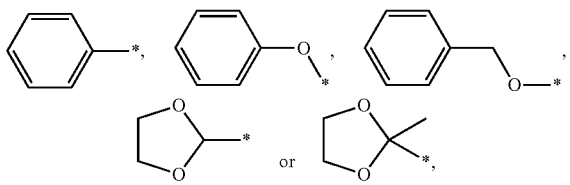

wherein * indicates the point of attachment of said group with the rest of the molecule.

In a further embodiment of the above-mentioned aspects, the invention relates to compounds of formula (I) or (Ia), wherein $R^6$ represents $C_1$-alkoxy.

In a further embodiment of the above-mentioned aspects, the invention relates to compounds of formula (I) or (Ia), wherein $R^6$ represents, independently from each other, halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl or $C_1$-$C_4$-haloalkoxy.

In a further embodiment of the above-mentioned aspects, the invention relates to compounds of formula (I) or (Ia), wherein $R^6$ represents hydrogen.

In a further embodiment of the above-mentioned aspects, the invention relates to compounds of formula (I) or (Ia), wherein $R^6$ represents, independently from each other, halogen, hydroxy, amino, nitro, cyano, $C_1$-$C_2$-alkyl, $C_1$-$C_2$-alkoxy, $C_1$-$C_2$-alkoxy-$C_1$-$C_2$-alkyl-, $C_1$-$C_2$-haloalkyl or $C_1$-$C_2$-haloalkoxy.

In a further embodiment of the above-mentioned aspects, the invention relates to compounds of formula (I) or (Ia), wherein ring B represents a group selected from:

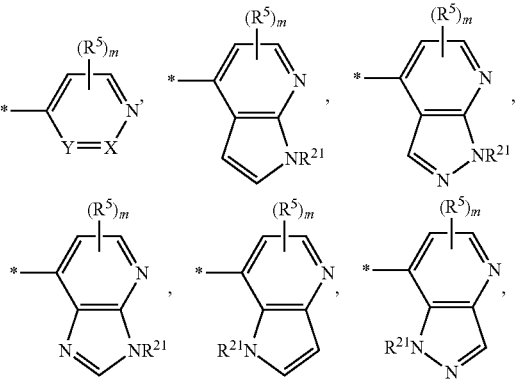

-continued

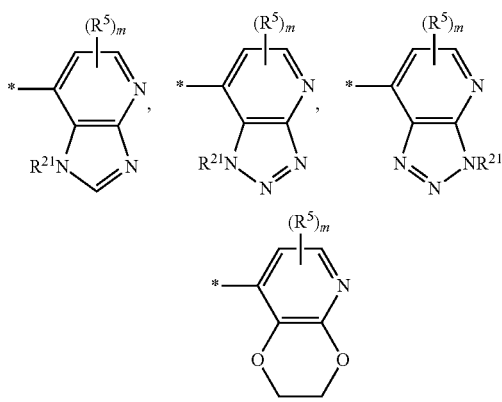

wherein * indicates the point of attachment of said group with the rest of the molecule.

In a further embodiment of the above-mentioned aspects, the invention relates to compounds of formula (I) or (Ia), wherein ring B represents a group selected from:

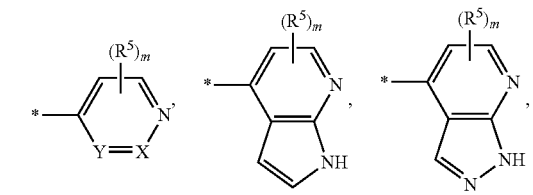

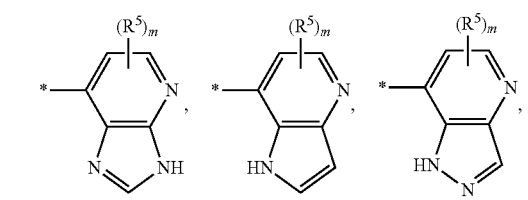

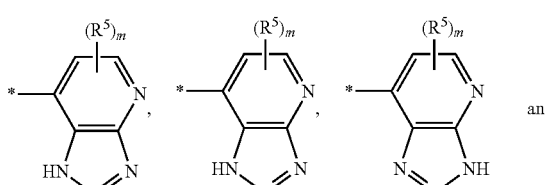

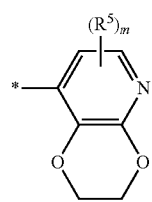

wherein * indicates the point of attachment of said group with the rest of the molecule.

In a further embodiment of the above-mentioned aspects, the invention relates to compounds of formula (I) or (Ia), wherein ring B represents a group selected from:

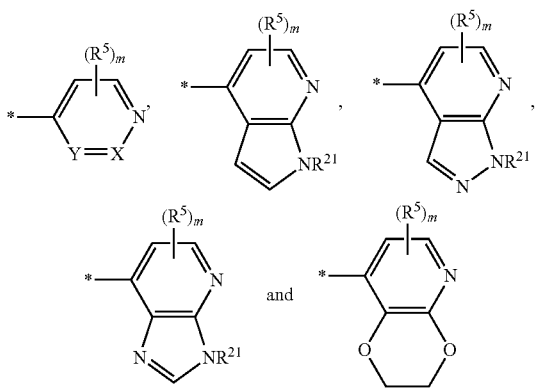

wherein * indicates the point of attachment of said group with the rest of the molecule.

In a further embodiment of the above-mentioned aspects, the invention relates to compounds of formula (I) or (Ia), wherein ring B represents a group selected from:

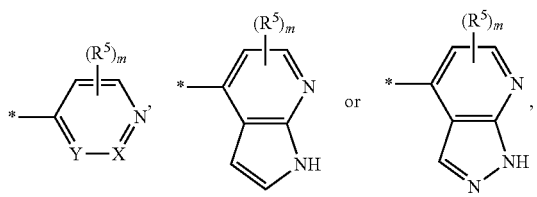

wherein * indicates the point of attachment of said group with the rest of the molecule.

In a further embodiment of the above-mentioned aspects, the invention relates to compounds of formula (I) or (Ia), wherein B represents a group selected from:

wherein * indicates the point of attachment of said group with the rest of the molecule.

In a further embodiment of the above-mentioned aspects, the invention relates to compounds of formula (I) or (Ia), wherein B represents a group selected from:

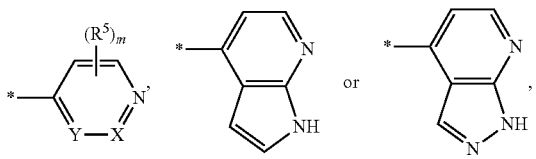

wherein * indicates the point of attachment of said group with the rest of the molecule.

In a further embodiment of the above-mentioned aspects, the invention relates to compounds of formula (I) or (Ia), wherein
B represents a group:

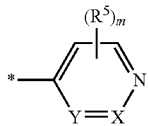

wherein * indicates the point of attachment of said group with the rest of the molecule.

In a further embodiment of the above-mentioned aspects, the invention relates to compounds of formula (I) or (Ia), wherein
B represents a group:

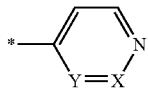

wherein * indicates the point of attachment of said group with the rest of the molecule.

In a further embodiment of the above-mentioned aspects, the invention relates to compounds of formula (I) or (Ia), wherein
X represents $CR^4$ and
Y represents $CR^4$.

In a further embodiment of the above-mentioned aspects, the invention relates to compounds of formula (I) or (Ia), wherein
X represents $CR^4$ or N.

In a further embodiment of the above-mentioned aspects, the invention relates to compounds of formula (I) or (Ia), wherein
Y represents $CR^4$ or N.

In a further embodiment of the above-mentioned aspects, the invention relates to compounds of formula (I) or (Ia), wherein
X represents $CR^4$ and Y represents N.

In a further embodiment of the above-mentioned aspects, the invention relates to compounds of formula (I) or (Ia), wherein
Y represents $CR^4$ and X represents N.

In a further embodiment of the above-mentioned aspects, the invention relates to compounds of formula (I) or (Ia), wherein
X represents $CR^4$.

In a further embodiment of the above-mentioned aspects, the invention relates to compounds of formula (I) or (Ia), wherein
$R^4$ represents, independently from each other, hydrogen, halogen, hydroxy, cyano, $C_1$-$C_4$-alkyl, $C_3$-$C_4$-cycloalkyl, $C_1$-$C_4$-alkoxy, $C_1$-$C_4$-alkyl-S—, $C_1$-$C_4$-alkyl-SO—, $C_1$-$C_4$-alkyl-$SO_2$—, $R^9R^{10}$N—, $R^{11}$—C(O)—($NR^7$)—, ($R^{11}$—C(O)—)($R^{12}$—C(O)—)N—, $R^9R^{10}$N—C(O)—($NR^7$)—, $R^9R^{10}$N—C(S)—($NR^7$)—, $R^{18}$—O—C(O)—($NR^7$)—, $R^9R^{10}$N—$SO_2$— or $C_1$-$C_4$-alkyl-$SO_2$—NH—,
wherein said $C_1$-$C_4$-alkyl is optionally substituted, one or more times, independently from each other, with a substituent selected from hydroxy and halogen; and
wherein said $C_1$-$C_4$-alkoxy is optionally substituted, one or more times, independently from each other, with a substituent selected from hydroxy, halogen, $C_1$-$C_4$-alkoxy, $C_3$-$C_6$-cycloalkyl and phenyl, wherein said phenyl is optionally substituted, one or more times, independently from each other, with $R^3$; and
wherein said $C_3$-$C_4$-cycloalkyl is optionally substituted, one or more times, independently from each other, with halogen.

In a further embodiment of the above-mentioned aspects, the invention relates to compounds of formula (I) or (Ia), wherein
$R^4$ represents, independently from each other, hydrogen, halogen, hydroxy, cyano, $C_1$-$C_4$-alkyl, $C_1$-$C_4$-alkoxy, $C_1$-$C_4$-alkyl-S—, $C_1$-$C_4$-alkyl-SO—, $C_1$-$C_4$-alkyl-$SO_2$—, $R^9R^{10}$N—, $R^{11}$—C(O)—($NR^7$)—, ($R^{11}$—C(O)—)($R^{12}$—C(O)—)N—, $R^9R^{10}$N—C(O)—($NR^7$)—, $R^9R^{10}$N—C(S)—($NR^7$)—, $R^{18}$—O—C(O)—($NR^7$)—, $R^9R^{10}$N—$SO_2$— or $C_1$-$C_2$-alkyl-$SO_2$—NH—,
wherein said $C_1$-$C_4$-alkyl is optionally substituted, one or more times, independently from each other, with a substitutent selected from hydroxy and halogen; and
wherein said $C_1$-$C_4$-alkoxy is optionally substituted, one or more times, independently from each other, with a substituent selected from hydroxy, halogen, $C_1$-$C_4$-alkoxy, $C_3$-$C_6$-cycloalkyl and phenyl, wherein said phenyl is optionally substituted, one or more times, independently from each other, with $R^3$.

In a further embodiment of the above-mentioned aspects, the invention relates to compounds of formula (I) or (Ia), wherein
$R^4$ represents, independently from each other, hydrogen, halogen, hydroxy, cyano, $C_1$-$C_3$-alkyl, $C_1$-$C_4$-alkoxy, $C_1$-$C_2$-alkyl-S—, $C_1$-$C_2$-alkyl-SO—, $C_1$-$C_2$-alkyl-$SO_2$—, $R^9R^{10}$N—, $R^{11}$—C(O)—($NR^7$)—, ($R^{11}$—C(O)—)($R^{12}$—C(O)—)N—, $R^9R^{10}$N—C(O)—($NR^7$)—, $R^9R^{10}$N—C(S)—($NR^7$)—, $R^{18}$—O—C(O)—($NR^7$)—, $R^9R^{10}$N—$SO_2$— or $C_1$-$C_2$-alkyl-$SO_2$—NH—,
wherein said $C_1$-$C_3$-alkyl is optionally substituted, one or more times, independently from each other, with a substituent selected from hydroxy and halogen; and
wherein said $C_1$-$C_4$-alkoxy is optionally substituted, one or more times, independently from each other, with hydroxy, halogen, $C_1$-$C_4$-alkoxy, $C_3$-$C_6$-cycloalkyl or phenyl, wherein said phenyl is optionally substituted, one or more times, independently from each other, with $R^3$.

In a further embodiment of the above-mentioned aspects, the invention relates to compounds of formula (I) or (Ia), wherein
$R^4$ represents, independently from each other, hydrogen, halogen, hydroxy, cyano, $C_1$-$C_2$-alkyl, $C_1$-$C_4$-alkoxy, $C_1$-$C_2$-alkyl-S—, $R^9R^{10}$N—, $R^{11}$—C(O)—(NH)—, ($R^{11}$—C(O)—)($R^{12}$—C(O)—)N—, $R^9R^{10}$N—C(O)—($NR^7$)—, $R^9R^{10}$N—C(S)—($NR^7$)—, $R^{18}$—O—C(O)—($NR^7$)—, $R^9R^{10}$N—$SO_2$— or $C_1$-$C_2$-alkyl-$SO_2$—NH—, wherein said $C_1$-$C_2$-alkyl is optionally substituted, one time with hydroxy and/or one, two or three times, independently from each other, with halogen; and wherein said $C_1$-$C_4$-alkoxy is optionally substituted, one or more times, independently from each other, with a substituent selected from hydroxy, halogen, $C_1$-$C_2$-alkoxy, and $C_3$-$C_4$-cycloalkyl.

In a further embodiment of the above-mentioned aspects, the invention relates to compounds of formula (I) or (Ia), wherein $R^4$ represents, independently from each other, hydrogen, halogen, hydroxy, cyano, $C_1$-alkyl, $C_1$-$C_3$-alkoxy, $C_1$-alkyl-S—, $R^9R^{10}N$—, $R^{11}$—C(O)—(NH)—, ($R^{11}$—C(O)—)($R^{12}$—C(O)—)N—, $R^9R^{10}N$—C(O)—($NR^7$)—, $R^9R^{10}N$—C(S)—($NR^7$)—, or $R^{18}$—O—C(O)—($NR^7$)—,
wherein said $C_1$-alkyl is optionally substituted, one, two or three times, independently from each other, with halogen; and
wherein said $C_1$-$C_3$-alkoxy is optionally substituted, one or more times, independently from each other, with a substituent selected from hydroxy, halogen, $C_1$-$C_2$-alkoxy, and $C_3$-$C_4$-cycloalkyl.

In a further embodiment of the above-mentioned aspects, the invention relates to compounds of formula (I) or (Ia), wherein $R^4$ represents, independently from each other, hydrogen, halogen, hydroxy, cyano, $C_1$-alkyl, $C_1$-$C_3$-alkoxy, $C_1$-alkyl-S—, $R^9R^{10}N$—, $R^{11}$—C(O)—(NH)—, ($R^{11}$—C(O)—)($R^{12}$—C(O)—)N—, $R^9R^{10}N$—C(O)—($NR^7$)—, $R^9R^{10}N$—C(S)—($NR^7$)—, or $R^{18}$—O—C(O)—($NR^7$)—,
wherein said $C_1$-alkyl is optionally substituted, one or two times, with fluorine; and
wherein said $C_1$-$C_3$-alkoxy is optionally substituted, one or more times, independently from each other, with a substituent selected from hydroxy, fluorine, $C_1$-alkoxy, and $C_3$-cycloalkyl.

In a further embodiment of the above-mentioned aspects, the invention relates to compounds of formula (I) or (Ia), wherein $R^4$ represents, independently from each other, hydrogen, halogen, hydroxy, cyano, $C_1$-$C_4$-alkyl, $C_1$-$C_4$-alkoxy, $R^9R^{10}N$—, $R^{11}$—C(O)—NH—, ($R^{11}$—C(O)—)($R^{12}$—C(O)—)N— or $C_1$-$C_4$-alkyl-$SO_2$—NH—.

In a further embodiment of the above-mentioned aspects, the invention relates to compounds of formula (I) or (Ia), wherein $R^4$ represents, independently from each other, hydrogen, F, Cl, Br, cyano, methyl, —$OCH_3$, amino, —$NHCH_3$, —NH—C(O)—$CH_3$, —NH—C(O)—$CHF_2$, —NH—C(O)—$CH_2CH_3$, —NH—C(O)—$CH(CH_3)_2$, —NH—C(O)-cyclopropyl, —N(—C(O)—$CH_3)_2$, —N(—C(O)-cyclopropyl)$_2$, —NH—$S(O)_2$—$CH_3$,

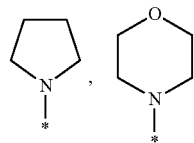

or phenyl-NH—, wherein said phenyl group is optionally substituted, one or more times, independently from each other, with $R^5$,
wherein * indicates the point of attachment of said group with the rest of the molecule.

In a further embodiment of the above-mentioned aspects, the invention relates to compounds of formula (I), wherein J represents hydrogen or hydroxyl.

In a further embodiment of the above-mentioned aspects, the invention relates to compounds of formula (I), wherein J represents hydrogen.

In a further embodiment of the above-mentioned aspects, the invention relates to compounds of formula (I), wherein J represents hydroxyl.

In a further embodiment of the above-mentioned aspects, the invention relates to compounds of formula (I), wherein E represents hydrogen, $C_1$-$C_4$-alkyl, $C_1$-$C_4$-alkoxy-$C_2$-$C_4$-alkyl, $R^{17a}R^{17b}R^{17c}Si$—O—$C_2$-$C_4$-alkyl, $C_1$-$C_4$-alkyl-$SO_2$—$C_1$-$C_4$-alkyl, $R^{18}$—O—C(O)—$C_1$-$C_4$-alkyl, $R^7R^8N$—$C_2$-$C_4$-alkyl, $R^7R^8N$—C(O)—$C_1$-$C_4$-alkyl or phenyl-$C_1$-$C_4$-alkyl,
wherein said $C_1$-$C_4$-alkyl is optionally substituted, one or more times, independently from each other, with a substituent selected from hydroxy and halogen; and
wherein said phenyl group is optionally substituted, one or more times, independently from each other, with $R^5$.

In a further embodiment of the above-mentioned aspects, the invention relates to compounds of formula (I), wherein E represents hydrogen, $C_1$-$C_4$-alkyl, $R^{17a}R^{17b}R^{17c}Si$—O—$C_2$-alkyl, $R^{18}$—O—C(O)—$C_1$-$C_2$-alkyl, $R^7R^8N$—C(O)—$C_1$-$C_2$-alkyl or phenyl-$C_1$-$C_2$-alkyl,
wherein said $C_1$-$C_4$-alkyl is optionally substituted, one or more times, independently from each other, with a substituent selected from hydroxy and halogen; and
wherein said phenyl group is optionally substituted, one or more times, independently from each other, with $R^5$.

In a further embodiment of the above-mentioned aspects, the invention relates to compounds of formula (I), wherein E represents hydrogen, $C_1$-$C_4$-alkyl, $R^{18}$—O—C(O)—$C_1$-$C_2$-alkyl, or $R^7R^8N$—C(O)—$C_1$-$C_2$-alkyl,
wherein said $C_1$-$C_4$-alkyl is optionally substituted, one or more times, independently from each other, with a substituent selected from hydroxy and halogen.

In a further embodiment of the above-mentioned aspects, the invention relates to compounds of formula (I), wherein E represents hydrogen, $C_1$-$C_3$-alkyl, $R^{18}$—O—C(O)—$C_1$-$C_2$-alkyl, or $R^7R^8N$—C(O)—$C_1$-$C_2$-alkyl,
wherein said $C_1$-$C_3$-alkyl is optionally substituted, one or more times, independently from each other, with a substituent selected from hydroxy and halogen.

In a further embodiment of the above-mentioned aspects, the invention relates to compounds of formula (I), wherein E represents hydrogen, $C_1$-$C_3$-alkyl, or $R^7R^8N$—C(O)—$C_1$-$C_2$-alkyl,
wherein said $C_1$-$C_3$-alkyl is optionally substituted one time with hydroxy and/or optionally substituted one, two or three times with fluorine.

In a further embodiment of the above-mentioned aspects, the invention relates to compounds of formula (I) or (Ia), wherein $R^5$ represents, independently from each other, halogen, hydroxy, amino, nitro, cyano, $C_1$-$C_4$-alkyl, $C_3$-$C_6$-cycloalkyl, $C_1$-$C_4$-alkoxy, $C_1$-$C_4$-haloalkyl, $C_1$-$C_4$-haloalkoxy or phenyl-$C_1$-$C_4$-alkyl,
wherein said phenyl group is optionally substituted, one or more times, independently from each other, with a substituent selected from halogen, hydroxy, $C_1$-$C_3$-alkyl, $C_1$-$C_3$-haloalkyl and $C_1$-$C_3$-alkoxy;
wherein said $C_3$-$C_6$-cycloalkyl group is optionally substituted, one or more times, independently from each other, with halogen.

In a further embodiment of the above-mentioned aspects, the invention relates to compounds of formula (I) or (Ia), wherein $R^5$ represents, independently from each other, halogen, hydroxy, amino, nitro, cyano, $C_1$-$C_4$-alkyl, $C_1$-$C_4$-alkoxy, $C_1$-$C_4$-haloalkyl, $C_1$-$C_4$-haloalkoxy or phenyl-$C_1$-$C_4$-alkyl,
wherein said phenyl group is optionally substituted, one or more times, independently from each other, with a substituent selected from halogen, hydroxy, $C_1$-$C_3$-alkyl, $C_1$-$C_3$-haloalkyl and $C_1$-$C_3$-alkoxy.

In a further embodiment of the above-mentioned aspects, the invention relates to compounds of formula (I) or (Ia), wherein $R^5$ represents, independently from each other, halogen, hydroxy, amino, nitro, cyano, $C_1$-$C_4$-alkyl, $C_1$-$C_3$-alkoxy, $C_1$-$C_3$-haloalkyl, $C_1$-$C_3$-haloalkoxy or phenyl-$C_1$-$C_4$-alkyl,
wherein said phenyl group is optionally substituted, one or more times, independently from each other, with $C_1$-$C_2$-alkoxy.

In a further embodiment of the above-mentioned aspects, the invention relates to compounds of formula (I) or (Ia), wherein $R^5$ represents, independently from each other, halogen, amino, $C_1$-$C_4$-alkyl, $C_1$-$C_2$-alkoxy, or phenyl-$C_1$-$C_2$-alkyl,
wherein said phenyl group is optionally substituted, one or more times, with $C_1$-alkoxy.

In a further embodiment of the above-mentioned aspects, the invention relates to compounds of formula (I) or (Ia), wherein $R^5$ represents, independently from each other, halogen, amino, $C_1$-$C_4$-alkyl, $C_1$-alkoxy, or phenyl-$C_1$-alkyl,
wherein said phenyl group is optionally substituted one time, with $C_1$-alkoxy.

In a further embodiment of the above-mentioned aspects, the invention relates to compounds of formula (I) or (Ia), wherein $R^5$ represents, independently from each other, fluorine, chlorine, amino, $C_1$-$C_4$-alkyl, $C_1$-alkoxy, or phenyl-$C_1$-alkyl.

In a further embodiment of the above-mentioned aspects, the invention relates to compounds of formula (I) or (Ia), wherein $R^5$ represents, independently from each other, halogen, hydroxy, amino, nitro, cyano, $C_1$-$C_4$-alkyl or $C_1$-$C_4$-alkoxy.

In a further embodiment of the above-mentioned aspects, the invention relates to compounds of formula (I) or (Ia), wherein $R^5$ represents, independently from each other, halogen, preferably F or Cl.

In a further embodiment of the above-mentioned aspects, the invention relates to compounds of formula (I) or (Ia), wherein $R^7$, $R^8$ represent, independently from each other, hydrogen, $C_1$-$C_4$-alkyl or tert-butyl-O—C(O)—.

In a further embodiment of the above-mentioned aspects, the invention relates to compounds of formula (I) or (Ia), wherein $R^7$, $R^8$ represent, independently from each other, hydrogen, $C_1$-$C_2$-alkyl or tert-butyl-O—C(O)—.

In a further embodiment of the above-mentioned aspects, the invention relates to compounds of formula (I) or (Ia), wherein $R^7$, $R^8$ represent, independently from each other, hydrogen, $C_1$-alkyl or tert-butyl-O—C(O)—;

In a further embodiment of the above-mentioned aspects, the invention relates to compounds of formula (I) or (Ia), wherein $R^7$, $R^8$ represent, independently from each other, hydrogen or $C_1$-$C_4$-alkyl.

In a further embodiment of the above-mentioned aspects, the invention relates to compounds of formula (I) or (Ia), wherein $R^7$, $R^8$ represent, independently from each other, hydrogen or $C_1$-$C_2$-alkyl.

In a further embodiment of the above-mentioned aspects, the invention relates to compounds of formula (I) or (Ia), wherein $R^7$ represents hydrogen.

In a further embodiment of the above-mentioned aspects, the invention relates to compounds of formula (I) or (Ia), wherein $R^9$, $R^{10}$ represent, independently from each other, hydrogen, $C_1$-$C_4$-alkyl, $C_3$-$C_6$-cyclo-alkyl-, $C_1$-$C_4$-haloalkyl-, phenyl or heteroaryl,
wherein said phenyl or heteroaryl group is optionally substituted, one or more times, independently from each other, with $R^5$; and
wherein said $C_1$-$C_4$-alkyl is optionally substituted, one or more times, independently from each other, with hydroxy, $C_1$-$C_4$-alkoxy, $C_1$-$C_4$-alkyl-S—, $C_3$-$C_6$-cycloalkyl, 4- to 6-membered heterocycloalkyl, phenyl, heteroaryl or $R^{18}$—O—C(O)—,
wherein said $C_3$-$C_6$-cycloalkyl or 4- to 6-membered heterocycloalkyl is optionally substituted, one or more times, independently from each other, with a substituent selected from halogen, $C_1$-$C_4$-alkyl and tert-butyl-O—C(O)—,
wherein said phenyl or heteroaryl group is optionally substituted, one or more times, independently from each other, with $R^5$.

In a further embodiment of the above-mentioned aspects, the invention relates to compounds of formula (I) or (Ia), wherein $R^9$ and $R^{10}$ together with the nitrogen atom to which they are attached form a 3- to 7-membered nitrogen containing heterocyclic ring, optionally containing one additional heteroatom selected from O, NH or S, and which may be optionally substituted, one or more times, independently from each other, with $R^5$.

In a further embodiment of the above-mentioned aspects, the invention relates to compounds of formula (I) or (Ia), wherein $R^9$ represents, hydrogen, $C_1$-$C_4$-alkyl, $C_3$-$C_6$-cyclo-alkyl-, $C_1$-$C_4$-haloalkyl-, phenyl or heteroaryl,
wherein said phenyl or heteroaryl group is optionally substituted, one or more times, independently from each other, with $R^5$; and
wherein said $C_1$-$C_4$-alkyl is optionally substituted, one or more times, independently from each other, with hydroxy, $C_1$-$C_4$-alkoxy, $C_1$-$C_4$-alkyl-S—, $C_3$-$C_6$-cycloalkyl, 4- to 6-membered heterocycloalkyl, phenyl, heteroaryl or $R^{18}$—O—C(O)—,
wherein said $C_3$-$C_6$-cycloalkyl or 4- to 6-membered heterocycloalkyl is optionally substituted, one or more times, independently from each other, with a substituent selected from halogen, $C_1$-$C_4$-alkyl and tert-butyl-O—C(O)—,
wherein said phenyl or heteroaryl group is optionally substituted, one or more times, independently from each other, with $R^5$; and $R^{10}$ represents hydrogen.

In a further embodiment of the above-mentioned aspects, the invention relates to compounds of formula (I) or (Ia), wherein
$R^{10}$ represents hydrogen.

In a further embodiment of the above-mentioned aspects, the invention relates to compounds of formula (I) or (Ia), wherein
$R^9$, $R^{10}$ represent, independently from each other, hydrogen, $C_1$-$C_4$-alkyl, $C_3$-$C_6$-cyclo-alkyl-, $C_1$-$C_4$-haloalkyl-, phenyl or heteroaryl,
    wherein said phenyl or heteroaryl group is optionally substituted, one or more times, independently from each other, with $R^5$; and
    wherein said $C_1$-$C_4$-alkyl is optionally substituted, one or more times, independently from each other, with hydroxy, $C_1$-$C_4$-alkoxy, $C_1$-$C_4$-alkyl-S—, $C_3$-$C_6$-cycloalkyl, 4- to 6-membered heterocycloalkyl, phenyl, heteroaryl or $R^{18}$—O—C(O)—,
        wherein said $C_3$-$C_6$-cycloalkyl or 4- to 6-membered heterocycloalkyl is optionally substituted, one or more times, independently from each other, with a substituent selected from halogen, $C_1$-$C_4$-alkyl and tert-butyl-O—C(O)—,
        wherein said phenyl or heteroaryl group is optionally substituted, one or more times, independently from each other, with $R^5$; or
$R^9$ and $R^{10}$ together with the nitrogen atom to which they are attached form a 3- to 7-membered nitrogen containing heterocyclic ring, optionally containing one additional heteroatom selected from O, NH or S, and which may be optionally substituted, one or more times, independently from each other, with $R^5$.

In a further embodiment of the above-mentioned aspects, the invention relates to compounds of formula (I) or (Ia), wherein
$R^9$, $R^{10}$ represent, independently from each other, hydrogen, $C_1$-$C_4$-alkyl, $C_3$-$C_6$-cyclo-alkyl-, $C_1$-$C_4$-haloalkyl-, phenyl or heteroaryl,
    wherein said phenyl or heteroaryl group is optionally substituted, one or more times, independently from each other, with $R^5$; and
    wherein said $C_1$-$C_4$-alkyl is optionally substituted, one or more times, independently from each other, with a substituent selected from hydroxy, $C_1$-$C_2$-alkoxy, $C_1$-$C_2$-alkyl-S—, $C_3$-$C_6$-cycloalkyl, 4- to 6-membered heterocycloalkyl, phenyl, heteroaryl and $R^{18}$—O—C(O)—,
        wherein said 4- to 6-membered heterocycloalkyl is optionally substituted, one or more times, independently from each other, with a substituent selected from $C_1$-$C_2$-alkyl and tert-butyl-O—C(O)—,
        wherein said phenyl or heteroaryl group is optionally substituted, one or more times, independently from each other, with $R^5$; or
$R^9$ and $R^{10}$ together with the nitrogen atom to which they are attached form a 3- to 7-membered nitrogen containing heterocyclic ring, optionally containing one additional heteroatom selected from O, and NH, and which may be optionally substituted, one or more times, independently from each other, with $R^5$.

In a further embodiment of the above-mentioned aspects, the invention relates to compounds of formula (I) or (Ia), wherein
$R^9$, $R^{10}$ represent, independently from each other, hydrogen, $C_1$-$C_4$-alkyl, $C_3$-$C_6$-cyclo-alkyl-, $C_1$-$C_4$-haloalkyl-, phenyl or heteroaryl,
    wherein said phenyl or heteroaryl group is optionally substituted, one or more times, independently from each other, with $R^5$; and
    wherein said $C_1$-$C_4$-alkyl is optionally substituted, one or more times, independently from each other, with a substituent selected from hydroxy, $C_1$-alkoxy, $C_1$-alkyl-S—, $C_3$-$C_6$-cycloalkyl, 4- to 6-membered heterocycloalkyl, phenyl, heteroaryl and $R^{18}$—O—C(O)—,
        wherein said 4- to 6-membered heterocycloalkyl is optionally substituted, one time with tert-butyl-O—C(O)—,
    wherein said phenyl or heteroaryl group is optionally substituted, one or more times, independently from each other, with $R^5$.

In a further embodiment of the above-mentioned aspects, the invention relates to compounds of formula (I) or (Ia), wherein
$R^9$, $R^{10}$ represent, independently from each other, hydrogen, $C_1$-$C_4$-alkyl, $C_3$-$C_4$-cyclo-alkyl-, $C_1$-$C_3$-haloalkyl-, phenyl or heteroaryl,
    wherein said phenyl or heteroaryl group is optionally substituted, one or more times, independently from each other, with $R^5$; and
    wherein said $C_1$-$C_4$-alkyl is optionally substituted, one or more times, independently from each other, with a substituent selected from hydroxy, $C_1$-alkoxy, $C_1$-alkyl-S—, $C_3$-cycloalkyl, heteroaryl and $R^{18}$—O—C(O)—.

In a further embodiment of the above-mentioned aspects, the invention relates to compounds of formula (I) or (Ia), wherein
$R^9$, $R^{10}$ represent, independently from each other, hydrogen, $C_1$-$C_3$-alkyl, $C_3$-$C_4$-cyclo-alkyl-, $C_1$-$C_3$-haloalkyl-, or heteroaryl,
    wherein said heteroaryl group is optionally substituted, one time with $R^5$; and
    wherein said $C_1$-$C_3$-alkyl is optionally substituted, one or more times, independently from each other, with a substituent selected from hydroxy, $C_1$-alkoxy, $C_1$-alkyl-S—, $C_3$-cycloalkyl, and heteroaryl.

In a further embodiment of the above-mentioned aspects, the invention relates to compounds of formula (I) or (Ia), wherein
$R^9$, $R^{10}$ represent, independently from each other, hydrogen, $C_1$-$C_4$-alkyl, $C_3$-$C_6$-cycloalkyl-, $C_1$-$C_4$-haloalkyl- or phenyl, wherein said phenyl group is optionally substituted, one or more times, independently from each other, with $R^5$; or
$R^9$ and $R^{10}$ together with the nitrogen atom to which they are attached form a 3- to 7-membered nitrogen containing heterocyclic ring, optionally containing at least one additional heteroatom selected from O, NH or S, and which may be optionally substituted, one or more times, independently from each other, with $R^5$.

In a further embodiment of the above-mentioned aspects, the invention relates to compounds of formula (I) or (Ia), wherein
$R^9$, $R^{10}$ represent, independently from each other, hydrogen, $C_1$-$C_4$-alkyl, $C_3$-$C_6$-cycloalkyl-, $C_1$-$C_4$-haloalkyl- or phenyl, wherein said phenyl group is optionally substituted, one or more times, independently from each other, with $R^5$.

In a further embodiment of the above-mentioned aspects, the invention relates to compounds of formula (I) or (Ia), wherein $R^9$, $R^{10}$ represent, independently from each other, hydrogen, $C_1$-$C_4$-alkyl or phenyl, wherein said phenyl group is optionally substituted, one or more times, independently from each other, with $R^5$.

In a further embodiment of the above-mentioned aspects, the invention relates to compounds of formula (I) or (Ia), wherein $R^9$, $R^{10}$ represent, independently from each other, hydrogen, $C_1$-$C_2$-alkyl or phenyl, wherein said phenyl group is optionally substituted, one or more times, independently from each other, with $R^5$, preferably hydrogen, methyl or phenyl substituted with F.

In a further embodiment of the above-mentioned aspects, the invention relates to compounds of formula (I) or (Ia), wherein $R^9$ represents hydrogen and $R^{10}$ represents hydrogen, $C_1$-$C_4$-alkyl or phenyl, wherein said phenyl group is optionally substituted, one or more times, independently from each other, with $R^5$.

In a further embodiment of the above-mentioned aspects, the invention relates to compounds of formula (I) or (Ia), wherein $R^9$ and $R^{10}$ together with the nitrogen atom to which they are attached form a 3- to 7-membered nitrogen containing heterocyclic ring, optionally containing at least one additional heteroatom selected from O, NH or S, and which may be optionally substituted, one or more times, independently from each other, with $R^5$.

In a further embodiment of the above-mentioned aspects, the invention relates to compounds of formula (I) or (Ia), wherein $R^9$ and $R^{10}$ together with the nitrogen atom to which they are attached form a 4- to 6-membered nitrogen containing heterocyclic ring, optionally containing at least one additional heteroatom selected from O, NH or S, and which may be optionally substituted, one or more times, independently from each other, with $R^5$.

In a further embodiment of the above-mentioned aspects, the invention relates to compounds of formula (I) or (Ia), wherein $R^9$ and $R^{10}$ together with the nitrogen atom to which they are attached form a 4- to 6-membered nitrogen containing heterocyclic ring, optionally containing at least one additional heteroatom selected from O, NH or S.

In a further embodiment of the above-mentioned aspects, the invention relates to compounds of formula (I) or (Ia), wherein $R^9$ and $R^{10}$ together with the nitrogen atom to which they are attached form a 5- to 6-membered nitrogen containing heterocyclic ring, optionally containing at least one additional heteroatom selected from O.

In a further embodiment of the above-mentioned aspects, the invention relates to compounds of formula (I) or (Ia), wherein $R^{11}$, $R^{12}$ represent, independently from each other, $C_1$-$C_4$-alkyl, $C_2$-$C_4$-alkenyl, $C_2$-$C_4$-alkynyl, $C_3$-$C_6$-cycloalkyl, 4- to 6-membered heterocycloalkyl, phenyl, heteroaryl, or $R^{13}$—($C_1$-$C_4$-alkyl)-O—$CH_2$—,
wherein said $C_1$-$C_4$-alkyl is optionally substituted, one or more times, independently from each other, with a substituent selected from halogen, hydroxy, cyano, $C_1$-$C_4$-alkoxy, $R^7R^8N$—, $R^{14}$, $R^{15}$—O—, and phenyl optionally substituted, one or more times, independently from each other, with $R^5$, and
wherein said $C_3$-$C_6$-cycloalkyl is optionally substituted, one or more times, independently from each other, with a substituent selected from halogen, cyano, $C_1$-$C_4$-alkyl, $C_1$-$C_4$-haloalkyl and phenyl optionally substituted, one or more times, independently from each other, with $R^5$, and
wherein said 4- to 6-membered heterocycloalkyl is optionally substituted, one or more times, independently from each other, with a substituent selected from hydroxy, $C_1$-$C_4$-alkyl, $C_1$-$C_4$-alkoxy, $R^7R^8N$— and $R^{18}$—O—C(O)—, and
wherein said phenyl or heteroaryl is optionally substituted, one or more times, independently from each other, with $R^5$.

In a further embodiment of the above-mentioned aspects, the invention relates to compounds of formula (I) or (Ia), wherein $R^{11}$, $R^{12}$ represent, independently from each other, $C_1$-$C_4$-alkyl, $C_2$-$C_4$-alkenyl, $C_2$-$C_4$-alkynyl, $C_3$-$C_6$-cycloalkyl, 4- to 6-membered heterocycloalkyl, or $R^{13}$—($C_1$-$C_4$-alkyl)-O—$CH_2$—,
wherein said $C_1$-$C_4$-alkyl is optionally substituted, one or more times, independently from each other, with a substituent selected from halogen, hydroxy, cyano, $C_1$-$C_4$-alkoxy, $R^7R^8N$—, $R^{14}$, $R^{15}$—O—, and phenyl optionally substituted, one or more times, independently from each other, with $R^5$, and
wherein said $C_3$-$C_6$-cycloalkyl is optionally substituted, one or more times, independently from each other, with a substituent selected from halogen, cyano, $C_1$-$C_4$-alkyl, $C_1$-$C_4$-haloalkyl and phenyl optionally substituted, one or more times, independently from each other, with $R^5$, and
wherein said 4- to 6-membered heterocycloalkyl is optionally substituted, one or more times, independently from each other, with a substituent selected from hydroxy, $C_1$-$C_4$-alkyl, $C_1$-$C_4$-alkoxy, $R^7R^8N$— and $R^{18}$—O—C(O)—.

In a further embodiment of the above-mentioned aspects, the invention relates to compounds of formula (I) or (Ia), wherein $R^{11}$, $R^{12}$ represent, independently from each other, phenyl, or heteroaryl,
wherein said phenyl or heteroaryl is optionally substituted, one or more times, independently from each other, with $R^5$.

In a further embodiment of the above-mentioned aspects, the invention relates to compounds of formula (I) or (Ia), wherein $R^{11}$, $R^{12}$ represent, independently from each other, $C_1$-$C_4$-alkyl, $C_3$-$C_6$-cycloalkyl, 4- to 6-membered heterocycloalkyl, phenyl, heteroaryl, $R^{13}$—$(CH_2)_o$—O—$CH_2$—, $R^{14}$—$(CH_2)_o$—, or $R^{15}$—O—$(CH_2)_o$—,
wherein said $C_1$-$C_4$-alkyl is optionally substituted, one or more times, independently from each other, with a substituent selected from halogen, hydroxy, cyano, $C_1$-$C_4$-alkoxy, $R^7R^8N$—, and phenyl optionally substituted, one or more times, independently from each other, with $R^5$, and
wherein said $C_3$-$C_6$-cycloalkyl is optionally substituted, one or more times, independently from each other, with a substituent selected from halogen, cyano, $C_1$-$C_2$-alkyl, $C_1$-$C_2$-haloalkyl and phenyl optionally substituted, one or more times, independently from each other, with $R^5$, and
wherein said 4- to 6-membered heterocycloalkyl is optionally substituted, one or more times, independently from each other, with a substituent selected from hydroxy, $C_1$-$C_2$-alkyl, $C_1$-$C_2$-alkoxy, $R^7R^8N$— and $R^{18}$—O—C(O)—, and wherein said phenyl or heteroaryl is optionally substituted, one or more times, independently from each other, with $R^5$.

In a further embodiment of the above-mentioned aspects, the invention relates to compounds of formula (I) or (Ia), wherein $R^{11}$, $R^{12}$ represent, independently from each other, $C_1$-$C_4$-alkyl, $C_3$-$C_6$-cycloalkyl, 4- to 6-membered heterocycloalkyl, phenyl, heteroaryl, $R^{13}$—$(CH_2)_o$—O—$CH_2$—, $R^{14}$—$(CH_2)_o$—, or $R^{15}$—O—$(CH_2)_o$—, wherein said $C_1$-$C_4$-alkyl is optionally substituted, one or more times, independently from each other, with a substituent selected from halogen, hydroxy, cyano, $C_1$-$C_4$-alkoxy, $R^7R^8N$—, and phenyl optionally substituted, one or more times, independently from each other, with $R^5$, and wherein said $C_3$-$C_6$-cycloalkyl is optionally substituted, one or two times, independently from each other, with a substituent selected from halogen, cyano, $C_1$-$C_2$-alkyl, $C_1$-$C_2$-haloalkyl and phenyl optionally substituted, one or more times, independently from each other, with $R^5$, and wherein said 4- to 6-membered heterocycloalkyl is optionally substituted, one or more times, independently from each other, with a substituent selected from $C_1$-$C_2$-alkyl, and $R^{18}$—O—C(O)—, and wherein said phenyl or heteroaryl is optionally substituted, one or more times, independently from each other, with $R^5$.

In a further embodiment of the above-mentioned aspects, the invention relates to compounds of formula (I) or (Ia), wherein $R^{11}$, $R^{12}$ represent, independently from each other, $C_1$-$C_4$-alkyl, $C_3$-$C_4$-cycloalkyl, 4- to 6-membered heterocycloalkyl, phenyl, heteroaryl, $R^{13}$—$(CH_2)_o$—O—$CH_2$—, $R^{14}$—$(CH_2)_o$—, or $R^{15}$—O—$(CH_2)_o$—, wherein said $C_1$-$C_4$-alkyl is optionally substituted, one or more times, independently from each other, with a substituent selected from halogen, hydroxy, cyano, $C_1$-$C_4$-alkoxy, $R^7R^8N$—, and phenyl optionally substituted, one or more times, independently from each other, with $R^5$, and wherein said $C_3$-$C_4$-cycloalkyl is optionally substituted, one or two times, independently from each other, with halogen, cyano, $C_1$-alkyl, $C_1$-haloalkyl or phenyl optionally substituted, one or more times, independently from each other, with $R^5$, and wherein said 4- to 6-membered heterocycloalkyl is optionally substituted, one or more times, independently from each other, with a substituent selected from $C_1$-alkyl, and $R^{18}$—O—C(O)—, and wherein said phenyl or heteroaryl is optionally substituted, one or two times, independently from each other, with $R^5$.

In a further embodiment of the above-mentioned aspects, the invention relates to compounds of formula (I) or (Ia), wherein $R^{11}$, $R^{12}$ represent, independently from each other, $C_1$-$C_4$-alkyl, $C_3$-$C_4$-cycloalkyl, 4- to 5-membered heterocycloalkyl, phenyl, heteroaryl, $R^{13}$—$(CH_2)_o$—O—$CH_2$—, $R^{14}$—$(CH_2)_o$—, or $R^{15}$—O—$(CH_2)_o$—, wherein said $C_1$-$C_4$-alkyl is optionally substituted, one or more times, independently from each other, with a substituent selected from halogen, hydroxy, cyano, $C_1$-$C_4$-alkoxy, $R^7R^8N$—, and phenyl optionally substituted, one or more times, independently from each other, with $R^5$, and wherein said $C_3$-$C_4$-cycloalkyl is optionally substituted, one or two times, independently from each other, with a substituent selected from fluorine, cyano, $C_1$-alkyl, —$CF_3$ and phenyl, and wherein said 4- to 6-membered heterocycloalkyl is optionally substituted, one or more times, independently from each other, with $C_1$-alkyl, or $R^{18}$—O—C(O)—, wherein said phenyl or heteroaryl is optionally substituted, one or two times, independently from each other, with $R^5$.

In a further embodiment of the above-mentioned aspects, the invention relates to compounds of formula (I) or (Ia), wherein $R^{11}$, $R^{12}$ represent, independently from each other, $C_1$-$C_4$-alkyl, $C_3$-$C_6$-cycloalkyl- or $C_1$-$C_4$-haloalkyl-.

In a further embodiment of the above-mentioned aspects, the invention relates to compounds of formula (I) or (Ia), wherein $R^{11}$, $R^{12}$ represent, independently from each other, $C_1$-$C_4$-alkyl, $C_3$-$C_6$-cycloalkyl- or $C_1$-$C_2$-haloalkyl-.

In a further embodiment of the above-mentioned aspects, the invention relates to compounds of formula (I) or (Ia), wherein $R^{11}$, $R^{12}$ represent, independently from each other, $C_1$-$C_4$-alkyl or $C_3$-$C_6$-cycloalkyl-.

In a further embodiment of the above-mentioned aspects, the invention relates to compounds of formula (I) or (Ia), wherein $R^{11}$, $R^{12}$ represent, independently from each other, methyl, ethyl, isopropyl, cyclopropyl or —$CHF_2$.

In a further embodiment of the above-mentioned aspects, the invention relates to compounds of formula (I) or (Ia), wherein $R^{11}$, $R^{12}$ represent, independently from each other, methyl, ethyl, isopropyl, cyclopropyl or —$CHF_2$.

In a further embodiment of the above-mentioned aspects, the invention relates to compounds of formula (I) or (Ia), wherein $R^{11}$ represents, independently from each other, $C_1$-$C_4$-alkyl, $C_3$-$C_6$-cycloalkyl- or $C_1$-$C_4$-haloalkyl-.

In a further embodiment of the above-mentioned aspects, the invention relates to compounds of formula (I), wherein $R^{13}$ represents branched $C_3$-$C_4$-alkyl, $C_1$-$C_4$-haloalkyl, $C_2$-$C_4$-alkenyl, $C_2$-$C_4$-alkynyl, $C_3$-$C_6$-cycloalkyl, 4- to 6-membered heterocycloalkyl, phenyl or heteroaryl, wherein said phenyl or heteroaryl is optionally substituted, one or more times, independently from each other, with $R^5$.

In a further embodiment of the above-mentioned aspects, the invention relates to compounds of formula (I), wherein $R^{13}$ represents branched $C_3$-$C_4$-alkyl, $C_1$-$C_2$-haloalkyl, $C_2$-$C_3$-alkenyl, $C_2$-$C_3$-alkynyl, $C_3$-$C_6$-cycloalkyl, 4- to 6-membered heterocycloalkyl, phenyl or heteroaryl, wherein said phenyl or heteroaryl is optionally substituted, one or more times, independently from each other, with $R^5$.

In a further embodiment of the above-mentioned aspects, the invention relates to compounds of formula (I), wherein $R^{13}$ represents branched $C_3$-$C_4$-alkyl, $C_1$-$C_2$-haloalkyl, $C_2$-$C_3$-alkenyl, $C_2$-$C_3$-alkynyl, 4- to 6-membered heterocycloalkyl, phenyl or heteroaryl,
  wherein said phenyl or heteroaryl is optionally substituted, one or more times, independently from each other, with $R^5$.

In a further embodiment of the above-mentioned aspects, the invention relates to compounds of formula (I), wherein $R^{13}$ represents branched $C_3$-alkyl, $C_1$-$C_2$-haloalkyl, $C_2$-alkenyl, $C_2$-alkynyl, 4- to 6-membered heterocycloalkyl, phenyl or heteroaryl,
  wherein said phenyl or heteroaryl is optionally substituted, one or two times, independently from each other, with $R^5$.

In a further embodiment of the above-mentioned aspects, the invention relates to compounds of formula (I), wherein $R^{13}$ represents branched $C_3$-alkyl, $C_1$-$C_2$-haloalkyl, $C_2$-alkenyl, $C_2$-alkynyl, 6-membered heterocycloalkyl, phenyl or heteroaryl,
  wherein said phenyl or heteroaryl is optionally substituted, one time, with $R^5$.

In a further embodiment of the above-mentioned aspects, the invention relates to compounds of formula (I), wherein $R^{14}$ represents $C_1$-$C_4$-alkyl-S—, $C_1$-$C_4$-alkyl-$SO_2$—, $C_3$-$C_6$-cycloalkyl, 4- to 6-membered heterocycloalkyl, phenyl or heteroaryl,
  wherein said phenyl or heteroaryl is optionally substituted, one or more times, independently from each other, with $R^5$.

In a further embodiment of the above-mentioned aspects, the invention relates to compounds of formula (I), wherein $R^{14}$ represents $C_1$-$C_2$-alkyl-S—, $C_1$-$C_2$-alkyl-$SO_2$—, $C_3$-$C_6$-cycloalkyl, 4- to 6-membered heterocycloalkyl, phenyl or heteroaryl,
  wherein said phenyl or heteroaryl is optionally substituted, one or more times, independently from each other, with $R^5$.

In a further embodiment of the above-mentioned aspects, the invention relates to compounds of formula (I), wherein $R^{14}$ represents $C_1$-alkyl-S—, $C_1$-alkyl-$SO_2$—, $C_3$-$C_4$-cycloalkyl, 4- to 6-membered heterocycloalkyl, phenyl or heteroaryl,
  wherein said phenyl or heteroaryl is optionally substituted, one or two times, independently from each other, with $R^5$.

In a further embodiment of the above-mentioned aspects, the invention relates to compounds of formula (I), wherein $R^{14}$ represents $C_1$-alkyl-S—, $C_1$-alkyl-$SO_2$—, $C_3$-cycloalkyl, 5-membered heterocycloalkyl, phenyl or heteroaryl,
  wherein said phenyl or heteroaryl is optionally substituted, one time, with $R^5$.

In a further embodiment of the above-mentioned aspects, the invention relates to compounds of formula (I), wherein $R^{15}$ represents phenyl or heteroaryl,
  wherein said phenyl or heteroaryl is optionally substituted, one or more times, independently from each other, with $R^5$.

In a further embodiment of the above-mentioned aspects, the invention relates to compounds of formula (I), wherein $R^{15}$ represents phenyl or heteroaryl,
  wherein said phenyl or heteroaryl is optionally substituted, one or more times, independently from each other, with $R^5$.

In a further embodiment of the above-mentioned aspects, the invention relates to compounds of formula (I), wherein $R^{15}$ represents phenyl or heteroaryl.

In a further embodiment of the above-mentioned aspects, the invention relates to compounds of formula (I) or (Ia), wherein
n represents 0, 1, or 2.

In a further embodiment of the above-mentioned aspects, the invention relates to compounds of formula (I) or (Ia), wherein
n represents 0, 1, 2 or 3.

In a further embodiment of the above-mentioned aspects, the invention relates to compounds of formula (I) or (Ia), wherein
n represents 0.

In a further embodiment of the above-mentioned aspects, the invention relates to compounds of formula (I), wherein $R^{16}$ represents hydrogen, $C_1$-$C_6$-alkyl, phenyl or $C_1$-$C_4$-alkyl-C(O)—,
  wherein said phenyl group is optionally substituted, one or more times, independently from each other, with $R^5$.

In a further embodiment of the above-mentioned aspects, the invention relates to compounds of formula (I), wherein $R^{16}$ represents hydrogen, $C_1$-$C_2$-alkyl, or $C_1$-$C_2$-alkyl-C(O)—.

In a further embodiment of the above-mentioned aspects, the invention relates to compounds of formula (I), wherein $R^{16}$ represents hydrogen, or $C_1$-$C_2$-alkyl-C(O)—.

In a further embodiment of the above-mentioned aspects, the invention relates to compounds of formula (I), wherein $R^{16}$ represents hydrogen, or $C_1$-alkyl-C(O)—.

In a further embodiment of the above-mentioned aspects, the invention relates to compounds of formula (I), wherein $R^{17a}$, $R^{17b}$, $R^{17c}$ represent, independently from each other, $C_1$-$C_4$-alkyl;

In a further embodiment of the above-mentioned aspects, the invention relates to compounds of formula (I), wherein $R^{18}$ represents hydrogen or $C_1$-$C_6$-alkyl.

In a further embodiment of the above-mentioned aspects, the invention relates to compounds of formula (I), wherein $R^{18}$ represents hydrogen or $C_1$-$C_4$-alkyl.

In a further embodiment of the above-mentioned aspects, the invention relates to compounds of formula (I), wherein:
$R^{21}$ represents hydrogen, $C_1$-$C_4$-alkyl, $C_1$-$C_4$-haloalkyl, or $C_1$-$C_6$-cycloalkyl optionally substituted, one or more times, independently from each other, with halogen.

In a further embodiment of the above-mentioned aspects, the invention relates to compounds of formula (I), wherein:
$R^{22}$ represents hydrogen, halogen, $C_1$-$C_4$-alkyl, $C_1$-$C_4$-haloalkyl, or $C_1$-$C_6$-cycloalkyl optionally substituted, one or more times, independently from each other, with halogen.

In a further embodiment of the above-mentioned aspects, the invention relates to compounds of formula (I) or (Ia), wherein
m represents 0, 1 or 2.

In a further embodiment of the above-mentioned aspects, the invention relates to compounds of formula (I) or (Ia), wherein
m represents 0 or 1.

In a further embodiment of the above-mentioned aspects, the invention relates to compounds of formula (I) or (Ia), wherein
m represents 0, 1 or 2.

In a further embodiment of the above-mentioned aspects, the invention relates to compounds of formula (I) or (Ia), wherein
m represents 0, or 1.

In a further embodiment of the above-mentioned aspects, the invention relates to compounds of formula (I), wherein
o represents 1, 2, 3 or 4.

In a further embodiment of the above-mentioned aspects, the invention relates to compounds of formula (I), wherein o represents 1, or 2.

A further aspect of the invention are compounds of formula (I), which are present as their salts.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

Another embodiment of the invention are compounds according to the claims as disclosed in the Claims section wherein the definitions are limited according to the preferred or more preferred definitions as disclosed below or specifically disclosed residues of the exemplified compounds and subcombinations thereof.

DEFINITIONS

Constituents which are optionally substituted as stated herein, may be substituted, unless otherwise noted, one or more times, independently from one another at any possible position. When any variable occurs more than one time in any constituent, each definition is independent. For example, when $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17a}$, $R^{17b}$, $R^{17c}$, $R^{18}$, $R^{21}$, $R^{22}$, X and/or Y occur more than one time in any compound of formula (I) each definition of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17a}$, $R^{17b}$, $R^{17c}$, $R^{18}$, $R^{21}$, $R^{22}$, X and Y is independent.

Should a constituent be composed of more than one part, e.g. $C_1$-$C_4$-alkoxy-$C_1$-$C_4$-alkyl-, the position of a possible substituent can be at any of these parts at any suitable position.

A hyphen at the beginning of the constituent marks the point of attachment to the rest of the molecule. Should a ring be substituted the substitutent could be at any suitable position of the ring, also on a ring nitrogen atom if suitable.

The term "comprising" when used in the specification includes "consisting of".

For the purpose of the present invention the terms "A" and "ring A" within the context of the structure of the compounds of formula (I) or (II) can be used interchangeably. Similarly, for the purpose of the present invention the terms "B" and "ring B" within the context of the structure of the compounds of formula (I) or (II) can be used interchangeably.

If it is referred to "as mentioned above" or "mentioned above" within the description it is referred to any of the disclosures made within the specification in any of the preceding pages.

"suitable" within the sense of the invention means chemically possible to be made by methods within the knowledge of a skilled person.

The terms as mentioned in the present text have preferably the following meanings:

The term "halogen atom", "halo-" or "Hal-" is to be understood as meaning a fluorine, chlorine, bromine or iodine atom, preferably a fluorine, chlorine, bromine or iodine atom.

The term "$C_1$-$C_4$-alkyl" is to be understood as preferably meaning a linear or branched, saturated, monovalent hydrocarbon group having 1, 2, 3 or 4 carbon atoms, e.g. a methyl, ethyl, propyl, butyl, iso-propyl, iso-butyl, sec-butyl, tert-butyl group, particularly 1, 2 or 3 carbon atoms ("$C_1$-$C_3$-alkyl"), e.g. a methyl, ethyl, n-propyl- or iso-propyl group.

The term "$C_2$-$C_4$-alkenyl" is to be understood as meaning a linear or branched, monovalent hydrocarbon group, which contains one or two double bonds, and which has 2, 3 or 4 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, iso-propenyl, 2-methylprop-2-enyl, 1-methylprop-2-enyl, 2-methylprop-1-enyl, (E)-1-methylprop-1-enyl, (Z)-1-methylprop-1-enyl, or buta-1,3-dienyl group. Particularly, said group is vinyl or allyl.

The term "$C_2$-$C_4$-alkynyl" is to be understood as meaning a linear or branched, monovalent hydrocarbon group which contains one triple bond, and which contains 2, 3, or 4 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, or 1-methylprop-2-ynyl group. Particularly, said alkynyl group is ethynyl, prop-1-ynyl or prop-2-ynyl.

The term "$C_1$-$C_4$-haloalkyl" is to be understood as preferably meaning a linear or branched, saturated, monovalent hydrocarbon group in which the term "$C_1$-$C_4$-alkyl" is defined supra, and in which one or more hydrogen atoms is replaced by a halogen atom, in identically or differently, i.e. one halogen atom being independent from another. Particularly, said halogen atom is F. Said $C_1$-$C_4$-haloalkyl group is, for example, —$CF_3$, —$CHF_2$, —$CH_2F$, —$CF_2CF_3$, or —$CH_2CF_3$.

The term "$C_1$-$C_4$-alkoxy" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy or sec-butoxy group, or an isomer thereof.

The term "$C_1$-$C_4$-haloalkoxy" is to be understood as preferably meaning a linear or branched, saturated, monovalent $C_1$-$C_4$-alkoxy group, as defined supra, in which one or more of the hydrogen atoms is replaced, in identically or differently, by a halogen atom. Particularly, said halogen atom is F. Said $C_1$-$C_4$-haloalkoxy group is, for example, —$OCF_3$, —$OCHF_2$, —$OCH_2F$, —$OCF_2CF_3$, or —$OCH_2CF_3$.

The term "$C_1$-$C_4$-alkoxy-$C_1$-$C_4$-alkyl" is to be understood as preferably meaning a linear or branched, saturated, monovalent alkyl group, as defined supra, in which one or more of the hydrogen atoms is replaced, in identically or differently, by a $C_1$-$C_4$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl or sec-butoxyalkyl group, in which the term "$C_1$-$C_4$-alkyl" is defined supra, or an isomer thereof.

The term "$C_3$-$C_6$-cycloalkyl" is to be understood as meaning a saturated, monovalent, mono-, or bicyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl, or a bicyclic hydrocarbon ring.

The term "heteroaryl" is understood as meaning a monovalent, monocyclic, aromatic ring system having 5, or 6, ring atoms (a "5- to 6-membered heteroaryl" group), which contains at least one ring heteroatom atom and optionally one, two or three further ring heteroatoms from the series N, $NR^5$, O and/or S, and which is bound via a ring carbon atom or, unless otherwise defined, optionally via a ring nitrogen atom (when allowed by valency). $R^5$ is as defined herein.

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl. In general, and unless otherwise mentioned, the heteroarylic or heteroarylenic radicals include all the possible isomeric forms thereof, e.g.: tautomers and positional isomers with respect to the point of linkage to the rest of the molecule. Thus, for some illustrative non-restricting example, the term pyridinyl includes pyridin-2-yl, pyridin-3-yl and pyridin-4-yl; or the term thienyl includes thien-2-yl and thien-3-yl.

The term "3- to 7-membered heterocycloalkyl" or "3- to 7-membered heterocyclic ring", is to be understood as meaning a saturated, monovalent, mono- or bicyclic hydrocarbon ring which contains 2, 3, 4, 5 or 6, carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl-, $C_1$-$C_6$-haloalkyl- or tert-butyl-O—C(O)— group; it being possible for said heterocycloalkyl group to be attached to the rest of the molecule via any one of the carbon atoms or, if present, the nitrogen atom.

Particularly, said 3- to 7-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, the term "4- to 6-membered heterocycloalkyl" is to be understood as meaning a monocyclic, saturated heterocycle with 4 to 6 ring atoms in total, which contains one or two identical or different ring heteroatoms from the series C(=O), O, S, S(=O), S(=O)$_2$, NR$^a$, in which R$^a$ represents a hydrogen atom, or a $C_1$-$C_6$-alkyl-, $C_1$-$C_6$-haloalkyl- or tert-butyl-O—C(O)— group; it being possible for said heterocycloalkyl group to be attached to the rest of the molecule via any one of the carbon atoms or, if present, a nitrogen atom. 4- to 6-Membered heterocycloalkyl containing one ring nitrogen atom and optionally one further ring heteroatom from the series N, NR$^a$, O or S(=O)$_2$ is preferred. 5- or 6-membered heterocycloalkyl containing one ring nitrogen atom and optionally one further ring heteroatom from the series N, NR$^a$, or O is particularly preferred.

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example. Optionally, said heterocycloalkyl can be benzo fused.

Said heterocyclyl can be bicyclic, such as, without being limited thereto, a 5,5-membered ring, e.g. a hexahydrocyclopenta[c]pyrrol-2(1H)-yl ring, or a 5,6-membered bicyclic ring, e.g. a hexahydropyrrolo[1,2-a]pyrazin-2(1H)-yl ring.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term "$C_1$-$C_4$", as used throughout this text, e.g. in the context of the definition of "$C_1$-$C_4$-alkyl", "$C_1$-$C_4$-haloalkyl", "$C_1$-$C_4$-alkoxy", or "$C_1$-$C_4$-haloalkoxy" is to be understood as meaning an alkyl group having a finite number of carbon atoms of 1 to 4, i.e. 1, 2, 3 or 4 carbon atoms. It is to be understood further that said term "$C_1$-$C_4$" is to be interpreted as any sub-range comprised therein, e.g. $C_1$-$C_4$, $C_2$-$C_4$, $C_3$-$C_4$, $C_1$-$C_2$, $C_1$-$C_3$, particularly $C_1$-$C_2$, $C_1$-$C_3$, $C_1$-$C_4$, in the case of "$C_1$-$C_6$-haloalkyl" or "$C_1$-$C_4$-haloalkoxy" even more particularly $C_1$-$C_2$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The $R^7R^8N$—C(O)— group include, for example, —C(O)NH$_2$, —C(O)N(H)CH$_3$, —C(O)N(CH$_3$)$_2$, —C(O)N(H)CH$_2$CH$_3$, —C(O)N(CH$_3$)CH$_2$CH$_3$ or —C(O)N(CH$_2$CH$_3$)$_2$.

The $R^9R^{10}N$-group includes, for example, —NH$_2$, —N(H)CH$_3$, —N(CH$_3$)$_2$, —N(H)CH$_2$CH$_3$ and —N(CH$_3$)CH$_2$CH$_3$. In the case of $R^9R^{10}N$—, when $R^9$ and $R^{10}$ together with the nitrogen atom to which they are attached form a 3- to 7-membered nitrogen containing heterocyclic ring optionally containing one further heteroatom (or a heteroatom-containing group) selected from the group consisting of O, S, N and NH, the term "heterocyclic ring" is defined above. Especially preferred is pyrrolidinyl and morpholinyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^{2}$H (deuterium), $^{3}$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^{3}$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel O D and Chiracel O J among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

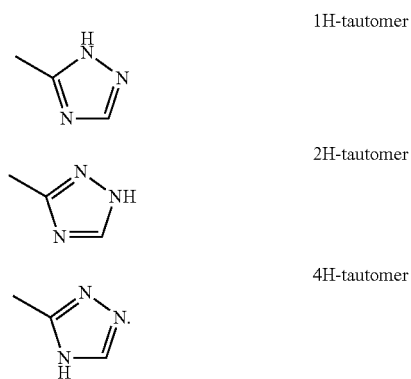

An example of tautomers of the present invention is shown below (these can exist alone or in any mixture of the three tautomers in any ratio).

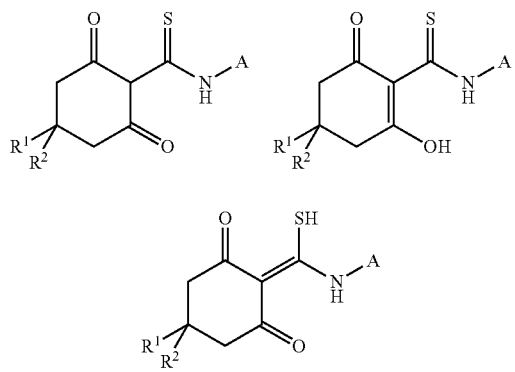

An example of tautomers of the present invention is shown below (these can exist alone or in any mixture of the three tautomers in any ratio).

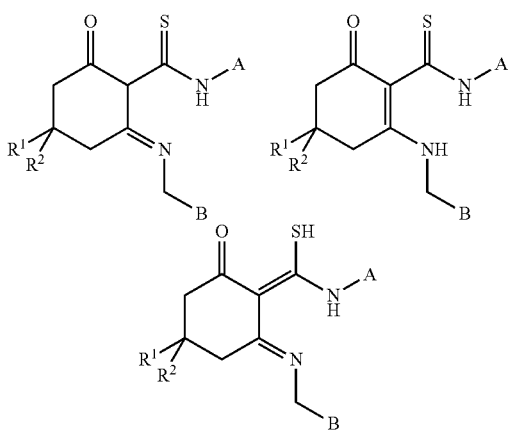

An example of tautomers of the present invention is shown below (these can exist alone or in any mixture of the three tautomers in any ratio).

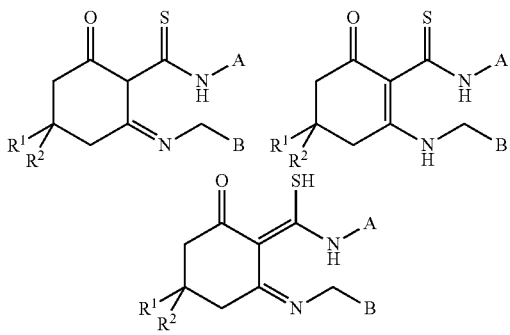

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Suitable pharmaceutically acceptable anions according to the present invention are, for example, the anion of an inorganic acid, such as hydrochloric, hydrobromic, hydroiodic, sulfuric, bisulfuric, phosphoric, or nitric acid, for example, or of an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example. Preferred anions according to the present invention are $Br^-$, $I^-$ and $CF_3SO_3^-$.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF$_3$COOH", "x Na+", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

The salts include water-insoluble and, particularly, water-soluble salts.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered. Any such combination of a compound of formula (I) of the present invention with an anti-cancer agent as defined below is an embodiment of the invention.

The term "(chemotherapeutic) anti-cancer agents", includes but is not limited to 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

It has now been found, and this constitutes the basis of the present invention, that said compounds of the present invention have surprising and advantageous properties.

In particular, said compounds of the present invention have surprisingly been found to effectively inhibit Bub1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1 kinase, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The intermediates used for the synthesis of the compounds of claims 1-6 as described below, as well as their use for the synthesis of the compounds of claims 1-6, are one further aspect of the present invention. Preferred intermediates are the Intermediate Examples as disclosed below.

General Procedures

The compounds according to the invention can be prepared according to the following Schemes 1 through 9.

The Schemes and procedures described below illustrate synthetic routes to the compounds of general formula (I) of the invention and are not intended to be limiting. It is obvious to the person skilled in the art that the order of transformations as exemplified in the Schemes can be modified in various ways. The order of transformations exemplified in the Schemes is therefore not intended to be limiting. In addition, interconversion of any of the substituents, $R^1$, $R^2$, A and B can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

One route for the preparation of compounds of general formula (I) is described in Scheme 1. In instances where this route is not feasible, Scheme 2 can be applied.

Scheme 1

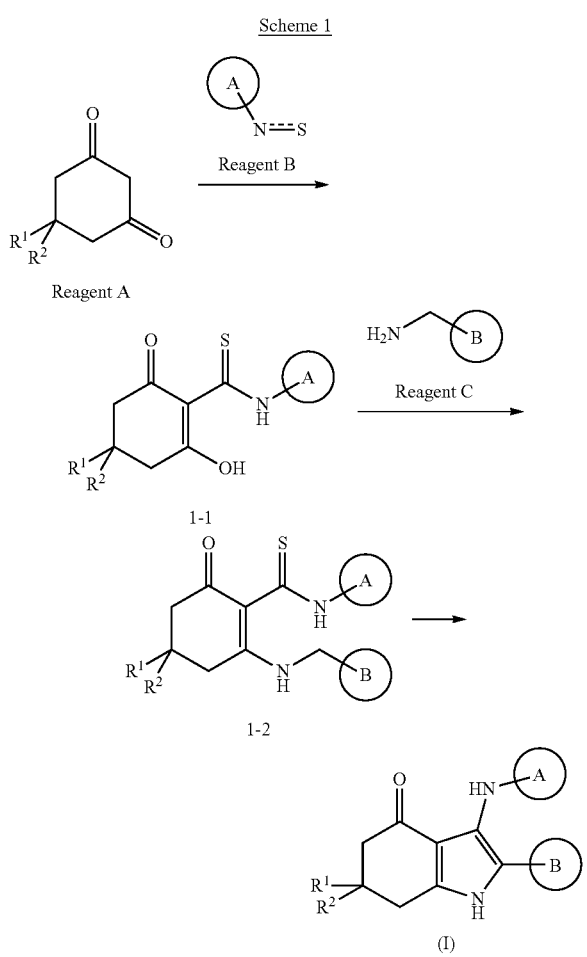

Scheme 1

Route for the preparation of compounds of general formula (I), wherein $R^1$, $R^2$, A and B have the meaning as given for general formula (I), supra. In addition, interconversion of any of the substituents, $R^1$, $R^2$, A or B can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see, for example, T. W. Greene and P. G. M. Wuts in Protective Groups in Organic Synthesis, 3rd edition, Wiley 1999). Specific examples are described in the subsequent paragraphs.

Reagent A, reagent B, and reagent C are either commercially available or can be prepared according to procedures available from the public domain, as understandable to the person skilled in the art. Specific examples are described in the subsequent paragraphs.

A suitably substituted 1,3-dicarbonyl cyclohexane of general formula (reagent A) can be reacted with a suitably substituted isothiocyanate (reagent B), such as, for example, 5,5-dimethyl-1,3-cyclohexanedione (dimedone), in a suitable solvent system, such as, for example, acetonitrile, in the presence of a suitable base, such as, for example, triethylamine or DBU, at temperatures ranging from −78° C. to +100° C., preferably the reaction is carried out at 0° C. or +100° C., to furnish general formula (1-1). Similar reactions have been performed in the literature (Muthusamy, S. et al. J. Heterocyclic Chem., 1991, 28, 759-763; Jagodzinski, S. and Wesolowska; H., Polish Journal of Chemistry, 2001, 75, 387-400; Bolvig, S. et al., Journal of Molecular Structure, 1996, 378, 45-59).

Intermediates of general formula (1-1) can be converted to intermediates of general formula (1-2) by reaction with a suitable amine, such as, for example 4-(aminomethyl)pyridine, in a suitable solvent system, such as, for example, ethanol and ethyl acetate, at a temperature between room temperature and the boiling point of the respective solvents, preferably the reaction is carried out at the boiling point of the respective solvents, whereby the water formed in the reaction is removed from the reaction by methods known to those skilled in the art, such as, for example, azeotropic removal of water (Dean-Stark conditions) or with molecular sieves, to furnish general formula (1-2).

Intermediates of general formula (1-2) are reacted with a base and/or oxidizing reagent, preferably an oxidizing agent, such as, for example hydrogen peroxide, in a suitable solvent system, such as, for example, methanol, in a temperature range from room temperature to the boiling point of the respective solvent, preferably the reaction is carried out at the boiling point of the respective solvent, to furnish compounds of general formula (I).

Scheme 2

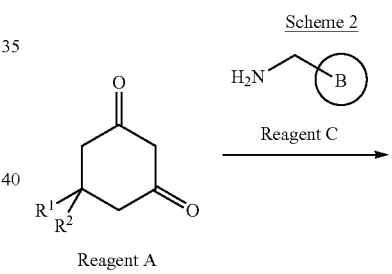

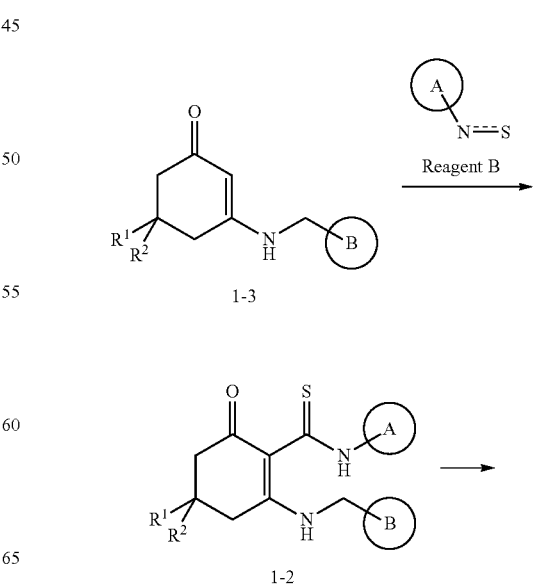

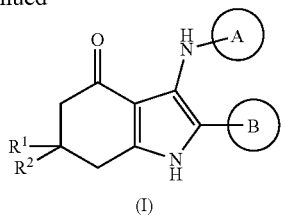

Scheme 2

Route for the preparation of compounds of general formula (I), wherein $R^1$, $R^2$, A and B have the meaning as given for general formula (I), supra. In addition, interconversion of any of the substituents, $R^1$, $R^2$, A and B can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Specific examples are described in the subsequent paragraphs.

Reagent A, reagent B, and reagent C are either commercially available or can be prepared according to procedures available from the public domain, as understandable to the person skilled in the art. Specific examples are described in the subsequent paragraphs.

A suitably substituted 1,3-dicarbonyl cyclohexane of general formula (reagent A) can be converted to intermediate s of general formula (1-3) by reaction with a suitable amine, such as, for example 4-(aminomethyl)pyridine, in a suitable solvent system, such as, for example, ethanol and ethyl acetate, at a temperature between room temperature and the boiling point of the respective solvents, preferably the reaction is carried out at the boiling point of the respective solvent, whereby the water formed in the reaction is removed from the reaction by methods known to those skilled in the art, such as, for example, azeotropic removal of water (Dean-Stark conditions) or with molecular sieves, to furnish general formula (1-3). Similar reactions have been performed in the literature (Fowler, F. et al., Angew. Chem. Int. Ed., 2000, 39, 2132-2135).

Intermediates of general formula (1-3) can be reacted with a suitably substituted isothiocyanate (B), such as, for example, dimedone, in a suitable solvent system, such as, for example, acetonitrile, in the presence of a suitable base, such as, for example, triethylamine or DBU, at temperatures ranging from −78° C. to +100° C., preferably the reaction is carried out at 0° C. or +100° C., to furnish general formula (1-2).

Intermediates of general formula (1-2) are reacted with a base and/or oxidizing reagent, preferably an oxidizing agent, such as, for example hydrogen peroxide, in a suitable solvent system, such as, for example, methanol, in a temperature range from room temperature to the boiling point of the respective solvent, preferably the reaction is carried out at the boiling point of the respective solvent, to furnish compounds of general formula (I).

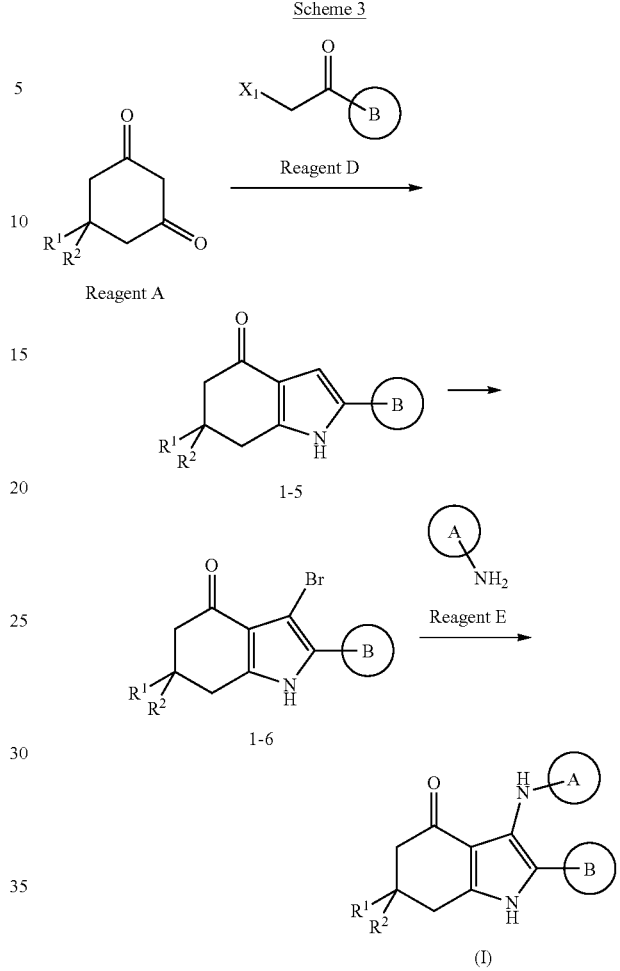

Scheme 3

Route for the preparation of compounds of general formula (I), wherein $R^1$, $R^2$, A and B have the meaning as given for general formula (I), supra. In addition, interconversion of any of the substituents, $R^1$, $R^2$, A and B can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Specific examples are described in the subsequent paragraphs.

Compounds of the formula (I) can also be prepared using the synthetic methods described in context of Scheme 3. Compounds reagent D and reagent E, are either commercially available or can be prepared according to procedures available from the public domain, as understandable to the person skilled in the art.

A suitably substituted 1,3-dicarbonyl cyclohexane of general formula (reagent A) can be reacted with suitably substituted compounds of general formula (reagent D) where X1 is a suitable leaving group, such as, for example, bromide, chloride, preferably bromide, in the presence of an ammonium salt, such as, for example, ammonium acetate, in a suitable solvent, such as, for example, ethanol, in a temperature range from 0° C. to the boiling point of the respective solvent, preferably the reaction is carried out at room temperature, to furnish general formula (1-5). Similar examples for the formation of a pyrrole ring in this manner have been previously published using cyclolactams instead of cyclohexanones (Anderson, D. R. et al., J. Med. Chem., 2007, 50, 2647-2654; Amici, R. et al., J. Med. Chem., 2008, 51, 487-501; Bargiotti, A. et al., J. Med. Chem., 2009, 52, 293-307).

Intermediates of general formula (1-5) can be reacted with a suitable halogenating reagent, such as, for example, copper (I) bromide and N-bromosuccinimide, preferably N-bromosuccinimide, in a suitable solvent system, such as, for example, acetonitrile, in a temperature range from 0° C. to the boiling point of the respective solvent, preferably the reaction is carried out at room temperature, to furnish general formula (1-6). Similar examples for the bromination of pyrroles have been previously published using lactams (Aiello, E. et al., J. Heterocyclic Chem., 1982, 19, 977-979; Duranti, A. et al., Bioorg. Med. Chem., 2003, 11, 3965-3973).

Intermediates of general formula (1-6) can be reacted with a suitable primary amines, such as, for example, primary aromatic amines and primary amines, preferably primary aromatic amines, such as, for example aniline or 3-aminothiophene, in the presence of a base, such as, for example, lithium bis(trimethylsilyl)amide (LHMDS), in the presence of a catalyst, such as, for example a suitable ligand, preferably 2-(di-tert-butylphosphino)-2',4',6'-triisopropyl-3,6-dimethoxy-1,1'-biphenyl (tBuBrettPhos) and in the presence of a pre-catalyst, such as, for example a palladium pre-catalyst, preferably chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct) in a suitable solvent system, such as, for example, tetrahydrofuran (THF), in a temperature range from 0° C. to the 200° C., preferably the reaction is carried out at 80° C., to furnish compounds of general formula (I).

Scheme 4

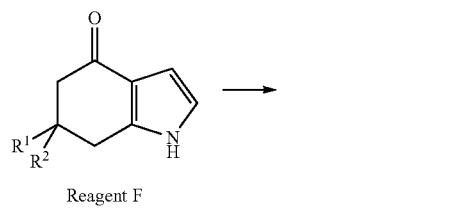

Reagent F

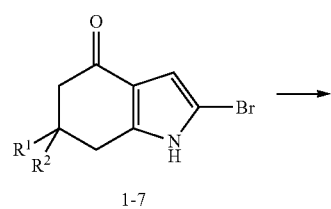

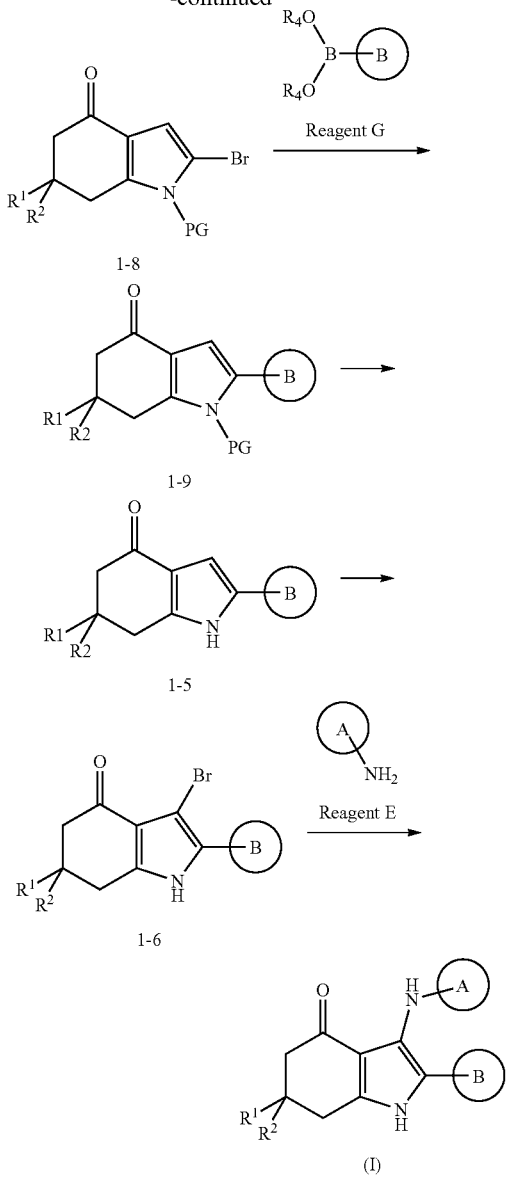

Scheme 4

Process for the preparation of compounds of general formula (I). In addition, interconversion of any of the substituents can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999).

Compounds of general formula reagent F are commercially available or can be synthesized by those skilled in the art. Compounds of general formula reagent G are commercially available or can be synthesized by those skilled in the art. Compounds of general formula reagent E are commercially available and have been referred to in the previous Schemes. Compounds of general formula reagent F are converted to compounds of general formula (1-7) by treatment with a suitable brominating agent, such as for example phenyltrimethyammonium tribromide, in a suitable solvent, such as, for example, tetrahydrofuran (THF), in a temperature range from 0° C. to the boiling point of the respective solvent, preferably the reaction is carried out at room temperature, to furnish general formula (1-7). Such brominations of 1,5,6,7-tetrahydro-4H-indol-4-ones have been previously reported (Davies, H. M. L. and Manning, J. R., J. Am. Chem. Soc., 2006, 128, 1060-1061; Remers, W. A. and Weiss, M. J., J. Org. Chem., 1971, 36, 1241-1247).

Compounds of general formula (1-7) are then reacted to introduce a suitable protecting group, such as, for example, t-butoxy carbonyl (Boc), onto the pyrrole nitrogen. Reagents for introducing these protecting groups are well-known to those skilled in the art (see for example T. W. Greene and P. G. M. Wuts in Protective Groups in Organic Synthesis, 3rd edition, Wiley 1999). The compounds of general formula (1-8) can be reacted with a compound of general formula (reagent G) as mentioned above, such as, for example, aromatic boronic acids, heteroaromatic boronic acids, aromatic boronic esters, heteroaromatic boronic esters, preferably primary heteroaromatic boronic acids and heteroaromatic boronic esters, such as, pyridin-4-ylboronic acid and 4-(4,4,5,5-tetramethyl-1,3,2-dioxaborolan-2-yl)pyridine, in the presence of a base, such as, for example, caesium carbonate, in the presence of a catalyst, such as, for example a palladium catalyst, preferably bis-(triphenylphosphine)palladium(II) dichloride in a suitable solvent system, such as, for example, dimethoxyethane and water, in a temperature range from room temperature to the boiling point of the respective solvent, preferably the reaction is carried out at 80-100° C., to furnish compounds of general formula (1-9).

Alternatively compounds of general formula (1-7) can be reacted with a compound of general formula (reagent G) as mentioned above, such as, for example, aromatic boronic acids, heteroaromatic boronic acids, aromatic boronic esters, heteroaromatic boronic esters, preferably primary heteroaromatic boronic acids and heteroaromatic boronic esters, such as, pyridin-4-ylboronic acid and 4-(4,4,5,5-tetramethyl-1,3,2-dioxaborolan-2-yl)pyridine, in the presence of a base, such as, for example, caesium carbonate, in the presence of a catalyst, such as, for example a palladium catalyst, preferably bis-(triphenylphosphine)palladium(II) dichloride in a suitable solvent system, such as, for example, dimethoxyethane and water, in a temperature range from room temperature to the boiling point of the respective solvent, preferably the reaction is carried out at 80-100° C., to furnish compounds of general formula (1-9).

Intermediates of general formula (1-9) can be reacted with a suitable reagent for removing the said protecting group, such methods and their suitable reagents for removing these protecting groups are well-known to those skilled in the art (see for example T. W. Greene and P. G. M. Wuts in Protective Groups in Organic Synthesis, 3rd edition, Wiley 1999). For example, with intermediates of general formula (1-9) where R⁵ is t-butoxy carbonyl (Boc), can be reacted with an acid, such as for example, hydrochloric acid or trifluoroacetic acid (TFA), in a suitable solvent system, such as, for example, dichloromethane or using the acid as solvent, in a temperature range from 0° C. to the boiling point of the respective solvent, preferably the reaction is carried out at room temperature to furnish compounds of general formula (1-5).

Intermediates of general formula (1-5) can be reacted with a suitable halogenating reagent, such as, for example, copper (I) bromide and N-bromosuccinimide, preferably N-bromosuccinimide, in a suitable solvent system, such as, for example, acetonitrile, in a temperature range from 0° C. to the boiling point of the respective solvent, preferably the reaction is carried out at room temperature, to furnish general formula (1-6). Similar examples for the bromination of pyrroles have been previously published using lactams (Aiello, E. et al., J. Heterocyclic Chem., 1982, 19, 977-979; Duranti, A. et al., Bioorg. Med. Chem., 2003, 11, 3965-3973).

Intermediates of general formula (1-6) can be reacted with a suitable primary amines, such as, for example, primary aromatic amines and primary amines, preferably primary aromatic amines, such as, for example aniline or 3-aminothiophene, in the presence of a base, such as, for example, lithium bis(trimethylsilyl)amide (LHMDS), in the presence of a catalyst, such as, for example a palladium catalyst, preferably 2-(di-tert-butylphosphino)-2',4',6'-triisopropyl-3,6-dimethoxy-1,1'-biphenyl (tBuBrettPhos) in a suitable solvent system, such as, for example, tetrahydrofuran (THF), in a temperature range from 0° C. to the 200° C., preferably the reaction is carried out at 80° C., to furnish compounds of general formula (I).

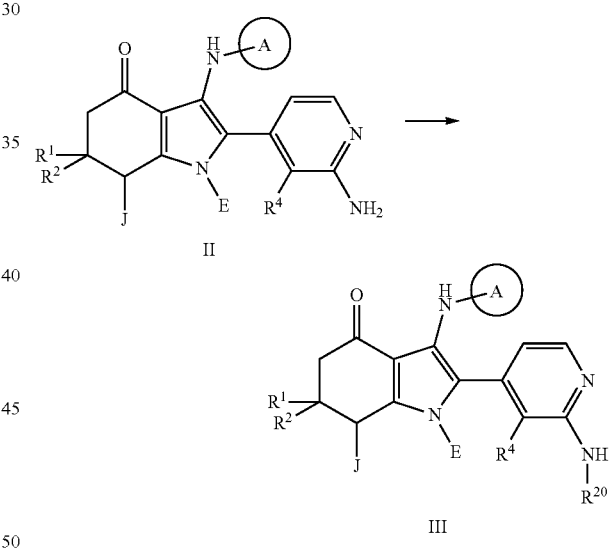

Scheme 5

Scheme 5:
Route for the preparation of compounds of general formula (III), wherein R¹, R², R³, R⁴, A and J have the meaning as given for general formula (I), supra and R²⁰ represents R¹¹—C(O)—, R¹⁸O—C(O)— or R⁹R¹⁰N—C(O)— or R⁹R¹⁰N—C(S)— or R¹¹—.

Intermediates of general formula (II) are reacted with an acylating reagent, an acylating agent which can be generated in situ, to furnish compounds of general formula (III). These types of reactions are well-known (selected literature examples are: S. Miwatashi, et al., J. Med. Chem., 2005, 48, 5966-5979; J. Zhao, et al., Bioorg. Med. Chem. Lett., 2014, 24, 2802-2806; M. P. Hay, et al., J. Med. Chem., 2010, 53, 787-797; J. M. Keith, et al., Med. Chem. Lett, 2012, 3, 823-827; J. Liang, et al., Eur. J. Med. Chem., 2013, 67, 175-187).

Not-limiting examples of these types of reagents are:
i) carboxylic acid with dehydrating reagents typically used in amide bond formation, such as, for example (HBTU, HATU, PyBOP, BOP, T3P, EDC, DIC, DCC)
ii) acid fluorides, acid chlorides, acid bromides, preferably in the presence of a base
iii) acid anhydrides, preferably in the presence of a base
iv) chloroformates, preferably in the presence of a base
v) isocyanates, preferably in the presence of a base
vi) isothiocyanates, preferably in the presence of a base Intermediates of general formula (II) are reacted with compounds or reagents, such as for example, alcohols, aldehydes and ketones, preferably aldehydes, in the presence of a reducing agent or a catalytic system, preferably a reducing agent, to furnish compounds of general formula (III). These types of reactions, also known as reductive aminations, are well-known (selected literature examples are: Martinez-Asencio et al., Tetrahedron Letts., 2010, 51, 325-327; Martinez-Asencio et al., Org. Biomol. Chem., 2009, 7, 2176-2181; Ikeda et al., Eur. J. Med. Chem., 2011, 46, 636-646.

Not-limiting examples of these types of reagents are:
i) alcohols with 2-aminopyridines in the presence of base, for example KO$^t$Bu, and copper acetate or nano-Fe$_3$O$_4$ (Martinez-Asencio et al., Tetrahedron Letts., 2010, 51, 325-327; Martinez-Asencio et al., Org. Biomol. Chem., 2009, 7, 2176-2181).
ii) Aldehydes with reducing agents, such as for example, sodium borohydride or sodium cyanoborohydride or sodium tris(acetoxy)borohydride, preferably in the presence of an acid, such as acetic acid; Ikeda et al., Eur. J. Med. Chem., 2011, 46, 636-646; Eur. J. Med. Chem., 2000, 35, 815-826; Betzel et al., Bioconjugate Chem., 2013, 24, 205-214.
iii) Aldehydes under catalytic hydrogenation conditions with a catalyst, such as for example Pd/NiO under an H2 atmosphere (Yang et al., Synth. Commun., 2014, 44, 1314-1322).

protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999).

Compounds of general formula reagent H and reagent J, whereby LG is a leaving group, such as, for example, F, Cl, Br, I or aryl sulfonate such as for example p-toluene sulfonate, or alkyl sulfonate such as for example methane sulfonate or trifluoromethane sulfonate, are commercially available or can be synthesized by those skilled in the art.

Compounds of general formula reagent H and reagent J can be converted to compounds of general formula (1-10) by treatment with a suitable nucleophile, such as for example, amines, alcohols, metal alkoxides, azides, thiols or metal thiolates, under either basic, neutral, acidic, catalytic conditions, preferably basic conditions, in a suitable solvent or using the nucleophile as solvent, such as, for example, DMF, tetrahydrofuran (THF), in a temperature range from −78° C. to the boiling point of the respective solvent, preferably the reaction is carried out −10° C. to the boiling point of the respective solvent, to furnish general formula (1-10). Such substitution reactions have been previously reported (Clark et al., J. Med. Chem., 2008, 51, 6631-6634; Guo et al., Tetrahedron Letts., 2013, 54, 3233-3237; Watterson et al., J. Med. Chem., 2007, 50, 3730-3742; Bellale et al., J. Med. Chem., 2014, 57, 6572-6582; Klimesova et al., Eur. J. Med. Chem., 1996, 31, 389-395; Leroy et al., Synth. Commun., 1997, 27, 2905-2916; LaMattina et al., J. Org. Chem., 1981, 46, 4179-4182; Beugelmans et al., Tetrahedron, 1983, 39, 4153-4162).

Compounds of general formula (1-10) can be converted to compounds of general formula (1-11) by many reducing methods known to those skilled in the art, using numerous Scheme 6

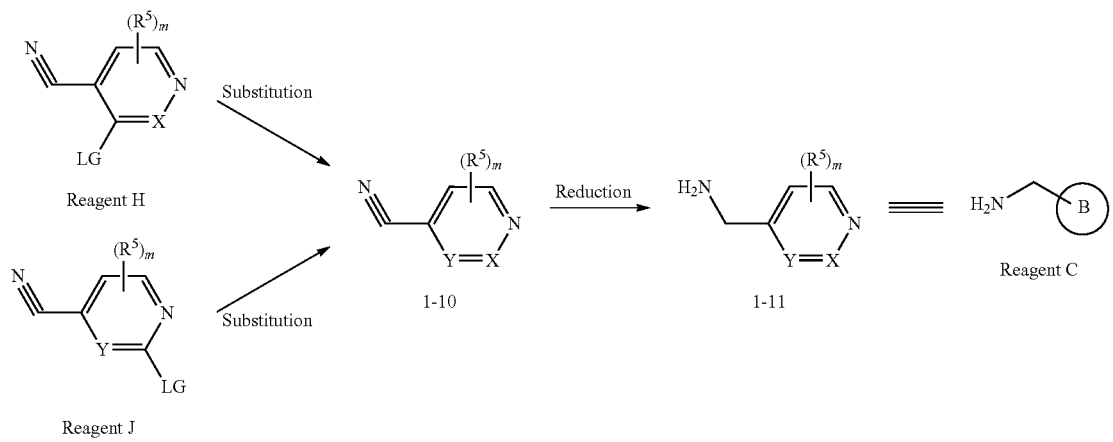

Scheme 6

Process for the preparation of reagents C of general formula 1-11, wherein B, R$^5$, X, Y and m have the meaning as given for general formula (I). In addition, interconversion of any of the substituents can be achieved before and/or after the exemplified transformations. These modifications can be such as the introduction of protecting groups, cleavage of different reagents and reaction conditions; such methods and reagents can be carried out with metal hydrides, such as, for example, lithium aluminium hydride in THF (Bullock et al., J. Am. Chem. Soc., 1956, 78, 490, Wang et al., J. Org. Chem., 2006, 71, 4021-3160), or using zinc in acetic acid (Rabe, Chem. Ber., 1913, 46, 1024), or using diborane (De Munno et al., Heterocycles, 1996, 43, 1893-1900), or using catalytic hydrogenation methods, for example, hydrogen and palladium on carbon under acidic conditions (Stokker et al., J. Med. Chem., 1981, 24, 115-117; Bertini et al., J. Med. Chem., 2005, 48, 664-670), hydrogen and nickel under basic conditions (Walpole et al., J. Med. Chem., 1993, 36, 2362-2372, Kuramochi et al., Bioorg. Med. Chem., 2005, 13, 4022-4036.)

Scheme 7

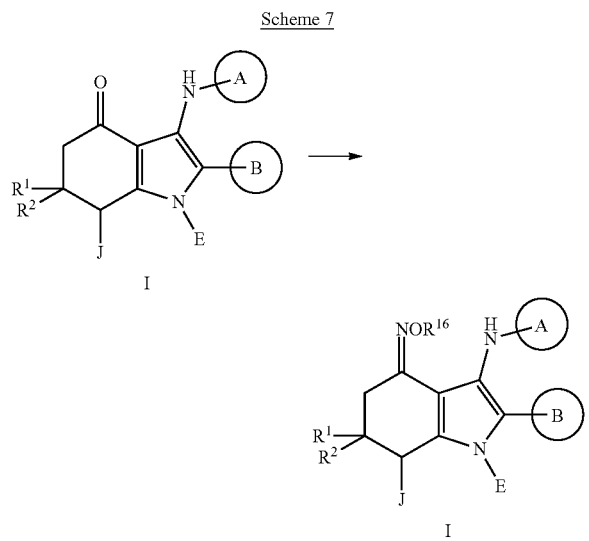

Scheme 8

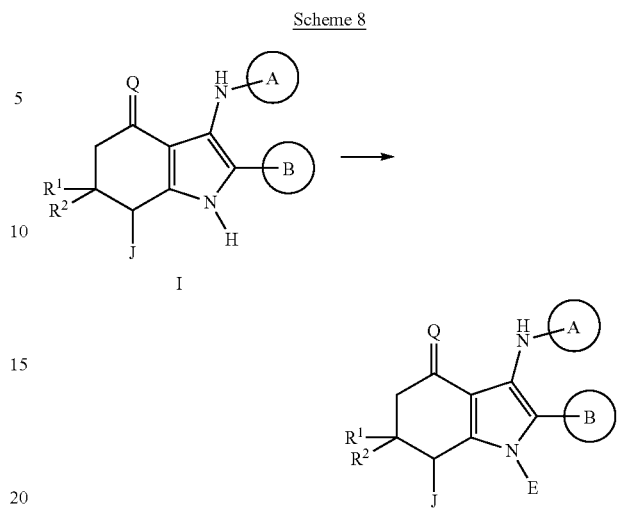

Scheme 7

Process for the preparation of compounds of general formula (I), wherein B, $R^1$, $R^2$, $R^4$, $R^{16}$, A, B, and J have the meaning as given for general formula (I). In addition, interconversion of any of the substituents can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999).

Compounds of general formula (I) wherein Q is O can be converted to compounds of general formula (I) wherein Q is $NOR^{16}$ by treatment with a suitable reagent containing one or more $NH_2$ group, such as for example, amines, oxyamines, hydroxylamines, hydrazones or hydrazines, in a suitable solvent, such as, for example, ethanol, methanol, water, DMF, tetrahydrofuran (THF), preferably, ethanol, in a temperature range from −78° C. to the boiling point of the respective solvent, preferably the reaction is carried out RT to the boiling point of the respective solvent, to furnish general formula (I). Such transformations have been previously reported (Kesten et al., J. Med. Chem., 1992, 35, 3429-3447; Bisejieks et al., Heteocyclic Comunn., 2005, 11, 9-12; Maillard et al., Eur. J. Med. Chem., 1984, 19, 451-456; Hassan, Molecules, 2013, 18, 2683-2711).

Scheme 8

Process for the preparation of compounds of general formula (I), wherein $R^1$, $R^2$, E, A, B, J and Q have the meaning as given for general formula (I). In addition, interconversion of any of the substituents can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999).

Compounds of general formula (I) wherein E is hydrogen can be converted to compounds of general formula (I) wherein E is as defined herein other than hydrogen, by treatment with a suitable base, such as, for example, alkali metal carbonate, alkali metal hydrogen carbonate, alkali metal hydroxide, sodium hydride, alkali metal alkoxide, LHMDS, optionally in the presence of a phase transfer catalyst, or a crown ether, with an alkylating reagent which contains a suitable leaving group, such as, for example, F, Cl, Br, I or aryl sulfonate such as for example para-toluene sulfonate, or alkyl sulfonate such as for example methane sulfonate or trifluoromethane sulfonate, are commercially available or can be synthesized by those skilled in the art, in a suitable solvent, such as, for example, ethanol, methanol, water, DMF, tetrahydrofuran (THF), preferably, DMF, in a temperature range from −78° C. to the boiling point of the respective solvent, preferably the reaction is carried out RT to the boiling point of the respective solvent, to furnish general formula (I).

Such transformations have been previously reported (Zhang et al., Bioorg. Med. Chem. Lett., 2006, 16, 3233-3237; WO2008/132434 A2, Kang et al., Bioorg. Med. Chem., 2010, 18, 6156-6169; Vanotti et al., J. Med. Chem., 2008, 51, 487-501).

Scheme 9

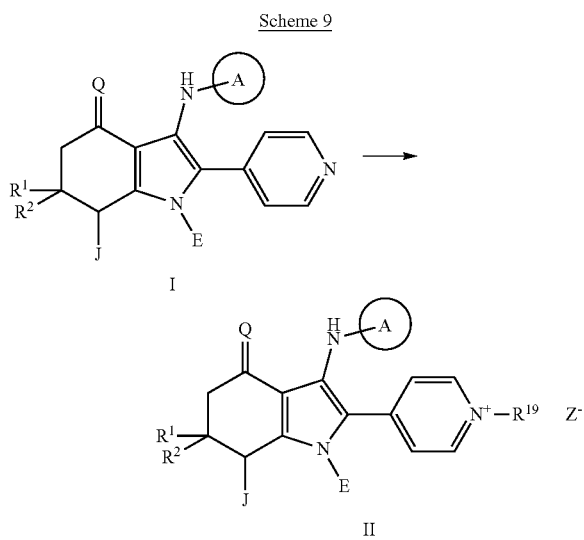

Scheme 9

Process for the preparation of compounds of general formula (II), wherein $R^1$, $R^2$, E, A, J and Q have the meaning as given for general formula (I) and $R^{19}$ and $Z^-$ are as defined herein. In addition, interconversion of any of the substituents can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999).

Compounds of general formula (I) can be converted to compounds of general formula (II) by treatment with an alkylating reagent which contains a suitable leaving group, such as, for example, F, Cl, Br, I or aryl sulfonate such as for example para-toluene sulfonate, or alkyl sulfonate such as for example methane sulfonate or trifluoromethane sulfonate, are commercially available or can be synthesized by those skilled in the art, optionally in the presence of a base, such as, for example, alkali metal carbonate, alkali metal hydrogen carbonate, alkali metal hydroxide, sodium hydride, alkali metal alkoxide, LHMDS, optionally in the presence of a phase transfer catalyst, or a crown ether, in a suitable solvent, such as, for example, ethanol, methanol, water, DMF, tetrahydrofuran (THF), preferably, DMF, in a temperature range from −78° C. to the boiling point of the respective solvent, preferably the reaction is carried out RT to the boiling point of the respective solvent, to furnish general formula (II).

Such transformations have been previously reported (Chahma et al., Synthesis, 2004, 4, 517-520; WO2008/65054 A1; Yu et al., Bioorg. Med. Chem., 1999, 7, 231-239; Ferlin et al., Farmaco., 1998, 53, 431-437).

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids vl formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-6 according to the examples, as well as the intermediates used for their preparation.

Optionally, compounds of the formula (I) can be converted into their salts, or, optionally, salts of the compounds of the formula (I) can be converted into the free compounds. Corresponding processes are customary for the skilled person.

Commercial Utility

As mentioned supra, the compounds of the present invention have surprisingly been found to effectively inhibit Bub1 finally resulting in cell death e.g. apoptosis and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, endocrine glands (e.g. thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumors in said organs and corresponding secondary tumors in distant organs ("tumor metastases"). Haematological tumors can e.g be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

A further aspect of the invention is the use of the compounds according to formula (I) for the treatment of cervical-, breast-, non-small cell lung-, prostate-, colon- and melanoma tumors and/or metastases thereof, especially preferred for the treatment thereof as well as a method of treatment of cervical-, breast-, non-small cell lung-, prostate-, colon- and melanoma tumors and/or metastases thereof comprising administering an effective amount of a compound of formula (I).

One aspect of the invention is the use of the compounds according to formula (I) for the treatment of cervix tumors as well as a method of treatment of cervix tumors comprising administering an effective amount of a compound of formula (I).

In accordance with an aspect of the present invention therefore the invention relates to a compound of general formula I, or an N-oxide, a salt, a tautomer or a stereoisomer of said compound, or a salt of said N-oxide, tautomer or stereoisomer particularly a pharmaceutically acceptable salt thereof, or a mixture of same, as described and defined herein, for use in the treatment or prophylaxis of a disease, especially for use in the treatment of a disease.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of hyperproliferative disorders or disorders responsive to induction of cell death i.e apoptosis.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, especially the treatment, wherein the diseases are haematological tumours, solid tumours and/or metastases thereof.

Another aspect is the use of a compound of formula (I) is for the treatment of cervical-, breast-, non-small cell lung-, prostate-, colon- and melanoma tumors and/or metastases thereof, especially preferred for the treatment thereof. A preferred aspect is the use of a compound of formula (I) for the prophylaxis and/or treatment of cervical tumors especially preferred for the treatment thereof.

Another aspect of the present invention is the use of a compound of formula (I) or a stereoisomer, a tautomer, an N-oxide, a hydrate, a solvate, or a salt thereof, particularly a pharmaceutically acceptable salt thereof, or a mixture of same, as described herein, in the manufacture of a medicament for the treatment or prophylaxis of a disease, wherein such disease is a hyperproliferative disorder or a disorder responsive to induction of cell death e.g. apoptosis. In an embodiment the disease is a haematological tumour, a solid tumour and/or metastases thereof. In another embodiment the disease is cervical-, breast-, non-small cell lung-, prostate-, colon- and melanoma tumor and/or metastases thereof, in a preferred aspect the disease is cervical tumor.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce cell death e.g. apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death e.g. apoptosis of such cell types.

Preferably, the diseases of said method are haematological tumours, solid tumour and/or metastases thereof.

The compounds of the present invention can be used in particular in therapy and prevention i.e. prophylaxis, especially in therapy of tumour growth and metastases, especially in solid tumours of all indications and stages with or without pre-treatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haematological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:
acidifying agents (examples include but are not limited to acetic acid, citric acid, fumaric acid, hydrochloric acid, nitric acid);
alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);
adsorbents (examples include but are not limited to powdered cellulose and activated charcoal);
aerosol propellants (examples include but are not limited to carbon dioxide, $CCl_2F_2$, $F_2ClC-CClF_2$ and $CClF_3$)
air displacement agents—examples include but are not limited to nitrogen and argon;
antifungal preservatives (examples include but are not limited to benzoic acid, butylparaben, ethylparaben, methylparaben, propylparaben, sodium benzoate);
antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);
antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate), flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to *arachis* oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas), plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, octoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, crosslinked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. solution: A 5 mg/mL solution of the desired compound of this invention can be made using sterile, injectable water, and the pH is adjusted if necessary. The solution is diluted for administration to 1-2 mg/mL with sterile 5% dextrose and is administered as an i.v. infusion over about 60 minutes.

Lyophilised powder for i.v. administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg. of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haematological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

EXPERIMENTAL PART

The following table lists the abbreviations used in this paragraph and in the Intermediate Examples and Examples section as far as they are not explained within the text body.

| Abbreviation | Meaning |
|---|---|
| AcOH | acetic acid (ethanoic acid) |
| $Ac_2O$ | Acetic anhydride |
| $AlMe_3$ | Trimethylaluminium |
| aq. | aqueous |
| Ar | Argon |
| Boc or boc | t-butoxycarbonyl |
| $Boc_2O$ | Di-tert-butyldicarbonate |
| br | broad |
| CI | chemical ionisation |
| CuCN | Copper(I) cyanide |
| d | doublet |
| DAD | diode array detector |
| DBU | 1,8-Diazabicyclo(5.4.0)undec-7-ene |
| DCM | dichloromethane |
| dd | double-doublet |
| DIAD | Diisopropyl auodicarboxylate |
| DIPEA | diisopropylethylamine |
| DMA | N,N-dimethylacetamide |
| DMAP | 4-Dimethylaminopyridine |
| DMF | N,N-dimethylformamide |
| DMSO | dimethyl sulfoxide |
| ELSD | Evaporative Light Scattering Detector |
| EtOAc | ethyl acetate |
| EtOH | ethanol |
| eq. | equivalent |
| ESI | electrospray (ES) ionisation |
| HATU | O-(7-Azabenzotriazol-1-yl)-N,N,N',N'-tetramethyluronium-hexafluorphosphate |
| HPLC | high performance liquid chromatography |
| $H_2O_2$ | Hydrogen peroxide |
| KO$^t$Bu | Potassium tert-butoxide |
| LC-MS | liquid chromatography mass spectrometry |
| LHMDS | Lithium bis(trimethylsilyl)amide |
| m | multiplet |
| MeCN | acetonitrile |
| MeOH | methanol |
| MS | mass spectrometry |
| MTBE | methyl tert-butylether |
| $NaBH_3CN$ | Sodium cyanoborohydride |
| NBS | N-Bromosuccinimide |
| NMP | N-Methylpyrrolidine |
| n-PrOH | Propan-1-ol |
| NMR | nuclear magnetic resonance spectroscopy: chemical shifts (δ) are given in ppm. The chemical shifts were corrected by setting the DMSO signal to 2.50 ppm using unless otherwise stated. |
| PDA | Photo Diode Array |
| $Pd(PPh_3)_4$ | Tetrakis(triphenylphosphine)palladium(0) |
| Pd/C | Palladium on carbon |
| PoraPak ™; | a HPLC column obtainable from Waters |
| PTSA | para-Toluenesulfonic acid |
| q | quartet |
| r.t. or rt | room temperature |
| Rt | retention time (as measured either with HPLC or UPLC) in minutes |
| s | singlet |
| SIBX | Stabilized 2-Iodoxybenzoic acid |
| SM | starting material |
| SQD | Single-Quadrupol-Detector |
| t | triplet |
| TBAF | Tetrabutylammonium fluoride |
| TEA | Triethylamine |
| TFA | Trifluoroacetic acid |
| THF | tetrahydrofuran |
| UPLC | ultra performance liquid chromatography |

Other abbreviations have their meanings customary per se to the skilled person.

The various aspects of the invention described in this application are illustrated by the following examples which are not meant to limit the invention in any way.

SPECIFIC EXPERIMENTAL DESCRIPTIONS

NMR peak forms in the following specific experimental descriptions are stated as they appear in the spectra, possible higher order effects have not been considered. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash $NH_2$ silica gel in combination with a Isolera® autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated in vacuo" refers to use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only, and are not to be construed as limiting the scope of the invention in any manner. All publications mentioned herein are incorporated by reference in their entirety.

Analytical LC-MS Conditions

LC-MS-data given in the subsequent specific experimental descriptions refer (unless otherwise noted) to the following conditions:

| | |
|---|---|
| System: | Waters Acquity UPLC-MS: Binary Solvent Manager, Sample Manager/Organizer, Column Manager, PDA, ELSD, SQD 3001 or ZQ4000 |
| Column: | Acquity UPLC BEH C18 1.7 50 × 2.1 mm |
| Solvent: | A1 = water + 0.1% vol. formic acid (99%) |
| | A2 = water + 0.2% vol. ammonia (32%) |
| | B1 = acetonitrile |
| Gradient: | 0-1.6 min 1-99% B, 1.6-2.0 min 99% B |
| Flow: | 0.8 mL/min |
| Temperature: | 60° C. |
| Injection: | 2.0 µl |
| Detection: | DAD scan range 210-400 nm -> Peaktable |
| | ELSD |
| Methods: | MS ESI+, ESI− Switch -> various scan ranges (Report Header) |
| | Method 1: A1 + B1 = C:\MassLynx\Mass_100_1000.flp |
| | Method 2: A1 + B1 = C:\MassLynx\NH$_3$_Mass_100_1000.flp |

Preparative HPLC Conditions

"Purification by preparative HPLC" in the subsequent specific experimental descriptions refers to (unless otherwise noted) the following conditions:

Analytics (Pre- and Post Analytics: Method A):

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.1% vol. formic acid (99%) |
| | B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 µl |
| Detection: | DAD scan range 210-400 nm |
| | MS ESI+, ESI−, scan range 160-1000 m/z |
| | ELSD |
| Methods: | Purify_pre.flp |
| | Purify_post.flp |

Analytics (Pre- and Post Analytics: Method B):

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.2% vol. ammonia (32%) |
| | B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 µl |
| Detection: | DAD scan range 210-400 nm |
| | MS ESI+, ESI−, scan range 160-1000 m/z |
| | ELSD |
| Methods: | Purify_pre.flp |
| | Purify_post.flp |

Preparative HPLC (Method Acidic):

| | |
|---|---|
| System: | Waters Autopurificationsystem: Pump 2545, Sample Manager 2767, CFO, DAD 2996, ELSD 2424, SQD 3001 |
| Column: | XBridge C18 5 µm 100 × 30 mm |
| Solvent: | A = water + 0.1% vol. formic acid (99%) |
| | B = acetonitrile |
| Gradient: | 0-1 min 1% B, 1-8 min 1-99% B, 8-10 min 99% B |
| Flow: | 50 mL/min |
| Temperature: | RT |
| Solution: | max. 250 mg/2.5 mL dimethyl sufoxide or DMF |
| Injection: | 1 × 2.5 mL |
| Detection: | DAD scan range 210-400 nm |
| | MS ESI+, ESI−, scan range 160-1000 m/z |

Preparative HPLC (Method Basic):

| | |
|---|---|
| System: | Waters Autopurificationsystem: Pump 2545, Sample Manager 2767, CFO, DAD 2996, ELSD 2424, SQD 3001 |
| Column: | XBridge C18 5 µm 100 × 30 mm |
| Solvent: | A = water + 0.2% vol. ammonia (32%) |
| | B = acetonitrile |
| Gradient: | 0-1 min 1% B, 1-8 min 1-99% B, 8-10 min 99% B |
| Flow: | 50 mL/min |
| Temperature: | RT |
| Solution: | max. 250 mg/2.5 mL dimethyl sufoxide or DMF |
| Injection: | 1 × 2.5 mL |
| Detection: | DAD scan range 210-400 nm |
| | MS ESI+, ESI−, scan range 160-1000 m/z |

Chiral HPLC Conditions

If not specified otherwise, chiral HPLC-data given in the subsequent specific experimental descriptions refer to the following conditions:

Analytics:

| | |
|---|---|
| System: | Waters: Alliance 2695, DAD 996, ESA: Corona |
| Column: | Chiralpak AD-H 5 µm 150 × 4.6 mm |
| Solvent: | Ethanol/Methanol/Diethylamine 50:50:0.1 (v/v/v) |
| Flow: | 1.0 mL/min |
| Temperature: | 25° C. |
| Solution: | 1.0 mg/mL ethanol/methanol 1:1 |
| Injection: | 5.0 µl |
| Detection: | UV 280 nm |

Preparation:

| | |
|---|---|
| System: | Agilent: Prep 1200, 2xPrep Pump, DLA, MWD, Gilson: Liquid Handler 215 |
| Column: | Chiralpak AD-H 5 µm 250 × 30 mm |
| Solvent: | Ethanol/Methanol/Diethylamine 50:50:0.1 (v/v/v) |
| Flow: | 30 mL/min |
| Temperature: | RT |
| Solution: | 50 mg/2 mL EtOH/MeOH |
| Injection: | 2 × 1 mL |
| Detection: | UV 280 nm |

Flash Column Chromatography Conditions

"Purification by (flash) column chromatography" as stated in the subsequent specific experimental descriptions refers to the use of a Biotage Isolera purification system. For technical specifications see "Biotage product catalogue" on www.biotage.com.

Determination of Optical Rotation Conditions

Optical rotations were measured in dimethyl sulfoxide at 589 nm wavelength, 20° C., concentration 1.0000 g/100 ml, integration time 10 s, film thickness 100.00 mm.

EXAMPLES

General Experimental Methods

Method A1 Preparation of 2-hydroxy-6-oxocyclohex-1-ene-1-carbothioamides (Formula 1-1)

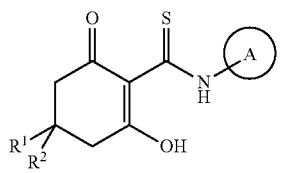

To an ice-cooled mixture of the cyclohexane-1,3-dione (compound of general formula A) and the isothiocyanate (compound of general formula B) in MeCN (approximately 1 ml/mmol) was added DBU (approximately 1.5 eq) slowly dropwise. The reaction was stirred overnight. The reaction mixture was poured into ice-water containing concentrated HCl (typically the same volume of concentrated HCl was used as the volume of DBU used in the reaction) and the solid formed was collected by filtration and dried in vacuo and was used directly without further purification. If a solid did not form then the the organics were extracted with EtOAc, the EtOAc layers were combined and washed with water, sat. NaCl(aq), dried over $Na_2SO_4$ or $MgSO_4$, filtered and concentrated. The crude residue was purified by column chromatography using hexane and EtOAc gradients.

Method A2 Preparation of 2-hydroxy-6-oxocyclohex-1-ene-1-carbothioamides (Formula 1-1)

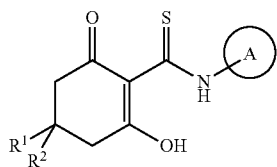

To a solution of the cyclohexane-1,3-dione (compound of general formula A) and the isothiocyanate (compound of general formula B) in MeCN (approximately 1 ml/mmol) was added a few drops of triethylamine (TEA) and the mixture was heated under reflux conditions overnight. The reaction was allowed to cool the solid formed was collected by filtration and dried in vacuo. When no solid formed the solvent was slowly removed under reduced pressure until a solid was formed and this solid was collected by filtration and dried in vacuo. When no solid formed upon concentrating then the residue was purified by column chromatography using hexane and EtOAc gradients.

Method B1 Preparation of 2-(amino)-6-oxocyclohex-1-ene-1-carbothioamides (Formula 1-2)

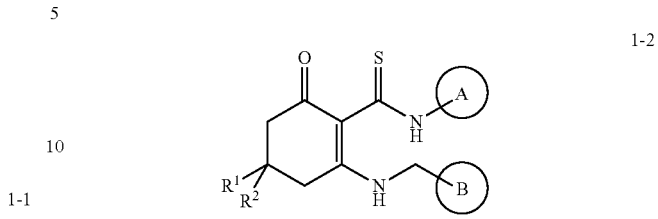

A mixture of the 2-hydroxy-6-oxocyclohex-1-ene-1-carbothioamides (Formula 1-1) and the 4-aminomethylheterocycle (Reagent B) was heated under an Argon atmosphere in either EtOH, EtOAc or DMSO optionally using 4 Å molecular sieves to remove water from the reaction mixture. The reaction was concentrated and purified either column chromatography or preparative HPLC.

Method C1 Preparation of N-protected 2-heterocyclo-1,5,6,7-tetrahydro-4H-indol-4-ones (Formula 1-5 and 1-6)

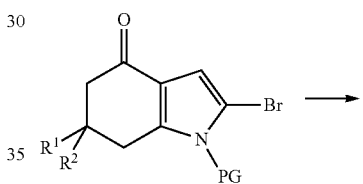

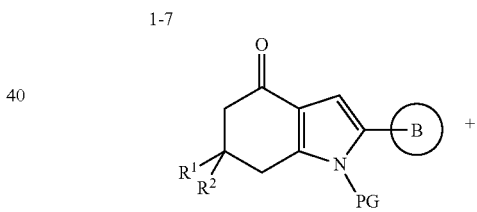

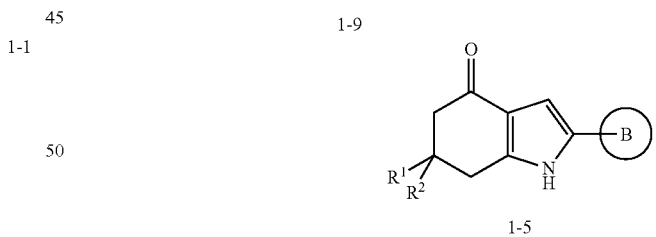

To a solution of the 1,5,6,7-tetrahydro-4H-indol-4-one (general formula 1-8) and the heterocyclic boronic acid or ester (general formula G) in dimethoxyethane (approximately 5 mL/mmol) and water (approximately 1 mL/mmol) was added either potassium carbonate or caesium carbonate (2.2 eq). The reaction mixture was degassed (×3). Under an Argon atmosphere was added the catalyst, either bis(triphenylphosphine)palladium(II) dichloride or Tetrakis(triphenylphosphin)-palladium(0). The reaction mixture was heated for at 85° C. and the reaction was monitored. The reaction was diluted with water and extracted with dichloromethane (×3). The organics phases were combined, washe dried over Na$_2$SO$_4$ or MgSO$_4$, filtered and concentrated. The crude residue was purified by silica chromatography using hexane and EtOAc to give

Method D1 Preparation of unprotected 2-heterocyclo-1,5,6,7-tetrahydro-4H-indol-4-ones (Formula 1-5)

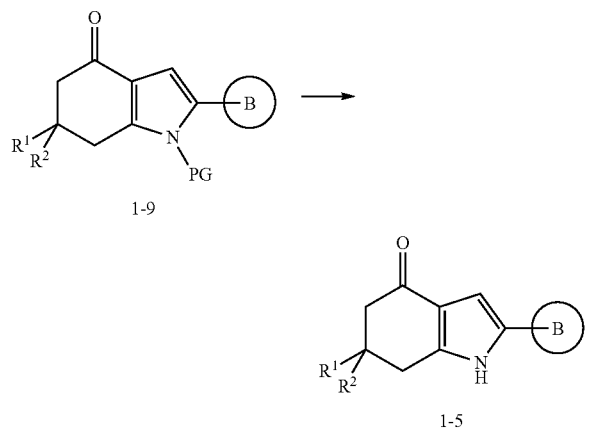

A solution of the N-Boc 2-heterocyclo-1,5,6,7-tetrahydro-4H-indol-4-one (general formula 1-9) in dichloromethane and/or trifluoroacetic acid was stirred at room temperature for 3 h. The reaction was concentrated in vacuo and was used directly without further purification.

Method E1 Preparation of 2-heterocyclo 3-bromo-1,5,6,7-tetrahydro-4H-indol-4-ones (Formula 1-6)

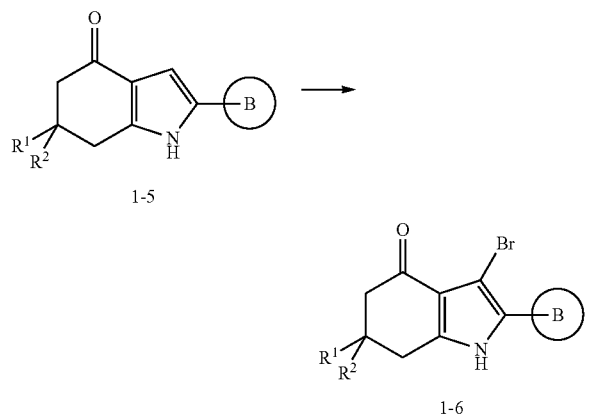

To a solution of 2-(heterocyclyl)-1,5,6,7-tetrahydro-4H-indol-4-ones in DMF (approximately 15 mL/mmol) under an atmosphere of Argon was added N-bromosuccinimide (NBS, 1.05 eq). The reaction mixture was stirred at room temperature for 16 and poured into an ice-water mixture. The solid formed was collected by filtration and the solid was dried in vacuo to yield the target compound, which was used without further purification.

Method F1 Preparation of 2-heterocyclo-3-amino-1,5,6,7-tetrahydro-4H-indol-4-ones (Formula Ia)

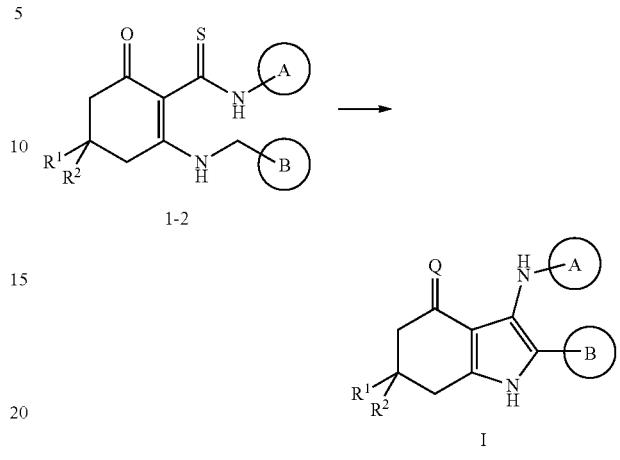

A mixture of the 2-(amino)-6-oxocyclohex-1-ene-1-carbothioamides (Formula 1-2) in either MeOH or EtOH or DMSO was added an aqueous 30% solution of hydrogen peroxide and the reaction heated under reflux conditions or in a sealed tube overnight. The reaction was concentrated and purified either by column chromatography or preparative HPLC.

Method F2 Preparation of 2-heterocyclo-3-amino-1,5,6,7-tetrahydro-4H-indol-4-ones (Formula Ia)

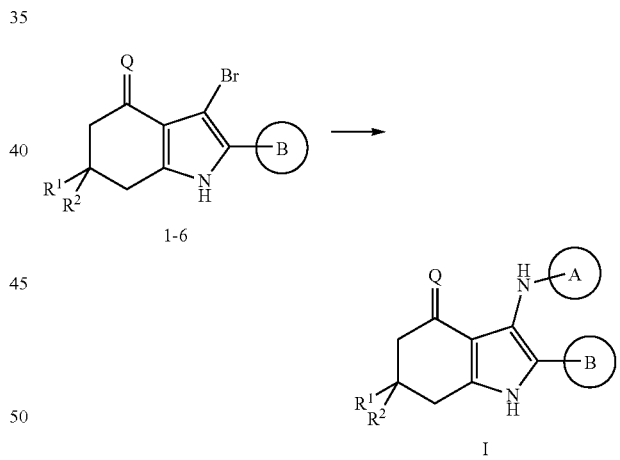

To a mixture of the 2-heterocyclo 3-bromo-1,5,6,7-tetrahydro-4H-indol-4-ones (general formula 1-6), amine (compound of general formula E), the pre-catalyst chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct, approximately 2 mol %), the ligand 2-(di-tert-butylphosphino)-2',4',6'-triisopropyl-3,6-dimethoxy-1,1'-biphenyl (tBuBrettPhos, 4 mol %) and lithium bis(trimethylsilyl)amide (LHMDS, 4-5 eq). The reaction mixture was degassed (×3) and heated under an Argon atmosphere at 80° C. and the reaction was monitored. The reaction was quenched by the addition of 1M HCl (1 mL) and the reaction diluted with EtOAc and washed with sat. NaHCO$_{3(aq)}$. The aqueous phase was extracted with EtOAc (×2). The organics phases were combined and washed with sat. NaCl$_{(aq)}$, dried over Na$_2$SO$_4$ or MgSO$_4$, filtered and concentrated. The crude residue was purified by preparative HPLC.

Method G1 Acylation of 2-(2-aminopyrid-4-yl)-3-amino-1,5,6,7-tetrahydro-4H-indol-4-ones (Formula Ia)

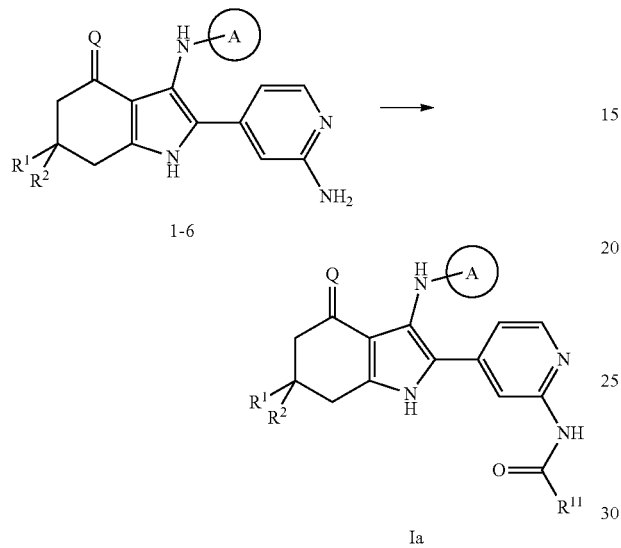

To a mixture of the 2-(2-aminopyrid-4-yl)-3-amino-1,5,6,7-tetrahydro-4H-indol-4-one, pyridine (10 eq) in THF (1 mL) was added the acyl chloride (2-10 eq) and stirred at room temperature. The reaction was quenched by the addition of MeOH (1 mL) and concentrated. The residue was purified either by column chromatography or preparative HPLC.

Method G2 Acylation of 2-(2-aminopyrid-4-yl)-3-amino-1,5,6,7-tetrahydro-4H-indol-4-ones (Formula Ia)

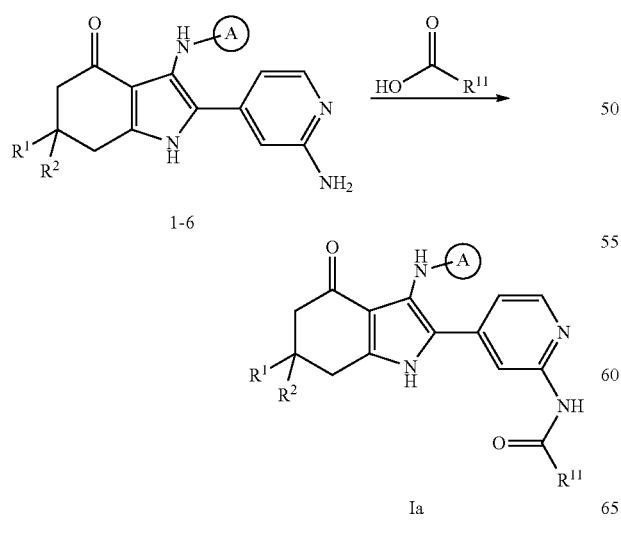

To a mixture of the carboxylic acid (2 eq) in DMF was added HATU (2 eq) followed by DIPEA (2 eq). Stirred at RT for 10-15 mins, then 2-(2-aminopyrid-4-yl)-3-amino-1,5,6,7-tetrahydro-4H-indol-4-one (1 eq) was added and stirred at room temperature unless otherwise stated. The reaction was concentrated and purified either by column chromatography or preparative HPLC.

Method G3 The formation of ureas from 2-(2-aminopyrid-4-yl)-3-amino-1,5,6,7-tetrahydro-4H-indol-4-ones (Formula Ia)

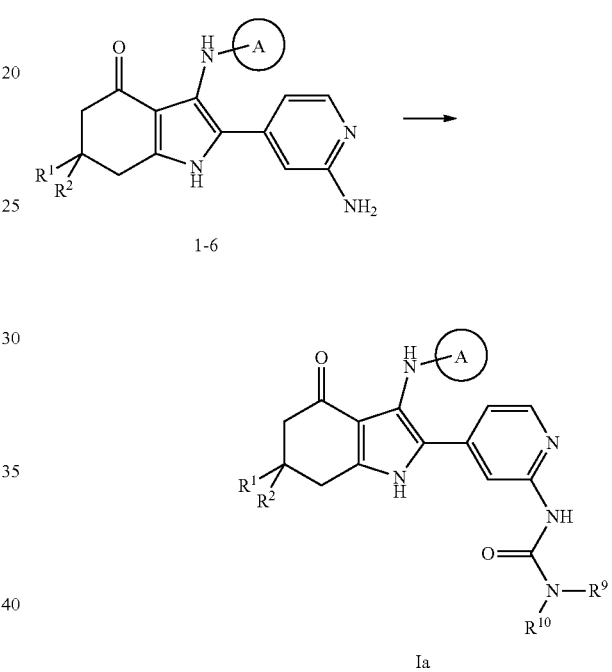

To a mixture of the 2-(2-aminopyrid-4-yl)-3-amino-1,5,6,7-tetrahydro-4H-indol-4-one in pyridine (1-2 mL) was added isocyanate (2 eq) and stirred at room temperature. The reaction was concentrated. The residue was purified either by column chromatography or preparative HPLC.

Method G4 The formation of thioureas from 2-(2-aminopyrid-4-yl)-3-amino-1,5,6,7-tetrahydro-4H-indol-4-ones (Formula Ia)

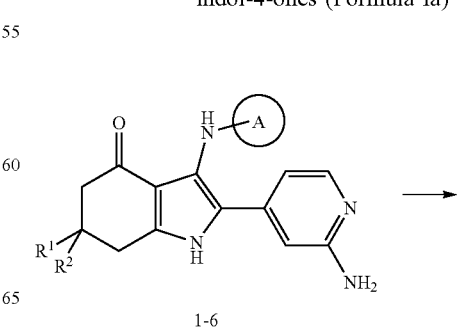

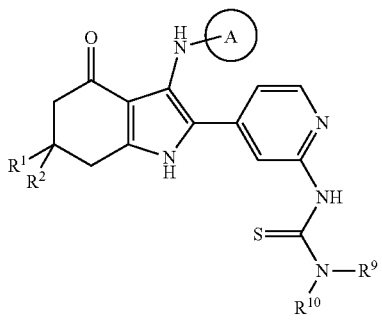

Ia

To a mixture of the 2-(2-aminopyrid-4-yl)-3-amino-1,5,6,7-tetrahydro-4H-indol-4-one in pyridine (1-2 mL) was added isothiocyanate (2 eq) and stirred at room temperature. The reaction was concentrated. The residue was purified either by column chromatography or preparative HPLC.

Method G5 Reductive amination of 2-(2-aminopyrid-4-yl)-3-amino-1,5,6,7-tetrahydro-4H-indol-4-ones (Formula Ia)

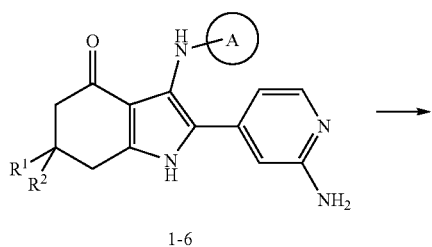

1-6

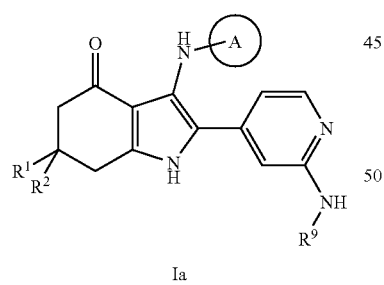

Ia

To a solution of Example 9 (1 eq) in MeOH (11 mL) was added a solution of aldehyde (5 eq) in AcOH (15 eq) and stirred at RT overnight. The reaction was cooled to 0° C. and NaBH₃CN (1.2 eq) added and stirred for 24 h. Additional NaBH₃CN (1.2 eq) was added if necessary to drive the reaction and stirred for 1-3 days. The reaction was diluted with sat. NaHCO₃, extracted with EtOAc. The organic layers were combined and washed with sat. NaCl, dried over Na₂SO₄, filtered and concentrated and purified by preparative HPLC or by silica chromatography.

Method H1 Alkylation of 2-(2-aminopyrid-4-yl)-3-amino-1,5,6,7-tetrahydro-4H-indol-4-ones (Formula Ia)

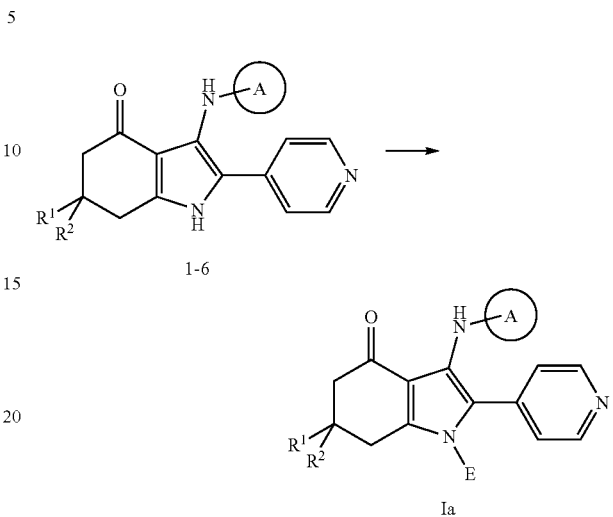

To a solution of 2-(2-aminopyrid-4-yl)-3-amino-1,5,6,7-tetrahydro-4H-indol-4-one (1 eq) in THF under Ar was added MeOH (5 eq) and PPh₃ (1.6 eq). To this solution was added DIAD (1.6 eq). Stirred for 16 h at RT. Concentrated and the residue was purified either by column chromatography or preparative HPLC.

Synthetic Intermediates

Intermediate 1-7-1 Preparation of 2-bromo-6,6-dimethyl-1,5,6,7-tetrahydro-indol-4-one

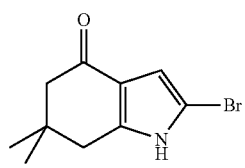

To a solution of 6,6-dimethyl-1,5,6,7-tetrahydroindol-4-one (16.32 g, 100 mmol) in anhydrous tetrahydrofuran (250 mL) was added slowly dropwise over 30 mins a solution of phenyl-trimethylammonium tribromide (37.59 g, 100 mmol) in anhydrous tetrahydrofuran (150 mL). The reaction was stirred at room temperature for 2 h and in this time a colourless solid precipitated. The solid was collected by filtration and dried in vacuo to give the desired product (11.98 g, 49%). The filtrate was concentrated and re-dissloved in dichloromethane (250 mL) and washed with 5% NaHCO₃₍ₐq₎, sat. NaCl₍ₐq₎, dried over Na₂SO₄, filtered and concentrated. The residue was crystallized methanol/water (60 mL, 1:1) to give the desired product (1.91 g, 8%).

1H NMR (400 MHz, DMSO-d₆) δ [ppm]=1.01 (s, 6H) 2.19 (s, 2H) 2.59 (s, 2H) 6.27 (d, 1H) 11.95 (br. s., 1H)

Intermediate 1-8-1 Preparation of tert-butyl 2-bromo-6,6-dimethyl-4-oxo-4,5,6,7-tetrahydro-1H-indole-1-carboxylate

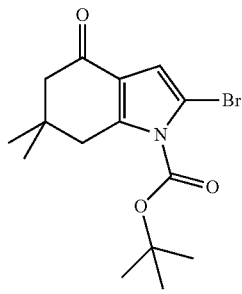 [SMILES: CC1(C)CC(=O)c2cc(Br)n(C(=O)OC(C)(C)C)c2C1]

To a solution of 2-bromo-6,6-dimethyl-1,5,6,7-tetrahydro-indol-4-one 1-7-1 (11.97 g, 49.4 mmol) and di-tert-butyl-dicarbonate (11.87 g, 54.4 mmol) in anhydrous acetonitrile (600 mL) was added 4-dimethylaminopyridine (60 mg, 0.49 mmol) and stirred at room temperature for 3 h. To the reaction mixture was added imidazole (673 mg, 9.9 mmol) and stirred for an additional 15 min. The reaction was diluted with chloroform (500 mL) and washed with 0.5% HCl solution (3×300 ml). The organics phase was dried over $Na_2SO_4$, filtered and concentrated. The crude residue (16.85 g, 99%), was used without further purification.

1H NMR (400 MHz, DMSO-$d_6$) δ [ppm]=1H NMR 1.04 (s, 6H) 1.60 (s, 9H) 2.29 (s, 2H) 2.88 (s, 2H) 6.60 (s, 1H).

Intermediate 1-5-1 Preparation of 6,6-dimethyl-2-(pyridin-4-yl)-1,5,6,7-tetrahydro-4H-indol-4-one

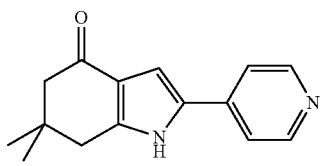 [SMILES: CC1(C)CC(=O)c2cc(-c3ccncc3)[nH]c2C1]

A mixture of 5,5-dimethyl-1,3-cyclohexanedione (37.1 g, 264 mmol), B und ammonium acetate (81.7 g, 1059 mmol) in EtOH (1000 mL) was stirred at room temperature for 16 h. The reaction mixture was concentrated and to the residue was added water. The solid formed was collected by filtration and the solid was dried in vacuo to yield 16 g of 38% pure target compound, which was used without further purification.

1H NMR (300 MHz, DMSO-$d_6$) δ [ppm]=0.97-1.19 (m, 6H) 2.27 (s, 2H) 2.74 (s, 2H) 7.05 (s, 1H) 7.51-7.74 (m, 2H) 8.43-8.60 (m, 2H) 11.98 (br. s., 1H).

Intermediate 1-6-1 Preparation of 3-bromo-6,6-dimethyl-2-(pyridin-4-yl)-1,5,6,7-tetrahydro-4H-indol-4-one

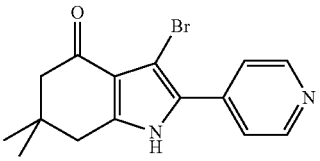 [SMILES: CC1(C)CC(=O)c2c([nH]c(-c3ccncc3)c2Br)C1]

To a solution of 6,6-dimethyl-2-(pyridin-4-yl)-1,5,6,7-tetrahydro-4H-indol-4-one 1-5-1 (10 g, 41.6 mmol) in DMF (600 mL) under an atmosphere of Argon was added N-bromosuccinimide (NBS, 7.77 g, 43.7 mmol). The reaction mixture was stirred at room temperature for 16 and poured into an ice-water mixture. The solid formed was collected by filtration and the solid was dried in vacuo to yield 11.4 g of 85% pure target compound, which was used without further purification.

1H NMR (300 MHz, DMSO-$d_6$) δ [ppm]=1.06 (s, 6H) 2.20-2.35 (m, 2H) 2.76 (s, 2H) 7.75 (m, 2H) 8.64 (br. s., 2H) 12.30 (br. s., 1H)

Intermediate 1-1-1 Preparation of 2-hydroxy-4,4-dimethyl-6-oxo-N-phenylcyclohex-1-ene-1-carbothioamide

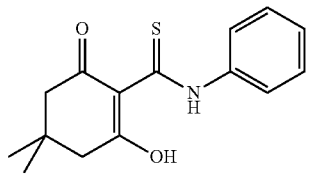

Synthesized according to Method A1. 5,5-Dimethyl-1,3-cyclohexanedione (50 g) gave the desired product (88.4 g, 90%).

1H NMR (400 MHz, DMSO-$d_6$) δ [ppm]=1.04 (s, 6H) 2.71 (br. s., 2H) 3.32 (br. s., 2H) 7.26-7.38 (m, 1H) 7.42-7.52 (m, 5H) 13.81 (s, 1H)

Intermediate 1-1-2 Preparation of N-(3-fluorophenyl)-2-hydroxy-4,4-dimethyl-6-oxocyclohex-1-ene-1-carbothioamide

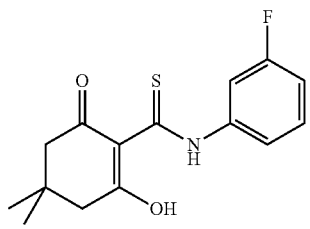 [SMILES: CC1(C)CC(=O)C(C(=S)Nc2cccc(F)c2)=C(O)C1]

Synthesized according to Method A1. 5,5-Dimethyl-1,3-cyclohexanedione (3 g) gave the desired product (5.6 g, 89%).

1H NMR (400 MHz, CDCl₃) δ [ppm]=1.13 (s, 6H), 1.78 (bs, 1H), 2.49 (s, 2H), 2.65 (s, 2H), 6.97-7.02 (m, 1H), 7.21-7.23 (m, 1H), 7.37-7.39 (m, 2H). 14.07 (bs, 1H)

Intermediate 1-1-3 Preparation of N-(4-fluorophenyl)-2-hydroxy-4,4-dimethyl-6-oxocyclohex-1-ene-1-carbothioamide

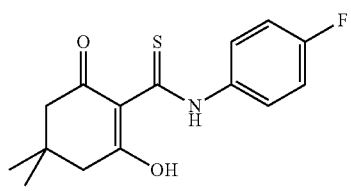 [SMILES: CC1(C)CC(=O)C(C(=S)Nc2ccc(F)cc2)=C(O)C1]

Synthesized according to Method A1. 5,5-Dimethyl-1,3-cyclohexanedione (3 g) gave the desired product (5.6 g, 90%).

1H NMR (400 MHz, CDCl₃) δ [ppm]=1.13 (s, 6H), 1.78, 2.49 (s, 2H), 2.64 (s, 2H), 7.08-7.12 (m, 2H), 7.39-7.43 (m, 2H), 13.90 (bs, 1H)

Intermediate 1-1-4 Preparation of N-(3,4-difluorophenyl)-2-hydroxy-4,4-dimethyl-6-oxocyclohex-1-ene-1-carbothioamide

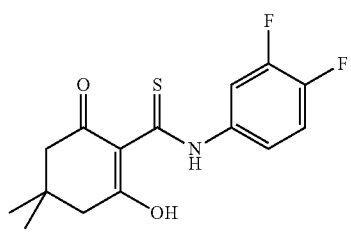 [SMILES: CC1(C)CC(=O)C(C(=S)Nc2ccc(F)c(F)c2)=C(O)C1]

Synthesized according to Method A1. 5,5-Dimethyl-1,3-cyclohexanedione (3 g) gave the desired product (6 g, 90%).

1H NMR (400 MHz, CDCl₃) δ [ppm]=1.13 (s, 6H), 1.78, 2.49 (s, 2H), 2.64 (s, 2H), 7.08-7.12 (m, 2H), 7.39-7.43 (m, 2H), 13.90 (bs, 1H)

Intermediate 1-1-5 Preparation of 2-hydroxy-6-oxo-N-phenylcyclohex-1-ene-1-carbothioamide

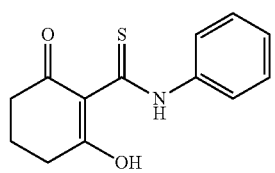 [SMILES: O=C1CCCC(O)=C1C(=S)Nc1ccccc1]

Synthesized according to Method A1. 1,3-Cyclohexanedione (43.7 g) gave the desired product (61.4 g, 63%).

1H NMR (400 MHz, DMSO-d₆) δ [ppm]=1.92 (m, 2H) 2.55-2.85 (m, 4H) 7.29-7.39 (m, 1H) 7.42-7.54 (m, 4H) 13.80 (s, 1H)

Intermediate 1-1-6 Preparation of N-(3-fluorophenyl)-2-hydroxy-6-oxocyclohex-1-ene-1-carbothioamide

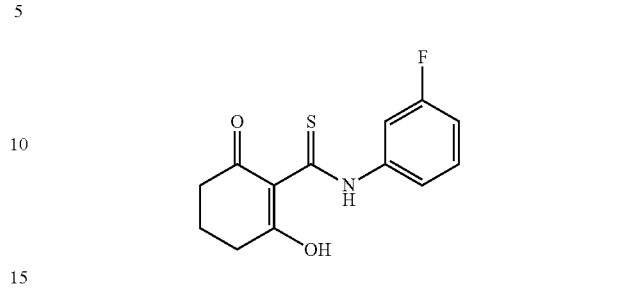

Synthesized according to Method A1. 1,3-Cyclohexanedione (3 g) gave the desired product after recrystallization form cyclohexane (5.4 g, 68%).

1H NMR (400 MHz, CDCl₃) δ [ppm]=2.00 (q, 2H), 2.64 (t, 2H), 2.79 (t, 2H), 6.97-7.03 (m, 1H), 7.19-7.23 (m, 1H), 7.32-7.40 (m, 2H), 14.10 (bs, 1H).

Intermediate 1-1-7 Preparation of N-(4-fluorophenyl)-2-hydroxy-6-oxocyclohex-1-ene-1-carbothioamide

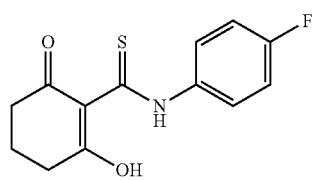 [SMILES: O=C1CCCC(O)=C1C(=S)Nc1ccc(F)cc1]

Synthesized according to Method A1. 1,3-Cyclohexanedione (3 g) gave the desired product (4.74 g, 67%) after column chromatography (EtOAc:cyclohexane (1:10)).

1H NMR (400 MHz, CDCl₃) δ [ppm]=1.97-2.04 (m, 2H), 2.62-2.65 (m, 2H), 2.77-2.79 (m, 2H), 7.07-7.14 (m, 2H), 7.36-7.41 (m, 2H), 13.93 (bs, 1H)

Intermediate 1-1-8 Preparation of N-(3,4-difluorophenyl)-2-hydroxy-6-oxocyclohex-1-ene-1-carbothioamide

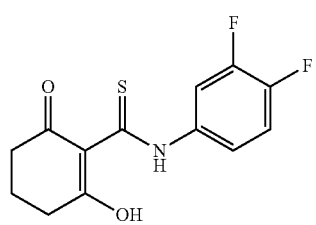 [SMILES: O=C1CCCC(O)=C1C(=S)Nc1ccc(F)c(F)c1]

Synthesized according to Method A1. 1,3-Cyclohexanedione (3 g) gave the desired product (5.1 g, 67%) after column chromatography (EtOAc:cyclohexane (1:10)).

1H NMR (400 MHz, CDCl₃) δ [ppm]=1.97-2.04 (m, 2H), 2.60-2.65 (m, 2H), 2.77-2.80 (m, 2H), 7.10-7.25 (m, 2H), 7.39-7.44 (m, 2H), 14.03 (bs, 1H)

Intermediate 1-1-9 Preparation of 2 2-hydroxy-4-isopropyl-6-oxo-N-phenylcyclohex-1-ene-1-carbothioamide

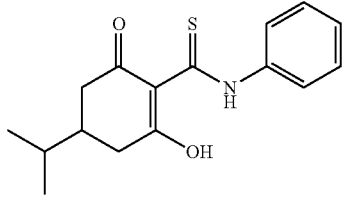 [SMILES: CC(C)C1CC(=O)C(C(=S)Nc2ccccc2)=C(O)C1]

Synthesized according to Method A1. 5-Isopropyl-3-cyclohexanedione (3 g) gave the desired product (2.9 g, 73%) after column chromatography (EtOAc:cyclohexane (1:19)).
1H NMR (400 MHz, CDCl$_3$) δ [ppm]=0.96 (d, 3H), 0.98 (d, 3H), 1.56-1.66 (m, 1H), 1.85-1.95 (m, 1H), 2.31-2.40 (m, 1H), 2.49-2.59 (m, 1H), 2.65-2.72 (m 1H), 2.74-2.82 (m, 1H), 7.27-7.33 (m, 1H), 7.39-7.48 (m, 4H), 13.98 (bs, 1H)

Intermediate 1-1-10 Preparation of N-(3-fluorophenyl)-2-hydroxy-4-isopropyl-6-oxocyclohex-1-ene-1-carbothioamide

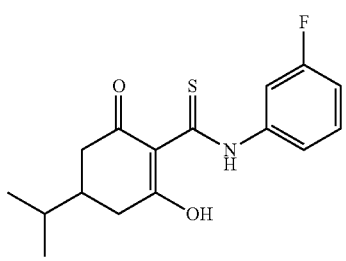 [SMILES: CC(C)C1CC(=O)C(C(=S)Nc2cccc(F)c2)=C(O)C1]

Synthesized according to Method A1. 5-Isopropyl-3-cyclohexanedione (4 g) gave the desired product (5 g, 62%) after column chromatography (EtOAc:cyclohexane (1:10)).
1H NMR (400 MHz, CDCl$_3$) δ [ppm]=0.96-0.98 (m, 6H), 1.59-1.64 (m, 1H), 1.87-1.94 (m, 1H), 2.32-2.39 (m, 1H), 2.51-2.58 (m, 1H), 2.66-2.82 (m, 2H), 6.98-7.02 (m, 1H), 7.20-7.22 (m, 1H), 7.33-7.40 (m, 2H), 14.09 (bs, 1H)

Intermediate 1-1-11 Preparation of N-(4-fluorophenyl)-2-hydroxy-4-isopropyl-6-oxocyclohex-1-ene-1-carbothioamide

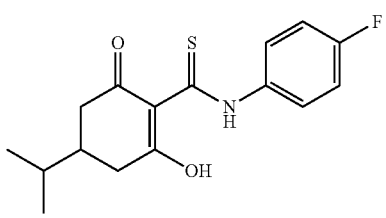 [SMILES: CC(C)C1CC(=O)C(C(=S)Nc2ccc(F)cc2)=C(O)C1]

Synthesized according to Method A1. 5-Isopropyl-3-cyclohexanedione (4 g) gave the desired product (4.7 g, 59%) after column chromatography (EtOAc:cyclohexane (1:10)).
1H NMR (400 MHz, CDCl$_3$) δ [ppm]=0.95-0.97 (m, 6H), 1.58-1.63 (m, 1H), 1.86-1.94 (m, 1H), 2.31-2.39 (m, 1H), 2.50-2.57 (m, 1H), 2.66-2.81 (m, 2H), 7.07-7.13 (m, 2H), 7.37-7.41 (m, 2H), 13.92 (bs, 1H)

Intermediate 1-1-12 Preparation of N-(3,4-difluorophenyl)-2-hydroxy-4-isopropyl-6-oxocyclohex-1-ene-1-carbothioamide

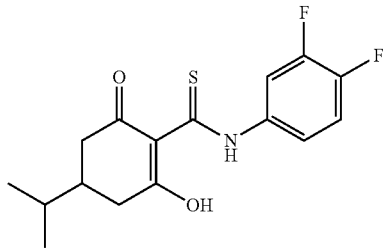 [SMILES: CC(C)C1CC(=O)C(C(=S)Nc2ccc(F)c(F)c2)=C(O)C1]

Synthesized according to Method A1. 4-Isopropyl-3-cyclohexanedione (4 g) gave the desired product (2.86 g, 59%) after crystallization (EtOAc:cyclohexane (1:10)).
1H NMR (400 MHz, CDCl$_3$) δ [ppm]=0.95-0.98 (m, 6H), 1.57-1.65 (m, 1H), 1.86-1.94 (m, 1H), 2.32-2.39 (m, 1H), 2.50-2.58 (m, 1H), 2.65-2.82 (m, 2H), 7.12-7.23 (m, 2H), 7.40-7.46 (m, 1H), 14.02 (bs, 1H)

Intermediate 1-1-13 Preparation of 2-hydroxy-4,4-dimethyl-6-oxo-N-(pyridin-2-yl)cyclohex-1-ene-1-carbothioamide

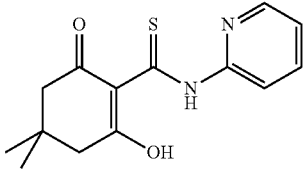 [SMILES: CC1(C)CC(=O)C(C(=S)Nc2ccccn2)=C(O)C1]

Synthesized according to Method A2. 5,5-Dimethyl-1,3-cyclohexanedione (906 mg) gave the desired product (738 mg, 41%).
1H NMR (300 MHz, DMSO-d$_6$) δ [ppm]=1.05 (s, 6H) 2.63 (br. s., 4H) 7.34 (m, 1H) 7.84-8.04 (m, 1H) 8.31 (d, 1H) 8.50 (d, 1H) 14.34 (br. s., 1H)

Intermediate 1-1-14 Preparation of N-(3-bromophenyl)-2-hydroxy-4,4-dimethyl-6-oxocyclohex-1-ene-1-carbothioamide

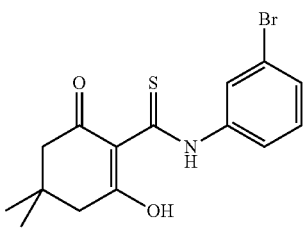 [SMILES: CC1(C)CC(=O)C(C(=S)Nc2cccc(Br)c2)=C(O)C1]

Synthesized according to Method A1. 5,5-Dimethyl-1,3-cyclohexanedione (7.8 g) gave the desired product (19.2 g, 97%).

1H NMR (300 MHz, DMSO-d$_6$) δ [ppm]=1.06 (s, 6H) 2.61 (br. s., 4H) 7.35-7.60 (m, 3H) 7.75-7.96 (m, 1H) 13.70 (s, 1H)

Intermediate 1-1-15 Preparation of N-(2-bromophenyl)-2-hydroxy-4,4-dimethyl-6-oxocyclohex-1-ene-1-carbothioamide

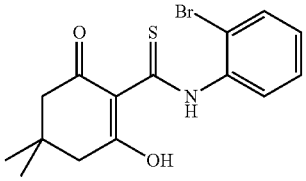 [SMILES: CC1(C)CC(=O)C(C(=S)Nc2ccccc2Br)=C(O)C1]

Synthesized according to Method A2. 5,5-Dimethyl-1,3-cyclohexanedione (1.84 g) gave the desired product (2.73 g, 59%).

1H NMR (300 MHz, DMSO-d$_6$) δ [ppm]=1.06 (s, 6H) 2.56 (br. s., 2H) 2.76 (br. s., 2H) 7.31 (m, 1H) 7.47 (m, 1H) 7.52-7.59 (m, 1H) 7.77 (m, 1H) 13.86 (s, 1H)

Intermediate 1-1-16 Preparation of N-(4-bromophenyl)-2-hydroxy-4,4-dimethyl-6-oxocyclohex-1-ene-1-carbothioamide

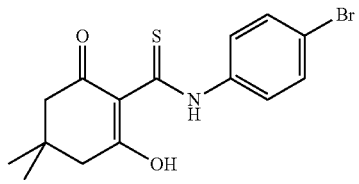 [SMILES: CC1(C)CC(=O)C(C(=S)Nc2ccc(Br)cc2)=C(O)C1]

Synthesized according to Method A2. 5,5-Dimethyl-1,3-cyclohexanedione (3.15 g) gave the desired product (3.07 g, 59%) after column chromatography (EtOAc:hexane (2:8)).

1H NMR (300 MHz, DMSO-d$_6$) δ [ppm]=1.05 (s, 6H) 2.60 (br. s., 4H) 7.41-7.56 (m, 2H) 7.56-7.71 (m, 2H) 13.71 (s, 1H)

Intermediate 1-1-17 Preparation of 2-hydroxy-4,4-dimethyl-N-(3-nitrophenyl)-6-oxocyclohex-1-ene-1-carbothioamide

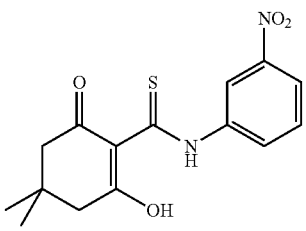 [SMILES: CC1(C)CC(=O)C(C(=S)Nc2cccc([N+](=O)[O-])c2)=C(O)C1]

Synthesized according to Method A2. 5,5-Dimethyl-1,3-cyclohexanedione (2.12 g) gave the desired product (1.66 g, 34%) after column chromatography (EtOAc:hexane (2:8)).

1H NMR (300 MHz, DMSO-d$_6$) δ [ppm]=1.07 (s, 6H) 2.59 (br. s., 4H) 7.63-7.85 (m, 1H) 7.99 (m, 1H) 8.17 (m, 1H) 8.58 (s, 1H) 13.68 (s, 1H)

Intermediate 1-1-18 Preparation of 6-hydroxy-8-oxo-N-phenylspiro[3.5]non-6-ene-7-carbothioamide

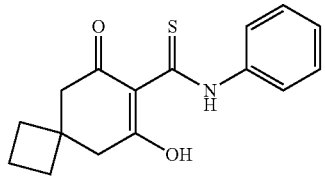 [SMILES: O=C1CC2(CCC2)CC(O)=C1C(=S)Nc1ccccc1]

Synthesized according to Method A2. 8-Hydroxyspiro[3.5]non-7-en-6-one (4 g) gave the desired product (2.71 g, 36%) after preparative HPLC (Chromatorex C18 5 μm 250×50.8 mm, Solvent: A=H$_2$O+0.1% Vol. AcOH (99%), B=Acetonitrile, isocratic 85% in A, flow: 200 mL/min).

1H NMR (300 MHz, DMSO-d$_6$) δ [ppm]=1.75-1.97 (s, 6H) 2.83 (br. s., 4H) 7.28-7.40 (m, 1H) 7.40-7.51 (m, 4H) 13.83 (s, 1H)

Intermediate 1-1-19 Preparation of 2-hydroxy-6-oxo-N-phenyl-4-(trifluoromethyl)cyclohex-1-ene-1-carbothioamide

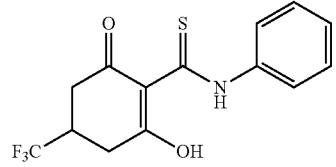 [SMILES: O=C1CC(C(F)(F)F)CC(O)=C1C(=S)Nc1ccccc1]

Synthesized according to Method A2. 5-trifluoromethyl-3-cyclohexanedione (4.6 g) gave the desired product (2.82 g, 35%) after column chromatography (EtOAc:hexane (1:4)).

1H NMR (400 MHz, DMSO-d$_6$) δ [ppm]=2.69-2.96 (m, 4H) 3.34-3.43 (m, 1H) 7.30-7.36 (m, 1H) 7.41-7.56 (m, 4H) 13.42 (s, 1H)

Intermediate 1-1-20 Preparation of 4-ethyl-2-hydroxy-6-oxo-N-phenylcyclohex-1-ene-1-carbothioamide

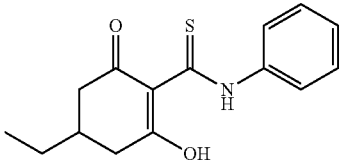 [SMILES: CCC1CC(=O)C(C(=S)Nc2ccccc2)=C(O)C1]

Synthesized according to Method A2. 5-Ethyl-3-cyclohexanedione (1.2 g) gave the desired product (820 mg, 35%) after column chromatography (EtOAc:hexane (1:9)).

1H NMR (400 MHz, DMSO-d$_6$) δ [ppm]=0.91 (t, 3H) 1.39 (q, 2H) 1.89-2.12 (m, 1H) 2.54 (br. s., 1H) 2.61-2.90 (m, 2H) 7.31-7.42 (m, 1H) 7.42-7.54 (m, 4H) 13.86 (s, 1H)

Intermediate 1-1-21 Preparation of 2-hydroxy-4-(2-methylpropyl)-6-oxo-N-phenylcyclohex-1-ene-1-carbothioamide

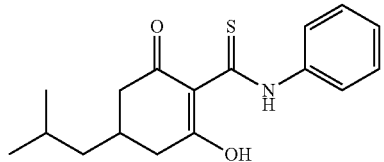 [SMILES: CC(C)CC1CC(=O)C(C(=S)Nc2ccccc2)=C(O)C1]

Synthesized according to Method A2. 5-Isobutylcyclohexane-1,3-dione (1.35 g (gave the desired product (969 mg, 40%) after column chromatography (EtOAc:hexane (1:9)).

1H NMR (400 MHz, DMSO-$d_6$) δ [ppm]=0.89 (d, Hz, 6H) 1.24 (t, 2H) 1.68 (m, 6.84 Hz, 1H) 2.22 (m, 1H) 2.54 (br. s., 1H) 2.59-2.85 (m, 2H) 7.25-7.41 (m, 1H) 7.41-7.53 (m, 4H) 13.84 (s, 1H)

Intermediate 1-1-22 Preparation of 2-hydroxy-6-oxo-4-phenyl-N-phenylcyclohex-1-en-1-carbothioamide

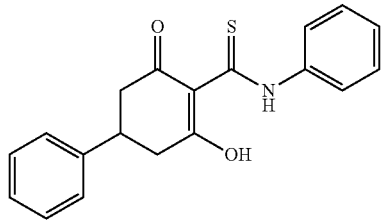 [SMILES: O=C1CC(c2ccccc2)CC(O)=C1C(=S)Nc1ccccc1]

Synthesized according to Method A2. 5-Phenylcyclohexane-1,3-dione (941 mg) gave the desired product (220 mg, 14%) after column chromatography (cyclohexan/EtOAc, 10:1).

m/z: [M+H]+=324.3

Intermediate 1-1-23 Preparation of 5-hydroxy-7-oxo-N-phenylspiro[2.5]oct-5-ene-6-carbothioamide

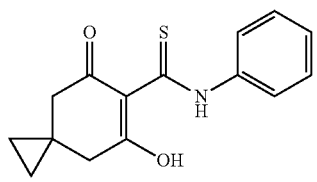 [SMILES: O=C1CC2(CC2)CC(O)=C1C(=S)Nc1ccccc1]

Synthesized according to Method A2. Spiro[2.5]octane-5,7-dione (1 g) gave the desired product (481 mg, 24%) after column chromatography (EtOAc:hexane (1:9)).

1H NMR (400 MHz, DMSO-$d_6$) δ [ppm]=0.49 (s, 4H) 2.58 (br. s., 1H) 2.62-2.92 (m, 2H) 7.26-7.41 (m, 1H) 7.41-7.58 (m, 4H) 13.80 (s, 1H)

Intermediate 1-1-24 Preparation of 5-hydroxy-7-oxo-N-phenylspiro[2.5]oct-5-ene-6-carbothioamide)

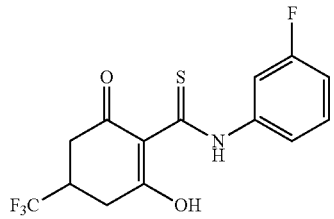 [SMILES: O=C1CC(C(F)(F)F)CC(O)=C1C(=S)Nc1cccc(F)c1]

Synthesized according to Method A2 and used directly in the next step.

Intermediate 1-1-25 Preparation of 2-hydroxy-4-methyl-6-oxo-N-phenylcyclohex-1-ene-1-carbothioamide

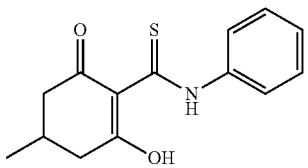 [SMILES: CC1CC(=O)C(C(=S)Nc2ccccc2)=C(O)C1]

Synthesized according to Method A2. 5-Methyl-3-cyclohexanedione (4 g) gave the desired product (1350 mg, 16%) after preparative HPLC (Chromatorex C18 10 μm 250×50.8 mm, Solvent: A=$H_2O$+0.1% Vol. $HCO_2H$ (99%), B=Acetonitrile, isocratic 80% B in A, flow: 200 mL/min).

1H NMR (300 MHz, DMSO-$d_6$) δ [ppm]=0.93-1.10 (m, 3H) 2.04-2.35 (m, 1H) 2.48-2.84 (m, 4H) 7.26-7.39 (m, 1H) 7.40-7.63 (m, 4H) 13.85 (s, 1H)

Intermediate 1-3-1 Preparation of 3-(benzylamino)-5,5-dimethylcyclohex-2-en-1-one

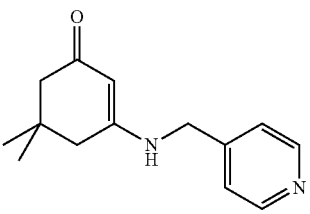 [SMILES: CC1(C)CC(=O)C=C(NCc2ccncc2)C1]

To a solution of 5,5-dimethyl-1,3-cyclohexanedione (1 g, 7.1 mmol) in toluene (7 mL) was added benzylamine (779 μL, 6.06 g, 7.1 mmol) and stirred overnight at room temperature. The reaction was then stirred overnight at 60° C. The reaction was diluted with sat. $NaCl_{(aq)}$, and EtOAc. The organic phase was filtered through a hydrophobic filter and Intermediate 1-3-2 Preparation of 3-{[(3-chloropyridin-4-yl)methyl]amino}-5,5-dimethylcyclohex-2-en-1-one

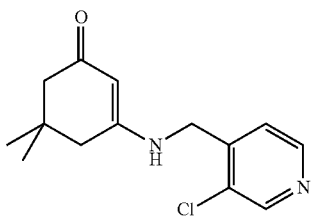 [SMILES: CC1(C)CC(=O)C=C(NCc2ccncc2Cl)C1]

To a suspension of 2-chloro-4-(aminomethyl)pyridine hydrochloride (2.81 g, 14.3 mmol) in toluene (40 mL) was added DBU (2.34 mL, 2.39 g, 15.7 mmol) and stirred at room temperature for 15 min. The 5,5-dimethyl-1,3-cyclohexanedione (2 g, 14.3 mmol) was added and stirred at room temperature for 12 h. The reaction was diluted with dichloromethane:isopropanol (9:1), washed with water and the organic phase and filtered through a hydrophobic filter and concentrated to give the desired product (2.77 g, 73%) and was used directly in the next step.

1H NMR (400 MHz, DMSO-$d_6$) δ [ppm]=0.97 (s, 6H) 2.10 (s, 4H) 5.15 (br. s., 2H) 7.60 (d, 1H) 8.49 (d, 1H) 8.51 (s, 1H)

Intermediate 1-2-1 Preparation of 4,4-dimethyl-6-oxo-N-phenyl-2-[(pyrimidin-4-ylmethyl)amino]cyclohex-1-ene-1-carbothioamide

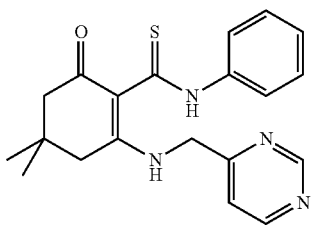 [SMILES: CC1(C)CC(=O)C(C(=S)Nc2ccccc2)=C(NCc2ccncn2)C1]

Synthesized according to Method B1. Intermediate 1-1-1 (906 mg) gave the desired product (500 mg, 34%) and 6,6-dimethyl-3-(phenylamino)-2-(pyrimidin-4-yl)-1,5,6,7-tetrahydro-4H-indol-4-one (34 mg, 6% Example 5) after preparative HPLC (XBrigde C18 5 μm 100×30 mm, Solvent: A=H$_2$O+0.2% Vol. NH$_3$ (32%), B=Acetonitrile, 33% B in A to 56% in A over 5.5 min, flow: 70 mL/min).

1H NMR (300 MHz, DMSO-$d_6$) δ [ppm]=0.90-1.07 (m, 6H) 2.39 (s, 2H) 2.62-2.79 (m, 2H) 4.96 (d, 2H) 7.17-7.28 (m, 1H) 7.39 (t, 2H) 7.47 (d, 2H) 7.55 (d, 1H) 8.83 (d, 1H) 9.18 (s, 1H) 14.00 (br. s., 1H) 14.58 (br. s., 1H)

Intermediate 1-2-2 Preparation of 6-oxo-N-phenyl-4-(propan-2-yl)-2-[(pyridin-4-ylmethyl)amino]cyclohex-1-ene-1-carbothioamide

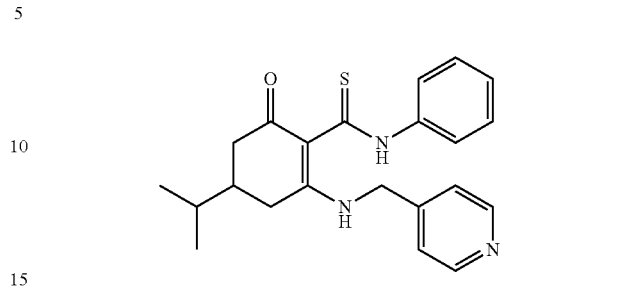

Synthesized according to Method B1. Intermediate 1-1-9 (9.8 g) gave the desired product (10.6 g, 82%).

1H NMR (300 MHz, DMSO-$d_6$) δ [ppm]=0.82-0.89 (6H), 1.51 (m, 1H), 1.66 (m, 1H), 2.28-2.50 (3H), 2.82 (1H), 4.86 (m, 2H), 7.22 (t, 1H), 7.36-7.45 (6H), 8.59 (d, 2H), 13.94 (s, 1H), 14.60 (s, 1H)

Intermediate 1-2-3 Preparation of 6-oxo-N,4-diphenyl-2-[(pyridin-4-ylmethyl)amino]cyclohex-1-ene-1-carbothioamide

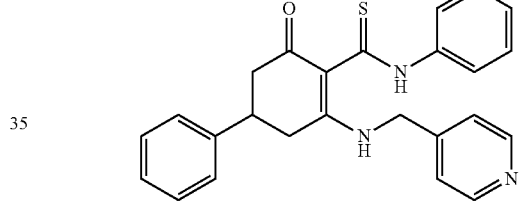

Synthesized according to Method B1. Intermediate 1-1-22 (210 mg) gave the desired product (95 mg, 34%) which crystallized from the reaction mixture on cooling.

1H NMR (400 MHz, DMSO-$d_6$) δ [ppm]=2.61 (d, 1H), 2.85-2.96 (m, 2H), 3.10 (d, 1H), 4.86 (m, 1H), 7.22-7.47 (10H), 7.44 (d, 2H), 8.57 (d, 2H), 13.89 (s, 1H), 14.57 (s, 1H)

Intermediate 1-2-4 Preparation of 6-oxo-N-phenyl-2-[(pyridin-4-ylmethyl)amino]cyclohex-1-ene-1-carbothioamide

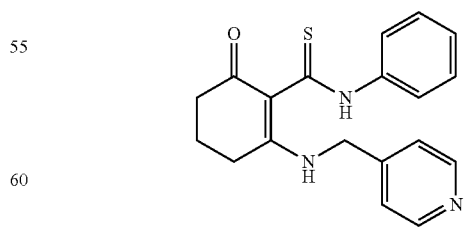

Synthesized according to Method B1. Intermediate 1-1-5 (61.3 g) gave the desired product (46.17 g, 55%) after concentrating the reaction mixture and heating in EtOAc (100 mL) at 50° C. and collecting the solid.

1H NMR (400 MHz, DMSO-d$_6$) δ [ppm]=1.80 (m, 2H), 2.46 (t, 2H), 2.74 (t, 2H), 4.82 (d, 2H), 7.21 (t, 1H), 7.27-7.41 (4H), 7.46 (d, 2H), 8.59 (d, 2H), 13.74 (s, 1H), 14.54 (s, 1H)

Intermediate 1-2-5 Preparation of N-(3-bromophenyl)-4,4-dimethyl-6-oxo-2-[(pyridin-4-ylmethyl)amino]cyclohex-1-ene-1-carbothioamide

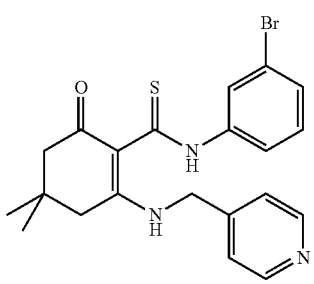 [SMILES: CC1(C)CC(=O)C(C(=S)Nc2cccc(Br)c2)=C(NCc2ccncc2)C1]

Synthesized according to Method B1. Intermediate 1-1-14 (300 mg) gave the desired product (185 mg, 48%) after preparative HPLC (XBrigde C18 5 μm 100×30 mm, Solvent: A=H$_2$O+0.2% Vol. NH$_3$ (32%), B=Acetonitrile, 0-0.5 min 25 mL/min increasing to 70 mL/min 39% solvent B; 0.5-5.5 min 39-69% solvent B, flow: 70 mL/min).

1H NMR (300 MHz, DMSO-d$_6$) δ [ppm]=0.97 (s, 6H) 2.39 (s, 2H) 2.66 (s, 2H) 4.86 (d, 2H) 7.27-7.50 (m, 5H) 7.82 (s, 1H) 8.59 (d2H) 13.83 (br. s., 1H) 14.68 (br. s., 1H)

Intermediate 1-2-6 Preparation of 3'-(phenylamino)-2'-(pyridin-4-yl)-1',7'-dihydrospiro[cyclobutane-1,6'-indol]-4'(5'H)-one

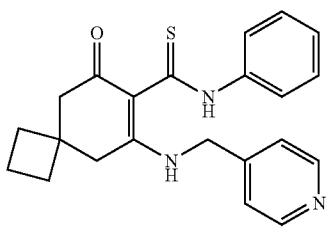 [SMILES: O=C1CC2(CCC2)CC(NCc2ccncc2)=C1C(=S)Nc1ccccc1]

Synthesized according to Method B1. Intermediate 1-1-18 (500 mg) gave the desired product (33 mg, 6%) after preparative HPLC (XBrigde C18 5 μm 150×50 mm, Solvent: A=H$_2$O+A+0.1% Vol. HCOOH (99%), B=Acetonitrile, 0-8 min 26-46% solvent B, flow: 150 mL/min).

1H NMR (300 MHz, DMSO-d$_6$) δ [ppm]=1.71-2.05 (m, 6H) 2.97 (s, 2H) 6.46-6.70 (m, 3H) 7.03 (t, 2H) 7.32-7.56 (m, 3H) 8.40 (d, 2H) 11.91 (s, 1H)

Intermediate 1-2-7 Preparation of 4,4-dimethyl-N-(3-nitrophenyl)-6-oxo-2-[(pyridin-4-ylmethyl)amino]cyclohex-1-ene-1-carbothioamide

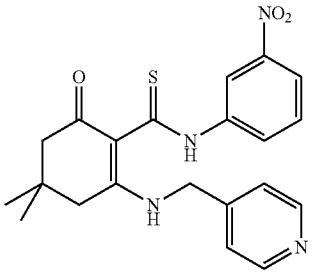

Synthesized according to Method B1. Intermediate 1-1-17 (300 mg) gave the desired product (30 mg, 8%) after preparative HPLC (XBrigde C18 5 μm 100×30 mm, Solvent: A=H$_2$O+0.2% Vol. NH$_3$ (32%), B=Acetonitrile, 0-0.5 min 25 mL/min increasing to 70 mL/min 42% solvent B; 0.5-5.5 min 42-58% solvent B, flow: 70 mL/min).

m/z: [M+H]+=411

Intermediate 1-2-8 Preparation of 6-oxo-N-phenyl-2-[(pyridin-4-ylmethyl)amino]-4-(trifluoromethyl)cyclohex-1-ene-1-carbothioamide

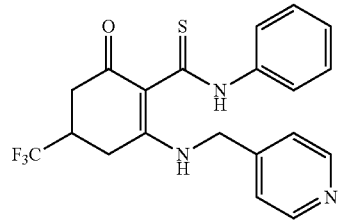 [SMILES: O=C1CC(C(F)(F)F)CC(NCc2ccncc2)=C1C(=S)Nc1ccccc1]

Synthesized according to Method B1. Intermediate 1-1-16 (370 mg) gave the desired product (243 mg, 51%) after column chromatography (EtOAc:Hexane).

1H NMR (400 MHz, DMSO-d$_6$) δ [ppm]=2.53-2.75 (m, 2H) 2.76-2.88 (m, 1H) 3.02-3.10 (m, 1H) 3.11-3.21 (m, 1H) 4.81-4.95 (m, 2H) 7.13-7.33 (m, 1H) 7.33-7.53 (m, 5H) 8.51-8.64 (m, 2H) 13.56 (br. s., 1H) 14.16 (br. s., 1H)

Intermediate 1-2-9 Preparation of 4,4-dimethyl-6-oxo-N-(pyridin-2-yl)-2-[(pyridin-4-ylmethyl)amino]cyclohex-1-ene-1-carbothioamide

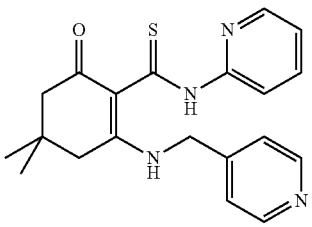 [SMILES: CC1(C)CC(=O)C(C(=S)Nc2ccccn2)=C(NCc2ccncc2)C1]

Synthesized according to Method B1. Intermediate 1-1-13 (648 mg) gave the desired product (60 mg, 7%) after preparative HPLC (Chromatorex C18 5 μm 250×50.8 mm, Solvent: A=H$_2$O+0.1% Vol. AcOH (99%), B=Acetonitrile, isocratic 85% in A, flow: 200 mL/min).

1H NMR (400 MHz, DMSO-d$_6$) δ [ppm]=0.94-0.99 (m, 6H) 2.41 (s, 2H) 2.69 (s, 2H) 4.89 (d, 2H) 7.21 (m, 1H) 7.37-7.41 (m, 2H) 7.82 (m, 1H) 8.38 (d, 1H) 8.42 (m, 1H) 8.57-8.64 (m, 2H) 14.19 (br. S., 1H) 15.17 (br. s., 1H)

Intermediate 1-2-10 Preparation of 4,4-dimethyl-6-oxo-N-phenyl-2-[(1H-pyrrolo[2,3-b]pyridin-4-ylmethyl)amino]cyclohex-1-ene-1-carbothioamide

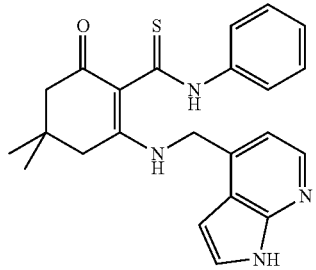 [SMILES: CC1(C)CC(=O)C(C(=S)Nc2ccccc2)=C(NCc2ccnc3[nH]ccc23)C1]

Synthesized according to Method B1. Intermediate 1-1-1 (780 mg) gave the desired product (73 mg, 6%) after preparative HPLC (XBrigde C18 5 μm 100×30 mm, Solvent: A=H$_2$O+0.1% Vol. HCO$_2$H (99%), B=Acetonitrile, 0-8 min 40-60% B, flow: 70 mL/min).

1H NMR (400 MHz, DMSO-d$_6$) δ [ppm]=0.86-1.00 (m, 6H) 2.33-2.46 (m, 2H) 2.73 (s, 2H) 5.07 (d, 2H) 6.64 (dd, 1H) 7.06 (d, 1H) 7.19-7.27 (m, 1H) 7.34-7.42 (m, 2H) 7.42-7.48 (m, 2H) 7.49-7.55 (m, 1H) 8.23 (d, 1H) 11.77 (br. s., 1H) 14.34 (br. s., 1H) 14.75 (s, 1H)

Intermediate 1-2-11 Preparation of 4-ethyl-6-oxo-N-phenyl-2-[(pyridin-4-ylmethyl)amino]cyclohex-1-ene-1-carbothioamide

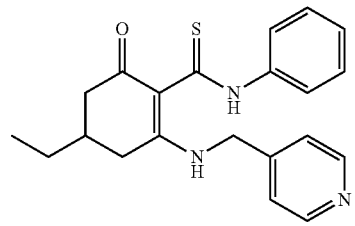 [SMILES: CCC1CC(=O)C(C(=S)Nc2ccccc2)=C(NCc2ccncc2)C1]

Synthesized according to Method B1. Intermediate 1-1-20 (810 mg) gave the desired product (566 mg, 53%) after column chromatography (EtOAc:Hexane).

1H NMR (400 MHz, DMSO-d$_6$) δ [ppm]=0.76-0.89 (m, 3H) 1.24-1.40 (m, 2H) 1.72-1.90 (m, 1H) 2.21-2.44 (m, 2H) 2.91 (dd, 1H) 4.70-4.99 (m, 2H) 7.18-7.27 (m, 1H) 7.33-7.49 (m, 6H) 8.52-8.71 (m, 2H) 13.91 (br. s., 1H) 14.61 (br. s., 1H)

Intermediate 1-2-12 Preparation of 4-(2-methylpropyl)-6-oxo-N-phenyl-2-[(pyridin-4-ylmethyl)amino]cyclohex-1-ene-1-carbothioamide

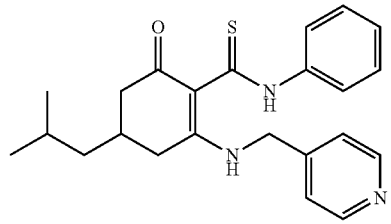 [SMILES: CC(C)CC1CC(=O)C(C(=S)Nc2ccccc2)=C(NCc2ccncc2)C1]

Synthesized according to Method B1. Intermediate 1-1-21 (960 mg) gave the desired product (680 mg, 55%) after column chromatography (EtOAc:Hexane).

1H NMR (400 MHz, DMSO-d$_6$) δ [ppm]=0.71-0.89 (m, 3H) 0.80 (d, 3H) 1.12-1.22 (m, 2H) 1.58 (m, 1H) 1.91-2.10 (m, 1H) 2.20-2.41 (m, 2H) 2.45 (d, 1H) 2.83-2.96 (m, 1H) 4.69-4.97 (m, 2H) 7.19-7.27 (m, 1H) 7.35-7.42 (m, 4H) 7.42-7.48 (m, 2H) 8.48-8.65 (m, 2H) 13.88 (br. s., 1H) 14.59 (s, 1H)

Intermediate 1-2-13 Preparation of 2-{[(3-fluoropyridin-4-yl)methyl]amino}-4,4-dimethyl-6-oxo-N-phenylcyclohex-1-ene-1-carbothioamide

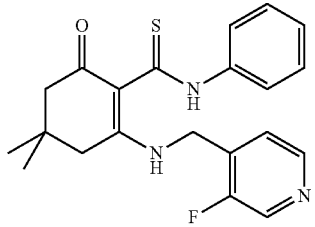 [SMILES: CC1(C)CC(=O)C(C(=S)Nc2ccccc2)=C(NCc2ccncc2F)C1]

Synthesized according to Method B1. Intermediate 1-1-1 (910 mg) gave the desired product (573 mg, 45%) after column chromatography (EtOAc:Hexane).

1H NMR (400 MHz, DMSO-d$_6$) δ [ppm]=0.99 (s, 7H) 2.39 (s, 2H) 2.67-2.74 (m, 2H) 4.92 (d, 2H) 7.18-7.26 (m, 1H) 7.35-7.42 (m, 2H) 7.42-7.51 (m, 3H) 8.48 (d, 1H) 8.58-8.65 (m, 1H) 13.91 (br. s., 1H) 14.55 (br. s., 1H)

Intermediate 1-2-14 Preparation of 2-{[(3-chloropyridin-4-yl)methyl]amino}-6-oxo-N-phenylcyclohex-1-ene-1-carbothioamide

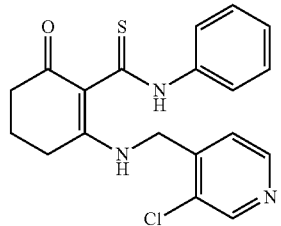 [SMILES: O=C1CCCC(NCc2ccncc2Cl)=C1C(=S)Nc1ccccc1]

Synthesized according to Method B1. Intermediate 1-1-1 (1870 mg) gave the desired product (418 mg, 15%) after column chromatography (EtOAc:Hexane).

1H NMR (400 MHz, DMSO-$d_6$) δ [ppm]=1.74-1.89 (m, 2H) 2.46 (t, 2H) 2.74 (t, 2H) 4.86 (d, 2H) 7.19-7.27 (m, 1H) 7.39 (t, 2H) 7.44-7.54 (m, 3H) 8.58 (d, 1H) 8.66 (s, 1H) 13.43 (br. s., 1H) 14.38 (br. s., 1H)

Intermediate 1-2-15 Preparation of 4,4-dimethyl-6-oxo-N-phenyl-2-[(1H-pyrazolo[3,4-b]pyridin-4-ylmethyl)amino]cyclohex-1-ene-1-carbothioamide

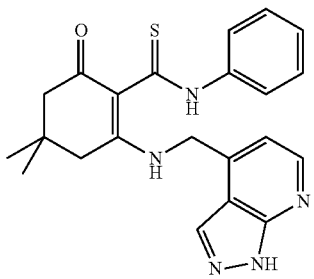 [SMILES: CC1(C)CC(=O)C(C(=S)Nc2ccccc2)=C(NCc2ccnc3[nH]ncc23)C1]

Synthesized according to Method B1. Intermediate 1-1-1 (232 mg) gave the desired product (180 mg, 50%) after column chromatography (EtOAc:Hexane).

1H NMR (400 MHz, DMSO-$d_6$) δ [ppm]=0.93 (s, 6H) 2.38 (s, 2H) 2.67-2.70 (m, 2H) 5.17-5.25 (m, 2H) 7.18 (d, 1H) 7.21-7.26 (m, 1H) 7.39 (t, 2H) 7.47 (d, 2H) 8.31 (d, 1H) 8.53 (d, 1H) 13.77 (s, 1H) 14.24 (br. s., 1H) 14.65 (s, 1H)

Intermediate 1-2-16 Preparation of 2-{[(2-aminopyridin-4-yl)methyl]amino}-4,4-dimethyl-6-oxo-N-phenylcyclohex-1-ene-1-carbothioamide

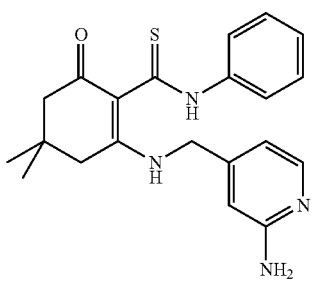 [SMILES: CC1(C)CC(=O)C(C(=S)Nc2ccccc2)=C(NCc2ccnc(N)c2)C1]

Synthesized according to Method B1. Intermediate 1-1-1 (1863 mg) gave the desired product (1165 mg, 45%) after column chromatography (MeOH:MeOH).

1H NMR (400 MHz, DMSO-$d_6$) δ [ppm]=0.90-1.08 (m, 6H) 2.40 (s, 2H) 2.63-2.69 (m, 2H) 4.65 (d, 2H) 6.02 (s, 2H) 6.36 (s, 1H) 6.44 (dd, 1H) 7.19-7.27 (m, 1H) 7.35-7.48 (m, 3H) 7.88 (d, 1H) 14.18 (br. s., 1H) 14.77 (s, 1H)

Intermediate 1-2-17 Preparation of 7-oxo-N-phenyl-5-[(pyridin-4-ylmethyl)amino]spiro[2.5]oct-5-ene-6-carbothioamide

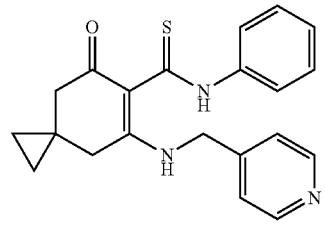 [SMILES: O=C1CC2(CC2)CC(NCc2ccncc2)=C1C(=S)Nc1ccccc1]

Synthesized according to Method B1. Intermediate 1-1-23 (200 mg) gave the desired product (23 mg, 9%) after preparative HPLC (Method acidic).

1H NMR (400 MHz, DMSO-$d_6$) δ [ppm]=0.33-0.49 (m, 4H) 2.41 (s, 2H) 2.66-2.75 (m, 2H) 4.78 (d, 2H) 7.20-7.27 (m, 1H) 7.34-7.43 (m, 4H) 7.43-7.48 (m, 2H) 8.59 (d, 2H) 13.94 (br. s., 1H) 14.57 (s, 1H)

Intermediate 1-2-18 Preparation of 2-{[(2-aminopyridin-4-yl)methyl]amino}-6-oxo-N-phenylcyclohex-1-ene-1-carbothioamide

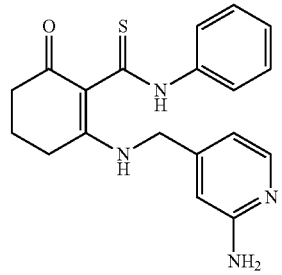 [SMILES: Nc1cc(CNC2=C(C(=S)Nc3ccccc3)C(=O)CCC2)ccn1]

Synthesized according to Method B1. Intermediate 1-1-5 (2231 mg) gave the desired product (1128 mg, 39%) after column chromatography (MeOH:DCM).

1H NMR (300 MHz, DMSO-$d_6$) δ [ppm]=1.72-1.89 (m, 2H) 2.41-2.48 (m, 2H) 2.75 (t, 2H) 4.62 (d, 2H) 6.02 (s, 2H) 6.37 (s, 1H) 6.45 (dd, 1H) 7.17-7.28 (m, 1H) 7.33-7.48 (m, 4H) 7.88 (d, 1H) 13.89 (br. s., 1H) 14.68 (s, 1H)

Intermediate 1-2-19 Preparation of 2-{[(2-aminopyridin-4-yl)methyl]amino}-N-(3-fluorophenyl)-6-oxocyclohex-1-ene-1-carbothioamide

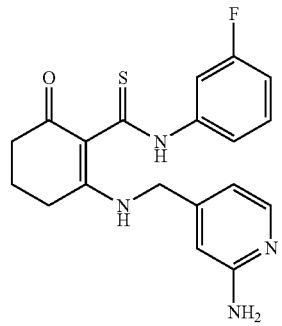 [SMILES: Nc1cc(CNC2=C(C(=S)Nc3cccc(F)c3)C(=O)CCC2)ccn1]

Synthesized according to Method B1. Intermediate 1-1-6 (2394 mg) gave the desired product (945 mg, 31%) after column chromatography (MeOH:DCM).

1H NMR (400 MHz, DMSO-$d_6$) δ [ppm]=1.73-1.89 (m, 2H) 2.43-2.48 (m, 2H) 2.75 (t, 2H) 4.63 (d, 2H) 6.00 (s, 2H) 6.38 (s, 1H) 6.42-6.49 (m, 1H) 7.07 (m, 1H) 7.21 (d, 1H) 7.37-7.46 (m, 1H) 7.52 (d, 1H) 7.89 (d, 1H) 13.75 (br. s., 1H) 14.78 (br. s., 1H)

Intermediate 1-2-20 Preparation of N-(3-fluorophenyl)-6-oxo-2-[(pyridin-4-ylmethyl)amino]cyclohex-1-ene-1-carbothioamide

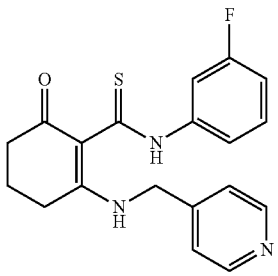 [SMILES: O=C1CCCC(NCc2ccncc2)=C1C(=S)Nc1cccc(F)c1]

Synthesized according to Method B1. Intermediate 1-1-6 (200 mg) gave the desired product (31 mg, 12%) after preparative HPLC (Method basic).

1H NMR (300 MHz, DMSO-$d_6$) δ [ppm]=1.75-1.86 (m, 2H) 2.46 (t, 2H) 2.75 (t, 2H) 4.83 (d, 2H) 7.07 (m, 1H) 7.23 (d, 1H) 7.34-7.46 (m, 3H) 7.55 (d, 1H) 8.59 (d, 2H) 13.53 (br. s., 1H) 14.62 (br. s., 1H)

Intermediate 1-2-21 Preparation of N-(4-fluorophenyl)-6-oxo-2-[(pyridin-4-ylmethyl)amino]cyclohex-1-ene-1-carbothioamide

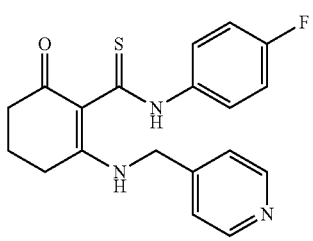 [SMILES: O=C1CCCC(NCc2ccncc2)=C1C(=S)Nc1ccc(F)cc1]

Synthesized according to Method B1. Intermediate 1-1-7 (200 mg) gave the desired product (33 mg, 12%) after preparative HPLC (Method acidic).

1H NMR (400 MHz, DMSO-$d_6$) δ [ppm]=1.80 (m, 2H) 2.42-2.46 (m, 2H) 2.74 (t, 2H) 4.82 (d, 2H) 7.18-7.27 (m, 2H) 7.35-7.42 (m, 2H) 7.45 (m, 2H) 8.14 (s, 1H) 8.59 (d, 2H) 13.66 (br. s., 1H) 14.46 (br. s., 1H)

Intermediate 1-2-22 Preparation of N-(3-fluorophenyl)-6-oxo-2-[(pyridin-4-ylmethyl)amino]-4-(trifluoromethyl)cyclohex-1-ene-1-carbothioamide

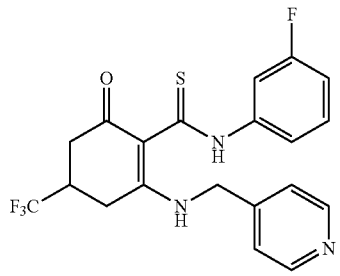 [SMILES: O=C1CC(C(F)(F)F)CC(NCc2ccncc2)=C1C(=S)Nc1cccc(F)c1]

Synthesized according to Method B1. Intermediate 1-1-24 (200 mg) gave the desired product (92 mg, 36%) after preparative HPLC (Method acidic).

1H NMR (300 MHz, DMSO-$d_6$) δ [ppm]=2.56-2.74 (m, 2H) 2.81 (m, 1H) 3.07 (d, 1H) 3.12-3.21 (m, 1H) 4.66-4.96 (m, 2H) 7.09 (m, 1H) 7.26 (d, 1H) 7.34-7.49 (m, 3H) 7.57 (d, 1H) 8.60 (d, 2H) 13.30 (br. s., 1H) 14.20 (br. s., 1H)

Intermediate 1-2-23 Preparation of 2-{[(2-fluoropyridin-4-yl)methyl]amino}-6-oxo-N-phenylcyclohex-1-ene-1-carbothioamide

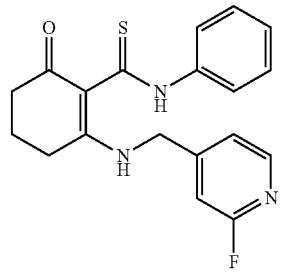 [SMILES: O=C1CCCC(NCc2ccnc(F)c2)=C1C(=S)Nc1ccccc1]

Synthesized according to Method B1. Intermediate 1-1-5 (500 mg) gave the desired product (266 mg, 39%) after column chromatography (MeOH:DCM).

1H NMR (400 MHz, DMSO-$d_6$) δ [ppm]=1.81 (m, 2H) 2.43-2.47 (m, 2H) 2.72 (t, 2H) 4.87 (d, 2H) 7.17 (s, 1H) 7.20-7.27 (m, 1H) 7.33-7.43 (m, 3H) 7.48 (d, 2H) 8.27 (d, 1H) 13.46 (br. s., 1H) 14.40 (br. s., 1H)

Intermediate Preparation of tert-butyl [(1-oxidopyridin-4-yl)methyl]carbamate

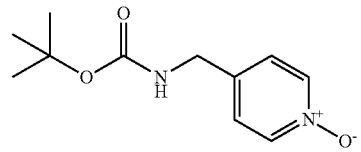 [SMILES: CC(C)(C)OC(=O)NCc1cc[n+]([O-])cc1]

To an ice-cooled solution of tert-butyl-(pyridin-4-ylmethyl)carbamate (15.8 g, 75.9 mmol) in DCM (80 mL) was added mCPBA (19.7 g, 87.9 mmol, 77%) and the reaction was stirred at room temperature for 3 h. The reaction mxture was washed with 1M ammonium hydroxide solution, the aqueous layers combined and re-extracted with DCM (×5). The combined DCM layers were dried over MgSO₄, filtered and concentrated and used directly without further purification (4.2 g, 25%).

1H NMR (400 MHz, DMSO-d₆) δ [ppm]=1.39 (s, 9H), 4.09 (d, 2H), 7.23 (d, 2H), 7.47 (t, 1H), 8.15 (d, 2H)

Intermediate Preparation of tert-butyl [(2-cyanopyridin-4-yl)methyl]carbamate

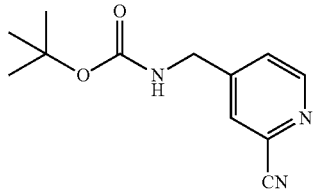 [SMILES: CC(C)(C)OC(=O)NCc1ccnc(C#N)c1]

To a solution of tert-butyl-[(1-oxidopyridin-4-yl)methyl] carbamate (4.2 g, 18.7 mmol) and trimethylsilanecarbonitrile (3.5 mL, 26.2 mmol) in DCM (20 mL) was added N-dimethylcarbamoyl chloride (2.0 mL, 21.7 mmol). The reaction was stirred at room temperature for 2 h. To the reaction was added sat NaHCO₃(aq) solution (50 mL). The organics were extracted with DCM (×4). The combined DCM layers were dried over MgSO4, filtered and concentrated. The residue was purified by column chromatography (diethylether to give the desired product as a white solid (900 mg, 20%).

1H NMR (400 MHz, DMSO-d₆) δ [ppm]=1.40 (s, 9H), 4.23 (d, 2H), 7.54 (t, 1H), 7.57 (d, 1H), 7.85 (d, 1H), 8.69 (d, 1H)

Intermediate Preparation of 4-(aminomethyl)pyridine-2-carbonitrile trifluoroacetate (1:2)

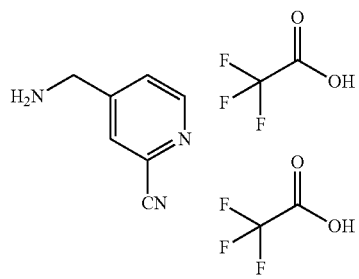

To a suspension of tert-butyl-[(2-cyanopyridin-4-yl)methyl]carbamate (440 mg, 26.4 mmol) in DCM (2 mL) was added TFA (2 mL) and stirred at room temperature for 3 h and concentrated to give the desired product as a brown oil which was used in the next step without further purification.

Intermediate 1-2-24 Preparation of 2-{[(2-cyanopyridin-4-yl)methyl]amino}-4,4-dimethyl-6-oxo-N-phenylcyclohex-1-ene-1-carbothioamide

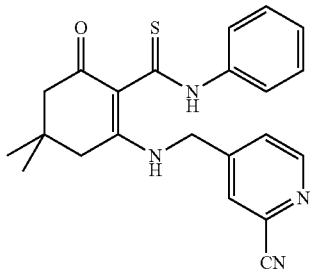 [SMILES: CC1(C)CC(=O)C(C(=S)Nc2ccccc2)=C(NCc2ccnc(C#N)c2)C1]

Synthesized according to Method B1 with DIPEA (0.8 mL). Intermediate 1-1-1 750 mg gave the desired product (105 mg, 29%) after column chromatography (diethyl ether).

1H NMR (400 MHz, DMSO-d₆) δ [ppm]=0.98 (s, 6H), 2.38 (s, 2H), 2.62 (s, 2H), 4.92 (d, 2H), 7.20-7.27 (m, 1H), 7.35-7.44 (m, 2H), 7.46-7.55 (m, 2H), 7.71 (d, 1H), 8.00 (s, 1H), 8.78 (d, 1H), 13.75 (s, 1H), 14.46 (s, 1H)

Intermediate 1-2-25 Preparation of 2-{[(2-aminopyridin-4-yl)methyl]amino}-6-oxo-N-phenyl-4-(propan-2-yl)cyclohex-1-ene-1-carbothioamide

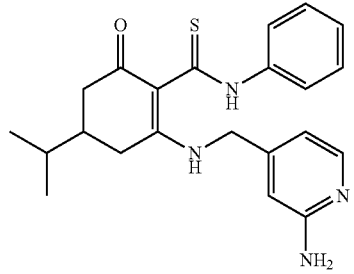 [SMILES: CC(C)C1CC(=O)C(C(=S)Nc2ccccc2)=C(NCc2ccnc(N)c2)C1]

Synthesized according to Method B1. Intermediate 1-1-9 (989 mg) gave the desired product (667 mg, 49%) after column chromatography (MeOH:DCM).

1H NMR (400 MHz, DMSO-d₆) δ [ppm]=0.85 (d, 3H) 0.84 (d, 3H) 1.52 (m, 1H) 1.61-1.75 (m, 1H) 2.26-2.36 (m, 1H) 2.36-2.47 (m, 2H) 2.85 (d, 1H) 4.65 (d, 2H) 6.00 (s, 2H) 6.38 (s, 1H) 6.46 (dd, 1H) 7.19-7.27 (m, 1H) 7.35-7.47 (m, 4H) 7.89 (d, 1H) 14.01 (br. s., 1H) 14.70 (s, 1H)

Intermediate 1-2-26 Preparation of 2-{[(2-aminopyridin-4-yl)methyl]amino}-N-(3-fluorophenyl)-6-oxo-4-(propan-2-yl)cyclohex-1-ene-1-carbothioamide

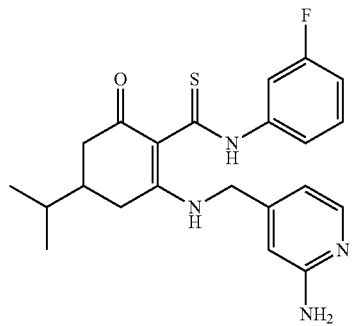 [SMILES: CC(C)C1CC(=O)C(C(=S)Nc2cccc(F)c2)=C(NCc2ccnc(N)c2)C1]

Synthesized according to Method B1. Intermediate 1-1-10 (988 mg) gave the desired product (537 mg, 38%) after column chromatography (MeOH:DCM).

1H NMR (400 MHz, DMSO-d$_6$) δ [ppm]=0.85 (dd, 6H) 1.52 (m, 1H) 1.59-1.74 (m, 1H) 2.26-2.38 (m, 1H) 2.38-2.48 (m, 2H) 2.86 (m, 1H) 4.61-4.74 (m, 2H) 6.00 (s, 2H) 6.38 (s, 1H) 6.46 (dd, 1H) 7.07 (m, 1H) 7.21 (d, 1H) 7.37-7.48 (m, 1H) 7.51 (d, 1H) 7.89 (d, 1H) 13.89 (br. s., 1H) 14.82 (s, 1H)

Intermediate 1-2-27 Preparation of 4-methyl-6-oxo-N-phenyl-2-[(pyridin-4-ylmethyl)amino]cyclohex-1-ene-1-carbothioamide

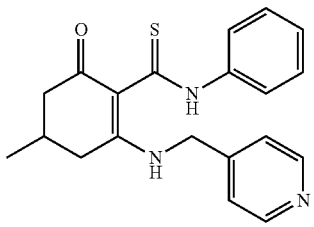 [SMILES: CC1CC(=O)C(C(=S)Nc2ccccc2)=C(NCc2ccncc2)C1]

Synthesized according to Method B1. Intermediate 1-1-25 (500 mg) gave the desired product (391 mg, 58%) after preparative HPLC (XBrigde C18 5 μm 150×50 mm, Solvent: A=H2O+0.2% Vol. NH$_3$ (32%), B=Acetonitrile, 40% B in A to 70% in A over 8 min, flow: 150 mL/min).

1H NMR (300 MHz, DMSO-d$_6$) δ [ppm]=0.98 (d, 3H) 1.95-2.17 (m, 1H) 2.21-2.46 (m, 2H) 2.91 (dd, 1H) 4.70-4.97 (m, 2H) 7.11-7.31 (m, 1H) 7.31-7.56 (m, 6H) 8.59 (d, 2H) 13.89 (br. s., 1H) 14.62 (s, 1H)

Intermediate 1-2-28 Preparation of N-(3,4-difluorophenyl)-6-oxo-2-[(pyridin-4-ylmethyl)amino]cyclohex-1-ene-1-carbothioamide

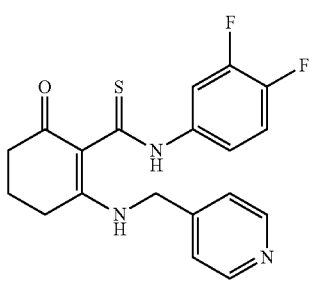 [SMILES: O=C1CCCC(NCc2ccncc2)=C1C(=S)Nc1ccc(F)c(F)c1]

Synthesized according to Method B1. Intermediate 1-1-10 (988 mg) gave the crude product which was used directly in the next step (see Example 38).

1H NMR (400 MHz, DMSO-d$_6$) δ [ppm]=1.74-1.84 (m, 2H) 2.45 (t, 2H) 2.74 (t, 2H) 4.82 (d, 2H) 7.15-7.26 (m, 1H) 7.32-7.51 (m, 3H) 7.64-7.75 (m, 1H) 8.58 (d, 2H) 13.51 (br. s., 1H) 14.54 (br. s., 1H)

Intermediate 1-9-1 Preparation of tert-butyl 2-(2-fluoropyridin-4-yl)-6,6-dimethyl-4-oxo-4,5,6,7-tetrahydro-1H-indole-1-carboxylate

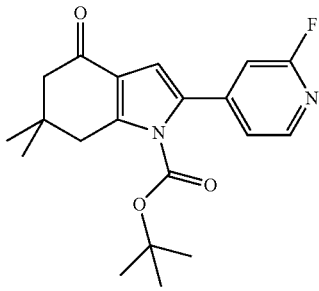 [SMILES: CC1(C)CC(=O)c2cc(-c3ccnc(F)c3)n(C(=O)OC(C)(C)C)c2C1]

Synthesized according to Method C1. Intermediate 1-8-1 (1369 mg) gave the desired product (711 mg, 50%) and the Boc-deprotected 2-(2-fluoropyridin-4-yl)-6,6-dimethyl-1,5,6,7-tetrahydro-4H-indol-4-one (167 mg, 16%) after column chromatography (EtOAc:cyclohexane)

1H NMR (400 MHz, DMSO-d$_6$) δ [ppm]=1.09 (s, 6H), 1.34 (s, 9H), 2.35 (s, 2H), 3.00 (s, 2H), 6.75 (s, 1H), 7.24 (s, 1H), 7.35 (d, 1H), 8.24 (d, 1H)

Intermediate 1-5-2 Preparation of 2-(2-fluoropyridin-4-yl)-6,6-dimethyl-1,5,6,7-tetrahydro-4H-indol-4-one

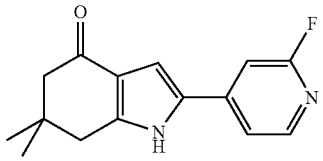 [SMILES: CC1(C)CC(=O)c2cc(-c3ccnc(F)c3)[nH]c2C1]

Synthesized according to Method D1. Intermediate 1-9-1 (685 mg) gave the desired product (424 mg, 88%).

1H NMR (400 MHz, DMSO-d$_6$) δ [ppm]=1.06 (s, 6H), 2.28 (s, 2H), 2.75 (s, 2H), 7.17 (s, 1H), 7.41 (m, 1H), 7.60 (m, 1H), 8.16 (m, 1H), 12.06 (s, 1H)

Intermediate 1-6-2 Preparation of 3-bromo-2-(2-fluoropyridin-4-yl)-6,6-dimethyl-1,5,6,7-tetrahydro-4H-indol-4-one

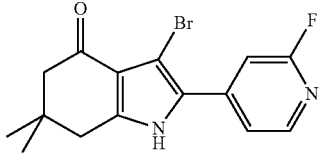 [SMILES: CC1(C)CC(=O)c2c([nH]c(-c3ccnc(F)c3)c2Br)C1]

Synthesized according to Method E1. Intermediate 1-5-2 (430 mg) gave the desired product (481 mg, 81%).

1H NMR (400 MHz, DMSO-d$_6$) δ [ppm]=1.06 (s, 6H), 2.30 (s, 2H), 2.75 (s, 2H), 7.48 (s, 1H), 7.76 (m, 1H), 8.30 (m, 1H), 12.35 (s, 1H)

Example Compounds

Example 1 Preparation of 6,6-dimethyl-3-(phenylamino)-2-(pyridin-4-yl)-1,5,6,7-tetrahydro-4H-indol-4-one

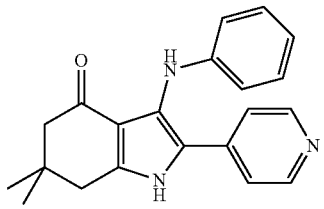 [SMILES: CC1(C)CC(=O)c2c([nH]c(-c3ccncc3)c2Nc2ccccc2)C1]

To a solution of 3-(benzylamino)-5,5-dimethylcyclohex-2-en-1-one (Intermediate 1-3-1) (1.39 g, 6.04 mmol) in DMF (3.6 mL) was added DBU (1.8 mL, 1.84 g, 12.1 mmol) and the reaction was heated at 120° C. for 8 h. The reaction was poured into ice-water and extracted with dichloromethane:isopropanol (4:1), the organics phase were combined and dried over $Na_2SO_4$, filtered and concentrated. The residue was subjected to column chromatography (dichloromethane:isopropanol (9:1). The product was re-crystallized from THF:dichloromethane to give the desired product (315 mg, 16%).

1H-NMR (400 MHz, DMSO-d6): δ [ppm]=1.06 (s, 6H), 2.22 (s, 2H), 2.74 (s, 2H), 6.48-6.66 (m, 3H), 6.96-7.07 (m, 2H), 7.40 (s, 1H), 7.43-7.49 (m, 2H), 8.35-8.42 (m, 2H), 11.83 (br. s., 1H).

Example 2 Preparation of 2-(3-chloropyridin-4-yl)-6,6-dimethyl-3-(phenylamino)-1,5,6,7-tetrahydro-4H-indol-4-one

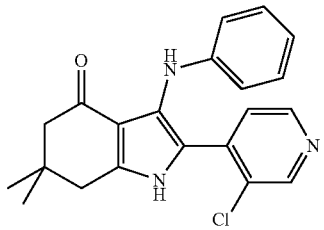 [SMILES: CC1(C)CC(=O)c2c([nH]c(-c3ccncc3Cl)c2Nc2ccccc2)C1]

To a solution of 3-{[(3-chloropyridin-4-yl)methyl]amino}-5,5-dimethylcyclohex-2-en-1-one (Intermediate 1-3-2) (2.77 g, 10.5 mmol) in DMF (20 mL) was heated at 120° C. for 4 h. DBU (3.12 mL, 3.19 g, 20.9 mmol) was then added and the reaction was heated at 120° C. for 3 h. The reaction was poured into ice-water and extracted with dichloromethane:isopropanol (4:1), the organics phase were combined and dried over $Na_2SO_4$, filtered and concentrated. The residue was subjected to column chromatography (dichloromethane:isopropanol (9:1). The purified product was then purified by preparative HPLC (Method basic) to give the desired product (185 mg, 5%).

1H-NMR (400 MHz, DMSO-d6): δ [ppm]=1.07 (s, 6H) 2.24 (s, 2H) 2.72 (s, 2H) 6.37-6.64 (m, 3H) 6.87-7.00 (m, 2H) 7.31 (d, 1H) 7.42 (s, 1H) 8.34 (d, 1H) 8.54 (s, 1H)

Example 3 Preparation of 6,6-dimethyl-3-[(3-methylphenyl)amino]-2-(pyridin-4-yl)-1,5,6,7-tetrahydro-4H-indol-4-one

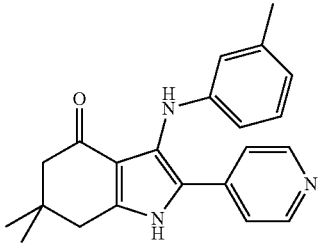 [SMILES: Cc1cccc(Nc2c(-c3ccncc3)[nH]c3c2C(=O)CC(C)(C)C3)c1]

Synthesized according to Method F2. Intermediate 1-6-1 (50 mg) gave the desired product (5 mg, 9%) after preparative HPLC (Method basic).

1H-NMR (300 MHz, METHANOL-d4): δ [ppm]=1.15 (s, 6H) 2.12 (s, 3H) 2.35 (s, 2H) 2.80 (s, 2H) 6.38-6.50 (m, 2H) 6.55 (d, 1H) 6.93 (t, 1H) 7.42 (br. s., 1H)

Example 4 Preparation of 6,6-dimethyl-3-[(3-chlorophenyl)amino]-2-(pyridin-4-yl)-1,5,6,7-tetrahydro-4H-indol-4-one

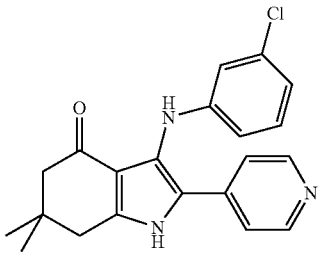

Synthesized according to Method F2. Intermediate 1-6-1 (100 mg) gave the desired product (47 mg, 41%) after preparative HPLC (Method acidic).

1H-NMR (400 MHz, DMSO-d6): δ [ppm]=1.07 (s, 6H) 2.23 (s, 2H) 2.76 (s, 2H) 6.46-6.55 (m, 2H) 6.57-6.63 (m, 1H) 7.03 (t, 1H) 7.52 (d, 2H) 7.72 (s, 1H) 8.46 (d, 2H) 11.91 (s, 1H)

Example 5 Preparation of 6,6-dimethyl-3-(phenylamino)-2-(pyrimidin-4-yl)-1,5,6,7-tetrahydro-4H-indol-4-one

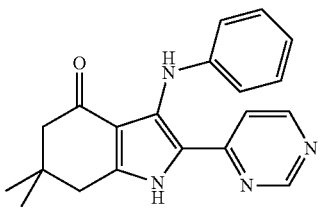 [SMILES: CC1(C)CC(=O)c2c([nH]c(-c3ccncn3)c2Nc2ccccc2)C1]

Synthesized according to Method B1. Intermediate 1-1-1 (500 mg) gave the desired product (34 mg, 5%) after preparative HPLC (XBridge C18 5 μm 100×30 mm, Solvent: A=$H_2O$+0.2% Vol. $NH_3$ (32%), B=Acetonitrile, gradient=0.5-5.5 min 33-56% B in A, flow: 70 mL/min).

1H-NMR (300 MHz, DMSO-d6): δ [ppm]=1.05 (s, 6H) 2.25 (s, 2H) 2.76 (s, 2H) 6.63-6.75 (m, 3H) 7.10 (t, 2H) 7.24 (m, 1H) 7.97 (s, 1H) 8.51 (d, 1H) 9.03 (d, 1H) 12.16 (br. s., 1H)

Example 6 Preparation of 2-(3-fluoropyridin-4-yl)-6,6-dimethyl-3-(phenylamino)-1,5,6,7-tetrahydro-4H-indol-4-one

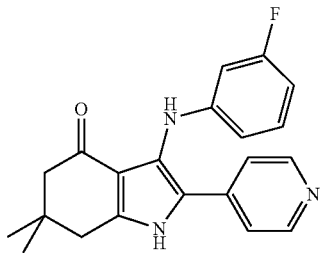 [SMILES: CC1(C)CC(=O)c2c([nH]c(-c3ccncc3)c2Nc2cccc(F)c2)C1]

Synthesized according to Method F2. Intermediate 1-6-1 (100 mg) gave the desired product (47 mg, 41%) after preparative HPLC (Method acidic).

1H-NMR (500 MHz, DMSO-d6): δ [ppm]=1.07 (s, 6H) 2.23 (s, 2H) 2.76 (s, 2H) 6.24 (m, 1H) 6.33-6.43 (m, 2H) 7.04 (m, 1H) 7.48-7.60 (m, 2H) 7.72 (s, 1H) 8.42-8.48 (m, 2H) 11.90 (s, 1H)

Example 7 Preparation of 3-(phenylamino)-6-(propan-2-yl)-2-(pyridin-4-yl)-1,5,6,7-tetrahydro-4H-indol-4-one

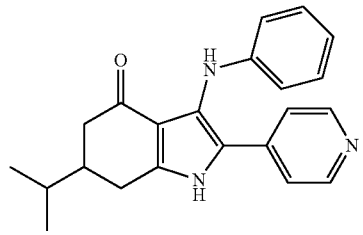

Synthesized according to Method F1. Intermediate 1-2-2 (10.6 g) gave the desired product (1.7 g, 17%) after column chromatography (EtOAc).

1H-NMR (400 MHz, CDCl3): δ [ppm]=0.94-0.96 (d, 6H) 1.67 (m, 1H), 2.10 (m, 1H) 2.2.8 (m, 1H) 2.48-2.83 (m, 2H) 2.86 (m, 1H) 6.22 (t, 1H) 6.67 (d, 2H) 6.77 (t, 1H) 7.05-7.09 (m, 2H) 7.22-7.25 (m, 2H) 8.32 (d, 2H) 10.32 (s, 1H)

Example 7 (50 mg) was submitted to preparative chiral HPLC to give:

Example 17 (Enantiomer 1 of 3-(phenylamino)-6-(propan-2-yl)-2-(pyridin-4-yl)-1,5,6,7-tetrahydro-4H-indol-4-one Enantiomer 1

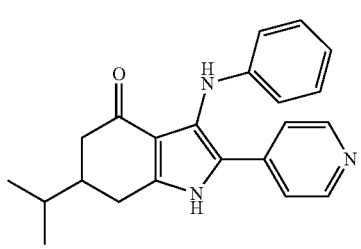 [SMILES: CC(C)C1CC(=O)c2c([nH]c(-c3ccncc3)c2Nc2ccccc2)C1]

18 mg (34%) after preparative chiral HPLC (retention time using the analytical chiral method was 2.91 min.

Optional rotation (1.0 mg/mL MeOH): −22.8°+/−1.48° (589 nm)

Example 18 (Enantiomer 2 of 3-(phenylamino)-6-(propan-2-yl)-2-(pyridin-4-yl)-1,5,6,7-tetrahydro-4H-indol-4-one Enantiomer 2

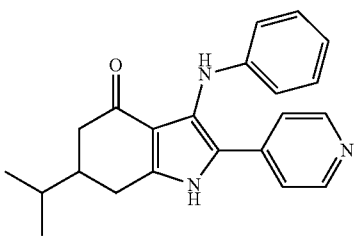

16 mg (30%) after preparative chiral HPLC (retention time using the analytical chiral method was 3.39 min.

Optional rotation (1.0 mg/mL DMSO): 25.6°+/−1.37° (589 nm)

Example 8 Preparation of 6-Phenyl-3-phenylamino-2-(pyridin-4-yl)-1,5,6,7-tetrahydroindol-4-one

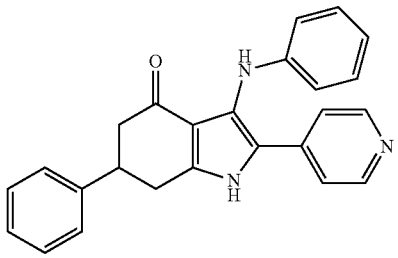 [SMILES: O=C1CC(c2ccccc2)Cc2[nH]c(-c3ccncc3)c(Nc3ccccc3)c21]

Synthesized according to Method F1. Intermediate 1-2-3 (90 mg) gave the desired product (60 mg, 72%) after column chromatography (EtOAc).

1H-NMR (400 MHz, CDCl3): δ [ppm]=2.71-2.80 (m, 2H) 3.02-3.08 (m, 2H) 3.52 (m, 1H) 6.67 (d, 2H) 6.75 (t, 1H) 7.06 (m, 1H) 7.23-7.38 (m, 8H) 8.30 (d, 2H) 10.26 (s, 1H)

Example 9 Preparation of 3-(phenylamino)-2-(pyridin-4-yl)-1,5,6,7-tetrahydro-4H-indol-4-one

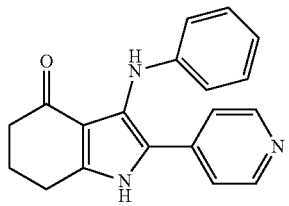 [SMILES: O=C1CCCc2[nH]c(-c3ccncc3)c(Nc3ccccc3)c21]

Synthesized according to Method F1. Intermediate 1-2-4 (28.8 g) gave the desired product (33.4 g, 85%) after column chromatography (EtOAc:MeOH, 10:1)).

1H-NMR (400 MHz, CDCl3): δ [ppm]=2.04 (m, 2H), 2.33 (t, 2H), 2.86 (t, 2H), 6.58 (d, 2H), 6.61 (t, 1H), 7.01-7.05 (m, 2H), 7.41 (s, 1H), 7.45 (d, 2H), 8.40 (d, 2H), 11.87 (s, 1H).

Example 10 Preparation of 3-[(4-chlorophenyl)amino]-6,6-dimethyl-2-(pyridin-4-yl)-1,5,6,7-tetrahydro-4H-indol-4-one

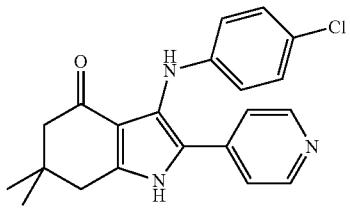 [SMILES: CC1(C)CC(=O)c2c([nH]c(-c3ccncc3)c2Nc2ccc(Cl)cc2)C1]

Synthesized according to Method F2. Intermediate 1-6-1 (100 mg) gave the desired product (21 mg, 18%) after preparative HPLC (Method acidic).

1H-NMR (500 MHz, DMSO-d6): δ [ppm]=1.07 (s, 6H) 2.22 (s, 2H) 2.75 (s, 2H) 6.51-6.58 (m, 2H) 7.03-7.08 (m, 2H) 7.46-7.51 (m, 2H) 7.60 (s, 1H) 8.41-8.46 (m, 2H) 11.88 (s, 1H)

Example 11 Preparation of 3-[(4-fluorophenyl)amino]-6,6-dimethyl-2-(pyridin-4-yl)-1,5,6,7-tetrahydro-4H-indol-4-one

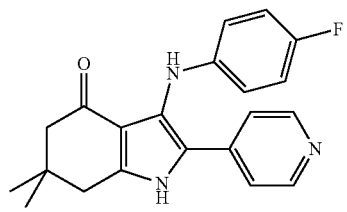 [SMILES: CC1(C)CC(=O)c2c([nH]c(-c3ccncc3)c2Nc2ccc(F)cc2)C1]

Synthesized according to Method F2. Intermediate 1-6-1 (100 mg) gave the desired product (29 mg, 27%) after preparative HPLC (Method acidic).

1H-NMR (500 MHz, DMSO-d6): δ [ppm]=0.94-1.13 (m, 6H) 2.23 (s, 2H) 2.75 (s, 2H) 6.53-6.58 (m, 2H) 6.85-6.91 (m, 2H) 7.40 (s, 1H) 7.44-7.48 (m, 2H) 8.33-8.48 (m, 2H) 11.85 (s, 1H)

Example 12 Preparation of 3-[(3-bromophenyl)amino]-6,6-dimethyl-2-(pyridin-4-yl)-1,5,6,7-tetrahydro-4H-indol-4-one

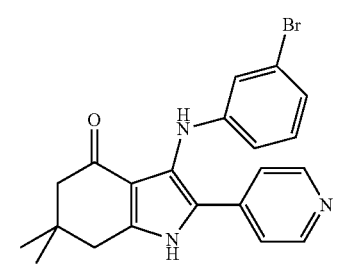 [SMILES: CC1(C)CC(=O)c2c([nH]c(-c3ccncc3)c2Nc2cccc(Br)c2)C1]

Synthesized according to Method F1. Intermediate 1-2-5 (133 mg) gave the desired product (74 mg, 57%) after preparative HPLC (Method acidic).

1H-NMR (400 MHz, DMSO-d6): δ [ppm]=1.07 (s, 6H) 2.23 (s, 2H) 2.76 (s, 2H) 6.51 (dd, 1H) 6.63-6.79 (m, 2H) 6.97 (t, 1H) 7.48-7.56 (m, 2H) 7.73 (s, 1H) 8.40-8.54 (m, 2H) 11.92 (s, 1H)

Example 13 Preparation of 3'-(phenylamino)-2'-(pyridin-4-yl)-1',7'-dihydrospiro[cyclobutane-1,6'-indol]-4'(5'H)-one

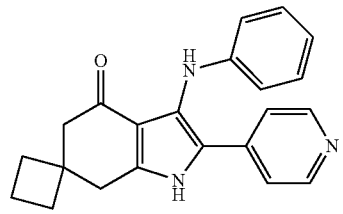 [SMILES: O=C1CC2(CCC2)Cc2[nH]c(-c3ccncc3)c(Nc3ccccc3)c21]

Synthesized according to Method B1. Intermediate 1-2-6 (500 mg) gave the desired product (33 mg, 6%) after preparative HPLC (Method acidic).

1H-NMR (300 MHz, DMSO-d6): δ [ppm]=1.71-2.05 (m, 6H) 2.97 (s, 2H) 6.46-6.70 (m, 3H) 7.03 (t, 2H) 7.32-7.56 (m, 3H) 8.40 (d, 2H) 11.91 (s, 1H)

Example 14 Preparation of 3-[(3-fluoro-5-methylphenyl)amino]-6,6-dimethyl-2-(pyridin-4-yl)-1,5,6,7-tetrahydro-4H-indol-4-one

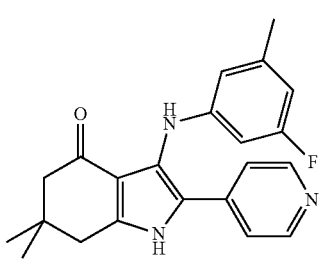 [SMILES: Cc1cc(F)cc(Nc2c(-c3ccncc3)[nH]c3c2C(=O)CC(C)(C)C3)c1]

Synthesized according to Method F2. Intermediate 1-6-1 (100 mg) gave the desired product (23 mg, 19%) after preparative HPLC (Method acidic).

1H-NMR (400 MHz, DMSO-d6): δ [ppm]=1.06 (s, 6H) 2.11 (s, 3H) 2.22 (s, 2H) 2.75 (s, 2H) 5.96-6.05 (m, 1H) 6.20 (d, 1H) 6.24 (s, 1H) 7.45-7.57 (m, 2H) 7.61 (s, 1H) 8.41-8.61 (m, 2H) 11.87 (s, 1H)

Example 15 Preparation of 3-[(3-ethylphenyl)amino]-6,6-dimethyl-2-(pyridin-4-yl)-1,5,6,7-tetrahydro-4H-indol-4-one

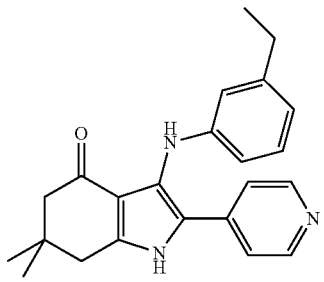 [SMILES: CCc1cccc(Nc2c(-c3ccncc3)[nH]c3c2C(=O)CC(C)(C)C3)c1]

Synthesized according to Method F2. Intermediate 1-6-1 (100 mg) gave the desired product (40 mg, 36%) after preparative HPLC (Method acidic).

1H-NMR (400 MHz, DMSO-d6): δ [ppm]=0.97 (t, 3H) 1.07 (s, 6H) 2.24 (s, 2H) 2.31-2.41 (m, 2H) 2.75 (s, 2H) 6.37-6.43 (m, 2H) 6.48 (d, 1H) 6.94 (t, 1H) 7.36-7.53 (m, 3H) 8.29-8.44 (m, 2H) 11.82 (br. s., 1H)

Example 16 Preparation of 6,6-dimethyl-3-[(3-nitrophenyl)amino]-2-(pyridin-4-yl)-1,5,6,7-tetrahydro-4H-indol-4-one

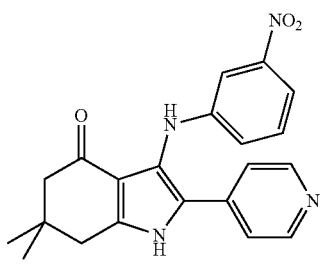 [SMILES: CC1(C)CC(=O)c2c([nH]c(-c3ccncc3)c2Nc2cccc([N+](=O)[O-])c2)C1]

Synthesized according to Method F1. Intermediate 1-2-7 (21 mg) gave the desired product (19 mg, 89%) after preparative HPLC (Method acidic).

1H-NMR (300 MHz, DMSO-d6): δ [ppm]=1.07 (s, 6H) 2.21 (s, 2H) 2.77 (s, 2H) 6.96 (d, 1H) 7.25-7.33 (m, 2H) 7.38-7.43 (m, 1H) 7.51-7.59 (m, 2H) 8.18 (s, 1H) 8.47 (d, 2H) 12.00 (s, 1H)

Example 19 Preparation of 3-[(3-chloro-5-fluorophenyl)amino]-6,6-dimethyl-2-(pyridin-4-yl)-1,5,6,7-tetrahydro-4H-indol-4-one

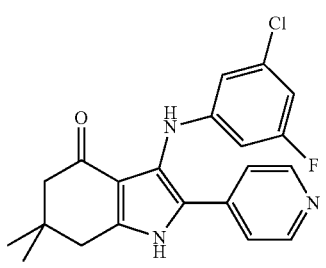 [SMILES: CC1(C)CC(=O)c2c([nH]c(-c3ccncc3)c2Nc2cc(F)cc(Cl)c2)C1]

Synthesized according to Method F2. Intermediate 1-6-1 (100 mg) gave the desired product (13 mg, 11%) after preparative HPLC (Method basic).

1H-NMR (400 MHz, DMSO-d6): δ [ppm]=1.07 (s, 6H) 2.23 (s, 2H) 2.77 (s, 2H) 6.20 (d, 1H) 6.39 (s, 1H) 6.49 (m, 1H) 7.48-7.59 (m, 2H) 8.06 (s, 1H) 8.47-8.53 (m, 2H) 11.97 (s, 1H)

Example 20 Preparation of 3-(phenylamino)-2-(pyridin-4-yl)-6-(trifluoromethyl)-1,5,6,7-tetrahydro-4H-indol-4-one

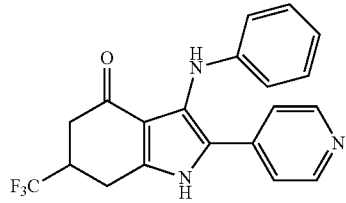 [SMILES: O=C1CC(C(F)(F)F)Cc2[nH]c(-c3ccncc3)c(Nc3ccccc3)c21]

Synthesized according to Method F1. Intermediate 1-2-8 (210 mg) gave the desired product (85 mg, 44%) after preparative HPLC (Method acidic).

1H-NMR (400 MHz, DMSO-d6): δ [ppm]=2.52-2.63 (m, 2H) 3.02 (dd, 1H) 3.14 (dd, 1H) 6.56-6.67 (m, 3H) 7.04 (dd, 2H) 7.44-7.52 (m, 3H) 8.39-8.50 (m, 2H) 12.10 (s, 1H)

Example 21 Preparation of 3-[(3,4-difluorophenyl)amino]-6,6-dimethyl-2-(pyridin-4-yl)-1,5,6,7-tetrahydro-4H-indol-4-one

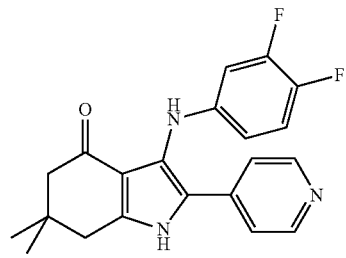 [SMILES: CC1(C)CC(=O)c2c([nH]c(-c3ccncc3)c2Nc2ccc(F)c(F)c2)C1]

Synthesized according to Method F2. Intermediate 1-6-1 (100 mg) gave the desired product (28 mg, 24%) after preparative HPLC (Method acidic).

1H-NMR (400 MHz, DMSO-d6): δ [ppm]=1.07 (s, 6H) 2.23 (s, 2H) 2.75 (s, 2H) 6.29-6.36 (m, 1H) 6.45 (m, m 1H) 7.08 (m, m 1H) 7.48-7.53 (m, 2H) 7.66 (s, 1H) 8.38-8.52 (m, 2H) 11.91 (s, 1H)

Example 22 Preparation of 6-methyl-3-(phenylamino)-2-(pyridin-4-yl)-1,5,6,7-tetrahydro-4H-indol-4-one

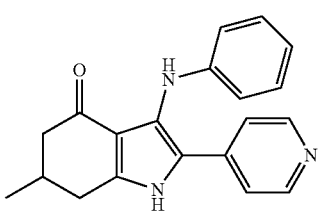 [SMILES: CC1CC(=O)c2c([nH]c(-c3ccncc3)c2Nc2ccccc2)C1]

Synthesized according to Method F1. Intermediate 1-2-27 (351 mg) gave the desired product (135 mg, 43%) after preparative HPLC (Method acidic).

1H-NMR (400 MHz, DMSO-d6): δ [ppm]=1.09 (d, 3H) 2.12-2.24 (m, 1H) 2.24-2.41 (m, 2H) 2.52-2.61 (m, 1H) 2.94 (dd, 1H) 6.54-6.60 (m, 2H) 6.63 (t, 1H) 7.04 (dd, 2H) 7.41 (s, 1H) 7.43-7.49 (m, 2H) 8.35-8.46 (m, 2H) 11.86 (s, 1H).

Example 24 Preparation of 3-[(3-fluorophenyl)amino]-2-(2-fluoropyridin-4-yl)-6,6-dimethyl-1,5,6,7-tetrahydro-4H-indol-4-one

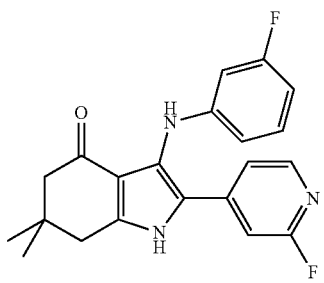 [SMILES: CC1(C)CC(=O)c2c([nH]c(-c3ccnc(F)c3)c2Nc2cccc(F)c2)C1]

Synthesized according to Method F2. Intermediate 1-5-2 (100 mg) gave the desired product (45 mg, 41%) after preparative HPLC (Method acidic).

1H-NMR (400 MHz, DMSO-d6): δ [ppm]=1.07 (s, 6H) 2.24 (s, 2H) 2.77 (s, 2H) 6.27 (m, 1H) 6.34-6.45 (m, 2H) 7.02-7.11 (m, 1H) 7.22 (s, 1H) 7.45-7.53 (m, 1H) 7.81 (s, 1H) 8.12 (d, 1H) 11.99 (s, 1H)

Example 25 Preparation of 6,6-dimethyl-2-(pyridin-4-yl)-3-(pyridin-2-ylamino)-1,5,6,7-tetrahydro-4H-indol-4-one

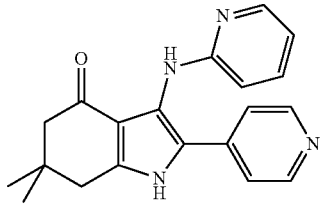 [SMILES: CC1(C)CC(=O)c2c([nH]c(-c3ccncc3)c2Nc2ccccn2)C1]

Synthesized according to Method F1. Intermediate 1-2-9 (60 mg) gave the desired product (24 mg, 44%) after preparative HPLC (Method basic).

1H-NMR (400 MHz, DMSO-d6): δ [ppm]=1.07 (s, 6H) 2.21 (s, 2H) 2.75 (s, 2H) 6.34 (d, 1H) 6.54-6.60 (m, 1H) 7.31-7.41 (m, 1H) 7.50-7.57 (m, 2H) 7.92-7.96 (m, 1H) 7.98 (s, 1H) 8.39-8.48 (m, 2H) 11.86 (s, 1H)

Example 26 Preparation of 3-(1-benzofuran-6-ylamino)-6,6-dimethyl-2-(pyridin-4-yl)-1,5,6,7-tetrahydro-4H-indol-4-one

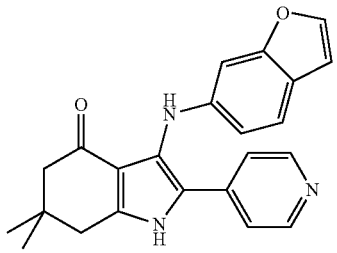 [SMILES: CC1(C)CC(=O)c2c([nH]c(-c3ccncc3)c2Nc2ccc3ccoc3c2)C1]

Synthesized according to Method F2. Intermediate 1-6-1 (100 mg) gave the desired product (23 mg, 20%) after preparative HPLC (Method basic).

1H-NMR (400 MHz, DMSO-d6): δ [ppm]=1.08 (s, 6H) 2.24 (s, 2H) 2.77 (s, 2H) 6.54 (s, 1H) 6.67-6.75 (m, 2H) 7.32 (d, 1H) 7.49-7.54 (m, 2H) 7.58 (s, 1H) 7.64 (d, 1H) 8.37-8.44 (m, 2H) 11.89 (s, 1H)

Example 27 Preparation of 6,6-dimethyl-3-(phenylamino)-2-(1H-pyrrolo[2,3-b]pyridin-4-yl)-1,5,6,7-tetrahydro-4H-indol-4-one

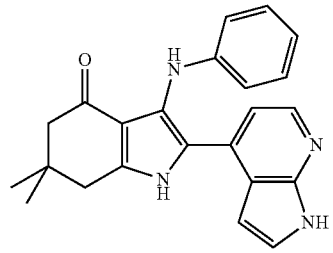 [SMILES: CC1(C)CC(=O)c2c([nH]c(-c3ccnc4[nH]ccc34)c2Nc2ccccc2)C1]

Synthesized according to Method F2. Intermediate 1-2-10 (70 mg) gave the desired product (2 mg, 3%) after preparative HPLC (Method acidic).

1H-NMR (400 MHz, DMSO-d6): δ [ppm]=1.06-1.12 (m, 6H) 2.25 (s, 2H) 2.78 (s, 2H) 6.43-6.51 (m, 2H) 6.62 (dd, 1H) 6.89 (dd, 2H) 7.07 (d, J=5.07 Hz, 1H) 7.35-7.40 (m, 2H) 8.08 (d, 1H) 11.56 (s, 2H)

Example 28 Preparation of 6-ethyl-3-(phenylamino)-2-(pyridin-4-yl)-1,5,6,7-tetrahydro-4H-indol-4-one

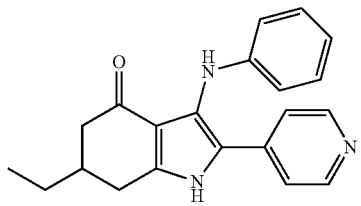 [SMILES: CCC1CC(=O)c2c([nH]c(-c3ccncc3)c2Nc2ccccc2)C1]

Synthesized according to Method F1. Intermediate 1-2-11 (535 mg) gave the desired product (339 mg, 70%) after column chromatography (MeOH:DCM).

1H-NMR (400 MHz, DMSO-d6): δ [ppm]=0.93 (t, 3H) 1.45 (m, 2H) 2.10-2.27 (m, 2H) 2.30-2.39 (m, 1H) 2.52-2.64 (m, 1H) 2.97 (dd, 1H) 6.54-6.67 (m, 3H) 7.03 (dd, 2H) 7.41 (s, 1H) 7.42-7.48 (m, 2H) 8.30-8.50 (m, 2H) 11.87 (s, 1H)

Example 29 Preparation of 6-(2-methylpropyl)-3-(phenylamino)-2-(pyridin-4-yl)-1,5,6,7-tetrahydro-4H-indol-4-one

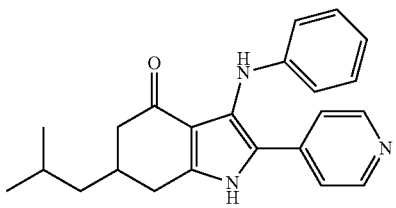 [SMILES: CC(C)CC1CC(=O)c2c([nH]c(-c3ccncc3)c2Nc2ccccc2)C1]

Synthesized according to Method F2. Intermediate 1-2-12 (650 mg) gave the desired product (293 mg, 49%) after column chromatography (MeOH:DCM).

1H-NMR (400 MHz, DMSO-d6): δ [ppm]=0.89 (d, 6H) 1.22-1.45 (m, 2H) 1.62-1.81 (m, 1H) 2.08 (s, 1H) 2.11-2.25 (m, 1H) 2.25-2.39 (m, 2H) 2.57 (d, 1H) 2.95 (d, 1H) 6.46-6.74 (m, 2H) 7.04 (t, 2H) 7.34-7.54 (m, 2H) 8.40 (d, 2H) 11.86 (br. s., 1H)

Example 30 Preparation of 2-(3-fluoropyridin-4-yl)-6,6-dimethyl-3-(phenylamino)-1,5,6,7-tetrahydro-4H-indol-4-one

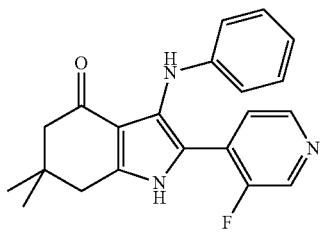

Synthesized according to Method F1. Intermediate 1-2-13 (536 mg) gave the desired product (209 mg, 43%) after column chromatography (MeOH:DCM).

1H-NMR (400 MHz, DMSO-d6): δ [ppm]=1.01-1.13 (m, 6H) 2.25 (s, 2H) 2.76 (s, 2H) 6.50-6.64 (m, 3H) 6.94-7.02 (m, 2H) 7.41 (dd, 1H) 7.50 (s, 1H) 8.23 (dd, 1H) 8.49 (d, 1H) 11.57 (s, 1H)

Example 31 Preparation of 3-[(3,5-difluorophenyl)amino]-6,6-dimethyl-2-(pyridin-4-yl)-1,5,6,7-tetrahydro-4H-indol-4-one

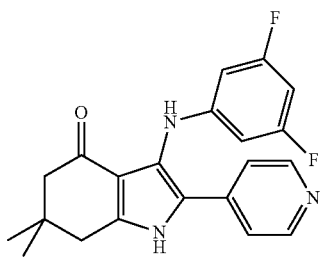 [SMILES: CC1(C)CC(=O)c2c([nH]c(-c3ccncc3)c2Nc2cc(F)cc(F)c2)C1]

Synthesized according to Method F2. Intermediate 1-6-1 (100 mg) gave the desired product (21 mg, 17%) after preparative HPLC (Method acidic).

1H-NMR (400 MHz, DMSO-d6): δ [ppm]=1.07 (s, 6H) 2.24 (s, 2H) 2.76 (s, 2H) 6.13 (d, 1H) 6.11 (d, 1H) 6.24-6.36 (m, 1H) 7.48-7.61 (m, 2H) 8.05 (s, 1H) 8.42-8.54 (m, 2H) 11.95 (s, 1H)

Example 32 6,6-dimethyl-2-(pyridin-4-yl)-3-[(3,4,5-trifluorophenyl)amino]-1,5,6,7-tetrahydro-4H-indol-4-one

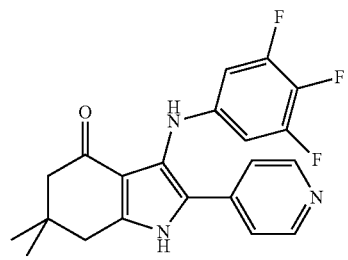 [SMILES: CC1(C)CC(=O)c2c([nH]c(-c3ccncc3)c2Nc2cc(F)c(F)c(F)c2)C1]

Synthesized according to Method F2. Intermediate 1-6-1 (100 mg) gave the desired product (21 mg, 17%) after preparative HPLC (Method basic).

1H-NMR (400 MHz, DMSO-d6): δ [ppm]=1.07 (s, 6H) 2.23 (s, 2H) 2.76 (s, 2H) 6.30 (d, 1H) 6.27 (d, 1H) 7.49-7.59 (m, 2H) 7.94 (s, 1H) 8.45-8.53 (m, 2H) 11.95 (s, 1H)

Example 33 Preparation of 6 2-(3-chloropyridin-4-yl)-3-(phenylamino)-1,5,6,7-tetrahydro-4H-indol-4-one

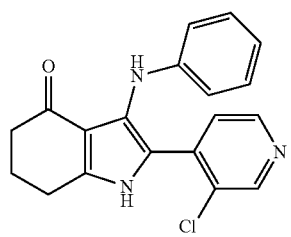 [SMILES: O=C1CCCc2[nH]c(-c3ccncc3Cl)c(Nc3ccccc3)c21]

Synthesized according to Method F1. Intermediate 1-2-14 (1018 mg) gave the desired product (371 mg, 37%) after column chromatography (MeOH:DCM).

1H-NMR (400 MHz, DMSO-d6): δ [ppm]=2.06 (m, 2H) 2.33-2.40 (m, 2H) 2.84 (t, 2H) 6.47-6.57 (m, 3H) 6.91 (dd, 2H) 7.31 (d, 1H) 7.48 (s, 1H) 8.35 (d, 1H) 8.54 (s, 1H) 11.61 (s, 1H)

Example 34 Preparation of 6,6-dimethyl-3-(phenylamino)-2-(1H-pyrazolo[3,4-b]pyridin-4-yl)-1,5,6,7-tetrahydro-4H-indol-4-one

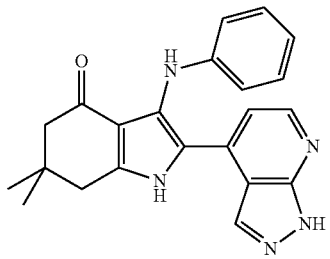 [SMILES: CC1(C)CC(=O)c2c([nH]c(-c3ccnc4[nH]ncc34)c2Nc2ccccc2)C1]

Synthesized according to Method F1. Intermediate 1-2-15 (150 mg) gave the desired product (54 mg, 39%) after column chromatography (MeOH:DCM).
1H-NMR (400 MHz, DMSO-d6): δ [ppm]=1.09 (s, 6H) 2.27 (s, 2H) 2.80 (s, 2H) 6.47-6.61 (m, 3H) 6.91 (t, 2H) 7.15 (d, 1H) 7.57 (s, 1H) 8.22 (d, 1H) 8.37 (d, 1H) 11.74 (s, 1H) 13.45 (s, 1H)

Example 35 Preparation of N-{4-[6,6-dimethyl-4-oxo-3-(phenylamino)-4,5,6,7-tetrahydro-1H-indol-2-yl]pyridin-2-yl}propanamide

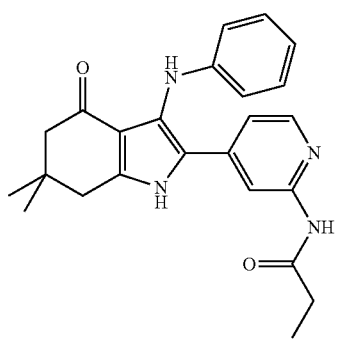 [SMILES: CCC(=O)Nc1cc(-c2[nH]c3c(c2Nc2ccccc2)C(=O)CC(C)(C)C3)ccn1]

Synthesized according to Method G1. Example 122 (70 mg) gave the desired product (46 mg, 57%) after column chromatography (MeOH:DCM).
1H-NMR (400 MHz, DMSO-d6): δ [ppm]=1.03-1.12 (m, 9H) 2.19-2.28 (m, 2H) 2.37 (q, 2H) 2.75 (s, 2H) 6.50-6.63 (m, 3H) 7.01 (t, 2H) 7.15 (dd, 1H) 7.35 (s, 1H) 8.06 (d, 1H) 8.24 (s, 1H) 10.27 (s, 1H) 11.86 (s, 1H)

Example 36 Preparation of N-{4-[6,6-dimethyl-4-oxo-3-(phenylamino)-4,5,6,7-tetrahydro-1H-indol-2-yl]pyridin-2-yl}acetamide

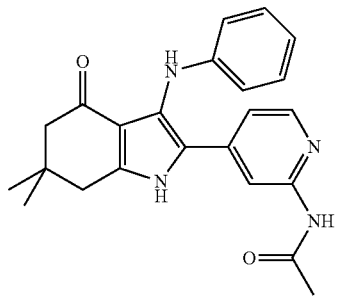 [SMILES: CC(=O)Nc1cc(-c2[nH]c3c(c2Nc2ccccc2)C(=O)CC(C)(C)C3)ccn1]

Synthesized according to Method G1. Example 122 (44 mg) gave the desired product (20 mg, 41%) after preparative HPLC (Method acidic).
1H-NMR (400 MHz, CDCl3): δ [ppm]=1.14 (s, 6H) 2.16-2.25 (m, 3H) 2.31-2.40 (m, 2H) 2.69 (s, 2H) 6.69 (d, 2H) 6.77 (t, 1H) 6.92 (d, 1H) 7.05-7.13 (m, 2H) 7.39 (s, 1H) 7.88-8.04 (m, 1H) 8.22 (br. s., 1H)

Example 37 Preparation of 3'-(phenylamino)-2'-(pyridin-4-yl)-1',7'-dihydrospiro[cyclopropane-1,6'-indol]-4'(5'H)-one

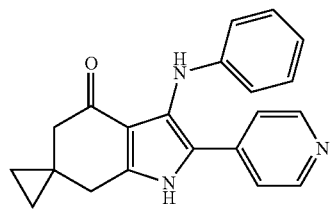 [SMILES: O=C1CC2(CC2)Cc2[nH]c(-c3ccncc3)c(Nc3ccccc3)c21]

Synthesized according to Method F1. Intermediate 1-2-17 (182 mg) gave the desired product (33 mg, 20%) after preparative HPLC (Method acidic).
1H-NMR (400 MHz, DMSO-d6): δ [ppm]=0.39-0.47 (m, 2H) 0.47-0.56 (m, 2H) 2.26 (s, 2H) 2.78 (s, 2H) 6.57-6.71 (m, 3H) 7.07 (t, 2H) 7.51-7.60 (m, 2H) 7.65 (s, 1H) 8.46 (d, 2H) 12.05 (s, 1H)

Example 38 3-[(3,4-difluorophenyl)amino]-2-(pyridin-4-yl)-1,5,6,7-tetrahydro-4H-indol-4-one

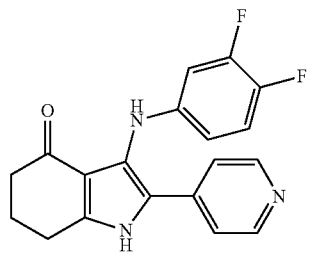 [SMILES: O=C1CCCc2[nH]c(-c3ccncc3)c(Nc3ccc(F)c(F)c3)c21]

Synthesized according to Method F1. Intermediate 1-2-28 (264 mg) gave the desired product (22 mg, 9%) after preparative HPLC (Method acidic).
1H-NMR (400 MHz, DMSO-d6): δ [ppm]=2.02-2.17 (m, 2H) 2.35 (t, 2H) 2.89 (t, 2H) 6.38 (d, 1H) 6.55 (m, 1H) 7.03-7.15 (m, 1H) 7.61 (d, 2H) 7.82 (s, 1H) 8.52 (d, 2H) 12.10 (s, 1H)

Example 39 Preparation of N-{4-[4-oxo-3-(phenylamino)-4,5,6,7-tetrahydro-1H-indol-2-yl]pyridin-2-yl}acetamide

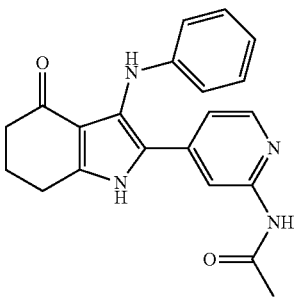 [SMILES: CC(=O)Nc1cc(-c2[nH]c3c(c2Nc2ccccc2)C(=O)CCC3)ccn1]

Synthesized according to Method G1. Example 139 (80 mg) gave the desired product (38 mg, 42%) after preparative HPLC (Method basic).

1H-NMR (400 MHz, DMSO-d6): δ [ppm]=0.98-2.09 (m, 5H) 2.32 (t, 2H) 2.86 (t, 2H) 6.52-6.66 (m, 3H) 7.01 (dd, 2H) 7.13-7.17 (m, 1H) 7.34 (s, 1H) 8.07 (d, 1H) 8.21 (s, 1H) 10.30 (s, 1H) 11.88 (s, 1H)

Example 40 Preparation of N-(4-{3-[(3-fluorophenyl)amino]-4-oxo-4,5,6,7-tetrahydro-1H-indol-2-yl}pyridin-2-yl)acetamide

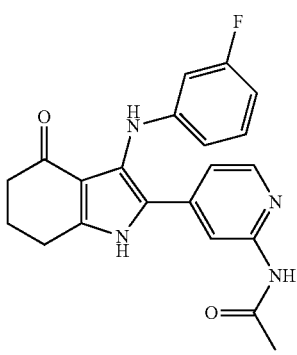 [SMILES: CC(=O)Nc1cc(-c2[nH]c3c(c2Nc2cccc(F)c2)C(=O)CCC3)ccn1]

Synthesized according to Method G1. Example 138 (90 mg) gave the desired product (45 mg, 44%) after preparative HPLC (Method basic).

1H-NMR (400 MHz, DMSO-d6): δ [ppm]=1.98-2.09 (m, 5H) 2.27-2.38 (m, 2H) 2.86 (t, 2H) 6.25 (m, 1H) 6.30-6.43 (m, 2H) 7.01 (q, 1H) 7.19 (dd, 1H) 7.61 (s, 1H) 8.13 (d, 1H) 8.24 (s, 1H) 10.33 (s, 1H) 11.93 (s, 1H)

Example 41 Preparation of 3-[(3-fluorophenyl)amino]-2-(pyridin-4-yl)-1,5,6,7-tetrahydro-4H-indol-4-one

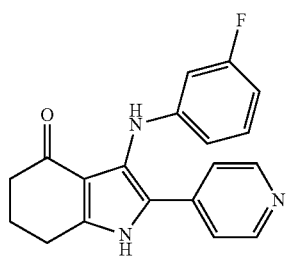 [SMILES: O=C1CCCc2[nH]c(-c3ccncc3)c(Nc3cccc(F)c3)c21]

Synthesized according to Method F1. Intermediate 1-2-20 (264 mg) gave the desired product (6 mg, 21%) after preparative HPLC (Method basic).

1H-NMR (400 MHz, DMSO-d6): δ [ppm]=2.00-2.12 (m, 2H) 2.33 (t, 2H) 2.87 (t, 2H) 6.26 (m, 1H) 6.32-6.47 (m, 2H) 6.98-7.08 (m, 1H) 7.48-7.52 (m, 2H) 7.70 (s, 1H) 8.42-8.47 (m, 2H) 11.94 (br. s., 1H)

Example 42 Preparation of 3-[(4-fluorophenyl)amino]-2-(pyridin-4-yl)-1,5,6,7-tetrahydro-4H-indol-4-one

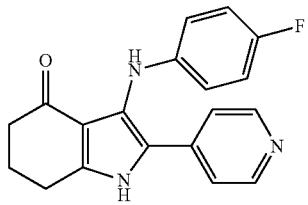 [SMILES: O=C1CCCc2[nH]c(-c3ccncc3)c(Nc3ccc(F)cc3)c21]

Synthesized according to Method F1. Intermediate 1-2-21 (33 mg) gave the desired product (8 mg, 27%) after preparative HPLC (Method basic).

1H-NMR (400 MHz, DMSO-d6): δ [ppm]=1.99-2.11 (m, 2H) 2.28-2.36 (m, 4H) 2.86 (t, 1H) 6.51-6.63 (m, 1H) 6.88 (t, 2H) 7.35-7.50 (m, 2H) 8.36-8.45 (m, 1H) 11.89 (br. s., 1H)

Example 43 Preparation of 3-[(3-fluorophenyl)amino]-2-(pyridin-4-yl)-6-(trifluoromethyl)-1,5,6,7-tetrahydro-4H-indol-4-one

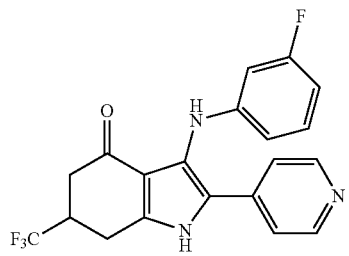 [SMILES: O=C1CC(C(F)(F)F)Cc2[nH]c(-c3ccncc3)c(Nc3cccc(F)c3)c21]

Synthesized according to Method F1. Intermediate 1-2-22 (92 mg) gave the desired product (7 mg, 8%) after preparative HPLC (Method basic).

1H-NMR (400 MHz, DMSO-d6): δ [ppm]=2.45 (d, 1H) 2.52-2.63 (m, 2H) 3.02 (dd, 1H) 3.14 (dd, 1H) 6.27 (m, 1H) 6.32-6.46 (m, 2H) 7.00-7.11 (m, 1H) 7.49-7.54 (m, 2H) 7.72-7.78 (m, 1H) 8.44-8.51 (m, 2H) 12.14 (br. s., 1H)

Example 44 Preparation of 2-(2-fluoropyridin-4-yl)-3-(phenylamino)-1,5,6,7-tetrahydro-4H-indol-4-one

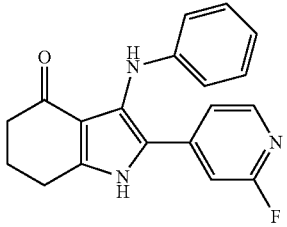 [SMILES: O=C1CCCc2[nH]c(-c3ccnc(F)c3)c(Nc3ccccc3)c21]

Synthesized according to Method F1. Intermediate 1-2-23 (240 mg) gave the desired product (101 mg, 47%) after column chromatography (MeOH:DCM).

1H-NMR (400 MHz, DMSO-d6): δ [ppm]=2.06 (m, 2H) 2.30-2.41 (m, 2H) 2.87 (t, 2H) 6.56-6.63 (m, 2H) 6.66 (t, 1H) 7.06 (dd, 2H) 7.11-7.16 (m, 1H) 7.42 (m, 1H) 7.50-7.57 (m, 1H) 8.07 (d, 1H) 11.98 (s, 1H)

Example 45 Preparation of 3-(biphenyl-3-ylamino)-6,6-dimethyl-2-(pyridin-4-yl)-1,5,6,7-tetrahydro-4H-indol-4-one

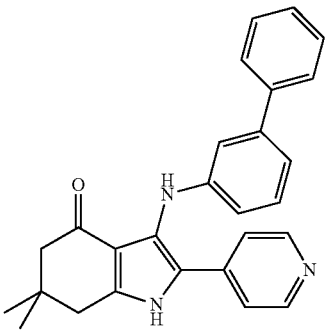 [SMILES: CC1(C)CC(=O)c2c([nH]c(-c3ccncc3)c2Nc2cccc(-c3ccccc3)c2)C1]

Synthesized according to Method F2. Intermediate 1-6-1 (100 mg) gave the desired product (42 mg, 33%) after preparative HPLC (Method basic).

1H-NMR (400 MHz, DMSO-d6): δ [ppm]=1.08 (s, 6H) 2.25 (s, 2H) 2.76 (s, 2H) 6.62 (d, 1H) 6.77 (s, 1H) 6.90 (d, 1H) 7.14 (t1H) 7.25-7.41 (m, 5H) 7.49 (d, 2H) 7.63 (s, 1H) 8.44 (d, 2H) 11.88 (s, 1H)

Example 46 Preparation of 4-[6,6-dimethyl-4-oxo-3-(phenylamino)-4,5,6,7-tetrahydro-1H-indol-2-yl]pyridine-2-carbonitrile

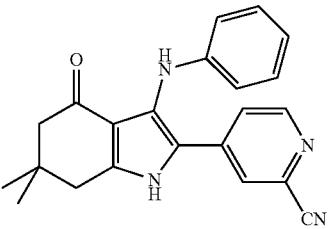 [SMILES: CC1(C)CC(=O)c2c([nH]c(-c3ccnc(C#N)c3)c2Nc2ccccc2)C1]

Synthesized according to Method F1. Intermediate 1-2-24 (90 mg) gave the desired product (10 mg, 12%) after column chromatography (Diethyl ether:EtOAc).

1H-NMR (400 MHz, DMSO-d6): δ [ppm]=1.08 (s, 6H), 2.23 (s, 2H), 2.77 (s, 2H), 6.55-6.64 (m, 2H), 6.64-6.72 (m, 1H), 7.02-7.13 (m, 2H), 7.63 (s, 1H), 7.96 (s, 1H), 8.49-8.56 (m, 1H), 12.01 (s, 1H)

Example 47 Preparation of N-(4-{3-[(3-fluorophenyl)amino]-4-oxo-4,5,6,7-tetrahydro-1H-indol-2-yl}pyridin-2-yl)cyclopropanecarboxamide

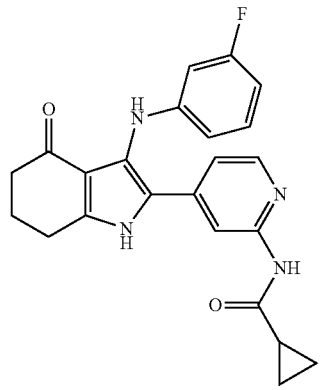 [SMILES: O=C1CCCc2[nH]c(-c3ccnc(NC(=O)C4CC4)c3)c(Nc3cccc(F)c3)c21]

Synthesized according to Method G1. Example 138 (80 mg) gave the desired product (20 mg, 18%) after preparative HPLC (Method basic).

1H-NMR (400 MHz, DMSO-d6): δ [ppm]=0.80 (d, 3H) 1.93-2.09 (m, 3H) 2.27-2.35 (m, 2H) 2.85 (t, 2H) 6.24 (m, 1H) 6.30-6.41 (m, 2H) 6.95-7.07 (m, 1H) 7.19 (dd, 1H) 7.63 (s, 1H) 8.12 (d, 1H) 8.21-8.27 (m, 1H) 10.66 (s, 1H) 11.93 (s, 1H)

Example 48 Preparation of N-{4-[4-oxo-3-(phenylamino)-4,5,6,7-tetrahydro-1H-indol-2-yl]pyridin-2-yl}cyclopropanecarboxamide

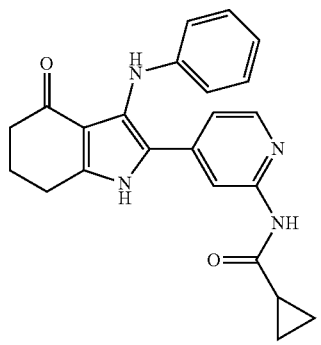 [SMILES: O=C1CCCc2[nH]c(-c3ccnc(NC(=O)C4CC4)c3)c(Nc3ccccc3)c21]

Synthesized according to Method G1. Example 139 (80 mg) gave the desired product (15 mg, 15%) after preparative HPLC (Method basic).

1H-NMR (400 MHz, DMSO-d6): δ [ppm 0.80 (d, 4H) 1.93-2.12 (m, 3H) 2.27-2.39 (m, 2H) 2.84 (t, 2H) 6.48-6.67 (m, 3H) 6.96-7.05 (m, 2H) 7.13 (dd, 1H) 7.36 (s, 1H) 8.06 (d, 1H) 8.19-8.26 (m, 1H) 10.64 (s, 1H) 11.87 (s, 1H)

Example 49 Preparation of 2-(2-aminopyridin-4-yl)-3-(phenylamino)-6-(propan-2-yl)-1,5,6,7-tetrahydro-4H-indol-4-one

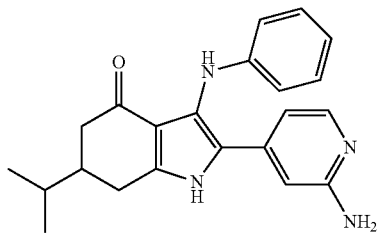 [SMILES: CC(C)C1CC(=O)c2c([nH]c(-c3ccnc(N)c3)c2Nc2ccccc2)C1]

Synthesized according to Method F1. Intermediate 1-2-25 (667 mg) gave the desired product (272 mg, 42%) after column chromatography (MeOH:DCM).

1H-NMR (400 MHz, DMSO-d6): δ [ppm]=0.81-0.88 (m, 6H) 1.53 (m, 1H) 1.62-1.76 (m, 1H) 2.17-2.42 (m, 3H) 2.74-2.85 (m, 1H) 4.60 (d, 2H) 6.01 (s, 2H) 6.34 (s, 1H) 6.43 (dd, 1H) 7.03 (t, 1H) 7.29 (t, 2H) 7.54 (dd, 2H) 7.89 (d, 1H) 12.33 (t, 1H) 12.62 (s, 1H)

Example 50 Preparation of 2-(2-aminopyridin-4-yl)-3-[(3-fluorophenyl)amino]-6-(propan-2-yl)-1,5,6,7-tetrahydro-4H-indol-4-one

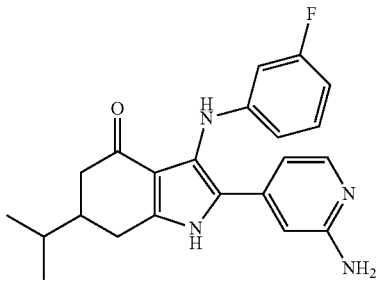 [SMILES: CC(C)C1CC(=O)c2c([nH]c(-c3ccnc(N)c3)c2Nc2cccc(F)c2)C1]

Synthesized according to Method F1. Intermediate 1-2-26 (515 mg) gave the desired product (184 mg, 37%) after column chromatography (MeOH:DCM).

1H-NMR (400 MHz, DMSO-d6): δ [ppm]=0.80-0.88 (m, 6H) 1.53 (m, 1H) 1.61-1.80 (m, 1H) 2.19-2.42 (m, 3H) 2.73-2.86 (m, 1H) 4.62 (d, 2H) 6.02 (s, 2H) 6.34 (s, 1H) 6.43 (dd, 1H) 6.79-6.91 (m, 1H) 7.17 (dd, 1H) 7.28-7.38 (m, 1H) 7.66 (m, 1H) 7.89 (d, 1H) 12.21 (t, 1H) 12.80 (s, 1H)

Example 122 Preparation of 2-(2-aminopyridin-4-yl)-6,6-dimethyl-3-(phenylamino)-1,5,6,7-tetrahydro-4H-indol-4-one

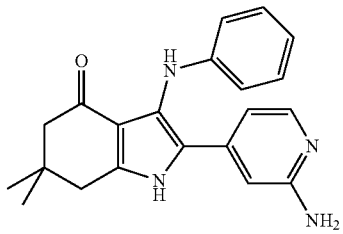 [SMILES: CC1(C)CC(=O)c2c([nH]c(-c3ccnc(N)c3)c2Nc2ccccc2)C1]

Synthesized according to Method F1. Intermediate 1-2-16 (680 mg) gave the desired product (586 mg, 94%) after column chromatography (MeOH:DCM).

1H-NMR (400 MHz, DMSO-d6): δ [ppm]=1.06 (s, 6H) 2.20 (s, 2H) 2.71 (s, 2H) 5.68 (s, 2H) 6.50-6.63 (m, 4H) 6.69 (dd, 1H) 7.01 (dd, 2H) 7.20 (s, 1H) 7.75 (d, 1H) 11.62 (s, 1H)

Example 138 Preparation of 2-(2-aminopyridin-4-yl)-3-[(3-fluorophenyl)amino]-1,5,6,7-tetrahydro-4H-indol-4-one

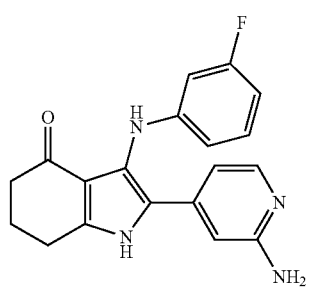 [SMILES: Nc1cc(-c2[nH]c3c(c2Nc2cccc(F)c2)C(=O)CCC3)ccn1]

Synthesized according to Method F1. Intermediate 1-2-19 (917 mg) gave the desired product (391 mg, 47%) after column chromatography (MeOH:DCM).

1H-NMR (400 MHz, DMSO-d6): δ [ppm]=1.97-2.09 (m, 2H) 2.24-2.36 (m, 2H) 2.83 (t, 2H) 5.79 (s, 2H) 6.24 (m, 1H) 6.30-6.43 (m, 2H) 6.58-6.62 (m, 1H) 6.71 (dd, 1H) 6.97-7.06 (m, 1H) 7.51 (s, 1H) 7.79 (d, 1H) 11.73 (s, 1H)

Example 139 Preparation of 2-(2-aminopyridin-4-yl)-3-(phenylamino)-1,5,6,7-tetrahydro-4H-indol-4-one

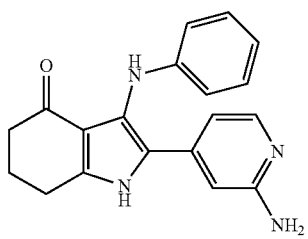 [SMILES: Nc1cc(-c2[nH]c3c(c2Nc2ccccc2)C(=O)CCC3)ccn1]

Synthesized according to Method F1. Intermediate 1-2-18 (1100 mg) gave the desired product (276 mg, 28%) after column chromatography (MeOH:DCM).

1H-NMR (400 MHz, DMSO-d6): δ [ppm]=1.96-2.14 (m, 2H) 2.26-2.38 (m, 2H) 2.83 (t, 2H) 5.84 (br. s., 2H) 6.52-6.66 (m, 4H) 6.71 (dd, 1H) 6.95-7.07 (m, 2H) 7.26 (s, 1H) 7.75 (d, 1H) 11.71 (s, 1H)

The following examples where prepared by the methods described supra.

| Example Nr. | Intermediate | Synthesis Method | Yield (%) | HPLC Retention time (min) | MS M + H+ |
|---|---|---|---|---|---|
| 51 | 1-6-1 | F2 | 68 | 1.18 | 400 |
| 52 | 1-6-1 | F2 | 50 | 0.81 | 362 |
| 53 | 1-6-1 | F2 | 56 | 1.15 | 346 |
| 54 | 1-6-1 | F2 | 40 | 0.88 | 346 |
| 55 | 1-1-1 | B1 | 30 | 0.97 | 333 |
| 56 | 1-6-1 | F2 | 32 | 0.84 | 392 |
| 58 | 1-6-1 | F2 | 29 | 0.79 | 392 |
| 59 | 1-6-1 | F2 | 44 | 0.86 | 362 |
| 60 | 1-6-1 | F2 | 42 | 1.15 | 350 |
| 61 | 1-6-1 | F2 | 15 | 1.16 | 366 |
| 62 | 1-6-1 | F2 | 40 | 1.08 | 392 |
| 63 | 1-6-1 | F2 | 30 | 0.50 | 333 |
| 64 | 1-6-1 | F2 | 30 | 1.01 | 383 |
| 65 | 1-6-1 | F2 | 14 | 0.60 | 347 |
| 66 | 1-6-1 | F2 | 37 | 0.99 | 383 |
| 67 | 1-6-1 | F2 | 39 | 1.10 | 372 |
| 68 | 1-6-1 | F2 | 38 | 1.04 | 371 |
| 69 | 1-6-1 | F2 | 35 | 1.16 | 388 |
| 70 | 1-6-1 | F2 | 43 | 1.01 | 371 |
| 71 | analogous | F1 | 65 | 1.18 | 410, 412 |
| 72 | analogous | F1 | 58 | 1.17 | 410, 412 |
| 73 | 1-6-1 | F2 | 26 | 0.84 | 372 |
| 74 | 1-6-1 | F2 | 58 | 1.24 | 372 |
| 75 | 1-6-1 | F2 | 30 | 1.28 | 383 |
| 76 | 1-6-1 | F2 | 33 | 1.08 | 392 |
| 77 | 1-6-1 | F2 | 10 | 0.97 | 400, 402 |
| 78 | 1-6-1 | F2 | 7 | 1.23 | 400, 402 |
| 79 | 1-6-1 | F2 | 25 | 1.01 | 357 |
| 80 | 1-6-1 | F2 | 44 | 1.24 | 438 |
| 81 | 1-6-1 | F2 | 53 | 1.15 | 364 |
| 82 | 1-6-1 | F2 | 30 | 1.16 | 364 |
| 83 | 1-6-1 | F2 | 25 | 1.21 | 360 |
| 84 | 1-6-1 | F2 | 18 | 1.23 | 360 |
| 85 | 1-6-1 | F2 | 34 | 1.25 | 374 |

-continued

| Example Nr. | Intermediate | Synthesis Method | Yield (%) | HPLC Retention time (min) | MS M + H⁺ |
|---|---|---|---|---|---|
| 86 | 1-6-1 | F2 | 51 | 1.27 | 374 |
| 87 | 1-6-1 | F2 | 38 | 1.17 | 384 |
| 88 | 1-6-1 | F2 | 34 | 1.28 | 374 |
| 89 | 1-6-1 | F2 | 33 | 0.73 | 348 |
| 90 | 1-6-1 | F2 | 6 | 1.00 | 377 |
| 91 | 1-6-1 | F2 | 10 | 1.25 | 380, 382 |
| 92 | 1-6-1 | F2 | 9 | 1.21 | 380, 382 |
| 93 | 1-6-1 | F2 | 28 | 1.22 | 380, 382 |
| 94 | 1-6-1 | F2 | 11 | 1.19 | 384, 386 |
| 95 | 1-6-1 | F2 | 7 | 1.16 | 384 |
| 96 | 1-6-1 | F2 | 32 | 1.17 | 346 |
| 97 | 1-6-1 | F2 | 40 | 1.00 | 417 |
| 98 | 1-6-1 | F2 | 3 | 0.74 | 403 |
| 99 | 1-6-1 | F2 | 23 | 0.89 | 389 |
| 100 | 1-6-1 | F2 | 15 | 0.92 | 372 |
| 101 | 1-6-1 | F2 | 19 | 0.85 | 375 |
| 102 | 1-6-1 | F2 | 21 | 1.00 | 417 |
| 103 | analogous | F1 | 18 | — | 365, 367 |
| 104 | 1-6-1 | F2 | 19 | 1.11 | 376 |
| 105 | 1-6-1 | F2 | 19 | 1.16 | 389 |
| 106 | 1-6-1 | F2 | 29 | 0.91 | 392 |
| 107 | 1-6-1 | F2 | 14 | 1.20 | 416 |
| 108 | 1-6-1 | F2 | 21 | 1.19 | 390 |
| 109 | 1-6-1 | F2 | 8 | 0.89 | 389 |
| 110 | 1-6-1 | F2 | 11 | 1.06 | 380 |
| 111 | 1-6-1 | F2 | 19 | 0.93 | 380 |
| 112 | 1-6-1 | F2 | 24 | 0.94 | 376 |
| 113 | 1-6-1 | F2 | 23 | 0.99 | 374 |
| 114 | 1-6-1 | F2 | 18 | 1.28 | 388 |
| 116 | 1-6-1 | F2 | 18 | 0.81 | 403 |
| 117 | 1-6-1 | F2 | 5 | 1.17 | 398 |
| 118 | 1-6-1 | F2 | 11 | 1.25 | 432 |
| 119 | 1-6-1 | F2 | 11 | 1.30 | 404 |
| 121 | 1-6-1 | F2 | 29 | 1.11 | 380 |
| 123 | 1-6-1 | F2 | 10 | 1.32 | 458 |
| 124 | 1-6-1 | F2 | 12 | 1.09 | 362 |
| 125 | 1-6-1 | F2 | 12 | 1.19 | 394 |
| 126 | analogous | F1 | 44 | 1.28 | 401 |
| 127 | analogous | F1 | 43 | 1.19 | 417 |
| 128 | 1-6-1 | F2 | 9 | 1.16 | 376 |
| 129 | 1-6-1 | F2 | 17 | 1.19 | 418 |
| 130 | 1-6-1 | F2 | 16 | 1.15 | 388 |
| 131 | analogous | F1 | 37 | 1.10 | 346 |
| 132 | 122 | G1 | 36 | 1.01 | 417 |
| 133 | 122 | G1 | 23 | 1.15 | 431 |
| 134 | analogous | F1 | 9 | 0.75 | 340 |
| 135 | analogous | F1 | 8 | 1.14 | 368 |
| 136 | analogous | F1 | 4 | 1.07 | 358 |
| 137 | analogous | F1 | 52 | 1.27 | 411 |
| 140 | analogous | F1 | 34 | 1.31 | 400 |
| 142 | analogous | F1 | 17 | 1.03 | 356 |
| 143 | analogous | F1 | 79 | 1.02 | 318 |
| 144 | 1-6-1 | F2 | 16 | 0.93 | 403 |
| 145 | 1-6-1 | F2 | 31 | 1.09 | 361 |
| 146 | 1-6-1 | F2 | 8 | 1.03 | 357 |
| 147 | 1-6-1 | F2 | 12 | 1.05 | 375 |
| 148 | 1-6-1 | F2 | 14 | 1.22 | 434 |
| 149 | analogous | F1 | 60 | 1.13 | 346 |
| 150 | analogous | F1 | 20 | 1.09 | 334 |
| 151 | 1-6-1 | F2 | 28 | 0.59 | 376 |
| 152 | analogous | F1 | 34 | 1.14 | 382 |
| 153 | 1-6-1 | F2 | 49 | 1.08 | 418 |
| 154 | 1-6-1 | F2 | 31 | 1.01 | 390 |
| 155 | 1-6-1 | F2 | 33 | 1.03 | 430 |
| 156 | 1-6-1 | F2 | 35 | 1.10 | 390 |
| 157 | 1-6-1 | F2 | 50 | 1.22 | 382 |
| 158 | 1-6-1 | F2 | 36 | 1.18 | 382 |
| 159 | 1-6-1 | F2 | 9 | 1.03 | 424 |
| 160 | 1-6-1 | F2 | 22 | 1.28 | 408 |
| 162 | 138 | G1 | 18 | 1.17 | 473 |
| 163 | 139 | G1 | 22 | 1.16 | 455 |
| 164 | 103 | F2 | 18 | 1.10 | 361 |
| 165 | analogous | F1 | 9 | 0.98 | 459 |
| 166 | 122 | G1 | 12 | 1.13 | 425 |
| 167 | analogous | F1 | 28 | 1.15 | 379 |
| 168 | analogous | B1 | 0.4 | 0.98 | 431 |

Example 161 Preparation of 6,6-dimethyl-2-(1-oxidopyridin-4-yl)-3-(phenylamino)-1,5,6,7-tetrahydro-4H-indol-4-one

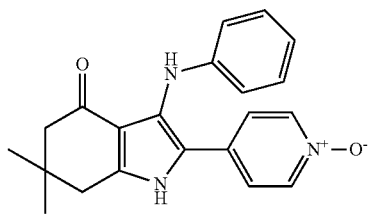 [SMILES: CC1(C)CC(=O)c2c([nH]c(-c3cc[n+]([O-])cc3)c2Nc2ccccc2)C1]

Synthesis of Example 161

Synthesis of 4,4-dimethyl-2-{[(1-oxidopyridin-4-yl)methyl]amino}-6-oxo-N-phenylcyclohex-1-ene-1-carbothioamide

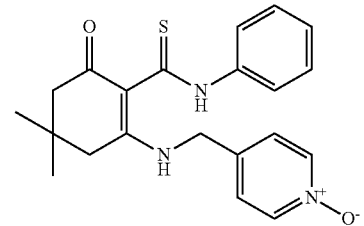 [SMILES: CC1(C)CC(=O)C(C(=S)Nc2ccccc2)=C(NCc2cc[n+]([O-])cc2)C1]

A suspension of intermediate 1-1-1 (3.6 g, 13.1 mmol), 1-(1-oxidopyridin-4-yl)methanamine dihydrochloride (synthesized according to WO2004/22561 A1) (1.8 g, 9.1 mmol) and DIPEA (3.6 mL, 20.7 mmol) in EtOH (9 mL) was heated in a sealed tube at 100° C. for 3 h. The reaction was allowed to cool, diluted with EtOAc and washed with sat. NaHCO3 (aq), dried over MgSO₄, filtered and concentrated. Purification by silica chromatography and re-crystallization (MeOH) gave 4,4-dimethyl-2-{[(1-oxidopyridin-4-yl)methyl]amino}-6-oxo-N-phenylcyclohex-1-ene-1-carbothioamide (1.25 g, 36%).

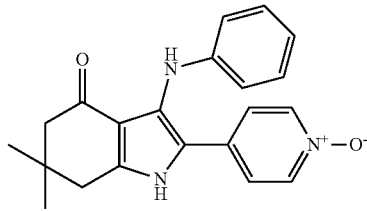 [SMILES: CC1(C)CC(=O)c2c([nH]c(-c3cc[n+]([O-])cc3)c2Nc2ccccc2)C1]

To a solution of 4,4-dimethyl-2-{[(1-oxidopyridin-4-yl)methyl]amino}-6-oxo-N-phenylcyclohex-1-ene-1-carbothioamide ( ) (1.20 g, 0.3.15 mmol) in EtOH (12 mL) was added H₂O₂ (34% in water, 8.22 mmol) and the reaction was heated at 100° C. for 6 h. The reaction was concentrated and the residue was subjected to column chromatography to give the desired product (360 mg, 31%).

¹H-NMR (400 MHz, DMSO-d₆): δ [ppm]=1.06 (s, 6H), 2.22 (s, 2H), 2.73 (s, 2H), 6.53-6.60 (m, 2H), 6.60-6.68 (m, 1H), 7.00-7.11 (m, 2H), 7.38 (s, 1H), 7.46-7.54 (m, 2H), 8.06-8.15 (m, 2H), 11.87 (s, 1H).

| Example Nr. | Chemical structure | Chemical name |
|---|---|---|
| 1 | 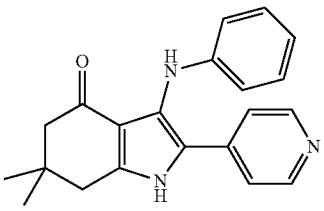 [SMILES: CC1(C)CC(=O)c2c([nH]c(-c3ccncc3)c2Nc2ccccc2)C1] | 6,6-dimethyl-3-(phenylamino)-2-(pyridin-4-yl)-1,5,6,7-tetrahydro-4H-indol-4-one |
| 51 | 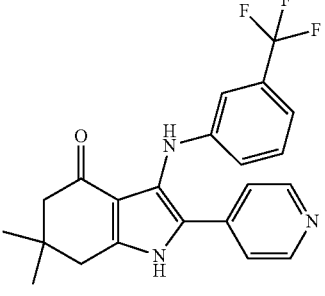 | 6,6-dimethyl-2-(pyridin-4-yl)-3-{[3-(trifluoromethyl)phenyl]amino}-1,5,6,7-tetrahydro-4H-indol-4-one |
| 52 | 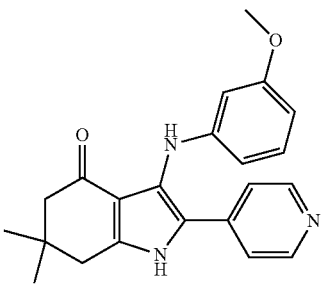 [SMILES: COc1cccc(Nc2c(-c3ccncc3)[nH]c3c2C(=O)CC(C)(C)C3)c1] | 3-[(3-methoxyphenyl)amino]-6,6-dimethyl-2-(pyridin-4-yl)-1,5,6,7-tetrahydro-4H-indol-4-one |
| 53 | 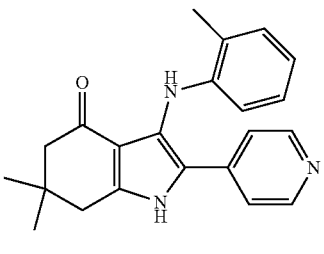 [SMILES: Cc1ccccc1Nc1c(-c2ccncc2)[nH]c2c1C(=O)CC(C)(C)C2] | 6,6-dimethyl-3-[(2-methylphenyl)amino]-2-(pyridin-4-yl)-1,5,6,7-tetrahydro-4H-indol-4-one |
| 54 | 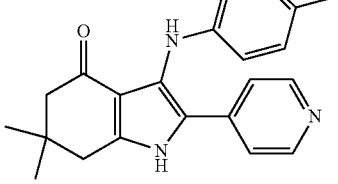 | 6,6-dimethyl-3-[(4-methylphenyl)amino]-2-(pyridin-4-yl)-1,5,6,7-tetrahydro-4H-indol-4-one |

-continued

| Example Nr. | Chemical structure | Chemical name |
|---|---|---|
| 55 | 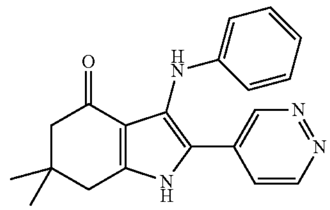 [SMILES: CC1(C)CC(=O)c2c([nH]c(-c3ccnnc3)c2Nc2ccccc2)C1] | 6,6-dimethyl-3-(phenylamino)-2-(pyridazin-4-yl)-1,5,6,7-tetrahydro-4H-indol-4-one |
| 56 | 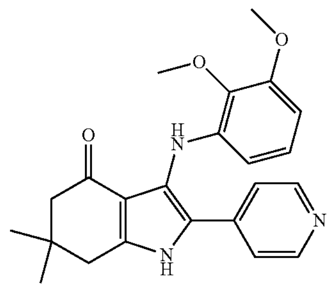 [SMILES: COc1cccc(Nc2c(-c3ccncc3)[nH]c3c2C(=O)CC(C)(C)C3)c1OC] | 3-[(2,3-dimethoxyphenyl)amino]-6,6-dimethyl-2-(pyridin-4-yl)-1,5,6,7-tetrahydro-4H-indol-4-one |
| 58 | 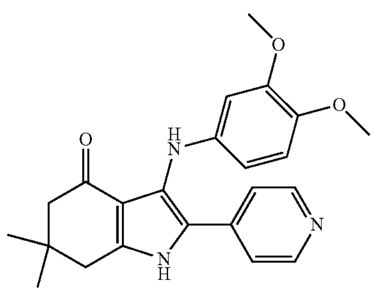 | 3-[(3,4-dimethoxyphenyl)amino]-6,6-dimethyl-2-(pyridin-4-yl)-1,5,6,7-tetrahydro-4H-indol-4-one |
| 59 | 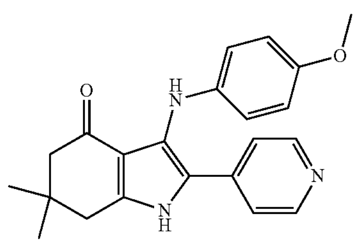 | 3-[(4-methoxyphenyl)amino]-6,6-dimethyl-2-(pyridin-4-yl)-1,5,6,7-tetrahydro-4H-indol-4-one |
| 60 | 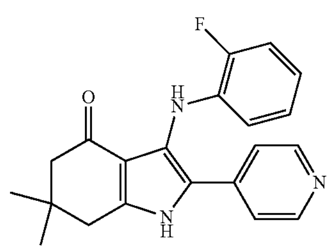 [SMILES: CC1(C)CC(=O)c2c([nH]c(-c3ccncc3)c2Nc2ccccc2F)C1] | 3-[(2-fluorophenyl)amino]-6,6-dimethyl-2-(pyridin-4-yl)-1,5,6,7-tetrahydro-4H-indol-4-one |
| 61 | 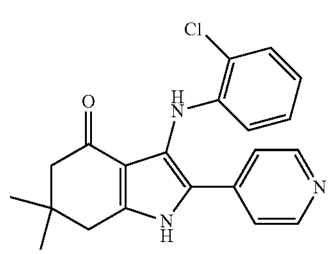 | 3-[(2-chlorophenyl)amino]-6,6-dimethyl-2-(pyridin-4-yl)-1,5,6,7-tetrahydro-4H-indol-4-one |

-continued

| Example Nr. | Chemical structure | Chemical name |
|---|---|---|
| 62 | 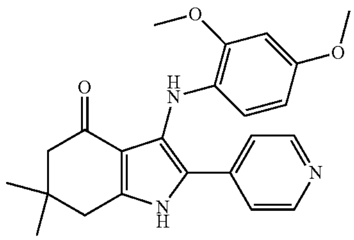 | 3-[(2,4-dimethoxyphenyl)amino]-6,6-dimethyl-2-(pyridin-4-yl)-1,5,6,7-tetrahydro-4H-indol-4-one |
| 63 | 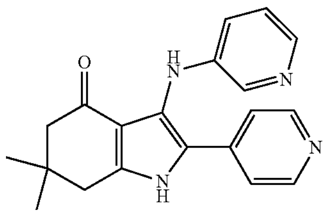 [SMILES: CC1(C)CC(=O)c2c([nH]c(-c3ccncc3)c2Nc2cccnc2)C1] | 6,6-dimethyl-2-(pyridin-4-yl)-3-(pyridin-3-ylamino)-1,5,6,7-tetrahydro-4H-indol-4-one |
| 64 | 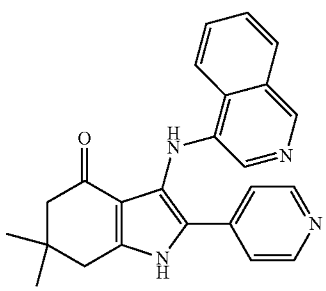 | 3-(isoquinolin-4-ylamino)-6,6-dimethyl-2-(pyridin-4-yl)-1,5,6,7-tetrahydro-4H-indol-4-one |
| 65 | 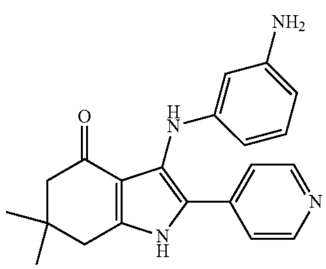 [SMILES: CC1(C)CC(=O)c2c([nH]c(-c3ccncc3)c2Nc2cccc(N)c2)C1] | 3-[(3-aminophenyl)amino]-6,6-dimethyl-2-(pyridin-4-yl)-1,5,6,7-tetrahydro-4H-indol-4-one |
| 66 | 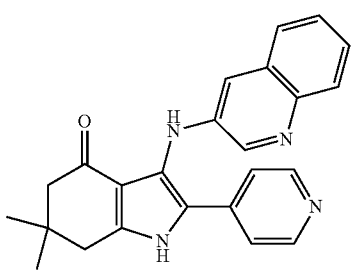 [SMILES: CC1(C)CC(=O)c2c([nH]c(-c3ccncc3)c2Nc2cnc3ccccc3c2)C1] | 6,6-dimethyl-2-(pyridin-4-yl)-3-(quinolin-3-ylamino)-1,5,6,7-tetrahydro-4H-indol-4-one |
| 67 | 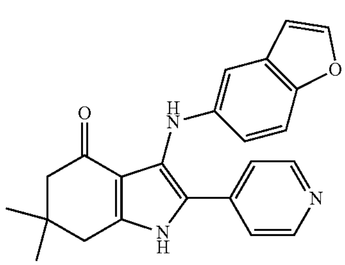 [SMILES: CC1(C)CC(=O)c2c([nH]c(-c3ccncc3)c2Nc2ccc3occc3c2)C1] | 3-(1-benzofuran-5-ylamino)-6,6-dimethyl-2-(pyridin-4-yl)-1,5,6,7-tetrahydro-4H-indol-4-one |

-continued

| Example Nr. | Chemical structure | Chemical name |
|---|---|---|
| 68 | 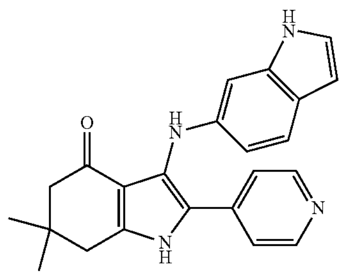 [SMILES: CC1(C)CC(=O)c2c([nH]c(-c3ccncc3)c2Nc2ccc3cc[nH]c3c2)C1] | 3-(1H-indol-6-ylamino)-6,6-dimethyl-2-(pyridin-4-yl)-1,5,6,7-tetrahydro-4H-indol-4-one |
| 69 | 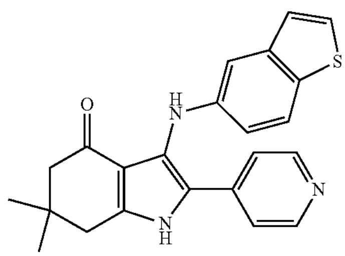 [SMILES: CC1(C)CC(=O)c2c([nH]c(-c3ccncc3)c2Nc2ccc3sccc3c2)C1] | 3-(1-benzothiophen-5-ylamino)-6,6-dimethyl-2-(pyridin-4-yl)-1,5,6,7-tetrahydro-4H-indol-4-one |
| 70 | 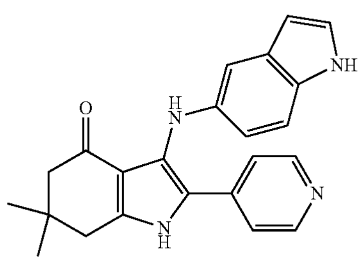 [SMILES: CC1(C)CC(=O)c2c([nH]c(-c3ccncc3)c2Nc2ccc3[nH]ccc3c2)C1] | 3-(1H-indol-5-ylamino)-6,6-dimethyl-2-(pyridin-4-yl)-1,5,6,7-tetrahydro-4H-indol-4-one |
| 71 | 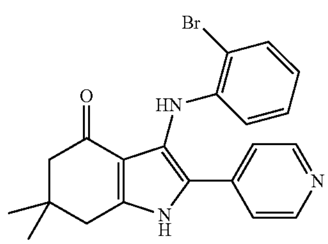 [SMILES: CC1(C)CC(=O)c2c([nH]c(-c3ccncc3)c2Nc2ccccc2Br)C1] | 3-[(2-bromophenyl)amino]-6,6-dimethyl-2-(pyridin-4-yl)-1,5,6,7-tetrahydro-4H-indol-4-one |
| 72 | 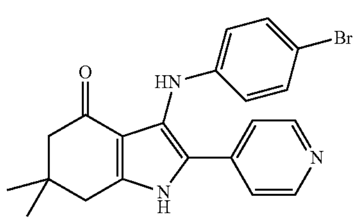 [SMILES: CC1(C)CC(=O)c2c([nH]c(-c3ccncc3)c2Nc2ccc(Br)cc2)C1] | 3-[(4-bromophenyl)amino]-6,6-dimethyl-2-(pyridin-4-yl)-1,5,6,7-tetrahydro-4H-indol-4-one |
| 73 | 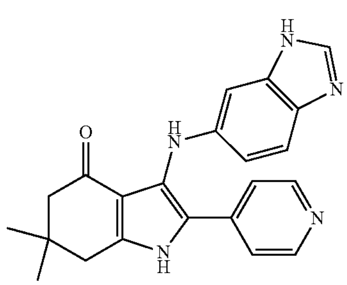 [SMILES: CC1(C)CC(=O)c2c([nH]c(-c3ccncc3)c2Nc2ccc3nc[nH]c3c2)C1] | 3-(1H-benzimidazol-6-ylamino)-6,6-dimethyl-2-(pyridin-4-yl)-1,5,6,7-tetrahydro-4H-indol-4-one |

-continued

| Example Nr. | Chemical structure | Chemical name |
|---|---|---|
| 74 | 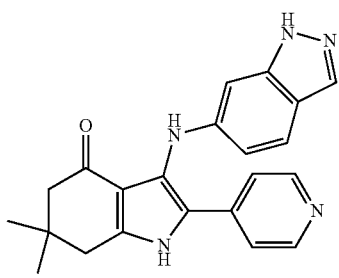 [SMILES: CC1(C)CC(=O)c2c([nH]c(-c3ccncc3)c2Nc2ccc3cn[nH]c3c2)C1] | 3-(1H-indazol-6-ylamino)-6,6-dimethyl-2-(pyridin-4-yl)-1,5,6,7-tetrahydro-4H-indol-4-one |
| 75 | 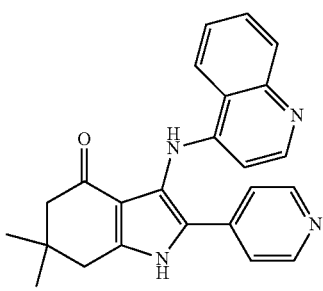 [SMILES: CC1(C)CC(=O)c2c([nH]c(-c3ccncc3)c2Nc2ccnc3ccccc23)C1] | 6,6-dimethyl-2-(pyridin-4-yl)-3-(quinolin-4-ylamino)-1,5,6,7-tetrahydro-4H-indol-4-one |
| 76 | 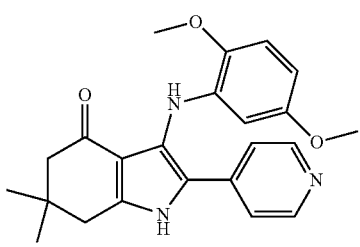 | 3-[(2,5-dimethoxyphenyl)amino]-6,6-dimethyl-2-(pyridin-4-yl)-1,5,6,7-tetrahydro-4H-indol-4-one |
| 77 | 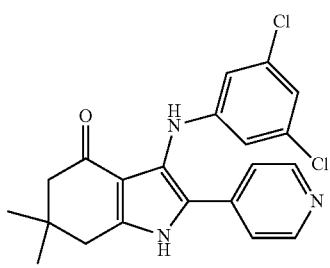 [SMILES: CC1(C)CC(=O)c2c([nH]c(-c3ccncc3)c2Nc2cc(Cl)cc(Cl)c2)C1] | 3-[(3,5-dichlorophenyl)amino]-6,6-dimethyl-2-(pyridin-4-yl)-1,5,6,7-tetrahydro-4H-indol-4-one |
| 78 | 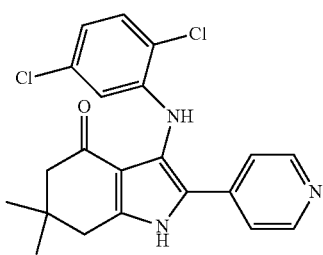 [SMILES: CC1(C)CC(=O)c2c([nH]c(-c3ccncc3)c2Nc2cc(Cl)ccc2Cl)C1] | 3-[(2,5-dichlorophenyl)amino]-6,6-dimethyl-2-(pyridin-4-yl)-1,5,6,7-tetrahydro-4H-indol-4-one |

| Example Nr. | Chemical structure | Chemical name |
|---|---|---|
| 79 | 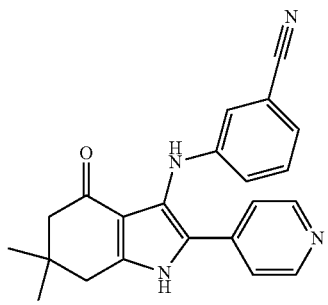 [SMILES: CC1(C)CC(=O)c2c([nH]c(-c3ccncc3)c2Nc2cccc(C#N)c2)C1] | 3-{[6,6-dimethyl-4-oxo-2-(pyridin-4-yl)-4,5,6,7-tetrahydro-1H-indol-3-yl]amino}benzonitrile |
| 80 | 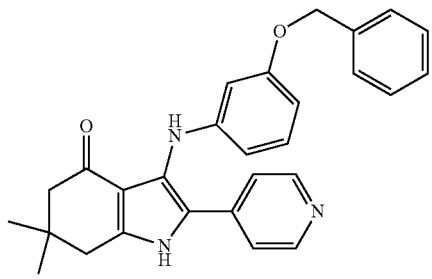 [SMILES: CC1(C)CC(=O)c2c([nH]c(-c3ccncc3)c2Nc2cccc(OCc3ccccc3)c2)C1] | 3-{[3-(benzyloxy)phenyl]amino}-6,6-dimethyl-2-(pyridin-4-yl)-1,5,6,7-tetrahydro-4H-indol-4-one |
| 81 | 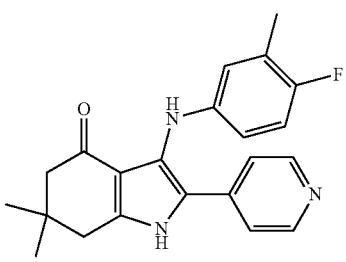 [SMILES: Cc1cc(Nc2c(-c3ccncc3)[nH]c3c2C(=O)CC(C)(C)C3)ccc1F] | 3-[(4-fluoro-3-methylphenyl)amino]-6,6-dimethyl-2-(pyridin-4-yl)-1,5,6,7-tetrahydro-4H-indol-4-one |
| 82 | 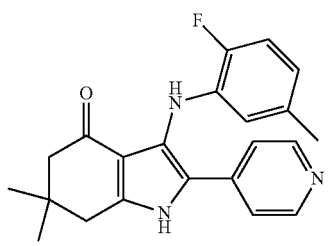 | 3-[(2-fluoro-5-methylphenyl)amino]-6,6-dimethyl-2-(pyridin-4-yl)-1,5,6,7-tetrahydro-4H-indol-4-one |
| 83 | 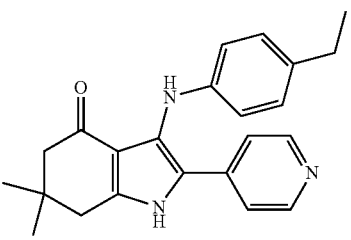 [SMILES: CCc1ccc(Nc2c(-c3ccncc3)[nH]c3c2C(=O)CC(C)(C)C3)cc1] | 3-[(4-ethylphenyl)amino]-6,6-dimethyl-2-(pyridin-4-yl)-1,5,6,7-tetrahydro-4H-indol-4-one |

| Example Nr. | Chemical structure | Chemical name |
|---|---|---|
| 84 | 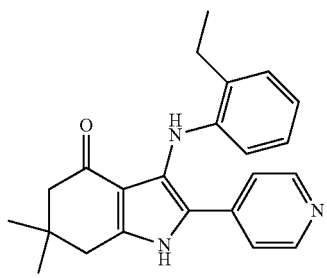 [SMILES: CCc1ccccc1Nc1c(-c2ccncc2)[nH]c2c1C(=O)CC(C)(C)C2] | 3-[(2-ethylphenyl)amino]-6,6-dimethyl-2-(pyridin-4-yl)-1,5,6,7-tetrahydro-4H-indol-4-one |
| 85 | 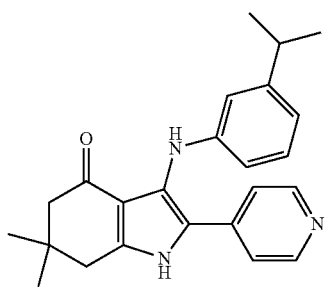 [SMILES: CC(C)c1cccc(Nc2c(-c3ccncc3)[nH]c3c2C(=O)CC(C)(C)C3)c1] | 6,6-dimethyl-3-{[3-(propan-2-yl)phenyl]amino}-2-(pyridin-4-yl)-1,5,6,7-tetrahydro-4H-indol-4-one |
| 86 | 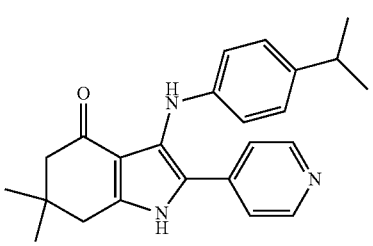 [SMILES: CC(C)c1ccc(Nc2c(-c3ccncc3)[nH]c3c2C(=O)CC(C)(C)C3)cc1] | 6,6-dimethyl-3-{[4-(propan-2-yl)phenyl]amino}-2-(pyridin-4-yl)-1,5,6,7-tetrahydro-4H-indol-4-one |
| 87 | 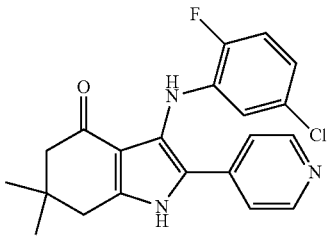 [SMILES: CC1(C)CC(=O)c2c([nH]c(-c3ccncc3)c2Nc2cc(Cl)ccc2F)C1] | 3-[(5-chloro-2-fluorophenyl)amino]-6,6-dimethyl-2-(pyridin-4-yl)-1,5,6,7-tetrahydro-4H-indol-4-one |
| 88 | 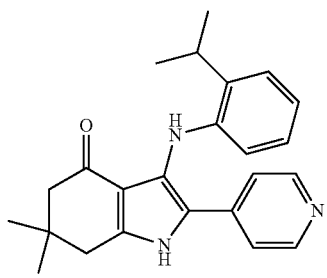 [SMILES: CC(C)c1ccccc1Nc1c(-c2ccncc2)[nH]c2c1C(=O)CC(C)(C)C2] | 6,6-dimethyl-3-{[2-(propan-2-yl)phenyl]amino}-2-(pyridin-4-yl)-1,5,6,7-tetrahydro-4H-indol-4-one |

-continued

| Example Nr. | Chemical structure | Chemical name |
|---|---|---|
| 89 | 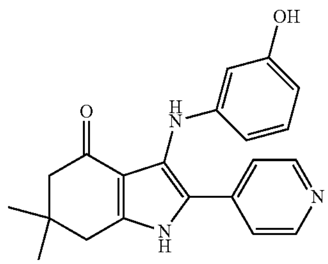 [SMILES: CC1(C)CC(=O)c2c([nH]c(-c3ccncc3)c2Nc2cccc(O)c2)C1] | 3-[(3-hydroxyphenyl)amino]-6,6-dimethyl-2-(pyridin-4-yl)-1,5,6,7-tetrahydro-4H-indol-4-one |
| 90 | 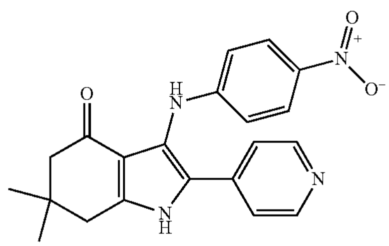 | 6,6-dimethyl-3-[(4-nitrophenyl)amino]-2-(pyridin-4-yl)-1,5,6,7-tetrahydro-4H-indol-4-one |
| 91 | 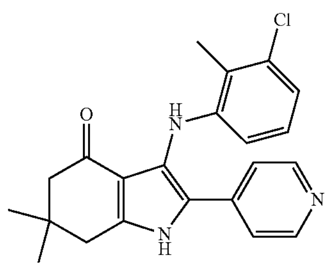 [SMILES: Cc1c(Cl)cccc1Nc1c(-c2ccncc2)[nH]c2c1C(=O)CC(C)(C)C2] | 3-[(3-chloro-2-methylphenyl)amino]-6,6-dimethyl-2-(pyridin-4-yl)-1,5,6,7-tetrahydro-4H-indol-4-one |
| 92 | 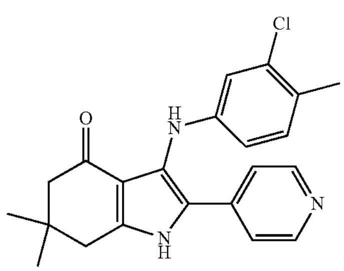 | 3-[(3-chloro-4-methylphenyl)amino]-6,6-dimethyl-2-(pyridin-4-yl)-1,5,6,7-tetrahydro-4H-indol-4-one |
| 93 | 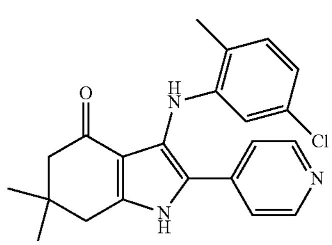 [SMILES: Cc1ccc(Cl)cc1Nc1c(-c2ccncc2)[nH]c2c1C(=O)CC(C)(C)C2] | 3-[(5-chloro-2-methylphenyl)amino]-6,6-dimethyl-2-(pyridin-4-yl)-1,5,6,7-tetrahydro-4H-indol-4-one |
| 94 | 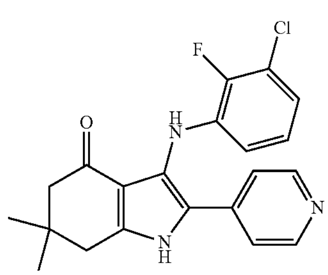 [SMILES: CC1(C)CC(=O)c2c([nH]c(-c3ccncc3)c2Nc2cccc(Cl)c2F)C1] | 3-[(3-chloro-2-fluorophenyl)amino]-6,6-dimethyl-2-(pyridin-4-yl)-1,5,6,7-tetrahydro-4H-indol-4-one |

| Example Nr. | Chemical structure | Chemical name |
|---|---|---|
| 95 | 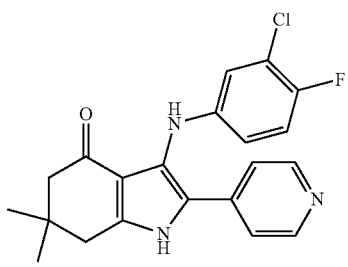 [SMILES: CC1(C)CC(=O)c2c([nH]c(-c3ccncc3)c2Nc2ccc(F)c(Cl)c2)C1] | 3-[(3-chloro-4-fluorophenyl)amino]-6,6-dimethyl-2-(pyridin-4-yl)-1,5,6,7-tetrahydro-4H-indol-4-one |
| 96 | 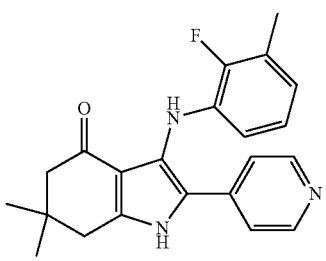 [SMILES: Cc1cccc(Nc2c(-c3ccncc3)[nH]c3c2C(=O)CC(C)(C)C3)c1F] | 3-[(2-fluoro-3-methylphenyl)amino]-6,6-dimethyl-2-(pyridin-4-yl)-1,5,6,7-tetrahydro-4H-indol-4-one |
| 97 | 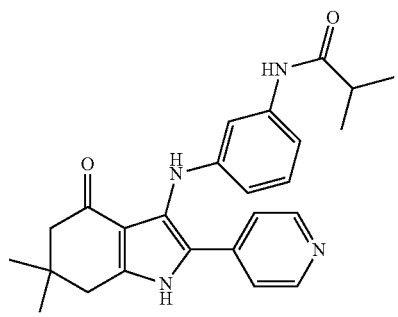 [SMILES: CC(C)C(=O)Nc1cccc(Nc2c(-c3ccncc3)[nH]c3c2C(=O)CC(C)(C)C3)c1] | N-(3-{[6,6-dimethyl-4-oxo-2-(pyridin-4-yl)-4,5,6,7-tetrahydro-1H-indol-3-yl]amino}phenyl)-2-methylpropanamide |
| 98 | 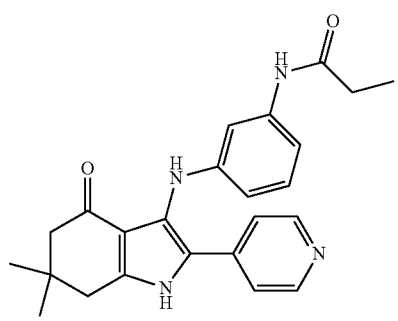 [SMILES: CCC(=O)Nc1cccc(Nc2c(-c3ccncc3)[nH]c3c2C(=O)CC(C)(C)C3)c1] | N-(3-{[6,6-dimethyl-4-oxo-2-(pyridin-4-yl)-4,5,6,7-tetrahydro-1H-indol-3-yl]amino}phenyl)propanamide |
| 99 | 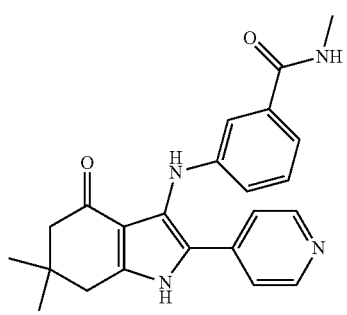 | 3-{[6,6-dimethyl-4-oxo-2-(pyridin-4-yl)-4,5,6,7-tetrahydro-1H-indol-3-yl]amino}-N-methylbenzamide |

-continued

| Example Nr. | Chemical structure | Chemical name |
| --- | --- | --- |
| 100 | 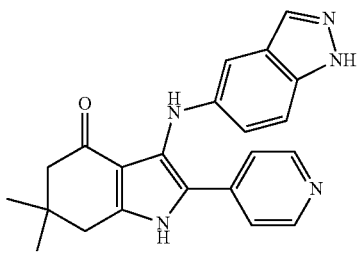 [SMILES: CC1(C)CC(=O)c2c([nH]c(-c3ccncc3)c2Nc2ccc3[nH]ncc3c2)C1] | 3-(1H-indazol-5-ylamino)-6,6-dimethyl-2-(pyridin-4-yl)-1,5,6,7-tetrahydro-4H-indol-4-one |
| 101 | 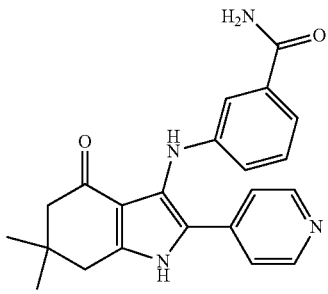 [SMILES: CC1(C)CC(=O)c2c([nH]c(-c3ccncc3)c2Nc2cccc(C(N)=O)c2)C1] | 3-{[6,6-dimethyl-4-oxo-2-(pyridin-4-yl)-4,5,6,7-tetrahydro-1H-indol-3-yl]amino}benzamide |
| 102 | 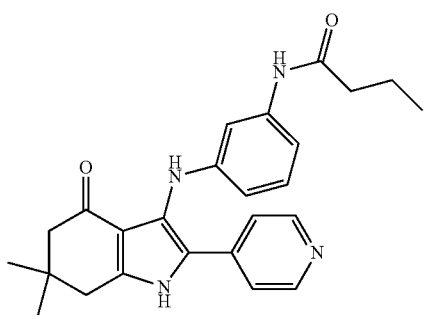 [SMILES: CCCC(=O)Nc1cccc(Nc2c(-c3ccncc3)[nH]c3c2C(=O)CC(C)(C)C3)c1] | N-(3-{[6,6-dimethyl-4-oxo-2-(pyridin-4-yl)-4,5,6,7-tetrahydro-1H-indol-3-yl]amino}phenyl)butanamide |
| 103 | 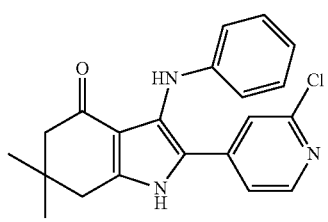 [SMILES: CC1(C)CC(=O)c2c([nH]c(-c3ccnc(Cl)c3)c2Nc2ccccc2)C1] | 2-(2-chloropyridin-4-yl)-6,6-dimethyl-3-(phenylamino)-1,5,6,7-tetrahydro-4H-indol-4-one |
| 104 | 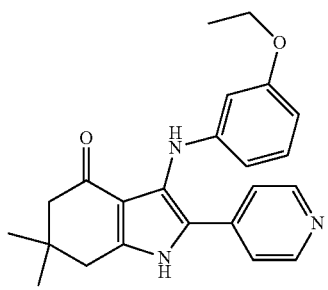 [SMILES: CCOc1cccc(Nc2c(-c3ccncc3)[nH]c3c2C(=O)CC(C)(C)C3)c1] | 3-[(3-ethoxyphenyl)amino]-6,6-dimethyl-2-(pyridin-4-yl)-1,5,6,7-tetrahydro-4H-indol-4-one |

-continued

| Example Nr. | Chemical structure | Chemical name |
|---|---|---|
| 105 | 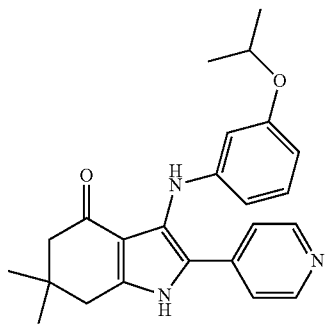 [SMILES: CC(C)Oc1cccc(Nc2c(-c3ccncc3)[nH]c3c2C(=O)CC(C)(C)C3)c1] | 6,6-dimethyl-3-{[3-(propan-2-yloxy)phenyl]amino}-2-(pyridin-4-yl)-1,5,6,7-tetrahydro-4H-indol-4-one |
| 106 | 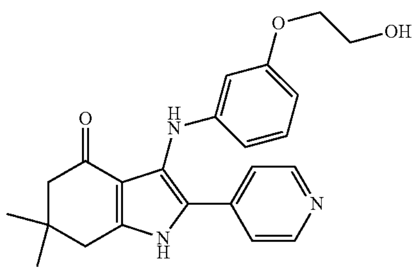 [SMILES: CC1(C)CC(=O)c2c([nH]c(-c3ccncc3)c2Nc2cccc(OCCO)c2)C1] | 3-{[3-(2-hydroxyethoxy)phenyl]amino}-6,6-dimethyl-2-(pyridin-4-yl)-1,5,6,7-tetrahydro-4H-indol-4-one |
| 107 | 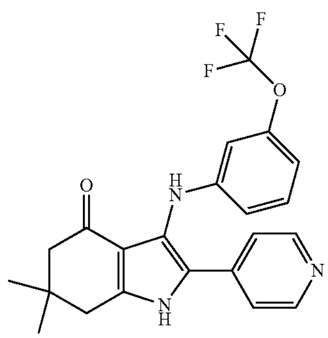 [SMILES: CC1(C)CC(=O)c2c([nH]c(-c3ccncc3)c2Nc2cccc(OC(F)(F)F)c2)C1] | 6,6-dimethyl-2-(pyridin-4-yl)-3-{[3-(trifluoromethoxy)phenyl]amino}-1,5,6,7-tetrahydro-4H-indol-4-one |
| 108 | 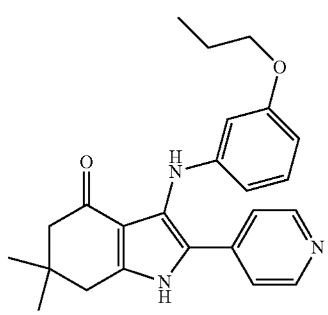 [SMILES: CCCOc1cccc(Nc2c(-c3ccncc3)[nH]c3c2C(=O)CC(C)(C)C3)c1] | 6,6-dimethyl-3-[(3-propoxyphenyl)amino]-2-(pyridin-4-yl)-1,5,6,7-tetrahydro-4H-indol-4-one |
| 109 | 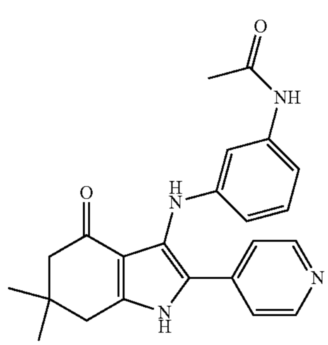 [SMILES: CC(=O)Nc1cccc(Nc2c(-c3ccncc3)[nH]c3c2C(=O)CC(C)(C)C3)c1] | N-(3-{[6,6-dimethyl-4-oxo-2-(pyridin-4-yl)-4,5,6,7-tetrahydro-1H-indol-3-yl]amino}phenyl)acetamide |

| Example Nr. | Chemical structure | Chemical name |
|---|---|---|
| 110 | 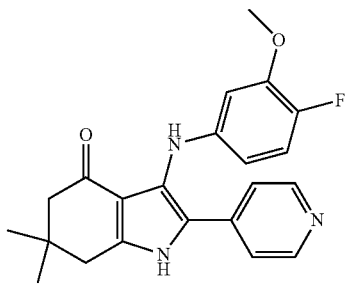 [SMILES: COc1cc(Nc2c(-c3ccncc3)[nH]c3c2C(=O)CC(C)(C)C3)ccc1F] | 3-[(4-fluoro-3-methoxyphenyl)amino]-6,6-dimethyl-2-(pyridin-4-yl)-1,5,6,7-tetrahydro-4H-indol-4-one |
| 111 | 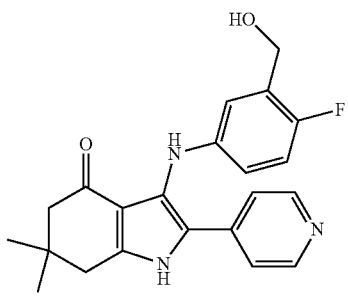 [SMILES: CC1(C)CC(=O)c2c([nH]c(-c3ccncc3)c2Nc2ccc(F)c(CO)c2)C1] | 3-{[4-fluoro-3-(hydroxymethyl)phenyl]amino}-6,6-dimethyl-2-(pyridin-4-yl)-1,5,6,7-tetrahydro-4H-indol-4-one |
| 112 | 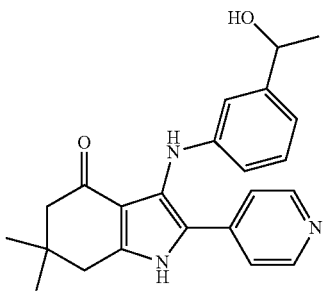 [SMILES: CC(O)c1cccc(Nc2c(-c3ccncc3)[nH]c3c2C(=O)CC(C)(C)C3)c1] | 3-{[3-(1-hydroxyethyl)phenyl]amino}-6,6-dimethyl-2-(pyridin-4-yl)-1,5,6,7-tetrahydro-4H-indol-4-one |
| 113 | 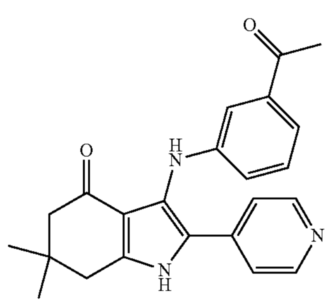 [SMILES: CC(=O)c1cccc(Nc2c(-c3ccncc3)[nH]c3c2C(=O)CC(C)(C)C3)c1] | 3-[(3-acetylphenyl)amino]-6,6-dimethyl-2-(pyridin-4-yl)-1,5,6,7-tetrahydro-4H-indol-4-one |
| 114 | 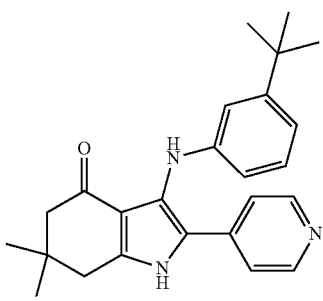 [SMILES: CC1(C)CC(=O)c2c([nH]c(-c3ccncc3)c2Nc2cccc(C(C)(C)C)c2)C1] | 3-[(3-tert-butylphenyl)amino]-6,6-dimethyl-2-(pyridin-4-yl)-1,5,6,7-tetrahydro-4H-indol-4-one |

-continued

| Example Nr. | Chemical structure | Chemical name |
|---|---|---|
| 117 | 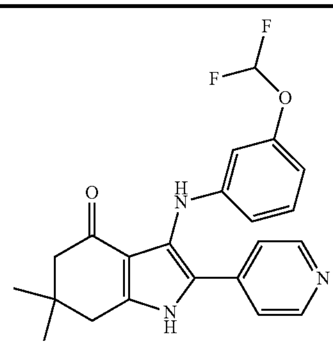 | 3-{[3-(difluoromethoxy)phenyl]amino}-6,6-dimethyl-2-(pyridin-4-yl)-1,5,6,7-tetrahydro-4H-indol-4-one |
| 118 | 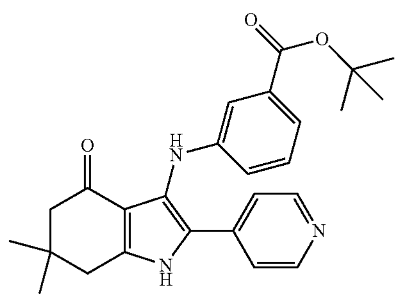 [SMILES: CC1(C)CC(=O)c2c([nH]c(-c3ccncc3)c2Nc2cccc(C(=O)OC(C)(C)C)c2)C1] | tert-butyl 3-{[6,6-dimethyl-4-oxo-2-(pyridin-4-yl)-4,5,6,7-tetrahydro-1H-indol-3-yl]amino}benzoate |
| 119 | 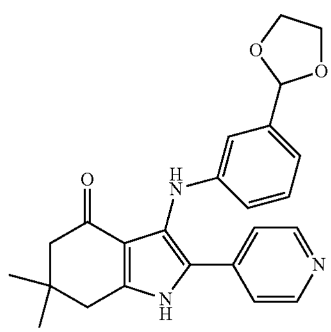 [SMILES: CC1(C)CC(=O)c2c([nH]c(-c3ccncc3)c2Nc2cccc(C3OCCO3)c2)C1] | 3-{[3-(1,3-dioxolan-2-yl)phenyl]amino}-6,6-dimethyl-2-(pyridin-4-yl)-1,5,6,7-tetrahydro-4H-indol-4-one |
| 121 | 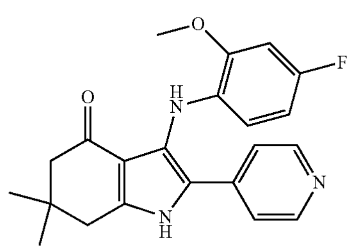 [SMILES: COc1cc(F)ccc1Nc1c(-c2ccncc2)[nH]c2c1C(=O)CC(C)(C)C2] | 3-[(4-fluoro-2-methoxyphenyl)amino]-6,6-dimethyl-2-(pyridin-4-yl)-1,5,6,7-tetrahydro-4H-indol-4-one |
| 123 | 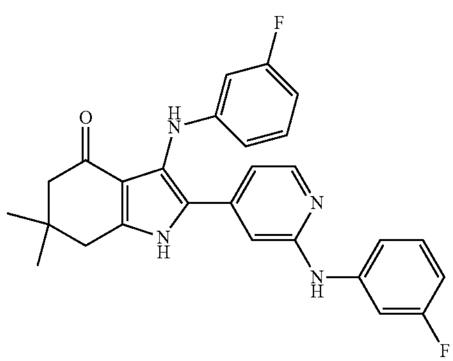 [SMILES: CC1(C)CC(=O)c2c([nH]c(-c3ccnc(Nc4cccc(F)c4)c3)c2Nc2cccc(F)c2)C1] | 3-[(3-fluorophenyl)amino]-2-{2-[(3-fluorophenyl)amino]pyridin-4-yl}-6,6-dimethyl-1,5,6,7-tetrahydro-4H-indol-4-one |

-continued

| Example Nr. | Chemical structure | Chemical name |
|---|---|---|
| 124 | 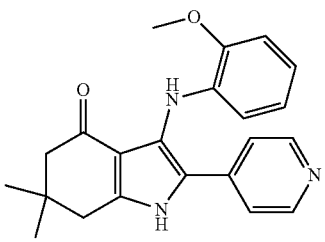 [SMILES: COc1ccccc1Nc1c(-c2ccncc2)[nH]c2c1C(=O)CC(C)(C)C2] | 3-[(2-methoxyphenyl)amino]-6,6-dimethyl-2-(pyridin-4-yl)-1,5,6,7-tetrahydro-4H-indol-4-one |
| 125 | 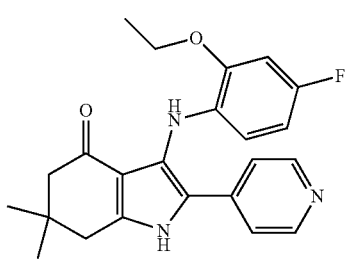 [SMILES: CCOc1cc(F)ccc1Nc1c(-c2ccncc2)[nH]c2c1C(=O)CC(C)(C)C2] | 3-[(2-ethoxy-4-fluorophenyl)amino]-6,6-dimethyl-2-(pyridin-4-yl)-1,5,6,7-tetrahydro-4H-indol-4-one |
| 126 | 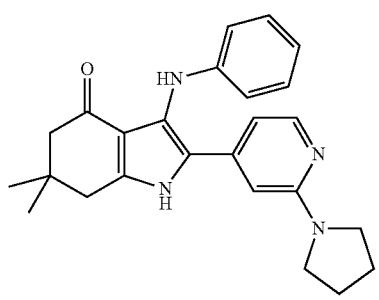 [SMILES: CC1(C)CC(=O)c2c([nH]c(-c3ccnc(N4CCCC4)c3)c2Nc2ccccc2)C1] | 6,6-dimethyl-3-(phenylamino)-2-[2-(pyrrolidin-1-yl)pyridin-4-yl]-1,5,6,7-tetrahydro-4H-indol-4-one |
| 127 | 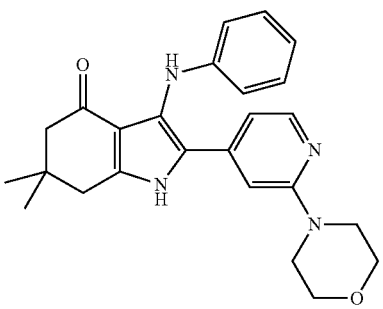 [SMILES: CC1(C)CC(=O)c2c([nH]c(-c3ccnc(N4CCOCC4)c3)c2Nc2ccccc2)C1] | 6,6-dimethyl-2-[2-(morpholin-4-yl)pyridin-4-yl]-3-(phenylamino)-1,5,6,7-tetrahydro-4H-indol-4-one |
| 128 | 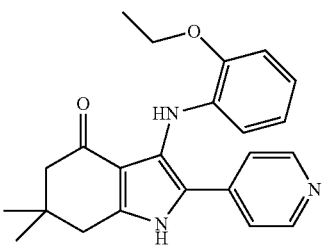 [SMILES: CCOc1ccccc1Nc1c(-c2ccncc2)[nH]c2c1C(=O)CC(C)(C)C2] | 3-[(2-ethoxyphenyl)amino]-6,6-dimethyl-2-(pyridin-4-yl)-1,5,6,7-tetrahydro-4H-indol-4-one |

-continued

| Example Nr. | Chemical structure | Chemical name |
|---|---|---|
| 129 | 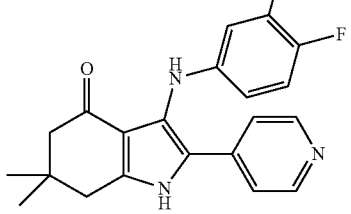 | 3-{[4-fluoro-3-(trifluoromethyl)phenyl]amino}-6,6-dimethyl-2-(pyridin-4-yl)-1,5,6,7-tetrahydro-4H-indol-4-one |
| 130 | 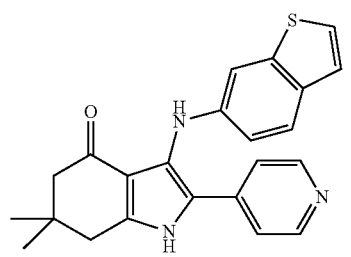 [SMILES: CC1(C)CC(=O)c2c([nH]c(-c3ccncc3)c2Nc2ccc3ccsc3c2)C1] | 3-(1-benzothiophen-6-ylamino)-6,6-dimethyl-2-(pyridin-4-yl)-1,5,6,7-tetrahydro-4H-indol-4-one |
| 131 | 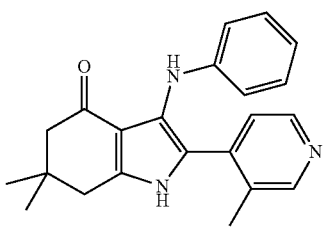 [SMILES: Cc1cnccc1-c1[nH]c2c(c1Nc1ccccc1)C(=O)CC(C)(C)C2] | 6,6-dimethyl-2-(3-methylpyridin-4-yl)-3-(phenylamino)-1,5,6,7-tetrahydro-4H-indol-4-one |
| 132 | 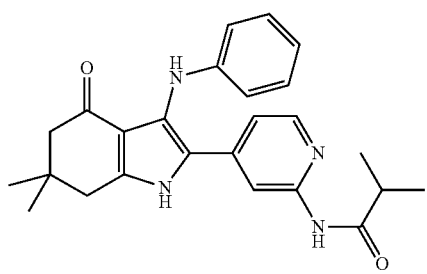 [SMILES: CC(C)C(=O)Nc1cc(-c2[nH]c3c(c2Nc2ccccc2)C(=O)CC(C)(C)C3)ccn1] | N-{4-[6,6-dimethyl-4-oxo-3-(phenylamino)-4,5,6,7-tetrahydro-1H-indol-2-yl]pyridin-2-yl}-2-methylpropanamide |
| 133 | 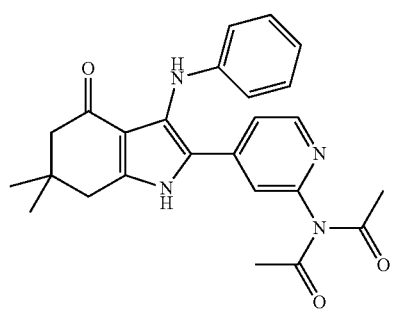 [SMILES: CC(=O)N(C(C)=O)c1cc(-c2[nH]c3c(c2Nc2ccccc2)C(=O)CC(C)(C)C3)ccn1] | N-acetyl-N-{4-[6,6-dimethyl-4-oxo-3-(phenylamino)-4,5,6,7-tetrahydro-1H-indol-2-yl]pyridin-2-yl}acetamide |

-continued

| Example Nr. | Chemical structure | Chemical name |
|---|---|---|
| 134 | 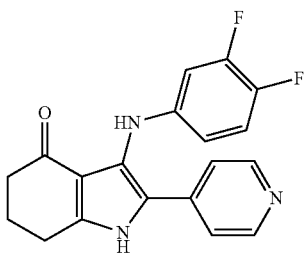 [SMILES: O=C1CCCc2[nH]c(-c3ccncc3)c(Nc3ccc(F)c(F)c3)c21] | 3-[(3,4-difluorophenyl)amino]-2-(pyridin-4-yl)-1,5,6,7-tetrahydro-4H-indol-4-one |
| 135 | 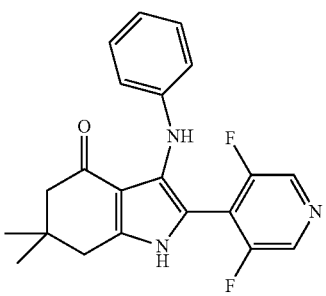 [SMILES: CC1(C)CC(=O)c2c([nH]c(-c3c(F)cncc3F)c2Nc2ccccc2)C1] | 2-(3,5-difluoropyridin-4-yl)-6,6-dimethyl-3-(phenylamino)-1,5,6,7-tetrahydro-4H-indol-4-one |
| 136 | 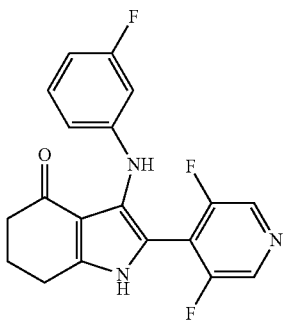 [SMILES: O=C1CCCc2[nH]c(-c3c(F)cncc3F)c(Nc3cccc(F)c3)c21] | 2-(3,5-difluoropyridin-4-yl)-3-[(3-fluorophenyl)amino]-1,5,6,7-tetrahydro-4H-indol-4-one |
| 137 | 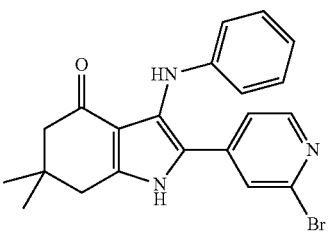 [SMILES: CC1(C)CC(=O)c2c([nH]c(-c3ccnc(Br)c3)c2Nc2ccccc2)C1] | 2-(2-bromopyridin-4-yl)-6,6-dimethyl-3-(phenylamino)-1,5,6,7-tetrahydro-4H-indol-4-one |
| 142 | 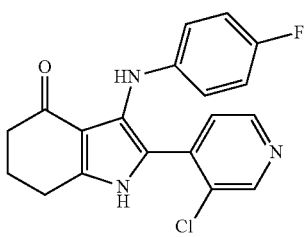 [SMILES: O=C1CCCc2[nH]c(-c3ccncc3Cl)c(Nc3ccc(F)cc3)c21] | 2-(3-chloropyridin-4-yl)-3-[(4-fluorophenyl)amino]-1,5,6,7-tetrahydro-4H-indol-4-one |

-continued

| Example Nr. | Chemical structure | Chemical name |
|---|---|---|
| 143 | 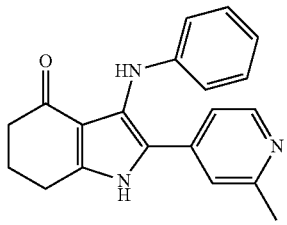 [SMILES: Cc1cc(-c2[nH]c3c(c2Nc2ccccc2)C(=O)CCC3)ccn1] | 2-(2-methylpyridin-4-yl)-3-(phenylamino)-1,5,6,7-tetrahydro-4H-indol-4-one |
| 144 | 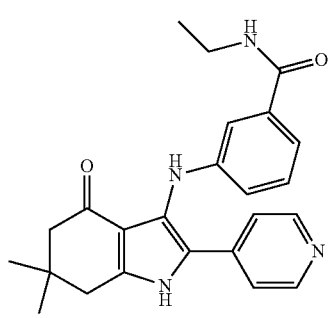 [SMILES: CCNC(=O)c1cccc(Nc2c(-c3ccncc3)[nH]c3c2C(=O)CC(C)(C)C3)c1] | 3-{[6,6-dimethyl-4-oxo-2-(pyridin-4-yl)-4,5,6,7-tetrahydro-1H-indol-3-yl]amino}-N-ethylbenzamide |
| 145 | 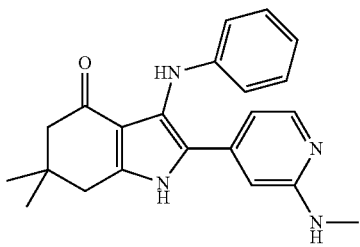 | 6,6-dimethyl-2-[2-(methylamino)pyridin-4-yl]-3-(phenylamino)-1,5,6,7-tetrahydro-4H-indol-4-one |
| 146 | 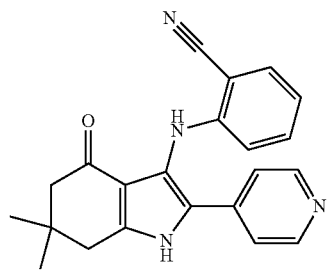 [SMILES: CC1(C)CC(=O)c2c([nH]c(-c3ccncc3)c2Nc2ccccc2C#N)C1] | 2-{[6,6-dimethyl-4-oxo-2-(pyridin-4-yl)-4,5,6,7-tetrahydro-1H-indol-3-yl]amino}benzonitrile |
| 147 | 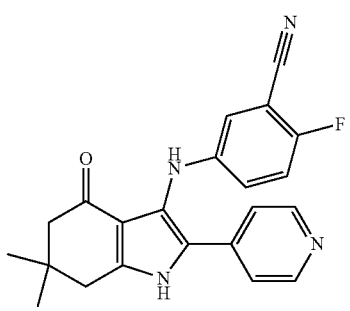 [SMILES: CC1(C)CC(=O)c2c([nH]c(-c3ccncc3)c2Nc2ccc(F)c(C#N)c2)C1] | 5-{[6,6-dimethyl-4-oxo-2-(pyridin-4-yl)-4,5,6,7-tetrahydro-1H-indol-3-yl]amino}-2-fluorobenzonitrile |

| Example Nr. | Chemical structure | Chemical name |
|---|---|---|
| 148 | 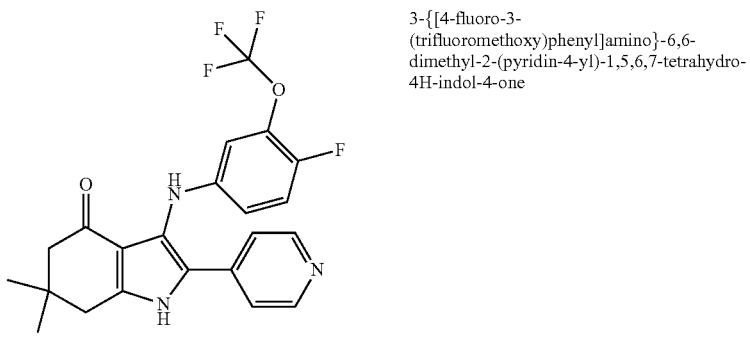 | 3-{[4-fluoro-3-(trifluoromethoxy)phenyl]amino}-6,6-dimethyl-2-(pyridin-4-yl)-1,5,6,7-tetrahydro-4H-indol-4-one |
| 149 | 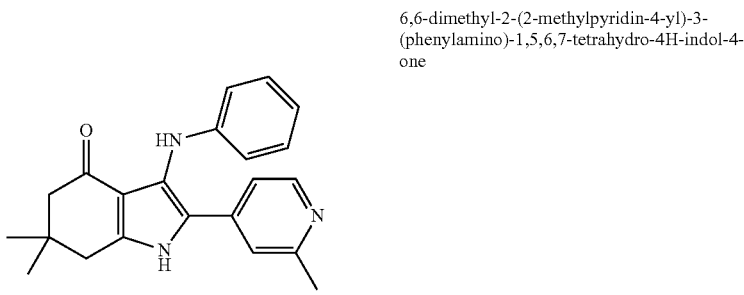 | 6,6-dimethyl-2-(2-methylpyridin-4-yl)-3-(phenylamino)-1,5,6,7-tetrahydro-4H-indol-4-one |
| 150 | 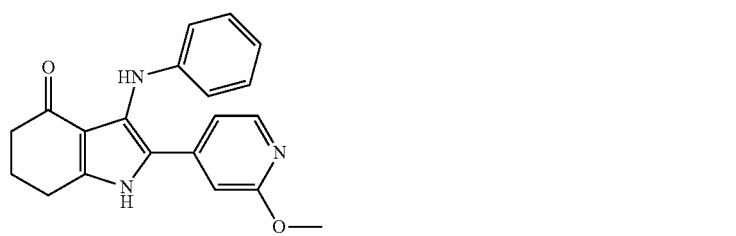 [SMILES: COc1cc(-c2[nH]c3c(c2Nc2ccccc2)C(=O)CCC3)ccn1] | 2-(2-methoxypyridin-4-yl)-3-(phenylamino)-1,5,6,7-tetrahydro-4H-indol-4-one |
| 152 | 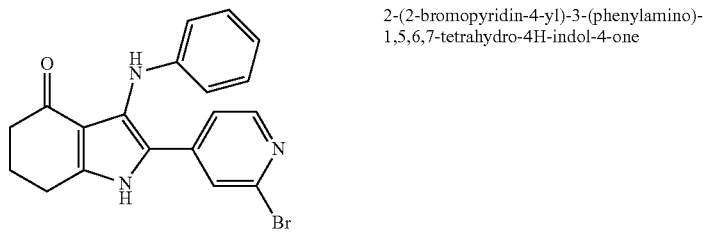 | 2-(2-bromopyridin-4-yl)-3-(phenylamino)-1,5,6,7-tetrahydro-4H-indol-4-one |
| 153 | 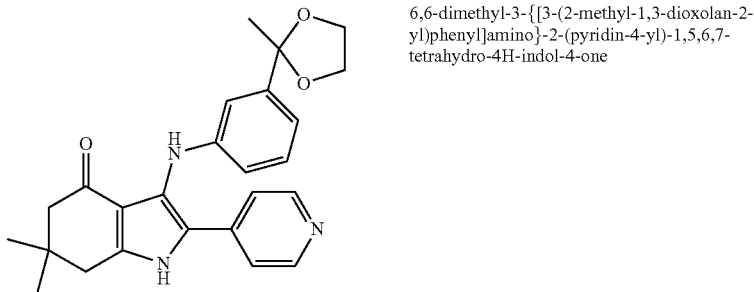 | 6,6-dimethyl-3-{[3-(2-methyl-1,3-dioxolan-2-yl)phenyl]amino}-2-(pyridin-4-yl)-1,5,6,7-tetrahydro-4H-indol-4-one |

-continued

| Example Nr. | Chemical structure | Chemical name |
|---|---|---|
| 154 | 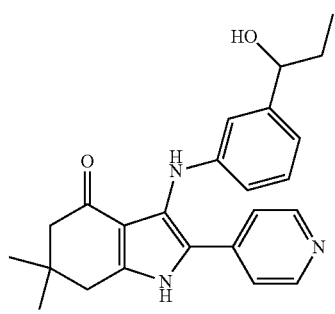 [SMILES: CCC(O)c1cccc(Nc2c(-c3ccncc3)[nH]c3c2C(=O)CC(C)(C)C3)c1] | 3-{[3-(1-hydroxypropyl)phenyl]amino}-6,6-dimethyl-2-(pyridin-4-yl)-1,5,6,7-tetrahydro-4H-indol-4-one |
| 155 | 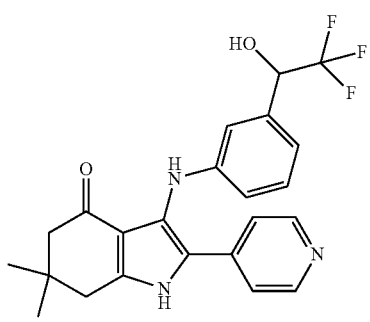 [SMILES: CC1(C)CC(=O)c2c([nH]c(-c3ccncc3)c2Nc2cccc(C(O)C(F)(F)F)c2)C1] | 6,6-dimethyl-2-(pyridin-4-yl)-3-{[3-(2,2,2-trifluoro-1-hydroxyethyl)phenyl]amino}-1,5,6,7-tetrahydro-4H-indol-4-one |
| 156 | 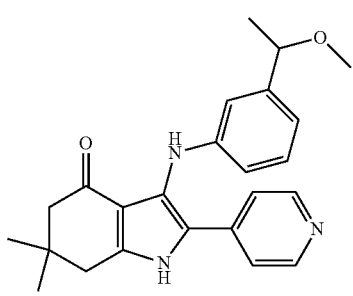 | 3-{[3-(1-methoxyethyl)phenyl]amino}-6,6-dimethyl-2-(pyridin-4-yl)-1,5,6,7-tetrahydro-4H-indol-4-one |
| 157 | 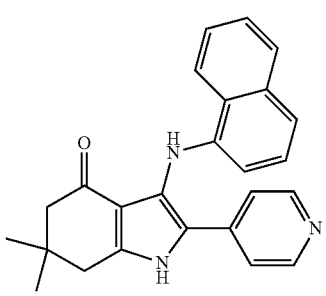 [SMILES: CC1(C)CC(=O)c2c([nH]c(-c3ccncc3)c2Nc2cccc3ccccc23)C1] | 6,6-dimethyl-3-(naphthalen-1-ylamino)-2-(pyridin-4-yl)-1,5,6,7-tetrahydro-4H-indol-4-one |
| 158 | 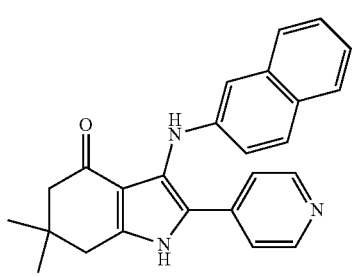 [SMILES: CC1(C)CC(=O)c2c([nH]c(-c3ccncc3)c2Nc2ccc3ccccc3c2)C1] | 6,6-dimethyl-3-(naphthalen-2-ylamino)-2-(pyridin-4-yl)-1,5,6,7-tetrahydro-4H-indol-4-one |

-continued

| Example Nr. | Chemical structure | Chemical name |
|---|---|---|
| 159 | 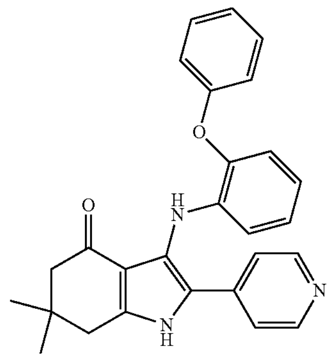 [SMILES: CC1(C)CC(=O)c2c([nH]c(-c3ccncc3)c2Nc2ccccc2Oc2ccccc2)C1] | 6,6-dimethyl-3-[(2-phenoxyphenyl)amino]-2-(pyridin-4-yl)-1,5,6,7-tetrahydro-4H-indol-4-one |
| 160 | 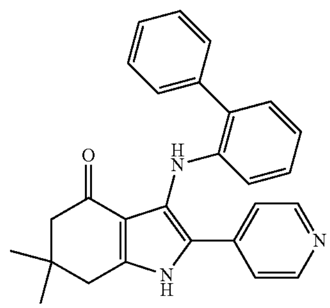 [SMILES: CC1(C)CC(=O)c2c([nH]c(-c3ccncc3)c2Nc2ccccc2-c2ccccc2)C1] | 3-(biphenyl-2-ylamino)-6,6-dimethyl-2-(pyridin-4-yl)-1,5,6,7-tetrahydro-4H-indol-4-one |
| 161 | 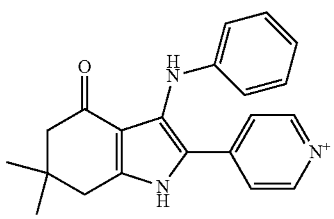 [SMILES: CC1(C)CC(=O)c2c([nH]c(-c3cc[nH+]cc3)c2Nc2ccccc2)C1] | 6,6-dimethyl-2-(1-oxidopyridin-4-yl)-3-(phenylamino)-1,5,6,7-tetrahydro-4H-indol-4-one |
| 162 | 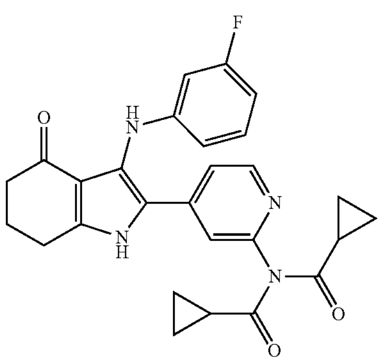 [SMILES: O=C1CCCc2[nH]c(-c3ccnc(N(C(=O)C4CC4)C(=O)C4CC4)c3)c(Nc3cccc(F)c3)c21] | N-(cyclopropylcarbonyl)-N-(4-{3-[(3-fluorophenyl)amino]-4-oxo-4,5,6,7-tetrahydro-1H-indol-2-yl}pyridin-2-yl)cyclopropanecarboxamide |
| 163 | 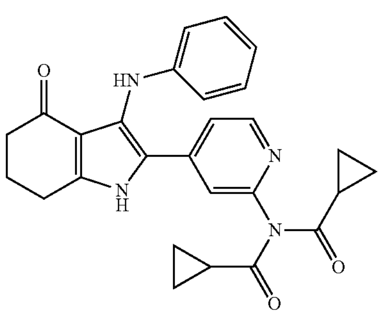 [SMILES: O=C1CCCc2[nH]c(-c3ccnc(N(C(=O)C4CC4)C(=O)C4CC4)c3)c(Nc3ccccc3)c21] | N-(cyclopropylcarbonyl)-N-{4-[4-oxo-3-(phenylamino)-4,5,6,7-tetrahydro-1H-indol-2-yl]pyridin-2-yl}cyclopropanecarboxamide |

| Example Nr. | Chemical structure | Chemical name |
|---|---|---|
| 165 | 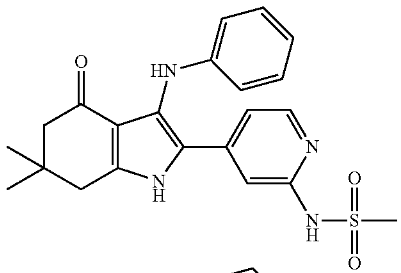 | N-{4-[6,6-dimethyl-4-oxo-3-(phenylamino)-4,5,6,7-tetrahydro-1H-indol-2-yl]pyridin-2-yl}methanesulfonamide |
| 166 | 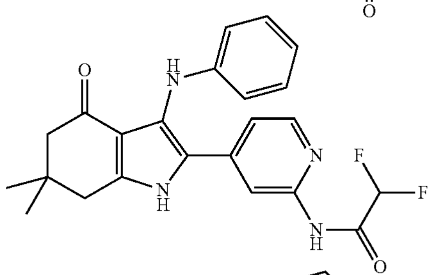 | N-{4-[6,6-dimethyl-4-oxo-3-(phenylamino)-4,5,6,7-tetrahydro-1H-indol-2-yl]pyridin-2-yl}-2,2-difluoroacetamide |
| 167 | 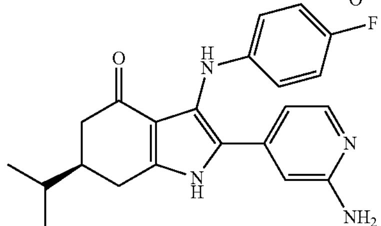 | 2-(2-aminopyridin-4-yl)-3-[(4-fluorophenyl)amino]-6-(propan-2-yl)-1,5,6,7-tetrahydro-4H-indol-4-one |
| 168 | 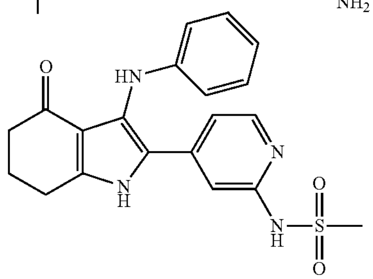 | N-{4-[4-oxo-3-(phenylamino)-4,5,6,7-tetrahydro-1H-indol-2-yl]pyridin-2-yl}methanesulfonamide |

Example 169 Preparation of 1-methyl-3-(phenylamino)-2-(pyridin-4-yl)-1,5,6,7-tetrahydro-4H-indol-4-one

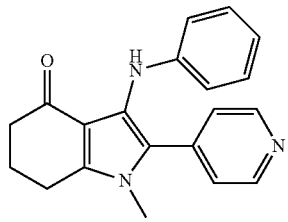 [SMILES: Cn1c2c(c(Nc3ccccc3)c1-c1ccncc1)C(=O)CCC2]

To a solution of Example 9 (50 mg, 15 μmol) in THF under Ar was added MeOH (5 eq) and PPh₃ (1.6 eq). To this solution was added DIAD (1.6 eq). Stirred for 16 h at RT. Concentrated and purified by silica chromatography and preparative HPLC (acidic method) to give the desired product (5 mg, 10%).

1H-NMR (400 MHz, DMSO-d6), d [ppm]=2.07 (2H), 2.25-2.38 (2H), 2.80-2.96 (2H), 3.36 (3H), 6.40-6.58 (3H), 6.86-7.01 (2H), 7.22 (1H), 7.30-7.38 (2H), 8.43-8.61 (2H).

Example 170 Preparation of 1-ethyl-3-(phenylamino)-2-(pyridin-4-yl)-1,5,6,7-tetrahydro-4H-indol-4-one

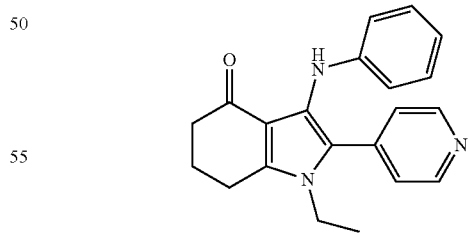

Using method H1: Example 9 (50 mg) with EtOH gave the desired product (10 mg, 18%) after purification by silica chromatography and preparative HPLC (acidic method).

1H-NMR (400 MHz, DMSO-d6), d [ppm]=1.14 (3H), 2.08 (2H), 2.28-2.42 (2H), 2.91 (2H), 3.92-4.12 (2H), 6.42-6.53 (3H), 6.88-6.97 (2H), 7.16 (1H), 7.29-7.35 (2H), 8.41-8.57 (2H)

Example 171 Preparation of 3-(phenylamino)-1-propyl-2-(pyridin-4-yl)-1,5,6,7-tetrahydro-4H-indol-4-one

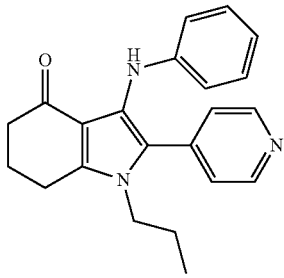 [SMILES: CCCn1c2c(c(Nc3ccccc3)c1-c1ccncc1)C(=O)CCC2]

Using method H1: Example 9 (50 mg) with n-PrOH gave the desired product (3 mg, 5%) after purification by silica chromatography and preparative HPLC (Column: XBridge C18 5μ 100×30 mm; Solvent A: Water+0.2 Vol-% NH$_4$OH (32%), Solvent B: Acetonitrile; Gradient: 0.00-0.50 min 34% B (25-70 mL/min), 0.51-5.50 min 34-54% B; Flow: 70 mL/min).

1H-NMR (400 MHz, DMSO-d6), d [ppm]=0.69 (3H), 1.45 (2H), 2.00-2.15 (2H), 2.33 (2H), 2.90 (2H), 3.97 (2H), 6.39-6.57 (3H), 6.93 (2H), 7.16 (1H), 7.32 (2H), 8.51 (2H).

Example 172 Preparation of methyl 3-[4-oxo-3-(phenylamino)-2-(pyridin-4-yl)-4,5,6,7-tetrahydro-1H-indol-1-yl]propanoate

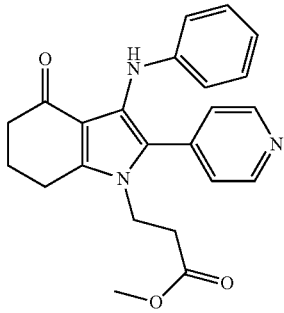 [SMILES: COC(=O)CCn1c2c(c(Nc3ccccc3)c1-c1ccncc1)C(=O)CCC2]

A mixture of Example 9 (1 g, 3.3 mmol), methyl 3-bromopropionate (826 mg, 4.9 mmol) and KO$^t$Bu (740 mg, 6.6 mmol) in THF (20 mL) was heated in a sealed tube at 80° C. for 24 h. The reaction was diluted with sat. NaHCO$_3$ and extracted with EtOAc. The organics were combined, concentrated and purified by silica chromatography) to give the desired product (190 mg, 13%).

1H-NMR (400 MHz, DMSO-d6), d [ppm]=2.06 (2H), 2.32 (2H), 2.50 (2H), 2.93 (2H), 3.49 (3H), 4.28 (2H), 6.45-6.53 (3H), 6.92 (2H), 7.12 (1H), 7.32 (2H), 8.52 (2H).

Example 173 Preparation of 3-[4-oxo-3-(phenylamino)-2-(pyridin-4-yl)-4,5,6,7-tetrahydro-1H-indol-1-yl]propanoic acid

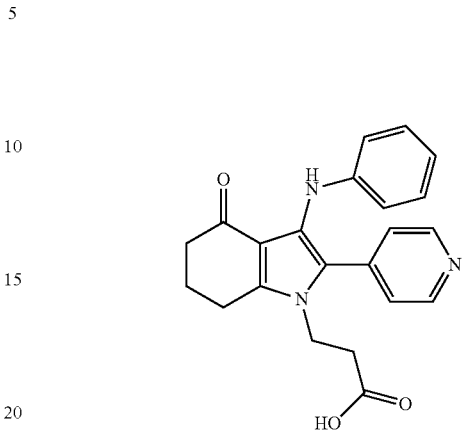

A mixture of Example 172 (62 mg, 159 μmol), 1M NaOH (320 μL) in MeOH (1 ml) was stirred at RT for 20 h. 2M HCl (160 μL, 320 μmol) was added and the reaction mixture concentrated. Purification by silica chromatography gave the desired product (11 mg, 16%).

1H-NMR (400 MHz, DMSO-d6), d [ppm]=2.06 (2H), 2.30 (4H), 2.93 (2H), 4.18 (2H), 6.45-6.52 (3H), 6.91 (2H), 7.12 (1H), 7.32 (2H), 8.48 (2H).

Example 174 Preparation 3-[4-oxo-3-(phenylamino)-2-(pyridin-4-yl)-4,5,6,7-tetrahydro-1H-indol-1-yl]propanamide

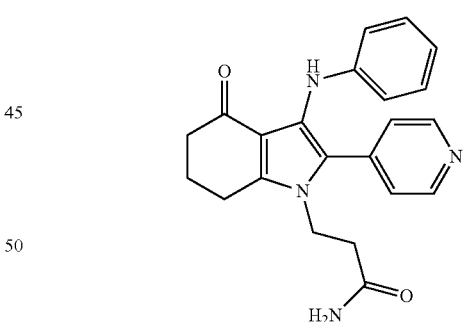

A mixture of Example 172 (140 mg, 359 μmol), 2M AlMe$_3$ in toluene (449 μL, 899 μmol) and NH$_4$Cl (48 mg, 899 μmol) in toluene (1 ml) was stirred at RT for 5 days. Reaction quenched by the addition of sat. NaHCO$_3$, extracted with EtOAc and washed with sat. NaCl. Concentrated and the residue purified by silica chromatography to give the desired product (15 mg, 11%).

1H-NMR (400 MHz, CDCl3), d [ppm]=2.16 (2H), 2.33 (2H), 2.45 (2H), 2.90 (2H) 4.34 (2H), 5.50 (1H), 5.87 (1H), 6.52-6.55 (2H), 6.63-6.67 (1H), 6.90 (2H), 7.15 (12), 8.34 (2H).

Example 175 Preparation 1-(3-hydroxypropyl)-3-(phenylamino)-2-(pyridin-4-yl)-1,5,6,7-tetrahydro-4H-indol-4-one

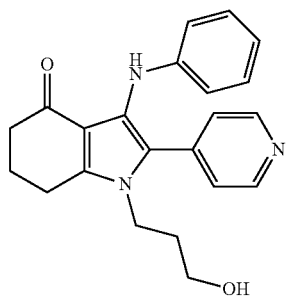 [SMILES: O=C1CCCc2c1c(Nc1ccccc1)c(-c1ccncc1)n2CCCO]

Synthesis of Example 175

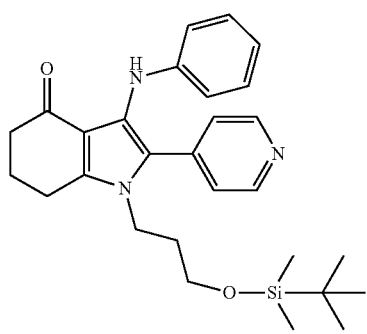 [SMILES: CC(C)(C)[Si](C)(C)OCCCn1c2c(c(Nc3ccccc3)c1-c1ccncc1)C(=O)CCC2]

A mixture of Example 9 (500 mg, 1.65 mmol), 2-bromopropoxy)(tert-butyl)dimethylsilane (460 mg, 1.82 mmol) and K₂CO₃ (500 mg, 3.62 mmol) in DMF (2 mL) was heated in a sealed tube at 80° C. for 1 h. The reaction was diluted with sat. NaHCO₃ and extracted with EtOAc. The organics were combined, concentrated and purified by silica chromatography to give 3-anilino-1-(3-{[tert-butyl(dimethyl)silyl]oxy}propyl)-2-(pyridin-4-yl)-1,5,6,7-tetrahydro-4H-indol-4-one (40 mg, 5%).

1H-NMR (400 MHz, CDCl3), d [ppm]=0.01 (6H), 0.87 (9H), 1.68 (2H), 2.19 (2H), 2.49 (2H), 2.88 (2H), 3.50 (2H), 4.09 (2H), 6.57 (2H), 6.66 (1H), 6.92 (2H), 7.17 (2H), 7.28 (1H), 8.39 (2H).

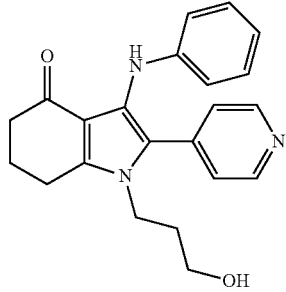 [SMILES: O=C1CCCc2c1c(Nc1ccccc1)c(-c1ccncc1)n2CCCO]

A mixture of 3-anilino-1-(3-{[tert-butyl(dimethyl)silyl]oxy}propyl)-2-(pyridin-4-yl)-1,5,6,7-tetrahydro-4H-indol-4-one Example 175 (35 mg, 74 μmol) in 1M HCl was heated at reflux for 1 min. Extracted with DCM and concentrated. Purified by preparative HPLC (Column: C18; Solvent: Water (+0.1% TFA)/Methanol (+2% Water, +0.1% TFA) 45:55]) to give the desired product (12 mg, 41%).

1H-NMR (400 MHz, DMSO-d6): δ [ppm]=1.59 (2H), 2.08 (2H), 2.34 (2H), 2.92 (2H), 3.26 (2H), 4.09 (2H), 4.52 (1H), 6.42-6.58 (3H), 6.88-6.99 (2H), 7.22 (1H), 7.34-7.47 (2H), 8.46-8.61 (2H).

Example 176 Preparation 1-[2-(methylsulfonyl)ethyl]-3-(phenylamino)-2-(pyridin-4-yl)-1,5,6,7-tetrahydro-4H-indol-4-one

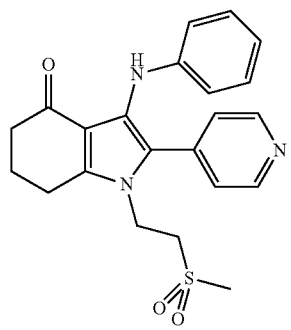 [SMILES: CS(=O)(=O)CCn1c2c(c(Nc3ccccc3)c1-c1ccncc1)C(=O)CCC2]

A mixture of Example 9 (737 mg, 2.43 mmol), 2-bromoethylmethylsulfone (500 mg, 2.67 mmol) and K₂CO₃ (739 mg, 5.35 mmol) in DMF (2 mL) was heated in a sealed tube at 80° C. for 4 h. The reaction was diluted with sat. NaHCO₃ and extracted with EtOAc. The organics were combined, concentrated and purified by silica chromatography) to give the desired product (190 mg, 13%).

1H-NMR (400 MHz, DMSO-d6), d [ppm]=2.09 (2H), 2.32 (2H), 2.92 (3H), 2.98 (2H), 3.41 (2H), 4.14 (2H), 6.47-6.54 (3H), 6.92 (2H), 7.17 (1H), 7.36 (2H), 8.52 (2H)

Example 177 Preparation of 2-(3-chloropyridin-4-yl)-1-ethyl-3-(phenylamino)-1,5,6,7-tetrahydro-4H-indol-4-one

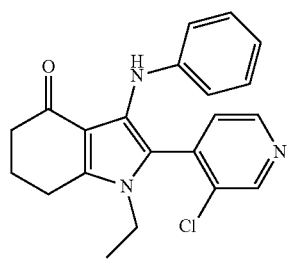 [SMILES: CCn1c2c(c(Nc3ccccc3)c1-c1ccncc1Cl)C(=O)CCC2]

A mixture of Example 33 (50 mg, 148 μmol), iodoethane (46 mg, 268 μmol) and K₂CO₃ (82 mg, 592 μmol) in DMF (2.2 mL) was stirred at RT for 96 h. The reaction was filtered, concentrated and purified by silica chromatography to give the desired product (41 mg, 71%).

1H-NMR (300 MHz, CHLOROFORM-d), d [ppm]=1.19 (6H), 2.37 (2H), 2.68 (2H), 3.56 (3H), 6.56 (2H), 6.66 (1H), 6.94 (2H), 7.16 (3H)

Example 178 Preparation of 1,6-dimethyl-3-(phenylamino)-2-(pyridin-4-yl)-1,5,6,7-tetrahydro-4H-indol-4-one

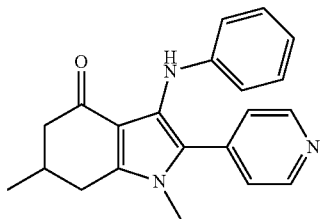 [SMILES: CC1CC(=O)c2c(Nc3ccccc3)c(-c3ccncc3)n(C)c2C1]

Using method H1: Example 22 (50 mg) with MeOH gave the desired product (7 mg, 13%) after purification by silica chromatography and preparative HPLC (Column: Phenomenex Kinetex C18 5μ 100×30 mm; Solvent A: Water+0.2 Vol-% TFA (99%), Solvent B: MeOH; Gradient: 0.00-0.50 min 32% B (25-70 mL/min), 0.51-5.50 min 32-52% B; Flow: 70 mL/min).

1H-NMR (400 MHz, DMSO-d6), d [ppm]=1.13 (3H), 2.15-2.28 (1H), 2.28-2.39 (2H), 2.52-2.58 (1H), 3.07 (1H), 3.65 (3H), 6.41-6.67 (3H), 6.97 (2H), 7.56 (1H), 7.63 (2H), 8.60 (2H).

Example 179 Preparation of 1,6,6-trimethyl-3-(phenylamino)-2-(pyridin-4-yl)-1,5,6,7-tetrahydro-4H-indol-4-one

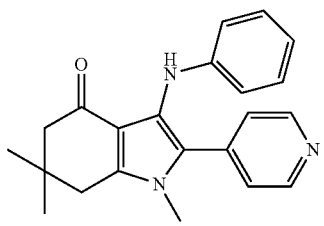 [SMILES: Cn1c2c(c(Nc3ccccc3)c1-c1ccncc1)C(=O)CC(C)(C)C2]

A mixture of Example 1 (29 mg, 87 μmol), iodomethane (2 eq), K$_2$CO$_3$ (4 eq) in DMF (2 mL) was stirred at RT for 40 h. Concentrated and purified by preparative HPLC (basic method) to give the desired product (10 mg, 15%).

1H-NMR (300 MHz, CHLOROFORM-d), d [ppm]=1.19 (6H), 2.37 (2H), 2.68 (2H), 3.56 (3H), 6.56 (2H), 6.66 (1H), 6.94 (2H), 7.16 (2H), 8.49 (2H).

Example 180 Preparation of 6,6-dimethyl-3-(phenylamino)-2-(pyridin-4-yl)-1-(2,2,2-trifluoroethyl)-1,5,6,7-tetrahydro-4H-indol-4-one

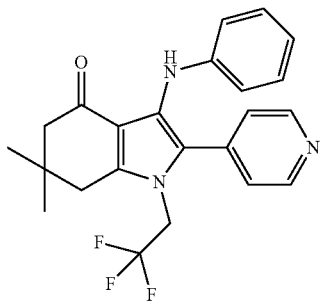 [SMILES: CC1(C)CC(=O)c2c(Nc3ccccc3)c(-c3ccncc3)n(CC(F)(F)F)c2C1]

A mixture of Example 1 (50 mg, 151 μmol), 2,2,2-trifluoroethyl trifluoromethanesulfonate (2 eq), K$_2$CO$_3$ (4 eq) in DMF (2 mL) was stirred at RT for 96 h. Concentrated and purified by silica chromatography to give the desired product (7 mg, 11%).

1H-NMR (400 MHz, DMSO-d6), d [ppm]=1.09 (6H), 2.28 (2H), 2.80-2.92 (2H), 5.02 (2H), 6.43 (2H), 6.51 (1H), 6.94 (2H), 7.19 (1H), 7.30-7.38 (2H), 8.52 (2H)

Example 181 Preparation of 1-ethyl-6,6-dimethyl-3-(phenylamino)-2-(pyridin-4-yl)-1,5,6,7-tetrahydro-4H-indol-4-one

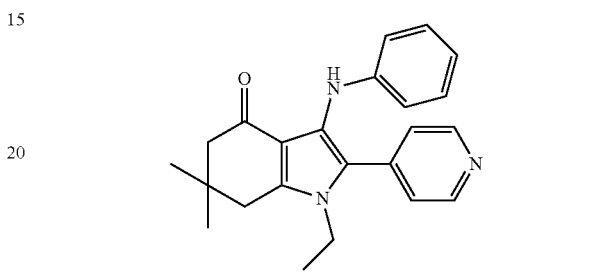

A mixture of Example 1 (500 mg, 1.51 mmol), iodoethane (1 eq), K$_2$CO$_3$ (3 eq) in DMF (3 mL) was heated at 60° C. for 30 min. Diluted with water, extracted EtOAc and concentrated. Purification by silica chromatography gave the desired product (45 mg, 8%).

1H-NMR (400 MHz, DMSO-d6), d [ppm]=1.17 (6H), 1.22 (3H), 2.35 (2H), 2.68 (2H), 3.96 (2H), 6.55 (2H), 6.63 (1H), 6.91 (2H), 7.12 (1H), 7.15 (2H), 8.43 (2H).

Example 182 Preparation of 6,6-dimethyl-3-(phenylamino)-1-propyl-2-(pyridin-4-yl)-1,5,6,7-tetrahydro-4H-indol-4-one

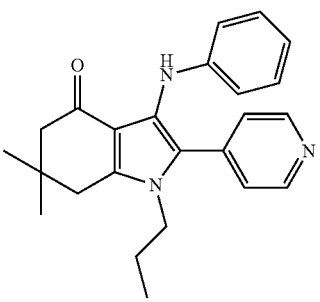 [SMILES: CCCn1c2c(c(Nc3ccccc3)c1-c1ccncc1)C(=O)CC(C)(C)C2]

A mixture of Example 1 (50 mg, 151 μmol), 1-iodopropane (2 eq), K$_2$CO$_3$ (4 eq) in DMF (2 mL) was stirred at RT for 16 h. Concentrated and purified by preparative HPLC (Column: XBridge C18 5 μm 100×30 mm; Solvent A: Water+0.2% NH$_4$OH; Solvent B: Acetonitrile; Gradient; 0.5-5.5 min 42-62% B: Flow: 70 mL/min) to give the desired product (9 mg, 10%).

1H-NMR (300 MHz, DMSO-d6), d [ppm]=0.66 (3H), 0.96-1.16 (7H), 1.30-1.50 (2H), 2.22 (2H), 2.80 (2H), 3.96 (2H), 6.34-6.62 (3H), 6.92 (2H), 7.14 (1H), 7.32 (2H), 8.49 (2H)

Example 183 Preparation of 3-anilino-2-(pyridin-4-yl)-1-[2-(tetrahydro-2H-pyran-2-yloxy)ethyl]-1,5,6,7-tetrahydro-4H-indol-4-one

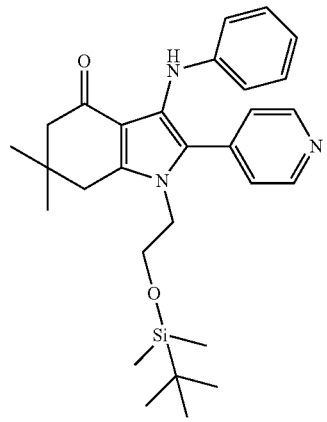 [SMILES: CC1(C)CC(=O)c2c(Nc3ccccc3)c(-c3ccncc3)n(CCO[Si](C)(C)C(C)(C)C)c2C1]

A mixture of Example 1 (2.38 g, 7.18 mmol), $K_2CO_3$ (4.96 g, 21.54 mmol) and 2-(2-bromoethoxy)tetrahydro-2H-pyran (1.80 g, 8.62 mmol) in DMF (36 mL) was heated at 60° C. for 72 h. Diluted with water and extracted with EtOAc. Concentrated and purified by silica chromatography to give the desired product (672 mg, 20%).

1H-NMR (400 MHz, CHLOROFORM-d), d [ppm]=1.16 (6H), 1.48-1.67 (6H), 2.35 (2H), 2.75 (2H), 3.42-3.48 (2H), 3.57 (1H), 3.80 (1H), 4.18 (2H), 4.45 (1H), 6.55 (2H), 6.66 (1H), 6.92 (2H), 7.09 (1H), 7.22 (2H), 8.42 (2H).

Example 184 Preparation of 1-(2-hydroxyethyl)-6,6-dimethyl-3-(phenylamino)-2-(pyridin-4-yl)-1,5,6,7-tetrahydro-4H-indol-4-one

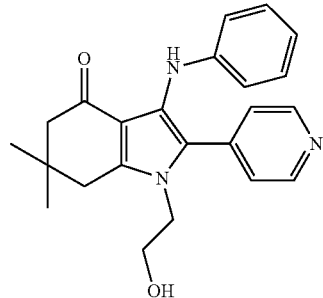 [SMILES: CC1(C)CC(=O)c2c(Nc3ccccc3)c(-c3ccncc3)n(CCO)c2C1]

To a mixture of 3-anilino-2-(pyridin-4-yl)-1-[2-(tetrahydro-2H-pyran-2-yloxy)ethyl]-1,5,6,7-tetrahydro-4H-indol-4-one (650 mg, 1.41 mmol) in THF (20 mL) was added 1M HCl (5 mL) and stirred at RT for 20 h. Extracted with EtOAc and concentrated. Purified by silica chromatography to give the desired product (413 mg, 74%)

1H-NMR (400 MHz, DMSO-d6), d [ppm]=1.09 (6H), 2.23 (2H), 2.83 (2H), 3.41 (2H), 4.05 (2H), 4.94 (1H), 6.45-6.52 (3H), 6.93 (2H), 7.38 (2H), 8.49 (2H).

Example 185 Preparation of 2-[3-anilino-6,6-dimethyl-4-oxo-2-(pyridin-4-yl)-4,5,6,7-tetrahydro-1H-indol-1-yl]acetamide formic acid salt

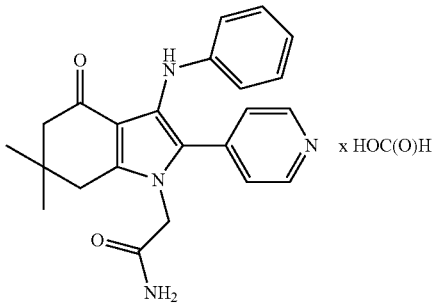 [SMILES: CC1(C)CC(=O)c2c(Nc3ccccc3)c(-c3ccncc3)n(CC(N)=O)c2C1]

A mixture of Example 1 (45 mg, 151 μmol), iodoacetamide (2 eq), $K_2CO_3$ (4 eq) in DMF (1 mL) was stirred at RT for 16 h. Concentrated and purified by preparative HPLC (Column: XBridge C18 5 μm 100×30 mm; Solvent A: Water+0.1% $HCO_2H$; Solvent B: Acetonitrile; Gradient; 0.5 min Inlet (7% B, 25 to 50 mL/min); 0.5-5.5 min 15-37%: Flow: 70 mL/min) to give the desired product (28 mg, 46%).

1H-NMR (400 MHz, DMSO-d6), d [ppm]=1.05 (5H), 2.25 (2H), 2.73 (2H), 4.96 (2H), 6.68-6.80 (3H), 7.13 (2H), 7.53 (1H), 7.89 (1H), 8.10 (1H), 8.28 (2H), 8.45 (1H).

Example 186 Preparation of 1-benzyl-6,6-dimethyl-3-(phenylamino)-2-(pyridin-4-yl)-1,5,6,7-tetrahydro-4H-indol-4-one

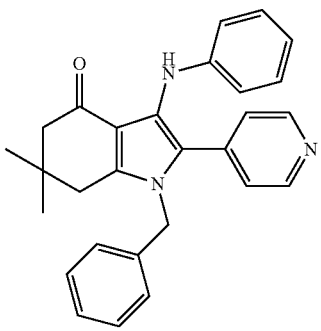 [SMILES: CC1(C)CC(=O)c2c(Nc3ccccc3)c(-c3ccncc3)n(Cc3ccccc3)c2C1]

A mixture of Example 1 (45 mg, 151 μmol), iodoacetamide (2 eq), $K_2CO_3$ (4 eq) in DMF (1 mL) was stirred at 90° C. for 16 h. Concentrated and purified by preparative HPLC (Column: XBridge C18 5 μm 100×30 mm; Solvent A: Water+0.2% $NH_4OH$; Solvent B: Acetonitrile; Gradient; 0.00-0.50 min 46% B (25-70 mL/min), 0.51-5.50 min 46-66% B: Flow: 70 mL/min) to give the desired product (25 mg, 19%).

1H-NMR (400 MHz, DMSO-d6), d [ppm]=0.92-1.10 (6H), 2.25 (2H), 2.66 (2H), 5.28 (2H), 6.43-6.55 (2H), 6.66-6.77 (1H), 6.86-6.99 (3H), 7.16-7.42 (6H), 8.40 (2H).

Example 187 Preparation of N-{4-[1-ethyl-6,6-dimethyl-4-oxo-3-(phenylamino)-4,5,6,7-tetrahydro-1H-indol-2-yl]pyridin-2-yl}acetamide

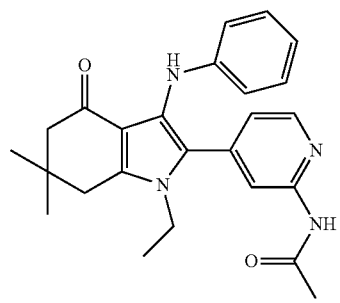 [SMILES: CCn1c2c(c(Nc3ccccc3)c1-c1ccnc(NC(C)=O)c1)C(=O)CC(C)(C)C2]

A mixture of Example 1 (20 mg, 51 μmol), iodoethane (2 eq), K$_2$CO$_3$ (4 eq) in DMF (3 mL) was stirred at RT for 96 h. Filtered, concentrated and purified by silica chromatography to give the desired product (15 mg, 63%).

1H-NMR (400 MHz, CHLOROFORM-d), d [ppm]=1.15-1.23 (6H), 1.32 (3H), 1.57 (3H), 2.16-2.28 (3H), 2.37 (2H), 2.71 (2H), 3.98-4.10 (2H), 6.59 (2H), 6.62-6.70 (1H), 6.90 (1H), 6.95 (2H), 7.16 (1H), 7.90 (1H), 7.97 (1H), 8.20 (1H).

Example 188 Preparation of 1-(2,2-difluoroethyl)-6,6-dimethyl-3-(phenylamino)-2-(pyridin-4-yl)-1,5,6,7-tetrahydro-4H-indol-4-one

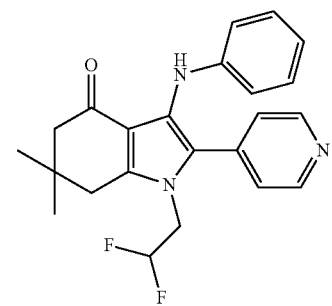 [SMILES: CC1(C)CC(=O)c2c(Nc3ccccc3)c(-c3ccncc3)n(CC(F)F)c2C1]

A mixture of Example 1 (45 mg, 151 μmol), 2,2-difluoroethyl trifluoromethanesulfone (2 eq), K$_2$CO$_3$ (4 eq) in DMF (1 mL) was stirred at RT for 96 h. Concentrated and purified by silica chromatography to give the desired product (7 mg, 12%).

1H-NMR (400 MHz, DMSO-d6), d [ppm]=1.00-1.16 (6H), 2.21-2.29 (2H), 2.83 (2H), 4.46-4.62 (2H), 6.38-6.60 (3H), 6.93 (2H), 7.16 (1H), 7.27-7.39 (2H), 8.51 (2H), 8.61 (1H).

Example 189 Preparation of 4-[6,6-dimethyl-4-oxo-3-(phenylamino)-4,5,6,7-tetrahydro-1H-indol-2-yl]-1-(propan-2-yl)pyridinium iodide

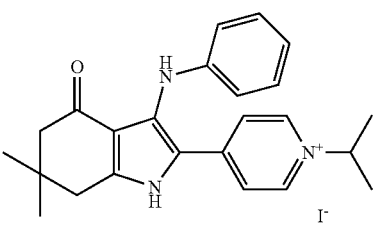 [SMILES: CC(C)[n+]1ccc(-c2[nH]c3c(c2Nc2ccccc2)C(=O)CC(C)(C)C3)cc1 ; [I-]]

A mixture of Example 1 (57 mg, 172 μmol), 2-iodopropane (2 eq), K$_2$CO$_3$ (4 eq) in DMF (1 mL) was stirred at RT for 16 h and then at 100° C. for 16 h. Filtered. concentrated and purified by preparative HPLC (Column: XBridge C18 5 μm 100×30 mm; Solvent A: Water+0.1% TFA; Solvent B: Acetonitrile; Gradient; 0-8 min, 30-45% B: Flow: 70 mL/min) to give the desired product (10 mg, 12%).

1H-NMR (400 MHz, DMSO-d6), d [ppm]=1.03-1.15 (6H), 1.47-1.55 (6H), 2.32 (2H), 2.83 (2H), 4.63-4.80 (1H), 6.71 (2H), 6.78 (1H), 7.10-7.18 (2H), 7.66-7.88 (2H), 8.11 (1H), 8.71-8.87 (2H), 12.45 (1H).

Example 190 Preparation of 4-[6,6-dimethyl-4-oxo-3-(phenylamino)-4,5,6,7-tetrahydro-1H-indol-2-yl]-1-(2,2,2-trifluoroethyl)pyridinium trifluoromethanesulfonate

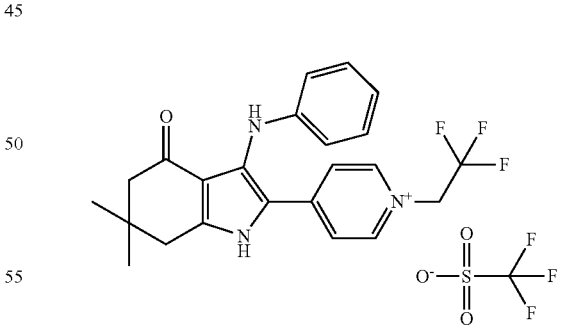

A mixture of Example 1 (50 mg, 151 μmol), 2,2,2-trifluoroethyl trifluoromethanesulfonate (2 eq), K$_2$CO$_3$ (4 eq) in DMF (2 mL) was stirred at RT for 96 h. Concentrated and purified by silica chromatography to give the desired product (19 mg, 21%).

1H-NMR (400 MHz, DMSO-d6), d [ppm]=1.09 (6H), 2.33-2.40 (2H), 2.84 (2H), 5.39 (2H), 6.74-6.90 (3H), 7.16 (2H), 7.71 (2H), 8.40 (1H), 8.61 (2H), 12.49 (1H).

Example 191 Preparation of 4-[6,6-dimethyl-4-oxo-3-(phenylamino)-4,5,6,7-tetrahydro-1H-indol-2-yl]-1-(3-hydroxypropyl)pyridinium iodide

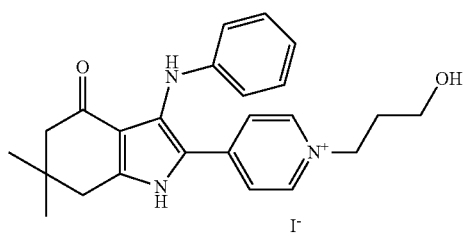 [SMILES: CC1(C)CC(=O)c2c([nH]c(-c3cc[n+](CCCO)cc3)c2Nc2ccccc2)C1 ; [I-]]

A mixture of Example 1 (57 mg, 172 μmol), 3-iodopropan-1-ol (2 eq), K$_2$CO$_3$ (4 eq) in DMF (1 mL) was stirred at RT for 16 h and then at 100° C. for 16 h. Filtered, concentrated and purified by preparative HPLC (Column: XBridge C18 5 μm 100×30 mm; Solvent A: Water+0.1% TFA; Solvent B: Acetonitrile; Gradient; 0-8 min, 20-40% B: Flow: 70 mL/min) to give the desired product (25 mg, 30%).

1H-NMR (400 MHz, DMSO-d6), d [ppm]=1.09 (6H), 1.97 (2H), 2.29-2.39 (3H), 2.82 (2H), 3.39 (2H), 4.38 (2H), 6.71 (2H), 6.78 (1H), 7.09-7.17 (2H), 7.73 (2H), 8.12 (1H), 8.66 (2H), 12.38 (1H).

Example 192 Preparation of 4-[6,6-dimethyl-4-oxo-3-(phenylamino)-4,5,6,7-tetrahydro-1H-indol-2-yl]-1-(2,2-difluoroethyl)pyridinium trifluoromethanesulfonate

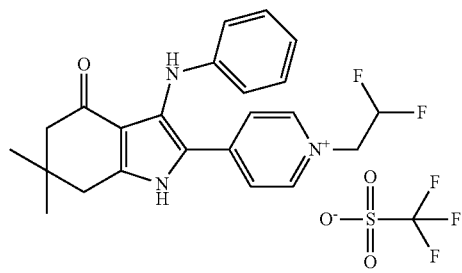 [SMILES: CC1(C)CC(=O)c2c([nH]c(-c3cc[n+](CC(F)F)cc3)c2Nc2ccccc2)C1 ; O=S(=O)([O-])C(F)(F)F]

A mixture of Example 1 (45 mg, 151 μmol), 2,2-difluoroethyl trifluoromethanesulfone (2 eq), K$_2$CO$_3$ (4 eq) in DMF (1 mL) was stirred at RT for 96 h. Concentrated and purified by silica chromatography to give the desired product (26 mg, 30%).

1H-NMR (400 MHz, DMSO-d6), d [ppm]=1.09 (6H), 2.29-2.36 (2H), 2.84 (2H), 4.81-4.98 (2H), 6.56 (1H), 6.72-6.85 (3H), 7.10-7.18 (2H), 7.73 (2H), 8.27 (1H), 8.58 (2H), 12.45 (1H).

Example 193 Preparation of 4-[6,6-dimethyl-4-oxo-3-(phenylamino)-4,5,6,7-tetrahydro-1H-indol-2-yl]-1-(2-methoxy-2-oxoethyl)pyridinium bromide

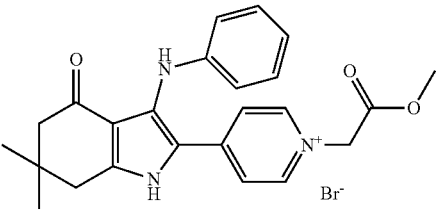

To a solution of Example 1 (33 mg, 100 μmol) in dry THF (500 μL) was added NaH (60% dispersion on mineral oil, 8 mg, 200 μmol) and stirred for 15 mins at RT. To the reaction was added methyl bromoacetate (30 mg, 200 μmol) and stirred at 50° C. for 30 h. Reaction quenched by addition of sat. NH$_4$Cl solution and extracted with DCM. Organics combined, dried Na$_2$SO$_4$ and concentrated to give the desired product (15 mg, 28%).

1H-NMR (400 MHz, DMSO-d6), d [ppm]=1.09 (6H), 2.33 (2H), 2.87 (2H), 3.74 (3H), 5.36 (2H), 6.74-6.81 (3H), 7.13-7.16 (2H), 7.87-7.89 (2H), 8.24 (1H), 8.55-8.56 (2H), 13.02 (1H).

Example 194 Preparation of 4-(hydroxyimino)-6,6-dimethyl-N-phenyl-2-(pyridin-4-yl)-4,5,6,7-tetrahydro-1H-indol-3-amine

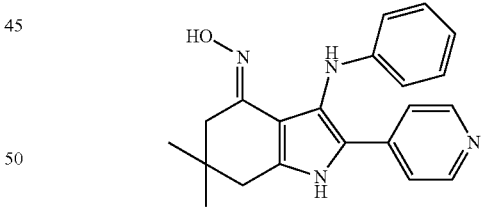

To a solution of Example 1 (21 mg, 63 μmol) in EtOH (1 mL) was added hydroxylamine hydrochloride (4.4 mg, 63 μmol) and DIPEA (11 μL, 63 μmol). After 2 h at RT additional hydroxylamine hydrochloride (4.4 mg, 63 μmol) and DIPEA (11 μL, 63 μmol) was added and heated at 80° C. for 16 h. Reaction allowed to cool and 1M HCl (2 mL) added and extracted with EtOAc. Organics combined, washed with water, sat. NaCl and concentrated. Purification by preparative HPLC (acidic method) gave the desired product (4.6 mg, 21%).

1H-NMR (600 MHz, DMSO-d6), d [ppm]=1.02 (6H), 2.44 (2H), 2.56 (2H), 6.55 (2H), 6.61-6.65 (1H), 7.02-7.07 (2H), 7.18 (1H), 7.40-7.44 (2H), 8.32 (2H), 10.31 (1H), 11.36 (1H).

Example 195 Preparation of 1-({(E)-[6,6-dimethyl-3-(phenylamino)-2-(pyridin-4-yl)-1,5,6,7-tetrahydro-4H-indol-4-ylidene]amino}oxy)ethanone

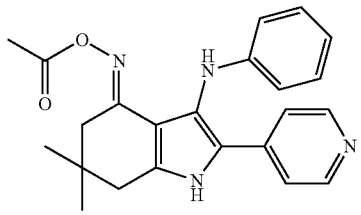 [SMILES: CC(=O)O/N=C1\CC(C)(C)Cc2[nH]c(-c3ccncc3)c(Nc3ccccc3)c21]

To a solution of (50 mg, 144 μmol) in THF (2 mL) was added Pd/C (10%, 15 mg) and Ac$_2$O (123 μL, 1.3 mmol) and stirred under an H$_2$ atmosphere (10.6 bar) for 17 h. Reaction filtered, concentrated and the residue was purified by preparative HPLC (basic method) to give the desired product (18.5 mg, 30%).

1H-NMR (500 MHz, DMSO-d6), d [ppm]=1.02-1.10 (6H), 2.02 (3H), 2.55-2.61 (2H), 2.64 (2H), 6.51-6.59 (2H), 6.60-6.66 (1H), 7.01-7.08 (2H), 7.31 (1H), 7.48-7.54 (2H), 8.37-8.42 (2H), 11.71 (1H).

Example 196 Preparation of 2-(3-bromopyridin-4-yl)-3-(phenylamino)-1,5,6,7-tetrahydro-4H-indol-4-one

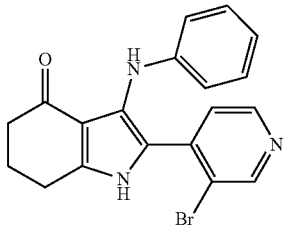 [SMILES: O=C1CCCc2[nH]c(-c3ccncc3Br)c(Nc3ccccc3)c21]

Synthesis of Example 196

Intermediate 1-2-29

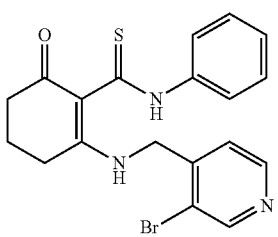 [SMILES: O=C1CCCC(NCc2ccncc2Br)=C1C(=S)Nc1ccccc1]

Using method F1: Intermediate 1-1-5 (1.587, 6.42 mmol) with 4-aminomethyl-3-bromopyridine (1 g, 5.35 mmol) in EtOH:EtOAc gave Intermediate 1-2-29 (1.348 g, 61%) after silica chromatography.

1H-NMR (400 MHz, DMSO-d6), d [ppm]=1.81 (2H), 2.45 (2H), 2.73 (2H), 4.81 (2H), 7.18-7.29 (1H), 7.33-7.44 (2H), 7.44-7.54 (3H), 8.60 (1H), 8.77 (1H), 13.37 (1H), 14.36 (1H).

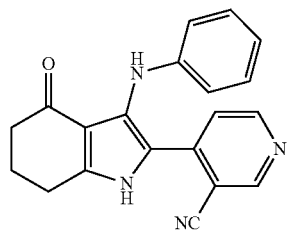 [SMILES: N#Cc1cnccc1-c1[nH]c2c(c1Nc1ccccc1)C(=O)CCC2]

A solution of intermediate 1-2-29 (1320 mg, 3.17 mmol) in MeOH (50 mL) was added H$_2$O$_2$ (34% aq, 571 μL, 6.34 mmol) and heated at reflux for 4 h. Concentrated and purified by silica chromatography to give the desired product (437 mg, 36%)

1H-NMR (400 MHz, DMSO-d6), d [ppm]=2.02-2.12 (2H), 2.30-2.41 (2H), 2.83 (2H), 6.43-6.59 (3H), 6.90 (2H), 7.27 (1H), 7.41 (1H), 8.37 (1H), 8.65-8.70 (1H), 11.59 (1H).

Example 197 Preparation of 4-[4-oxo-3-(phenylamino)-4,5,6,7-tetrahydro-1H-indol-2-yl]pyridine-3-carbonitrile

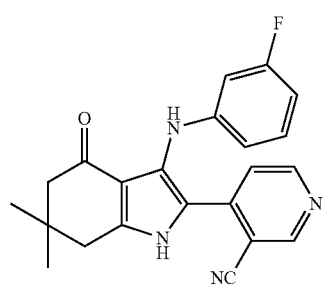 [SMILES: CC1(C)CC(=O)c2c([nH]c(-c3ccncc3C#N)c2Nc2cccc(F)c2)C1]

A mixture of Example 196 (50 mg, 131 μmol) and CuCN (12.3 mg, 137 μmol) in NMP (1 mL) was heated at 150° C. for 1 h. Reaction filtered through Celite and purified by preparative HPLC (basic method) to give the desired product (4.3 mg, 9%).

1H-NMR (400 MHz, DMSO-d6), d [ppm]=1.86-1.97 (2H), 2.06-2.16 (2H), 2.86 (2H), 7.28 (2H), 7.45-7.58 (3H), 7.69-7.80 (1H), 8.63 (1H), 9.43 (1H).

Example 198 Preparation of 4-{3-[(3-fluorophenyl)amino]-6,6-dimethyl-4-oxo-4,5,6,7-tetrahydro-1H-indol-2-yl}pyridine-3-carbonitrile Synthesis of Example 198

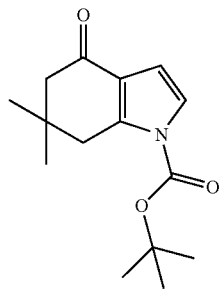 [SMILES: CC1(C)CC(=O)c2ccn(C(=O)OC(C)(C)C)c2C1]

To a suspension of 6,6-dimethyl-1,5,6,7-tetrahydro-4H-indol-4-one (10 g, 61.3 mmol) and DMAP (7.49 g, 61.3 mmol) in MeCN (50 mL) was added slowly dropwise Boc₂O (28.2 mL, 122.5 mmol). Reaction stirred at RT for 16 h and concentrated. Purification by silica chromatography gave tert-butyl 6,6-dimethyl-4-oxo-4,5,6,7-tetrahydro-1H-indole-1-carboxylate (13.175 g, 78%).

1H-NMR (400 MHz, DMSO-d6), d [ppm]=1.04 (6H), 1.57 (9H), 2.28 (2H), 2.98 (2H), 6.43 (1H), 7.23 (1H).

Intermediate 1-8-1

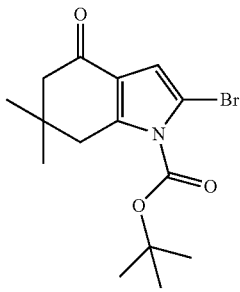 [SMILES: CC1(C)CC(=O)c2cc(Br)n(C(=O)OC(C)(C)C)c2C1]

To a solution of intermediate tert-butyl 6,6-dimethyl-4-oxo-4,5,6,7-tetrahydro-1H-indole-1-carboxylate (13.17 g, 50 mmol) in DMF (50 mL) was added NBS (9.35 g, 52.51 mmol) and stirred at RT for 16 h. Reaction poured into water, extracted EtOAc. Organics combined, washed water, sat. NaCl and concentrated. Purification by silica chromatography gave tert-butyl 2-bromo-6,6-dimethyl-4-oxo-4,5,6,7-tetrahydro-1H-indole-1-carboxylate intermediate 1-8-1 (11.37 g, 66%).

1H-NMR (400 MHz, DMSO-d6), d [ppm]=1.04 (6H), 1.60 (9H), 2.29 (2H), 2.88 (2H), 6.60 (1H).

Intermediate 1-5-3

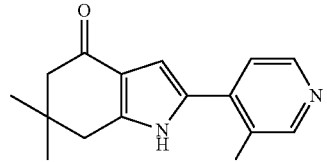

A mixture of intermediate 1-8-1 tert-butyl 2-bromo-6,6-dimethyl-4-oxo-4,5,6,7-tetrahydro-1H-indole-1-carboxylate (205 mg, 600 μmol), 3-cyanopyridine-4-boronic acid pinacol ester (690 mg, 3 mmol), Pd(PPh₃)₄ (69 mg, 60 μmol) and K₂CO₃ (414 mg, 3 mmol) in dioxane (5.1 mL) was heated at 150° C. for 90 min using a microwave. Reaction was filtered and concentrated and purified by preparative HPLC (basic method) to give the intermediate 1-5-3 4-(6,6-dimethyl-4-oxo-4,5,6,7-tetrahydro-1H-indol-2-yl)nicotinonitrile (49 mg, 31%).

1H-NMR (300 MHz, DMSO-d6), d [ppm]=1.07 (6H), 2.30 (2H), 2.77 (2H), 7.38 (1H), 7.77 (1H), 8.77 (1H), 8.94 (1H), 12.26 (1H).

Intermediate 1-6-3

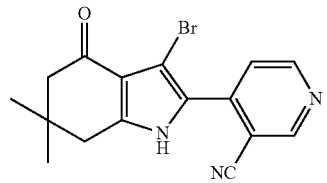 [SMILES: CC1(C)CC(=O)c2c([nH]c(-c3ccncc3C#N)c2Br)C1]

To a solution of intermediate 1-5-3 (45 mg, 170 μmol) in DMF (2 mL) was added NBS (32 mg, 178 μmol) and stirred at RT for 16 h. Reaction poured into water and the solid product, 4-(3-bromo-6,6-dimethyl-4-oxo-4,5,6,7-tetrahydro-1H-indol-2-yl)nicotinonitrile, was collected and dried in vacuo (33 mg, 57%).

1H-NMR (400 MHz, DMSO-d6), d [ppm]=1.07 (6H), 2.33 (2H), 2.77 (2H), 7.71 (1H), 8.91 (1H), 9.13 (1H), 12.48 (1H).

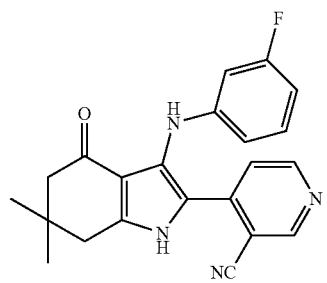 [SMILES: CC1(C)CC(=O)c2c([nH]c(-c3ccncc3C#N)c2Nc2cccc(F)c2)C1]

Using method F2: intermediate 4-(3-bromo-6,6-dimethyl-4-oxo-4,5,6,7-tetrahydro-1H-indol-2-yl)nicotinonitrile (18 mg, 52 μmol) gave the desired product (3.5 mg, 16%) after preparative HPLC (basic method).

1H-NMR (400 MHz, METHANOL-d4), d [ppm]=1.06 (6H), 2.16 (2H), 2.85 (2H), 7.23-7.33 (2H), 7.34-7.44 (1H), 7.64 (1H), 7.96 (1H), 8.66 (1H), 9.52 (1H).

Example 199 Preparation of 2-(3-bromopyridin-4-yl)-6,6-dimethyl-3-(phenylamino)-1,5,6,7-tetrahydro-4H-indol-4-one

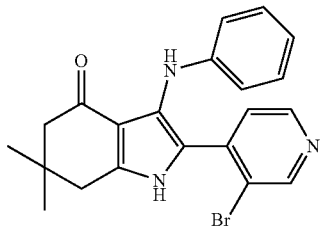 [SMILES: CC1(C)CC(=O)c2c([nH]c(-c3ccncc3Br)c2Nc2ccccc2)C1]

Synthesis of Example 199

Intermediate 1-2-30

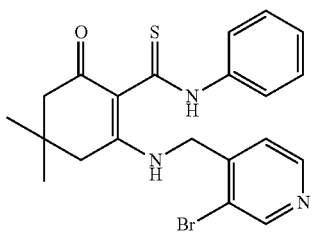 [SMILES: CC1(C)CC(=O)C(C(=S)Nc2ccccc2)=C(NCc2ccncc2Br)C1]

A solution of Intermediate 1-1-1 (1.64 g, 5.96 mmol) and 4-aminomethyl-3-bromopyridine (2.23 g, 11.92 mmol) in DMA (3.3 mL) was heated in a sealed tube at 120° C. for 90 mins using a microwave. Concentrated and purified by silica chromatography to give the intermediate 1-2-30 (1.21 g, 46%).

1H-NMR (400 MHz, DMSO-d6), d [ppm]=0.99 (6H), 2.39 (2H), 2.66 (2H), 4.83 (2H), 7.19-7.29 (1H), 7.39 (2H), 7.43-7.54 (3H), 8.60 (1H), 8.77 (1H), 13.76 (1H), 14.48 (1H).

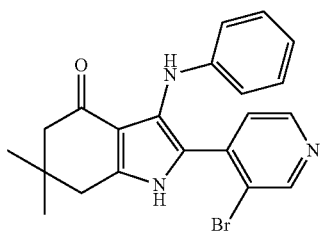 [SMILES: CC1(C)CC(=O)c2c([nH]c(-c3ccncc3Br)c2Nc2ccccc2)C1]

Using method F1: intermediate 1-2-30 (134 mg, 302 μmol) gave the desired product (26 mg, 20%) after preparative HPLC (acidic method).

1H-NMR (400 MHz, DMSO-d6), d [ppm]=1.08 (6H), 2.25 (2H), 2.72 (2H), 6.45-6.57 (3H), 6.91 (2H), 7.29 (1H), 7.38 (1H), 8.38 (1H), 8.68 (1H), 11.57 (1H).

Example 200 Preparation of 6,6-dimethyl-2-[2-(methylsulfanyl)pyridin-4-yl]-3-(phenylamino)-1,5,6,7-tetrahydro-4H-indol-4-one

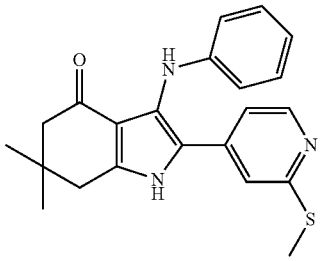 [SMILES: CSc1cc(-c2[nH]c3c(c2Nc2ccccc2)C(=O)CC(C)(C)C3)ccn1]

Synthesis of Example 200

Intermediate 1-2-31

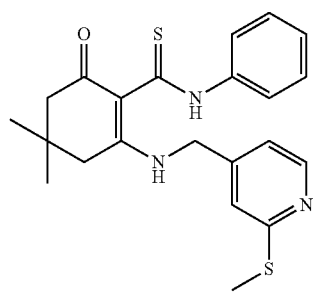 [SMILES: CSc1cc(CNC2=C(C(=S)Nc3ccccc3)C(=O)CC(C)(C)C2)ccn1]

A solution of Intermediate 1-1-1 (1.62 g, 1.62 mmol) and [2-(methylsulfanyl)pyridin-4-yl]methanamine (125 mg, 810 μmol) in DMA (2.5 mL) was heated in a sealed tube at 130° C. for 90 mins using a microwave. Purified by preparative HPLC (basic method) to give the intermediate 1-2-31 (96 mg, 29%).

1H-NMR (400 MHz, DMSO-d6), d [ppm]=0.98 (6H), 2.39 (2H), 2.51 (3H), 2.61-2.67 (2H), 4.80 (2H), 6.92 (1H), 7.09 (1H), 7.20-7.27 (1H), 7.29 (1H), 7.36-7.43 (2H), 7.43-7.50 (2H), 8.39-8.50 (1H), 13.91 (1H), 14.59 (1H).

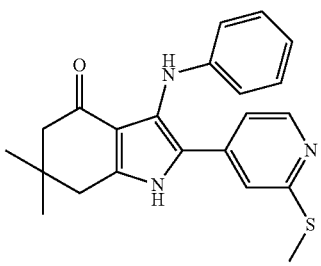 [SMILES: CSc1cc(-c2[nH]c3c(c2Nc2ccccc2)C(=O)CC(C)(C)C3)ccn1]

Using method F1: intermediate 1-2-31 (90 mg, 219 μmol) gave the desired product (13 mg, 16%) after preparative HPLC (basic method).

1H-NMR (400 MHz, DMSO-d6), d [ppm]=1.07 (6H), 2.24 (2H), 2.28 (3H), 2.75 (2H), 6.53-6.60 (2H), 6.60-6.68 (1H), 7.05 (2H), 7.22 (1H), 7.30 (1H), 7.49 (1H), 8.16-8.29 (1H), 11.86 (1H).

Example 201 Preparation of 6,6-dimethyl-2-[3-(methylsulfanyl)pyridin-4-yl]-3-(phenylamino)-1,5,6,7-tetrahydro-4H-indol-4-one

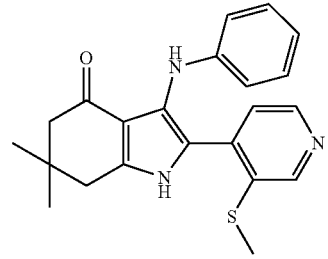 [SMILES: CSc1cnccc1-c1[nH]c2c(c1Nc1ccccc1)C(=O)CC(C)(C)C2]

Synthesis of Example 201

Intermediate 1-2-32

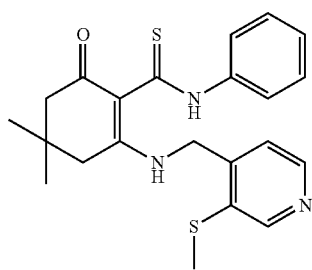 [SMILES: CSc1cnccc1CNC1=C(C(=S)Nc2ccccc2)C(=O)CC(C)(C)C1]

A solution of Intermediate 1-1-1 (300 mg, 1.09 mmol) and [3-(methylsulfanyl)pyridin-4-yl]methanamine (202 mg, 1.31 mmol) in DMA (4 mL) was heated in a sealed tube at 130° C. for 60 mins using a microwave. Purified by preparative HPLC (basic method) to give the intermediate 1-2-32 (155 mg, 35%).

1H-NMR (400 MHz, DMSO-d6), d [ppm]=0.98 (6H), 2.39 (2H), 2.60 (3H), 2.64 (2H), 4.77 (2H), 7.19-7.27 (1H), 7.32 (1H), 7.34-7.43 (2H), 7.43-7.49 (2H), 8.44 (1H), 8.57 (1H), 13.86 (1H), 14.57 (1H).

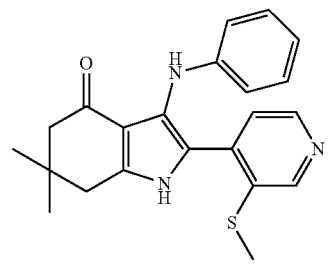 [SMILES: CSc1cnccc1-c1[nH]c2c(c1Nc1ccccc1)C(=O)CC(C)(C)C2]

Using method F1: intermediate 1-2-32 (150 mg, 364 μmol) gave the desired product (20 mg, 15%) after silica chromatography.

1H-NMR (400 MHz, DMSO-d6), d [ppm]=1.06 (6H), 2.23 (2H), 2.45 (3H), 2.69 (2H), 6.42-6.54 (3H), 6.85-6.94 (2H), 7.14 (1H), 7.21 (1H), 8.22 (1H), 8.44 (1H), 11.49 (1H).

Example 202 Preparation of {4-[6,6-dimethyl-4-oxo-3-(phenylamino)-4,5,6,7-tetrahydro-1H-indol-2-yl]pyridin-3-yl}(methyl)sulfoniumolate

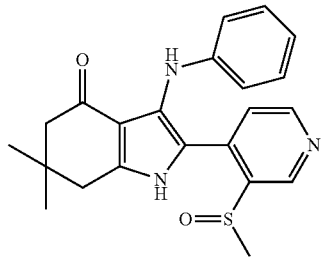 [SMILES: CS(=O)c1cnccc1-c1[nH]c2c(c1Nc1ccccc1)C(=O)CC(C)(C)C2]

Using method F1: intermediate 1-2-32 (150 mg, 364 μmol) gave the desired product (56 mg, 39%) after silica chromatography.

1H-NMR (400 MHz, DMSO-d6), d [ppm]=1.07 (6H), 2.17-2.29 (2H), 2.59 (3H), 2.67-2.80 (2H), 6.41-6.48 (2H), 6.53 (1H), 6.90-6.98 (2H), 7.36 (1H), 7.41 (1H), 8.65 (1H), 8.93 (1H), 11.86 (1H).

Example 203 Preparation of 2-(2-aminopyridin-4-yl)-3-[(3-bromophenyl)amino]-6,6-dimethyl-1,5,6,7-tetrahydro-4H-indol-4-one

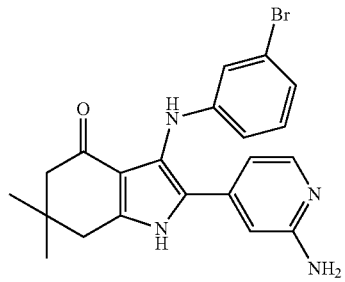 [SMILES: CC1(C)CC(=O)c2c([nH]c(-c3ccnc(N)c3)c2Nc2cccc(Br)c2)C1]

Synthesis of Example 203

Intermediate 1-2-33

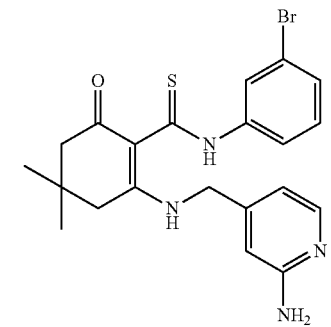 [SMILES: CC1(C)CC(=O)C(C(=S)Nc2cccc(Br)c2)=C(NCc2ccnc(N)c2)C1]

A solution of intermediate 1-1-14 (2.025 g, 5.72 mmol), 2-amino-4-(aminomethyl)pyridine (845 mg, 6.9 mmol) and DBU (427 μL, 2.86 mmol) in EtOH:EtOAc (1:1, 100 mL)

was heated at reflux for 16 h. Concentrated and purified by preparative HPLC (Column: XBridge C18 5 μm 100×30 mm; Solvent A: Water+0.2% NH₄OH; Solvent B: Acetonitrile; Gradient; 0-8 min 50-78% B: Flow: 70 mL/min) to give the intermediate 1-2-33 (684 mg, 26%)

1H-NMR (400 MHz, DMSO-d6), d [ppm]=0.98 (5H), 2.40 (2H), 2.66 (2H), 4.65 (2H), 6.02 (2H), 6.37 (1H), 7.35 (1H), 7.41 (1H), 7.89 (1H).

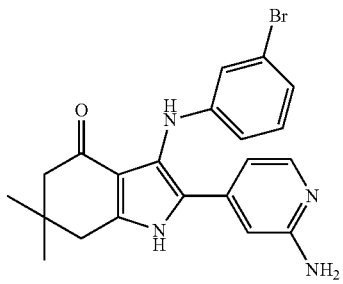 [SMILES: CC1(C)CC(=O)c2c([nH]c(-c3ccnc(N)c3)c2Nc2cccc(Br)c2)C1]

Using method F1 intermediate 1-2-33 (595 mg, 1.3 mmol) gave the desired product (110 mg, 20%) after preparative HPLC (basic method).

1H-NMR (500 MHz, DMSO-d6), d [ppm]=1.05 (5H), 2.20 (2H), 2.72 (2H), 5.76 (2H), 6.49 (1H), 6.61 (1H), 6.63-6.74 (2H), 6.95 (1H), 7.52 (1H), 7.80 (1H), 11.70 (1H).

Example 204 Preparation of 2-{2-[(1-benzyl-1H-pyrazol-4-yl)amino]pyridin-4-yl}-6,6-dimethyl-3-(phenylamino)-1,5,6,7-tetrahydro-4H-indol-4-one

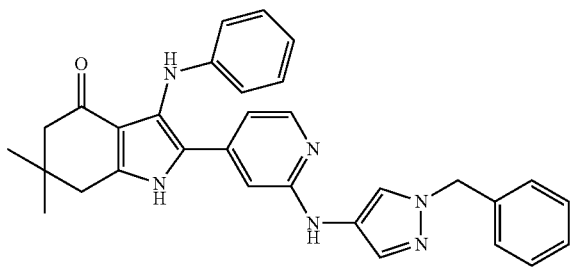 [SMILES: CC1(C)CC(=O)c2c([nH]c(-c3ccnc(Nc4cnn(Cc5ccccc5)c4)c3)c2Nc2ccccc2)C1]

Synthesis of Example 204

Intermediate 1-10-1

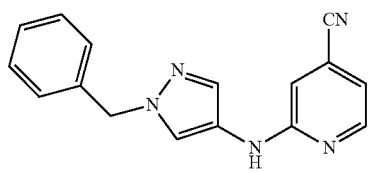 [SMILES: N#Cc1ccnc(Nc2cnn(Cc3ccccc3)c2)c1]

A mixture of 2-fluoro-4-cyanopyridine (535 mg, 4.4 mmol), 1-benzyl-1H-pyrazol-4-amine (759 mg, 4.4 mmol) and DIPEA (763 μL, 4.4 mmol) in THF (3 mL) was heated at 120° C. for 16 h in a sealed tube. Concentrated and purified by silica chromatography to give the intermediate 1-10-1 (164 mg, 14%)

1H-NMR (400 MHz, DMSO-d6), d [ppm]=5.30 (2H), 6.93 (1H), 6.97 (1H), 7.19-7.25 (2H), 7.25-7.31 (1H), 7.31-7.37 (2H), 7.51 (1H), 8.10 (1H), 8.28 (1H), 9.38 (1H).

Intermediate 1-11-1

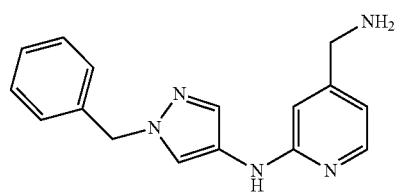 [SMILES: NCc1ccnc(Nc2cnn(Cc3ccccc3)c2)c1]

To a solution of intermediate 1-10-1 (160 mg, 581 μmol) in 7M NH₃ in MeOH (3.3 mL) was added Raney-Nickel (50% wet, 171 mg, 2.9 mmol) and stirred at RT under an H₂ atmosphere (28.6 bar) for 20 h. The reaction was filtered and concentrated to give the intermediate 1-11-1 product (153 mg, 94%) which was used without further purification.

1H-NMR (400 MHz, DMSO-d6), d [ppm]=3.61 (2H), 5.27 (2H), 6.57 (1H), 6.63 (1H), 7.19-7.24 (2H), 7.24-7.30 (1H), 7.30-7.37 (2H), 7.37-7.46 (1H), 7.96 (1H), 8.04 (1H), 8.74 (1H).

Intermediate 1-2-34

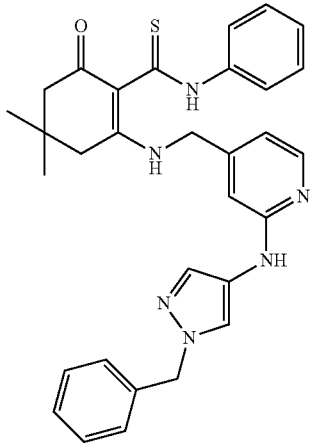 [SMILES: CC1(C)CC(=O)C(C(=S)Nc2ccccc2)=C(NCc2ccnc(Nc3cnn(Cc4ccccc4)c3)c2)C1]

A solution of intermediate 1-1-1 (123 mg, 447 μmol) and intermediate 1-11-1 (150 mg, 537, μmol) in DMA (2.5 mL) was heated in a sealed tube at 130° C. for 60 mins using a microwave. Concentrated and purified by preparative HPLC (basic method) to give the intermediate 1-2-34 (62 mg, 25%).

1H-NMR (400 MHz, DMSO-d6), d [ppm]=0.98 (6H), 2.40 (2H), 2.61-2.68 (2H), 4.73 (2H), 5.27 (2H), 6.55-6.63 (2H), 6.92 (1H), 7.16-7.29 (4H), 7.29-7.35 (2H), 7.36-7.42 (2H), 7.42-7.49 (3H), 8.05 (1H), 8.08 (1H), 8.98 (1H), 14.21 (1H), 14.77 (1H).

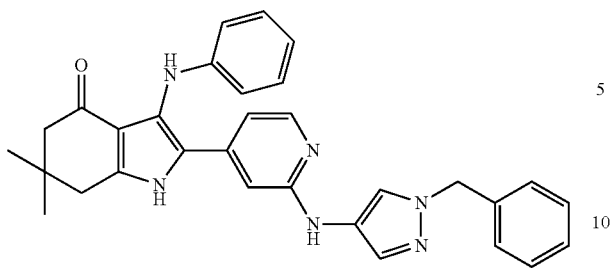

Using method F1 intermediate 1-2-34 (62 mg, 116 µmol) gave the desired product (17 mg, 28%) after preparative HPLC (basic method).

1H-NMR (400 MHz, DMSO-d6), d [ppm]=1.06 (5H), 2.21 (2H), 2.73 (2H), 5.24 (2H), 6.50-6.64 (3H), 6.77-6.88 (2H), 7.01 (2H), 7.14-7.24 (2H), 7.24-7.37 (5H), 7.81 (1H), 7.96 (1H), 8.62 (1H), 11.72 (1H).

Example 205 Preparation of 6,6-dimethyl-2-{2-[(1-methyl-1H-pyrazol-4-yl)amino]pyridin-4-yl}-3-(phenylamino)-1,5,6,7-tetrahydro-4H-indol-4-one

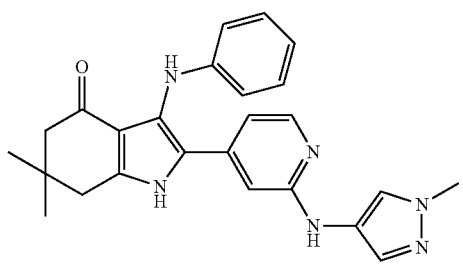

Synthesis of Example 205

Intermediate 1-10-2

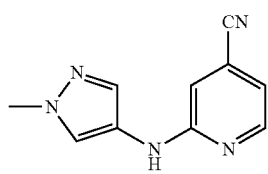

A mixture of 2-fluoro-4-cyanopyridine (549 mg, 4.5 mmol), 1-methyl-1H-pyrazol-4-amine (437 mg, 4.5 mmol) and DIPEA (784 µL, 4.5 mmol) in THF (3 mL) was heated at 120° C. for 16 h in a sealed tube. Concentrated and purified by silica chromatography to give the intermediate 1-10-2 (196 mg, 22%).

1H-NMR (400 MHz, DMSO-d6), d [ppm]=3.80 (3H), 6.93 (1H), 6.96 (1H), 7.40-7.51 (1H), 7.96 (1H), 8.25-8.33 (1H), 9.30 (1H).

Intermediate 1-11-2

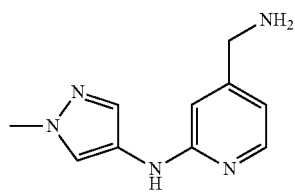

To a solution of intermediate 1-10-2 (190 mg, 954 µmol) in 7M NH₃ in MeOH (5.5 mL) was added Raney-Nickel (50% wet, 196 mg, 3.3 mmol) and stirred at RT under an H₂ atmosphere (28.6 bar) for 20 h. The reaction was filtered and concentrated to give the intermediate 1-11-2 (194 mg, 100%) which was used without further purification.

1H-NMR (400 MHz, DMSO-d6), d [ppm]=1.82 (2H), 3.61 (2H), 3.72-3.86 (3H), 6.57 (1H), 6.62 (1H), 7.31-7.42 (1H), 7.91 (1H), 7.97 (1H), 8.66 (1H).

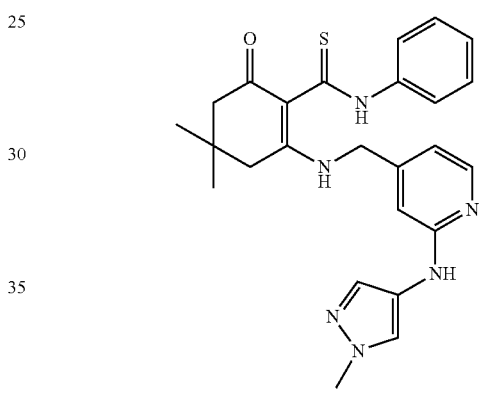

A solution of intermediate 1-1-1 (219 mg, 75 µmol) and intermediate 1-11-2 (194 mg, 954 µmol) in DMA (2.5 mL) was heated in a sealed tube at 130° C. for 60 mins using a microwave. Filtered and purified by preparative HPLC (basic method) to give the intermediate 1-2-35 (92 mg, 24%).

1H-NMR (400 MHz, DMSO-d6), d [ppm]=0.96-1.02 (6H), 2.41 (2H), 2.65-2.72 (3H), 3.79 (3H), 4.73 (2H), 6.54-6.64 (2H), 7.20-7.29 (1H), 7.36-7.44 (3H), 7.44-7.50 (2H), 7.92 (1H), 8.06-8.14 (1H), 8.90 (1H), 14.11-14.31 (1H), 14.77 (1H).

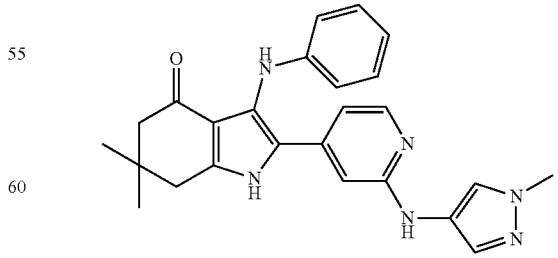

Using method F1 intermediate 1-2-35 (92 mg, 201 µmol) gave the desired product (25 mg, 28%) after preparative HPLC (basic method).

1H-NMR (400 MHz, DMSO-d6), d [ppm]=1.06 (6H), 2.21 (2H), 2.73 (2H), 3.74 (3H), 6.54-6.65 (3H), 6.78 (1H), 6.83 (1H), 7.04 (2H), 7.25 (1H), 7.32 (1H), 7.59 (1H), 7.97 (1H), 8.50 (1H), 11.71 (1H).

Example 206 Preparation of 2'-(2-aminopyridin-4-yl)-3'-(phenylamino)-1',7'-dihydrospiro[cyclopropane-1,6'-indol]-4'(5'H)-one

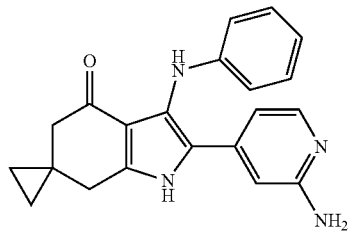 [SMILES: Nc1cc(-c2[nH]c3c(c2Nc2ccccc2)C(=O)CC2(CC2)C3)ccn1]

Synthesis of Example 206

Intermediate 1-2-36

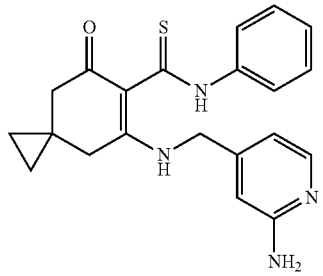 [SMILES: Nc1cc(CNC2=C(C(=S)Nc3ccccc3)C(=O)CC3(CC3)C2)ccn1]

A solution of intermediate 1-1-23 (2.74 g, 10 mmol) and 2-amino-4-(aminomethyl)pyridine (1.48 g, 12 mmol) in EtOH:EtOAc (1:1, 50 mL) was heated at reflux for 16 h under Dean-Stark conditions with 4 Å molecular sieves. Concentrated and purified by silica chromatography to give the intermediate 1-2-36 (1.01 g, 27%)

1H-NMR (400 MHz, DMSO-d6), d [ppm]=0.35-0.48 (4H), 2.37-2.43 (2H), 2.64-2.77 (2H), 4.58 (2H), 6.02 (2H), 6.35 (1H), 6.43 (1H), 7.18-7.34 (1H), 7.35-7.48 (4H), 7.88 (1H), 14.00-14.18 (1H), 14.70 (1H).

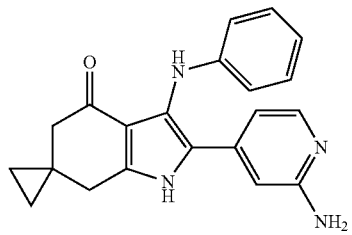 [SMILES: Nc1cc(-c2[nH]c3c(c2Nc2ccccc2)C(=O)CC2(CC2)C3)ccn1]

Using method F1 intermediate 1-2-36 (1.01 g, 2.6 mmol) gave the desired product (226 mg, 25%) after silica chromatography.

1H-NMR (400 MHz, DMSO-d6), d [ppm]=0.37-0.54 (4H), 2.22 (2H), 2.73 (2H), 3.17 (2H), 5.99 (2H), 6.55-6.67 (4H), 6.74 (1H), 7.03 (2H), 7.31 (1H), 7.76 (1H), 11.75 (1H).

Example 207 Preparation of 2'-(2-fluoropyridin-4-yl)-3'-(phenylamino)-1',7'-dihydrospiro[cyclopropane-1,6'-indol]-4'(5'H)-one

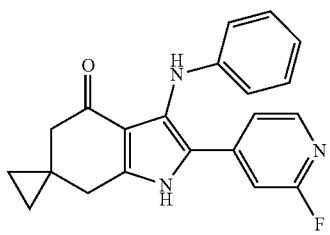 [SMILES: O=C1CC2(CC2)Cc2[nH]c(-c3ccnc(F)c3)c(Nc3ccccc3)c21]

Synthesis of Example 207

Intermediate 1-2-37

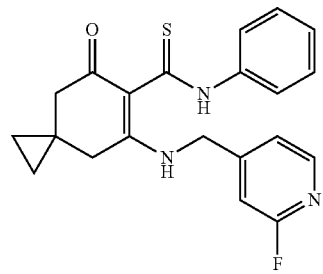 [SMILES: O=C1CC2(CC2)CC(NCc2ccnc(F)c2)=C1C(=S)Nc1ccccc1]

A solution of intermediate 1-1-23 (400 mg, 1.5 mmol) and 2-fluoro-4-(aminomethyl)pyridine (370 mg, 2.9 mmol) in DMA (2 mL) was heated in a sealed tube at 120° C. for 90 mins using a microwave. Filtered and purified by preparative HPLC (basic method) to give the intermediate 1-2-37 (46 mg, 8%).

1H-NMR (400 MHz, DMSO-d6), d [ppm]=0.32-0.48 (4H), 2.40 (2H), 2.67 (2H), 4.83 (2H), 7.14 (1H), 7.20-7.28 (1H), 7.33 (1H), 7.35-7.44 (2H), 7.44-7.50 (2H), 8.27 (1H), 13.69 (1H), 14.44 (1H).

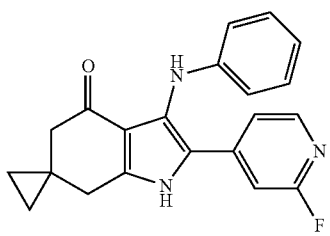 [SMILES: O=C1CC2(CC2)Cc2[nH]c(-c3ccnc(F)c3)c(Nc3ccccc3)c21]

Using method F1 intermediate 1-2-37 (46 mg, 121 µmol) gave the desired product (4.8 mg, 11%) after preparative HPLC (basic method).

1H-NMR (400 MHz, DMSO-d6), d [ppm]=0.37-0.47 (2H), 0.47-0.59 (2H), 2.25 (2H), 2.77 (2H), 6.61 (2H), 6.66 (1H), 7.07 (2H), 7.13 (1H), 7.42 (1H), 7.57 (1H), 8.07 (1H), 11.96 (1H).

Example 208 Preparation of 2'-(3-fluoropyridin-4-yl)-3'-(phenylamino)-1',7'-dihydrospiro[cyclopropane-1,6'-indol]-4'(5'H)-one

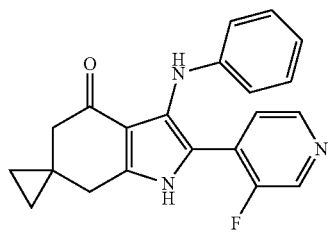 [SMILES: O=C1CC2(CC2)Cc2[nH]c(-c3ccncc3F)c(Nc3ccccc3)c21]

Synthesis of Example 207

Intermediate 1-2-38

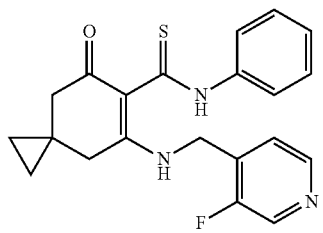 [SMILES: O=C1CC2(CC2)CC(NCc2ccncc2F)=C1C(=S)Nc1ccccc1]

A solution of intermediate 1-1-23 (250 mg, 92 μmol) and 3-fluoro-4-(aminomethyl)pyridine (231 mg, 1.8 mmol) in DMA (5 mL) was heated in a sealed tube at 120° C. for 90 mins using a microwave. Filtered and purified by preparative HPLC (basic method) to give the intermediate 1-2-38 (47 mg, 13%).

1H-NMR (400 MHz, DMSO-d6), d [ppm]=0.42 (4H), 2.41 (2H), 2.73 (2H), 4.85 (2H), 7.20-7.28 (1H), 7.35-7.42 (2H), 7.42-7.52 (3H), 8.48 (1H), 8.60 (1H), 13.76 (1H), 14.48 (1H).

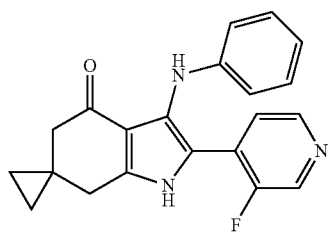 [SMILES: O=C1CC2(CC2)Cc2[nH]c(-c3ccncc3F)c(Nc3ccccc3)c21]

Using method F1 intermediate 1-2-38 (47 mg, 123 μmol) gave the desired product (9.7 mg, 23%) after preparative HPLC (basic method).

1H-NMR (400 MHz, DMSO-d6), d [ppm]=0.38-0.58 (4H), 2.26 (2H), 2.76 (2H), 6.50-6.66 (3H), 6.94-7.05 (2H), 7.40 (1H), 7.57 (1H), 8.24 (1H), 8.49 (1H), 11.64 (1H).

Example 209 Preparation of 2-(2,6-dimethylpyridin-4-yl)-6,6-dimethyl-3-(phenylamino)-1,5,6,7-tetrahydro-4H-indol-4-one

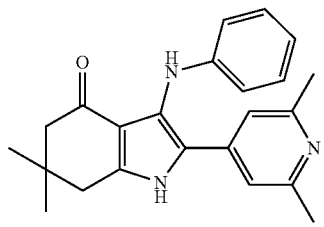

Synthesis of Example 209

Intermediate 1-2-39

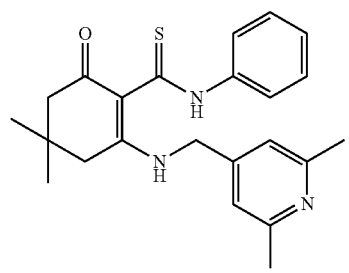

A solution of Intermediate 1-1-1 (1685 mg, 6.1 mmol) and 2,6-dimethyl-4-(aminomethyl)pyridine (1 g, 7.3 mmol) in EtOH:EtOAc (1:1, 100 mL) was heated at reflux for 16 h. Concentrated and purified by silica chromatography followed by preparative HPLC (Column: XBridge C18 5 μm 100×30 mm; Solvent A: Water+0.2% NH4OH; Solvent B: Acetonitrile; Gradient; 0-0.5 min 45% B (25 to 70 mL/Min), then 0.51-5.5 min 45-65% B: Flow: 70 mL/min) to give the intermediate 1-2-39 (84 mg, 3%)

1H-NMR (400 MHz, DMSO-d6), d [ppm]=0.93-1.09 (6H), 2.33-2.45 (8H), 2.66 (2H), 4.75 (2H), 7.01 (2H), 7.19-7.27 (1H), 7.38 (2H), 7.45 (2H), 14.08 (1H), 14.69 (1H).

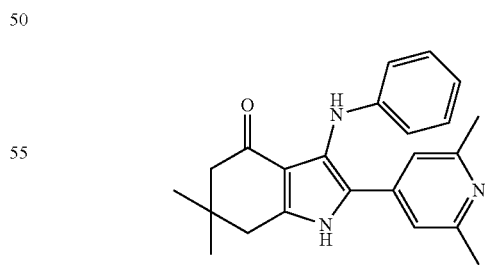

Using method F1 intermediate 1-2-39 (77 mg, 196 μmol) gave the desired product (25 mg, 36%) after preparative HPLC (basic method).

1H-NMR (400 MHz, DMSO-d6), d [ppm]=1.02-1.09 (6H), 2.23 (2H), 2.24-2.30 (6H), 2.73 (2H), 6.55 (2H), 6.61 (1H), 6.98-7.07 (2H), 7.14 (2H), 7.37 (1H), 11.74 (1H).

Example 210 Preparation of 2-(2,3-dihydro[1,4]dioxino[2,3-b]pyridin-8-yl)-6,6-dimethyl-3-(phenylamino)-1,5,6,7-tetrahydro-4H-indol-4-one

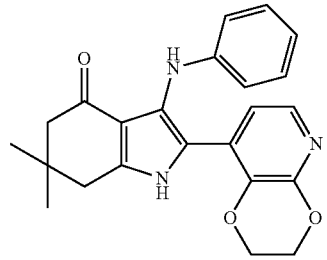 [SMILES: CC1(C)CC(=O)c2c([nH]c(-c3ccnc4c3OCCO4)c2Nc2ccccc2)C1]

Synthesis of Example 210

Intermediate 1-11-3

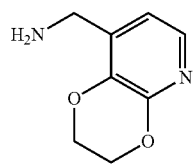 [SMILES: NCc1ccnc2c1OCCO2]

To a solution of 2,3-dihydro[1,4]dioxino[2,3-b]pyridine-8-carbonitrile (500 mg, 2.9 mmol) in 7M $NH_3$ in MeOH (16.7 mL) was added Raney-Nickel (50% wet, 429 mg, 7.3 mmol) and stirred at RT under an $H_2$ atmosphere (25.5 bar) for 20 h. The reaction was filtered and concentrated to give the intermediate 1-11-3 (quantitative) which was used without further purification.

1H-NMR (400 MHz, CHLOROFORM-d), d [ppm]=1.43 (2H), 3.76-3.90 (2H), 4.25-4.39 (2H), 4.44 (2H), 6.89 (1H), 7.71-7.88 (1H).

Intermediate 1-2-40

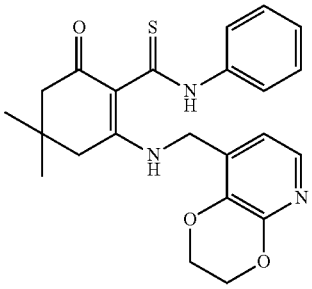 [SMILES: CC1(C)CC(=O)C(C(=S)Nc2ccccc2)=C(NCc2ccnc3c2OCCO3)C1]

A solution of Intermediate 1-1-1 (984 mg, 3.6 mmol) and intermediate 1-11-3 (540 mg, 3.2 mmol) in DMA (10 mL) was heated in a sealed tube at 130° C. for 120 mins using a microwave. Concentrated and purified by silica chromatography to give the intermediate 1-2-40 (476 mg, 35%)

1H-NMR (400 MHz, DMSO-d6), d [ppm]=1.00 (6H), 2.39 (2H), 2.70 (2H), 4.31 (2H), 4.37-4.47 (2H), 4.71 (2H), 6.96 (1H), 7.18-7.27 (1H), 7.38 (2H), 7.44 (2H), 7.76 (1H), 14.00 (1H), 14.66 (1H).

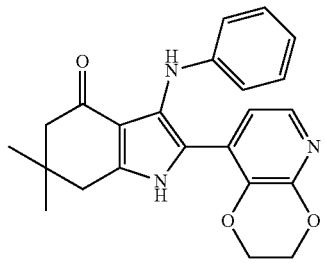 [SMILES: CC1(C)CC(=O)c2c([nH]c(-c3ccnc4c3OCCO4)c2Nc2ccccc2)C1]

Using method F1 at 50° C. plus DBU (116 µL, 774 µmol) and intermediate 1-2-40 (82 mg, 194 µmol) gave the desired product (7 mg, 8%) after preparative HPLC (basic method).

1H-NMR (400 MHz, DMSO-d6), d [ppm]=1.04-1.11 (6H), 2.23 (2H), 2.74 (2H), 4.09-4.21 (2H), 4.22-4.33 (2H), 6.43-6.63 (3H), 6.93-7.03 (3H), 7.41 (1H), 7.54 (1H), 11.31 (1H).

Example 211 Preparation of 2-(2-aminopyridin-4-yl)-3-[(4-fluorophenyl)amino]-1,5,6,7-tetrahydro-4H-indol-4-one

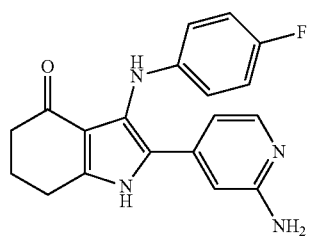 [SMILES: Nc1cc(-c2[nH]c3c(c2Nc2ccc(F)cc2)C(=O)CCC3)ccn1]

Synthesis of Example 211

Intermediate 1-2-41

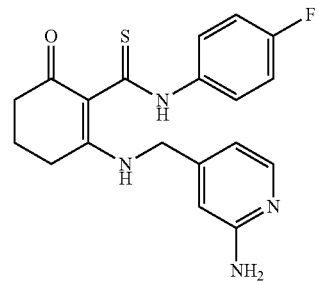 [SMILES: Nc1cc(CNC2=C(C(=S)Nc3ccc(F)cc3)C(=O)CCC2)ccn1]

A solution of Intermediate 1-1-7 (1 g, 3.8 mmol) and 2-amino-4-(aminomethyl)pyridine (557 mg, 4.5 mmol) in EtOH:EtOAc (1:1, 120 mL) was heated at reflux under Dean-Stark conditions with 4 Å molecular sieves for 72 h. Concentrated and purified by silica chromatography to give the intermediate 1-2-41 (410 mg, 28%)

1H-NMR (400 MHz, DMSO-d6), d [ppm]=1.80 (2H), 2.42-2.48 (2H), 2.75 (2H), 4.62 (2H), 6.01 (2H), 6.37 (1H), 6.45 (1H), 7.18-7.25 (2H), 7.43 (2H), 7.88 (1H), 13.83 (1H), 14.60 (1H).

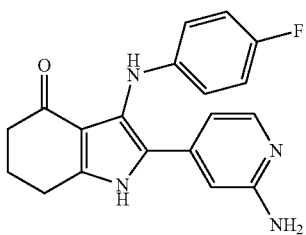 [SMILES: Nc1cc(-c2[nH]c3c(c2Nc2ccc(F)cc2)C(=O)CCC3)ccn1]

Using method F1: intermediate 1-2-41 (195 mg, 1.1 mmol) gave the desired product (145 mg, 38%) after silica chromatography.

1H-NMR (400 MHz, DMSO-d6), d [ppm]=1.96-2.09 (2H), 2.23-2.36 (2H), 2.82 (2H), 5.92 (2H), 6.49-6.61 (3H), 6.71 (1H), 6.82-6.91 (2H), 7.27 (1H), 7.76 (1H), 11.73 (1H).

Example 212 Preparation of 2-(2-aminopyridin-4-yl)-3-[(3,4-difluorophenyl)amino]-1,5,6,7-tetrahydro-4H-indol-4-one

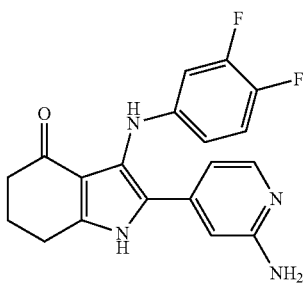 [SMILES: Nc1cc(-c2[nH]c3c(c2Nc2ccc(F)c(F)c2)C(=O)CCC3)ccn1]

Synthesis of Example 212

Intermediate 1-2-42

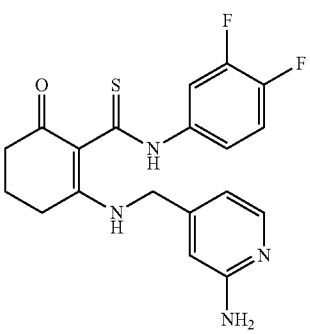 [SMILES: Nc1cc(CNC2=C(C(=S)Nc3ccc(F)c(F)c3)C(=O)CCC2)ccn1]

A solution of Intermediate 1-1-8 (1 g, 356 mmol) and 2-amino-4-(aminomethyl)pyridine (522 mg, 4.2 mmol) in EtOH:EtOAc (1:1, 40 mL) was heated at reflux under Dean-Stark conditions with 4 Å molecular sieves for 24 h. Concentrated and purified by silica chromatography to give the intermediate 1-2-42 (595 mg, 41%)

1H-NMR (400 MHz, DMSO-d6), d [ppm]=1.66-1.89 (2H), 2.43-2.48 (2H), 2.76 (2H), 4.63 (2H), 6.00 (2H), 6.37 (1H), 6.41-6.51 (1H), 7.20 (1H), 7.35-7.52 (1H), 7.62-7.74 (1H), 7.82-7.96 (1H), 13.73 (1H), 14.71 (1H)

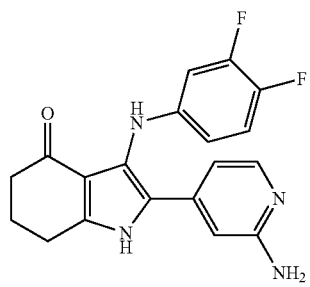

Using method F1: intermediate 1-2-42 (590 mg, 1.5 mmol) gave the desired product (241 mg, 42%) after silica chromatography.

1H-NMR (400 MHz, DMSO-d6), d [ppm]=1.93-2.15 (2H), 2.27-2.38 (2H), 2.83 (2H), 5.90 (2H), 6.26-6.37 (1H), 6.45 (1H), 6.54-6.63 (1H), 6.71 (1H), 6.97-7.16 (1H), 7.48 (1H), 7.77-7.86 (1H), 11.76 (1H)

Example 213 Preparation of 2-(2-fluoropyridin-4-yl)-6,6-dimethyl-3-(phenylamino)-1,5,6,7-tetrahydro-4H-indol-4-one

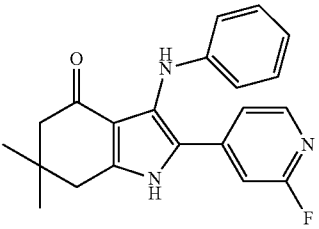 [SMILES: CC1(C)CC(=O)c2c([nH]c(-c3ccnc(F)c3)c2Nc2ccccc2)C1]

Synthesis of Example 213

Intermediate 1-2-43

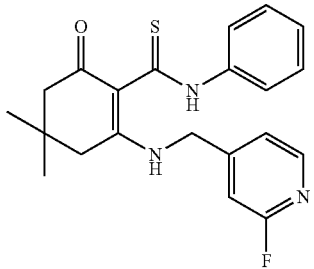 [SMILES: CC1(C)CC(=O)C(C(=S)Nc2ccccc2)=C(NCc2ccnc(F)c2)C1]

A solution of Intermediate 1-1-1 (250 mg, 908 μmol) and 2-fluoro-4-(aminomethyl)pyridine (229 mg, 1.8 mmol) in DMA (2 mL) was heated in a sealed tube at 120° C. for 90 mins using a microwave. Filtered and purified by preparative HPLC (basic method) to give the intermediate 1-2-43 (59 mg, 17%).

1H-NMR (400 MHz, DMSO-d6), Shift [ppm]=0.93-1.02 (5H), 2.38 (2H), 2.63 (2H), 4.91 (2H), 7.15 (1H), 7.19-7.28 (1H), 7.31-7.43 (3H), 7.47 (2H), 8.28 (1H), 13.82 (1H), 14.51 (1H).

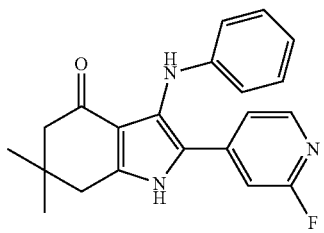 [SMILES: CC1(C)CC(=O)c2c([nH]c(-c3ccnc(F)c3)c2Nc2ccccc2)C1]

Using method F1 intermediate 1-2-43 (59 mg, 154 µmol) gave the desired product (4.1 mg, 8%) after preparative HPLC (acidic method).

1H-NMR (400 MHz, DMSO-d6), Shift [ppm]=1.07 (6H), 2.25 (2H), 2.76 (2H), 6.59 (2H), 6.65 (1H), 7.06 (2H), 7.15 (1H), 7.43 (1H), 7.54 (1H), 8.07 (1H), 11.97 (1H).

Example 214 Preparation of 2-(2,3-dichloropyridin-4-yl)-6,6-dimethyl-3-(phenylamino)-1,5,6,7-tetrahydro-4H-indol-4-one

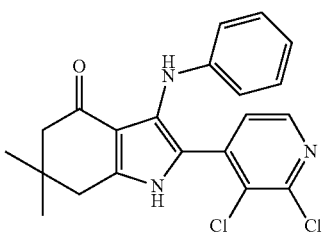

Synthesis of Example 214

Intermediate 1-2-44

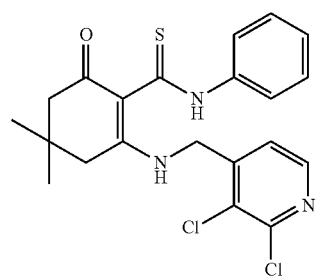 [SMILES: CC1(C)CC(=O)C(C(=S)Nc2ccccc2)=C(NCc2ccnc(Cl)c2Cl)C1]

A solution of intermediate 1-1-1 (3.37 g, 12.3 mmol) and 2,3-dichloro-4-(aminomethyl)pyridine (2.18 g, 10.2 mmol) with DBU (1.53 mL, 12.2 mmol) in EtOH:EtOAc (1:1, 100 mL) was heated at reflux for 96 h under Dean-Stark conditions with 4 Å molecular sieves. Concentrated and purified by silica chromatography to give the intermediate 1-2-44 (541 mg, 12%) and purification by preparative HPLC (basic method) to give Example 214 (63 mg, 1%).

1H-NMR (400 MHz, DMSO-d6), Shift [ppm]=0.96-1.04 (6H), 2.38 (2H), 2.64 (2H), 4.92 (2H), 7.20-7.26 (1H), 7.39 (2H), 7.45-7.52 (3H), 8.44 (1H), 13.62 (1H), 14.41 (1H).

Example 214: 1H-NMR (500 MHz, DMSO-d6), Shift [ppm]=1.08 (7H), 2.26 (2H), 2.73 (2H), 6.51 (2H), 6.56 (1H), 6.88-6.99 (2H), 7.32 (1H), 7.53 (1H), 8.20 (1H), 11.64 (1H).

Example 215 Preparation of 2-(2,5-dichloropyridin-4-yl)-6,6-dimethyl-3-(phenylamino)-1,5,6,7-tetrahydro-4H-indol-4-one

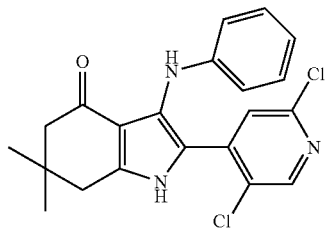 [SMILES: CC1(C)CC(=O)c2c([nH]c(-c3cc(Cl)ncc3Cl)c2Nc2ccccc2)C1]

A solution of intermediate 1-1-1 (2.97 g, 10.9 mmol) and 2,5-dichloro-4-(aminomethyl)pyridine hydrochloride (1.92 g, 9 mmol) with DBU (1.35 mL, 9 mmol) in EtOH:EtOAc (1:1, 140 mL) was heated at reflux for 96 h under Dean-Stark conditions with 4 Å molecular sieves. An additional portion of DBU (670 µL, 4.5 mmol) was added and heated as above for 24 h. Concentrated and purified by silica chromatography to give the desired product (1169 mg, 29%).

1H-NMR (400 MHz, DMSO-d6), Shift [ppm]=1.08 (6H), 2.27 (2H), 2.73 (2H), 6.48-6.62 (3H), 6.95 (2H), 7.40 (1H), 7.58 (1H), 8.39 (1H), 11.65 (1H).

Example 216 Preparation of 2-(2,6-dichloropyridin-4-yl)-6,6-dimethyl-3-(phenylamino)-1,5,6,7-tetrahydro-4H-indol-4-one

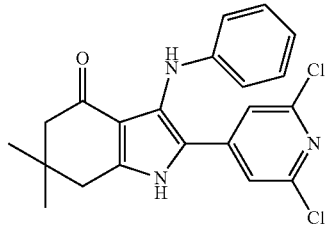 [SMILES: CC1(C)CC(=O)c2c([nH]c(-c3cc(Cl)nc(Cl)c3)c2Nc2ccccc2)C1]

Synthesis of Example 216

Intermediate 1-2-45

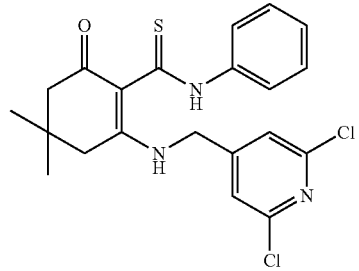 [SMILES: CC1(C)CC(=O)C(C(=S)Nc2ccccc2)=C(NCc2cc(Cl)nc(Cl)c2)C1]

A solution of intermediate 1-1-1 (3.4 g, 12.4 mmol) and 2,6-dichloro-4-(aminomethyl)pyridine (2 g, 11.3 mmol) in EtOH:EtOAc (1:1, 150 mL) was heated at reflux for 72 h under Dean-Stark conditions with 4 Å molecular sieves.

Concentrated and purified by silica chromatography to give the intermediate 1-2-45 (2550 mg, 52%).

1H-NMR (400 MHz, DMSO-d6), Shift [ppm]=0.95-1.03 (7H), 2.37 (2H), 2.60 (2H), 4.87 (2H), 7.19-7.29 (1H), 7.40 (2H), 7.50 (2H), 7.54 (2H), 13.47 (1H), 14.35 (1H).

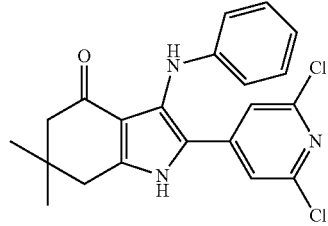 [SMILES: CC1(C)CC(=O)c2c([nH]c(-c3cc(Cl)nc(Cl)c3)c2Nc2ccccc2)C1]

Using method F1 intermediate 1-2-45 (2.41 g, 5.5 mmol) gave the desired product (460 mg, 21%) after silica chromatography.

1H-NMR (400 MHz, DMSO-d6), Shift [ppm]=1.02-1.11 (6H), 2.26 (2H), 2.75 (2H), 6.61 (2H), 6.70 (1H), 7.09 (2H), 7.50 (2H), 7.69 (1H), 12.02 (1H).

Example 217 Preparation of 2-(2,6-dichloropyridin-4-yl)-3-(phenylamino)-1,5,6,7-tetrahydro-4H-indol-4-one

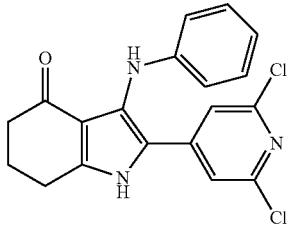 [SMILES: O=C1CCCc2[nH]c(-c3cc(Cl)nc(Cl)c3)c(Nc3ccccc3)c21]

Synthesis of Example 217

Intermediate 1-2-46

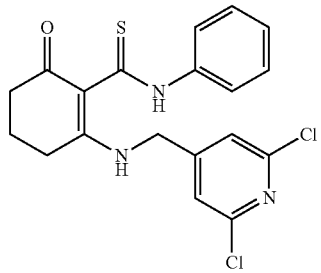 [SMILES: O=C1CCCC(NCc2cc(Cl)nc(Cl)c2)=C1C(=S)Nc1ccccc1]

A solution of intermediate 1-1-5 (3.07 g, 12.4 mmol) and 2,6-dichloro-4-(aminomethyl)pyridine (2 g, 11.3 mmol) in EtOH:EtOAc (1:1, 150 mL) was heated at reflux for 72 h under Dean-Stark conditions with 4 Å molecular sieves. Concentrated and purified by silica chromatography to give the intermediate 1-2-46 (2460 mg, 54%).

1H-NMR (400 MHz, DMSO-d6), Shift [ppm]=1.81 (2H), 2.44 (2H), 2.69 (2H), 4.83 (2H), 7.20-7.28 (1H), 7.35-7.44 (2H), 7.47-7.54 (2H), 7.56 (2H), 13.09 (1H), 14.24 (1H).

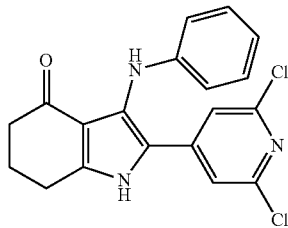 [SMILES: O=C1CCCc2[nH]c(-c3cc(Cl)nc(Cl)c3)c(Nc3ccccc3)c21]

Using method F1: intermediate 1-2-46 (2.4 g, 5.9 mmol) gave the desired product (850 mg, 39%) after silica chromatography.

1H-NMR (400 MHz, DMSO-d6), Shift [ppm]=1.97-2.14 (2H), 2.29-2.41 (2H), 2.87 (2H), 6.62 (2H), 6.71 (1H), 7.10 (2H), 7.48 (2H), 7.70 (1H), 12.06 (1H).

Example 218 Preparation of 2-(2,5-difluoropyridin-4-yl)-3-(phenylamino)-1,5,6,7-tetrahydro-4H-indol-4-one

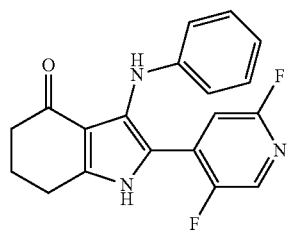 [SMILES: O=C1CCCc2[nH]c(-c3cc(F)ncc3F)c(Nc3ccccc3)c21]

Synthesis of Example 218

Intermediate 1-2-47

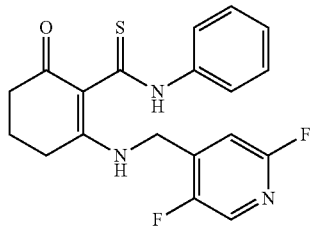 [SMILES: O=C1CCCC(NCc2cc(F)ncc2F)=C1C(=S)Nc1ccccc1]

To a suspension of 2,5-difluoro-4-(aminomethyl)pyridine hydrochloride (141 mg, 781 μmol) in EtOH (10 mL) was added Amberlyst 21 (381 mg) and stirred at RT for 1 h. The reaction was filtered and concentrated. The residue was dissolved in EtOH:EtOAc (1:1, 4 mL) and to this was added intermediate 1-1-5 (193 mg, 781 μmol) and the reaction was heated without stirring at reflux for 120 h with 4 Å molecular sieves. Concentrated and purified by silica chromatography to give the intermediate 1-2-47 (101 mg, 33%).

1H-NMR (400 MHz, DMSO-d6), Shift [ppm]=1.82 (2H), 2.40-2.46 (2H), 2.76 (2H), 4.89 (2H), 7.20-7.29 (2H), 7.34-7.43 (2H), 7.49 (2H), 8.29 (1H), 13.19 (1H), 14.27 (1H).

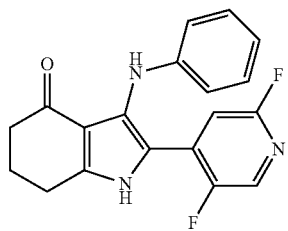 [SMILES: O=C1CCCc2[nH]c(-c3cc(F)ncc3F)c(Nc3ccccc3)c21]

Using method F1: intermediate 1-2-47 (95 mg, 254 µmol) gave the desired product (63 mg, 68%) after silica chromatography and preparative HPLC (basic method).

1H-NMR (400 MHz, DMSO-d6), Shift [ppm]=2.06 (2H), 2.33-2.43 (2H), 2.87 (2H), 6.54-6.69 (3H), 6.98-7.07 (3H), 7.68 (1H), 8.12-8.18 (1H), 11.68 (1H).

Example 219 Preparation of 2-(2-chloro-3-fluoro-pyridin-4-yl)-6,6-dimethyl-3-(phenylamino)-1,5,6,7-tetrahydro-4H-indol-4-one

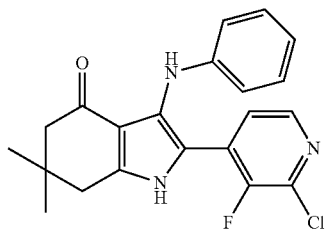 [SMILES: CC1(C)CC(=O)c2c([nH]c(-c3ccnc(Cl)c3F)c2Nc2ccccc2)C1]

Synthesis of Example 219

Intermediate 1-2-48

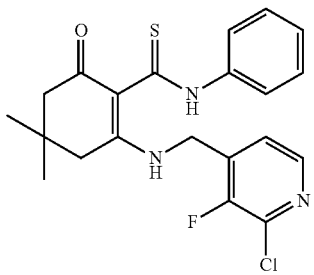 [SMILES: CC1(C)CC(=O)C(C(=S)Nc2ccccc2)=C(NCc2ccnc(Cl)c2F)C1]

A mixture of 2-chloro-3-fluoro-4-(aminomethyl)pyridine hydrochloride (150 mg, 761 µmol) in NH$_3$ in dioxane (4.6 mL) was stirred at RT for 30 mins, filtered and concentrated. The reside was dissolved in DMA (2.5 mL) and intermediate 1-1-1 (420 mg, 1.5 mmol) and in DMA (2 mL) was added was heated in a sealed tube at 130° C. for 30 mins using a microwave. Filtered and purified by silica chromatography to give the intermediate 1-2-48 (66 mg, 21%).

1H-NMR (400 MHz, DMSO-d6), Shift [ppm]=0.99 (6H), 2.38 (2H), 2.67 (3H), 4.96 (2H), 7.20-7.28 (1H), 7.35-7.44 (2H), 7.44-7.52 (3H), 8.33 (1H), 13.75 (1H), 14.47 (1H).

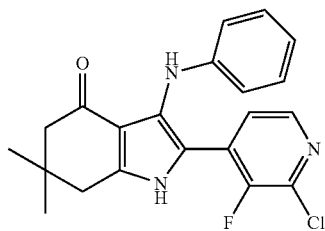 [SMILES: CC1(C)CC(=O)c2c([nH]c(-c3ccnc(Cl)c3F)c2Nc2ccccc2)C1]

To a solution of intermediate 1-2-48 (51 mg, 122 µmol) in MeOH (5.1 mL) was added urea hydrogen peroxide (17.2 mg, 183 µmol) and stirred at 50° C. for 16 h. Purification by preparative HPLC (basic method) gave the desired product (28 mg, 60%).

1H-NMR (400 MHz, DMSO-d6), Shift [ppm]=1.07 (6H), 2.26 (2H), 2.75 (2H), 6.53-6.59 (2H), 6.62 (1H), 6.96-7.07 (2H), 7.39 (1H), 7.64 (1H), 8.06 (1H), 11.70 (1H).

Example 220 Preparation of 2-(2-chloro-5-fluoro-pyridin-4-yl)-6,6-dimethyl-3-(phenylamino)-1,5,6,7-tetrahydro-4H-indol-4-one

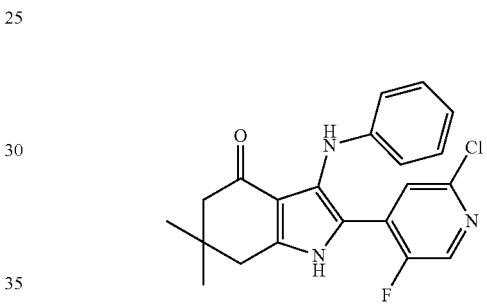

Synthesis of Example 220

Intermediate 1-2-49

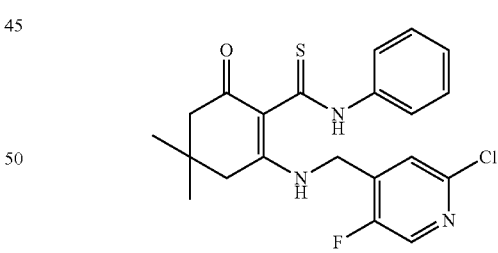

A mixture of 2-chloro-5-fluoro-4-(aminomethyl)pyridine hydrochloride (150 mg, 761 µmol) in NH$_3$ in dioxane (4.6 mL) was stirred at RT for 30 mins, filtered and concentrated. The reside was dissolved in DMA (2.5 mL) and intermediate 1-1-1 (420 mg, 1.5 mmol) and in DMA (2 mL) was added was heated in a sealed tube at 130° C. for 30 mins using a microwave. Filtered and purified by silica chromatography to give the intermediate 1-2-49 (93 mg, 29%).

1H-NMR (400 MHz, DMSO-d6), Shift [ppm]=0.98-1.02 (6H), 2.38 (2H), 2.64-2.73 (2H), 4.90 (2H), 7.19-7.28 (1H), 7.35-7.43 (2H), 7.48 (2H), 7.57 (1H), 8.50 (1H), 13.54 (1H), 14.39 (1H).

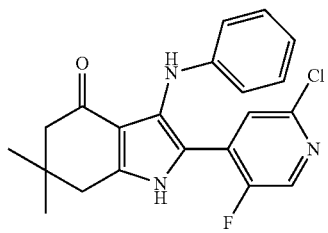 [SMILES: CC1(C)CC(=O)c2c([nH]c(-c3cc(Cl)ncc3F)c2Nc2ccccc2)C1]

Using method F1: intermediate 1-2-49 (85 mg, 203 μmol) gave the desired product (26 mg, 33%) after silica chromatography and preparative HPLC (basic method).

1H-NMR (400 MHz, DMSO-d6), Shift [ppm]=1.07 (6H), 2.27 (2H), 2.76 (2H), 6.59 (2H), 6.62-6.68 (1H), 6.98-7.07 (2H), 7.43 (1H), 7.68 (1H), 8.34 (1H), 11.65 (1H).

Example 221 Preparation of 2-(3H-imidazo[4,5-b]pyridin-7-yl)-6,6-dimethyl-3-(phenylamino)-1,5,6,7-tetrahydro-4H-indol-4-one

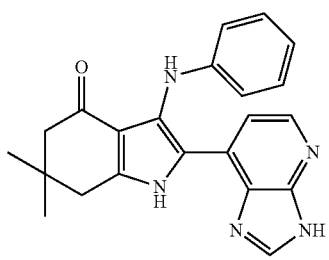 [SMILES: CC1(C)CC(=O)c2c([nH]c(-c3ccnc4[nH]cnc34)c2Nc2ccccc2)C1]

Synthesis of Example 221

Intermediate 1-2-50

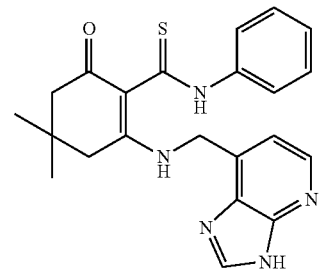 [SMILES: CC1(C)CC(=O)C(C(=S)Nc2ccccc2)=C(NCc2ccnc3[nH]cnc23)C1]

A solution of intermediate 1-1-1 (500 mg, 1.8 mmol) and 1-(3H-imidazo[4,5-b]pyridin-7-yl)methanamine (538 mg, 3.6 mmol) in DMA (10 mL) was heated in a sealed tube at 120° C. for 90 mins using a microwave. Filtered and purified by preparative HPLC (Column: XBridge C18 5 μm 100×30 mm; Solvent A: Water+0.1% HCO₂H; Solvent B: Acetonitrile; Gradient; 0.00-0.50 min 31% B (25-70 mL/min), 0.51-5.50 min 31-44% B: Flow: 70 mL/min) to give the intermediate 1-2-50 (199 mg, 27%).

1H-NMR (400 MHz, DMSO-d6), Shift [ppm]=0.91-1.03 (6H), 2.39 (2H), 2.79 (2H), 5.15 (2H), 7.16-7.29 (2H), 7.33-7.51 (4H), 8.37 (1H), 8.49 (1H), 13.20 (1H), 14.15 (1H), 14.66 (1H).

To a solution of intermediate 1-2-50 (70 mg, 173 μmol) in MeOH (5.1 mL) was added urea hydrogen peroxide (24.4 mg, 259 μmol) and stirred at 50° C. for 16 h. Purification by silica chromatography gave the desired product (47 mg, 73%)

1H-NMR (400 MHz, DMSO-d6), Shift [ppm]=1.09 (6H), 2.27 (2H), 2.85 (2H), 6.51-6.68 (3H), 7.02 (2H), 7.23 (1H), 8.17 (1H), 8.57 (1H), 8.72 (1H), 11.89 (1H), 13.31 (1H).

Example 222 Preparation of 2-(2-aminopyridin-4-yl)-3-[(3,4-difluorophenyl)amino]-6-(propan-2-yl)-1,5,6,7-tetrahydro-4H-indol-4-one

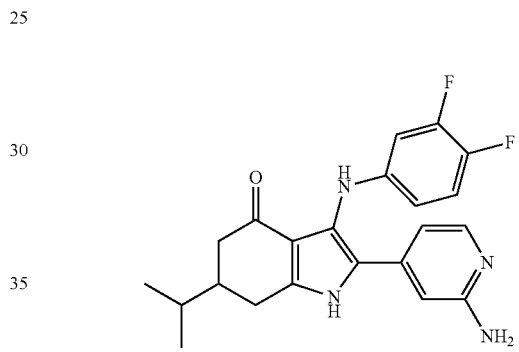

Synthesis of Example 222

Intermediate 1-2-51

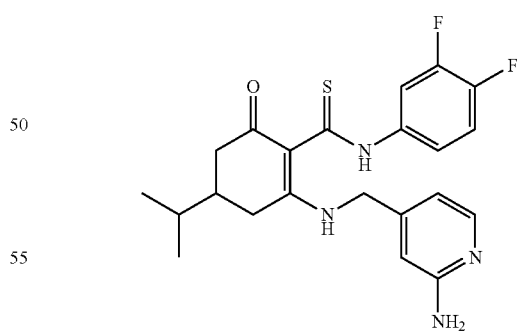

A solution of intermediate 1-1-12 (1 g, 3.1 mmol) and 2-amino-4-(aminomethyl)pyridine (454 mg, 3.7 mmol) in EtOH:EtOAc (1:1, 120 mL) was heated at reflux for 72 h under Dean-Stark conditions with 4 Å molecular sieves. Concentrated and purified by silica chromatography to give the intermediate 1-2-51 (649 mg, 49%).

1H-NMR (400 MHz, DMSO-d6), Shift [ppm]=0.85 (3H), 0.84 (3H), 1.52 (1H), 1.60-1.78 (1H), 2.21-2.48 (4H), 2.86

(1H), 4.59-4.73 (2H), 6.00 (2H), 6.38 (1H), 6.42-6.49 (1H), 7.12-7.23 (1H), 7.36-7.51 (1H), 7.67 (1H), 13.86 (1H), 14.74 (1H).

Intermediate 1-2-52

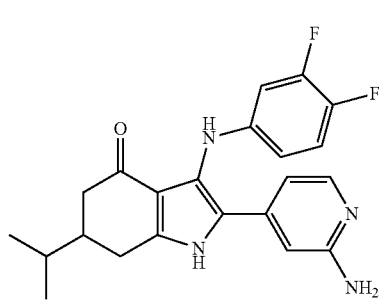 [SMILES: CC(C)C1CC(=O)c2c([nH]c(-c3ccnc(N)c3)c2Nc2ccc(F)c(F)c2)C1]

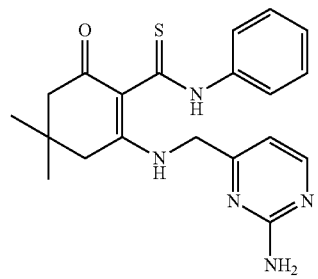

Using method F1: intermediate 1-2-51 (630 mg, 1.5 mmol) gave the desired product (221 mg, 38%) after silica chromatography.

1H-NMR (400 MHz, DMSO-d6), Shift [ppm]=0.94 (3H), 0.93 (3H), 1.65 (1H), 1.99 (1H), 2.16-2.31 (2H), 2.60 (1H), 2.88 (1H), 5.91 (2H), 6.27-6.35 (1H), 6.44 (1H), 6.55-6.61 (1H), 6.71 (1H), 7.06 (1H), 7.48 (1H), 7.80 (1H), 11.75 (1H).

Example 223 Preparation of 2-(2-aminopyrimidin-4-yl)-6,6-dimethyl-3-(phenylamino)-1,5,6,7-tetrahydro-4H-indol-4-one A solution of intermediate 1-1-1 (1.76 g, 6.4 mmol) and intermediate 1-11-4 (954 mg, 7.7 mmol) in EtOH:EtOAc (1:1, 80 mL) was heated at reflux for 72 h under Dean-Stark conditions with 4 Å molecular sieves. Concentrated and purified by silica chromatography to give the intermediate 1-2-52 (275 mg, 11%).

1H-NMR (400 MHz, DMSO-d6), Shift [ppm]=0.99 (5H), 2.38 (2H), 2.65-2.70 (2H), 4.64 (2H), 6.55 (1H), 6.64 (2H), 7.17-7.26 (1H), 7.37 (2H), 7.45 (2H), 8.23 (1H), 13.98 (1H), 14.65 (1H).

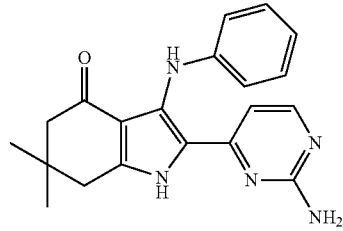 [SMILES: CC1(C)CC(=O)c2c([nH]c(-c3ccnc(N)n3)c2Nc2ccccc2)C1]

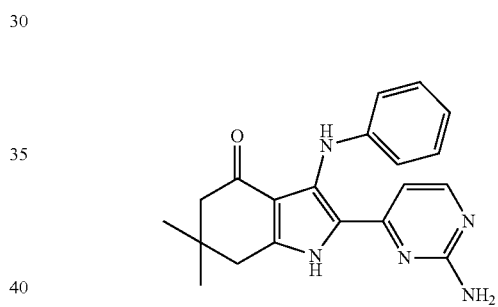

Synthesis of Example 223

Intermediate 1-11-4

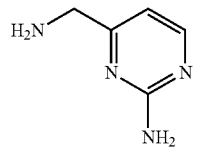

Using method F1 intermediate 1-2-52 (255 mg, 668 µmol) gave the desired product (68 mg, 29%) after preparative HPLC (basic method).

1H-NMR (400 MHz, DMSO-d6), Shift [ppm]=1.06 (6H), 2.24 (2H), 2.75 (2H), 6.45 (2H), 6.65 (1H), 6.69 (1H), 6.75 (2H), 7.07 (2H), 8.08 (1H), 8.62 (1H), 11.70 (1H).

Example 224 Preparation of 2-(6-aminopyrimidin-4-yl)-6,6-dimethyl-3-(phenylamino)-1,5,6,7-tetrahydro-4H-indol-4-one To a solution of 2-aminopyrimidine-4-carbonitrile (1 g, 8.3 mmol) in 7M NH₃ in MeOH (25.5 mL) was added Raney-Nickel (50% wet, 1.955 g, 33 mmol) and stirred at RT under an H₂ atmosphere (32.5 bar) for 22 h. The reaction was filtered and concentrated to give the intermediate 1-11-4 (954 mg, 92%) which was used without further purification.

1H-NMR (400 MHz, DMSO-d6), Shift [ppm]=3.55 (2H), 6.34-6.54 (2H), 6.63 (1H), 8.09-8.21 (1H).

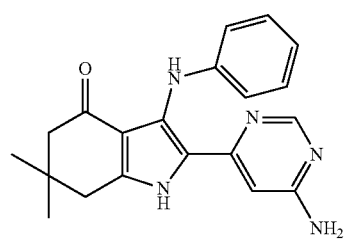

Synthesis of Example 224

Intermediate 1-2-53

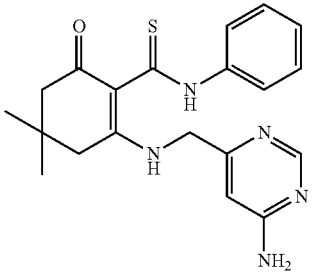 [SMILES: CC1(C)CC(=O)C(C(=S)Nc2ccccc2)=C(NCc2ccnc(N)n2)C1]

To a suspension of 6-(aminomethyl)pyrimidin-4-amine hydrochloride (1.47 g, 7.5 mmol) in EtOH (100 mL) was added Amberlyst 21 (5 g) and stirred at RT for 1 h. The reaction was filtered and concentrated. The residue was dissolved in EtOH:EtOAc (1:1, 50 mL) and to this was added intermediate 1-1-1 (896 mg, 3.3 mmol) and the reaction was heated without stirring at reflux for 24 h with 4 Å molecular sieves. DBU (243 μL, 1.63 mmol) added and heated for 72 h at reflux. Concentrated and purified by preparative HPLC (basic method) to give the intermediate 1-2-53 (161 mg, 13%).

1H-NMR (400 MHz, DMSO-d6), Shift [ppm]=1.00 (6H), 2.40 (2H), 2.65-2.74 (2H), 3.17 (2H), 4.63 (2H), 6.39 (1H), 6.97 (2H), 7.16-7.27 (1H), 7.38 (2H), 7.45 (2H), 8.32 (1H), 14.13 (1H), 14.73 (1H).

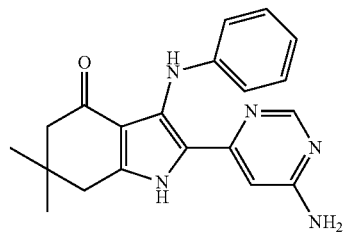 [SMILES: CC1(C)CC(=O)c2c([nH]c(-c3cc(N)ncn3)c2Nc2ccccc2)C1]

To a mixture of intermediate 1-1-1 (924 mg, 3.4 mmol), 6-(aminomethyl)pyrimidin-4-amine hydrochloride (794 mg, 4 mmol) and DBU (1.2 mL, 8 mmol) in EtOH:EtOAc (1:1.50 mL) was heated without stirring at reflux for 24 h with 4 Å molecular sieves. Concentrated and purified by preparative HPLC (Column: XBridge C18 5 μm 100×30 mm; Solvent A: Water+0.2% NH₄OH; Solvent B: Acetonitrile; Gradient; 0.00-0.50 min 30% B (25→70 mL/min), 0.51-5.50 min 30-40% B: Flow: 70 mL/min) to give the desired product (93 mg, 8%).

Alternatively, using method F1: intermediate 1-2-53 (115 mg, 301 μmol) gave the desired product (39 mg, 37%) after preparative HPLC (basic method).

1H-NMR (400 MHz, DMSO-d6), Shift [ppm]=1.04 (6H), 2.20 (2H), 2.72 (2H), 6.44 (1H), 6.58-6.71 (5H), 7.07 (2H), 7.77 (1H), 8.31 (1H), 11.82 (1H).

Example 225 Preparation of N-{4-[4-oxo-3-(phenylamino)-4,5,6,7-tetrahydro-1H-indol-2-yl]pyridin-2-yl}propanamide

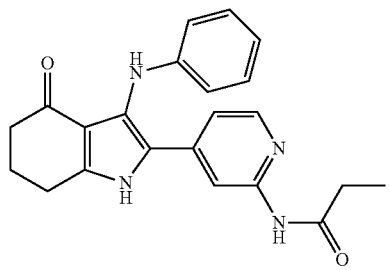 [SMILES: CCC(=O)Nc1cc(-c2[nH]c3c(c2Nc2ccccc2)C(=O)CCC3)ccn1]

To a solution of Example 139 (50 mg, 157 μmol) in pyridine (1 mL) was added propanoyl chloride (275 μL, 314 μmol) and stirred at RT for 16 h. Additional propanoyl chloride (27.5 μL, 314 μmol) added and stirred at RT for 72 h. Concentrated and purified by preparative HPLC (basic method) to give the desired product (24 mg, 41%).

1H-NMR (400 MHz, DMSO-d6), Shift [ppm]=1.06 (3H), 1.98-2.10 (2H), 2.29-2.41 (4H), 2.85 (2H), 6.50-6.65 (3H), 7.01 (2H), 7.13 (1H), 7.36 (1H), 8.05 (1H), 8.25 (1H), 10.27 (1H), 11.90 (1H).

Example 226 Preparation of N-{4-[4-oxo-3-(phenylamino)-4,5,6,7-tetrahydro-1H-indol-2-yl]pyridin-2-yl}butanamide

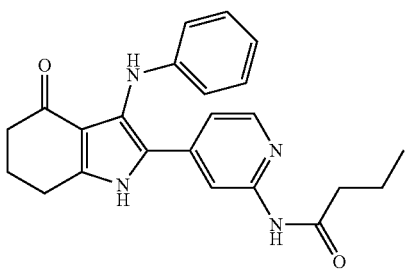 [SMILES: CCCC(=O)Nc1cc(-c2[nH]c3c(c2Nc2ccccc2)C(=O)CCC3)ccn1]

To a solution of Example 139 (50 mg, 157 μmol) in pyridine (1 mL) was added butanoyl chloride (32 μL, 314 μmol) and stirred at RT for 16 h. Concentrated and purified by preparative HPLC (basic method) to give the desired product (8 mg, 13%).

1H-NMR (400 MHz, DMSO-d6), Shift [ppm]=0.90 (3H), 1.59 (2H), 1.98-2.17 (2H), 2.26-2.39 (4H), 2.86 (2H), 6.52-6.64 (3H), 6.97-7.05 (2H), 7.14 (1H), 7.36 (1H), 8.06 (1H), 8.24 (1H), 10.26 (1H), 11.90 (1H).

Example 227 Preparation of 2,2-dimethyl-N-{4-[4-oxo-3-(phenylamino)-4,5,6,7-tetrahydro-1H-indol-2-yl]pyridin-2-yl}propanamide

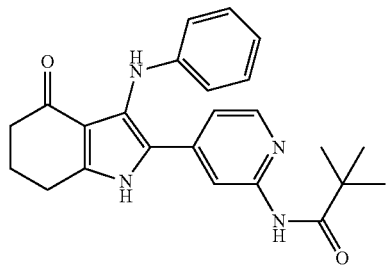 [SMILES: CC(C)(C)C(=O)Nc1cc(-c2[nH]c3c(c2Nc2ccccc2)C(=O)CCC3)ccn1]

To a solution of Example 139 (50 mg, 157 μmol) in pyridine (1 mL) was added 2,2-dimethylpropanoyl chloride (39 μL, 314 μmol) and stirred at RT for 16 h. Additional 2,2-dimethylpropanoyl chloride (39 μL, 314 μmol) added and stirred at RT for 72 h. Concentrated and purified by preparative HPLC (basic method) to give the desired product (20 mg, 32%).

1H-NMR (400 MHz, DMSO-d6), Shift [ppm]=1.18-1.28 (8H), 2.05 (2H), 2.33 (2H), 2.86 (2H), 6.53-6.65 (3H), 7.01 (2H), 7.16 (1H), 7.37 (1H), 8.07 (1H), 8.17-8.20 (1H), 9.60 (1H), 11.89 (1H).

Example 228 Preparation of 1-methyl-N-{4-[4-oxo-3-(phenylamino)-4,5,6,7-tetrahydro-1H-indol-2-yl]pyridin-2-yl}cyclopropanecarboxamide

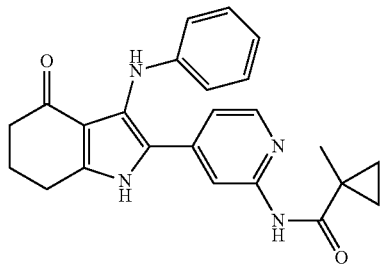 [SMILES: CC1(C(=O)Nc2cc(-c3[nH]c4c(c3Nc3ccccc3)C(=O)CCC4)ccn2)CC1]

To a solution of Example 139 (50 mg, 157 μmol) in pyridine (1 mL) was added 1-methylcyclopropanecarbonyl chloride (37 μL, 314 μmol) and stirred at RT for 16 h. Additional 1-methylcyclopropanecarbonyl chloride (37 μL, 314 μmol) added and stirred at RT for 72 h. Concentrated and purified by preparative HPLC (basic method) to give the desired product (21 mg, 33%).

1H-NMR (400 MHz, DMSO-d6), Shift [ppm]=0.61-0.70 (2H), 1.06-1.15 (2H), 1.36-1.43 (3H), 1.99-2.09 (2H), 2.27-2.38 (2H), 2.85 (2H), 6.52-6.66 (3H), 7.01 (2H), 7.16 (1H), 7.36 (1H), 8.08 (1H), 8.12-8.16 (1H), 9.34 (1H), 11.88 (1H).

Example 229 Preparation of N-{4-[4-oxo-3-(phenylamino)-4,5,6,7-tetrahydro-1H-indol-2-yl]pyridin-2-yl}cyclobutanecarboxamide

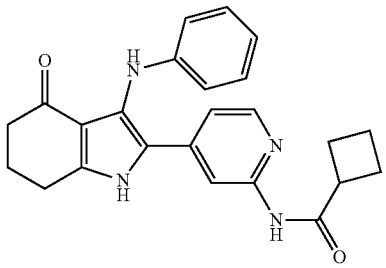 [SMILES: O=C1CCCc2[nH]c(-c3ccnc(NC(=O)C4CCC4)c3)c(Nc3ccccc3)c21]

To a solution of Example 139 (50 mg, 157 μmol) in pyridine (1 mL) was added cyclobutanecarbonyl chloride (36 μL, 314 μmol) and stirred at RT for 16 h. Concentrated and purified by preparative HPLC (basic method) to give the desired product (18 mg, 29%).

1H-NMR (400 MHz, DMSO-d6), Shift [ppm]=1.74-2.00 (2H), 2.00-2.14 (4H), 2.14-2.29 (2H), 2.33 (2H), 2.86 (2H), 6.45-6.73 (3H), 7.01 (2H), 7.13 (1H), 7.37 (1H), 8.04 (1H), 8.26 (1H), 10.14 (1H), 11.91 (1H).

Example 230 Preparation of 2-methyl-N-{4-[4-oxo-3-(phenylamino)-4,5,6,7-tetrahydro-1H-indol-2-yl]pyridin-2-yl}propanamide

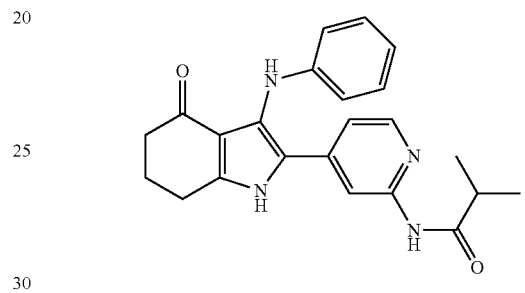

Using Method G2: Example 139 (100 mg, 314 μmol) gave the desired product (20 mg, 16%) after preparative HPLC (basic method).

1H-NMR (400 MHz, DMSO-d6), Shift [ppm]=1.08 (6H), 2.05 (2H), 2.33 (2H), 2.73 (1H), 2.85 (2H), 6.51-6.64 (3H), 6.96-7.05 (2H), 7.13 (1H), 7.38 (1H), 8.05 (1H), 8.25 (1H), 10.29 (1H), 11.92 (1H).

Example 231 Preparation of 2-cyclopropyl-N-{4-[4-oxo-3-(phenylamino)-4,5,6,7-tetrahydro-1H-indol-2-yl]pyridin-2-yl}acetamide

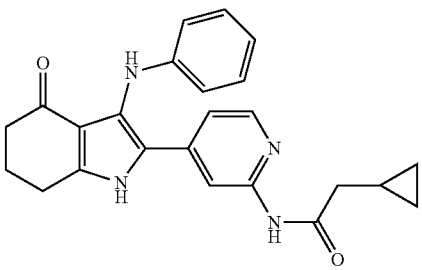 [SMILES: O=C(CC1CC1)Nc1cc(-c2[nH]c3c(c2Nc2ccccc2)C(=O)CCC3)ccn1]

Using Method G2: Example 139 (50 mg, 157 μmol) gave the desired product (29 mg, 44%) after preparative HPLC (basic method).

1H-NMR (400 MHz, DMSO-d6), Shift [ppm]=0.11-0.25 (2H), 0.41-0.52 (2H), 0.97-1.12 (1H), 1.98-2.11 (2H), 2.26 (2H), 2.33 (2H), 2.79-2.92 (2H), 6.52-6.63 (3H), 6.96-7.05 (2H), 7.14 (1H), 7.37 (1H), 8.03-8.08 (1H), 8.25-8.30 (1H), 10.21 (1H), 11.92 (1H).

Example 232 Preparation of 2,2-dimethyl-N-{4-[4-oxo-3-(phenylamino)-4,5,6,7-tetrahydro-1H-indol-2-yl]pyridin-2-yl}cyclopropanecarboxamide

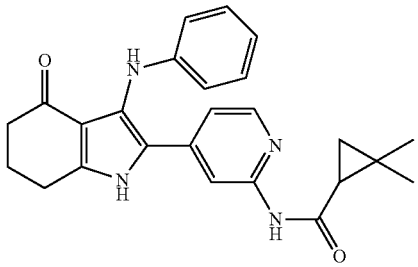 [SMILES: CC1(C)CC1C(=O)Nc1cc(-c2[nH]c3c(c2Nc2ccccc2)C(=O)CCC3)ccn1]

Using Method G2: Example 139 (100 mg, 314 µmol) gave the desired product (46 mg, 35%) after preparative HPLC (basic method).
1H-NMR (400 MHz, DMSO-d6), Shift [ppm]=0.79 (1H), 0.97 (1H), 1.13 (5H), 1.85 (1H), 1.98-2.16 (2H), 2.32 (2H), 2.85 (2H), 6.50-6.66 (3H), 6.95-7.04 (2H), 7.13 (1H), 7.37 (1H), 8.06 (1H), 8.22 (1H), 10.45 (1H), 11.88 (1H).

Example 233 Preparation of N-{4-[4-oxo-3-(phenylamino)-4,5,6,7-tetrahydro-1H-indol-2-yl]pyridin-2-yl}-2-phenylacetamide

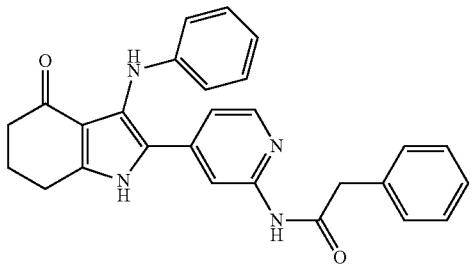 [SMILES: O=C(Cc1ccccc1)Nc1cc(-c2[nH]c3c(c2Nc2ccccc2)C(=O)CCC3)ccn1]

Using Method G2: Example 139 (100 mg, 314 µmol) gave the desired product (41 mg, 34%) after preparative HPLC (basic method).
1H-NMR (400 MHz, DMSO-d6), Shift [ppm]=2.01-2.12 (2H), 2.30-2.39 (2H), 2.43 (2H), 2.85-2.92 (2H), 6.21 (1H), 6.62-6.70 (3H), 7.08 (2H), 7.19-7.30 (2H), 7.53-7.64 (1H), 8.10 (1H), 12.12 (1H).

Example 234 Preparation of N-{4-[4-oxo-3-(phenylamino)-4,5,6,7-tetrahydro-1H-indol-2-yl]pyridin-2-yl}but-3-ynamide

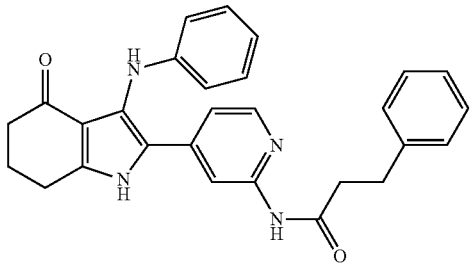 [SMILES: O=C(CCc1ccccc1)Nc1cc(-c2[nH]c3c(c2Nc2ccccc2)C(=O)CCC3)ccn1]

Using Method G2: Example 139 (100 mg, 314 µmol) gave the desired product (41 mg, 34%) after preparative HPLC (basic method).
1H-NMR (400 MHz, DMSO-d6), Shift [ppm]=2.01-2.12 (2H), 2.30-2.39 (2H), 2.43 (2H), 2.85-2.92 (2H), 6.21 (1H), 6.62-6.70 (3H), 7.08 (2H), 7.19-7.30 (2H), 7.53-7.64 (1H), 8.10 (1H), 12.12 (1H).

Example 235 Preparation of N-{4-[4-oxo-3-(phenylamino)-4,5,6,7-tetrahydro-1H-indol-2-yl]pyridin-2-yl}-3-phenylpropanamide

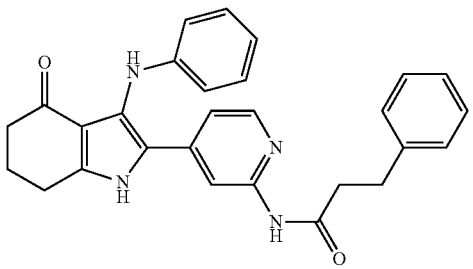 [SMILES: O=C(CCc1ccccc1)Nc1cc(-c2[nH]c3c(c2Nc2ccccc2)C(=O)CCC3)ccn1]

Using Method G2: Example 139 (100 mg, 314 µmol) gave the desired product (30 mg, 21%) after preparative HPLC (basic method).
1H-NMR (400 MHz, DMSO-d6), Shift [ppm]=1.98-2.10 (2H), 2.33 (2H), 2.63-2.75 (2H), 2.80-2.96 (4H), 6.51-6.65 (3H), 6.96-7.06 (2H), 7.11-7.22 (2H), 7.22-7.33 (4H), 7.38 (1H), 8.06 (1H), 8.26 (1H), 10.36 (1H), 11.92 (1H).

Example 236 Preparation of N-{4-[4-oxo-3-(phenylamino)-4,5,6,7-tetrahydro-1H-indol-2-yl]pyridin-2-yl}-4-phenylbutanamide

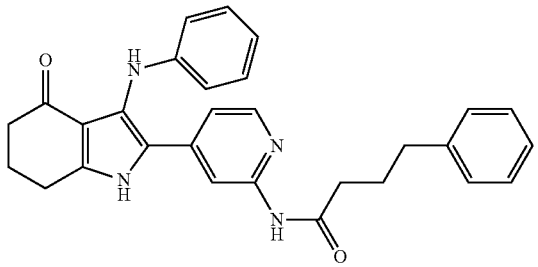 [SMILES: O=C(CCCc1ccccc1)Nc1cc(-c2[nH]c3c(c2Nc2ccccc2)C(=O)CCC3)ccn1]

Using Method G2: Example 139 (100 mg, 314 µmol) gave the desired product (30 mg, 21%) after preparative HPLC (basic method).
1H-NMR (400 MHz, DMSO-d6), Shift [ppm]=1.86 (2H), 1.98-2.12 (2H), 2.33 (2H), 2.39 (2H), 2.56-2.62 (2H), 2.86 (2H), 6.49-6.64 (3H), 7.00 (2H), 7.12-7.24 (4H), 7.26-7.35 (2H), 7.38 (1H), 8.06 (1H), 8.25 (1H), 10.32 (1H), 11.92 (1H).

Example 237 Preparation of 2-methyl-N-{4-[4-oxo-3-(phenylamino)-4,5,6,7-tetrahydro-1H-indol-2-yl]pyridin-2-yl}cyclopropanecarboxamide

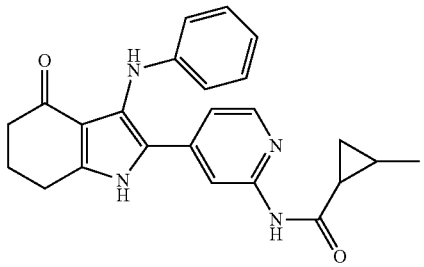 [SMILES: CC1CC1C(=O)Nc1cc(-c2[nH]c3c(c2Nc2ccccc2)C(=O)CCC3)ccn1]

Using Method G2: Example 139 (100 mg, 314 μmol) gave the desired product (20 mg, 16%) after preparative HPLC (basic method).

1H-NMR (400 MHz, DMSO-d6), Shift [ppm]=0.65 (1H), 0.95-1.04 (1H), 1.04-1.11 (3H), 1.17-1.30 (1H), 1.74 (1H), 1.99-2.11 (2H), 2.26-2.37 (2H), 2.80-2.90 (2H), 6.50-6.67 (3H), 6.95-7.06 (2H), 7.06-7.19 (1H), 7.33-7.41 (1H), 8.02-8.09 (1H), 8.20-8.24 (1H), 10.47-10.63 (1H), 11.88 (1H).

Example 238 Preparation of N-{4-[4-oxo-3-(phenylamino)-4,5,6,7-tetrahydro-1H-indol-2-yl]pyridin-2-yl}benzamide

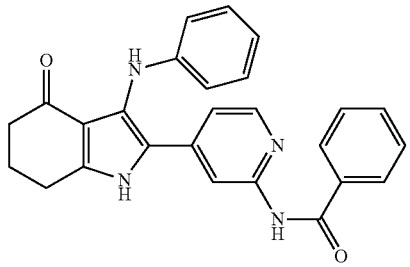 [SMILES: O=C(Nc1cc(-c2[nH]c3c(c2Nc2ccccc2)C(=O)CCC3)ccn1)c1ccccc1]

Using Method G2: Example 139 (50 mg, 157 μmol) in pyridine (1 mL) was added benzoyl chloride (36 μL, 314 μmol) and stirred at RT for 16 h. Additional benzoyl chloride (36 μL, 314 μmol) added and stirred at RT for 72 h. Concentrated and purified by preparative HPLC (basic method) to give the desired product (20 mg, 30%).

1H-NMR (400 MHz, DMSO-d6), Shift [ppm]=1.99-2.10 (2H), 2.28-2.39 (2H), 2.88 (2H), 6.55-6.66 (3H), 7.03 (2H), 7.23 (1H), 7.40 (1H), 7.51 (2H), 7.56-7.63 (1H), 7.98-8.05 (2H), 8.16 (1H), 8.31-8.38 (1H), 10.62 (1H), 11.95 (1H).

Example 239 Preparation of N-{4-[4-oxo-3-(phenylamino)-4,5,6,7-tetrahydro-1H-indol-2-yl]pyridin-2-yl}-2-phenylcyclopropanecarboxamide

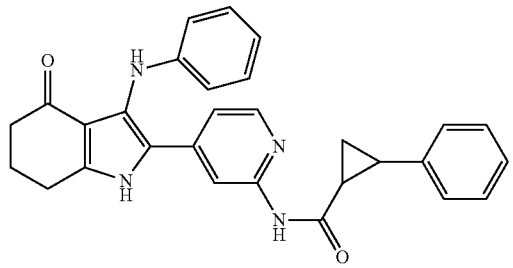 [SMILES: O=C1CCCc2[nH]c(-c3ccnc(NC(=O)C4CC4c4ccccc4)c3)c(Nc3ccccc3)c21]

Using Method G2: Example 139 (100 mg, 314 μmol) gave the desired product (30 mg, 21%) after preparative HPLC (basic method).

1H-NMR (400 MHz, DMSO-d6), Shift [ppm]=1.36 (1H), 1.42-1.53 (1H), 1.97-2.10 (2H), 2.24-2.40 (4H), 2.86 (2H), 6.48-6.67 (3H), 7.02 (2H), 7.12-7.24 (3H), 7.25-7.34 (2H), 7.39 (1H), 8.06 (1H), 8.25 (1H), 10.67 (1H), 11.91 (1H).

Example 240 Preparation of N-{4-[6,6-dimethyl-4-oxo-3-(phenylamino)-4,5,6,7-tetrahydro-1H-indol-2-yl]pyridin-2-yl}-N-methylacetamide

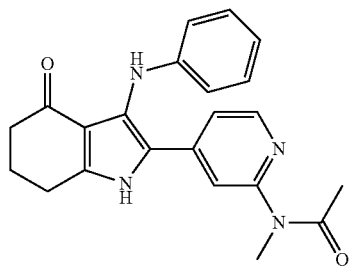 [SMILES: CC(=O)N(C)c1cc(-c2[nH]c3c(c2Nc2ccccc2)C(=O)CCC3)ccn1]

Using Method G2: Example 145 (26 mg, 72 μmol) pyridine (58 μL, 721 μmol) in THF (2 mL) was added acetyl chloride (10.3 μL, 144 μmol) and stirred at RT for 1 h. Additional acetyl chloride (10.3 μL, 144 μmol) was added and stirred at RT for 120 h. Additional acetyl chloride (10.3 μL, 144 μmol) and a crystal of DMAP were added and stirred at 60° C. for 4 h. Concentrated and purified by silica chromatography to give the desired product (16 mg, 55%).

1H-NMR (400 MHz, DMSO-d6), Shift [ppm]=1.07 (6H), 1.76 (3H), 2.25 (2H), 2.76 (2H), 3.00 (3H), 6.55-6.66 (3H), 7.05 (2H), 7.33-7.38 (1H), 7.42 (1H), 7.53 (1H), 8.32 (1H), 11.90 (1H).

Example 241 Preparation of 2-fluoro-N-{4-[4-oxo-3-(phenylamino)-4,5,6,7-tetrahydro-1H-indol-2-yl]pyridin-2-yl}propanamide

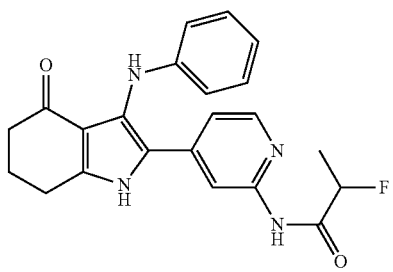 [SMILES: CC(F)C(=O)Nc1cc(-c2[nH]c3c(c2Nc2ccccc2)C(=O)CCC3)ccn1]

Using Method G2: Example 139 (50 mg, 157 μmol) gave the desired product (14 mg, 22%) after preparative HPLC (basic method).

1H-NMR (400 MHz, DMSO-d6), Shift [ppm]=1.45 (1H), 1.52 (1H), 1.94-2.16 (2H), 2.26-2.41 (2H), 2.77-2.93 (2H), 6.52-6.69 (3H), 7.01 (2H), 7.21 (1H), 7.40 (1H), 8.11 (1H), 8.20 (1H), 10.34 (1H), 11.95 (1H).

Example 242 Preparation of 2-fluoro-2-methyl-N-{4-[4-oxo-3-(phenylamino)-4,5,6,7-tetrahydro-1H-indol-2-yl]pyridin-2-yl}propanamide

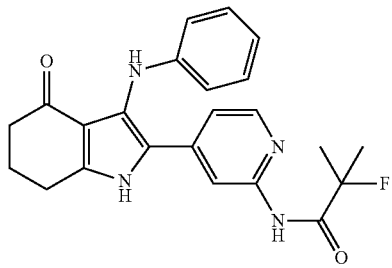 [SMILES: CC(C)(F)C(=O)Nc1cc(-c2[nH]c3c(c2Nc2ccccc2)C(=O)CCC3)ccn1]

Using Method G2: Example 139 (50 mg, 157 µmol) gave the desired product (7 mg, 11%) after preparative HPLC (basic method).
1H-NMR (400 MHz, DMSO-d6), Shift [ppm]=1.54 (3H), 1.60 (3H), 2.01-2.10 (2H), 2.30-2.37 (2H), 2.86 (2H), 6.51-6.68 (3H), 7.02 (2H), 7.20-7.26 (1H), 7.41 (1H), 8.10-8.15 (2H), 9.65 (1H), 11.93 (1H).

Example 243 Preparation of 3-hydroxy-2,2-dimethyl-N-{4-[4-oxo-3-(phenylamino)-4,5,6,7-tetrahydro-1H-indol-2-yl]pyridin-2-yl}propanamide

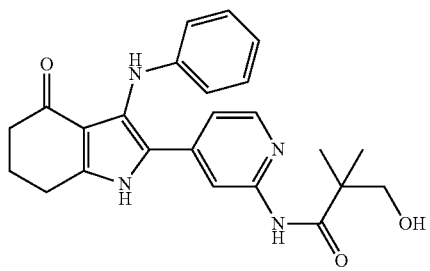 [SMILES: CC(C)(CO)C(=O)Nc1cc(-c2[nH]c3c(c2Nc2ccccc2)C(=O)CCC3)ccn1]

Using Method G2: Example 139 (50 mg, 157 µmol) gave the desired product (5 mg, 7%) after preparative HPLC (basic method).
1H-NMR (400 MHz, DMSO-d6), Shift [ppm]=1.05-1.22 (6H), 1.99-2.12 (2H), 2.33 (2H), 2.86 (2H), 3.50-3.56 (2H), 5.65 (1H), 6.52-6.65 (3H), 6.96-7.06 (2H), 7.13 (1H), 7.37 (1H), 8.03 (1H), 8.24 (1H), 9.84 (1H), 11.91 (1H).

Example 244 Preparation of 2-(methylsulfanyl)-N-{4-[4-oxo-3-(phenylamino)-4,5,6,7-tetrahydro-1H-indol-2-yl]pyridin-2-yl}acetamide

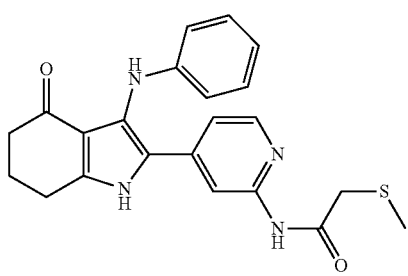 [SMILES: CSCC(=O)Nc1cc(-c2[nH]c3c(c2Nc2ccccc2)C(=O)CCC3)ccn1]

Using Method G2: Example 139 (50 mg, 157 µmol) gave the desired product (19 mg, 28%) after preparative HPLC (basic method).
1H-NMR (400 MHz, DMSO-d6), Shift [ppm]=1.98-2.08 (2H), 2.14 (3H), 2.28-2.38 (2H), 2.86 (2H), 6.51-6.64 (3H), 7.01 (2H), 7.17 (1H), 7.38 (1H), 8.09 (1H), 8.22 (1H), 10.38 (1H), 11.93 (1H).

Example 245 Preparation of 2-cyano-2-methyl-N-{4-[4-oxo-3-(phenylamino)-4,5,6,7-tetrahydro-1H-indol-2-yl]pyridin-2-yl}propanamide

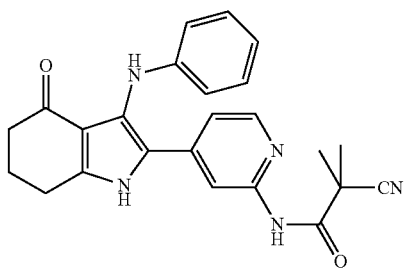 [SMILES: CC(C)(C#N)C(=O)Nc1cc(-c2[nH]c3c(c2Nc2ccccc2)C(=O)CCC3)ccn1]

Using Method G2: Example 139 (50 mg, 157 µmol) gave the desired product (10 mg, 14%) after preparative HPLC (basic method).
1H-NMR (400 MHz, DMSO-d6), Shift [ppm]=1.66 (5H), 1.99-2.12 (2H), 2.27-2.40 (2H), 2.78-2.93 (2H), 6.52-6.65 (3H), 6.97-7.06 (2H), 7.23 (1H), 7.43 (1H), 8.06-8.20 (1H), 10.49 (1H), 11.96 (1H).

Example 246 Preparation of 1-cyano-N-{4-[4-oxo-3-(phenylamino)-4,5,6,7-tetrahydro-1H-indol-2-yl]pyridin-2-yl}cyclopropanecarboxamide

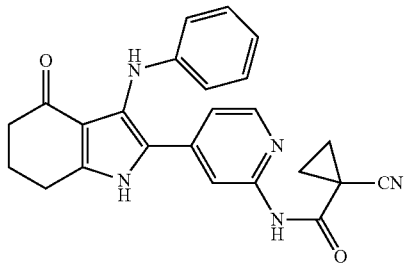 [SMILES: N#CC1(C(=O)Nc2cc(-c3[nH]c4c(c3Nc3ccccc3)C(=O)CCC4)ccn2)CC1]

Using Method G2: Example 139 (50 mg, 157 µmol) gave the desired product (9 mg, 15%) after preparative HPLC (basic method).
1H-NMR (400 MHz, DMSO-d6), Shift [ppm]=1.68 (4H), 1.98-2.12 (2H), 2.27-2.38 (2H), 2.78-2.91 (2H), 6.51-6.66 (3H), 7.02 (2H), 7.22 (1H), 7.41 (1H), 8.04 (1H), 8.13 (1H), 10.10 (1H), 11.93 (1H).

Example 247 Preparation of 3,3,3-trifluoro-2-methyl-N-{4-[4-oxo-3-(phenylamino)-4,5,6,7-tetrahydro-1H-indol-2-yl]pyridin-2-yl}propanamide

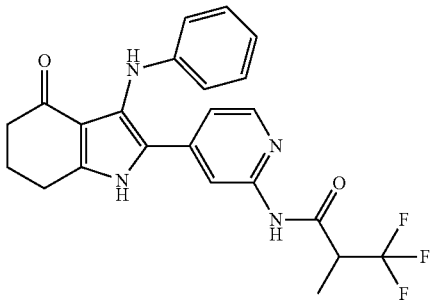 [SMILES: CC(C(=O)Nc1cc(-c2[nH]c3c(c2Nc2ccccc2)C(=O)CCC3)ccn1)C(F)(F)F]

Using Method G2: Example 139 (100 mg, 314 µmol) gave the desired product (20 mg, 14%) after preparative HPLC (basic method).
1H-NMR (400 MHz, DMSO-d6), Shift [ppm]=1.34 (2H), 2.05 (2H), 2.30-2.37 (3H), 2.86 (2H), 6.52-6.64 (2H), 6.98-7.05 (2H), 7.19 (1H), 7.41 (1H), 8.10 (1H), 8.22 (1H), 10.76 (1H).

Example 248 Preparation of 2-(methylsulfonyl)-N-{4-[4-oxo-3-(phenylamino)-4,5,6,7-tetrahydro-1H-indol-2-yl]pyridin-2-yl}acetamide

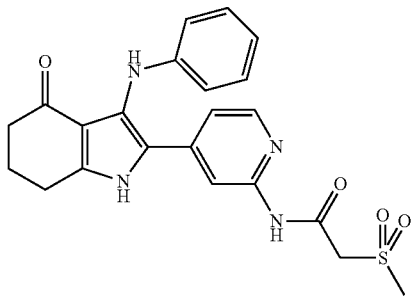 [SMILES: CS(=O)(=O)CC(=O)Nc1cc(-c2[nH]c3c(c2Nc2ccccc2)C(=O)CCC3)ccn1]

Using Method G2: Example 139 (50 mg, 157 µmol) gave the desired product (12 mg, 17%) after preparative HPLC (basic method).
1H-NMR (400 MHz, DMSO-d6), Shift [ppm]=2.01-2.10 (2H), 2.30-2.36 (2H), 2.87 (2H), 3.16 (2H), 4.39 (2H), 6.52-6.65 (3H), 7.02 (2H), 7.21 (1H), 7.40 (1H), 8.12 (1H), 8.23 (1H), 10.75 (1H), 11.96 (1H).

Example 249 Preparation of rel-(R,S/S,R)-2-fluoro-N-{4-[4-oxo-3-(phenylamino)-4,5,6,7-tetrahydro-1H-indol-2-yl]pyridin-2-yl}cyclopropanecarboxamide

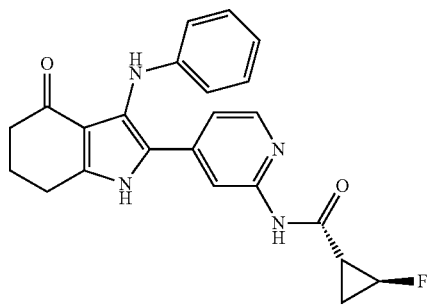

trans-racemic

Using Method G2: Example 139 (50 mg, 157 µmol) gave the desired racemic trans isomer product (27 mg, 41%) after preparative HPLC (basic method).
1H-NMR (400 MHz, DMSO-d6), Shift [ppm]=1.15-1.26 (1H), 1.43-1.62 (1H), 1.96-2.12 (2H), 2.26-2.37 (3H), 2.42-2.48 (2H), 2.52-2.59 (2H), 2.84 (2H), 4.68-4.83 (1H), 4.83-4.98 (1H), 6.51-6.63 (3H), 7.01 (2H), 7.15 (1H), 7.37 (1H), 8.09 (1H), 8.16 (1H), 10.79 (1H), 11.89 (1H).

Example 250 and Example 251 Separation of the Enantiomers (R,S/S,R)-2-fluoro-N-{4-[4-oxo-3-(phenylamino)-4,5,6,7-tetrahydro-1H-indol-2-yl]pyridin-2-yl}cyclopropanecarboxamide Example 249 (16 mg) was purified by chiral preparative HPLC purification (Column: Chiralpak IA 5µ 250×30 mm; Solvent A: Methanol+0.1% Diethylamine; Solvent B: Ethanol; Gradient: isocratic 50% A: 50% B; Flow: 25 mL/min) gave (Enantiomer 1 Example 250-5 mg, 30%>95% e.e.) and (Enantiomer 2 Example 251-5 mg, 30% 93% e.e). Chiral analytics: Column: Chiralpak IA 3µ 100×4.6 mm; Solvent A: Methanol+0.1% Diethylamine; Solvent B: Ethanol; Gradient: isocratic 50% A: 50% B; Flow: 1 mL/min)

Example 252 Preparation of rel-(S,S/R,R)-2-fluoro-N-{4-[4-oxo-3-(phenylamino)-4,5,6,7-tetrahydro-1H-indol-2-yl]pyridin-2-yl}cyclopropanecarboxamide

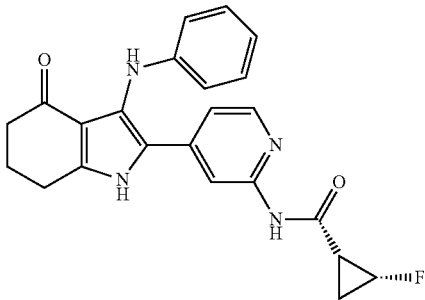

cis-racemic

Using Method G2: Example 139 (50 mg, 157 µmol) gave the desired racemic cis isomer product (25 mg, 37%) after preparative HPLC (basic method).
1H-NMR (400 MHz, DMSO-d6), Shift [ppm]=1.16 (1H), 1.53-1.71 (1H), 1.99-2.10 (2H), 2.13-2.25 (1H), 2.28-2.38 (2H), 2.85 (2H), 6.52-6.66 (3H), 7.01 (2H), 7.14 (1H), 7.37 (1H), 8.07 (1H), 8.25 (1H), 10.69 (1H), 11.93 (1H).

Example 253 Preparation of (1R,2R)-2-fluoro-N-{4-[4-oxo-3-(phenylamino)-4,5,6,7-tetrahydro-1H-indol-2-yl]pyridin-2-yl}cyclopropanecarboxamide

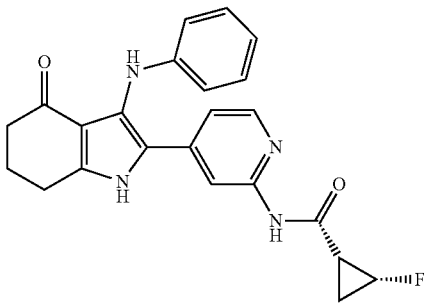

Using Method G2: Example 139 (100 mg, 314 µmol) with the (1R,2R)-2-fluorocyclopropanecarboxylic acid gave the desired cis product (59 mg, 45%) after preparative HPLC (basic method).

1H-NMR (400 MHz, DMSO-d6), Shift [ppm]=1.05-1.33 (1H), 1.51-1.73 (1H), 1.96-2.13 (2H), 2.13-2.28 (1H), 2.28-2.37 (2H), 2.77-2.91 (2H), 6.49-6.66 (2H), 6.94-7.07 (2H), 7.14 (1H), 7.37 (1H), 8.07 (1H), 8.25 (1H), 10.71 (1H), 11.94 (1H).

Optical rotation: 10 mg/ml in DMSO=43.3°+/−1.81°

Example 254 Preparation of (S,R)—N-{4-[6,6-dimethyl-4-oxo-3-(phenylamino)-4,5,6,7-tetrahydro-1H-indol-2-yl]pyridin-2-yl}-2-fluorocyclopropanecarboxamide

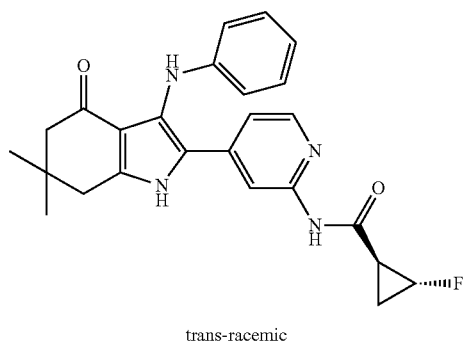 [SMILES: CC1(C)CC(=O)c2c([nH]c(-c3ccnc(NC(=O)[C@@H]4C[C@H]4F)c3)c2Nc2ccccc2)C1]

trans-racemic

Using Method G2 at 50° C.: Example 122 (250 mg, 722 µmol) gave the desired racemic trans-product (181 mg, 58%) after silica chromatography.

1H-NMR (400 MHz, DMSO-d6), Shift [ppm]=1.06 (6H), 1.20 (1H), 1.44-1.60 (1H), 2.22 (2H), 2.52-2.60 (1H), 2.73 (2H), 4.75 (1H), 4.84-5.01 (1H), 6.49-6.56 (2H), 6.59 (1H), 7.01 (2H), 7.17 (1H), 7.36 (1H), 8.09 (1H), 8.16 (1H), 10.81 (1H), 11.86 (1H).

Example 255 and Example 256 Separation of the Enantiomers (R,S/S,R)-2-fluoro-N-{4-[4-oxo-3-(phenylamino)-4,5,6,7-tetrahydro-1H-indol-2-yl]pyridin-2-yl}cyclopropanecarboxamide Example 254 (151 mg, 349 µmol) was purified by chiral preparative HPLC (Instrument: Sepiatec: Prep SFC100; Column: Chiralpak IB 5 µm 250×30 mm; Solvent A: CO2; Solvent B: 2-Propanol+0.2% Diethylamine; Isocratic 16% B; Flow: 100 mL/min; Temperature: 40° C.; Pressure 150 bar) to give the two enantiomers:

Enantiomer 1 Example 255 (55 mg, 36%)

Enantiomer 2 Example 256 (60 mg, 37%)

Chiral HPLC Analysis was performed (Instrument: Agilent: 1260, Aurora SFC-Module; Column: Chiralpak IB 5 µm 100×4.6 mm; Solvent A: CO₂; Solvent B: 2-Propanol+0.2% Diethylamine; Isocratic 16% B; Flow: 4 mL/min; Temperature: 37.5° C.; Pressure 100 bar).

Enantiomer 1 (Example 255): Rt 2.89 min (>95% e.e.)

Enantiomer 2 (Example 256): Rt 4.28 min (>95% e.e.)

Example 257 Preparation of (R,R)—N-{4-[6,6-dimethyl-4-oxo-3-(phenylamino)-4,5,6,7-tetrahydro-1H-indol-2-yl]pyridin-2-yl}-2-fluorocyclopropanecarboxamide

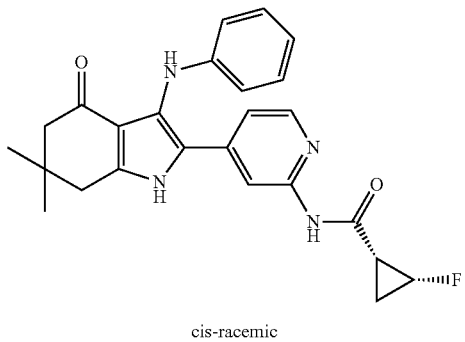 [SMILES: CC1(C)CC(=O)c2c([nH]c(-c3ccnc(NC(=O)[C@H]4C[C@H]4F)c3)c2Nc2ccccc2)C1]

cis-racemic

Using Method G2 at 50° C.: Example 122 (250 mg, 722 µmol) gave the desired racemic cis-product (180 mg, 58%) after silica chromatography.

1H-NMR (400 MHz, DMSO-d6), Shift [ppm]=1.00-1.09 (6H), 1.09-1.27 (1H), 1.55-1.71 (1H), 2.13-2.27 (3H), 2.74 (2H), 4.82-5.07 (1H), 6.49-6.63 (3H), 6.97-7.06 (2H), 7.16 (1H), 7.36 (1H), 8.08 (1H), 8.24 (1H), 10.71 (1H), 11.90 (1H).

Example 258 and Example 259 Separation of the Enantiomers (R,R/S,S)-2-fluoro-N-{4-[4-oxo-3-(phenylamino)-4,5,6,7-tetrahydro-1H-indol-2-yl]pyridin-2-yl}cyclopropanecarboxamide Example 257 (151 mg, 349 µmol) was purified by chiral preparative HPLC (Instrument: Sepiatec: Prep SFC100; Column: Chiralpak IB 5 µm 250×30 mm; Solvent A: CO₂; Solvent B: 2-Propanol+0.2% Diethylamine; Isocratic 16% B; Flow: 100 mL/min; Temperature: 40° C.; Pressure 150 bar) to give the two enantiomers:

Enantiomer 1 Example 258 (50 mg, 33%)

Optical Rotation: DMSO 2.7 mg/ml: −31.1°+/−0.58°

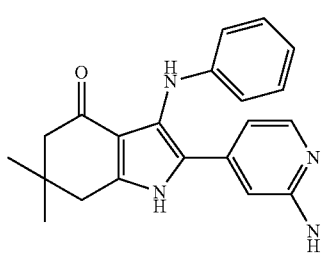

Enantiomer 2 Example 259 (50 mg, 33%)

Optical Rotation: DMSO 2.5 mg/ml: 29.7°+/−0.56°

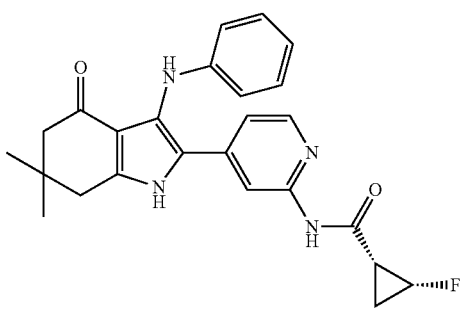 [SMILES: CC1(C)CC(=O)c2c([nH]c(-c3ccnc(NC(=O)[C@H]4C[C@H]4F)c3)c2Nc2ccccc2)C1]

Chiral HPLC Analysis was performed (Instrument: Agilent: 1260, Aurora SFC-Module; Column: Chiralpak IB 5 μm 100×4.6 mm; Solvent A: $CO_2$; Solvent B: 2-Propanol+ 0.2% Diethylamine; Isocratic 16% B; Flow: 4 mL/min; Temperature: 37.5° C.; Pressure 100 bar).

Enantiomer 1 (Example 258): Rt 2.99 min (>95% e.e.)
Enantiomer 2 (Example 259): Rt 4.29 min (>95% e.e.).

Example 259

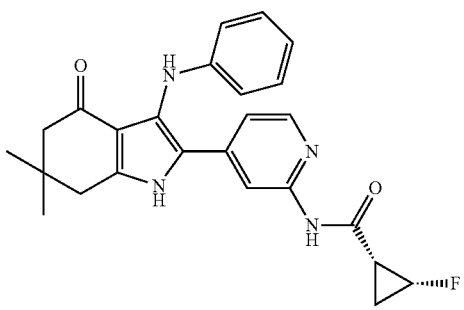 [SMILES: CC1(C)CC(=O)c2c([nH]c(-c3ccnc(NC(=O)[C@H]4C[C@H]4F)c3)c2Nc2ccccc2)C1]

Using Method G2: Example 122 (100 mg, 289 μmol) with (1R,2R)-2-fluorocyclopropanecarboxylic acid gave the desired product (47 mg, 38%) after preparative HPLC (basic method).

Optical Rotation: DMSO 3 mg/ml: 20.0°+/−0.76°.

Example 260 Preparation of 2,2-difluoro-N-{4-[4-oxo-3-(phenylamino)-4,5,6,7-tetrahydro-1H-indol-2-yl]pyridin-2-yl}cyclopropanecarboxamide

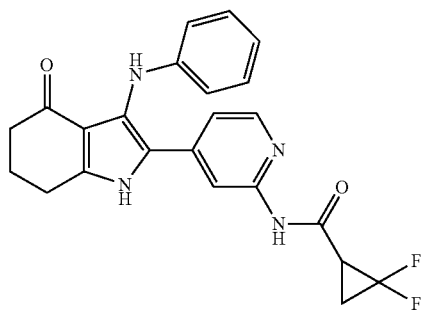 [SMILES: O=C1CCCc2[nH]c(-c3ccnc(NC(=O)C4CC4(F)F)c3)c(Nc3ccccc3)c21]

Using Method G2: Example 139 (50 mg, 157 μmol) gave the desired racemic product (16 mg, 24%) after preparative HPLC (basic method).

1H-NMR (400 MHz, DMSO-d6), Shift [ppm]=1.93-2.12 (4H), 2.28-2.37 (2H), 2.85 (2H), 2.94-3.01 (1H), 6.50-6.64 (3H), 7.01 (2H), 7.18 (1H), 7.39 (1H), 8.10 (1H), 8.21 (1H), 10.87 (1H), 11.94 (1H).

Example 261 Preparation of 1-fluoro-N-{4-[4-oxo-3-(phenylamino)-4,5,6,7-tetrahydro-1H-indol-2-yl]pyridin-2-yl}cyclopropanecarboxamide

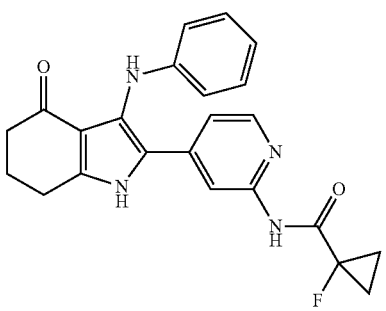 [SMILES: O=C1CCCc2[nH]c(-c3ccnc(NC(=O)C4(F)CC4)c3)c(Nc3ccccc3)c21]

Using Method G2: Example 139 (100 mg, 314 μmol) gave the desired product (17 mg, 13%) after preparative HPLC (basic method).

1H-NMR (400 MHz, DMSO-d6), Shift [ppm]=1.26-1.37 (2H), 1.37-1.53 (2H), 1.98-2.11 (2H), 2.29-2.37 (2H), 2.86 (2H), 6.56 (2H), 6.59-6.65 (1H), 7.02 (2H), 7.24 (1H), 7.41 (1H), 8.11 (1H), 8.15 (1H), 10.09 (1H), 11.94 (1H)

Example 262 Preparation of N-{4-[4-oxo-3-(phenylamino)-4,5,6,7-tetrahydro-1H-indol-2-yl]pyridin-2-yl}-2-(trifluoromethyl)cyclopropanecarboxamide

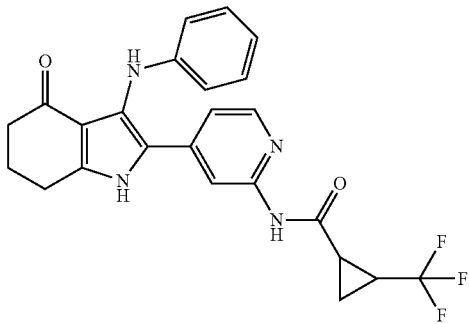 [SMILES: O=C1CCCc2[nH]c(-c3ccnc(NC(=O)C4CC4C(F)(F)F)c3)c(Nc3ccccc3)c21]

Using Method G2: Example 139 (100 mg, 314 μmol) gave the desired racemic product (46 mg, 32%) after preparative HPLC (basic method).

1H-NMR (400 MHz, DMSO-d6), Shift [ppm]=1.31 (1H), 1.45-1.56 (1H), 1.99-2.11 (2H), 2.15-2.29 (1H), 2.30-2.41 (3H), 2.86 (2H), 6.50-6.66 (3H), 6.96-7.05 (2H), 7.16 (1H), 7.37 (1H), 8.08 (1H), 8.19 (1H), 10.79 (1H), 11.92 (1H).

Example 263 Preparation of 3-fluoro-2,2-dimethyl-N-{4-[4-oxo-3-(phenylamino)-4,5,6,7-tetrahydro-1H-indol-2-yl]pyridin-2-yl}propanamide

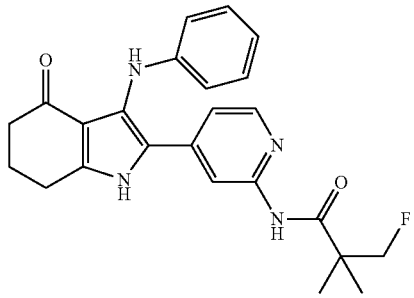 [SMILES: CC(C)(CF)C(=O)Nc1cc(-c2[nH]c3c(c2Nc2ccccc2)C(=O)CCC3)ccn1]

Using Method G2: Example 139 (100 mg, 314 µmol) gave the desired product (20 mg, 15%) after preparative HPLC (basic method)

1H-NMR (400 MHz, DMSO-d6), Shift [ppm]=1.25 (6H), 1.94-2.13 (2H), 2.33 (2H), 2.86 (2H), 4.50 (1H), 4.62 (1H), 6.54-6.66 (3H), 7.02 (2H), 7.17 (1H), 7.39 (1H), 8.09 (1H), 8.16-8.22 (1H), 9.84 (1H), 11.93 (1H).

Example 264 Preparation of 2-fluoro-N-{4-[4-oxo-3-(phenylamino)-4,5,6,7-tetrahydro-1H-indol-2-yl]pyridin-2-yl}benzamide

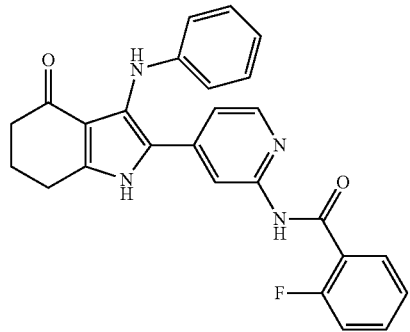 [SMILES: O=C(Nc1cc(-c2[nH]c3c(c2Nc2ccccc2)C(=O)CCC3)ccn1)c1ccccc1F]

Using Method G2: Example 139 (50 mg, 157 µmol) gave the desired product (13 mg, 19%) after preparative HPLC (basic method).

1H-NMR (400 MHz, DMSO-d6), Shift [ppm]=1.99-2.17 (2H), 2.30-2.39 (2H), 2.88 (2H), 6.56-6.66 (2H), 7.03 (2H), 7.22 (1H), 7.28-7.37 (2H), 7.41 (1H), 7.53-7.63 (1H), 7.66 (1H), 8.13 (1H), 8.34 (1H), 10.60 (1H), 11.97 (1H).

Example 265 Preparation of 3-fluoro-N-{4-[4-oxo-3-(phenylamino)-4,5,6,7-tetrahydro-1H-indol-2-yl]pyridin-2-yl}benzamide

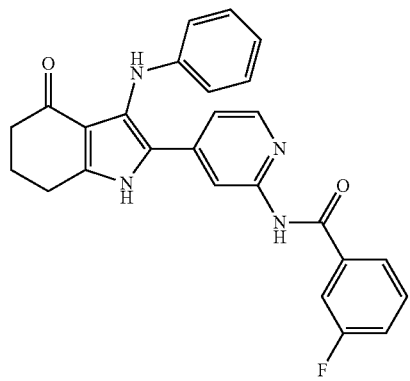 [SMILES: O=C(Nc1cc(-c2[nH]c3c(c2Nc2ccccc2)C(=O)CCC3)ccn1)c1cccc(F)c1]

Using Method G2: Example 139 (50 mg, 157 µmol) in pyridine (1 mL) was added 3-fluorobenzoyl chloride (50 mg, 314 µmol) and stirred at RT for 16 h. Additional 3-fluorobenzoyl chloride (56 mg, 314 µmol) added and stirred at RT for 72 h. Concentrated and purified by preparative HPLC (Column: XBridge C18 5µ 100×30 mm; Solvent A: Water+ 0.2 Vol-% NH4OH (32%), Solvent B: Acetonitrile; Gradient: 0.00-0.50 min 40% B (25-70 mL/min), 0.51-5.50 min 40-70% B; Flow: 70 mL/min) to give the desired product (27 mg, 39%).

1H-NMR (400 MHz, DMSO-d6), Shift [ppm]=1.99-2.14 (2H), 2.31-2.41 (2H), 2.88 (2H), 6.56-6.64 (3H), 7.03 (2H), 7.24 (1H), 7.41 (1H), 7.45 (1H), 7.57 (1H), 7.79-7.91 (2H), 8.17 (1H), 8.33 (1H), 10.75 (1H), 11.96 (1H).

Example 266 Preparation of 4-fluoro-N-{4-[4-oxo-3-(phenylamino)-4,5,6,7-tetrahydro-1H-indol-2-yl]pyridin-2-yl}benzamide

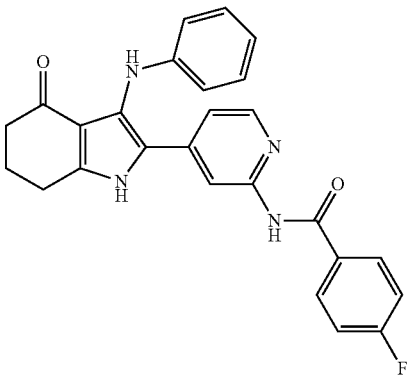 [SMILES: O=C(Nc1cc(-c2[nH]c3c(c2Nc2ccccc2)C(=O)CCC3)ccn1)c1ccc(F)cc1]

Using Method G2: Example 139 (50 mg, 157 µmol) in pyridine (1 mL) was added 3-fluorobenzoyl chloride (50 mg, 314 µmol) and stirred at RT for 16 h. Additional 3-fluorobenzoyl chloride (56 mg, 314 µmol) added and stirred at RT for 72 h. Concentrated and purified by preparative HPLC (Column: XBridge C18 5µ 100×30 mm; Solvent A: Water+ 0.2 Vol-% NH4OH (32%), Solvent B: Acetonitrile; Gradient: 0.00-0.50 min 40% B (25-70 mL/min), 0.51-5.50 min 40-70% B; Flow: 70 mL/min) to give the desired product (24 mg, 33%).

1H-NMR (400 MHz, DMSO-d6), Shift [ppm]=1.98-2.13 (2H), 2.29-2.39 (2H), 2.87 (2H), 6.55-6.66 (3H), 7.02 (2H), 7.23 (1H), 7.31-7.39 (2H), 7.40 (1H), 8.06-8.13 (2H), 8.16 (1H), 8.32 (1H), 10.68 (1H), 11.95 (1H).

Example 267 Preparation of N-{4-[6,6-dimethyl-4-oxo-3-(phenylamino)-4,5,6,7-tetrahydro-1H-indol-2-yl]pyridin-2-yl}-4-fluorobenzamide

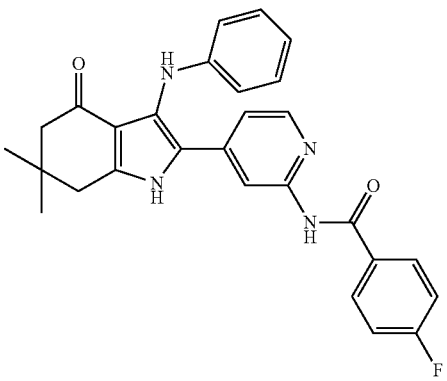 [SMILES: CC1(C)CC(=O)c2c([nH]c(-c3ccnc(NC(=O)c4ccc(F)cc4)c3)c2Nc2ccccc2)C1]

Using Method G2: Example 122 (100 mg, 314 µmol) gave the desired product (50 mg, 37%) after preparative HPLC (basic method).

1H-NMR (400 MHz, DMSO-d6), Shift [ppm]=1.07 (6H), 2.24 (2H), 2.76 (2H), 6.53-6.64 (3H), 6.97-7.05 (2H), 7.25 (1H), 7.30-7.38 (2H), 7.41 (1H), 8.05-8.14 (2H), 8.17 (1H), 8.29-8.35 (1H), 10.73 (1H), 11.93 (1H).

Example 268 Preparation of N-{4-[4-oxo-3-(phenylamino)-4,5,6,7-tetrahydro-1H-indol-2-yl]pyridin-2-yl}pyridine-4-carboxamide

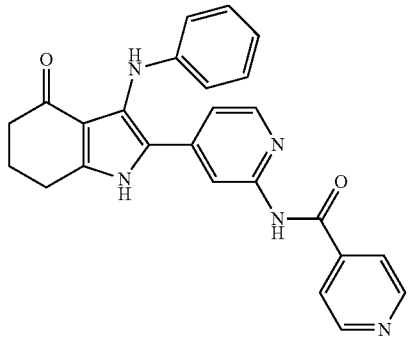 [SMILES: O=C(Nc1cc(-c2[nH]c3c(c2Nc2ccccc2)C(=O)CCC3)ccn1)c1ccncc1]

Using Method G2: Example 139 (50 mg, 157 µmol) in pyridine (1 mL) was added 4-pyridinecarbonyl chloride hydrochloride (56 mg, 314 µmol) and stirred at RT for 16 h. Additional 4-pyridinecarbonyl chloride hydrochloride (56 mg, 314 µmol) added and stirred at RT for 72 h. Concentrated and purified by preparative HPLC (basic method) to give the desired product (32 mg, 48%).

1H-NMR (400 MHz, DMSO-d6), Shift [ppm]=1.96-2.12 (2H), 2.29-2.42 (2H), 2.88 (2H), 6.52-6.66 (3H), 6.97-7.09 (2H), 7.26 (1H), 7.42 (1H), 7.87-7.91 (2H), 8.19 (1H), 8.32-8.36 (1H), 8.66-8.86 (2H), 10.96 (1H), 11.97 (1H).

Example 269 Preparation of N-{4-[4-oxo-3-(phenylamino)-4,5,6,7-tetrahydro-1H-indol-2-yl]pyridin-2-yl}pyridine-2-carboxamide

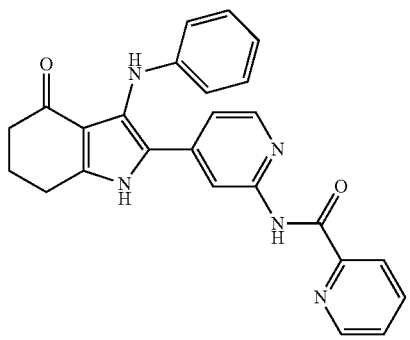 [SMILES: O=C(Nc1cc(-c2[nH]c3c(c2Nc2ccccc2)C(=O)CCC3)ccn1)c1ccccn1]

Using Method G2: Example 139 (50 mg, 157 µmol) gave the desired product (35 mg, 54%) after preparative HPLC (basic method).

1H-NMR (400 MHz, DMSO-d6), Shift [ppm]=1.97-2.13 (2H), 2.27-2.40 (2H), 2.89 (2H), 6.54-6.66 (3H), 6.96-7.08 (2H), 7.26 (1H), 7.44 (1H), 7.73 (1H), 8.12 (1H), 8.16-8.24 (2H), 8.45 (1H), 8.70-8.83 (1H), 10.31 (1H), 12.02 (1H).

Example 270 Preparation of N-{4-[4-oxo-3-(phenylamino)-4,5,6,7-tetrahydro-1H-indol-2-yl]pyridin-2-yl}-1,3-thiazole-2-carboxamide

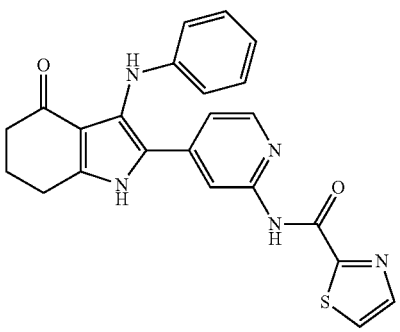 [SMILES: O=C(Nc1cc(-c2[nH]c3c(c2Nc2ccccc2)C(=O)CCC3)ccn1)c1nccs1]

Using Method G2: Example 139 (50 mg, 157 µmol) gave the desired product (19 mg, 28%) after preparative HPLC (basic method).

1H-NMR (400 MHz, DMSO-d6), Shift [ppm]=2.00-2.13 (2H), 2.32-2.39 (2H), 2.88 (2H), 6.52-6.70 (3H), 7.03 (2H), 7.22-7.34 (1H), 7.44 (1H), 8.12 (1H), 8.15-8.23 (2H), 8.27-8.32 (1H), 9.99 (1H), 12.00 (1H).

Example 271 Preparation of N-{4-[4-oxo-3-(phenylamino)-4,5,6,7-tetrahydro-1H-indol-2-yl]pyridin-2-yl}-1,3-thiazole-4-carboxamide

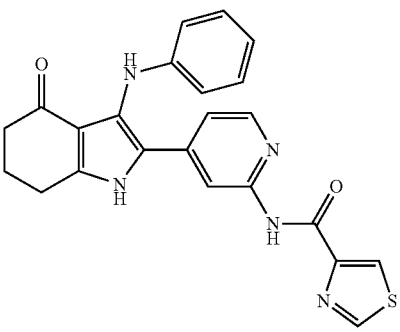 [SMILES: O=C(Nc1cc(-c2[nH]c3c(c2Nc2ccccc2)C(=O)CCC3)ccn1)c1cscn1]

Using Method G2: Example 139 (50 mg, 157 µmol) gave the desired product (26 mg, 39%) after preparative HPLC (basic method).

1H-NMR (400 MHz, DMSO-d6), Shift [ppm]=1.98-2.12 (2H), 2.28-2.38 (2H), 2.88 (2H), 6.56-6.67 (3H), 6.98-7.09 (2H), 7.25 (1H), 7.43 (1H), 8.16 (1H), 8.38 (1H), 8.60 (1H), 9.28 (1H), 9.80 (1H), 12.01 (1H).

Example 272 Preparation of N-{4-[6,6-dimethyl-4-oxo-3-(phenylamino)-4,5,6,7-tetrahydro-1H-indol-2-yl]pyridin-2-yl}-1,3-thiazole-4-carboxamide

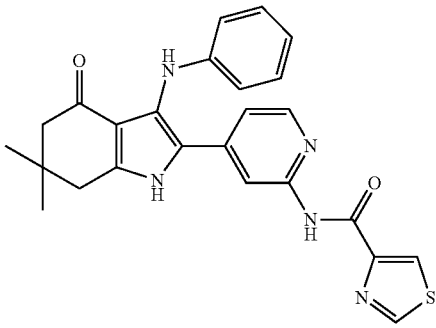 [SMILES: CC1(C)CC(=O)c2c([nH]c(-c3ccnc(NC(=O)c4cscn4)c3)c2Nc2ccccc2)C1]

Using Method G2: Example 122 (100 mg, 289 μmol) gave the desired product (36 mg, 26%) after preparative HPLC (basic method).
1H-NMR (400 MHz, DMSO-d6), Shift [ppm]=1.07 (6H), 2.24 (2H), 2.77 (2H), 6.52-6.64 (3H), 7.02 (2H), 7.27 (1H), 7.43 (1H), 8.17 (1H), 8.35-8.41 (1H), 8.61 (1H), 9.28 (1H), 9.81 (1H), 11.98 (1H).

Example 273 Preparation of N-{4-[4-oxo-3-(phenylamino)-4,5,6,7-tetrahydro-1H-indol-2-yl]pyridin-2-yl}-1,3-thiazole-5-carboxamide

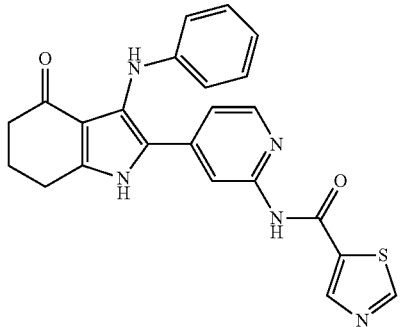 [SMILES: O=C(Nc1cc(-c2[nH]c3c(c2Nc2ccccc2)C(=O)CCC3)ccn1)c1cncs1]

Using Method G2: Example 139 (50 mg, 157 μmol) gave the desired product (14 mg, 21%) after preparative HPLC (basic method).
1H-NMR (400 MHz, DMSO-d6), Shift [ppm]=1.99-2.13 (2H), 2.31-2.37 (2H), 2.87 (2H), 6.53-6.68 (3H), 7.02 (2H), 7.24 (1H), 7.42 (1H), 8.18 (1H), 8.28 (1H), 8.87 (1H), 9.32 (1H), 11.07 (1H), 11.96 (1H).

Example 274 Preparation of N-{4-[4-oxo-3-(phenylamino)-4,5,6,7-tetrahydro-1H-indol-2-yl]pyridin-2-yl}-1H-imidazole-2-carboxamide

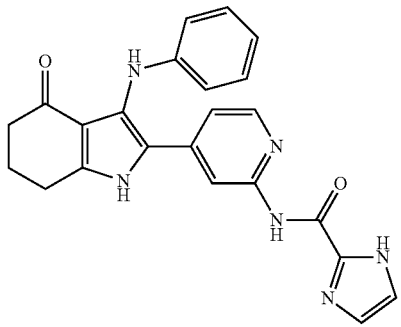 [SMILES: O=C(Nc1cc(-c2[nH]c3c(c2Nc2ccccc2)C(=O)CCC3)ccn1)c1ncc[nH]1]

Using Method G2: Example 139 (50 mg, 157 μmol) gave the desired product (6 mg, 9%) after preparative HPLC (basic method).
1H-NMR (400 MHz, DMSO-d6), Shift [ppm]=2.00-2.12 (2H), 2.29-2.37 (2H), 2.87 (1H), 6.51-6.65 (3H), 6.96-7.06 (2H), 7.16 (1H), 7.25 (1H), 7.43 (1H), 8.17 (1H), 8.27-8.34 (1H), 9.53 (1H), 11.99 (1H), 13.40 (1H).

Example 275 Preparation of N-{4-[4-oxo-3-(phenylamino)-4,5,6,7-tetrahydro-1H-indol-2-yl]pyridin-2-yl}-1H-pyrazole-5-carboxamide

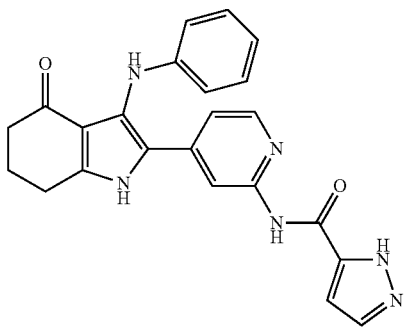 [SMILES: O=C(Nc1cc(-c2[nH]c3c(c2Nc2ccccc2)C(=O)CCC3)ccn1)c1ccn[nH]1]

Using Method G2: Example 139 (50 mg, 157 μmol) gave the desired product (3.5 mg, 5%) after preparative HPLC (basic method).
1H-NMR (400 MHz, DMSO-d6), Shift [ppm]=1.95-2.12 (2H), 2.28-2.37 (2H), 2.82-2.94 (2H), 6.52-6.66 (3H), 7.02 (2H), 7.22 (1H), 7.41 (1H), 7.79-8.00 (1H), 8.14 (1H), 8.35 (1H), 9.48 (1H), 11.98 (1H), 13.54 (1H).

Example 276 Preparation of N-{4-[4-oxo-3-(phenylamino)-4,5,6,7-tetrahydro-1H-indol-2-yl]pyridin-2-yl}-1,2-thiazole-3-carboxamide

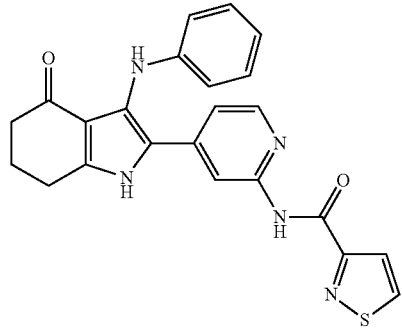 [SMILES: O=C(Nc1cc(-c2[nH]c3c(c2Nc2ccccc2)C(=O)CCC3)ccn1)c1ccsn1]

Using Method G2: Example 139 (50 mg, 157 μmol) gave the desired product (20 mg, 30%) after preparative HPLC (basic method).
1H-NMR (400 MHz, DMSO-d6), Shift [ppm]=2.00-2.13 (2H), 2.28-2.37 (3H), 2.88 (2H), 6.55-6.66 (2H), 7.02 (2H), 7.26 (1H), 7.43 (1H), 7.91 (1H), 8.18 (1H), 8.33 (1H), 9.24 (1H), 9.96 (1H), 12.00 (1H).

Example 277 Preparation of N-{4-[4-oxo-3-(phenylamino)-4,5,6,7-tetrahydro-1H-indol-2-yl]pyridin-2-yl}-1,2-thiazole-4-carboxamide

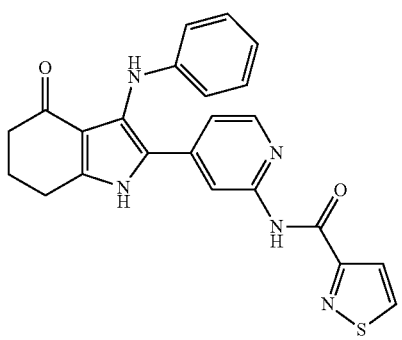 [SMILES: O=C(Nc1cc(-c2[nH]c3c(c2Nc2ccccc2)C(=O)CCC3)ccn1)c1ccsn1]

Using Method G2: Example 139 (50 mg, 157 µmol) gave the desired product (17 mg, 25%) after preparative HPLC (basic method).

1H-NMR (400 MHz, DMSO-d6), Shift [ppm]=1.99-2.14 (2H), 2.29-2.42 (2H), 2.87 (2H), 6.54-6.68 (2H), 7.02 (2H), 7.24 (1H), 7.40 (1H), 8.17 (1H), 8.34 (1H), 9.06 (1H), 9.88 (1H), 10.85 (1H), 11.96 (1H).

Example 278 Preparation of N-{4-[4-oxo-3-(phenylamino)-4,5,6,7-tetrahydro-1H-indol-2-yl]pyridin-2-yl}-1,3-oxazole-4-carboxamide

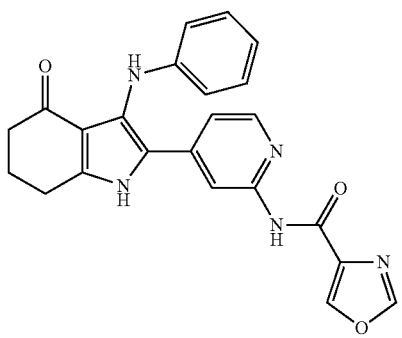 [SMILES: O=C(Nc1cc(-c2[nH]c3c(c2Nc2ccccc2)C(=O)CCC3)ccn1)c1cocn1]

Using Method G2: Example 139 (50 mg, 157 µmol) gave the desired product (14 mg, 22%) after preparative HPLC (basic method).

1H-NMR (400 MHz, DMSO-d6), Shift [ppm]=1.94-2.15 (2H), 2.28-2.38 (2H), 2.87 (2H), 6.51-6.66 (3H), 7.02 (2H), 7.25 (1H), 7.41 (1H), 8.16 (1H), 8.32 (1H), 8.61 (1H), 8.92 (1H), 9.69 (1H), 11.98 (1H).

Example 279 Preparation of N-{4-[4-oxo-3-(phenylamino)-4,5,6,7-tetrahydro-1H-indol-2-yl]pyridin-2-yl}pyridine-3-carboxamide

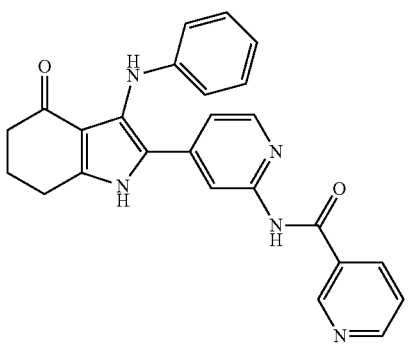 [SMILES: O=C(Nc1cc(-c2[nH]c3c(c2Nc2ccccc2)C(=O)CCC3)ccn1)c1cccnc1]

Using Method G2: Example 139 (50 mg, 157 µmol) gave the desired product (13 mg, 19%) after preparative HPLC (basic method).

1H-NMR (400 MHz, DMSO-d6), Shift [ppm]=6.54-6.66 (4H), 6.97-7.12 (3H), 7.21-7.30 (1H), 7.42 (1H), 7.55 (1H), 8.18 (1H), 8.31-8.41 (2H), 8.75 (1H), 9.12 (1H), 10.94 (1H), 11.98 (1H).

Example 280 Preparation of N-{4-[4-oxo-3-(phenylamino)-4,5,6,7-tetrahydro-1H-indol-2-yl]pyridin-2-yl}-1,2-thiazole-5-carboxamide

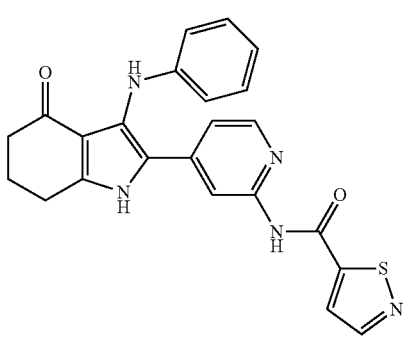 [SMILES: O=C(Nc1cc(-c2[nH]c3c(c2Nc2ccccc2)C(=O)CCC3)ccn1)c1ccns1]

Using Method G2: Example 139 (50 mg, 157 µmol) gave the desired product (12 mg, 18%) after preparative HPLC (basic method).

1H-NMR (400 MHz, DMSO-d6), Shift [ppm]=2.01-2.11 (2H), 2.30-2.42 (2H), 2.84-2.90 (2H), 6.56-6.67 (3H), 7.02 (2H), 7.27 (1H), 7.42 (1H), 8.20 (1H), 8.28-8.33 (2H), 8.72 (1H), 11.22 (1H), 11.97 (1H).

Example 281 Preparation of N-{4-[4-oxo-3-(phenylamino)-4,5,6,7-tetrahydro-1H-indol-2-yl]pyridin-2-yl}-1H-1,2,3-triazole-5-carboxamide

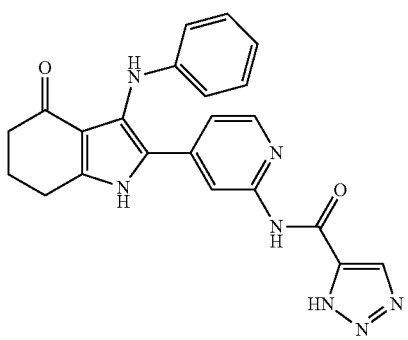 [SMILES: O=C(Nc1cc(-c2[nH]c3c(c2Nc2ccccc2)C(=O)CCC3)ccn1)c1cnn[nH]1]

Using Method G2: Example 139 (50 mg, 157 µmol) gave the desired product (8 mg, 12%) after preparative HPLC (basic method).

1H-NMR (400 MHz, DMSO-d6), Shift [ppm]=1.99-2.11 (2H), 2.33 (2H), 2.87 (2H), 6.54-6.65 (2H), 7.02 (2H), 7.22 (1H), 7.41 (1H), 8.11-8.18 (1H), 8.30-8.40 (1H), 8.46 (1H), 9.89 (1H), 11.98 (1H).

Example 282 Preparation of N-{4-[4-oxo-3-(phenylamino)-4,5,6,7-tetrahydro-1H-indol-2-yl]pyridin-2-yl}-1,3-oxazole-5-carboxamide

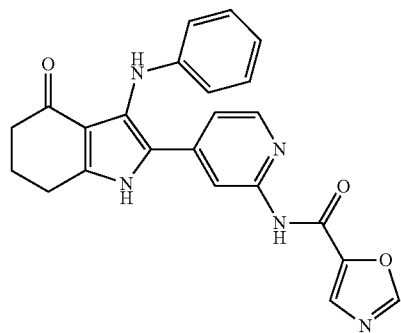 [SMILES: O=C(Nc1cc(-c2[nH]c3c(c2Nc2ccccc2)C(=O)CCC3)ccn1)c1cnco1]

Using Method G2: Example 139 (50 mg, 157 µmol) gave the desired product (10 mg, 15%) after preparative HPLC (basic method).

1H-NMR (400 MHz, DMSO-d6), Shift [ppm]=1.98-2.08 (2H), 2.28-2.37 (2H), 2.87 (2H), 6.51-6.65 (3H), 6.96-7.08 (2H), 7.24 (1H), 7.41 (1H), 8.11-8.23 (1H), 8.28 (1H), 8.64 (1H), 10.86 (1H), 11.98 (1H).

Example 283 Preparation of N-{4-[4-oxo-3-(phenylamino)-4,5,6,7-tetrahydro-1H-indol-2-yl]pyridin-2-yl}-1H-tetrazole-5-carboxamide

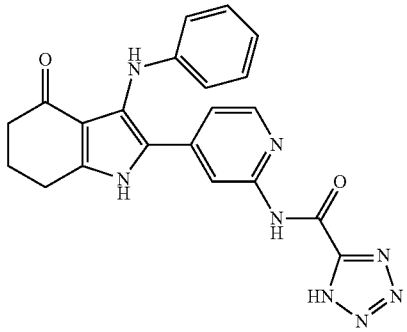 [SMILES: O=C(Nc1cc(-c2[nH]c3c(c2Nc2ccccc2)C(=O)CCC3)ccn1)c1nnn[nH]1]

Using Method G2: Example 139 (50 mg, 157 µmol) gave the desired product (5.6 mg, 9%) after preparative HPLC (Column: XBridge C18 5µ 100×30 mm; Solvent A: Water+0.2 Vol-% NH$_4$OH (32%), Solvent B: Acetonitrile; Gradient: 0.00-0.50 min 5% B (25-70 mL/min), 0.51-5.50 min 5-25% B; Flow: 70 mL/min).

1H-NMR (400 MHz, DMSO-d6), Shift [ppm]=1.21-1.28 (3H), 1.98-2.14 (2H), 2.88 (2H), 6.54-6.66 (3H), 7.03 (2H), 7.21-7.31 (1H), 7.44 (1H), 8.15 (1H), 8.33 (1H), 9.88 (1H), 12.02 (1H).

Example 284 Preparation of N-{4-[4-oxo-3-(phenylamino)-4,5,6,7-tetrahydro-1H-indol-2-yl]pyridin-2-yl}-2-(1H-pyrrol-2-yl)acetamide

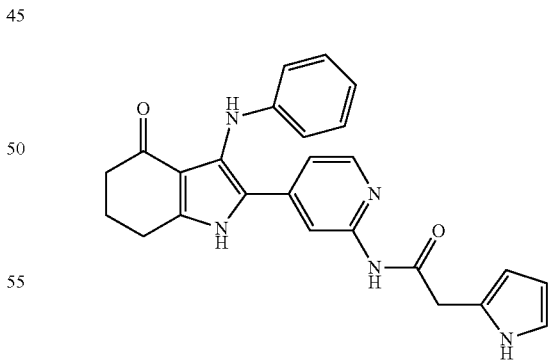

Using Method G2: Example 139 (100 mg, 314 µmol) gave the desired product (21 mg, 16%) after preparative HPLC (basic method).

1H-NMR (400 MHz, DMSO-d6), Shift [ppm]=1.98-2.09 (2H), 2.27-2.37 (2H), 2.83 (2H), 3.63 (2H), 5.84-5.98 (2H), 6.49-6.66 (3H), 7.01 (2H), 7.14 (1H), 7.37 (1H), 8.04-8.09 (1H), 8.23 (1H), 10.28 (1H), 10.61 (1H), 11.92 (1H).

Example 285 Preparation of N-{4-[4-oxo-3-(phenylamino)-4,5,6,7-tetrahydro-1H-indol-2-yl]pyridin-2-yl}-2-(1,3-thiazol-2-yl)acetamide

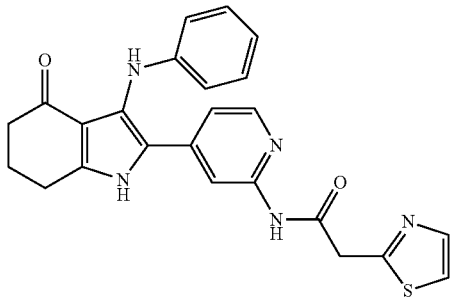 [SMILES: O=C(Cc1nccs1)Nc1cc(-c2[nH]c3c(c2Nc2ccccc2)C(=O)CCC3)ccn1]

Using Method G2: Example 139 (100 mg, 314 µmol) gave the desired product (25 mg, 18%) after preparative HPLC (basic method).

1H-NMR (400 MHz, DMSO-d6), Shift [ppm]=1.97-2.11 (2H), 2.26-2.39 (2H), 2.85 (2H), 4.23 (2H), 6.51-6.65 (3H), 7.01 (2H), 7.17 (1H), 7.39 (1H), 7.67 (1H), 7.75 (1H), 8.10 (1H), 8.23 (1H), 10.74 (1H), 11.94 (1H).

Example 286 Preparation of N-{4-[4-oxo-3-(phenylamino)-4,5,6,7-tetrahydro-1H-indol-2-yl]pyridin-2-yl}-2-(1H-pyrrol-3-yl)acetamide

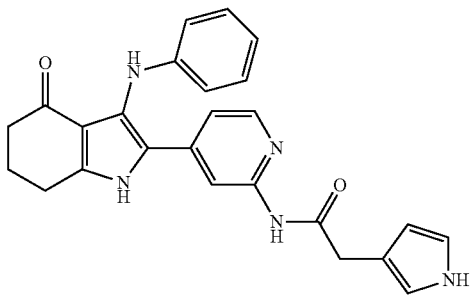 [SMILES: O=C(Cc1cc[nH]c1)Nc1cc(-c2[nH]c3c(c2Nc2ccccc2)C(=O)CCC3)ccn1]

Using Method G2: Example 139 (100 mg, 314 µmol) gave the desired product (25 mg, 18%) after preparative HPLC (basic method).

1H-NMR (400 MHz, DMSO-d6), Shift [ppm]=1.95-2.11 (2H), 2.26-2.36 (2H), 2.83 (2H), 3.59-3.68 (2H), 5.82-6.01 (1H), 6.48-6.69 (3H), 7.01 (2H), 7.14 (1H), 7.36 (1H), 8.07 (1H), 8.23 (1H), 10.28 (1H), 10.61 (1H), 11.92 (1H).

Example 287 Preparation of N-{4-[4-oxo-3-(phenylamino)-4,5,6,7-tetrahydro-1H-indol-2-yl]pyridin-2-yl}-2-(1,3-thiazol-4-yl)acetamide

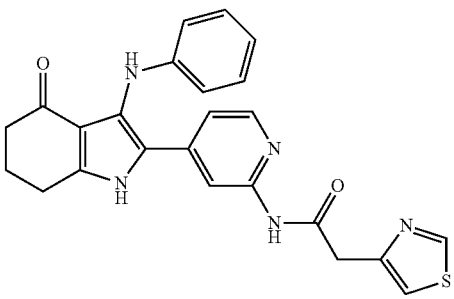 [SMILES: O=C(Cc1cscn1)Nc1cc(-c2[nH]c3c(c2Nc2ccccc2)C(=O)CCC3)ccn1]

Using Method G2: Example 139 (100 mg, 314 µmol) gave the desired product (20 mg, 14%) after preparative HPLC (basic method).

1H-NMR (400 MHz, DMSO-d6), Shift [ppm]=1.97-2.12 (2H), 2.28-2.35 (2H), 2.83 (2H), 3.93 (2H), 6.48-6.68 (3H), 6.93-7.09 (2H), 7.16 (1H), 7.38 (1H), 7.50 (1H), 8.04-8.16 (1H), 8.24 (1H), 9.05 (1H), 10.55 (1H), 11.92 (1H).

Example 288 Preparation of 2-(furan-2-yl)-N-{4-[4-oxo-3-(phenylamino)-4,5,6,7-tetrahydro-1H-indol-2-yl]pyridin-2-yl}acetamide

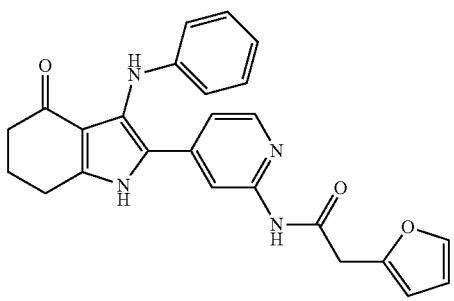 [SMILES: O=C(Cc1ccco1)Nc1cc(-c2[nH]c3c(c2Nc2ccccc2)C(=O)CCC3)ccn1]

Using Method G2: Example 139 (100 mg, 314 µmol) gave the desired product (30 mg, 22%) after preparative HPLC (basic method).

1H-NMR (400 MHz, DMSO-d6), Shift [ppm]=1.99-2.09 (2H), 2.28-2.40 (2H), 2.84 (2H), 3.79 (2H), 6.26 (1H), 6.40 (1H), 6.51-6.64 (3H), 7.01 (2H), 7.16 (1H), 7.37 (1H), 7.55-7.60 (1H), 8.08 (1H), 8.23 (1H), 10.53 (1H), 11.91 (1H).

Example 289 Preparation of 2-(3-methyl-1,2-oxazol-5-yl)-N-{4-[4-oxo-3-(phenylamino)-4,5,6,7-tetrahydro-1H-indol-2-yl]pyridin-2-yl}acetamide

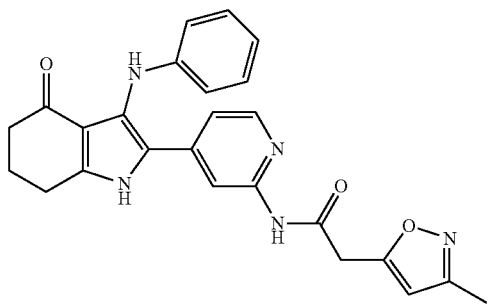 [SMILES: Cc1cc(CC(=O)Nc2cc(-c3[nH]c4c(c3Nc3ccccc3)C(=O)CCC4)ccn2)on1]

Using Method G2: Example 139 (100 mg, 314 µmol) gave the desired product (20 mg, 14%) after preparative HPLC (basic method).

1H-NMR (400 MHz, DMSO-d6), Shift [ppm]=1.95-2.11 (2H), 2.22 (3H), 2.32 (2H), 2.84 (2H), 3.95 (2H), 6.23 (1H), 6.51-6.65 (3H), 7.01 (2H), 7.18 (1H), 7.38 (1H), 8.10 (1H), 8.21 (1H), 10.68 (1H), 11.91 (1H).

Example 290 Preparation of N-{4-[4-oxo-3-(phenylamino)-4,5,6,7-tetrahydro-1H-indol-2-yl]pyridin-2-yl}-2-(thiophen-2-yl)acetamide

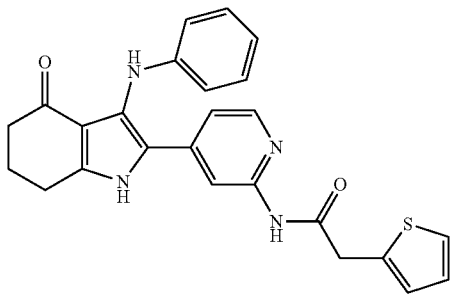 [SMILES: O=C(Cc1cccs1)Nc1cc(-c2[nH]c3c(c2Nc2ccccc2)C(=O)CCC3)ccn1]

Using Method G2: Example 139 (100 mg, 314 μmol) gave the desired product (30 mg, 22%) after preparative HPLC (basic method).

1H-NMR (400 MHz, DMSO-d6), Shift [ppm]=1.96-2.09 (2H), 2.32 (2H), 2.84 (2H), 3.93 (2H), 6.51-6.63 (3H), 6.92-7.07 (4H), 7.15 (1H), 7.35-7.43 (2H), 8.08 (1H), 8.22 (1H), 10.59 (1H), 11.91 (1H).

Example 291 Preparation of N-{4-[4-oxo-3-(phenylamino)-4,5,6,7-tetrahydro-1H-indol-2-yl]pyridin-2-yl}-2-(thiophen-3-yl)acetamide

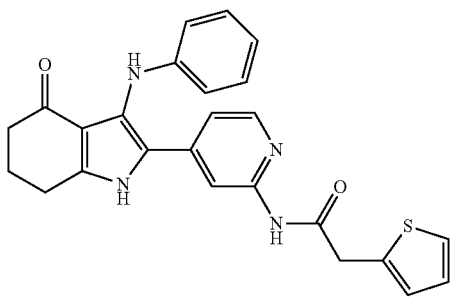 [SMILES: O=C(Cc1cccs1)Nc1cc(-c2[nH]c3c(c2Nc2ccccc2)C(=O)CCC3)ccn1]

Using Method G2: Example 139 (100 mg, 314 μmol) gave the desired product (40 mg, 29%) after preparative HPLC (basic method).

1H-NMR (400 MHz, DMSO-d6), Shift [ppm]=1.98-2.08 (2H), 2.28-2.37 (2H), 2.84 (2H), 3.71 (2H), 6.51-6.64 (3H), 6.95-7.05 (2H), 7.07 (1H), 7.15 (1H), 7.27-7.33 (1H), 7.38 (1H), 7.48 (1H), 8.08 (1H), 8.22 (1H), 10.53 (1H), 11.91 (1H).

Example 292 Preparation of 2-(1-methyl-1H-pyrazol-5-yl)-N-{4-[4-oxo-3-(phenylamino)-4,5,6,7-tetrahydro-1H-indol-2-yl]pyridin-2-yl}acetamide

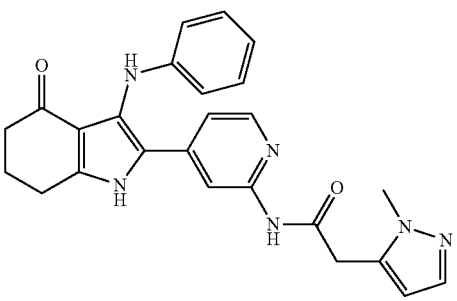 [SMILES: Cn1nccc1CC(=O)Nc1cc(-c2[nH]c3c(c2Nc2ccccc2)C(=O)CCC3)ccn1]

Using Method G2: Example 139 (100 mg, 314 μmol) gave the desired product (30 mg, 22%) after preparative HPLC (basic method).

1H-NMR (400 MHz, DMSO-d6), Shift [ppm]=1.96-2.10 (2H), 2.24-2.40 (2H), 2.84 (2H), 3.77 (3H), 3.86 (2H), 6.13 (1H), 6.50-6.64 (3H), 7.00 (2H), 7.17 (1H), 7.31 (1H), 7.39 (1H), 8.09 (1H), 8.20 (1H), 10.62 (1H), 11.91 (1H).

Example 293 Preparation of N-{4-[4'-oxo-3'-(phenylamino)-1',4',5',7'-tetrahydrospiro[cyclopropane-1,6'-indol]-2'-yl]pyridin-2-yl}acetamide

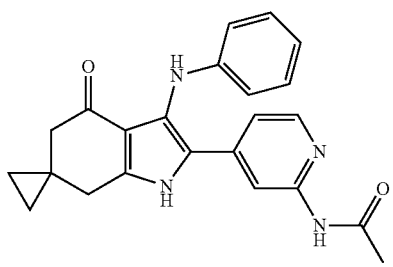 [SMILES: CC(=O)Nc1cc(-c2[nH]c3c(c2Nc2ccccc2)C(=O)CC2(CC2)C3)ccn1]

Using Method G2: Example 206 (50 mg, 15 μmol) in pyridine (1 mL) was added acetyl chloride (21 μL, 290 μmol) and stirred at RT for 16 h. Additional acetyl chloride (21 μL, 290 μmol) added and stirred at RT for 72 h. Concentrated and purified by preparative HPLC (acidic method) to give the desired product (31 mg, 55%).

1H-NMR (400 MHz, DMSO-d6), Shift [ppm]=0.38-0.56 (4H), 2.06 (3H), 2.23 (2H), 2.75 (2H), 6.53-6.64 (3H), 7.01 (2H), 7.15 (1H), 7.36 (1H), 8.07 (1H), 8.21 (1H), 10.30 (1H), 11.90 (1H).

Example 294 Preparation of N-{4-[4'-oxo-3'-(phenylamino)-1',4',5',7'-tetrahydrospiro[cyclopropane-1,6'-indol]-2'-yl]pyridin-2-yl}cyclopropanecarboxamide

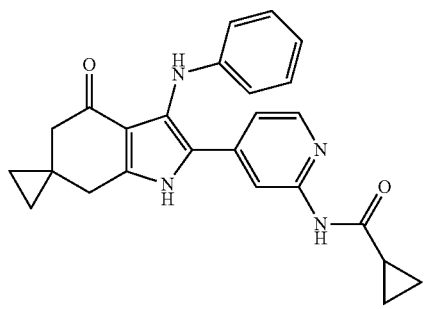 [SMILES: O=C1CC2(CC2)Cc2[nH]c(-c3ccnc(NC(=O)C4CC4)c3)c(Nc3ccccc3)c21]

Using Method G2: Example 206 (50 mg, 15 μmol) in pyridine (1 mL) was added cyclopropanecarbonyl chloride (26 μL, 290 μmol) and stirred at RT for 16 h. Concentrated and purified by preparative HPLC (acidic method) to give the desired product (34 mg, 57%).

1H-NMR (400 MHz, DMSO-d6), Shift [ppm]=0.35-0.54 (4H), 0.80 (4H), 1.98 (1H), 2.23 (2H), 2.74 (2H), 6.51-6.67 (3H), 6.96-7.05 (2H), 7.14 (1H), 7.37 (1H), 8.06 (1H), 8.21 (1H), 10.62 (1H), 11.88 (1H).

Example 295 Preparation of tert-butyl 3-({4-[4-oxo-3-(phenylamino)-4,5,6,7-tetrahydro-1H-indol-2-yl]pyridin-2-yl}carbamoyl)azetidine-1-carboxylate

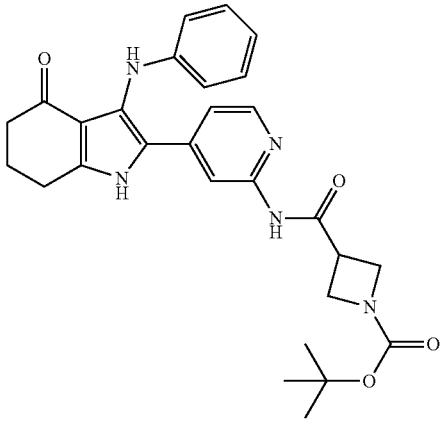 [SMILES: CC(C)(C)OC(=O)N1CC(C(=O)Nc2cc(-c3[nH]c4c(c3Nc3ccccc3)C(=O)CCC4)ccn2)C1]

Using Method G2: Example 139 (50 mg, 157 µmol) gave the desired product (33 mg, 42%) after preparative HPLC (basic method).

1H-NMR (400 MHz, DMSO-d6), Shift [ppm]=0.95 (2H), 1.36-1.45 (8H), 1.99-2.12 (2H), 2.28-2.39 (2H), 2.86 (2H), 3.91 (2H), 3.98 (2H), 6.50-6.67 (2H), 6.96-7.06 (2H), 7.17 (1H), 7.39 (1H), 8.07 (1H), 10.44 (1H), 11.92 (1H).

Example 296 Preparation of N-{4-[4-oxo-3-(phenylamino)-4,5,6,7-tetrahydro-1H-indol-2-yl]pyridin-2-yl}azetidine-3-carboxamide

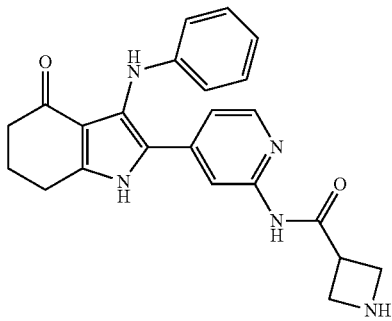 [SMILES: O=C1CCCc2[nH]c(-c3ccnc(NC(=O)C4CNC4)c3)c(Nc3ccccc3)c21]

Example 295 (33 mg, 66 µmol) in 4M HCl in dioxane (2 mL) was stirred at RT for 16 h. Concentrated and purified by preparative HPLC (Column: XBridge C18 5µ 100×30 mm; Solvent A: Water+0.2 Vol-% NH4OH (32%), Solvent B: Acetonitrile; Gradient: 0.00-0.50 min 10% B (25-70 mL/min), 0.51-5.50 min 10-45% B; Flow: 70 mL/min) to give the desired product (5 mg, 19%).

1H-NMR (400 MHz, DMSO-d6), Shift [ppm]=1.97-2.12 (2H), 2.27-2.37 (3H), 2.76 (1H), 2.86 (2H), 4.09 (1H), 4.20 (1H), 6.57-6.73 (3H), 6.82-6.91 (2H), 7.08 (2H), 7.53 (1H), 7.67 (1H).

Example 297 Preparation of tert-butyl methyl[2-oxo-2-({4-[4-oxo-3-(phenylamino)-4,5,6,7-tetrahydro-1H-indol-2-yl]pyridin-2-yl}amino)ethyl]carbamate

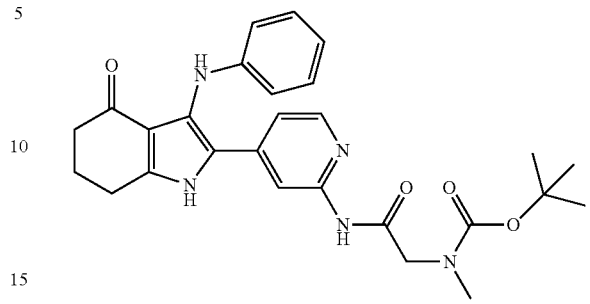

Using Method G2: Example 139 (50 mg, 157 µmol) gave the desired product (24 mg, 28%) after preparative HPLC (basic method).

1H-NMR (400 MHz, DMSO-d6), Shift [ppm]=1.27-1.42 (9H), 1.98-2.14 (2H), 2.33 (2H), 2.78-2.93 (5H), 4.02 (2H), 6.51-6.67 (3H), 6.94-7.06 (2H), 7.16 (1H), 7.37 (1H), 8.00-8.11 (1H), 8.23 (1H), 10.37 (1H), 11.92 (1H).

Example 298 Preparation of $N^2$-methyl-N-{4-[4-oxo-3-(phenylamino)-4,5,6,7-tetrahydro-1H-indol-2-yl]pyridin-2-yl}glycinamide

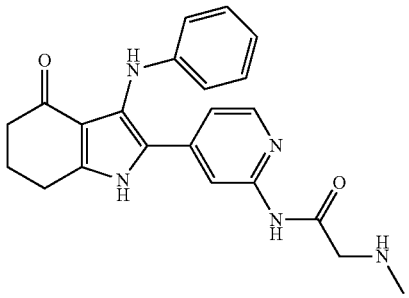 [SMILES: CNCC(=O)Nc1cc(-c2[nH]c3c(c2Nc2ccccc2)C(=O)CCC3)ccn1]

Example 297 (16 mg, 33 µmol) in 4M HCl in dioxane (4 mL) was stirred at RT for 2 h. Concentrated to give the desired product as a HCl salt (10 mg, 71%).

1H-NMR (400 MHz, DMSO-d6), Shift [ppm]=2.00-2.13 (2H), 2.29-2.38 (2H), 2.59 (3H), 2.88 (2H), 3.43-3.54 (1H), 3.55-3.66 (1H), 6.55-6.67 (2H), 6.98-7.09 (2H), 7.33 (1H), 8.11 (1H), 8.19 (1H), 8.99 (2H), 11.06 (1H), 12.12 (1H).

Example 299 Preparation of tert-butyl methyl[3-oxo-3-({4-[4-oxo-3-(phenylamino)-4,5,6,7-tetrahydro-1H-indol-2-yl]pyridin-2-yl}amino)propyl]carbamate

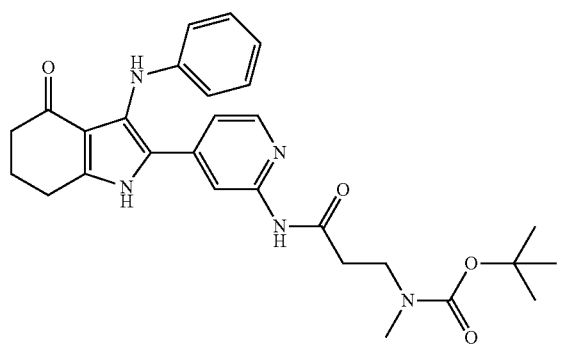 [SMILES: CN(CCC(=O)Nc1cc(-c2[nH]c3c(c2Nc2ccccc2)C(=O)CCC3)ccn1)C(=O)OC(C)(C)C]

Using Method G2: Example 139 (150 mg, 471 µmol) gave the desired product (74 mg, 31%) after preparative HPLC (basic method).

1H-NMR (400 MHz, DMSO-d6), Shift [ppm]=1.36 (9H), 1.98-2.12 (2H), 2.33 (2H), 2.57 (2H), 2.77 (3H), 2.86 (2H), 3.44 (2H), 6.44-6.68 (3H), 7.00 (2H), 7.15 (1H), 7.35 (1H), 8.07 (1H), 8.24 (1H), 10.40 (1H), 11.89 (1H).

Example 300 Preparation of $N^2$-methyl-N-{4-[4-oxo-3-(phenylamino)-4,5,6,7-tetrahydro-1H-indol-2-yl]pyridin-2-yl}-beta-alaninamide

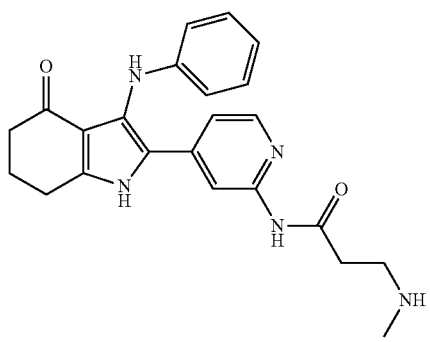 [SMILES: CNCCC(=O)Nc1cc(-c2[nH]c3c(c2Nc2ccccc2)C(=O)CCC3)ccn1]

Example 299 (53 mg, 15 µmol) in 4M HCl in dioxane (4 mL) was stirred at RT for 2 h. Concentrated to give the desired product as a HCl salt (30 mg, 64%).

1H-NMR (400 MHz, DMSO-d6), Shift [ppm]=2.02-2.10 (2H), 2.37 (2H), 2.55 (3H), 2.86-2.99 (4H), 3.10-3.20 (2H), 6.57-6.75 (3H), 7.07 (2H), 7.46 (1H), 7.81 (1H), 8.18 (1H), 8.98-9.16 (2H), 11.59 (1H), 12.44 (1H).

Example 301 Preparation of tert-butyl methyl[(2R)-1-oxo-1-({4-[4-oxo-3-(phenylamino)-4,5,6,7-tetrahydro-1H-indol-2-yl]pyridin-2-yl}amino)propan-2-yl]carbamate

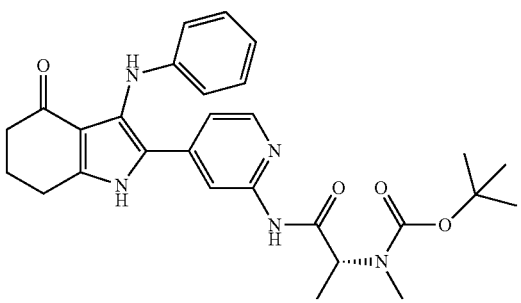 [SMILES: C[C@H](C(=O)Nc1cc(-c2[nH]c3c(c2Nc2ccccc2)C(=O)CCC3)ccn1)N(C)C(=O)OC(C)(C)C]

Using Method G2: Example 139 (150 mg, 471 µmol) gave the desired product (39 mg, 16%) after preparative HPLC (basic method).

1H-NMR (400 MHz, DMSO-d6), Shift [ppm]=1.20-1.40 (12H), 1.94-2.15 (2H), 2.33 (2H), 2.80-2.91 (5H), 4.67 (1H), 6.49-6.68 (3H), 7.01 (2H), 7.16 (1H), 7.38 (1H), 8.07 (1H), 8.19 (1H), 10.21 (1H), 11.91 (1H).

Example 302 Preparation of $N^2$-methyl-N-{4-[4-oxo-3-(phenylamino)-4,5,6,7-tetrahydro-1H-indol-2-yl]pyridin-2-yl}-D-alaninamide

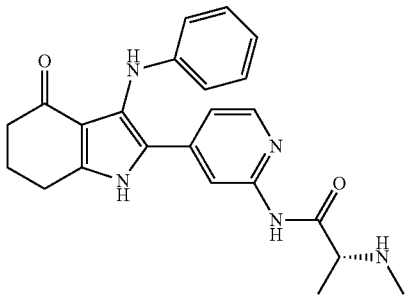 [SMILES: CN[C@H](C)C(=O)Nc1cc(-c2[nH]c3c(c2Nc2ccccc2)C(=O)CCC3)ccn1]

Example 301 (37 mg, 73 µmol) in 4M HCl in dioxane (4 mL) was stirred at RT for 2 h. Concentrated to give the desired product (10.5 mg, 35%) after preparative HPLC (basic method).

1H-NMR (500 MHz, DMSO-d6), Shift [ppm]=1.21 (3H), 1.99-2.08 (2H), 2.27 (3H), 2.33 (2H), 2.86 (2H), 3.24 (1H), 6.52-6.64 (3H), 7.01 (2H), 7.18 (1H), 7.39 (1H), 8.05-8.13 (1H), 8.21 (1H), 8.23 (1H), 11.93 (1H).

Example 303 Preparation of tert-butyl methyl[(2S)-1-oxo-1-({4-[4-oxo-3-(phenylamino)-4,5,6,7-tetrahydro-1H-indol-2-yl]pyridin-2-yl}amino)propan-2-yl]carbamate

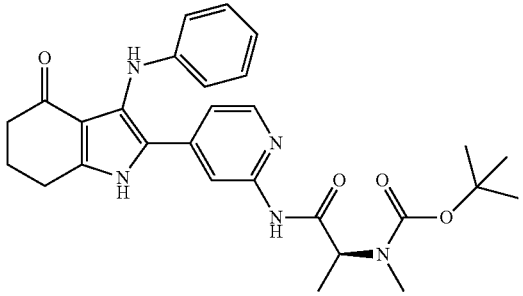 [SMILES: C[C@@H](C(=O)Nc1cc(-c2[nH]c3c(c2Nc2ccccc2)C(=O)CCC3)ccn1)N(C)C(=O)OC(C)(C)C]

Using Method G2: Example 139 (150 mg, 471 µmol) gave the desired product (32.5 mg, 14%) after preparative HPLC (basic method).

1H-NMR (400 MHz, DMSO-d6), Shift [ppm]=1.25-1.47 (12H), 1.99-2.09 (2H), 2.29-2.38 (2H), 2.80-2.90 (5H), 6.51-6.65 (3H), 7.01 (2H), 7.16 (1H), 7.38 (1H), 8.07 (1H), 8.19 (1H), 10.21 (1H), 11.92 (1H).

Example 304 Preparation of $N^2$-methyl-N-{4-[4-oxo-3-(phenylamino)-4,5,6,7-tetrahydro-1H-indol-2-yl]pyridin-2-yl}-L-alaninamide

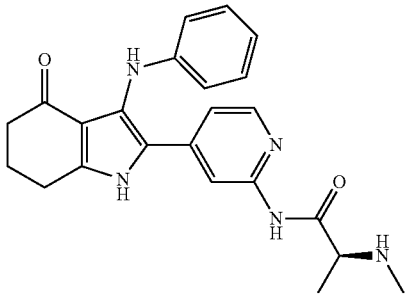 [SMILES: CN[C@@H](C)C(=O)Nc1cc(-c2[nH]c3c(c2Nc2ccccc2)C(=O)CCC3)ccn1]

Example 303 (29 mg, 58 μmol) in 4M HCl in dioxane (4 mL) was stirred at RT for 2 h. Concentrated to give the desired product (6.5 mg, 28%) after preparative HPLC (basic method).

1H-NMR (500 MHz, DMSO-d6), Shift [ppm]=1.21 (3H), 2.05 (2H), 2.27 (3H), 2.31-2.36 (2H), 2.86 (2H), 3.18-3.28 (2H), 6.53-6.64 (3H), 7.01 (2H), 7.18 (1H), 7.39 (1H), 8.08 (1H), 8.19 (1H), 8.24 (1H), 11.93 (1H).

Example 305 Preparation of $N^2,N^2$;-dimethyl-N-{4-[4-oxo-3-(phenylamino)-4,5,6,7-tetrahydro-1H-indol-2-yl]pyridin-2-yl}-alaninamide

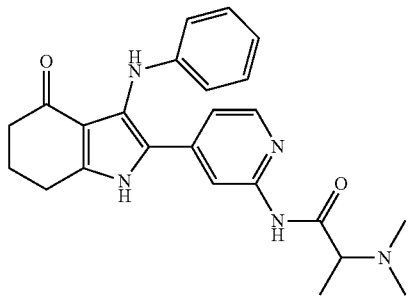 [SMILES: CC(C(=O)Nc1cc(-c2[nH]c3c(c2Nc2ccccc2)C(=O)CCC3)ccn1)N(C)C]

Using Method G2: Example 139 (50 mg, 157 μmol) gave the desired product (3 mg, 5%) after preparative HPLC (basic method).

1H-NMR (400 MHz, DMSO-d6), Shift [ppm]=0.90-0.97 (3H), 1.14 (3H), 1.99-2.10 (2H), 2.23 (5H), 2.86 (2H), 6.51-6.66 (3H), 7.01 (2H), 7.17 (1H), 7.39 (1H), 8.07 (1H), 8.23 (1H), 9.84 (1H), 11.93 (1H).

Example 306 Preparation of $N^2$,2-dimethyl-N-{4-[4-oxo-3-(phenylamino)-4,5,6,7-tetrahydro-1H-indol-2-yl]pyridin-2-yl}alaninamide

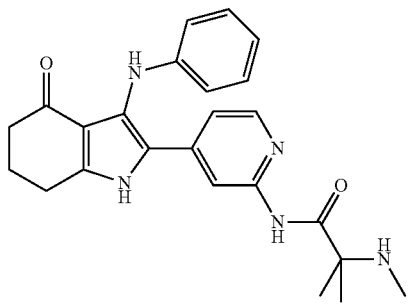 [SMILES: CNC(C)(C)C(=O)Nc1cc(-c2[nH]c3c(c2Nc2ccccc2)C(=O)CCC3)ccn1]

To a solution of N-(tert-butoxycarbonyl)-N,2-dimethylalanine (34 mg, 157 μmol) in DMF (1 mL) was added HATU (27 mg, 71 μmol) and stirred for 10 min at RT. To the reaction was added Example 139 (50 mg, 157 μmol) and DIPEA (27 μL, 157 μmol) and stirred for 5 h at 50° C. Additional N-(tert-butoxycarbonyl)-N,2-dimethylalanine (34 mg, 157 μmol), HATU (27 mg, 71 μmol) and Example 139 (50 mg, 157 μmol) and DIPEA (27 μL, 157 μmol) were added and heated at 100° C. for 16 h. Additional N-(tert-butoxycarbonyl)-N,2-dimethylalanine (34 mg, 157 μmol), HATU (27 mg, 71 μmol) and Example 139 (50 mg, 157 μmol) and DIPEA (27 μL, 157 μmol) were added and heated at 100° C. for 5 h.

Purification by preparative HPLC (basic method) gave the desired product (3 mg, 5%). 1H-NMR (400 MHz, DMSO-d6), Shift [ppm]=1.23 (6H), 1.97-2.12 (2H), 2.18 (3H), 2.29-2.39 (2H), 2.86 (2H), 6.52-6.65 (2H), 6.95-7.05 (2H), 7.16 (1H), 7.39 (1H), 8.05 (1H), 8.24 (1H), 11.94 (1H).

Example 307 Preparation of $N^2,N^2$;-dimethyl-N-{4-[4-oxo-3-(phenylamino)-4,5,6,7-tetrahydro-1H-indol-2-yl]pyridin-2-yl}glycinamide

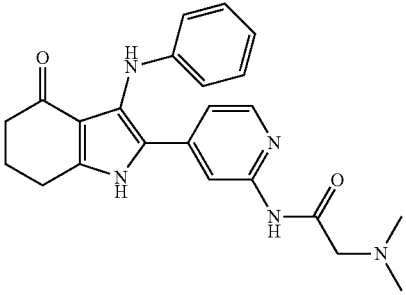

Using Method G2: Example 139 (50 mg, 157 μmol) gave the desired product (13 mg, 19%) after preparative HPLC (basic method).

1H-NMR (400 MHz, DMSO-d6), Shift [ppm]=1.97-2.10 (2H), 2.28 (6H), 2.33 (2H), 2.86 (2H), 3.09 (2H), 6.48-6.73 (3H), 6.96-7.09 (2H), 7.18 (1H), 7.38 (1H), 8.08 (1H), 8.17-8.29 (1H), 9.72 (1H), 11.93 (1H).

Example 308 Preparation of N-{4-[4-oxo-3-(phenylamino)-4,5,6,7-tetrahydro-1H-indol-2-yl]pyridin-2-yl}-2-(pyrrolidin-1-yl)acetamide

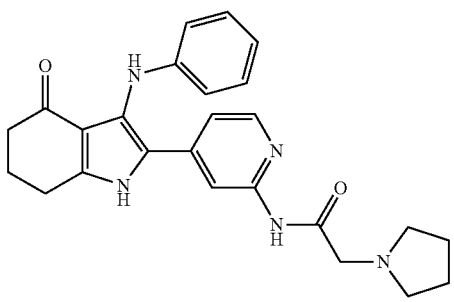 [SMILES: O=C(CN1CCCC1)Nc1cc(-c2[nH]c3c(c2Nc2ccccc2)C(=O)CCC3)ccn1]

Using Method G2: Example 139 (50 mg, 157 μmol) gave the desired product (3 mg, 4%) after preparative HPLC (basic method).

1H-NMR (400 MHz, DMSO-d6), Shift [ppm]=1.74 (4H), 1.99-2.11 (2H), 2.26-2.36 (2H), 2.55-2.63 (4H), 2.81-2.90 (2H), 3.27 (2H), 6.51-6.64 (3H), 6.95-7.05 (2H), 7.18 (1H), 7.38 (1H), 8.07 (1H), 8.23 (1H), 9.72 (1H), 11.93 (1H).

Example 309 Preparation of 1-methyl-N-{4-[4-oxo-3-(phenylamino)-4,5,6,7-tetrahydro-1H-indol-2-yl]pyridin-2-yl}-prolinamide

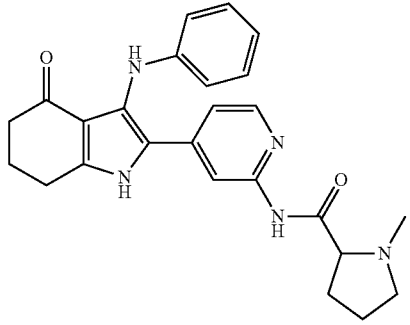 [SMILES: CN1CCCC1C(=O)Nc1cc(-c2[nH]c3c(c2Nc2ccccc2)C(=O)CCC3)ccn1]

Using Method G2: Example 139 (100 mg, 314 µmol) gave the desired product (10 mg, 7%) after preparative HPLC (basic method).

1H-NMR (400 MHz, DMSO-d6), Shift [ppm]=1.67-1.85 (3H), 1.99-2.12 (2H), 2.13-2.24 (1H), 2.30-2.42 (6H), 2.82-2.92 (2H), 2.94-3.03 (1H), 3.06-3.20 (1H), 6.51-6.67 (3H), 6.96-7.09 (2H), 7.18 (1H), 7.41 (1H), 8.02-8.13 (1H), 8.23 (1H), 9.72 (1H), 11.95 (1H).

Example 310 Preparation of 1-methyl-5-oxo-N-{4-[4-oxo-3-(phenylamino)-4,5,6,7-tetrahydro-1H-indol-2-yl]pyridin-2-yl}-prolinamide

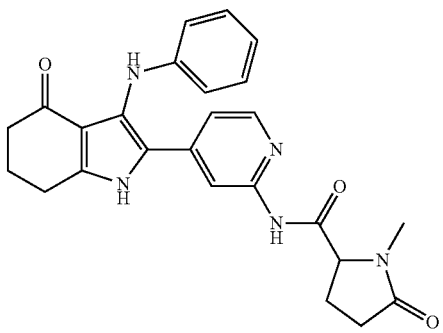 [SMILES: CN1C(=O)CCC1C(=O)Nc1cc(-c2[nH]c3c(c2Nc2ccccc2)C(=O)CCC3)ccn1]

Using Method G2: Example 139 (100 mg, 314 µmol) gave the desired product (20 mg, 14%) after preparative HPLC (acidic method).

1H-NMR (400 MHz, DMSO-d6), Shift [ppm]=1.74-1.97 (1H), 1.99-2.14 (2H), 2.15-2.39 (5H), 2.62-2.70 (3H), 2.76-2.97 (2H), 4.23-4.45 (1H), 6.51-6.65 (3H), 7.01 (2H), 7.18-7.29 (1H), 8.06-8.21 (2H), 10.76 (1H), 11.97 (1H).

Example 311 Preparation of 5-oxo-N-{4-[4-oxo-3-(phenylamino)-4,5,6,7-tetrahydro-1H-indol-2-yl]pyridin-2-yl}-prolinamide

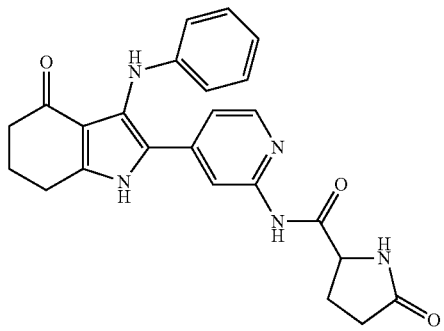 [SMILES: O=C1CCC(C(=O)Nc2cc(-c3[nH]c4c(c3Nc3ccccc3)C(=O)CCC4)ccn2)N1]

Using Method G2: Example 139 (100 mg, 314 µmol) gave the desired product (60 mg, 44%) after preparative HPLC (Column: XBridge C18 5µ 100×30 mm; Solvent A: Water+0.1 Vol-% HCO$_2$H, Solvent B: Acetonitrile; Gradient: 0.00-0.50 min 15% B (25-70 mL/min), 0.51-5.50 min 15-30% B; Flow: 70 mL/min).

1H-NMR (400 MHz, DMSO-d6), Shift [ppm]=1.94 (1H), 2.00-2.09 (2H), 2.10-2.28 (2H), 2.29-2.38 (3H), 2.86 (2H), 4.30 (2H), 6.53-6.66 (3H), 7.02 (2H), 7.19-7.25 (1H), 7.89 (1H), 8.11 (1H), 8.15 (1H), 10.59 (1H), 12.00 (1H).

Example 312 Preparation of methyl (4-{3-[(3-fluorophenyl)amino]-4-oxo-4,5,6,7-tetrahydro-1H-indol-2-yl}pyridin-2-yl)carbamate

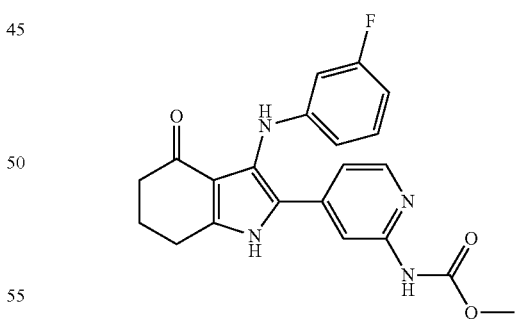

Example 138 (60 mg, 178 µmol in THF (1.5 mL) was added pyridine (144 µL, 1.78 mmol) followed by a solution of methyl chloroformate (33.7 mg, 357 µmol) in THF (0.5 mL). Heated at 60° C. for 16 h and then poured onto water (20 mL) and the solid collected. Purification by Biotage (silica, using DCM:MeOH) gave the desired product (15 mg, 21%). 1H-NMR (400 MHz, DMSO-d6), d [ppm]=1.98-2.11 (2H), 2.28-2.36 (2H), 2.86 (2H), 3.60-3.68 (3H), 6.26 (1H), 6.30-6.45 (2H), 6.95-7.08 (1H), 7.18 (1H), 7.63 (1H), 8.00 (1H), 8.10 (1H), 10.01 (1H), 11.94 (1H).

Example 313 Preparation of methyl N-(4-{3-[(4-fluorophenyl)amino]-4-oxo-4,5,6,7-tetrahydro-1H-indol-2-yl}pyridin-2-yl)acetamide

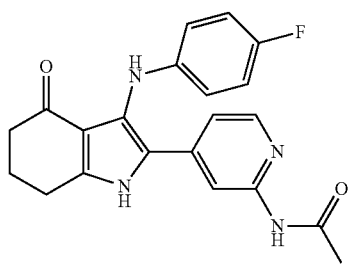 [SMILES: CC(=O)Nc1cc(-c2[nH]c3c(c2Nc2ccc(F)cc2)C(=O)CCC3)ccn1]

Example 211 (60 mg, 178 µmol in THF (1.5 mL) was added pyridine (144 µL, 1.78 mmol) followed by a solution of acetyl chloride (28 mg, 357 µmol) in THF (0.5 mL) and stirred at RT for 2 h. MeOH (2 mL) added and concentrated. Purification by silica chromatography gave the desired product (35 mg, 49%).

1H-NMR (400 MHz, DMSO-d6), Shift [ppm]=2.00-2.12 (5H), 2.29-2.34 (2H), 2.85 (2H), 6.49-6.62 (2H), 6.78-6.90 (2H), 7.14 (1H), 7.34 (1H), 8.09 (1H), 8.20 (1H), 10.31 (1H), 11.89 (1H).

Example 314 Preparation of N-(4-{3-[(4-fluorophenyl)amino]-4-oxo-4,5,6,7-tetrahydro-1H-indol-2-yl}pyridin-2-yl)cyclopropanecarboxamide

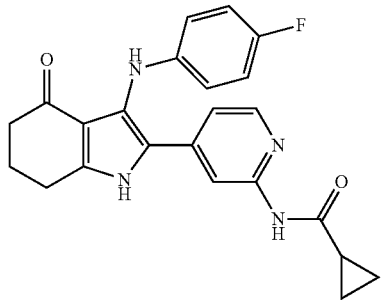 [SMILES: O=C1CCCc2[nH]c(-c3ccnc(NC(=O)C4CC4)c3)c(Nc3ccc(F)cc3)c21]

Using Method G2: Example 211 (60 mg, 178 µmol in THF (1.5 mL) was added pyridine (144 µL, 1.78 mmol) followed by a solution of cyclopropanecarbonyl chloride (37 mg, 357 µmol) in THF (0.5 mL) and stirred at RT for 2 h. MeOH (2 mL) added and concentrated. Purification by silica chromatography gave the desired product (32 mg, 42%).

1H-NMR (400 MHz, DMSO-d6), Shift [ppm]=0.68-0.87 (4H), 1.90-2.13 (3H), 2.26-2.40 (2H), 2.84 (2H), 6.49-6.60 (2H), 6.77-6.91 (2H), 7.12 (1H), 7.35 (1H), 8.08 (1H), 8.20 (1H), 10.63 (1H), 11.87 (1H).

Example 315 Preparation of N-(4-{3-[(3,4-difluorophenyl)amino]-4-oxo-4,5,6,7-tetrahydro-1H-indol-2-yl}pyridin-2-yl)acetamide

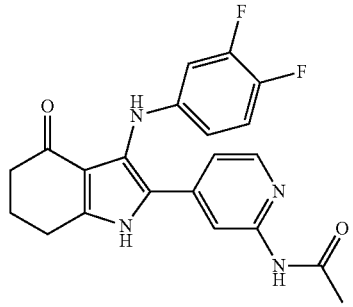 [SMILES: CC(=O)Nc1cc(-c2[nH]c3c(c2Nc2ccc(F)c(F)c2)C(=O)CCC3)ccn1]

To a solution of Example 212 (80 mg, 226 µmol in THF (1.5 mL) was added pyridine (183 µL, 2.26 mmol) followed by a solution of acetyl chloride (35 mg, 451 µmol) in THF (0.5 mL) and stirred at RT for 2 h. MeOH (2 mL) added and concentrated. Purification by silica chromatography gave the desired product (68 mg, 72%).

1H-NMR (400 MHz, DMSO-d6), Shift [ppm]=1.99-2.10 (5H), 2.27-2.37 (2H), 2.86 (2H), 6.25-6.37 (1H), 6.46 (1H), 7.04 (1H), 7.19 (1H), 7.56 (1H), 8.15 (1H), 8.23 (1H), 10.34 (1H), 11.94 (1H).

Example 316 Preparation of N-(4-{3-[(3,4-difluorophenyl)amino]-4-oxo-4,5,6,7-tetrahydro-1H-indol-2-yl}pyridin-2-yl)cyclopropanecarboxamide

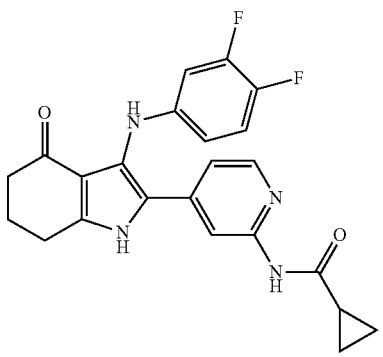 [SMILES: O=C1CCCc2[nH]c(-c3ccnc(NC(=O)C4CC4)c3)c(Nc3ccc(F)c(F)c3)c21]

To a solution of Example 212 (80 mg, 226 µmol in THF (1.5 mL) was added pyridine (183 µL, 2.26 mmol) followed by a solution of cyclopropanecarbonyl chloride (47 mg, 451 µmol) in THF (0.5 mL) and stirred at RT for 2 h. MeOH (2 mL) added and concentrated. Purification by silica chromatography gave the desired product (37 mg, 37%).

1H-NMR (400 MHz, DMSO-d6), Shift [ppm]=0.73-0.85 (4H), 1.93-2.11 (3H), 2.27-2.39 (2H), 2.85 (2H), 6.24-6.37 (1H), 6.46 (1H), 6.97-7.08 (1H), 7.18 (1H), 7.57 (1H), 8.14 (1H), 8.22 (1H), 10.65 (1H), 11.92 (1H).

Example 317 Preparation of N-{4-[4-oxo-3-(phenylamino)-6-(propan-2-yl)-4,5,6,7-tetrahydro-1H-indol-2-yl]pyridin-2-yl}acetamide

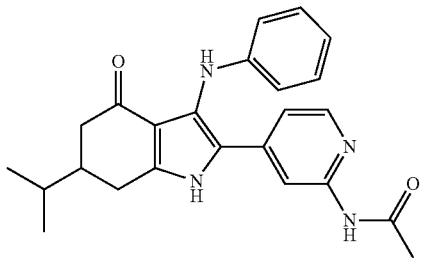 [SMILES: CC(=O)Nc1cc(-c2[nH]c3c(c2Nc2ccccc2)C(=O)CC(C(C)C)C3)ccn1]

To a solution of Example 49 (80 mg, 221 μmol in THF (1.5 mL) was added pyridine (180 μL, 2.22 mmol) followed by a solution of acetyl chloride (35 mg, 444 μmol) in THF (0.5 mL) and stirred at RT for 2 h. MeOH (2 mL) added and concentrated. Purification by preparative HPLC (basic method) gave the desired product (43 mg, 48%).

1H-NMR (400 MHz, DMSO-d6), Shift [ppm]=0.94 (3H), 0.94 (3H), 1.55-1.74 (1H), 1.99 (1H), 2.06 (3H), 2.18-2.31 (2H), 2.61 (1H), 2.92 (1H), 6.50-6.65 (3H), 7.01 (2H), 7.15 (1H), 7.32 (1H), 8.07 (1H), 8.21 (1H), 10.30 (1H), 11.88 (1H).

Example 318 Preparation of N-{4-[4-oxo-3-(phenylamino)-6-(propan-2-yl)-4,5,6,7-tetrahydro-1H-indol-2-yl]pyridin-2-yl}cyclopropanecarboxamide

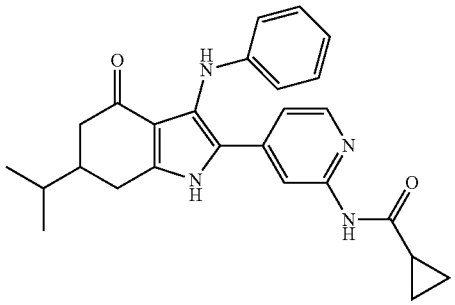 [SMILES: CC(C)C1CC(=O)c2c([nH]c(-c3ccnc(NC(=O)C4CC4)c3)c2Nc2ccccc2)C1]

To a solution of Example 49 (80 mg, 221 μmol in THF (1.5 mL) was added pyridine (180 μL, 2.22 mmol) followed by a solution of cyclopropanecarbonyl chloride (46 mg, 444 μmol) in THF (0.5 mL) and stirred at RT for 2 h. MeOH (2 mL) added and concentrated. Purification by preparative HPLC (basic method) gave the desired product (61 mg, 61%).

1H-NMR (400 MHz, DMSO-d6), Shift [ppm]=0.80 (4H), 0.94 (3H), 0.93 (3H), 1.60-1.74 (1H), 1.91-2.04 (2H), 2.17-2.31 (2H), 2.60 (1H), 2.92 (1H), 6.49-6.67 (3H), 7.01 (2H), 7.14 (1H), 7.32 (1H), 8.06 (1H), 8.18-8.26 (1H), 10.62 (1H), 11.86 (1H).

Example 319 Preparation of N-{4-[3-[(3-fluorophenyl)amino]-4-oxo-6-(propan-2-yl)-4,5,6,7-tetrahydro-1H-indol-2-yl]pyridin-2-yl}acetamide

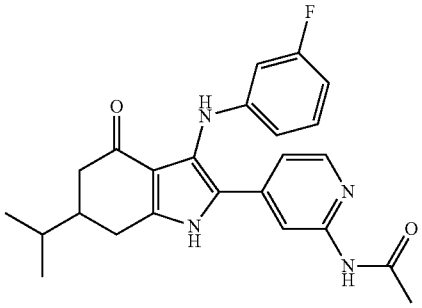 [SMILES: CC(=O)Nc1cc(-c2[nH]c3c(c2Nc2cccc(F)c2)C(=O)CC(C(C)C)C3)ccn1]

To a solution of Example 50 (80 mg, 211 μmol in THF (1.5 mL) was added pyridine (171 μL, 2.11 mmol) followed by a solution of acetyl chloride (33 mg, 423 μmol) in THF (0.5 mL) and stirred at RT for 3 h. MeOH (2 mL) added and concentrated. Purification by preparative HPLC (basic method) gave the desired product (61 mg, 65%).

1H-NMR (400 MHz, DMSO-d6), Shift [ppm]=0.94 (3H), 0.94 (3H), 1.56-1.75 (1H), 1.99 (1H), 2.04-2.11 (3H), 2.17-2.31 (2H), 2.56-2.67 (1H), 2.83-3.02 (1H), 6.24 (1H), 6.28-6.41 (2H), 6.93-7.07 (1H), 7.20 (1H), 7.61 (1H), 8.09-8.16 (1H), 8.25 (1H), 10.33 (1H), 11.92 (1H).

Example 320 Preparation of N-{4-[3-[(3-fluorophenyl)amino]-4-oxo-6-(propan-2-yl)-4,5,6,7-tetrahydro-1H-indol-2-yl]pyridin-2-yl}cyclopropanecarboxamide

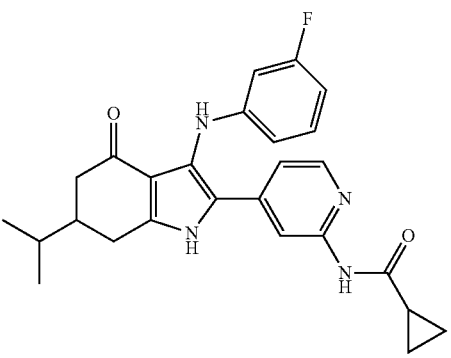 [SMILES: CC(C)C1CC(=O)c2c([nH]c(-c3ccnc(NC(=O)C4CC4)c3)c2Nc2cccc(F)c2)C1]

To a solution of Example 50 (80 mg, 211 μmol in THF (1.5 mL) was added pyridine (171 μL, 2.11 mmol) followed by a solution of cyclopropanecarbonyl chloride (44 mg, 423 μmol) in THF (0.5 mL) and stirred at RT for 3 h. MeOH (2 mL) added and concentrated. Purification by preparative HPLC (basic method) gave the desired product (64 mg, 64%).

1H-NMR (400 MHz, DMSO-d6), Shift [ppm]=0.80 (4H), 0.94 (3H), 0.93 (3H), 1.65 (1H), 1.86-2.09 (2H), 2.16-2.31 (2H), 2.61 (1H), 2.92 (1H), 6.24 (1H), 6.28-6.39 (2H), 6.93-7.07 (1H), 7.19 (1H), 7.61 (1H), 8.13 (1H), 8.24 (1H), 10.65 (1H), 11.91 (1H).

Example 321 Preparation of N-{4-[3-[(4-fluorophenyl)amino]-4-oxo-6-(propan-2-yl)-4,5,6,7-tetrahydro-1H-indol-2-yl]pyridin-2-yl}acetamide

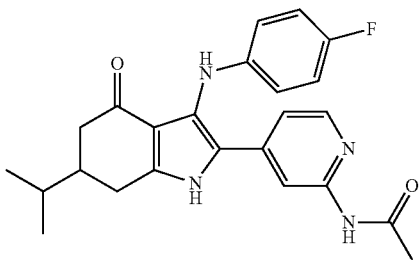 [SMILES: CC(=O)Nc1cc(-c2[nH]c3c(c2Nc2ccc(F)cc2)C(=O)CC(C(C)C)C3)ccn1]

To a solution of Example 167 (80 mg, 211 μmol in THF (1.5 mL) was added pyridine (171 μL, 2.11 mmol) followed by a solution of acetyl chloride (33 mg, 423 μmol) in THF (0.5 mL) and stirred at RT for 3 h. MeOH (2 mL) added and concentrated. Purification by silica chromatography gave the desired product (69 mg, 78%).

1H-NMR (400 MHz, DMSO-d6), Shift [ppm]=0.94 (3H), 0.93 (3H), 1.57-1.75 (1H), 1.99 (1H), 2.06 (3H), 2.15-2.32 (2H), 2.56-2.66 (1H), 2.92 (1H), 6.50-6.59 (2H), 6.78-6.91 (2H), 7.14 (1H), 7.32 (1H), 8.09 (1H), 8.21 (1H), 10.31 (1H), 11.89 (1H).

Example 322 Preparation of N-{4-[3-[(4-fluorophenyl)amino]-4-oxo-6-(propan-2-yl)-4,5,6,7-tetrahydro-1H-indol-2-yl]pyridin-2-yl}cyclopropanecarboxamide

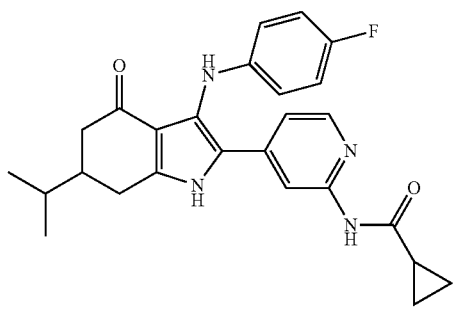 [SMILES: CC(C)C1CC(=O)c2c([nH]c(-c3ccnc(NC(=O)C4CC4)c3)c2Nc2ccc(F)cc2)C1]

To a solution of Example 167 (80 mg, 211 μmol in THF (1.5 mL) was added pyridine (171 μL, 2.11 mmol) followed by a solution of cyclopropanecarbonyl chloride (44 mg, 423 μmol) in THF (0.5 mL) and stirred at RT for 3 h. MeOH (2 mL) added and concentrated. Purification by silica chromatography and crystallization from EtOH:H2O gave the desired product (59 mg, 63%).

1H-NMR (400 MHz, DMSO-d6), Shift [ppm]=0.79 (4H), 0.93 (6H), 1.59-1.76 (1H), 1.98 (2H), 2.17-2.31 (2H), 2.60 (1H), 2.91 (1H), 6.48-6.59 (2H), 6.79-6.90 (2H), 7.13 (1H), 7.33 (1H), 8.09 (1H), 8.18-8.24 (1H), 10.63 (1H), 11.87 (1H).

Example 323 Preparation of N-{4-[3-[(3,4-difluorophenyl)amino]-4-oxo-6-(propan-2-yl)-4,5,6,7-tetrahydro-1H-indol-2-yl]pyridin-2-yl}acetamide

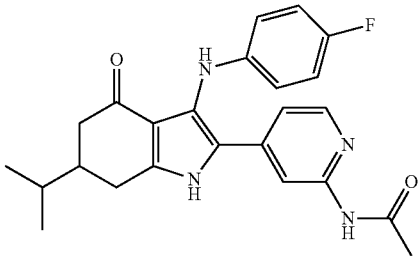 [SMILES: CC(=O)Nc1cc(-c2[nH]c3c(c2Nc2ccc(F)cc2)C(=O)CC(C(C)C)C3)ccn1]

To a solution of Example 222 (80 mg, 202 μmol in THF (1.5 mL) was added pyridine (171 μL, 2.11 mmol) followed by a solution of acetyl chloride (32 mg, 404 μmol) in THF (0.5 mL) and stirred at RT for 3 h. MeOH (2 mL) added and concentrated. Purification by silica chromatography and crystallization from EtOH:H2O gave the desired product (62 mg, 70%).

1H-NMR (400 MHz, DMSO-d6), Shift [ppm]=0.94 (6H), 1.58-1.72 (1H), 2.00 (1H), 2.06 (3H), 2.17-2.31 (2H), 2.57-2.66 (1H), 2.92 (1H), 6.20-6.36 (1H), 6.45 (1H), 6.95-7.12 (1H), 7.19 (1H), 7.56 (1H), 8.15 (1H), 8.24 (1H), 10.34 (1H), 11.93 (1H).

Example 324 Preparation of N-{4-[3-[(3,4-difluorophenyl)amino]-4-oxo-6-(propan-2-yl)-4,5,6,7-tetrahydro-1H-indol-2-yl]pyridin-2-yl}cyclopropanecarboxamide

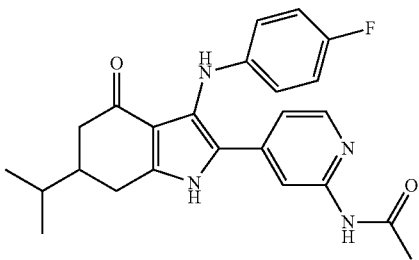 [SMILES: CC(=O)Nc1cc(-c2[nH]c3c(c2Nc2ccc(F)cc2)C(=O)CC(C(C)C)C3)ccn1]

To a solution of Example 222 (80 mg, 202 μmol in THF (1.5 mL) was added pyridine (171 μL, 2.11 mmol) followed by a solution of cyclopropanecarbonyl chloride (42 mg, 404 μmol) in THF (0.5 mL) and stirred at RT for 3 h. MeOH (2 mL) added and concentrated. Purification by silica chromatography and crystallization from EtOH:H$_2$O gave the desired product (64 mg, 65%).

1H-NMR (400 MHz, DMSO-d6), Shift [ppm]=0.73-0.86 (4H), 0.93 (6H), 1.65 (1H), 1.98 (2H), 2.17-2.32 (2H), 2.61 (1H), 2.91 (1H), 6.24-6.34 (1H), 6.45 (1H), 6.97-7.09 (1H), 7.18 (1H), 7.56 (1H), 8.14 (1H), 8.20-8.26 (1H), 10.65 (1H), 11.92 (1H).

Example 325 Preparation of 2-methoxy-N-{4-[4-oxo-3-(phenylamino)-4,5,6,7-tetrahydro-1H-indol-2-yl]pyridin-2-yl}acetamide

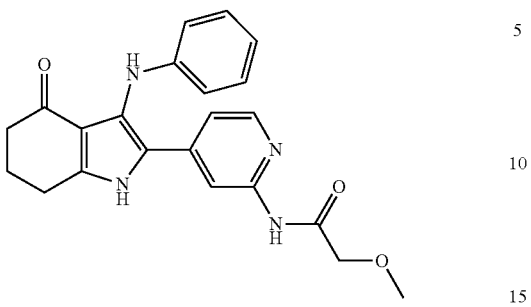

Using Method G2: Example 139 (50 mg, 157 µmol) gave the desired product (8.5 mg, 14%) after preparative HPLC (basic method).
1H-NMR (400 MHz, DMSO-d6), Shift [ppm]=1.99-2.14 (2H), 2.30-2.40 (2H), 2.86 (2H), 3.36 (3H), 4.03 (2H), 6.49-6.68 (3H), 7.01 (2H), 7.18 (1H), 7.38 (1H), 8.09 (1H), 8.22 (1H), 9.78 (1H), 11.93 (1H).

Example 326 Preparation of 2-methoxy-2-methyl-N-{4-[4-oxo-3-(phenylamino)-4,5,6,7-tetrahydro-1H-indol-2-yl]pyridin-2-yl}propanamide

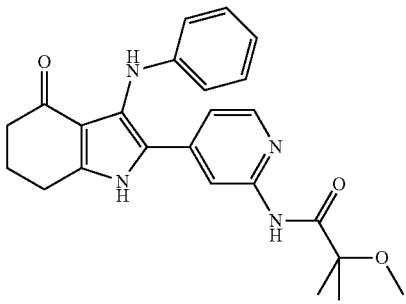 [SMILES: COC(C)(C)C(=O)Nc1cc(-c2[nH]c3c(c2Nc2ccccc2)C(=O)CCC3)ccn1]

Using Method G2: Example 139 (50 mg, 157 µmol) gave the desired product (9.5 mg, 14%) after preparative HPLC (basic method).
1H-NMR (400 MHz, DMSO-d6), Shift [ppm]=0.92-0.98 (1H), 1.36 (5H), 2.01-2.11 (2H), 2.29-2.38 (2H), 2.86 (2H), 3.25 (2H), 6.51-6.64 (3H), 7.01 (2H), 7.20 (1H), 7.41 (1H), 8.08 (1H), 8.18 (1H), 9.18 (1H), 11.94 (1H).

Example 327 Preparation of 2-hydroxy-2-methyl-N-{4-[4-oxo-3-(phenylamino)-4,5,6,7-tetrahydro-1H-indol-2-yl]pyridin-2-yl}propanamide

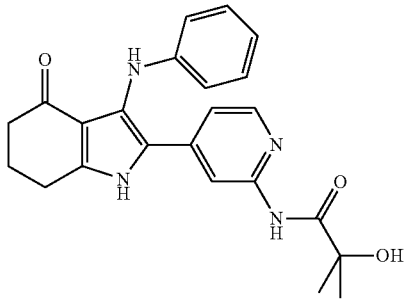 [SMILES: CC(C)(O)C(=O)Nc1cc(-c2[nH]c3c(c2Nc2ccccc2)C(=O)CCC3)ccn1]

Using Method G2: Example 139 (50 mg, 157 µmol) gave the desired product (5.5 mg, 9%) after preparative HPLC (Column: XBridge C18 5µ 100×30 mm; Solvent A: Water+ 0.2 Vol-% NH4OH, Solvent B: Acetonitrile; Gradient: 0-8 min 26-46% B; Flow: 70 mL/min).
1H-NMR (400 MHz, DMSO-d6), Shift [ppm]=1.35 (6H), 1.98-2.13 (2H), 2.28-2.38 (2H), 2.86 (2H), 5.98 (1H), 6.51-6.65 (3H), 7.01 (2H), 7.18 (1H), 7.40 (1H), 8.07 (1H), 8.25 (1H), 9.28 (1H), 11.94 (1H).

Example 328 Preparation of (2-ethoxy-2-methyl-N-{4-[4-oxo-3-(phenylamino)-4,5,6,7-tetrahydro-1H-indol-2-yl]pyridin-2-yl}propanamide

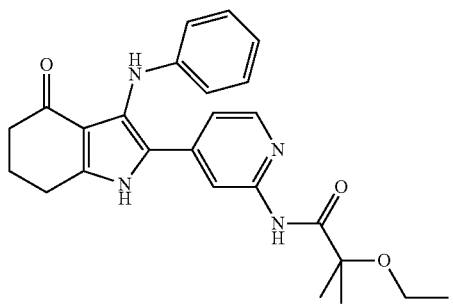 [SMILES: CCOC(C)(C)C(=O)Nc1cc(-c2[nH]c3c(c2Nc2ccccc2)C(=O)CCC3)ccn1]

Using Method G2: Example 139 (50 mg, 157 µmol) gave the desired product (27 mg, 38%) after preparative HPLC (basic method).
1H-NMR (400 MHz, DMSO-d6), Shift [ppm]=1.19 (3H), 1.37 (6H), 1.91-2.13 (2H), 2.25-2.39 (2H), 2.86 (2H), 3.45 (2H), 6.53-6.69 (3H), 7.01 (2H), 7.20 (1H), 7.42 (1H), 8.09 (1H), 8.19 (1H), 9.15 (1H), 11.95 (1H).

Example 329 Preparation of (2-methoxy-N-{4-[4-oxo-3-(phenylamino)-4,5,6,7-tetrahydro-1H-indol-2-yl]pyridin-2-yl}propanamide

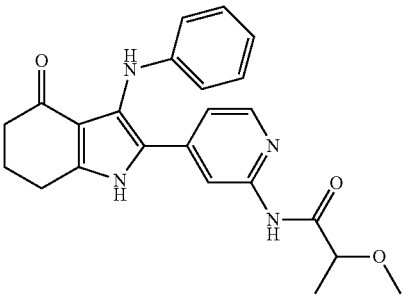 [SMILES: COC(C)C(=O)Nc1cc(-c2[nH]c3c(c2Nc2ccccc2)C(=O)CCC3)ccn1]

Using Method G2: Example 139 (50 mg, 157 µmol) gave the desired product (28 mg, 42%) after preparative HPLC (basic method).
1H-NMR (400 MHz, DMSO-d6), Shift [ppm]=1.28 (3H), 1.99-2.11 (2H), 2.28-2.37 (2H), 2.86 (2H), 3.28 (3H), 3.97 (1H), 6.53-6.67 (3H), 7.01 (2H), 7.19 (1H), 7.39 (1H), 8.09 (1H), 8.15-8.30 (1H), 9.85 (1H), 11.93 (1H).

Example 330 Preparation of N-{4-[4-oxo-3-(phenylamino)-4,5,6,7-tetrahydro-1H-indol-2-yl]pyridin-2-yl}-2-propoxyacetamide

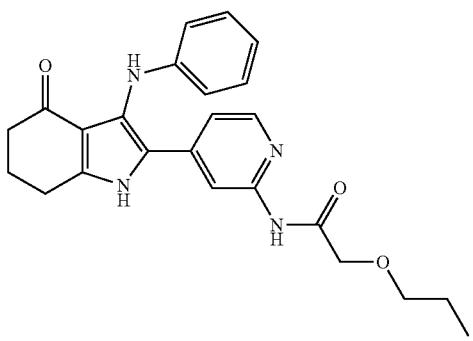 [SMILES: CCCOCC(=O)Nc1cc(-c2[nH]c3c(c2Nc2ccccc2)C(=O)CCC3)ccn1]

Using Method G2: Example 139 (100 mg, 314 µmol) gave the desired product (33 mg, 25%) after preparative HPLC (basic method).

1H-NMR (400 MHz, DMSO-d6), Shift [ppm]=0.84-0.98 (3H), 1.58 (2H), 2.00-2.11 (2H), 2.28-2.38 (2H), 2.87 (2H), 3.47 (2H), 4.07 (2H), 6.52-6.67 (3H), 6.97-7.06 (2H), 7.19 (1H), 7.40 (1H), 8.10 (1H), 8.24 (1H), 9.70 (1H), 11.96 (1H)

Example 331 Preparation of 2-(2-methylpropoxy)-N-{4-[4-oxo-3-(phenylamino)-4,5,6,7-tetrahydro-1H-indol-2-yl]pyridin-2-yl}acetamide

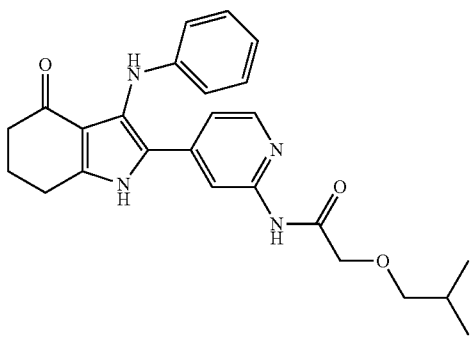 [SMILES: CC(C)COCC(=O)Nc1cc(-c2[nH]c3c(c2Nc2ccccc2)C(=O)CCC3)ccn1]

Using Method G2: Example 139 (100 mg, 314 µmol) gave the desired product (39 mg, 29%) after preparative HPLC (basic method).

1H-NMR (400 MHz, DMSO-d6), Shift [ppm]=0.90 (6H), 1.86 (1H), 1.98-2.14 (2H), 2.33 (2H), 2.86 (2H), 3.28 (2H), 4.07 (2H), 6.52-6.64 (3H), 7.01 (2H), 7.19 (1H), 7.39 (1H), 8.09 (1H), 8.24 (1H), 9.67 (1H), 11.95 (1H).

Example 332 Preparation of N-{4-[4-oxo-3-(phenylamino)-4,5,6,7-tetrahydro-1H-indol-2-yl]pyridin-2-yl}-2-(2,2,3,3-tetrafluoropropoxy)acetamide

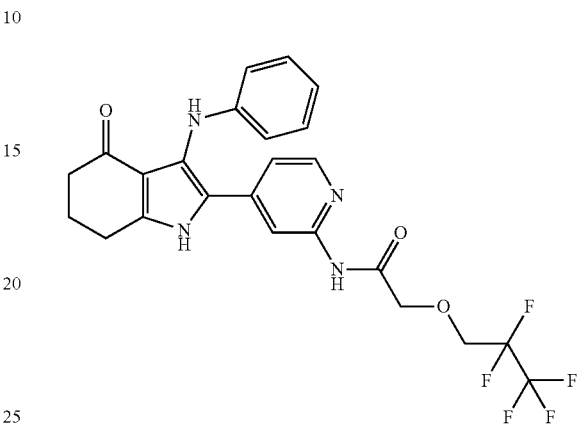

Using Method G2: Example 139 (100 mg, 314 µmol) gave the desired product (19 mg, 12%) after preparative HPLC (basic method).

1H-NMR (400 MHz, DMSO-d6), Shift [ppm]=2.00-2.14 (2H), 2.27-2.36 (2H), 2.86 (2H), 4.10 (2H), 4.29 (2H), 6.52-6.67 (3H), 7.01 (2H), 7.19 (1H), 7.40 (1H), 8.09 (1H), 8.22 (1H), 10.13 (1H), 11.96 (1H).

Example 333 Preparation of 2-butoxy-N-{4-[4-oxo-3-(phenylamino)-4,5,6,7-tetrahydro-1H-indol-2-yl]pyridin-2-yl}acetamide

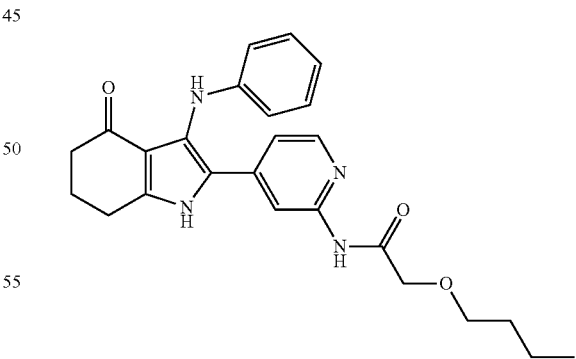

Using Method G2: Example 139 (100 mg, 314 µmol) gave the desired product (30 mg, 22%) after preparative HPLC (basic method).

1H-NMR (400 MHz, DMSO-d6), Shift [ppm]=0.91 (3H), 1.28-1.44 (2H), 1.49-1.63 (2H), 1.98-2.14 (2H), 2.33 (2H), 2.87 (2H), 3.51 (2H), 4.07 (2H), 6.51-6.67 (3H), 6.96-7.08 (2H), 7.19 (1H), 7.40 (1H), 8.10 (1H), 8.24 (1H), 9.69 (1H), 11.96 (1H).

Example 334 Preparation of 2-ethoxy-N-{4-[4-oxo-3-(phenylamino)-4,5,6,7-tetrahydro-1H-indol-2-yl]pyridin-2-yl}acetamide

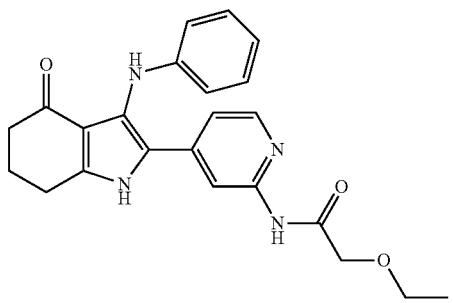 [SMILES: CCOCC(=O)Nc1cc(-c2[nH]c3c(c2Nc2ccccc2)C(=O)CCC3)ccn1]

Using Method G2: Example 139 (100 mg, 314 µmol) gave the desired product (40 mg, 31%) after preparative HPLC (basic method).

1H-NMR (400 MHz, DMSO-d6), Shift [ppm]=1.17 (3H), 1.94-2.10 (2H), 2.26-2.38 (2H), 2.86 (2H), 3.55 (2H), 4.06 (2H), 6.51-6.64 (3H), 6.97-7.06 (2H), 7.19 (1H), 7.40 (1H), 8.06-8.12 (1H), 8.20-8.26 (1H), 9.72 (1H), 11.95 (1H).

Example 335 Preparation of N-{4-[4-oxo-3-(phenylamino)-4,5,6,7-tetrahydro-1H-indol-2-yl]pyridin-2-yl}-2-(prop-2-en-1-yloxy)acetamide

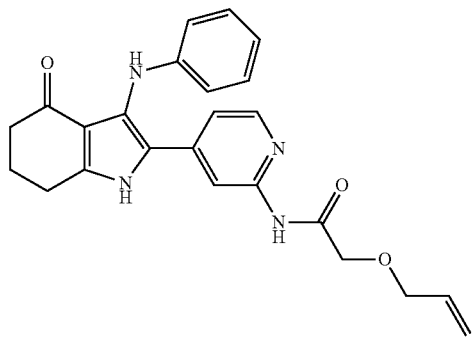 [SMILES: C=CCOCC(=O)Nc1cc(-c2[nH]c3c(c2Nc2ccccc2)C(=O)CCC3)ccn1]

Using Method G2: Example 139 (100 mg, 314 µmol) gave the desired product (20 mg, 15%) after preparative HPLC (basic method).

1H-NMR (400 MHz, DMSO-d6), Shift [ppm]=2.05 (2H), 2.33 (2H), 2.86 (2H), 4.07 (2H), 4.09 (2H), 5.20 (1H), 5.30 (1H), 5.93 (1H), 6.52-6.64 (3H), 6.97-7.08 (2H), 7.19 (1H), 7.39 (1H), 8.09 (1H), 8.23 (1H), 9.78 (1H), 11.94 (1H).

Example 336 Preparation of N-{4-[4-oxo-3-(phenylamino)-4,5,6,7-tetrahydro-1H-indol-2-yl]pyridin-2-yl}-2-(prop-2-yn-1-yloxy)acetamide

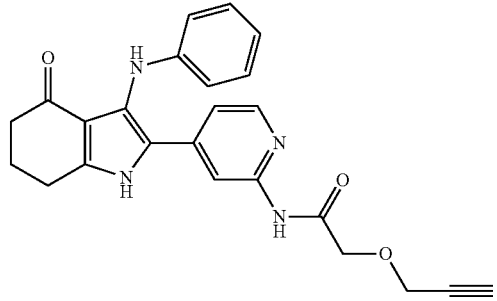 [SMILES: C#CCOCC(=O)Nc1cc(-c2[nH]c3c(c2Nc2ccccc2)C(=O)CCC3)ccn1]

Using Method G2: Example 139 (100 mg, 314 µmol) gave the desired product (20 mg, 15%) after preparative HPLC (basic method).

1H-NMR (400 MHz, DMSO-d6), Shift [ppm]=1.94-2.13 (2H), 2.29-2.37 (2H), 2.86 (2H), 3.53 (1H), 4.13-4.20 (2H), 4.29 (2H), 6.50-6.67 (3H), 6.96-7.05 (2H), 7.18 (1H), 7.39 (1H), 8.09 (1H), 8.21 (1H), 9.94 (1H), 11.94 (1H).

Example 337 Preparation of N-{4-[4-oxo-3-(phenylamino)-4,5,6,7-tetrahydro-1H-indol-2-yl]pyridin-2-yl}-2-phenoxyacetamide

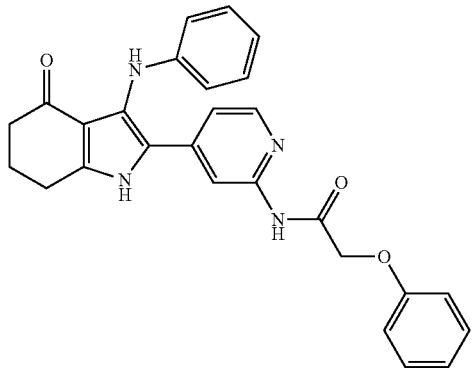

Using Method G2: Example 139 (100 mg, 314 µmol) gave the desired product (10 mg, 7%) after preparative HPLC (basic method).

1H-NMR (400 MHz, DMSO-d6), Shift [ppm]=1.97-2.10 (2H), 2.27-2.38 (2H), 2.84 (2H), 4.78 (2H), 6.50-6.67 (3H), 6.91-7.05 (5H), 7.19 (1H), 7.27-7.34 (2H), 7.39 (1H), 8.08-8.14 (1H), 10.38 (1H), 11.95 (1H).

Example 338 Preparation of 2-(3-fluorophenoxy)-N-{4-[4-oxo-3-(phenylamino)-4,5,6,7-tetrahydro-1H-indol-2-yl]pyridin-2-yl}acetamide

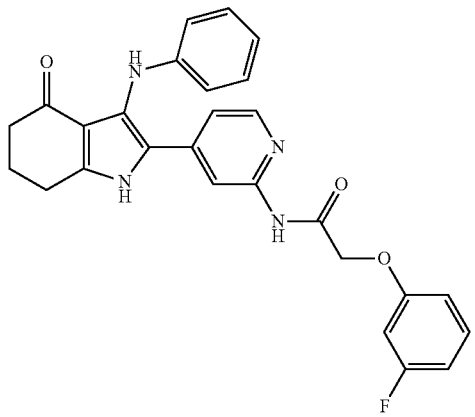 [SMILES: O=C(COc1cccc(F)c1)Nc1cc(-c2[nH]c3c(c2Nc2ccccc2)C(=O)CCC3)ccn1]

Using Method G2: Example 139 (100 mg, 314 µmol) gave the desired product (31 mg, 21%) after preparative HPLC (basic method).

1H-NMR (400 MHz, DMSO-d6), Shift [ppm]=1.97-2.11 (2H), 2.26-2.36 (2H), 2.84 (2H), 4.82 (2H), 6.52-6.66 (3H), 6.74-6.89 (3H), 7.01 (2H), 7.19 (1H), 7.28-7.37 (1H), 7.39 (1H), 8.11 (1H), 8.22 (1H), 10.43 (1H), 11.94 (1H).

Example 339 Preparation of 2-(2-fluorophenoxy)-N-{4-[4-oxo-3-(phenylamino)-4,5,6,7-tetrahydro-1H-indol-2-yl]pyridin-2-yl}acetamide

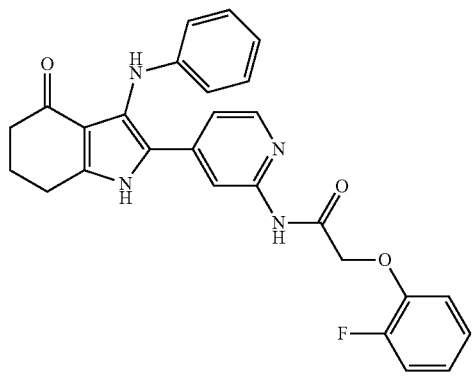 [SMILES: O=C(COc1ccccc1F)Nc1cc(-c2[nH]c3c(c2Nc2ccccc2)C(=O)CCC3)ccn1]

Using Method G2: Example 139 (100 mg, 314 µmol) gave the desired product (18 mg, 12%) after preparative HPLC (basic method).

1H-NMR (400 MHz, DMSO-d6), Shift [ppm]=1.97-2.10 (2H), 2.27-2.37 (2H), 2.84 (2H), 4.89 (2H), 6.51-6.66 (3H), 6.93-7.06 (3H), 7.06-7.17 (2H), 7.19 (1H), 7.22-7.30 (1H), 7.40 (1H), 8.11 (1H), 8.24 (1H), 10.46 (1H), 11.95 (1H).

Example 340 Preparation of 2-(benzyloxy)-N-{4-[4-oxo-3-(phenylamino)-4,5,6,7-tetrahydro-1H-indol-2-yl]pyridin-2-yl}acetamide

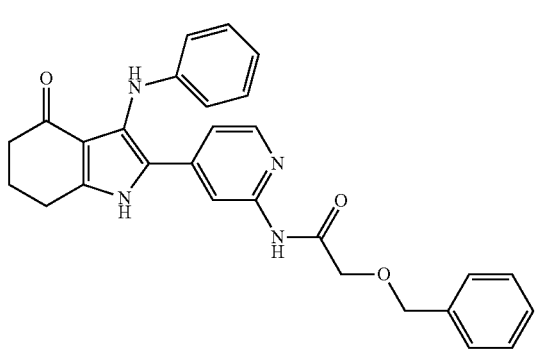 [SMILES: O=C(COCc1ccccc1)Nc1cc(-c2[nH]c3c(c2Nc2ccccc2)C(=O)CCC3)ccn1]

Using Method G2: Example 139 (200 mg, 618 µmol) gave the desired product (90 mg, 31%) after preparative HPLC (basic method).

1H-NMR (400 MHz, DMSO-d6), Shift [ppm]=1.97-2.11 (2H), 2.33 (2H), 2.86 (2H), 4.15 (2H), 4.60 (2H), 6.52-6.68 (3H), 7.01 (2H), 7.19 (1H), 7.29-7.44 (6H), 8.09 (1H), 8.25 (1H), 9.88 (1H), 11.96 (1H).

Example 341 Preparation of 2-[(4-fluorobenzyl)oxy]-N-{4-[4-oxo-3-(phenylamino)-4,5,6,7-tetrahydro-1H-indol-2-yl]pyridin-2-yl}acetamide

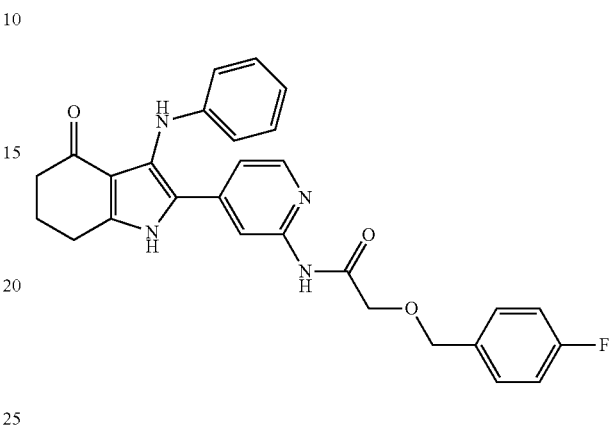

Using Method G2: Example 139 (100 mg, 314 µmol) gave the desired product (20 mg, 13%) after preparative HPLC (basic method).

1H-NMR (400 MHz, DMSO-d6), Shift [ppm]=1.98-2.12 (2H), 2.33 (2H), 2.86 (2H), 4.15 (2H), 4.58 (2H), 6.52-6.67 (3H), 6.96-7.07 (2H), 7.15-7.27 (3H), 7.35-7.52 (3H), 8.04-8.13 (1H), 8.24 (1H), 9.89 (1H), 11.94 (1H).

Example 342 Preparation of 2-[(4-methoxybenzyl)oxy]-N-{4-[4-oxo-3-(phenylamino)-4,5,6,7-tetrahydro-1H-indol-2-yl]pyridin-2-yl}acetamide

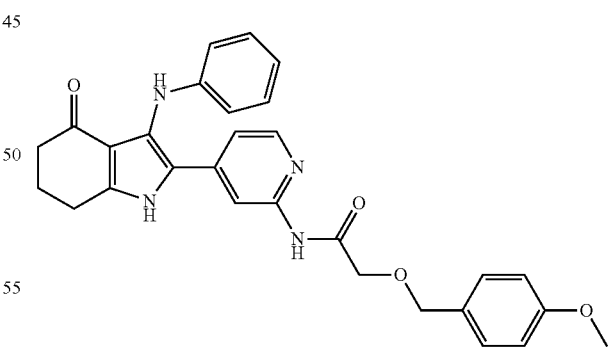

Using Method G2: Example 139 (100 mg, 314 µmol) gave the desired product (10 mg, 6%) after preparative HPLC (basic method).

1H-NMR (400 MHz, DMSO-d6), Shift [ppm]=1.98-2.10 (2H), 2.25-2.36 (2H), 2.79-2.92 (2H), 4.10 (2H), 4.48-4.59 (2H), 6.50-6.66 (3H), 6.88-6.98 (2H), 6.98-7.05 (2H), 7.15-7.22 (1H), 7.28-7.35 (2H), 7.36-7.42 (1H), 8.09 (1H), 8.24 (1H), 9.81 (1H), 11.95 (1H).

Example 343 Preparation of N-{4-[4-oxo-3-(phenylamino)-4,5,6,7-tetrahydro-1H-indol-2-yl]pyridin-2-yl}-2-[(2S)-tetrahydro-2H-pyran-2-ylmethoxy]acetamide

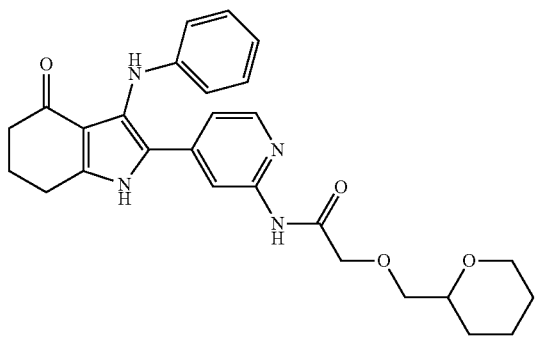 [SMILES: O=C(COCC1CCCCO1)Nc1cc(-c2[nH]c3c(c2Nc2ccccc2)C(=O)CCC3)ccn1]

Using Method G2: Example 139 (100 mg, 314 µmol) gave the desired product (31 mg, 21%) after preparative HPLC (basic method).
1H-NMR (400 MHz, DMSO-d6), Shift [ppm]=1.22 (1H), 1.37-1.60 (4H), 1.77 (1H), 1.96-2.13 (2H), 2.33 (2H), 2.86 (2H), 3.42-3.61 (4H), 3.93 (1H), 4.09 (2H), 6.51-6.65 (3H), 7.01 (2H), 7.16-7.23 (1H), 7.39 (1H), 8.09 (1H), 8.25 (1H), 9.81 (1H), 11.95 (1H).

Example 344 Preparation of N-{4-[4-oxo-3-(phenylamino)-4,5,6,7-tetrahydro-1H-indol-2-yl]pyridin-2-yl}-2-(thiophen-3-yloxy)acetamide

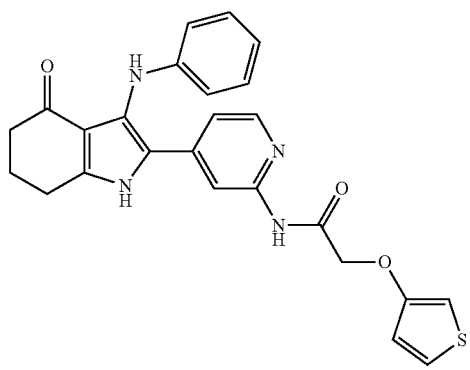 [SMILES: O=C(COc1ccsc1)Nc1cc(-c2[nH]c3c(c2Nc2ccccc2)C(=O)CCC3)ccn1]

Using Method G2: Example 139 (100 mg, 314 µmol) gave the desired product (30 mg, 21%) after preparative HPLC (basic method).
1H-NMR (400 MHz, DMSO-d6), Shift [ppm]=1.98-2.11 (2H), 2.27-2.37 (2H), 2.85 (2H), 4.71 (2H), 6.51-6.67 (4H), 6.87 (1H), 6.96-7.08 (2H), 7.19 (1H), 7.39 (1H), 7.45 (1H), 8.10 (1H), 8.24 (1H), 10.32 (1H), 11.95 (1H).

Example 345 Preparation of 2-[(2-chlorothiophen-3-yl)oxy]-N-{4-[4-oxo-3-(phenylamino)-4,5,6,7-tetrahydro-1H-indol-2-yl]pyridin-2-yl}acetamide

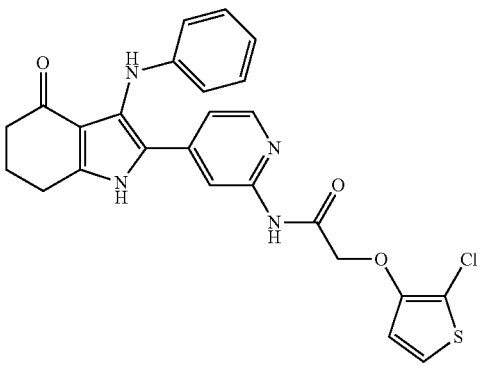 [SMILES: O=C(COc1ccsc1Cl)Nc1cc(-c2[nH]c3c(c2Nc2ccccc2)C(=O)CCC3)ccn1]

Using Method G2: Example 139 (100 mg, 314 µmol) gave the desired product (30 mg, 19%) after preparative HPLC (basic method).
1H-NMR (400 MHz, DMSO-d6), Shift [ppm]=1.93-2.15 (2H), 2.26-2.40 (2H), 2.73-2.95 (2H), 4.85 (2H), 6.52-6.64 (3H), 6.97 (1H), 7.01 (2H), 7.18 (1H), 7.36-7.45 (2H), 8.10 (1H), 8.23 (1H), 10.39 (1H), 11.95 (1H).

Example 346 Preparation of 2-[(5-methyl-1,2-oxazol-3-yl)oxy]-N-{4-[4-oxo-3-(phenylamino)-4,5,6,7-tetrahydro-1H-indol-2-yl]pyridin-2-yl}acetamide

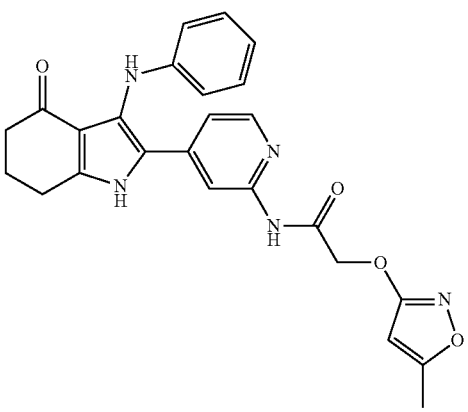 [SMILES: Cc1cc(OCC(=O)Nc2cc(-c3[nH]c4c(c3Nc3ccccc3)C(=O)CCC4)ccn2)no1]

Using Method G2: Example 139 (100 mg, 314 µmol) gave the desired product (30 mg, 21%) after preparative HPLC (basic method).
1H-NMR (400 MHz, DMSO-d6), Shift [ppm]=1.93-2.13 (2H), 2.25-2.39 (5H), 2.84 (2H), 4.88 (2H), 6.06 (1H), 6.52-6.66 (3H), 6.95-7.07 (2H), 7.17 (1H), 7.37 (1H), 8.09 (1H), 8.22 (1H), 10.52 (1H), 11.94 (1H).

Example 347 Preparation of N-{4-[4-oxo-3-(phenylamino)-4,5,6,7-tetrahydro-1H-indol-2-yl]pyridin-2-yl}-2-(pyridin-2-yloxy)acetamide

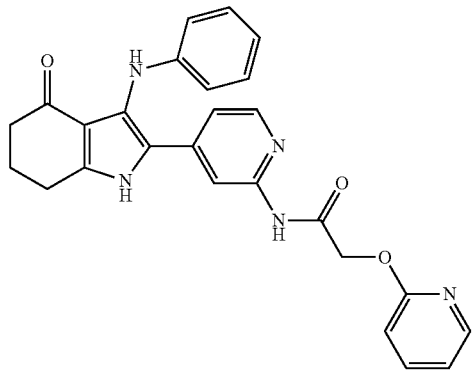 [SMILES: O=C(COc1ccccn1)Nc1cc(-c2[nH]c3c(c2Nc2ccccc2)C(=O)CCC3)ccn1]

Using Method G2: Example 139 (100 mg, 314 µmol) gave the desired product (30 mg, 21%) after preparative HPLC (basic method).

1H-NMR (400 MHz, DMSO-d6), Shift [ppm]=1.95-2.08 (2H), 2.27-2.40 (2H), 2.79-2.89 (2H), 4.81 (2H), 6.25 (1H), 6.40 (1H), 6.53-6.66 (3H), 6.97-7.06 (2H), 7.19 (1H), 7.47 (1H), 7.67 (1H), 8.09 (1H), 8.14 (1H), 10.92 (1H), 11.97 (1H).

Example 348 Preparation of 2-(1,2-oxazol-3-yloxy)-N-{4-[4-oxo-3-(phenylamino)-4,5,6,7-tetrahydro-1H-indol-2-yl]pyridin-2-yl}acetamide

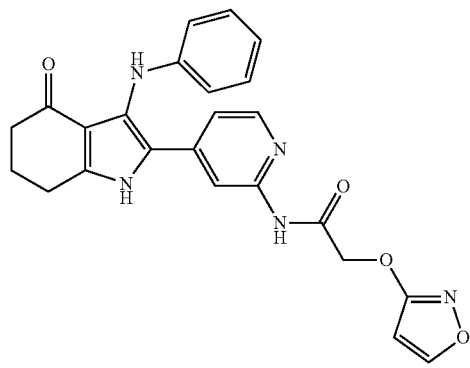 [SMILES: O=C(COc1ccon1)Nc1cc(-c2[nH]c3c(c2Nc2ccccc2)C(=O)CCC3)ccn1]

Using Method G2: Example 139 (100 mg, 314 µmol) gave the desired product (30 mg, 22%) after preparative HPLC (basic method).

1H-NMR (400 MHz, DMSO-d6), Shift [ppm]=1.96-2.12 (2H), 2.28-2.36 (2H), 2.84 (2H), 4.93 (2H), 6.41 (1H), 6.52-6.64 (3H), 6.97-7.07 (2H), 7.17 (1H), 7.39 (1H), 8.09 (1H), 8.18-8.26 (1H), 8.64-8.73 (1H), 10.58 (1H), 11.95 (1H).

Example 349 Preparation of 2-[(3-methyl-1,2,4-oxadiazol-5-yl)methoxy]-N-{4-[4-oxo-3-(phenylamino)-4,5,6,7-tetrahydro-1H-indol-2-yl]pyridin-2-yl}acetamide

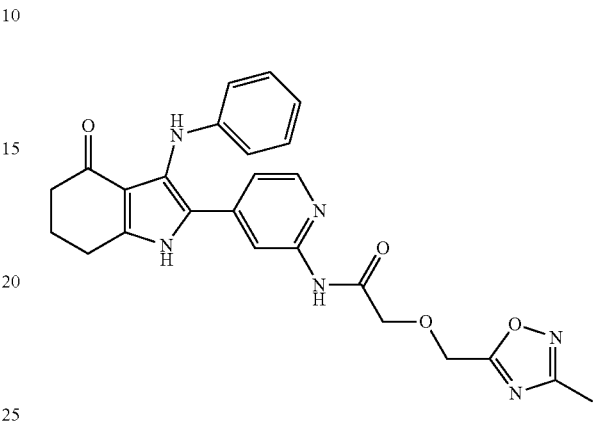

Using Method G2: Example 139 (100 mg, 314 µmol) gave the desired product (26 mg, 18%) after preparative HPLC (basic method).

1H-NMR (400 MHz, DMSO-d6), Shift [ppm]=1.97-2.10 (2H), 2.28-2.35 (2H), 2.36 (3H), 2.86 (2H), 4.30 (2H), 4.93 (2H), 6.52-6.63 (3H), 7.01 (2H), 7.19 (1H), 7.40 (1H), 8.09 (1H), 8.22 (1H), 10.11 (1H), 11.95 (1H).

Example 350 Preparation of 2-[(3-methyl-1,2-oxazol-5-yl)methoxy]-N-{4-[4-oxo-3-(phenylamino)-4,5,6,7-tetrahydro-1H-indol-2-yl]pyridin-2-yl}acetamide

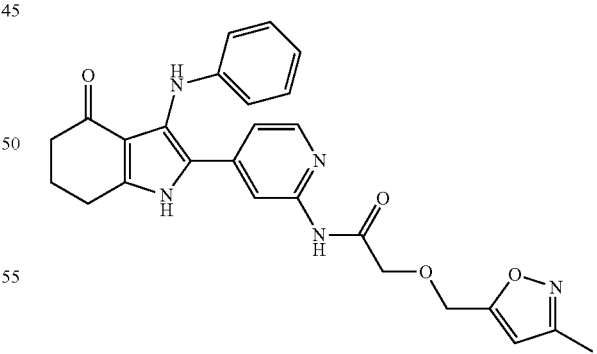

Using Method G2: Example 139 (100 mg, 314 µmol) gave the desired product (30 mg, 20%) after preparative HPLC (basic method).

1H-NMR (400 MHz, DMSO-d6), Shift [ppm]=1.96-2.13 (2H), 2.20-2.28 (3H), 2.28-2.39 (2H), 2.86 (2H), 4.19 (2H), 4.71 (2H), 6.42 (1H), 6.52-6.67 (3H), 6.96-7.07 (2H), 7.19 (1H), 7.40 (1H), 8.09 (1H), 8.23 (1H), 10.00 (1H), 11.95 (1H).

Example 351 Preparation of 2-[(1-methyl-1H-pyrazol-5-yl)methoxy]-N-{4-[4-oxo-3-(phenylamino)-4,5,6,7-tetrahydro-1H-indol-2-yl]pyridin-2-yl}acetamide

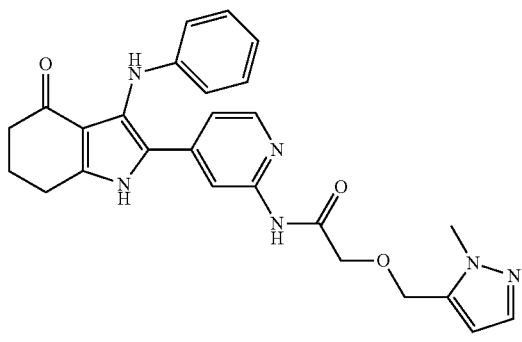 [SMILES: Cn1nccc1COCC(=O)Nc1cc(-c2[nH]c3c(c2Nc2ccccc2)C(=O)CCC3)ccn1]

Using Method G2: Example 139 (100 mg, 314 μmol) gave the desired product (50 mg, 34%) after preparative HPLC (basic method).
1H-NMR (400 MHz, DMSO-d6), Shift [ppm]=2.05 (2H), 2.27-2.38 (2H), 2.87 (2H), 3.86 (3H), 4.14 (2H), 4.64 (2H), 6.28 (1H), 6.54-6.66 (3H), 7.01 (2H), 7.19 (1H), 7.36 (1H), 7.40 (1H), 8.09 (1H), 8.23 (1H), 10.02 (1H), 11.95 (1H).

Example 352 Preparation of 2-(furan-2-ylmethoxy)-N-{4-[4-oxo-3-(phenylamino)-4,5,6,7-tetrahydro-1H-indol-2-yl]pyridin-2-yl}acetamide

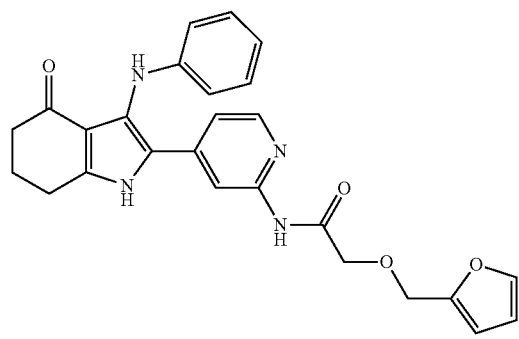 [SMILES: O=C(COCc1ccco1)Nc1cc(-c2[nH]c3c(c2Nc2ccccc2)C(=O)CCC3)ccn1]

Using Method G2: Example 139 (100 mg, 314 μmol) gave the desired product (50 mg, 34%) after preparative HPLC (basic method).
1H-NMR (400 MHz, DMSO-d6), Shift [ppm]=1.96-2.13 (2H), 2.25-2.39 (2H), 2.86 (2H), 4.05-4.18 (2H), 4.56 (2H), 6.42-6.52 (2H), 6.54-6.65 (3H), 7.01 (2H), 7.16-7.24 (1H), 7.40 (1H), 7.67 (1H), 8.05-8.14 (1H), 8.23 (1H), 9.81 (1H), 11.95 (1H).

Example 353 Preparation of 2-[(5-methyl-1,3,4-oxadiazol-2-yl)methoxy]-N-{4-[4-oxo-3-(phenylamino)-4,5,6,7-tetrahydro-1H-indol-2-yl]pyridin-2-yl}acetamide

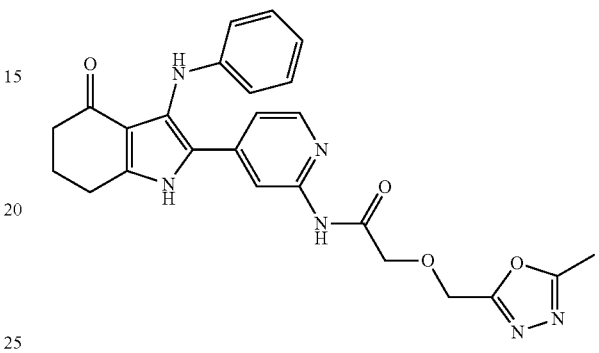

Using Method G2: Example 139 (100 mg, 314 μmol) gave the desired product (30 mg, 20%) after preparative HPLC (basic method).
1H-NMR (400 MHz, DMSO-d6), Shift [ppm]=1.99-2.12 (2H), 2.26-2.38 (2H), 2.52 (3H), 2.86 (2H), 4.24 (2H), 4.82 (2H), 6.53-6.65 (3H), 7.01 (2H), 7.18 (1H), 7.40 (1H), 8.09 (1H), 8.22 (1H), 10.08 (1H), 11.95 (1H).

Example 354 Preparation of 2-[(5-methyl-1,2-oxazol-3-yl)methoxy]-N-{4-[4-oxo-3-(phenylamino)-4,5,6,7-tetrahydro-1H-indol-2-yl]pyridin-2-yl}acetamide

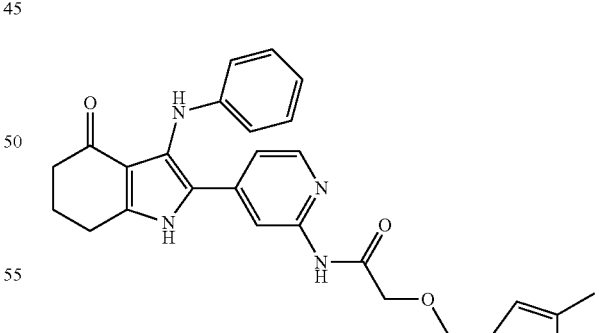

Using Method G2: Example 139 (100 mg, 314 μmol) gave the desired product (30 mg, 20%) after preparative HPLC (basic method).
1H-NMR (400 MHz, DMSO-d6), Shift [ppm]=1.98-2.12 (2H), 2.28-2.36 (2H), 2.37-2.44 (3H), 2.86 (2H), 4.17 (2H), 4.63 (2H), 6.32 (1H), 6.51-6.66 (3H), 7.01 (2H), 7.19 (1H), 7.40 (1H), 8.09 (1H), 8.23 (1H), 9.97 (1H), 11.95 (1H).

Example 355 Preparation of 2-[(5-methyl-1,3-oxazol-2-yl)methoxy]-N-{4-[4-oxo-3-(phenylamino)-4,5,6,7-tetrahydro-1H-indol-2-yl]pyridin-2-yl}acetamide

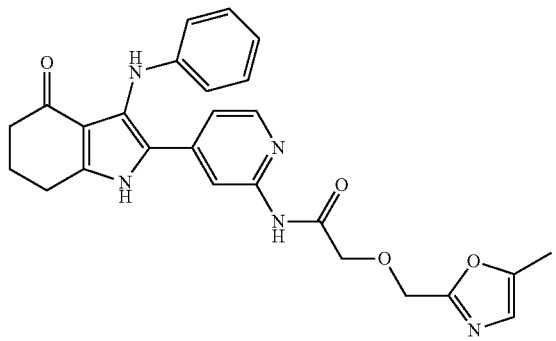 [SMILES: Cc1cnc(COCC(=O)Nc2cc(-c3[nH]c4c(c3Nc3ccccc3)C(=O)CCC4)ccn2)o1]

Using Method G2: Example 139 (100 mg, 314 μmol) gave the desired product (30 mg, 20%) after preparative HPLC (Column: XBridge C18 5μ 100×30 mm; Solvent A: Water+ 0.2 Vol-% NH₄OH, Solvent B: Acetonitrile; Gradient: 0.00-0.50 min 26% B (25-70 mL/min), 0.51-5.50 min 26-50% B; Flow: 70 mL/min).

1H-NMR (400 MHz, DMSO-d6), Shift [ppm]=1.97-2.14 (2H), 2.29 (3H), 2.30-2.36 (2H), 2.86 (2H), 4.19 (2H), 4.63 (2H), 6.52-6.64 (3H), 6.84 (1H), 6.96-7.06 (2H), 7.18 (1H), 7.40 (1H), 8.09 (1H), 8.22 (1H), 9.98 (1H), 11.96 (1H).

Example 356 Preparation of 2-[(5-methyl-1,3,4-thiadiazol-2-yl)methoxy]-N-{4-[4-oxo-3-(phenylamino)-4,5,6,7-tetrahydro-1H-indol-2-yl]pyridin-2-yl}acetamide

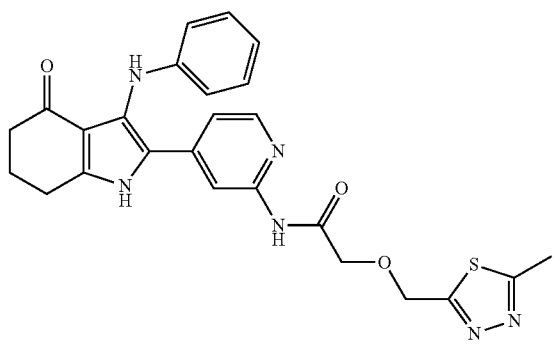 [SMILES: Cc1nnc(COCC(=O)Nc2cc(-c3[nH]c4c(c3Nc3ccccc3)C(=O)CCC4)ccn2)s1]

Using Method G2: Example 139 (100 mg, 314 μmol) gave the desired product (40 mg, 26%) after preparative HPLC (basic method).

1H-NMR (400 MHz, DMSO-d6), Shift [ppm]=1.97-2.11 (2H), 2.27-2.38 (2H), 2.71-2.77 (3H), 2.86 (2H), 4.27 (2H), 4.99 (2H), 6.51-6.65 (3H), 7.01 (2H), 7.18 (1H), 7.40 (1H), 8.09 (1H), 8.23 (1H), 10.14 (1H), 11.95 (1H).

Example 357 Preparation of N-{6-[6,6-dimethyl-4-oxo-3-(phenylamino)-4,5,6,7-tetrahydro-1H-indol-2-yl]pyrimidin-4-yl}acetamide

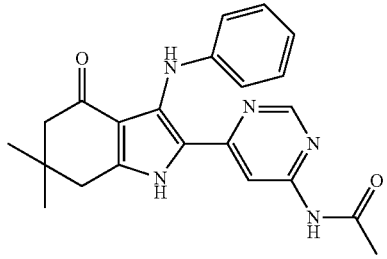 [SMILES: CC(=O)Nc1cc(-c2[nH]c3c(c2Nc2ccccc2)C(=O)CC(C)(C)C3)ncn1]

Example 224 (70 mg, 201 μmol) in pyridine (1 mL) was added acetyl chloride (29 μL, 403 μmol) and stirred at RT for 16 h. Concentrated and purified by preparative HPLC (acidic method) to give the desired product (40 mg, 51%).

1H-NMR (400 MHz, DMSO-d6), Shift [ppm]=1.05 (6H), 2.03 (3H), 2.23 (2H), 2.75 (2H), 6.53-6.76 (3H), 7.05 (2H), 8.02-8.21 (2H), 8.61-8.79 (1H), 10.57 (1H), 12.05 (1H).

Example 358 Preparation of 2-[2-(methylamino)pyridin-4-yl]-3-(phenylamino)-1,5,6,7-tetrahydro-4H-indol-4-one

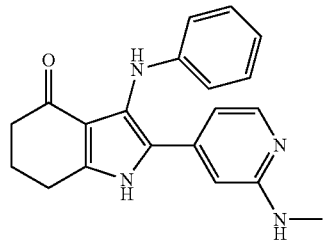 [SMILES: CNc1cc(-c2[nH]c3c(c2Nc2ccccc2)C(=O)CCC3)ccn1]

Synthesis of Example 358

Intermediate 1-10-3

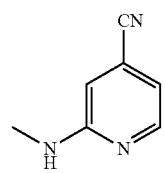

A solution of 2-chloro-4-cyanopyridine (2.4 g, 17.3 mmol) in 2M methylamine in THF (24 mL, 48 mmol) was heated in a sealed tube at 80° C. for 16 h. Allowed to cooled, diluted with water and extracted with EtOAc, the organics were combined, washed with water, sat. NaCl, dried over Na2SO4 and concentrated to give 2-(methylamino)isonicotinonitrile intermediate 1-10-3 which was used directly without further purification.

1H-NMR (300 MHz, DMSO-d6), Shift [ppm]=2.77 (3H), 6.67-6.90 (2H), 7.06 (1H), 8.09-8.29 (1H).

Intermediate 1-11-5

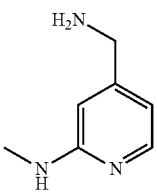

To a solution of Intermediate 1-10-3 2-(methylamino)isonicotinonitrile (2.1 g, 15.8 mmol) in 7M NH$_3$ in MeOH (52 mL) was added Raney-Nickel (50% wet, 3.24 g, 55.2 mmol) and stirred at RT under an H$_2$ atmosphere (25 bar) for 16 h. The reaction was filtered and concentrated to give intermediate 1-11-5 4-(aminomethyl)-N-methylpyridin-2-amine (2.16 g, 99%) which was used without further purification.

Intermediate 1-2-53

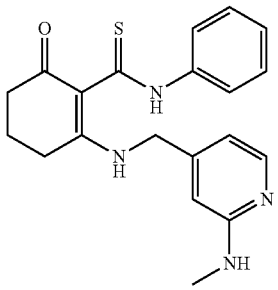 [SMILES: CNc1cc(CNC2=C(C(=S)Nc3ccccc3)C(=O)CCC2)ccn1]

A solution of Intermediate 1-1-5 (3.21 g, 13 mmol) and intermediate 1-11-5 4-(aminomethyl)-N-methylpyridin-2-amine (2.137 g, 15.6 mmol) in EtOH:EtOAc (1:1.40 mL) was heated at reflux for 24 h. Concentrated and purified by silica chromatography and preparative HPLC (Column: XBridge C18 5µ 150×50 mm; Solvent A: Water+0.1 Vol-% HCO$_2$H, Solvent B: Acetonitrile; Gradient: 0.00-9.50 min 20-60% B; Flow: 200 mL/min) to give the intermediate 1-2-53 (77 mg, 2%).

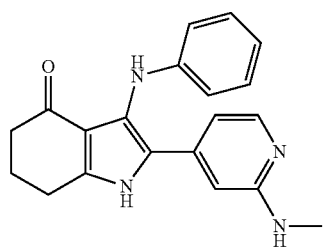 [SMILES: CNc1cc(-c2[nH]c3c(c2Nc2ccccc2)C(=O)CCC3)ccn1]

Using method F1 intermediate 1-2-53 (77 mg, 210 µmol) gave the desired product (16 mg, 23%) after preparative HPLC (acidic method).

1H-NMR (400 MHz, DMSO-d6), Shift [ppm]=2.00-2.10 (2H), 2.26-2.39 (2H), 2.61 (3H), 2.87 (2H), 4.10 (1H), 6.53-6.63 (3H), 6.66 (1H), 6.86 (1H), 7.06 (2H), 7.53 (1H), 7.81 (1H), 11.89 (1H).

Example 359 Preparation of 2-[2-(cyclobutylamino)pyridin-4-yl]-6,6-dimethyl-3-(phenylamino)-1,5,6,7-tetrahydro-4H-indol-4-one

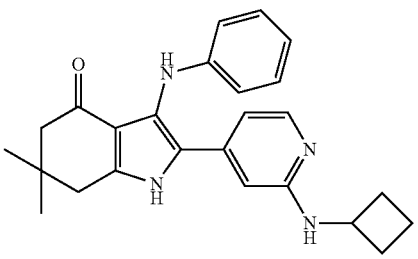 [SMILES: CC1(C)CC(=O)c2c([nH]c(-c3ccnc(NC4CCC4)c3)c2Nc2ccccc2)C1]

Synthesis of Example 359

Intermediate 1-10-4

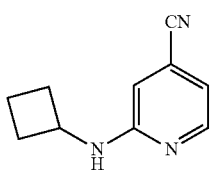 [SMILES: N#Cc1ccnc(NC2CCC2)c1]

A solution of 2-fluoro-4-cyanopyridine (1.1 g, 9.1 mmol) and cyclobutylamine (1.89 g, 18.1 mmol) in THF (10 mL) was stirred at RT for 16 h, then heated in a sealed tube at 50° C. for 16 h. Allowed to cooled, diluted with water and extracted with EtOAc, the organics were combined, washed with water, sat. NaCl, dried over Na$_2$SO$_4$ and concentrated. Purified by silica chromatography to give Intermediate 1-10-4 2-(cyclobutylamino)isonicotinonitrile (1.047 g, 67%).

1H-NMR (400 MHz, DMSO-d6), Shift [ppm]=1.57-1.74 (2H), 1.79-1.92 (2H), 2.21-2.33 (2H), 4.24 (1H), 6.68-6.78 (2H), 7.34 (1H), 8.13 (1H).

Intermediate 1-11-6

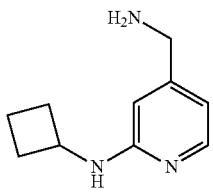 [SMILES: NCc1ccnc(NC2CCC2)c1]

To a solution of Intermediate 1-10-4 2-(cyclobutylamino)isonicotinonitrile (672 mg, 3.9 mmol) in 7M NH$_3$ in MeOH (11.9 mL) was added Raney-Nickel (50% wet, 911 mg, 15.5 mmol) and stirred at RT under an H$_2$ atmosphere (32 bar) for 22 h. The reaction was filtered and concentrated to give Intermediate 1-11-6 4-(aminomethyl)-N-cyclobutylpyridin-2-amine (650 mg, 95%) which was used without further purification.

Intermediate 1-2-54

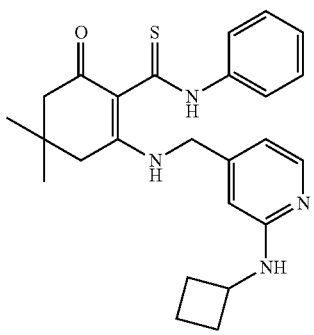 [SMILES: CC1(C)CC(=O)C(C(=S)Nc2ccccc2)=C(NCc2ccnc(NC3CCC3)c2)C1]

A solution of Intermediate 1-1-1 (777 mg, 2.8 mmol) and Intermediate 1-11-6 4-(aminomethyl)-N-cyclobutylpyridin-2-amine (500 mg, 2.8 mmol) in EtOH:EtOAc (1:1.40 mL) was heated at reflux for 24 h under Dean-Stark conditions using 4 Å molecular sieves. Concentrated and purified by preparative HPLC (Column: XBridge C18 5µ 150×50 mm; Solvent A: Water+0.2 Vol-% NH$_4$OH, Solvent B: Acetonitrile; Gradient: 0.00-8.00 min 45-75% B; Flow: 150 mL/min) to give the Intermediate 1-2-54 (341 mg, 28%).

1H-NMR (500 MHz, DMSO-d6), Shift [ppm]=0.93-1.04 (6H), 1.54-1.75 (2H), 1.78-1.93 (2H), 2.20-2.30 (2H), 2.40 (2H), 2.66 (2H), 4.16-4.27 (1H), 4.65 (2H), 6.34 (1H), 6.44 (1H), 6.87 (1H), 7.20-7.29 (1H), 7.34-7.42 (2H), 7.43-7.48 (2H), 7.93 (1H), 14.15 (1H), 14.75 (1H).

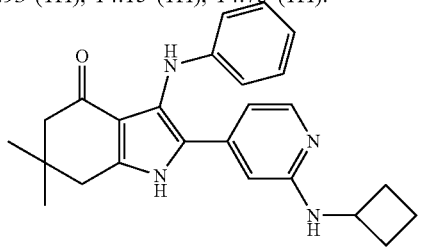

Using method F1 Intermediate 1-2-54 (340 mg, 782 µmol) gave the desired product (65 mg, 21%) after preparative HPLC (basic method).

1H-NMR (400 MHz, DMSO-d6), Shift [ppm]=1.06 (6H), 1.44-1.67 (2H), 1.67-1.84 (2H), 2.00-2.14 (2H), 2.22 (2H), 2.73 (2H), 3.73 (1H), 6.40-6.49 (2H), 6.53-6.64 (3H), 6.72 (1H), 7.00-7.09 (2H), 7.29 (1H), 7.83 (1H), 11.65 (1H).

Example 360 Preparation of 2-[2-(azetidin-1-yl)pyridin-4-yl]-6,6-dimethyl-3-(phenylamino)-1,5,6,7-tetrahydro-4H-indol-4-one

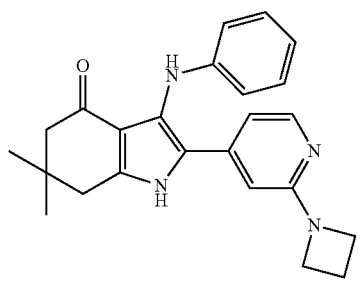 [SMILES: CC1(C)CC(=O)c2c([nH]c(-c3ccnc(N4CCC4)c3)c2Nc2ccccc2)C1]

Synthesis of Example 360

Intermediate 1-10-5

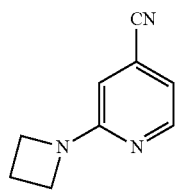 [SMILES: N#Cc1ccnc(N2CCC2)c1]

To a solution of 2-fluoro-4-cyanopyridine (535 mg, 4.4 mmol) in THF (1 mL) was added slowly (CARE—exothermic) cyclobutylamine (500 mg, 8.8 mmol) and was stirred at RT for 1 h. Diluted with sat. NaHCO$_3$ and extracted with EtOAc, the organics were combined, washed with water, sat. NaCl, dried over Na$_2$SO$_4$ and concentrated to give Intermediate 1-10-5 2-(azetidin-1-yl)isonicotinonitrile (651 mg, 93%) which was used without further purification.

1H-NMR (400 MHz, DMSO-d6), Shift [ppm]=2.22-2.41 (2H), 3.98 (4H), 6.78 (1H), 6.90 (1H), 8.12-8.32 (1H).

Intermediate 1-11-7

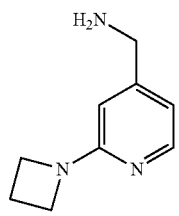 [SMILES: NCc1ccnc(N2CCC2)c1]

To a solution of 2-(azetidin-1-yl)isonicotinonitrile (1.27 g, 8 mmol) in 7M NH$_3$ in MeOH (24 mL) was added Raney-Nickel (50% wet, 1.87 g, 31.9 mmol) and stirred at RT under an H$_2$ atmosphere (32 bar) for 22 h. The reaction was filtered and concentrated to give Intermediate 1-11-7 1-[2-(azetidin-1-yl)pyridin-4-yl]methanamine (1.1 g, 84%) which was used without further purification.

Intermediate 1-2-55

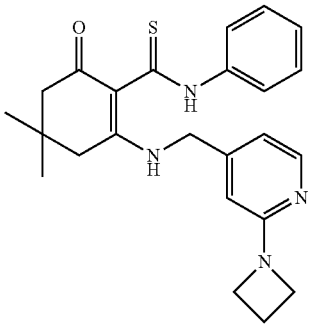 [SMILES: CC1(C)CC(=O)C(C(=S)Nc2ccccc2)=C(NCc2ccnc(N3CCC3)c2)C1]

A solution of Intermediate 1-1-1 (456 mg, 1.65 mmol) and Intermediate 1-11-7 2-[2-(azetidin-1-yl)pyridin-4-yl]methanamine (540 mg, 3.3 mmol) in DMA (10 mL) was heated at 120° C. for 90 mins using a microwave. Concentrated and purified by preparative HPLC (Column: XBridge C18 5µ 150×50 mm; Solvent A: Water+0.2 Vol-% NH₄OH, Solvent B: Acetonitrile; Gradient: 0.00-8.00 min 40-70% B; Flow: 150 mL/min) to give the Intermediate 1-2-55 (611 mg, 88%)

1H-NMR (500 MHz, DMSO-d6), Shift [ppm]=1.00 (6H), 2.26-2.34 (2H), 2.39 (2H), 2.68 (2H), 3.91 (4H), 4.70 (2H), 6.36 (1H), 6.59 (1H), 7.19-7.28 (1H), 7.35-7.42 (2H), 7.45 (2H), 8.04 (1H), 14.00 (1H), 14.67 (1H).

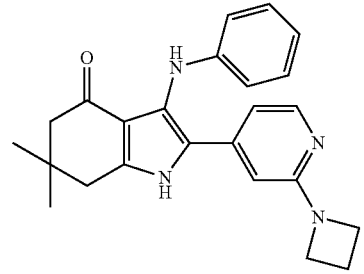 [SMILES: CC1(C)CC(=O)c2c([nH]c(-c3ccnc(N4CCC4)c3)c2Nc2ccccc2)C1]

Using method F1 Intermediate 1-2-55 (610 mg, 1.45 mmol) gave the desired product (153 mg, 27%) after preparative HPLC (basic method).

1H-NMR (400 MHz, DMSO-d6), Shift [ppm]=1.06 (6H), 2.15-2.29 (4H), 2.74 (2H), 3.70 (4H), 6.35-6.40 (1H), 6.55 (2H), 6.62 (1H), 6.83 (1H), 6.98-7.10 (2H), 7.37 (1H), 7.89 (1H), 11.73 (1H).

Example 361 Preparation of 6,6-dimethyl-3-(phenylamino)-2-{2-[(2,2,2-trifluoroethyl)amino]pyridin-4-yl}-1,5,6,7-tetrahydro-4H-indol-4-one

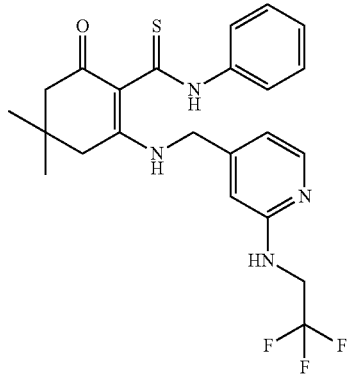

Synthesis of Example 361

Intermediate 1-10-6

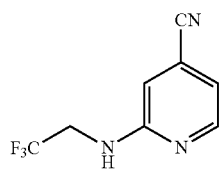 [SMILES: N#Cc1ccnc(NCC(F)(F)F)c1]

A mixture of 2-fluoro-4-cyanopyridine (468 mg, 3.8 mmol) and 2,2,2-trifluoro-1-aminoethane (1.26 g, 12.7 mmol) was heated at 160° C. in a sealed tube for 16 h. Concentrated and purified by silica chromatography to give Intermediate 1-10-6 2-[(2,2,2-trifluoroethyl)amino]isonicotinonitrile (432 mg, 56%).

1H-NMR (400 MHz, DMSO-d6), Shift [ppm]=4.20 (2H), 6.88-7.10 (2H), 7.68 (1H), 8.16-8.31 (1H).

Intermediate 1-11-8

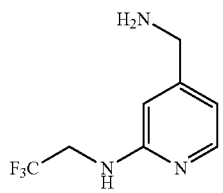 [SMILES: NCc1ccnc(NCC(F)(F)F)c1]

To a solution of Intermediate 1-10-6 2-[(2,2,2-trifluoroethyl)amino]isonicotinonitrile (654 mg, 3.2 mmol) in 7M NH₃ in MeOH (9.8 mL) was added Raney-Nickel (50% wet, 749 mg, 12.8 mmol) and stirred at RT under an H₂ atmosphere (32 bar) for 22 h. The reaction was filtered and concentrated to give Intermediate 1-11-8 4-(aminomethyl)-N-(2,2,2-trifluoroethyl)pyridin-2-amine (645 mg, 98%) which was used without further purification.

Intermediate 1-2-56

A solution of Intermediate 1-1-1 (537 mg, 1.9 mmol) and Intermediate 1-11-8 4-(aminomethyl)-N-(2,2,2-trifluoroethyl)pyridin-2-amine (400 mg, 1.9 mmol) in EtOH:EtOAc (1:1, 60 mL) was heated at reflux for 72 h under Dean-Stark conditions using 4 Å molecular sieves. Concentrated and purified by silica chromatography to give the Intermediate 1-2-5 (138 mg, 15%).

1H-NMR (400 MHz, DMSO-d6), Shift [ppm]=0.98 (6H), 2.40 (2H), 2.63-2.69 (2H), 4.15 (2H), 4.70 (2H), 6.56 (1H), 6.59 (1H), 7.18-7.26 (1H), 7.30 (1H), 7.35-7.42 (2H), 7.42-7.48 (2H), 8.01 (1H), 14.17 (1H), 14.74 (1H).

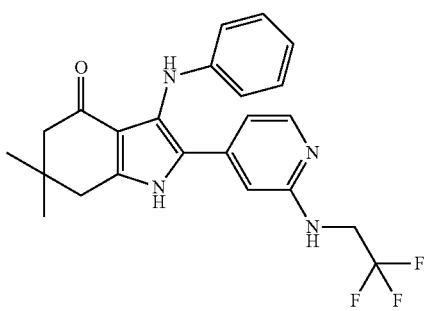 [SMILES: CC1(C)CC(=O)c2c([nH]c(-c3ccnc(NCC(F)(F)F)c3)c2Nc2ccccc2)C1]

Using method F1 Intermediate 1-2-56 (205 mg, 443 µmol) gave the desired product (48 mg, 25%) after preparative HPLC (basic method).

1H-NMR (400 MHz, DMSO-d6), Shift [ppm]=1.06 (6H), 2.21 (2H), 2.73 (2H), 3.88-4.11 (2H), 6.52-6.63 (3H), 6.72 (1H), 6.82 (1H), 6.94 (1H), 6.99-7.07 (2H), 7.29 (1H), 7.88 (1H), 11.70 (1H).

Example 362 Preparation of 6,6-dimethyl-3-(phenylamino)-2-{2-[(3,3,3-trifluoropropyl)amino]pyridin-4-yl}-1,5,6,7-tetrahydro-4H-indol-4-one

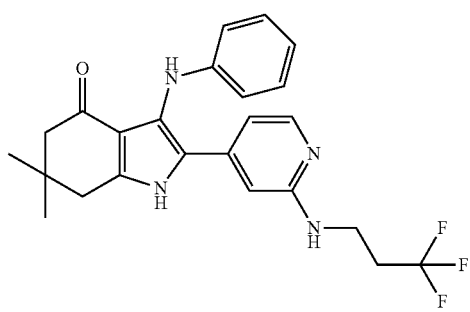 [SMILES: CC1(C)CC(=O)c2c([nH]c(-c3ccnc(NCCC(F)(F)F)c3)c2Nc2ccccc2)C1]

Synthesis of Example 362

Intermediate 1-10-7

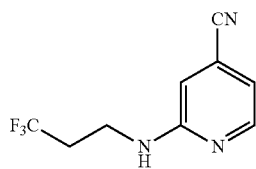 [SMILES: N#Cc1ccnc(NCCC(F)(F)F)c1]

A mixture of 2-fluoro-4-cyanopyridine (226 mg, 1.85 mmol) and 3,3,3-trifluoropropylamine (419 mg, 3.7 mmol) was stirred at RT for 16 h then heated at 50° C. in a sealed tube for 16 h and then heated at 80° C. in a sealed tube for 6 h Concentrated and purified by silica chromatography to give Intermediate 1-10-7 2-[(3,3,3-trifluoropropyl)amino]-isonicotinonitrile (233 mg, 38%).

1H-NMR (400 MHz, DMSO-d6), Shift [ppm]=2.52-2.61 (1H), 3.47-3.57 (2H), 6.76-6.95 (2H), 7.29 (1H), 8.20 (1H).

Intermediate 1-11-9

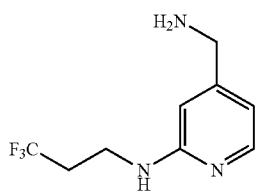 [SMILES: NCc1ccnc(NCCC(F)(F)F)c1]

To a solution of Intermediate 1-10-7 2-[(3,3,3-trifluoropropyl)amino]isonicotinonitrile (466 mg, 2.2 mmol) in 7M $NH_3$ in MeOH (6.6 mL) was added Raney-Nickel (50% wet, 508 mg, 8.7 mmol) and stirred at RT under an $H_2$ atmosphere (32 bar) for 22 h. The reaction was filtered and concentrated to give Intermediate 1-11-9 4-(aminomethyl)-N-(3,3,3-trifluoropropyl)pyridin-2-amine (450 mg, 95%) which was used without further purification.

Intermediate 1-2-57

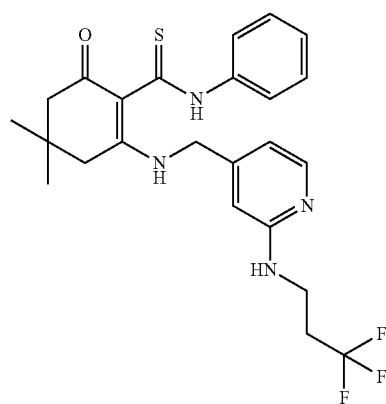 [SMILES: CC1(C)CC(=O)C(C(=S)Nc2ccccc2)=C(NCc2ccnc(NCCC(F)(F)F)c2)C1]

A solution of Intermediate 1-1-1 (377 mg, 1.4 mmol) and Intermediate 1-11-9 4-(aminomethyl)-N-(3,3,3-trifluoropropyl)pyridin-2-amine (300 mg, 1.4 mmol) in EtOH:EtOAc (1:1, 120 mL) was heated at reflux for 48 h under Dean-Stark conditions using 4 Å molecular sieves. Concentrated and preparative HPLC (Column: XBridge C18 5µ100×30 mm; Solvent A: Water+0.1 Vol-% $HCO_2H$, Solvent B: Acetonitrile; Gradient: 0.00-0.50 min 33% B (25->70 mL/min), 0.51-5.50 min 33-53% B (70 mL/min)) to give the Intermediate 1-2-57 (107 mg, 17%).

1H-NMR (400 MHz, DMSO-d6), Shift [ppm]=0.98 (6H), 2.40 (2H), 2.65 (2H), 3.42-3.53 (2H), 4.67 (2H), 6.43 (1H), 6.50 (1H), 6.89 (1H), 7.19-7.26 (1H), 7.38 (2H), 7.44 (2H), 7.99 (1H), 14.16 (1H), 14.75 (1H).

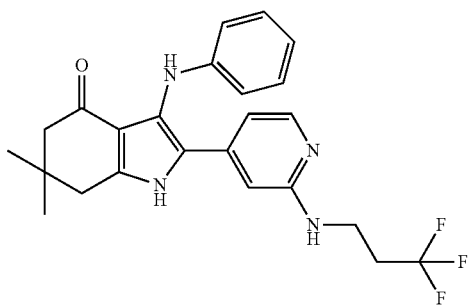 [SMILES: CC1(C)CC(=O)c2c([nH]c(-c3ccnc(NCCC(F)(F)F)c3)c2Nc2ccccc2)C1]

Using method F1 Intermediate 1-2-57 (106 mg, 222 µmol) gave the desired product (21 mg, 21%) after preparative HPLC (basic method).

1H-NMR (400 MHz, DMSO-d6), Shift [ppm]=1.06 (6H), 2.21 (2H), 2.35-2.46 (2H), 2.72 (2H), 3.29-3.36 (2H), 6.44 (1H), 6.50-6.64 (4H), 6.76 (1H), 6.96-7.10 (2H), 7.28 (1H), 7.86 (1H), 11.68 (1H).

Example 363 Preparation of 2-(2-{[1,1-difluoropropan-2-yl]amino}pyridin-4-yl)-6,6-dimethyl-3-(phenylamino)-1,5,6,7-tetrahydro-4H-indol-4-one

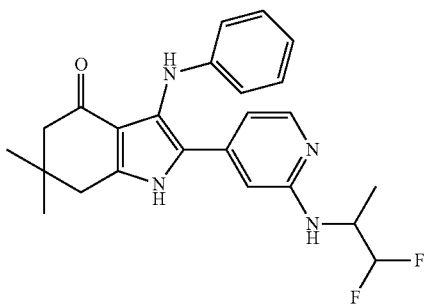 [SMILES: CC(Nc1cc(-c2[nH]c3c(c2Nc2ccccc2)C(=O)CC(C)(C)C3)ccn1)C(F)F]

Synthesis of Example 363

Intermediate 1-10-8

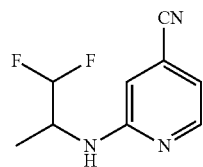

A mixture of 2-fluoro-4-cyanopyridine (1.07 g, 8.7 mmol), 1,1-difluoropropane-2-amine hydrochloride (1.15 g, 8.7 mmol) and DIPEA (1.52 mL, 8.7 mmol) in THF (20 mL) was heated at 120° C. in a sealed tube for 16 h. Concentrated and purified by silica chromatography to give Intermediate 1-10-8 2-[(1,1-difluoropropan-2-yl)amino]isonicotinonitrile (451 mg, 26%).

1H-NMR (400 MHz, DMSO-d6), Shift [ppm]=1.04-1.31 (3H), 4.29-4.54 (1H), 6.79-6.99 (2H), 7.31 (1H), 8.19 (1H).

Intermediate 1-11-10

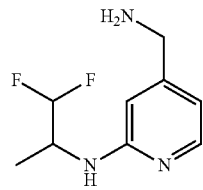

To a solution of Intermediate 1-10-8 2-[(1,1-difluoropropan-2-yl)amino]isonicotinonitrile (451 mg, 2.3 mmol) in 7M NH3 in MeOH (46 mL) was added Raney-Nickel (50% wet, 537 mg, 9.1 mmol) and stirred at RT under an H2 atmosphere (35 bar) for 23 h. The reaction was filtered and concentrated to give Intermediate 1-11-10 4-(aminomethyl)-N-(1,1-difluoropropan-2-yl)pyridin-2-amine (460 mg, 100%) which was used without further purification.

Intermediate 1-2-58

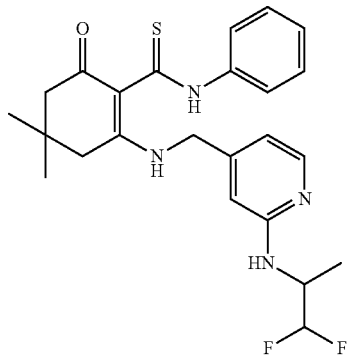 [SMILES: CC(Nc1cc(CNC2=C(C(=S)Nc3ccccc3)C(=O)CC(C)(C)C2)ccn1)C(F)F]

A solution of Intermediate 1-1-1 (68 mg, 248 µmol) and Intermediate 1-11-10 4-(aminomethyl)-N-(1,1-difluoropropan-2-yl)pyridin-2-amine (100 mg, 500 µmol) in DMA (2 mL) was heated at 120° C. for 90 mins using a microwave. Concentrated and preparative HPLC (basic method) to give the Intermediate 1-2-58 (24 mg, 21%).

1H-NMR (400 MHz, DMSO-d6), Shift [ppm]=0.99 (6H), 1.16 (3H), 2.40 (2H), 2.62-2.73 (2H), 4.29-4.55 (1H), 4.68 (2H), 6.01 (1H), 6.45-6.58 (2H), 6.85-6.97 (1H), 7.17-7.27 (1H), 7.34-7.51 (4H), 7.97 (1H), 14.19 (1H), 14.77 (1H).

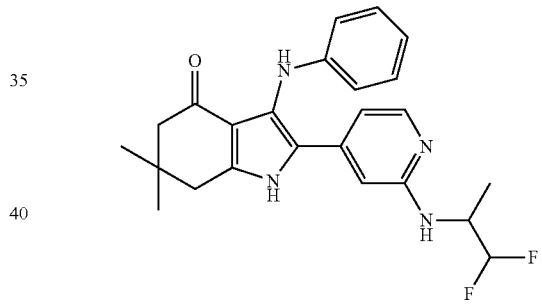

Using method F1 Intermediate 1-2-58 (24 mg, 52 µmol) gave the desired product (5.5 mg, 25%) after preparative HPLC (basic method).

1H-NMR (400 MHz, DMSO-d6), Shift [ppm]=1.06 (6H), 1.12 (3H), 2.21 (2H), 2.72 (2H), 4.21 (1H), 5.92 (1H), 6.47-6.63 (4H), 6.67 (1H), 6.76 (1H), 7.02 (2H), 7.25 (1H), 7.85 (1H), 11.68 (1H).

Example 364 Preparation of 3-(phenylamino)-2-[2-(propan-2-ylamino)pyridin-4-yl]-1,5,6,7-tetrahydro-4H-indol-4-one

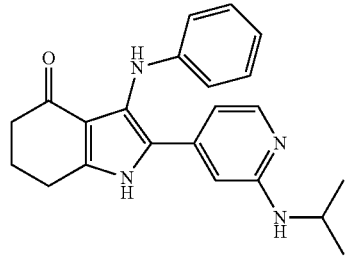 [SMILES: CC(C)Nc1cc(-c2[nH]c3c(c2Nc2ccccc2)C(=O)CCC3)ccn1]

Synthesis of Example 363

Intermediate 1-10-9

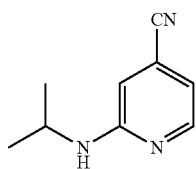

A mixture of 2-chloro-4-cyanopyridine (1.05 g, 7.6 mmol) and isopropylamine (2.57 mL, 30.2 mmol) was heated at 80° C. in a sealed tube for 72 h. Concentrated and purified by silica chromatography to give Intermediate 1-10-9 2-(isopropylamino)isonicotinonitrile (219 mg, 18%).
1H-NMR (300 MHz, DMSO-d6), Shift [ppm]=1.13 (6H), 3.98 (1H), 6.62-6.86 (2H), 6.96 (1H), 8.04-8.26 (1H).

Intermediate 1-11-11

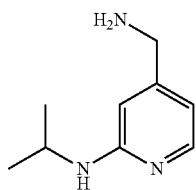

To a solution of Intermediate 1-10-9 2-(isopropylamino) isonicotinonitrile (200 mg, 1.2 mmol) in 7M $NH_3$ in MeOH (5.3 mL) was added Raney-Nickel (50% wet, 291 mg, 5 mmol) and stirred at RT under an $H_2$ atmosphere (31 bar) for 20 h. The reaction was filtered and concentrated to give Intermediate 1-11-11 4-(aminomethyl)-N-isopropylpyridin-2-amine (110 mg, 100%) which was used without further purification.

Intermediate 1-2-59

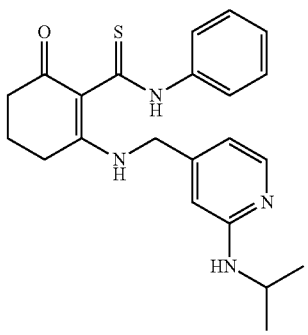 [SMILES: CC(C)Nc1cc(CNC2=C(C(=S)Nc3ccccc3)C(=O)CCC2)ccn1]

A solution of Intermediate 1-1-5 (283 mg, 1.1 mmol) and Intermediate 1-11-11 4-(aminomethyl)-N-isopropylpyridin-2-amine (227 mg, 1.4 mmol) in EtOH:EtOAc (4 mL) was heated in a sealed tube at 90° C. with 4 Å molecular sieves for 72 h without stirring. The reaction was filtered, concentrated and purified by preparative HPLC (Column: XBridge C18 5μ 100×30 mm; Solvent A: Water+0.2 Vol-% $NH_4OH$, Solvent B: Acetonitrile; Gradient: 0-0.5 min 25 mL/min auf 70 mL/min 43% B; 0.5-5.5 min 43-63% B (70 mL/min)) to give the Intermediate 1-2-59 (97 mg, 21%).
1H-NMR (300 MHz, DMSO-d6), Shift [ppm]=1.11 (6H), 1.70-1.88 (2H), 2.41-2.48 (2H), 2.75 (2H), 3.84-4.07 (1H), 4.61 (2H), 6.31-6.52 (3H), 7.15-7.30 (1H), 7.33-7.50 (4H), 7.93 (1H), 13.88 (1H), 14.68 (1H).

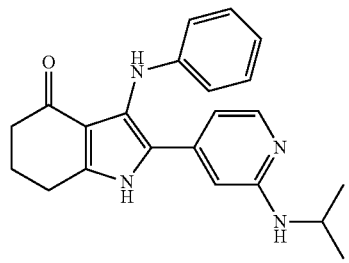 [SMILES: CC(C)Nc1cc(-c2[nH]c3c(c2Nc2ccccc2)C(=O)CCC3)ccn1]

Using method F1 Intermediate 1-2-59 (97 mg, 246 μmol) gave the desired product (5 mg, 6%) after preparative HPLC (Column: XBridge C18 5μ 100×30 mm; Solvent A: Water+0.2 Vol-% $NH_4OH$, Solvent B: Acetonitrile; Gradient:0-0.5 min 25 mL/min auf 70 mL/min 33% B; 0.5-5.5 min 33-53% B (70 mL/min)).
1H-NMR (400 MHz, DMSO-d6), Shift [ppm]=1.01 (6H), 1.93-2.10 (2H), 2.24-2.36 (2H), 2.84 (2H), 3.64 (1H), 5.96 (1H), 6.49-6.64 (4H), 6.68 (1H), 7.02 (2H), 7.24 (1H), 7.81 (1H), 11.67 (1H).

Example 365 Preparation of 3-(phenylamino)-2-{2-[(3,3,3-trifluoropropyl)amino]pyridin-4-yl}-1,5,6,7-tetrahydro-4H-indol-4-one

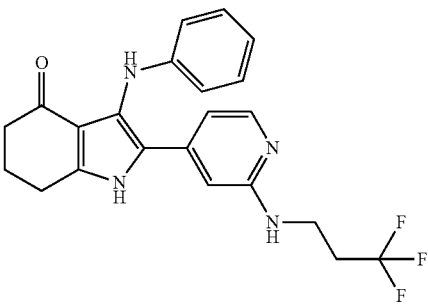 [SMILES: O=C1CCCc2[nH]c(-c3ccnc(NCCC(F)(F)F)c3)c(Nc3ccccc3)c21]

To a solution of Example 139 (150 mg, 471 μmol) in MeOH (11 mL) was added a solution of 3,3,3-trifluoropropanal (264 mg, 2.4 mmol) in AcOH (431 μL, 7.5 mmol) and stirred at RT for 19 h. The reaction was cooled to 0° C. and $NaBH_3CN$ (35.5 mg, 55 μmol) added and stirred for 24 h. Additional $NaBH_3CN$ (35.5 mg, 55 μmol) and stirred for 72 h. Diluted with sat. $NaHCO_3$, extracted with EtOAc. The organic layers were combined and washed with sat. NaCl, dried over $Na_2SO_4$, filtered and concentrated. Purification by silica chromatography gave the desired product (63 mg, 31%).
1H-NMR (400 MHz, DMSO-d6), Shift [ppm]=1.96-2.11 (2H), 2.31 (2H), 2.41 (2H), 2.84 (2H), 3.26-3.40 (2H), 6.44 (1H), 6.52-6.65 (4H), 6.76 (1H), 7.02 (2H), 7.28 (1H), 7.86 (1H), 11.72 (1H).

Example 366 Preparation of 2-[2-(benzylamino)pyridin-4-yl]-3-(phenylamino)-1,5,6,7-tetrahydro-4H-indol-4-one

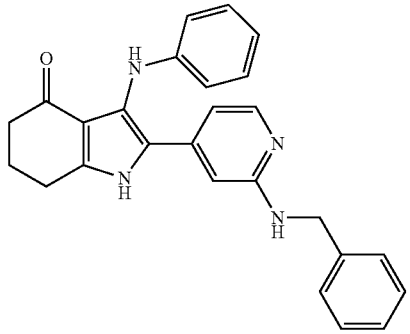 [SMILES: O=C1CCCc2[nH]c(-c3ccnc(NCc4ccccc4)c3)c(Nc3ccccc3)c21]

To a solution of Example 139 (50 mg, 157 μmol) in DCM (1 mL) under Ar was added benzaldehyde (50 mg, 48 μL, 471 μmol), AcOH (28 mg, 27 μL, 471 μmol) and stirred at RT for 15 mins. The reaction was cooled to 0° C. and NaBH$_3$CN (50 mg, 236 μmol) was added and stirred at RT for 16 h. Additional benzaldehyde (50 mg, 48 μL, 471 μmol), AcOH (28 mg, 27 μL, 471 μmol) were added and stirred at RT for 15 mins. The reaction was cooled to 0° C. and NaBH$_3$CN (50 mg, 236 μmol) was added and stirred at RT for 24 h. Concentrated and purified by preparative HPLC (basic method) to give the desired product (24 mg, 37%).

1H-NMR (400 MHz, DMSO-d6), Shift [ppm]=1.98-2.06 (2H), 2.25-2.38 (2H), 2.82 (2H), 4.26 (2H), 6.51-6.59 (3H), 6.59-6.66 (1H), 6.71 (1H), 6.84 (1H), 7.04 (2H), 7.14-7.32 (7H), 7.81 (1H), 11.70 (1H).

Example 367 Preparation of 3-(phenylamino)-2-{2-[(pyridin-4-ylmethyl)amino]pyridin-4-yl}-1,5,6,7-tetrahydro-4H-indol-4-one

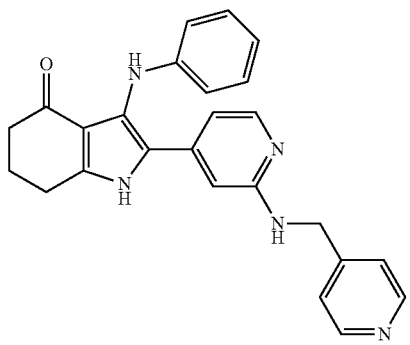 [SMILES: O=C1CCCc2[nH]c(-c3ccnc(NCc4ccncc4)c3)c(Nc3ccccc3)c21]

To a solution of Example 139 (100 mg, 314 μmol) in MeOH (3 mL) was added a solution of pyridine-4-aldehyde (336 mg, 3.1 mmol) in AcOH (55 μL, 10 mmol) and stirred at RT for 72 h. To the reaction under Ar was added Pd/C (10%, 17 mg) and the reaction vessel flushed with H$_2$ (×3). The reaction was stirred for 16 h. The reaction was filtered and added to 4M HCl (aq). The reaction mixture was diluted with water and 25% NH$_4$OH (aq) added and extracted with EtOAc. The organics were combined and washed with sat. NaCl, dried over Na$_2$SO$_4$, filtered and concentrated. Purification by preparative TLC gave the desired product (36 mg, 25%).

1H-NMR (400 MHz, DMSO-d6), Shift [ppm]=1.89-2.11 (2H), 2.31 (2H), 2.83 (2H), 4.31 (2H), 6.52-6.59 (3H), 6.63 (1H), 6.73 (1H), 6.96 (1H), 7.04 (2H), 7.16 (2H), 7.27-7.34 (1H), 7.81 (1H), 8.37-8.47 (2H), 11.71 (1H).

Example 368 Preparation of 2-{2-[(cyclopropylmethyl)amino]pyridin-4-yl}-3-(phenylamino)-1,5,6,7-tetrahydro-4H-indol-4-one

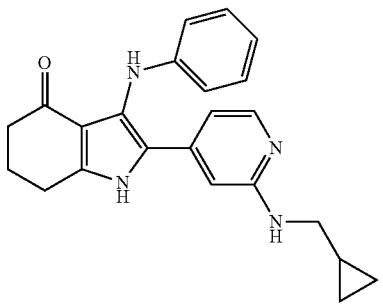 [SMILES: O=C1CCCc2[nH]c(-c3ccnc(NCC4CC4)c3)c(Nc3ccccc3)c21]

To a solution of Example 139 (150 mg, 471 μmol) in MeOH (11 mL) was added a solution of cyclopropancarboxaldehyde (165 mg, 2.4 mmol) in AcOH (431 μL, 7.5 mmol) and stirred at RT for 19 h. The reaction was cooled to 0° C. and NaBH$_3$CN (35.5 mg, 55 μmol) added and stirred for 24 h. Diluted with sat. NaHCO$_3$, extracted with EtOAc. The organic layers were combined and washed with sat. NaCl, dried over Na$_2$SO$_4$, filtered and concentrated. Purification by silica chromatography gave the desired product (63 mg, 31%).

1H-NMR (500 MHz, DMSO-d6), Shift [ppm]=−0.01-0.14 (2H), 0.29-0.43 (2H), 0.89 (1H), 1.97-2.11 (2H), 2.25-2.35 (2H), 2.78-2.93 (4H), 6.27 (1H), 6.48-6.63 (4H), 6.70 (1H), 7.02 (2H), 7.28 (1H), 7.81 (1H), 11.69 (1H).

Example 369 Preparation of N-{4-[4-oxo-3-(phenylamino)-4,5,6,7-tetrahydro-1H-indol-2-yl]pyridin-2-yl}glycine

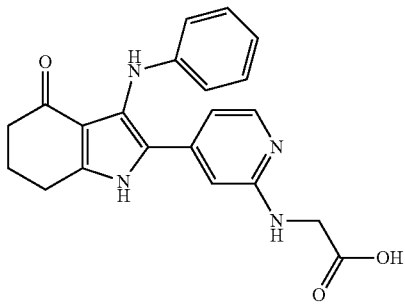 [SMILES: O=C(O)CNc1cc(-c2[nH]c3c(c2Nc2ccccc2)C(=O)CCC3)ccn1]

To a solution of Example 139 (150 mg, 471 μmol) in MeOH (11 mL) was added a solution of glyoxylic acid (174 mg, 2.4 mmol) in AcOH (431 μL, 7.5 mmol) and stirred at RT for 19 h. The reaction was cooled to 0° C. and NaBH$_3$CN (35.5 mg, 55 μmol) added and stirred for 24 h. Additional NaBH$_3$CN (35.5 mg, 55 μmol) was added at 0° C. and stirred for 24 h. Diluted with sat. NaHCO$_3$, extracted with EtOAc. The organic layers were combined and washed with sat. NaCl, dried over Na$_2$SO$_4$, filtered and concentrated to give the desired product (74 mg, 39%).

1H-NMR (400 MHz, DMSO-d6), Shift [ppm]=1.97-2.11 (2H), 2.24-2.36 (2H), 2.84 (2H), 3.82 (2H), 6.49-6.64 (4H), 6.66 (1H), 6.75 (1H), 7.03 (2H), 7.25 (1H), 7.75-7.85 (1H), 11.74 (1H).

Example 370 Preparation of 2-[2-({[(4S)-2,2-dimethyl-1,3-dioxolan-4-yl]methyl}amino)pyridin-4-yl]-3-(phenylamino)-1,5,6,7-tetrahydro-4H-indol-4-one

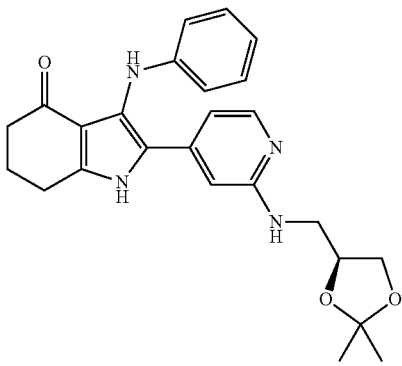 [SMILES: CC1(C)OC[C@H](CNc2cc(-c3[nH]c4c(c3Nc3ccccc3)C(=O)CCC4)ccn2)O1]

To a solution of Example 139 (250 mg, 75 µmol) in MeOH (19 mL) was added a solution of (4R)-2,2-dimethyl-1,3-dioxolane-4-carbaldehyde (511 mg, 3.9 mmol) in AcOH (719 µL, 12.6 mmol) and stirred at RT for 19 h. The reaction was cooled to 0° C. and NaBH₃CN (59 mg, 942 µmol) added and stirred for 24 h. Diluted with sat. NaHCO₃, extracted with EtOAc. The organic layers were combined and washed with sat. NaCl, dried over Na₂SO₄, filtered and concentrated. Purification by silica chromatography gave the desired product (162 mg, 45%).

1H-NMR (400 MHz, DMSO-d6), Shift [ppm]=1.24 (3H), 1.32 (3H), 1.98-2.08 (2H), 2.26-2.37 (2H), 2.84 (2H), 3.09-3.19 (1H), 3.19-3.29 (1H), 3.60 (1H), 3.91 (1H), 4.12 (1H), 6.33 (1H), 6.52-6.64 (4H), 6.72 (1H), 7.02 (2H), 7.28 (1H), 7.82 (1H), 11.70 (1H).

Example 371 Preparation of 2 2-(2-{[(2S)-2,3-dihydroxypropyl]amino}pyridin-4-yl)-3-(phenylamino)-1,5,6,7-tetrahydro-4H-indol-4-one

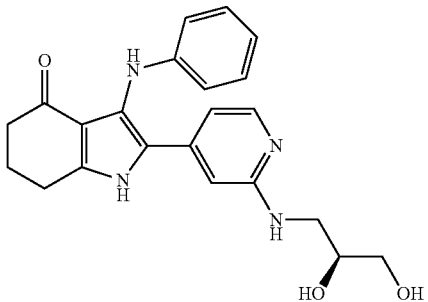 [SMILES: O=C1CCCc2[nH]c(-c3ccnc(NC[C@H](O)CO)c3)c(Nc3ccccc3)c21]

To a solution of Example 370 (115 mg, 266 µmol) in EtOH (3.1 mL) was added PTSA (76 mg, 399 µmol) and stirred at RT for 16 h. Triethylamine (74 µL, 532 µmol) was added and the reaction was concentrated. Purification by preparative TLC (silica), preparative HPLC (basic and acidic methods), followed by silica chromatography and another preparative TLC (silica) gave the desired product (31.4 mg, 29%).

1H-NMR (400 MHz, DMSO-d6), Shift [ppm]=1.94-2.10 (2H), 2.24-2.35 (2H), 2.77-2.87 (2H), 2.96-3.12 (1H), 3.12-3.28 (2H), 3.41-3.69 (2H), 4.67 (1H), 5.01 (1H), 6.09 (1H), 6.47-6.66 (4H), 6.70 (1H), 7.02 (2H), 7.25 (1H), 7.76 (1H).

Example 372 Preparation of 3-(phenylamino)-2-{2-[(pyridin-3-ylmethyl)amino]pyridin-4-yl}-1,5,6,7-tetrahydro-4H-indol-4-one

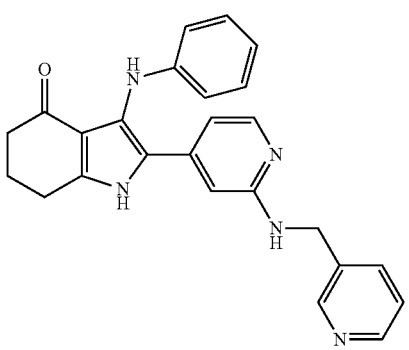 [SMILES: O=C1CCCc2[nH]c(-c3ccnc(NCc4cccnc4)c3)c(Nc3ccccc3)c21]

To a solution of Example 139 (150 mg, 471 µmol) in MeOH (17 mL) was added a solution of pyridine-3-carbaldehyde (252 mg, 2.4 mmol) in AcOH (431 µL, 7.5 mmol) and stirred at RT for 19 h. The reaction was cooled to 0° C. and NaBH₃CN (35.5 mg, 55 µmol) added and stirred for 24 h. Diluted with sat. NaHCO₃, extracted with EtOAc. The organic layers were combined and washed with sat. NaCl, dried over Na₂SO₄, filtered and concentrated. Purification by silica chromatography followed by a preparative TLC gave the desired product (7.8 mg, 4%).

1H-NMR (400 MHz, DICHLOROMETHANE-d2), Shift [ppm]=2.08-2.19 (2H), 2.44 (3H), 2.83 (2H), 3.77 (2H), 5.99 (1H), 6.13 (1H), 6.68 (2H), 6.80-6.94 (2H), 7.13-7.32 (3H), 7.49 (1H), 7.80 (1H), 7.90 (1H), 8.37 (1H), 8.49 (1H), 10.13 (1H).

Example 373 Preparation of tert-butyl 3-[({4-[4-oxo-3-(phenylamino)-4,5,6,7-tetrahydro-1H-indol-2-yl]pyridin-2-yl}amino)methyl]azetidine-1-carboxylate

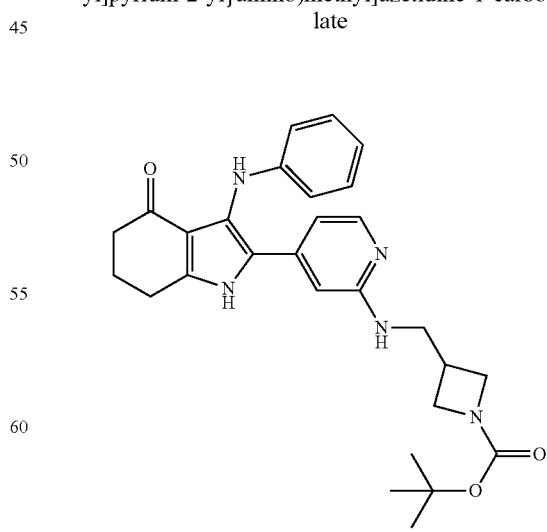

To a solution of Example 139 (150 mg, 471 µmol) in MeOH (11 mL) was added a solution of 1-Boc-3-Azetidinecarboxaldehyde (436 mg, 2.4 mmol) in AcOH (431 µL, 7.5 mmol) and stirred at RT for 19 h. The reaction was cooled to 0° C. and NaBH$_3$CN (35.5 mg, 55 µmol) added and stirred for 19 h. Diluted with sat. NaHCO$_3$, extracted with EtOAc. The organic layers were combined and washed with sat. NaCl, dried over Na$_2$SO$_4$, filtered and concentrated. Purification by silica chromatography gave the desired product (184 mg, 80%).

1H-NMR (400 MHz, DMSO-d6), Shift [ppm]=1.37 (9H), 1.98-2.11 (2H), 2.26-2.36 (2H), 2.52-2.61 (1H), 2.84 (2H), 3.15 (2H), 3.46 (2H), 3.77 (2H), 6.43-6.50 (2H), 6.53-6.64 (3H), 6.72 (1H), 7.03 (2H), 7.30 (1H), 7.82 (1H), 11.70 (1H).

Example 374 Preparation of 2-{2-[(1-methyl-1H-tetrazol-5-yl)amino]pyridin-4-yl}-3-(phenylamino)-1,5,6,7-tetrahydro-4H-indol-4-one

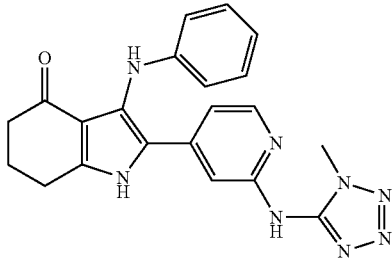 [SMILES: Cn1nnnc1Nc1cc(-c2[nH]c3c(c2Nc2ccccc2)C(=O)CCC3)ccn1]

To a mixture of Example 152 (20 mg, 52 µmol), 1-methyl-1H-tetrazol-5-amine (10 mg, 104 µmol) chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct, 4.6 mg, 5 µmol), 2-(di-tert-butylphosphino)-2',4',6'-triisopropyl-3,6-dimethoxy-1,1'-biphenyl (tBuBrettPhos, 2.5 mg, 5 µmol), lithium chloride (26.6 mg, 627 µmol) in dioxane (400 µL) under an Ar atmosphere was added 1M LHMDS in THF (262 µL, 262 µmol). The reaction mixture was heated under an Argon atmosphere at 80° C. for 16 h. The reaction was quenched by the addition of 1M HCl (2 mL) and the reaction diluted with EtOAc and washed with sat. NaHCO$_3$(aq). The aqueous phase was extracted with EtOAc (×2). The organics phases were combined and washed with sat. NaCl(aq), dried over Na$_2$SO$_4$ or MgSO4, filtered, concentrated and purified by preparative HPLC (basic method) to give the desired product (5.6 mg, 24%).

1H-NMR (400 MHz, CHLOROFORM-d), Shift [ppm]=2.22 (2H), 2.51 (2H), 2.79-3.09 (2H), 3.93 (3H), 6.67-7.60 (8H).

Example 375 Preparation of 2-{2-[(3-fluorophenyl)amino]pyridin-4-yl}-3-(phenylamino)-1,5,6,7-tetrahydro-4H-indol-4-one

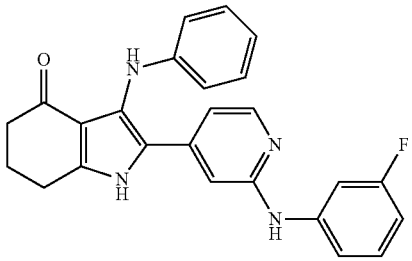 [SMILES: O=C1CCCc2[nH]c(-c3ccnc(Nc4cccc(F)c4)c3)c(Nc3ccccc3)c21]

To a mixture of Example 152 (20 mg, 52 µmol), 3-fluoroaniline (10 µL, 15 µmol) chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct, 4.6 mg, 5 µmol), 2-(di-tert-butylphosphino)-2',4',6'-triisopropyl-3,6-dimethoxy-1,1'-biphenyl (tBuBrettPhos, 2.5 mg, 5 µmol), lithium chloride (26.6 mg, 627 µmol) in dioxane (422 µL) under an Ar atmosphere was added 1M LHMDS in THF (262 µL, 262 µmol). The reaction mixture was heated under an Argon atmosphere at 80° C. for 16 h. The reaction was quenched by the addition of 1M HCl (2 mL) and the reaction diluted with EtOAc and washed with sat. NaHCO$_3$(aq). The aqueous phase was extracted with EtOAc (×2). The organics phases were combined and washed with sat. NaCl(aq), dried over Na2SO4 or MgSO4, filtered, concentrated and purified by preparative HPLC (basic method) to give the desired product (5.7 mg, 24%).

1H-NMR (400 MHz, CHLOROFORM-d), Shift [ppm]=2.10 (2H), 2.31-2.47 (2H), 2.72-2.88 (2H), 6.57-6.64 (4H), 6.68-6.93 (4H), 6.96-7.16 (3H), 7.29 (2H), 7.93 (1H).

Example 376 Preparation of 3-(phenylamino)-2-[3-(propan-2-ylamino)pyridin-4-yl]-1,5,6,7-tetrahydro-4H-indol-4-one

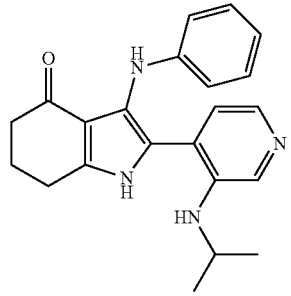 [SMILES: CC(C)Nc1cnccc1-c1[nH]c2c(c1Nc1ccccc1)C(=O)CCC2]

Synthesis of Example 376

Intermediate 1-10-10

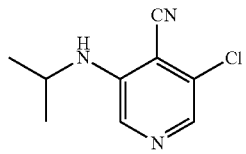

A mixture of 3,5-dichloro-4-cyanopyridine (1.01 g, 5.9 mmol) and isopropylamine (2 mL, 23 mmol) was heated at 80° C. in a sealed tube for 72 h. Concentrated and purified by silica chromatography to give Intermediate 1-10-10 3-chloro-5-(isopropylamino)isonicotinonitrile (923 mg, 81%).

1H-NMR (300 MHz, DMSO-d6), Shift [ppm]=1.21 (6H), 3.97 (1H), 6.51 (1H), 7.93 (1H), 8.25 (1H).

Intermediate 1-11-12

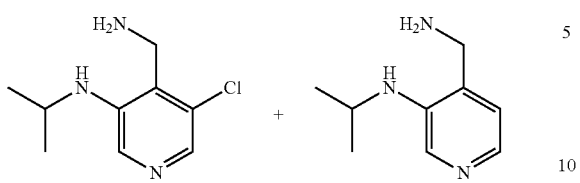

To a solution of Intermediate 1-10-10 3-chloro-5-(isopropylamino)isonicotinonitrile (900 mg, 4.6 mmol) in 7M NH$_3$ in MeOH (25 mL) was added Raney-Nickel (50% wet, 1.08 g, 18.4 mmol) and stirred at RT under an H$_2$ atmosphere (31 bar) for 20 h. The reaction was filtered and concentrated to give the Intermediate 1-11-12 as a mixture of 4-(aminomethyl)-5-chloro-N-(propan-2-yl)pyridin-3-amine and 4-(aminomethyl)-N-(propan-2-yl)pyridin-3-amine (850 mg) which was used without further purification.

Intermediate 1-2-60

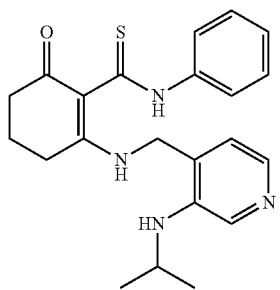 [SMILES: CC(C)Nc1cnccc1CNC1=C(C(=S)Nc2ccccc2)C(=O)CCC1]

A solution of Intermediate 1-1-5 (850 mg, 3.4 mmol) and a Intermediate 1-11-12 (824 mg, 4.1 mmol) in EtOH:EtOAc (40 mL) was heated at 90° C. for 48 h. The reaction was filtered, concentrated and purified by preparative HPLC (Column: XBridge C18 5μ 100×30 mm; Solvent A: Water+ 0.2 Vol-% NH$_4$OH, Solvent B: Acetonitrile; Gradient: 0-9.5 min 32-70% B (200 mL/min)) to give the Intermediate 1-2-60 (251 mg, 17%):

1H-NMR (400 MHz, DMSO-d6), Shift [ppm]=1.20 (6H), 1.74-1.89 (2H), 2.43-2.48 (2H), 2.76 (2H), 3.76 (1H), 4.61 (2H), 4.92 (1H), 7.11 (1H), 7.19-7.30 (1H), 7.34-7.41 (2H), 7.41-7.51 (2H), 7.85 (1H), 8.01 (1H), 13.64 (1H), 14.59 (1H).

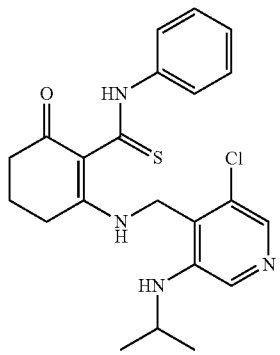 [SMILES: CC(C)Nc1cncc(Cl)c1CNC1=C(C(=S)Nc2ccccc2)C(=O)CCC1]

The chloro containing analog shown above was also obtained from the preparative HPLC purification (290 mg, 21%).

1H-NMR (400 MHz, DMSO-d6), Shift [ppm]=1.19 (6H), 1.80-1.95 (2H), 2.48 (1H), 2.93 (2H), 3.80 (1H), 4.76 (2H), 5.51 (1H), 7.14-7.27 (1H), 7.30-7.45 (4H), 7.87 (1H), 8.01 (1H), 13.70 (1H), 14.65 (1H).

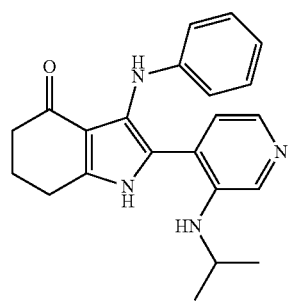 [SMILES: CC(C)Nc1cnccc1-c1[nH]c2c(c1Nc1ccccc1)C(=O)CCC2]

Using method F1 Intermediate 1-2-60 (210 mg, 532 μmol) gave the desired product (29 mg, 14%) after preparative HPLC basic method).

1H-NMR (400 MHz, DMSO-d6), Shift [ppm]=0.87 (6H), 2.00-2.16 (2H), 2.30-2.39 (2H), 2.83 (2H), 3.54 (1H), 5.06 (1H), 6.52-6.63 (3H), 6.91-7.01 (2H), 7.21 (1H), 7.65 (1H), 7.82-7.87 (2H), 11.56 (1H).

Example 377 Preparation of 1-ethyl-3-{4-[4-oxo-3-(phenylamino)-4,5,6,7-tetrahydro-1H-indol-2-yl]pyridin-2-yl}urea

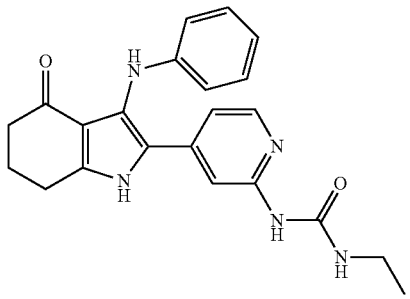 [SMILES: CCNC(=O)Nc1cc(-c2[nH]c3c(c2Nc2ccccc2)C(=O)CCC3)ccn1]

Using Method G3: To a solution of Example 139 (61 mg, 192 μmol) in pyridine (1 mL) was added ethylisocyanate (30 μL, 383 μmol) and stirred at RT for 16 h. Concentrated and purified by preparative HPLC (basic method) to give the desired product (29 mg, 37%) as a solid.

1H-NMR (400 MHz, DMSO-d6), d [ppm]=1.07 (2H), 1.98-2.13 (2H), 2.28-2.36 (2H), 2.85 (2H), 3.12-3.22 (2H), 6.51-6.65 (3H), 6.96-7.07 (2H), 7.32 (1H), 7.46 (1H), 7.97 (1H), 8.02 (1H), 9.03 (1H), 11.82 (1H).

Example 378 Preparation of 1-{4-[4-oxo-3-(phenylamino)-4,5,6,7-tetrahydro-1H-indol-2-yl]pyridin-2-yl}-3-propan-2-ylurea

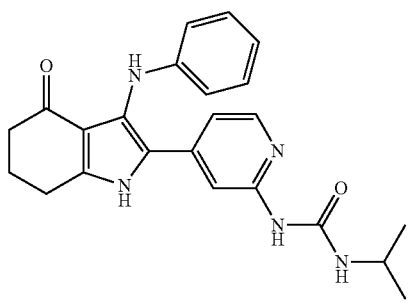 [SMILES: CC(C)NC(=O)Nc1cc(-c2[nH]c3c(c2Nc2ccccc2)C(=O)CCC3)ccn1]

Using Method G3: To a solution of Example 139 (64 mg, 201 μmol) in pyridine (1 mL) was added isopropyl isocyanate (40 μL, 402 μmol) and stirred at RT for 16 h. Concentrated and purified by preparative HPLC (basic method) to give the desired product (32 mg, 42%) as a solid.

1H-NMR (400 MHz, DMSO-d6), d [ppm]=1.12 (5H), 1.97-2.11 (2H), 2.27-2.38 (2H), 2.85 (2H), 3.73-3.86 (1H), 6.51-6.66 (3H), 6.97-7.08 (3H), 7.31 (1H), 7.51 (1H), 7.85 (1H), 7.96 (1H), 8.92 (1H), 11.81 (1H).

Example 379 Preparation of 1-cyclopropyl-3-{4-[4-oxo-3-(phenylamino)-4,5,6,7-tetrahydro-1H-indol-2-yl]pyridin-2-yl}urea

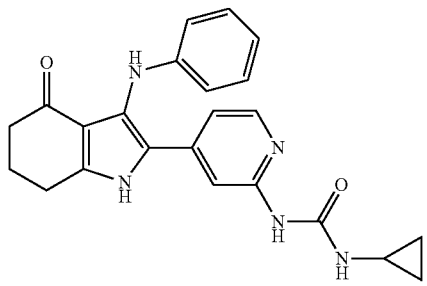 [SMILES: O=C(Nc1cc(-c2[nH]c3c(c2Nc2ccccc2)C(=O)CCC3)ccn1)NC1CC1]

Using Method G3: To a solution of Example 139 (71 mg, 223 μmol) in pyridine (1 mL) was added cyclopropyl isocyanate (31 μL, 446 μmol) and stirred at RT for 16 h. Concentrated and purified by preparative HPLC (basic method) to give the desired product (31 mg, 35%) as a solid.

1H-NMR (400 MHz, DMSO-d6), d [ppm]=0.37-0.51 (2H), 0.57-0.69 (2H), 1.97-2.10 (2H), 2.32 (2H), 2.52-2.63 (1H), 2.85 (2H), 6.52-6.64 (3H), 6.96-7.06 (2H), 7.32 (1H), 7.53 (1H), 7.96 (1H), 8.04 (1H), 8.96 (1H), 11.83 (1H).

Example 380 Preparation of 1-tert-butyl-3-{4-[4-oxo-3-(phenylamino)-4,5,6,7-tetrahydro-1H-indol-2-yl]pyridin-2-yl}urea

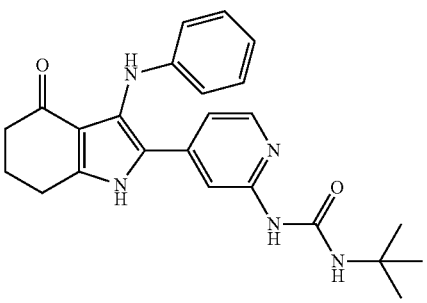 [SMILES: CC(C)(C)NC(=O)Nc1cc(-c2[nH]c3c(c2Nc2ccccc2)C(=O)CCC3)ccn1]

Using Method G3: To a solution of Example 139 (61 mg, 192 μmol) in pyridine (1 mL) was added tert-butylisocyanate (44 μL, 383 μmol) and stirred at RT for 16 h. Concentrated and purified by preparative HPLC (basic method) to give the desired product (29 mg, 36%).

1H-NMR (400 MHz, DMSO-d6), Shift [ppm]=1.31 (9H), 1.98-2.10 (2H), 2.28-2.37 (2H), 2.85 (2H), 6.51-6.67 (2H), 6.97-7.06 (2H), 7.32 (1H), 7.52 (1H), 7.86 (1H), 7.94 (1H), 8.81 (1H), 11.82 (1H).

Example 381 Preparation of 1-(2-methylpropyl)-3-{4-[4-oxo-3-(phenylamino)-4,5,6,7-tetrahydro-1H-indol-2-yl]pyridin-2-yl}urea

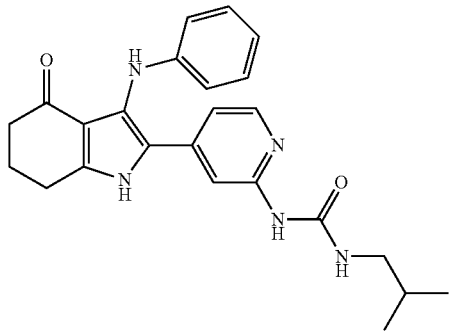 [SMILES: CC(C)CNC(=O)Nc1cc(-c2[nH]c3c(c2Nc2ccccc2)C(=O)CCC3)ccn1]

Using Method G3: To a solution of Example 139 (64 mg, 192 μmol) in pyridine (1 mL) was added 1-isocyanato-2-methylpropane (5 μL, 402 μmol) and stirred at RT for 40 h. Concentrated and purified by preparative HPLC (basic method) to give the desired product (39 mg, 46%).

1H-NMR (400 MHz, DMSO-d6), Shift [ppm]=0.88 (6H), 1.71 (1H), 1.98-2.10 (2H), 2.32 (2H), 2.85 (2H), 2.99 (2H), 6.50-6.70 (3H), 6.93-7.11 (3H), 7.32 (1H), 7.47 (1H), 7.97 (1H), 8.15 (1H), 9.04 (1H), 11.81 (1H).

Example 382 Preparation of 1-{4-[4-oxo-3-(phenylamino)-4,5,6,7-tetrahydro-1H-indol-2-yl]pyridin-2-yl}-3-(2,2,2-trifluoroethyl)urea

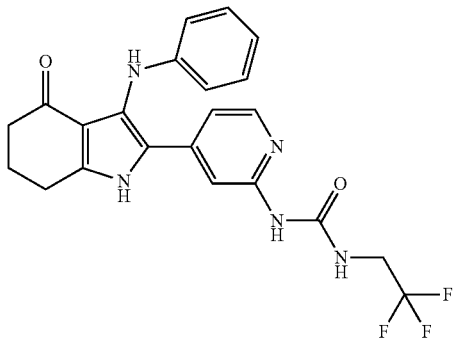 [SMILES: O=C(NCC(F)(F)F)Nc1cc(-c2[nH]c3c(c2Nc2ccccc2)C(=O)CCC3)ccn1]

Using Method G3: To a solution of Example 139 (67 mg, 210 µmol) in pyridine (1 mL) was added 2,2,2-trifluoroethyl isothiocyanate (37 µL, 421 µmol) and stirred at RT for 16 h. Concentrated and purified by preparative HPLC (basic method) to give the desired product (29 mg, 36%).

1H-NMR (500 MHz, DMSO-d6), Shift [ppm]=1.99-2.10 (2H), 2.22-2.40 (2H), 2.85 (2H), 3.92-4.09 (2H), 6.56 (2H), 6.61 (1H), 7.02 (2H), 7.08 (1H), 7.35 (1H), 7.50 (1H), 8.01 (1H), 8.58 (1H), 9.39 (1H), 11.85 (1H).

Example 383 Preparation of 1-(2-methoxyethyl)-3-{4-[4-oxo-3-(phenylamino)-4,5,6,7-tetrahydro-1H-indol-2-yl]pyridin-2-yl}urea

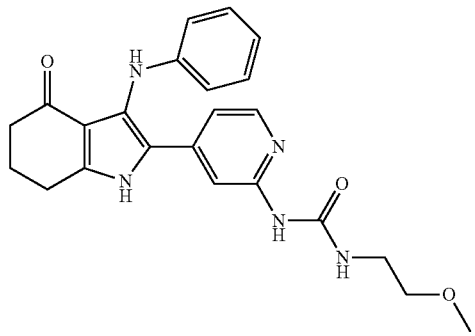 [SMILES: COCCNC(=O)Nc1cc(-c2[nH]c3c(c2Nc2ccccc2)C(=O)CCC3)ccn1]

Using Method G3: To a solution of Example 139 (64 mg, 201 µmol) in pyridine (1 mL) was added tert-butylisocyanate (42 µL, 402 µmol) and stirred at RT for 16 h. Concentrated and purified by preparative HPLC (basic method) to give the desired product (16 mg, 19%).

1H-NMR (400 MHz, DMSO-d6), Shift [ppm]=1.96-2.10 (2H), 2.26-2.37 (2H), 2.85 (2H), 3.27 (3H), 3.35-3.43 (2H), 6.53-6.64 (3H), 6.98-7.06 (3H), 7.33 (1H), 7.48 (1H), 7.97 (1H), 8.13 (1H), 9.11 (1H).

Example 384 Preparation of 1-(furan-2-ylmethyl)-3-{4-[4-oxo-3-(phenylamino)-4,5,6,7-tetrahydro-1H-indol-2-yl]pyridin-2-yl}urea

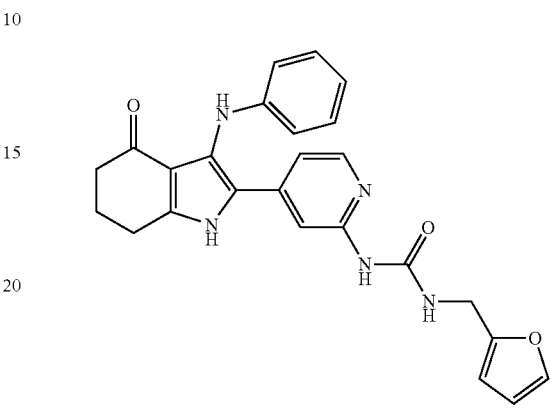

Using Method G3: To a solution of Example 139 (61 mg, 192 µmol) in pyridine (1 mL) was added furfuryl isocyanate (41 µL, 383 µmol) and stirred at RT for 16 h. Concentrated and purified by preparative HPLC (basic method) to give the desired product (18 mg, 20%).

1H-NMR (400 MHz, DMSO-d6), Shift [ppm]=1.99-2.09 (2H), 2.28-2.37 (2H), 2.84 (2H), 4.36 (2H), 6.25 (1H), 6.35-6.43 (1H), 6.51-6.65 (3H), 6.97-7.06 (3H), 7.34 (1H), 7.50 (1H), 7.55-7.60 (1H), 7.97 (1H), 8.41 (1H), 9.18 (1H), 11.84 (1H).

Example 385 Preparation of 1-{4-[4-oxo-3-(phenylamino)-4,5,6,7-tetrahydro-1H-indol-2-yl]pyridin-2-yl}-3-pyridin-4-ylurea

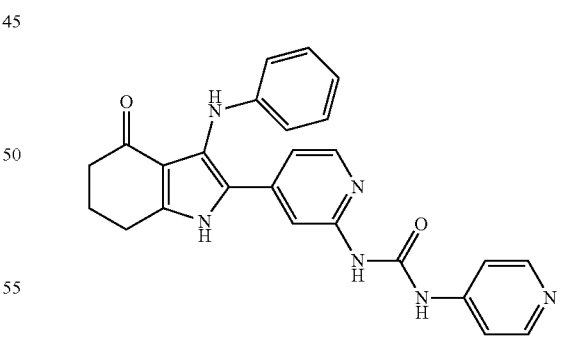

Using Method G3: To a solution of Example 139 (62 mg, 15 µmol) in pyridine (1 mL) was added 4-isocyanatopyridine (47 mg, 389 µmol) and stirred at RT for 16 h. Concentrated and purified by preparative HPLC (basic method) to give the desired product (13 mg, 14%).

1H-NMR (400 MHz, DMSO-d6), Shift [ppm]=1.97-2.12 (2H), 2.28-2.39 (2H), 2.87 (2H), 6.54-6.68 (3H), 6.98-7.08 (2H), 7.14 (1H), 7.39 (1H), 7.45-7.52 (2H), 7.70 (1H), 8.10 (1H), 8.39 (2H), 9.48 (1H), 10.59 (1H), 11.91 (1H).

Example 386 Preparation of 1-{4-[4-oxo-3-(phenylamino)-4,5,6,7-tetrahydro-1H-indol-2-yl]pyridin-2-yl}-3-pyridin-2-ylurea

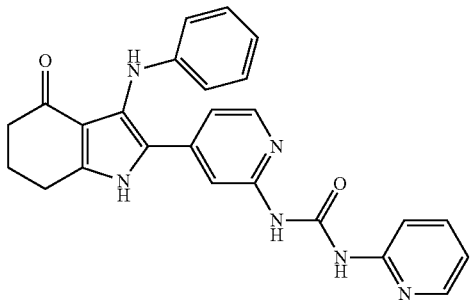 [SMILES: O=C(Nc1ccccn1)Nc1cc(-c2[nH]c3c(c2Nc2ccccc2)C(=O)CCC3)ccn1]

Using Method G3: To a solution of Example 139 (60 mg, 188 µmol) in pyridine (1 mL) was added 2-isocyanatopyridine (45 mg, 377 µmol) and stirred at RT for 16 h. Concentrated and purified by preparative HPLC (basic method) to give the desired product (44 mg, 51%).

1H-NMR (400 MHz, DMSO-d6), Shift [ppm]=1.98-2.12 (2H), 2.28-2.38 (2H), 2.87 (2H), 6.53-6.64 (3H), 6.98-7.07 (3H), 7.14 (1H), 7.38 (1H), 7.68 (1H), 7.76 (1H), 7.86 (1H), 8.09 (1H), 8.24-8.31 (1H), 10.50 (1H), 11.91 (1H).

Example 387 Preparation of 1-(2,2-difluoroethyl)-3-{4-[4-oxo-3-(phenylamino)-4,5,6,7-tetrahydro-1H-indol-2-yl]pyridin-2-yl}urea

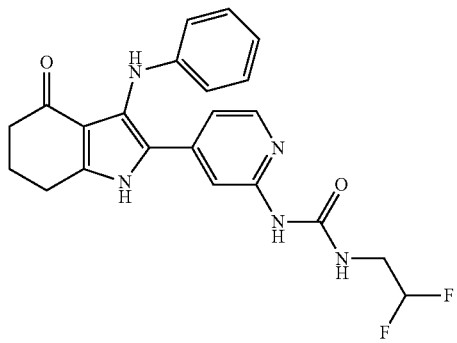 [SMILES: O=C(NCC(F)F)Nc1cc(-c2[nH]c3c(c2Nc2ccccc2)C(=O)CCC3)ccn1]

Using Method G3: To a solution of Example 139 (50 mg, 157 µmol) in pyridine (1 mL) was added 1,1-difluoro-2-isocyanatoethane (34 mg, 314 µmol) and stirred at RT for 16 h. Concentrated and purified by preparative HPLC (basic method) to give the desired product (18 mg, 27%).

1H-NMR (400 MHz, DMSO-d6), Shift [ppm]=1.96-2.11 (2H), 2.32 (2H), 2.85 (2H), 3.60 (2H), 6.08 (1H), 6.49-6.68 (3H), 6.97-7.09 (3H), 7.35 (1H), 7.46 (1H), 8.00 (1H), 8.44 (1H), 9.34 (1H), 11.85 (1H).

Example 388 Preparation of 1-(2-chloroethyl)-3-{4-[4-oxo-3-(phenylamino)-4,5,6,7-tetrahydro-1H-indol-2-yl]pyridin-2-yl}urea

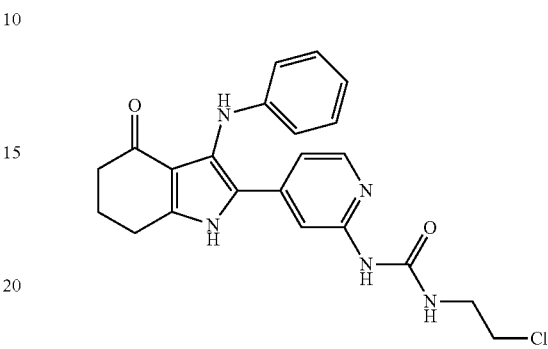

Using Method G3: To a solution of Example 139 (169 mg, 531 µmol) in pyridine (1 mL) was added 2-chloroethylisocyanate (91 µL, 1.06 mmol) and stirred at RT for 16 h. Concentrated and purified by preparative HPLC (basic method) to give the desired product (70 mg, 31%).

1H-NMR (400 MHz, DMSO-d6), Shift [ppm]=1.96-2.16 (2H), 2.32 (2H), 2.85 (2H), 3.49 (2H), 3.62-3.75 (2H), 6.52-6.64 (3H), 6.97-7.07 (3H), 7.33 (1H), 7.45 (1H), 7.99 (1H), 8.41 (1H), 9.24 (1H), 11.83 (1H).

Example 389 Preparation of 1-[2-(methylsulfanyl)ethyl]-3-{4-[4-oxo-3-(phenylamino)-4,5,6,7-tetrahydro-1H-indol-2-yl]pyridin-2-yl}urea

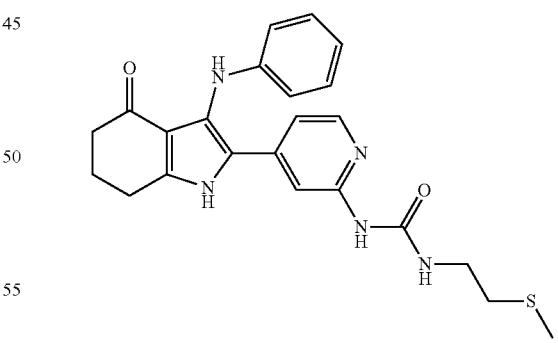

Using Method G3: To a solution of Example 139 (50 mg, 157 µmol) in pyridine (1 mL) was added isocyanatomethyl methyl sulfide (37 mg) and stirred at RT for 16 h. Concentrated and purified by preparative HPLC (basic method) to give the desired product (30 mg, 44%).

1H-NMR (400 MHz, DMSO-d6), Shift [ppm]=1.98-2.12 (5H), 2.29-2.35 (2H), 2.58 (2H), 2.85 (2H), 3.22-3.43 (2H), 6.52-6.65 (3H), 6.98-7.05 (3H), 7.33 (1H), 7.45 (1H), 7.97 (1H), 8.29 (1H), 9.17 (1H), 11.83 (1H).

Example 390 Preparation of 1-(1-methyl-1H-pyrazol-4-yl)-3-{4-[4-oxo-3-(phenylamino)-4,5,6,7-tetrahydro-1H-indol-2-yl]pyridin-2-yl}urea

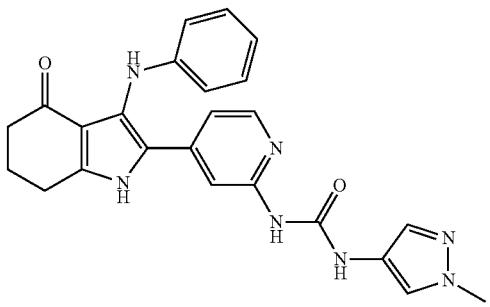 [SMILES: Cn1cc(NC(=O)Nc2cc(-c3[nH]c4c(c3Nc3ccccc3)C(=O)CCC4)ccn2)cn1]

Using Method G3: To a solution of Example 139 (99 mg, 311 μmol) in pyridine (1 mL) was added 4-isocyanato-1-methyl-1H-pyrazole (77 mg, 622 μmol) and stirred at RT for 64 h. Concentrated and purified by preparative HPLC (basic method) to give the desired product (57 mg, 39%).

1H-NMR (400 MHz, DMSO-d6), Shift [ppm]=1.96-2.15 (2H), 2.33 (2H), 2.86 (2H), 3.78 (3H), 6.53-6.65 (3H), 6.99-7.06 (2H), 7.08 (1H), 7.37 (1H), 7.42 (1H), 7.50 (1H), 7.78 (1H), 8.04 (1H), 9.37 (1H), 10.24 (1H), 11.88 (1H).

Example 391 Preparation of 1-{4-[6,6-dimethyl-4-oxo-3-(phenylamino)-4,5,6,7-tetrahydro-1H-indol-2-yl]pyridin-2-yl}-3-(1-methyl-1H-pyrazol-4-yl)urea

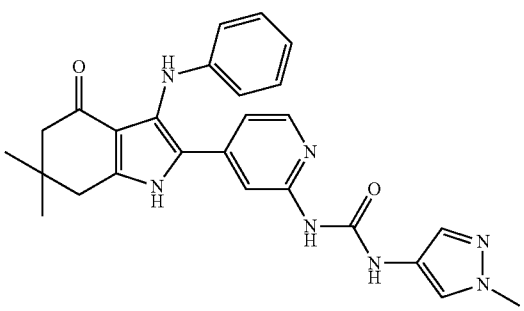

Using Method G3: To a solution of Example 122 (102 mg, 294 μmol) in pyridine (1 mL) was added 4-isocyanato-1-methyl-1H-pyrazole (72 mg, 589 μmol) and stirred at RT for 64 h. Concentrated and purified by preparative HPLC (basic method) to give the desired product (38 mg, 26%).

1H-NMR (400 MHz, DMSO-d6), Shift [ppm]=1.06 (6H), 2.23 (2H), 2.75 (2H), 3.78 (3H), 6.49-6.65 (3H), 7.02 (2H), 7.09 (1H), 7.36 (1H), 7.42 (1H), 7.50 (1H), 7.78 (1H), 8.05 (1H), 9.37 (1H), 10.24 (1H), 11.85 (1H).

Example 392 Preparation of 1-methyl-3-{4-[4-oxo-3-(phenylamino)-4,5,6,7-tetrahydro-1H-indol-2-yl]pyridin-2-yl}thiourea

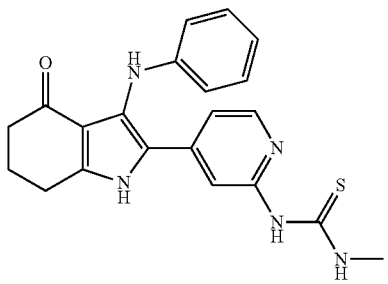 [SMILES: CNC(=S)Nc1cc(-c2[nH]c3c(c2Nc2ccccc2)C(=O)CCC3)ccn1]

Using Method G4: To a solution of Example 139 (76 mg, 239 μmol) in pyridine (1 mL) was added methylisothiocyanate (33 μL, 477 μmol) and stirred at RT for 64 h. Additional methylisothiocyanate (165 μL, 238 μmol) was added and heated at 50° C. for 24 h. Concentrated and purified by preparative HPLC (basic method) to give the desired product (43 mg, 46%).

1H-NMR (400 MHz, DMSO-d6), Shift [ppm]=1.98-2.11 (2H), 2.27-2.39 (2H), 2.85 (2H), 3.05 (3H), 6.52-6.68 (3H), 7.02 (2H), 7.11 (1H), 7.18 (1H), 7.37 (1H), 8.05 (1H), 10.47 (1H), 11.51 (1H), 11.81 (1H).

Example 393 Preparation of 1-ethyl-3-{4-[4-oxo-3-(phenylamino)-4,5,6,7-tetrahydro-1H-indol-2-yl]pyridin-2-yl}thiourea

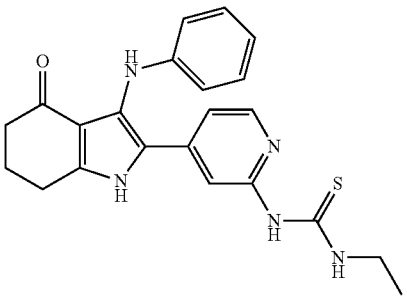

Using Method G4: To a solution of Example 139 (64 mg, 201 μmol) in pyridine (1 mL) was added ethylisothiocyanate (5 μL, 402 μmol) and stirred at RT for 16 h. Additional ethylisothiocyanate (175 μL, 201 μmol) was added and heated at 50° C. for 24 h. Again additional ethylisothiocyanate (175 μL, 201 μmol) was added and heated at 50° C. for 40 h. Concentrated and purified by preparative HPLC (basic method) to give the desired product (41 mg, 48%).

1H-NMR (400 MHz, DMSO-d6), Shift [ppm]=1.17 (3H), 1.99-2.14 (2H), 2.28-2.38 (2H), 2.85 (2H), 3.52-3.64 (2H), 6.53-6.67 (3H), 7.02 (2H), 7.11 (1H), 7.18 (1H), 7.38 (1H), 8.06 (1H), 10.42 (1H), 11.64 (1H), 11.81 (1H).

Example 394 Preparation of 1-{4-[4-oxo-3-(phenylamino)-4,5,6,7-tetrahydro-1H-indol-2-yl]pyridin-2-yl}-3-(2,2,2-trifluoroethyl)thiourea

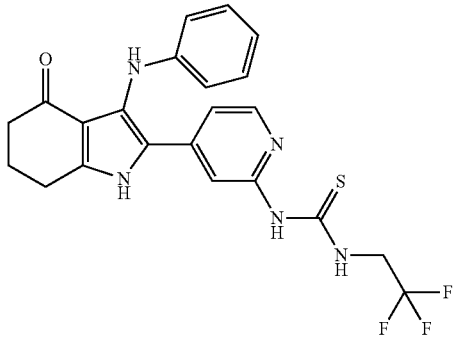

Using Method G4: To a solution of Example 139 (50 mg, 157 µmol) in pyridine (1 mL) was added 1,1,1-trifluoro-2-isothiocyanatoethane (44 mg, 314 µmol) and stirred at RT for 16 h. Concentrated and purified by preparative HPLC (basic method) to give the desired product (40 mg, 55%).

1H-NMR (400 MHz, DMSO-d6), Shift [ppm]=2.00-2.08 (2H), 2.29-2.37 (2H), 2.85 (2H), 4.52-4.74 (2H), 6.50-6.67 (3H), 6.97-7.07 (2H), 7.18 (1H), 7.25 (1H), 7.42 (1H), 8.10 (1H), 10.97 (1H), 11.86 (1H), 12.22 (1H).

Example 395 Preparation of 1-cyclopropyl-3-{4-[4-oxo-3-(phenylamino)-4,5,6,7-tetrahydro-1H-indol-2-yl]pyridin-2-yl}thiourea

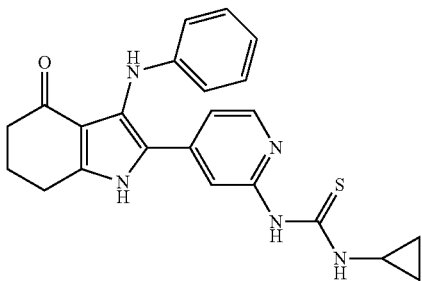

Using Method G4: To a solution of Example 139 (67 mg, 210 µmol) in pyridine (1 mL) was added cyclopropylisothiocyanate (42 mg, 421 µmol) and stirred at RT for 16 h. Additional cyclopropylisothiocyanate (21 mg, 210 µmol) was added and heated at 50° C. for 24 h. Again additional cyclopropylisothiocyanate (21 mg, 210 µmol) was added and heated at 50° C. for 40 h. Concentrated and purified by preparative HPLC (basic method) to give the desired product (46 mg, 50%).

1H-NMR (400 MHz, DMSO-d6), Shift [ppm]=0.52-0.66 (2H), 0.75-0.83 (2H), 1.97-2.10 (2H), 2.29-2.37 (2H), 2.84 (2H), 3.09 (1H), 6.56 (2H), 6.62 (1H), 7.02 (2H), 7.10 (1H), 7.18 (1H), 7.37 (1H), 8.03 (1H), 10.49 (1H), 11.71 (1H), 11.80 (1H).

Example 396 Preparation of 1-tert-butyl-3-{4-[4-oxo-3-(phenylamino)-4,5,6,7-tetrahydro-1H-indol-2-yl]pyridin-2-yl}thiourea

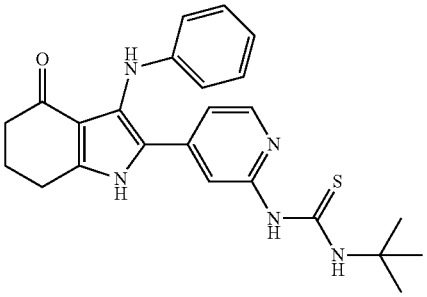

Using Method G4: To a solution of Example 139 (66 mg, 207 µmol) in pyridine (1 mL) was added tert-butylisothiocyanate (53 µL, 45 µmol) and stirred at RT for 16 h. Additional tert-butylisothiocyanate (26 µL, 207 µmol) was added and heated at 50° C. for 24 h. Again additional cyclopropylisothiocyanate (53 µL, 45 µmol) was added and heated at 100° C. for 24 h. Concentrated and purified by preparative HPLC (basic method) to give the desired product (9 mg, 10%).

1H-NMR (400 MHz, DMSO-d6), Shift [ppm]=1.51 (9H), 1.99-2.11 (2H), 2.30-2.37 (2H), 2.84 (2H), 6.56 (2H), 6.62 (1H), 7.02 (2H), 7.09 (1H), 7.17 (1H), 7.36 (1H), 8.03 (1H), 10.09 (1H), 11.94 (1H).

Example 397 Preparation of 1-cyclopentyl-3-{4-[4-oxo-3-(phenylamino)-4,5,6,7-tetrahydro-1H-indol-2-yl]pyridin-2-yl}thiourea

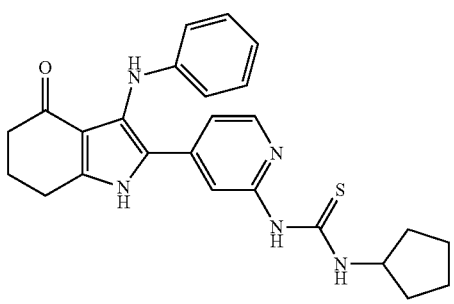 [SMILES: O=C1CCCc2[nH]c(-c3ccnc(NC(=S)NC4CCCC4)c3)c(Nc3ccccc3)c21]

Using Method G4: To a solution of Example 139 (69 mg, 217 µmol) in pyridine (1 mL) was added cyclopentyl isothiocyanate (54 µL, 433 µmol) and stirred at RT for 16 h. Additional cyclopentyl isothiocyanate (27 µL, 217 µmol) was added and heated at 50° C. for 24 h. Again additional cyclopentyl isothiocyanate (27 µL, 217 µmol) was added and heated at 100° C. for 24 h. Concentrated and purified by preparative HPLC (basic method) to give the desired product (42 mg, 43%).

1H-NMR (400 MHz, DMSO-d6), Shift [ppm]=1.46-2.13 (10H), 2.28-2.38 (2H), 2.85 (2H), 4.51 (1H), 6.54-6.59 (2H), 6.62 (1H), 6.97-7.06 (2H), 7.10 (1H), 7.17 (1H), 7.37 (1H), 8.05 (1H), 10.38 (1H), 11.74-11.88 (1H).

Example 398 Preparation of 1-(cyclopropylmethyl)-3-{4-[4-oxo-3-(phenylamino)-4,5,6,7-tetrahydro-1H-indol-2-yl]pyridin-2-yl}thiourea

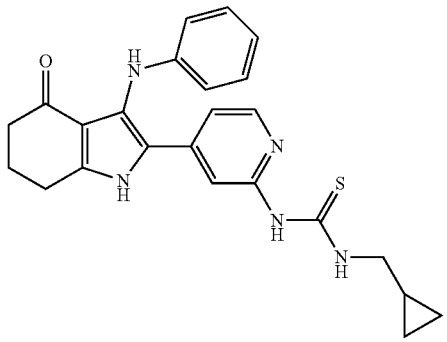 [SMILES: O=C1CCCc2[nH]c(-c3ccnc(NC(=S)NCC4CC4)c3)c(Nc3ccccc3)c21]

Using Method G4: To a solution of Example 139 (60 mg, 188 μmol) in pyridine (1 mL) was added cyclopropylmethylisothiocyanate (43 mg, 377 μmol) and stirred at RT for 16 h. Additional cyclopropylmethylisothiocyanate (22 mg, 188 μmol) was added and heated at 50° C. for 24 h. Concentrated and purified by preparative HPLC (basic method) to give the desired product (30 mg, 37%).

1H-NMR (400 MHz, DMSO-d6), Shift [ppm]=0.19-0.32 (2H), 0.42-0.52 (2H), 1.01-1.19 (1H), 1.99-2.10 (2H), 2.28-2.37 (2H), 2.85 (2H), 3.45 (2H), 6.53-6.66 (3H), 7.03 (2H), 7.12 (1H), 7.17-7.22 (1H), 7.39 (1H), 8.07 (1H), 10.46 (1H), 11.77 (2H).

Example 399 Preparation of 1-{4-[4-oxo-3-(phenylamino)-4,5,6,7-tetrahydro-1H-indol-2-yl]pyridin-2-yl}-3-propylthiourea

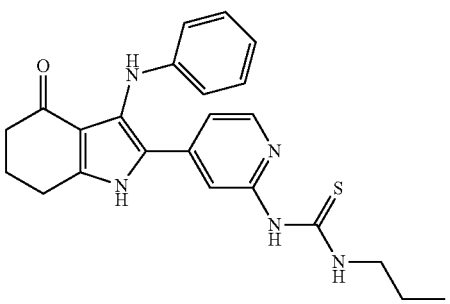 [SMILES: CCCNC(=S)Nc1cc(-c2[nH]c3c(c2Nc2ccccc2)C(=O)CCC3)ccn1]

Using Method G4: To a solution of Example 139 (67 mg, 210 μmol) in pyridine (1 mL) was added propylisothiocyanate (43 mg, 421 μmol) and stirred at RT for 16 h. Additional propylisothiocyanate (21 mg, 210 μmol) was added and heated at 50° C. for 24 h. Again additional propylisothiocyanate (21 mg, 210 μmol) was added and heated at 50° C. for 24 h. Concentrated and purified by preparative HPLC (basic method) to give the desired product (14 mg, 15%).

1H-NMR (400 MHz, DMSO-d6), Shift [ppm]=0.91 (3H), 1.59 (2H), 1.96-2.09 (2H), 2.30-2.37 (2H), 2.85 (2H), 3.47-3.57 (2H), 6.50-6.67 (3H), 6.97-7.07 (2H), 7.11 (1H), 7.18 (1H), 7.38 (1H), 8.06 (1H), 10.44 (1H), 11.73 (1H), 11.81 (1H).

Example 400 Preparation of 2-[2-(difluoromethyl)pyridin-4-yl]-6,6-dimethyl-3-(phenylamino)-1,5,6,7-tetrahydro-4H-indol-4-one

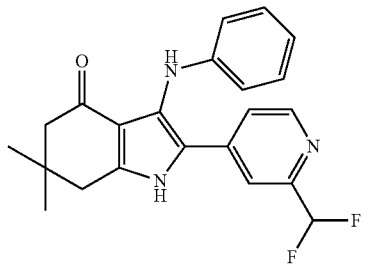 [SMILES: CC1(C)CC(=O)c2c([nH]c(-c3ccnc(C(F)F)c3)c2Nc2ccccc2)C1]

Synthesis of Example 400

Intermediate 1-11-13

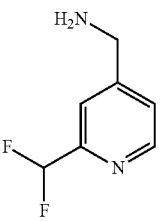 [SMILES: NCc1ccnc(C(F)F)c1]

To a mixture of 2-(difluoromethyl)pyridine-4-carbonitrile (1 g, 6.5 mmol) in EtOH (21 mL) was added HCl (37%, 2.4 mL) and 5% Pd/C (428 mg). Reaction flushed with H₂ and stirred at RT under an H₂ atmosphere (10 bar) for 15 h. The reaction was filtered and concentrated to give 1-[2-(difluoromethyl)pyridin-4-yl]methanamine as the hydrochloride salt (1.17 g, 93%) which was used without further purification. To a suspension of this salt (1.17 g, 6 mmol) in EtOH (50 mL) was Amberlyst 21 (7 g) and shaken at RT for 1 h. The reaction was filtered and concentrated to give the free base, Intermediate 1-11-13 1-[2-(difluoromethyl)pyridin-4-yl]methanamine (830 mg, 87%) which was used without further purification.

Intermediate 1-2-61

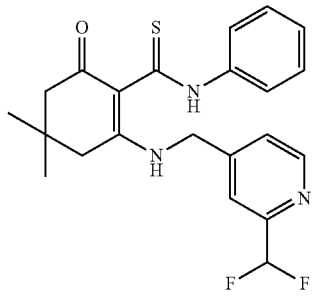 [SMILES: CC1(C)CC(=O)C(C(=S)Nc2ccccc2)=C(NCc2ccnc(C(F)F)c2)C1]

A solution of Intermediate 1-1-1 (857 mg, 3.1 mmol) and Intermediate 1-11-13 1-[2-(difluoromethyl)pyridin-4-yl]methanamine (410 mg, 2.6 mmol) in EtOH:EtOAc (28 mL)

was heated at reflux conditions for 72 h under Dean-Stark conditions with 4 Å molecular sieves. Concentrated and purified by silica chromatography gave the Intermediate 1-2-61 (177 mg, 8%) contaminated with an impurity and was used directly in the next step without further purification.

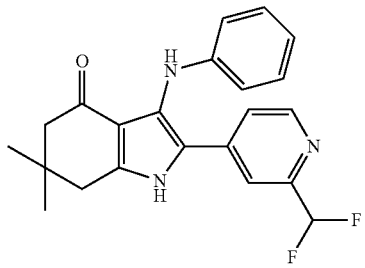 [SMILES: CC1(C)CC(=O)c2c([nH]c(-c3ccnc(C(F)F)c3)c2Nc2ccccc2)C1]

Using method F1 Intermediate 1-2-61 (175 mg, 421 µmol) gave the desired product (25 mg, 15%) after silica chromatography.

1H-NMR (400 MHz, DMSO-d6), Shift [ppm]=1.07 (6H), 2.25 (2H), 2.76 (2H), 6.55-6.61 (2H), 6.64 (1H), 6.80 (1H), 7.05 (2H), 7.52 (1H), 7.57 (1H), 7.78-7.84 (1H), 8.46 (1H), 12.01 (1H).

Example 401 Preparation of 2-[2-(difluoromethyl)pyridin-4-yl]-3-(phenylamino)-1,5,6,7-tetrahydro-4H-indol-4-one

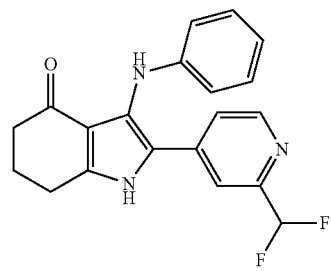 [SMILES: O=C1CCCc2[nH]c(-c3ccnc(C(F)F)c3)c(Nc3ccccc3)c21]

Synthesis of Example 401

Intermediate 1-2-62

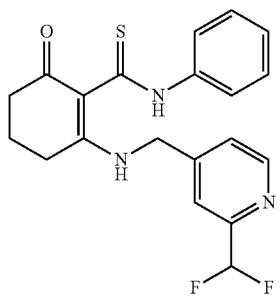 [SMILES: O=C1CCCC(NCc2ccnc(C(F)F)c2)=C1C(=S)Nc1ccccc1]

A solution of Intermediate 1-1-5 (769 mg, 2.6 mmol) and Intermediate 1-11-13 1-[2-(difluoromethyl)pyridin-4-yl]methanamine (410 mg, 2.6 mmol) in EtOH:EtOAc (28 mL)

was heated at reflux conditions for 72 h under Dean-Stark conditions with 4 Å molecular sieves. Concentrated and purified by silica chromatography gave the Intermediate 1-2-62 (178 mg, 18%).

1H-NMR (400 MHz, DMSO-d6), Shift [ppm]=1.81 (2H), 2.42-2.47 (2H), 2.73 (2H), 4.91 (2H), 6.98 (1H), 7.20-7.26 (1H), 7.39 (2H), 7.46 (2H), 7.57 (1H), 7.72 (1H), 8.70 (1H), 13.62 (1H), 14.47 (1H).

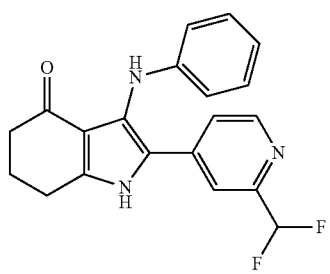 [SMILES: O=C1CCCc2[nH]c(-c3ccnc(C(F)F)c3)c(Nc3ccccc3)c21]

Using method F1 Intermediate 1-2-62 (175 mg, 452 µmol) gave the desired product (85 mg, 53%) after silica chromatography.

1H-NMR (400 MHz, DMSO-d6), Shift [ppm]=1.97-2.13 (2H), 2.30-2.41 (2H), 2.88 (2H), 6.56-6.62 (2H), 6.62-6.66 (1H), 6.80 (1H), 6.98-7.09 (2H), 7.48-7.60 (2H), 7.78-7.83 (1H), 8.46 (1H), 12.05 (1H).

Example 402 Preparation of 2-[2-(difluoromethyl)pyridin-4-yl]-3-[(3-fluorophenyl)amino]-6,6-dimethyl-1,5,6,7-tetrahydro-4H-indol-4-one

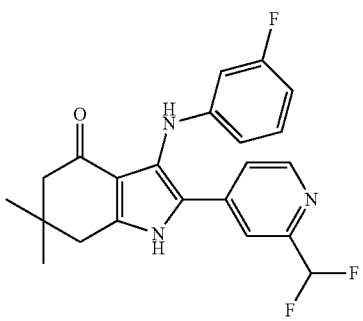

Synthesis of Example 402

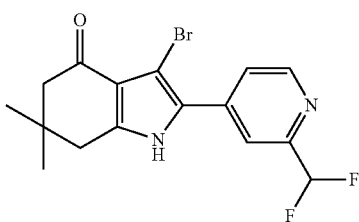 [SMILES: CC1(C)CC(=O)c2c([nH]c(-c3ccnc(C(F)F)c3)c2Br)C1]

To a solution of Intermediate 1-6-1 (50 mg, 157 µmol) and zinc difluoromethanesulfinate (93 mg, 313 µmol) in DMSO (1 mL) and water (0.4 mL) was added TFA (12 µL, 157 µmol) followed by the the slow addition of tert-butylhydroperoxide (80% aq, 10 μL) with vigorous stirring. Heated with vigorous stirring at 50° C. for 30 min. Another portion of tert-butylhydroperoxide (80% aq, 10 μL) and heated at 50° C. for 30 mins. This process with adding tert-butylhydroperoxide was repeated four more times. Reaction concentrated and purified by preparative HPLC (acid method) to give 3-bromo-2-[2-(difluoromethyl)pyridin-4-yl]-6,6-dimethyl-1,5,6,7-tetrahydro-4H-indol-4-one (24 mg, 42%).

1H-NMR (400 MHz, DMSO-d6), Shift [ppm]=1.06 (6H), 2.31 (2H), 2.77 (2H), 7.00 (1H), 7.95 (1H), 8.07 (1H), 8.73 (1H), 12.44 (1H).

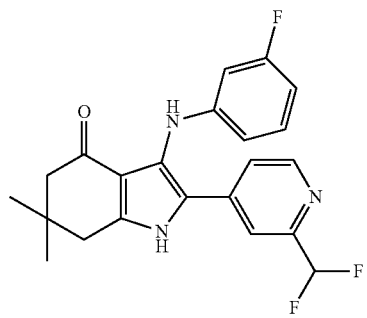 [SMILES: CC1(C)CC(=O)c2c([nH]c(-c3ccnc(C(F)F)c3)c2Nc2cccc(F)c2)C1]

To a mixture of 3-bromo-2-[2-(difluoromethyl)pyridin-4-yl]-6,6-dimethyl-1,5,6,7-tetrahydro-4H-indol-4-one (21 mg, 57 μmol), 3-fluoroaniline (7.6 mg, 68 μmol) chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct, 2 mg, 2.3 μmol), 2-(di-tert-butylphosphino)-2',4',6'-triisopropyl-3,6-dimethoxy-1,1'-biphenyl (tBuBrettPhos, 2 mg, 4.1 μmol) in THF (500 μL) under an Ar atmosphere was added 1M LHMDS in THF (228 μL, 228 μmol). The reaction mixture was heated under an Argon atmosphere at 80° C. for 16 h. The reaction was quenched by the addition of 1M HCl (1 mL) and the reaction diluted with EtOAc and washed with sat. NaHCO3 (aq). The aqueous phase was extracted with EtOAc (×2). The organics phases were combined and washed with sat. NaCl(aq), dried over Na2SO4 or MgSO4, filtered, concentrated and purified by preparative HPLC (basic method) to give the desired product (2.1 mg, 9%).

1H-NMR (400 MHz, CHLOROFORM-d), Shift [ppm] =1.14-1.24 (6H), 2.35-2.44 (2H), 2.75 (2H), 6.34 (1H), 6.41-6.69 (3H), 7.06 (1H), 7.19-7.24 (1H), 7.41 (1H), 7.44-7.51 (1H), 8.43 (1H), 8.55 (1H).

Example 403 Preparation of 2-(3-methoxypyridin-4-yl)-6,6-dimethyl-3-(phenylamino)-1,5,6,7-tetrahydro-4H-indol-4-one

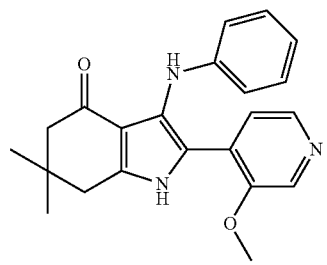

Synthesis of Example 403

Intermediate 1-10-11

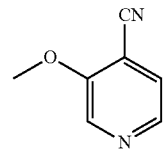

To an ice-cooled solution of 3-Chloro-4-cyanopyridine (18.26 g, 131.8 mmol) in DMF (100 mL) was slowly added portionwise NaOMe (7.12 g, 131.8 mmol). Reaction stirred for 4 h. Concentrated and purified by silica chromatography to give Intermediate 1-10-11 3-methoxyisonicotinonitrile (14.232 g, 81%) which was used without further purification.

1H-NMR (400 MHz, DMSO-d6), Shift [ppm]=4.05 (3H), 7.78 (1H), 8.39 (1H), 8.70 (1H).

Intermediate 1-11-14

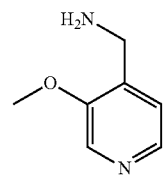

To a solution of Intermediate 1-10-11 3-methoxyisonicotinonitrile (3.84 g, 28.6 mmol) in 7M NH3 in MeOH (100 mL) was added Raney-Nickel (50% wet, 4.2 g, 71.6 mmol) and stirred at RT under an H2 atmosphere (25 bar) for 18 h. The reaction was filtered and concentrated to give Intermediate 1-11-14 1-(3-methoxypyridin-4-yl)methanamine (3.8 g, 96%) which was used without further purification.

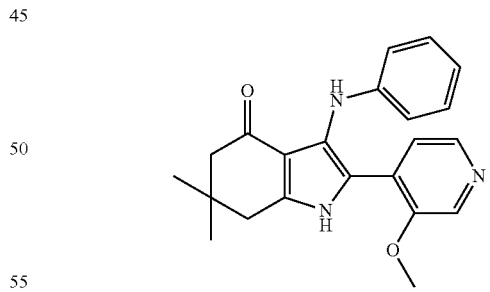

A solution of Intermediate 1-1-1 (1 g, 3.6 mmol) and Intermediate 1-11-14 1-(3-methoxypyridin-4-yl)methanamine (418 mg, 3 mmol) in EtOH:EtOAc (28 mL) was heated at reflux conditions for 72 h under Dean-Stark conditions with 4 Å molecular sieves. Concentrated and purified by silica chromatography gave the desired cyclized product (56 mg, 5%).

1H-NMR (400 MHz, DMSO-d6), Shift [ppm]=1.07 (6H), 2.23 (2H), 2.75 (2H), 3.88 (3H), 6.48-6.61 (3H), 6.98 (2H), 7.32 (1H), 7.39 (1H), 8.00 (1H), 8.33 (1H), 11.26 (1H).

Example 404 Preparation of 2-(3-ethoxypyridin-4-yl)-6,6-dimethyl-3-(phenylamino)-1,5,6,7-tetrahydro-4H-indol-4-one

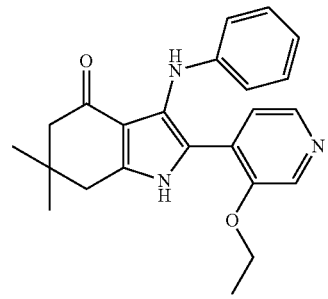 [SMILES: CCOc1cnccc1-c1[nH]c2c(c1Nc1ccccc1)C(=O)CC(C)(C)C2]

Synthesis of Example 404

Intermediate 1-2-64

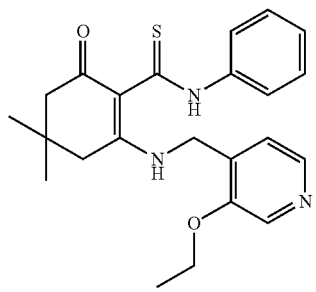 [SMILES: CCOc1cnccc1CNC1=C(C(=S)Nc2ccccc2)C(=O)CC(C)(C)C1]

A solution of Intermediate 1-1-1 (452 mg, 1.64 mmol) and (3-ethoxypyridin-4-yl)methanamine (125 mg, 821 µmol) in DMA (2.5 mL) was heated at 130° C. for 30 mins using a microwave. Concentrated and purified by preparative HPLC (basic method) to give the Intermediate 1-2-64 (48 mg, 14%).

1H-NMR (400 MHz, DMSO-d6), Shift [ppm]=0.99 (6H), 1.38 (3H), 2.38 (2H), 2.71 (2H), 4.23 (2H), 4.71 (2H), 7.18-7.25 (1H), 7.32-7.41 (3H), 7.41-7.46 (2H), 8.23 (1H), 8.39 (1H), 13.94-14.18 (1H), 14.68 (1H).

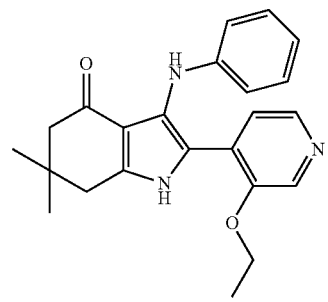 [SMILES: CCOc1cnccc1-c1[nH]c2c(c1Nc1ccccc1)C(=O)CC(C)(C)C2]

Using method F1 Intermediate 1-2-64 (46 mg, 112 µmol) gave the desired product (15 mg, 35%) after preparative HPLC (basic method).

1H-NMR (400 MHz, DMSO-d6), Shift [ppm]=1.07 (6H), 1.33 (3H), 2.24 (2H), 2.74 (2H), 4.10 (2H), 6.50 (2H), 6.53-6.58 (1H), 6.92-7.00 (2H), 7.28 (1H), 7.38 (1H), 8.02 (1H), 8.30 (1H), 11.22 (1H).

Example 405 Preparation of 6,6-dimethyl-3-(phenylamino)-2-(3-propoxypyridin-4-yl)-1,5,6,7-tetrahydro-4H-indol-4-one

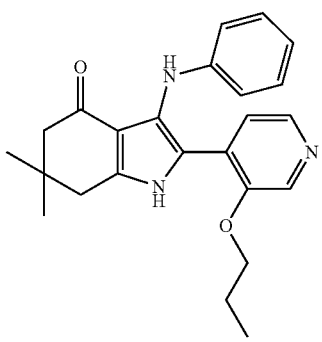 [SMILES: CCCOc1cnccc1-c1[nH]c2c(c1Nc1ccccc1)C(=O)CC(C)(C)C2]

Synthesis of Example 405

Intermediate 1-2-65

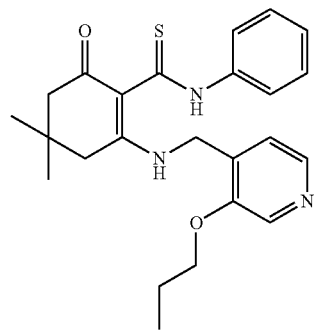 [SMILES: CCCOc1cnccc1CNC1=C(C(=S)Nc2ccccc2)C(=O)CC(C)(C)C1]

A solution of Intermediate 1-1-1 (250 mg, 908 µmol) and (3-propoxypyridin-4-yl)methanamine (181 mg, 1.09 mmol) in DMA (4 mL) was heated at 130° C. for 60 mins using a microwave. Concentrated and purified by preparative HPLC (basic method) to give the Intermediate 1-2-65 (82 mg, 20%).

1H-NMR (400 MHz, DMSO-d6), Shift [ppm]=0.94-1.06 (9H), 1.79 (2H), 2.38 (2H), 2.70 (2H), 4.13 (2H), 4.72 (2H), 7.16-7.27 (1H), 7.29-7.47 (5H), 8.23 (1H), 8.39 (1H), 14.01 (1H), 14.67 (1H).

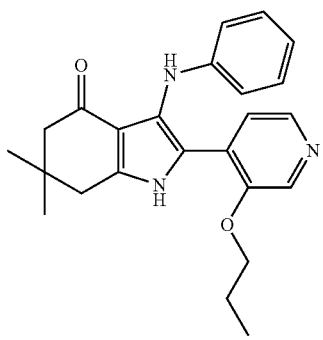 [SMILES: CCCOc1cnccc1-c1[nH]c2c(c1Nc1ccccc1)C(=O)CC(C)(C)C2]

Using method F1 Intermediate 1-2-65 (82 mg, 194 µmol) gave the desired product (19 mg, 24%) after preparative HPLC (basic method).

1H-NMR (400 MHz, DMSO-d6), Shift [ppm]=0.93 (3H), 1.06 (6H), 1.66-1.88 (2H), 2.23 (2H), 2.73 (2H), 4.01 (2H), 6.44-6.59 (3H), 6.96 (2H), 7.27 (1H), 7.34 (1H), 8.03 (1H), 8.33 (1H), 11.20 (1H).

Example 406 Preparation of 6,6-dimethyl-3-(phenylamino)-2-[3-(propan-2-yloxy)pyridin-4-yl]-1,5,6,7-tetrahydro-4H-indol-4-one

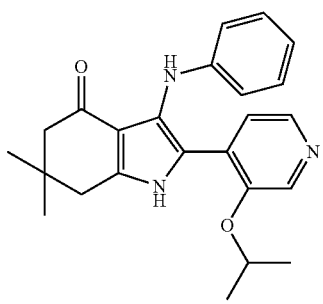 [SMILES: CC(C)Oc1cnccc1-c1[nH]c2c(c1Nc1ccccc1)C(=O)CC(C)(C)C2]

Synthesis of Example 406

Intermediate 1-2-66

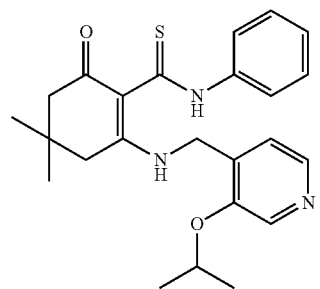 [SMILES: CC(C)Oc1cnccc1CNC1=C(C(=S)Nc2ccccc2)C(=O)CC(C)(C)C1]

A solution of Intermediate 1-1-1 (414 mg, 1.5 mmol) and [3-(propan-2-yloxy)pyridin-4-yl]methanamine (125 mg, 752 µmol) in DMA (2.5 mL) was heated at 130° C. for 30 mins using a microwave. Concentrated and purified by preparative HPLC (basic method) to give the Intermediate 1-2-66 (60 mg, 18%)

1H-NMR (400 MHz, DMSO-d6), Shift [ppm]=0.97 (6H), 1.33 (6H), 2.38 (2H), 2.65-2.71 (2H), 4.68 (2H), 4.78-4.89 (1H), 7.17-7.26 (1H), 7.31-7.47 (4H), 8.20 (1H), 8.41 (1H), 14.01 (1H), 14.68 (1H).

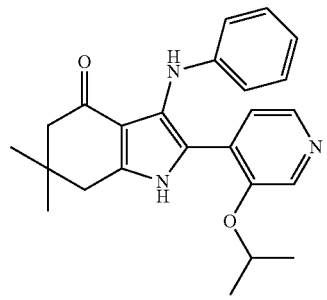 [SMILES: CC(C)Oc1cnccc1-c1[nH]c2c(c1Nc1ccccc1)C(=O)CC(C)(C)C2]

Using method F1 Intermediate 1-2-66 (60 mg, 143 µmol) gave the desired product (14 mg, 25%) after preparative HPLC (basic method).

1H-NMR (400 MHz, DMSO-d6), Shift [ppm]=1.07 (6H), 1.25 (6H), 2.23 (2H), 2.74 (2H), 4.61 (1H), 6.46-6.60 (3H), 6.91-7.00 (2H), 7.28 (1H), 7.31 (1H), 8.03 (1H), 8.33 (1H), 11.17 (1H).

Example 407 Preparation of 2-(3-tert-butoxypyridin-4-yl)-6,6-dimethyl-3-(phenylamino)-1,5,6,7-tetrahydro-4H-indol-4-one

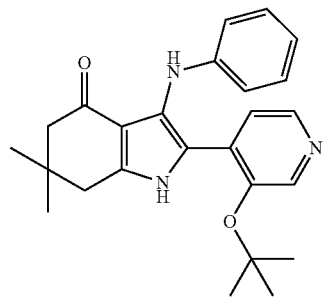 [SMILES: CC1(C)CC(=O)c2c([nH]c(-c3ccncc3OC(C)(C)C)c2Nc2ccccc2)C1]

Synthesis of Example 407

Intermediate 1-2-67

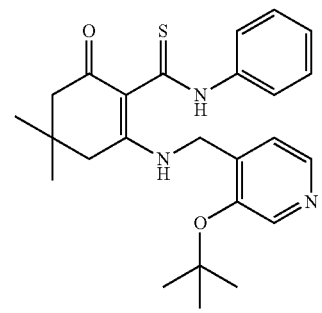 [SMILES: CC1(C)CC(=O)C(C(=S)Nc2ccccc2)=C(NCc2ccncc2OC(C)(C)C)C1]

A solution of Intermediate 1-1-1 (382 mg, 1.4 mmol) and [3-(tert-butoxy)pyridin-4-yl]methanamine (125 mg, 693

µmol) in DMA (2.5 mL) was heated at 130° C. for 30 mins using a microwave. Concentrated and purified by preparative HPLC (basic method) to give the Intermediate 1-2-67 (48 mg, 15%).

1H-NMR (400 MHz, DMSO-d6), Shift [ppm]=0.97 (6H), 1.43 (9H), 2.38 (2H), 2.67 (2H), 4.72 (2H), 7.18-7.27 (1H), 7.32-7.41 (3H), 7.41-7.48 (2H), 8.27 (1H), 8.44 (1H), 13.83-14.10 (1H), 14.65 (1H).

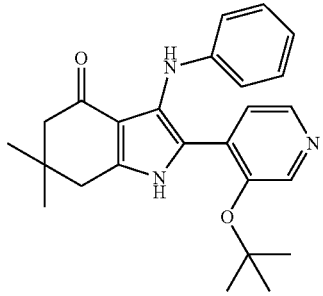 [SMILES: CC1(C)CC(=O)c2c([nH]c(-c3ccncc3OC(C)(C)C)c2Nc2ccccc2)C1]

Using method F1 Intermediate 1-2-67 (46.7 mg, 107 µmol) gave the desired product (8 mg, 19%) after preparative HPLC (basic method).

1H-NMR (400 MHz, DMSO-d6), Shift [ppm]=1.06 (6H), 1.19-1.24 (9H), 2.23 (2H), 2.74 (2H), 6.46-6.61 (3H), 6.98 (2H), 7.30-7.36 (2H), 8.15 (1H), 8.33 (1H), 11.32 (1H).

Example 408 Preparation of 2-[3-(2,2-difluoroethoxy)pyridin-4-yl]-6,6-dimethyl-3-(phenylamino)-1,5,6,7-tetrahydro-4H-indol-4-one

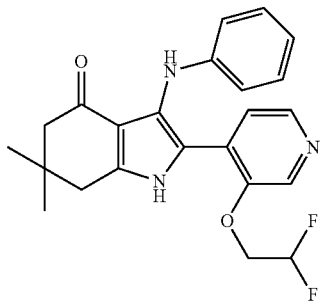 [SMILES: CC1(C)CC(=O)c2c([nH]c(-c3ccncc3OCC(F)F)c2Nc2ccccc2)C1]

Synthesis of Example 408

Intermediate 1-2-68

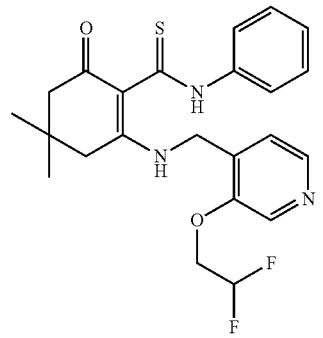 [SMILES: CC1(C)CC(=O)C(C(=S)Nc2ccccc2)=C(NCc2ccncc2OCC(F)F)C1]

A solution of Intermediate 1-1-1 (250 mg, 908 µmol) and [3-(2,2-difluoroethoxy)pyridin-4-yl]methanamine (205 mg, 1.09 mmol) in DMA (4 mL) was heated at 130° C. for 60 mins using a microwave. Concentrated and purified by preparative HPLC (basic method) to give the Intermediate 1-2-68 (96.6 mg, 23%)

1H-NMR (400 MHz, DMSO-d6), Shift [ppm]=0.98 (6H), 2.38 (2H), 2.67 (2H), 4.56 (2H), 4.75 (2H), 6.44 (1H), 7.19-7.27 (1H), 7.32-7.41 (3H), 7.41-7.48 (2H), 8.31 (1H), 8.48 (1H), 13.96 (1H), 14.63 (1H).

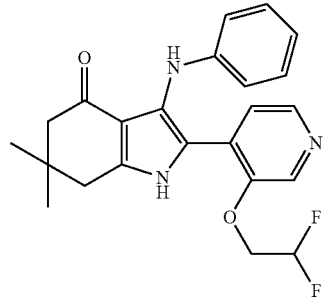 [SMILES: CC1(C)CC(=O)c2c([nH]c(-c3ccncc3OCC(F)F)c2Nc2ccccc2)C1]

Using method F1 Intermediate 1-2-68 (96.6 mg, 217 µmol) gave the desired product (20 mg, 21%) after preparative HPLC (basic method).

1H-NMR (400 MHz, DMSO-d6), Shift [ppm]=1.00-1.15 (6H), 2.24 (2H), 2.74 (2H), 4.33 (2H), 6.32 (1H), 6.47-6.59 (3H), 6.96 (2H), 7.31 (1H), 7.41 (1H), 8.11 (1H), 8.37 (1H), 11.25 (1H).

Example 409 Preparation of 2-[3-(2-hydroxyethoxy)pyridin-4-yl]-6,6-dimethyl-3-(phenylamino)-1,5,6,7-tetrahydro-4H-indol-4-one

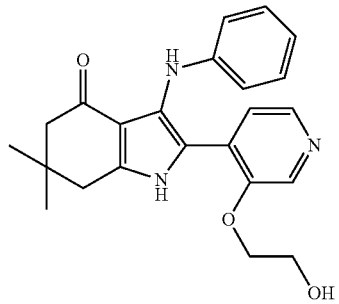 [SMILES: CC1(C)CC(=O)c2c([nH]c(-c3ccncc3OCCO)c2Nc2ccccc2)C1]

Synthesis of Example 409

Intermediate 1-2-68

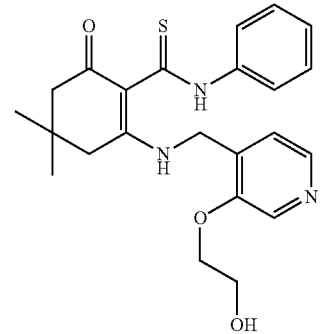 [SMILES: CC1(C)CC(=O)C(C(=S)Nc2ccccc2)=C(NCc2ccncc2OCCO)C1]

A solution of Intermediate 1-1-1 (250 mg, 908 µmol) and 2-{[4-(aminomethyl)pyridin-3-yl]oxy}ethanol (305 mg, 1.82 mmol) in DMA (3 mL) was heated at 130° C. for 120 mins using a microwave. Concentrated and purified by preparative HPLC (basic method) to give the Intermediate 1-2-68 (85 mg, 22%)

1H-NMR (400 MHz, DMSO-d6), Shift [ppm]=0.99 (6H), 2.39 (2H), 2.70 (2H), 3.77 (2H), 4.19 (2H), 4.77 (2H), 4.92 (1H), 7.19-7.25 (1H), 7.32 (1H), 7.34-7.41 (2H), 7.42-7.48 (2H), 8.24 (1H), 8.40 (1H), 14.02 (1H), 14.69 (1H).

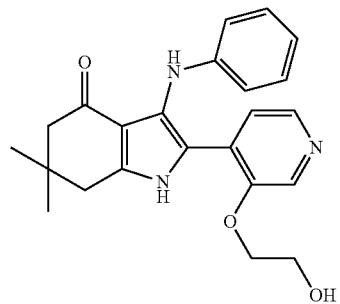 [SMILES: CC1(C)CC(=O)c2c([nH]c(-c3ccncc3OCCO)c2Nc2ccccc2)C1]

Using method F1 Intermediate 1-2-68 (82 mg, 193 µmol) gave the desired product (54 mg, 68%) after silica chromatography.

1H-NMR (400 MHz, DMSO-d6), Shift [ppm]=1.06 (6H), 2.24 (2H), 2.72 (2H), 3.84 (2H), 4.17-4.31 (2H), 5.60 (1H), 6.46-6.63 (3H), 6.99 (2H), 7.33 (1H), 7.42 (1H), 8.00 (1H), 8.35-8.46 (1H), 11.47 (1H).

Example 410 Preparation of 2-[3-(2-methoxyethoxy)pyridin-4-yl]-6,6-dimethyl-3-(phenylamino)-1,5,6,7-tetrahydro-4H-indol-4-one

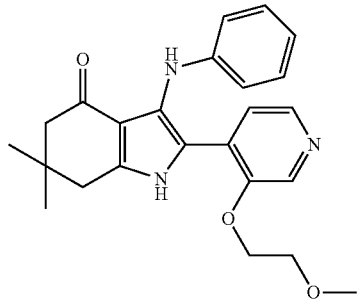

Synthesis of Example 410

Intermediate 1-2-69

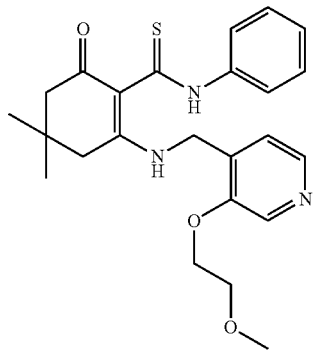 [SMILES: COCCOc1cnccc1CNC1=C(C(=S)Nc2ccccc2)C(=O)CC(C)(C)C1]

A solution of Intermediate 1-1-1 (378 mg, 1.37 µmol) and [3-(2-methoxyethoxy)pyridin-4-yl]methanamine (125 mg, 686 µmol) in DMA (4 mL) was heated at 130° C. for 30 mins using a microwave. Concentrated and purified by preparative HPLC (basic method) to give the Intermediate 1-2-69 (47 mg, 15%)

1H-NMR (400 MHz, DMSO-d6), Shift [ppm]=0.96-1.03 (6H), 2.38 (2H), 2.67-2.71 (2H), 3.32 (3H), 3.68-3.75 (2H), 4.24-4.35 (2H), 4.72 (2H), 7.18-7.26 (1H), 7.29-7.41 (3H), 7.41-7.48 (2H), 8.25 (1H), 8.42 (1H), 13.99 (1H), 14.67 (1H)

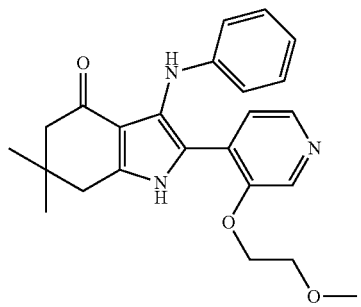

Using method F1 Intermediate 1-2-69 (40 mg, 91 µmol) gave the desired product (15 mg, 37%) after preparative HPLC (Column: XBridge C18 5µ 100×30 mm; Solvent A: Water+0.2 Vol-% NH4OH (32%), Solvent B: MeOH; Gradient: 0.00-0.50 min 50% B (25→70 mL/min), 0.51-5.50 min 50-90% B (70 mL/min)).

1H-NMR (400 MHz, DMSO-d6), Shift [ppm]=1.07 (6H), 2.24 (2H), 2.74 (2H), 3.39 (3H) 3.70-3.87 (2H), 4.20-4.41 (3H), 6.45-6.65 (3H), 6.99 (2H), 7.31-7.36 (1H), 7.39 (1H), 8.03 (1H), 8.39 (1H), 11.12 (1H)

Example 411 Preparation of 2-[3-(cyclopropylmethoxy)pyridin-4-yl]-6,6-dimethyl-3-(phenylamino)-1,5,6,7-tetrahydro-4H-indol-4-one

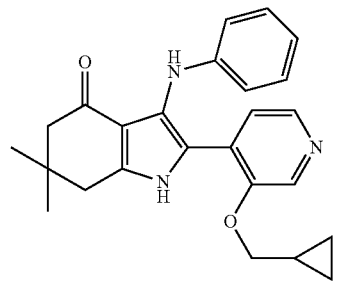 [SMILES: CC1(C)CC(=O)c2c([nH]c(-c3ccncc3OCC3CC3)c2Nc2ccccc2)C1]

Synthesis of Example 411

Intermediate 1-2-70

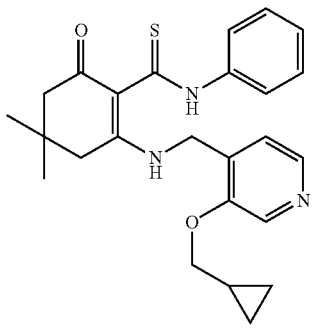 [SMILES: CC1(C)CC(=O)C(C(=S)Nc2ccccc2)=C(NCc2ccncc2OCC2CC2)C1]

A solution of Intermediate 1-1-1 (386 mg, 1.4 mmol) and [3-(cyclopropylmethoxy)pyridin-4-yl]methanamine (125 mg, 701 µmol) in DMA (3 mL) was heated at 130° C. for 30 mins using a microwave. Concentrated and purified by preparative HPLC (basic method) to give the Intermediate 1-2-70 (70 mg, 22%)

1H-NMR (400 MHz, DMSO-d6), Shift [ppm]=0.29-0.44 (2H), 0.51-0.62 (2H), 0.99 (6H), 1.20-1.37 (1H), 2.39 (2H), 2.72 (2H), 4.03 (2H), 4.74 (2H), 7.17-7.28 (1H), 7.29-7.49 (4H), 8.23 (1H), 8.37 (1H), 14.01 (1H), 14.68 (1H).

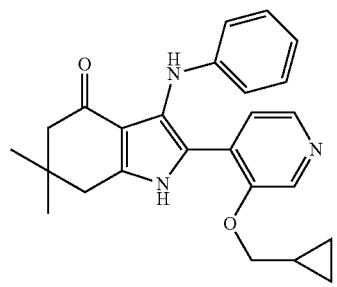 [SMILES: CC1(C)CC(=O)c2c([nH]c(-c3ccncc3OCC3CC3)c2Nc2ccccc2)C1]

Using method F1 Intermediate 1-2-70 (63 mg, 15 µmol) gave the desired product (17 mg, 29%) after preparative HPLC (basic method).

1H-NMR (400 MHz, DMSO-d6), Shift [ppm]=0.29-0.43 (2H), 0.51-0.64 (2H), 1.07 (6H), 1.19-1.34 (1H), 2.24 (2H), 2.74 (2H), 3.94 (2H), 6.48-6.60 (3H), 6.93-7.02 (2H), 7.28 (1H), 7.34 (1H), 8.03 (1H), 8.32 (1H), 11.21 (1H).

Example 412 Preparation of 6,6-dimethyl-3-(phenylamino)-2-[3-(2,2,2-trifluoroethoxy)pyridin-4-yl]-1,5,6,7-tetrahydro-4H-indol-4-one

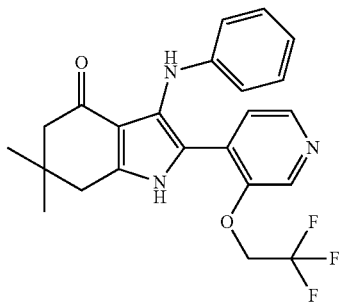 [SMILES: CC1(C)CC(=O)c2c([nH]c(-c3ccncc3OCC(F)(F)F)c2Nc2ccccc2)C1]

Synthesis of Example 412

Intermediate 1-2-71

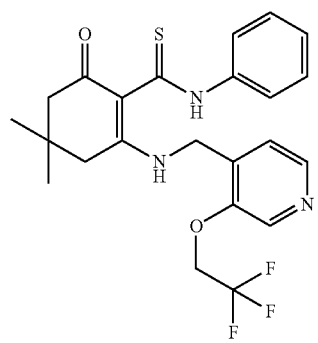 [SMILES: CC1(C)CC(=O)C(C(=S)Nc2ccccc2)=C(NCc2ccncc2OCC(F)(F)F)C1]

A solution of Intermediate 1-1-1 (334 mg, 1.2 mmol) and [3-(2,2,2-trifluoroethoxy)pyridin-4-yl]methanamine (125 mg, 606 µmol) in DMA (3 mL) was heated at 130° C. for 30 mins using a microwave. Concentrated and purified by preparative HPLC (basic method) to give the desired product (68 mg, 23%)

1H-NMR (400 MHz, DMSO-d6), Shift [ppm]=0.97 (6H), 2.38 (2H), 2.66 (2H), 4.76 (2H), 4.93-5.10 (2H), 7.17-7.28 (1H), 7.33-7.42 (3H), 7.42-7.49 (2H), 8.35 (1H), 8.52 (1H), 13.91 (1H), 14.59 (1H).

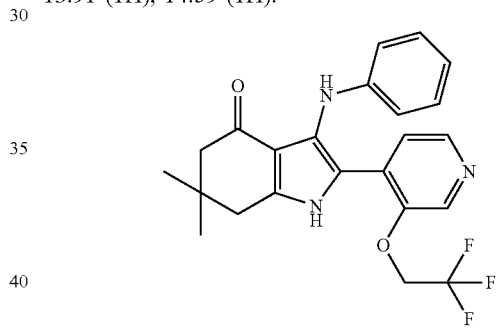

Using method F1 intermediate (59.4 mg, 128 µmol) gave the desired product (13 mg, 24%) after preparative HPLC (basic method).

1H-NMR (400 MHz, DMSO-d6), Shift [ppm]=1.06 (6H), 2.24 (2H), 2.72 (2H), 4.81 (2H), 6.49 (2H), 6.52-6.58 (1H), 6.92-6.99 (2H), 7.29 (1H), 7.32 (1H), 8.14 (1H), 8.46 (1H), 11.26 (1H).

Example 413 Preparation of 2-(3-methoxypyridin-4-yl)-3-(phenylamino)-1,5,6,7-tetrahydro-4H-indol-4-one

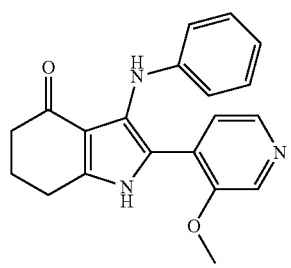 [SMILES: COc1cnccc1-c1[nH]c2c(c1Nc1ccccc1)C(=O)CCC2]

Synthesis of Example 413

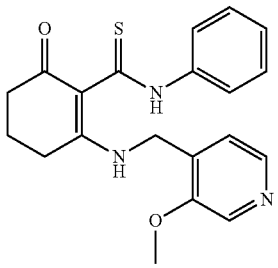 [SMILES: COc1cnccc1CNC1=C(C(=S)Nc2ccccc2)C(=O)CCC1]

A solution of Intermediate 1-1-5 (1 g, 4 mmol) and intermediate (466 mg, 3.4 mmol) in EtOH:EtOAc (40 mL) was heated at reflux conditions for 72 h under Dean-Stark conditions with 4 Å molecular sieves. Concentrated and purified by silica chromatography to give the Intermediate 1-2-71 (186 mg, 15%).

1H-NMR (400 MHz, DMSO-d6), Shift [ppm]=1.69-1.87 (2H), 2.45 (2H), 2.78 (2H), 3.94 (3H), 4.70 (2H), 7.19-7.28 (1H), 7.32-7.41 (3H), 7.41-7.46 (2H), 8.25 (1H), 8.40 (1H), 13.70 (1H), 14.58 (1H).

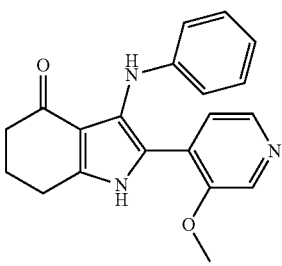 [SMILES: COc1cnccc1-c1[nH]c2c(c1Nc1ccccc1)C(=O)CCC2]

Using method F1 Intermediate 1-2-71 (185 mg, 503 µmol) gave the desired product (58 mg, 35%) after silica chromatography.

1H-NMR (500 MHz, DMSO-d6), Shift [ppm]=2.00-2.09 (2H), 2.33 (2H), 2.86 (2H), 3.85-3.90 (3H), 6.52 (2H), 6.54-6.61 (1H), 6.97 (2H), 7.29 (1H), 7.40 (1H), 7.99 (1H), 8.32 (1H), 11.28 (1H).

Example 414 Preparation of 3-(biphenyl-4-ylamino)-6,6-dimethyl-2-(pyridin-4-yl)-1,5,6,7-tetrahydro-4H-indol-4-one

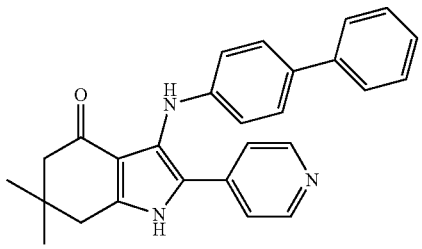 [SMILES: CC1(C)CC(=O)c2c([nH]c(-c3ccncc3)c2Nc2ccc(-c3ccccc3)cc2)C1]

Synthesized according to Method F2. Intermediate 1-6-1 (100 mg) gave the desired product (33 mg, 26%) after preparative HPLC (Column: XBridge C18 5µ 100×30 mm; Solvent A: Water+0.2 Vol-% NH4OH (32%), Solvent B: Acetonitrile; Gradient: 0.00-0.50 min 44% B (25-50 mL/min), 0.51-5.50 min 44-64% B; Flow: 70 mL/min).

1H-NMR (400 MHz, DMSO-d6), Shift [ppm]=1.08 (6H), 2.24 (2H), 2.77 (2H), 6.65 (2H), 7.22 (1H), 7.30-7.43 (4H), 7.49-7.57 (4H), 7.59 (1H), 8.44 (2H), 11.90 (1H).

Example 415 Preparation of 3-[(3-benzylphenyl)amino]-6,6-dimethyl-2-(pyridin-4-yl)-1,5,6,7-tetrahydro-4H-indol-4-one

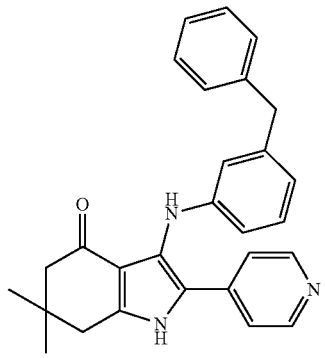

Synthesized according to Method F2. Intermediate 1-6-1 (100 mg) gave the desired product (22 mg, 15%) after preparative HPLC (acidic method) and silica chromatography.

1H-NMR (400 MHz, DMSO-d6), Shift [ppm]=1.06 (6H), 2.22 (2H), 2.74 (2H), 3.69 (2H), 6.35-6.46 (2H), 6.48 (1H), 6.95 (1H), 6.99-7.05 (2H), 7.09-7.16 (1H), 7.16-7.23 (2H), 7.42 (3H), 8.36-8.43 (2H), 11.81 (1H).

Example 416 Preparation of 3-[(2-benzylphenyl)amino]-6,6-dimethyl-2-(pyridin-4-yl)-1,5,6,7-tetrahydro-4H-indol-4-one

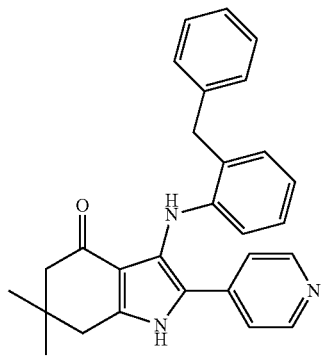 [SMILES: CC1(C)CC(=O)c2c([nH]c(-c3ccncc3)c2Nc2ccccc2Cc2ccccc2)C1]

Synthesized according to Method F2. Intermediate 1-6-1 (100 mg) gave the desired product (8 mg, 6%) after preparative HPLC (Column: XBridge C18 5µ 100×30 mm; Solvent A: Water+0.1 Vol-% HCO2H, Solvent B: Acetonitrile; Gradient: 0-0.5 min 25 mL/min auf 70 mL/min 30% B; 0.5-5.5 min 30-100% B).

1H-NMR (400 MHz, DMSO-d6), Shift [ppm]=1.07 (6H), 2.25 (2H), 2.74 (2H), 4.07 (2H), 6.28 (1H), 6.65-6.73 (1H), 6.82 (1H), 7.00 (1H), 7.08 (1H), 7.14-7.26 (3H), 7.27-7.39 (4H), 8.25 (2H), 11.83 (1H).

Example 417 Preparation of 6,6-dimethyl-3-{[3-(1-methyl-1H-pyrazol-5-yl)phenyl]amino}-2-(pyridin-4-yl)-1,5,6,7-tetrahydro-4H-indol-4-one

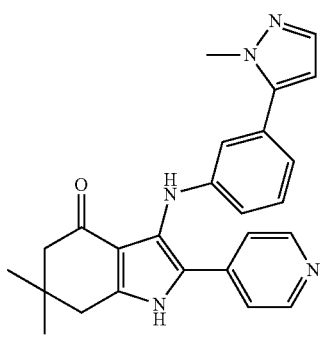 [SMILES: Cn1nccc1-c1cccc(Nc2c(-c3ccncc3)[nH]c3c2C(=O)CC(C)(C)C3)c1]

Synthesized according to Method F2. Intermediate 1-6-1 (100 mg) gave the desired product (23 mg, 17%) after preparative HPLC (basic method).

1H-NMR (400 MHz, DMSO-d6), Shift [ppm]=1.01-1.15 (6H), 2.24 (2H), 2.75 (2H), 3.60 (3H), 6.05 (1H), 6.55 (1H), 6.68-6.78 (2H), 7.18 (1H), 7.36 (1H), 7.47-7.53 (2H), 7.69 (1H), 8.42-8.49 (2H), 11.89 (1H).

Example 418 Preparation of 6,6-dimethyl-2-(pyridin-4-yl)-3-{[3-(thiophen-3-yl)phenyl]amino}-1,5,6,7-tetrahydro-4H-indol-4-one

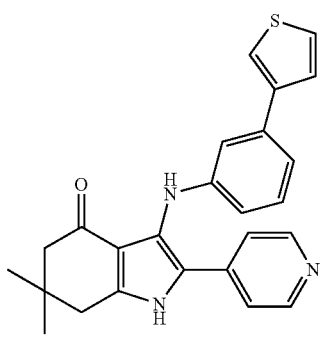 [SMILES: CC1(C)CC(=O)c2c([nH]c(-c3ccncc3)c2Nc2cccc(-c3ccsc3)c2)C1]

Synthesized according to Method F2. Intermediate 1-6-1 (100 mg) gave the desired product (40 mg, 30%) after preparative HPLC (basic method).

1H-NMR (400 MHz, DMSO-d6), Shift [ppm]=1.08 (6H), 2.25 (2H), 2.76 (2H), 6.49 (1H), 6.88 (1H), 6.96 (1H), 7.07 (1H), 7.21 (1H), 7.45-7.52 (3H), 7.54-7.63 (2H), 8.39-8.48 (2H), 11.87 (1H).

Example 419 Preparation of 3-{[3-(furan-2-yl)phenyl]amino}-6,6-dimethyl-2-(pyridin-4-yl)-1,5,6,7-tetrahydro-4H-indol-4-one

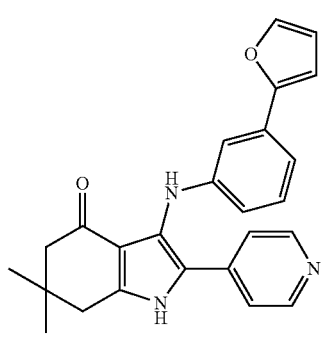 [SMILES: CC1(C)CC(=O)c2c([nH]c(-c3ccncc3)c2Nc2cccc(-c3ccco3)c2)C1]

Synthesized according to Method F2. Intermediate 1-6-1 (100 mg) gave the desired product (44 mg, 34%) after preparative HPLC (basic method).

1H-NMR (400 MHz, DMSO-d6), Shift [ppm]=1.08 (6H), 2.24 (2H), 2.77 (2H), 6.48 (1H), 6.51 (1H), 6.64 (1H), 6.91 (1H), 6.96 (1H), 7.07 (1H), 7.48-7.56 (2H), 7.59 (1H), 7.64 (1H), 8.36-8.48 (2H), 11.89 (1H).

Example 420 Preparation of 6,6-dimethyl-2-(pyridin-4-yl)-3-{[3-(thiophen-2-yl)phenyl]amino}-1,5,6,7-tetrahydro-4H-indol-4-one

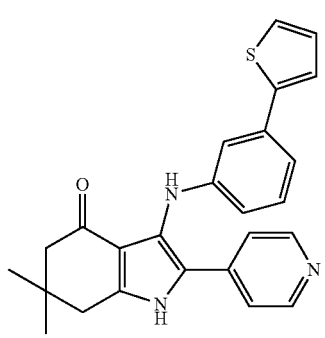 [SMILES: CC1(C)CC(=O)c2c([nH]c(-c3ccncc3)c2Nc2cccc(-c3cccs3)c2)C1]

Synthesized according to Method F2. Intermediate 1-6-1 (100 mg) gave the desired product (30 mg, 23%) after preparative HPLC (basic method).

1H-NMR (400 MHz, DMSO-d6), Shift [ppm]=1.08 (6H), 2.24 (2H), 2.77 (2H), 6.52 (1H), 6.82 (1H), 6.90-6.97 (1H), 7.02-7.12 (2H), 7.20 (1H), 7.44 (1H), 7.48-7.54 (2H), 7.65 (1H), 8.39-8.46 (2H), 11.89 (1H).

Example 421 Preparation of 6,6-dimethyl-3-[(3-phenoxyphenyl)amino]-2-(pyridin-4-yl)-1,5,6,7-tetrahydro-4H-indol-4-one

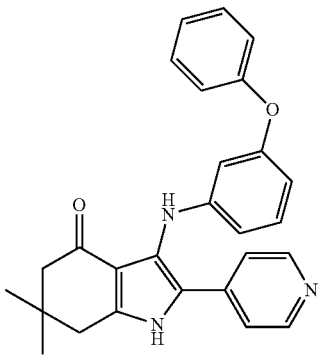 [SMILES: CC1(C)CC(=O)c2c([nH]c(-c3ccncc3)c2Nc2cccc(Oc3ccccc3)c2)C1]

Synthesized according to Method F2. Intermediate 1-6-1 (100 mg) gave the desired product (12.3 mg, 9%) after preparative HPLC (Column: XBridge C18 5µ 100×30 mm; Solvent A: Water+0.1 Vol-% HCO₂H, Solvent B: Acetonitrile; Gradient: 0.00-0.50 min 50% B (25->70 mL/min), 0.51-5.50 min 50-100% B (70 mL/min)).

1H-NMR (400 MHz, DMSO-d6), Shift [ppm]=1.04 (6H), 2.22 (2H), 2.72 (2H), 6.10 (1H), 6.78-6.87 (2H), 7.00-7.10 (2H), 7.21-7.33 (2H), 7.43-7.51 (2H), 7.62 (1H), 8.44 (2H), 11.83 (1H).

Example 422 Preparation of 6,6-dimethyl-3-[(4-phenylpyridin-2-yl)amino]-2-(pyridin-4-yl)-1,5,6,7-tetrahydro-4H-indol-4-one

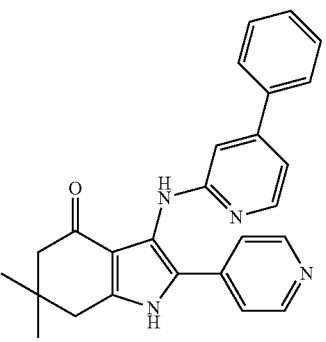 [SMILES: CC1(C)CC(=O)c2c([nH]c(-c3ccncc3)c2Nc2cc(-c3ccccc3)ccn2)C1]

Synthesized according to Method F2. Intermediate 1-6-1 (100 mg) gave the desired product (36 mg, 28%) after preparative HPLC (basic method).

1H-NMR (400 MHz, DMSO-d6), Shift [ppm]=1.08 (6H), 2.24 (2H), 2.77 (2H), 6.55 (1H), 6.90 (1H), 7.35-7.45 (5H), 7.55 (2H), 8.03 (1H), 8.18 (1H), 8.46 (2H), 11.89 (1H).

Example 423 Preparation of 6,6-dimethyl-3-[(6-phenylpyridin-2-yl)amino]-2-(pyridin-4-yl)-1,5,6,7-tetrahydro-4H-indol-4-one

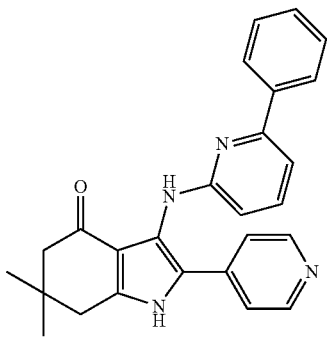 [SMILES: CC1(C)CC(=O)c2c([nH]c(-c3ccncc3)c2Nc2cccc(-c3ccccc3)n2)C1]

Synthesized according to Method F2. Intermediate 1-6-1 (100 mg) gave the desired product (19 mg, 15%) after preparative HPLC (basic method).

1H-NMR (400 MHz, DMSO-d6), Shift [ppm]=1.09 (6H), 2.24 (2H), 2.77 (2H), 6.45 (1H), 7.16 (1H), 7.27-7.40 (3H), 7.45-7.57 (3H), 7.73 (2H), 8.20 (1H), 8.39-8.48 (2H), 11.86 (1H).

Example 426 Preparation of 3-{[2-(hydroxymethyl)phenyl]amino}-6,6-dimethyl-2-(pyridin-4-yl)-1,5,6,7-tetrahydro-4H-indol-4-one

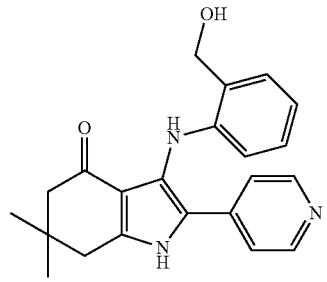 [SMILES: CC1(C)CC(=O)c2c([nH]c(-c3ccncc3)c2Nc2ccccc2CO)C1]

Synthesized according to Method F2. Intermediate 1-6-1 (100 mg) gave the desired product (18 mg, 15%) after preparative HPLC (basic method).

1H-NMR (400 MHz, DMSO-d6), Shift [ppm]=1.08 (6H), 2.25 (2H), 2.76 (2H), 4.61 (2H), 5.33 (1H), 6.30 (1H), 6.67 (1H), 6.79-6.90 (1H), 7.20 (1H), 7.27-7.35 (2H), 7.60 (1H), 8.26-8.37 (2H), 11.84 (1H).

Example 427 Preparation of 3-{[2-(2-hydroxyethyl)phenyl]amino}-6,6-dimethyl-2-(pyridin-4-yl)-1,5,6,7-tetrahydro-4H-indol-4-one

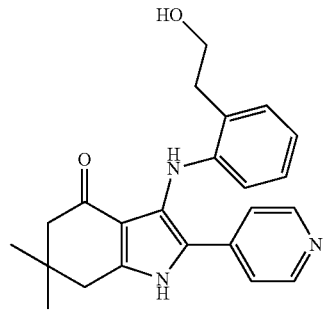 [SMILES: CC1(C)CC(=O)c2c([nH]c(-c3ccncc3)c2Nc2ccccc2CCO)C1]

Synthesized according to Method F2. Intermediate 1-6-1 (100 mg) gave the desired product (12 mg, 10%) after preparative HPLC (basic method).

1H-NMR (400 MHz, DMSO-d6), Shift [ppm]=1.04-1.11 (6H), 2.25 (2H), 2.76 (2H), 2.86 (2H), 3.69-3.81 (2H), 4.78 (1H), 6.24-6.31 (1H), 6.66 (1H), 6.75-6.83 (1H), 7.11 (1H), 7.22 (1H), 7.31-7.38 (2H), 8.30-8.38 (2H), 11.87 (1H).

Example 428 Preparation of 3-[(3-ethynylphenyl)amino]-6,6-dimethyl-2-(pyridin-4-yl)-1,5,6,7-tetrahydro-4H-indol-4-one

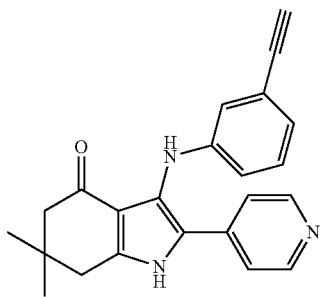 [SMILES: C#Cc1cccc(Nc2c(-c3ccncc3)[nH]c3c2C(=O)CC(C)(C)C3)c1]

Synthesized according to Method F2. Intermediate 1-6-1 (100 mg) gave the desired product (31 mg, 26%) after preparative HPLC (basic method).

1H-NMR (400 MHz, DMSO-d6), Shift [ppm]=1.08 (6H), 2.29 (2H), 2.75 (2H), 5.27 (2H), 6.58 (1H), 6.66 (1H), 6.70-6.75 (1H), 7.06 (1H), 7.86-8.03 (2H), 8.51-8.71 (2H), 12.25 (1H).

Example 429 Preparation of 2-{[6,6-dimethyl-4-oxo-2-(pyridin-4-yl)-4,5,6,7-tetrahydro-1H-indol-3-yl]amino}benzamide

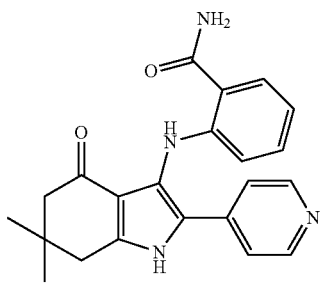 [SMILES: CC1(C)CC(=O)c2c([nH]c(-c3ccncc3)c2Nc2ccccc2C(N)=O)C1]

Synthesized according to Method F2. Intermediate 1-6-1 (100 mg) gave the desired product (6 mg, 5%) after preparative HPLC (basic method).

1H-NMR (400 MHz, DMSO-d6), Shift [ppm]=1.07 (6H), 2.22 (2H), 2.76 (2H), 6.35 (1H), 6.56-6.68 (1H), 7.01-7.12 (1H), 7.34 (1H), 7.42-7.52 (2H), 7.67 (1H), 8.00 (1H), 8.39-8.44 (2H), 9.91 (1H), 11.92 (1H).

Example 432 Preparation of 4-{[6,6-dimethyl-4-oxo-2-(pyridin-4-yl)-4,5,6,7-tetrahydro-1H-indol-3-yl]amino}benzenesulfonamide

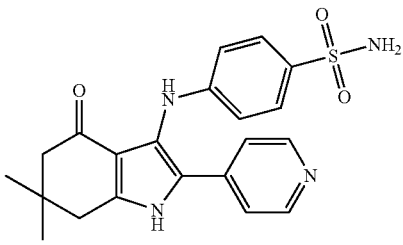 [SMILES: CC1(C)CC(=O)c2c([nH]c(-c3ccncc3)c2Nc2ccc(S(N)(=O)=O)cc2)C1]

Synthesis of Example 432

Intermediate 1-1-28

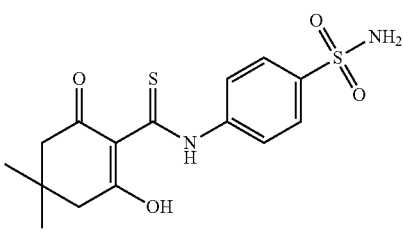 [SMILES: CC1(C)CC(=O)C(C(=S)Nc2ccc(S(N)(=O)=O)cc2)=C(O)C1]

To a ice-cooled mixture of dimedone (500 mg, 3.6 mmol) and 4-isothiocyanate-benzenesulfonamide (764 mg, 3.6 mmol) in MeCN (4 mL) was slowly added DBU (889 µL) and stirred for 16 h. Reaction poured into water (25 mL) containing conc. HCl (0.9 mL), the organics were extracted with DCM, concentrated and purified by silica chromatography to give the Intermediate 1-1-28 (83 mg, 7%).

Intermediate 1-2-74

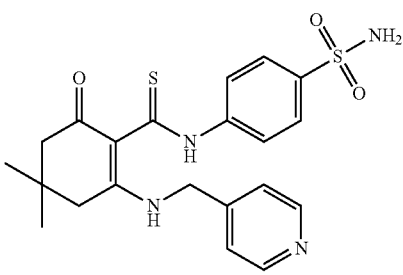 [SMILES: CC1(C)CC(=O)C(C(=S)Nc2ccc(S(N)(=O)=O)cc2)=C(NCc2ccncc2)C1]

A mixture of Intermediate 1-1-28 (74 mg, 209 µmol), 4-(aminomethyl)pyridine (45 mg, 418 µmol) in EtOH: EtOAc (1:1, 1 mL) was heated in a sealed tube at 100° C. for 72 h. Concentrated and purified by silica chromatography to give the Intermediate 1-2-74 (21.5 mg, 23%). 1H-NMR (400 MHz, DMSO-d6), Shift [ppm]=0.98 (6H), 2.40 (2H), 2.67 (2H), 4.87 (2H), 7.38 (4H), 7.69 (2H), 7.81 (2H), 8.55-8.64 (2H), 13.93 (1H), 14.87 (1H).

387

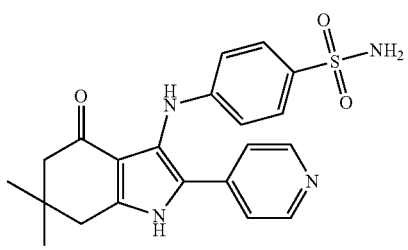 [SMILES: CC1(C)CC(=O)c2c([nH]c(-c3ccncc3)c2Nc2ccc(S(N)(=O)=O)cc2)C1]

To a solution of Intermediate 1-2-74 (20 mg, 5 µmol) in EtOH (1 mL) was added SIBX (28 mg, 5 µmol) and heated at 40° C. for 72 h. TEA (0.1 mL) added and concentrated. Purification by preparative HPLC (basic method) gave the desired product (20 mg, 18%). 1H-NMR (400 MHz, METHANOL-d4), Shift [ppm]=1.09-1.20 (6H), 2.34 (2H), 2.82 (2H), 6.60-6.81 (2H), 7.49-7.71 (4H), 8.37 (2H).

Example 433 Preparation of 4-{[6,6-dimethyl-4-oxo-2-(pyridin-4-yl)-4,5,6,7-tetrahydro-1H-indol-3-yl]amino}benzonitrile Synthesis of Example 433

Intermediate 1-1-29

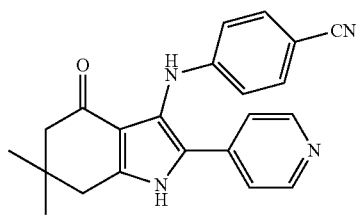 [SMILES: CC1(C)CC(=O)c2c([nH]c(-c3ccncc3)c2Nc2ccc(C#N)cc2)C1]

To a ice-cooled mixture of dimedone (500 mg, 3.6 mmol) and 4-isothiocyanate-benzolsulfonamide (571 mg, 3.6 mmol) in MeCN (4 mL) was slowly added DBU (889 µL) and stirred for 16 h. Reaction poured into water (25 mL) containing conc. HCl (0.9 mL), the organics were extracted with DCM, concentrated and purified by silica chromatography to give the Intermediate 1-1-29 (715 mg, 67%).

1H-NMR (400 MHz, DMSO-d6), Shift [ppm]=1.05 (6H), 2.51-2.69 (4H), 7.83 (2H), 7.91 (2H), 13.74 (1H).

388

Intermediate 1-2-75

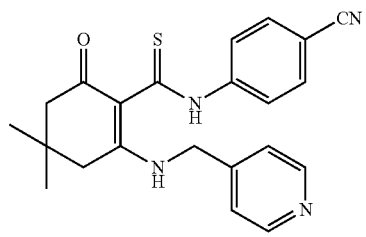

A mixture of Intermediate 1-1-29 (200 mg, 666 µmol), 4-(aminomethyl)pyridine (144 mg, 1.3 mmol) in EtOH:EtOAc (1:1, 2 mL) was heated in a sealed tube at 100° C. for 72 h. Concentrated and crystallized from EtOAc to give the Intermediate 1-2-75 (86 mg, 33%). 1H-NMR (400 MHz, DMSO-d6), Shift [ppm]=0.97 (6H), 2.36-2.43 (2H), 2.66 (2H), 4.87 (2H), 7.37 (2H), 7.74-7.81 (2H), 7.81-7.87 (2H), 8.56-8.65 (2H), 13.79 (1H), 14.92 (1H).

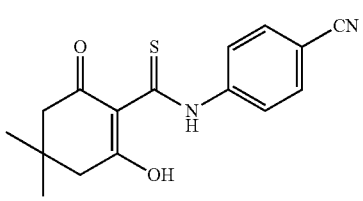 [SMILES: CC1(C)CC(=O)C(C(=S)Nc2ccc(C#N)cc2)=C(O)C1]

To a solution of Intermediate 1-2-75 (82 mg, 210 µmol) in EtOH (4 mL) was added SIBX (131 mg, 210 µmol) and heated at 40° C. for 16 h. TEA (0.1 mL) added and concentrated. Purification by preparative HPLC (basic method) gave the desired product (45 mg, 57%).

1H-NMR (400 MHz, DMSO-d6), Shift [ppm]=1.06 (6H), 2.21 (2H), 2.75 (2H), 6.59 (2H), 7.42 (2H), 7.48-7.58 (2H), 8.36 (1H), 8.42-8.52 (2H).

Example 435 Preparation of 3-{[4-(dimethylamino)phenyl]amino}-6,6-dimethyl-2-(pyridin-4-yl)-1,5,6,7-tetrahydro-4H-indol-4-one

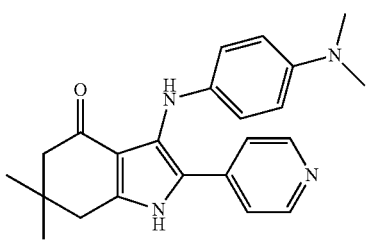

Synthesis of Example 435

Intermediate 1-1-31

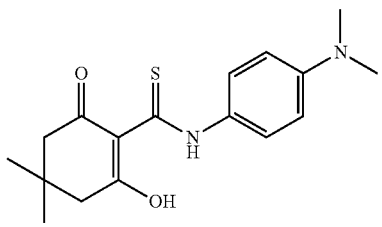

To a ice-cooled mixture of dimedone (500 mg, 3.6 mmol) and (4-dimethylamino)phenylisothiocyanate (496 mg, 3.6 mmol) in MeCN (4 mL) was slowly added DBU (889 µL) and stirred for 16 h. Reaction poured into water (25 mL) containing conc. HCl (0.9 mL) and resulting solid collected by filtration and dried in vacuo at 60° C. to give the Intermediate 1-1-31 (854 mg, 75%).

1H-NMR (400 MHz, DMSO-d6), Shift [ppm]=1.04 (6H), 2.52 (4H), 2.92 (6H), 6.64-6.81 (2H), 7.18-7.42 (2H), 13.71 (1H).

Intermediate 1-2-77

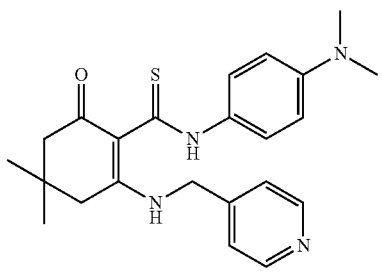

A mixture of Intermediate 1-1-31 (200 mg, 628 µmol), 4-(aminomethyl)pyridine (136 mg, 1.3 mmol) in EtOH:EtOAc (1:1, 2 mL) was heated in a sealed tube at 100° C. for 72 h. Concentrated and crystallized from EtOAc to give the Intermediate 1-2-77 (101 mg, 39%).

1H-NMR (400 MHz, DMSO-d6), Shift [ppm]=0.97 (6H), 2.37 (2H), 2.62 (2H), 2.90 (6H), 4.83 (2H), 6.63-6.80 (2H), 7.27 (2H), 7.33-7.44 (2H), 8.56-8.65 (2H), 14.10 (1H), 14.37 (1H).

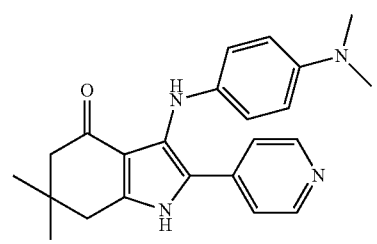

To a solution of Intermediate 1-2-77 (96 mg, 25 µmol) in EtOH (4.5 mL) was added SIBX (146 mg, 25 µmol) and heated at 40° C. for 16 h. TEA (0.1 mL) added and concentrated. Purification by preparative HPLC (basic method) followed by preparative TLC gave the desired product (10.7 mg, 12%).

1H-NMR (400 MHz, DMSO-d6), Shift [ppm]=1.07 (6H), 2.24 (2H), 2.69-2.77 (8H), 6.48-6.62 (4H), 7.11 (1H), 7.34-7.42 (2H), 8.29-8.40 (2H), 11.79 (1H).

Example 436 Preparation of 2-(3-chloropyridin-4-yl)-3-[(3-fluorophenyl)amino]-6-(trifluoromethyl)-1,5,6,7-tetrahydro-4H-indol-4-one

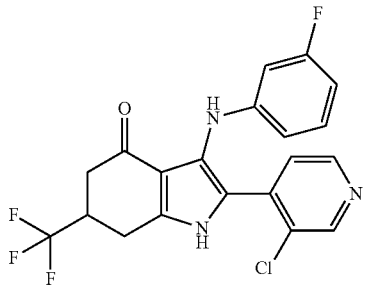 [SMILES: O=C1CC(C(F)(F)F)Cc2[nH]c(-c3ccncc3Cl)c(Nc3cccc(F)c3)c21]

Synthesis of Example 435

Intermediate 1-2-78

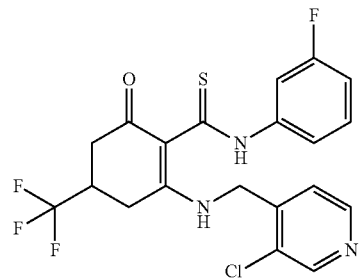 [SMILES: O=C1CC(C(F)(F)F)CC(NCc2ccncc2Cl)=C1C(=S)Nc1cccc(F)c1]

A mixture of Intermediate 1-1-24 (200 mg, 600 µmol), 1-(3-chloropyridin-4-yl)methanamine (103 mg, 720 µmol), DBU (90 µL, 600 µmol) in DMF (4 mL) was heated in a sealed tube at 90° C. for 16 h. Purified by preparative HPLC (Column: XBridge C18 5µ 100×30 mm; Solvent A: Water+0.1 Vol-% HCO₂H, Solvent B: Acetonitrile; Gradient: 0.00-8.00 min 50-68% B (70 mL/min)) gave the Intermediate 1-2-78 (35 mg, 13%).

1H-NMR (400 MHz, DMSO-d6), Shift [ppm]=2.52-2.72 (2H), 2.82 (1H), 3.07 (1H), 3.15 (1H), 4.91 (2H), 7.09 (1H), 7.28 (1H), 7.38-7.49 (1H), 7.51 (1H), 7.61 (1H), 8.58 (1H), 8.67 (1H), 12.87 (1H), 13.99 (1H).

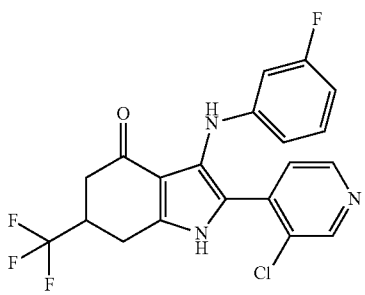 [SMILES: O=C1CC(C(F)(F)F)Cc2[nH]c(-c3ccncc3Cl)c(Nc3cccc(F)c3)c21]

Using method F1 Intermediate 1-2-78 (35 mg, 76 µmol) gave the desired product (7 mg, 22%) after preparative HPLC (acidic method).

1H-NMR (400 MHz, DMSO-d6), Shift [ppm]=2.55-2.66 (2H), 3.00 (1H), 3.11 (1H), 3.42 (1H), 6.22 (1H), 6.25-6.34 (1H), 6.37 (1H), 6.95 (1H), 7.33 (1H), 7.70 (1H), 8.44 (1H), 8.62 (1H), 11.92 (1H).

Example 437 Preparation of 2-[2-(hydroxymethyl) pyridin-4-yl]-6,6-dimethyl-3-(phenylamino)-1,5,6,7-tetrahydro-4H-indol-4-one

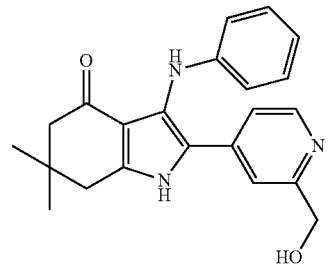 [SMILES: CC1(C)CC(=O)c2c([nH]c(-c3ccnc(CO)c3)c2Nc2ccccc2)C1]

A mixture of Intermediate 1-1-1 (500 mg, 1.8 mmol), [2-(hydroxymethyl)pyridin-4-yl]methanamine hydrochloride (317 mg, 1.8 mmol), DBU (407 µL, 2.7 mmol) in EtOH:EtOAc (1:1, 40 mL) was heated at reflux under Dean-Stark conditions with 4 Å molecular sieves for 16 h. Concentrated and purified by silica chromatography and preparative HPLC (basic method) to give the desired cyclized product (23 mg, 4%).

1H-NMR (400 MHz, DMSO-d6), Shift [ppm]=1.07 (6H), 2.23 (2H), 2.75 (2H), 4.48 (2H), 5.30 (1H), 6.51-6.67 (3H), 7.02 (2H), 7.31 (1H), 7.37 (1H), 7.65-7.71 (1H), 8.25 (1H), 11.91 (1H).

Example 438 Preparation of 6,6-dimethyl-3-(phenylamino)-2-[3-(trifluoromethyl)pyridin-4-yl]-1,5,6,7-tetrahydro-4H-indol-4-one

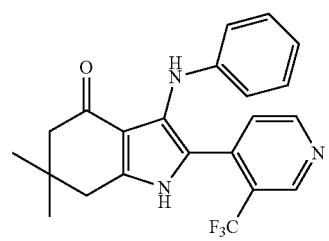 [SMILES: CC1(C)CC(=O)c2c([nH]c(-c3ccncc3C(F)(F)F)c2Nc2ccccc2)C1]

A mixture of Intermediate 1-1-1 (663 mg, 2.4 mmol), (3-trifluoromethyl)pyridin-4-yl]methanamine dihydrochloride (125 mg, 502 µmol), DBU (150 µL, 802 µmol) in EtOH:EtOAc (1:1, 30 mL) was heated at reflux under Dean-Stark conditions with 4 Å molecular sieves for 90 mins. Additional (3-trifluoromethyl)pyridin-4-yl]methanamine dihydrochloride (125 mg, 502 µmol) and DBU (150 µL, 802 µmol) were added and heated for 90 mins. This additional of (3-trifluoromethyl)pyridin-4-yl]methanamine dihydrochloride (125 mg, 502 µmol) and DBU (150 µL, 802 µmol) was repeated two more times and heated for 16 h. Concentrated and purified by silica chromatography to give the desired cyclized product (133 mg, 16%).

1H-NMR (400 MHz, DMSO-d6), Shift [ppm]=1.07 (6H), 2.24 (2H), 2.72 (2H), 6.45-6.55 (3H), 6.86-6.96 (2H), 7.20 (1H), 7.39 (1H), 8.69 (1H), 8.92 (1H), 11.30 (1H).

Example 439 Preparation of 4-[6,6-dimethyl-4-oxo-3-(phenylamino)-4,5,6,7-tetrahydro-1H-indol-2-yl] pyridine-2-sulfonamide

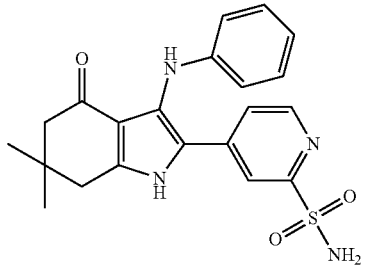 [SMILES: CC1(C)CC(=O)c2c([nH]c(-c3ccnc(S(N)(=O)=O)c3)c2Nc2ccccc2)C1]

Synthesis of Example 439

Intermediate 1-11-15

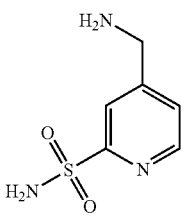

To a solution of 4-cyanopyridine-2-sulfonamide (500 mg, 2.7 mmol) in 7M NH$_3$ in MeOH (11.9 mL) was added Raney-Nickel (50% wet, 641 mg, 10.9 mmol) and stirred at RT under an H$_2$ atmosphere (30 bar) for 24 h. The reaction was filtered and concentrated to give the Intermediate 1-11-15 4-(aminomethyl)pyridine-2-sulfonamide (460 mg, 90%) which was used without further purification.

Intermediate 1-2-79

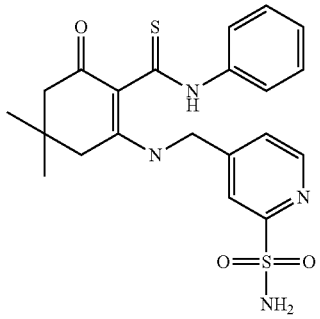 [SMILES: CC1(C)CC(=O)C(C(=S)Nc2ccccc2)=C(NCc2ccnc(S(N)(=O)=O)c2)C1]

A solution of Intermediate 1-1-1 (338 mg, 1.2 mmol) and Intermediate 1-11-15 4-(aminomethyl)pyridine-2-sulfonamide (460 mg, 2.5 mmol) in DMA (6 mL) was heated at 130° C. for 2 h using a microwave. Concentrated and purified by silica chromatography gave the Intermediate 1-2-7 (329 mg, 60%).

1H-NMR (400 MHz, DMSO-d6), Shift [ppm]=0.98 (6H), 2.40 (2H), 2.65 (2H), 4.91-5.03 (2H), 7.21-7.27 (1H), 7.35-7.43 (2H), 7.43-7.50 (2H), 7.52 (2H), 7.57-7.64 (1H), 7.94 (1H), 8.73 (1H), 14.04 (1H), 14.59 (1H).

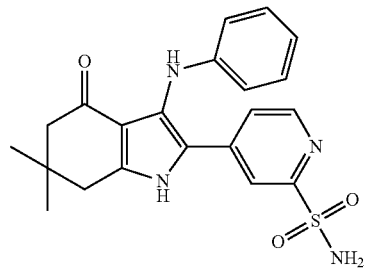 [SMILES: CC1(C)CC(=O)c2c([nH]c(-c3ccnc(S(N)(=O)=O)c3)c2Nc2ccccc2)C1]

Using method F1 Intermediate 1-2-7 (315 mg, 709 µmol) gave the desired product (87 mg, 28%) after silica chromatography.

1H-NMR (400 MHz, DMSO-d6), Shift [ppm]=1.07 (6H), 2.25 (2H), 2.76 (2H), 6.57-6.67 (3H), 6.99-7.13 (2H), 7.36 (2H), 7.54-7.57 (2H), 12.18 (1H).

Example 440 and Example 441 Separation of the Enantiomers of 3-(phenylamino)-2-(pyridin-4-yl)-6-(trifluoromethyl)-1,5,6,7-tetrahydro-4H-indol-4-one

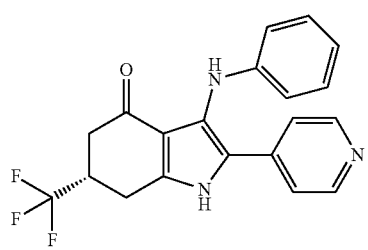

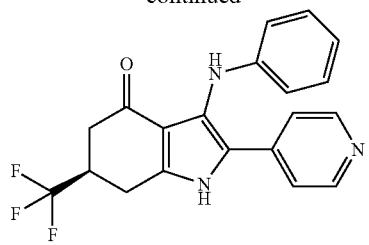

Example 20 (50 mg, 15 µmol) was purified by chiral preparative HPLC (Column: Chiralpak IC 5 µm 250×30 mm; Solvent Hexane/Ethanol/Diethylamine 95:5:0.1 (v/v/v); Flow: 50 mL/min) to give the two enantiomers Enantiomer 1 Example 440 (16 mg, 31%)
Enantiomer 2 Example 441 (18 mg, 32%)

Chiral HPLC Analysis was performed (Column: Chiralpak IC 3 µm 100×4.6 mm; Solvent Hexane/Ethanol/Diethylamine 95:5:0.1 (v/v/v); Flow: 1 mL/min).

Enantiomer 1: Rt=11.56 min (>95% e.e.)
Enantiomer 2: Rt=12.48 min (>90% e.e.)

Example 442 Preparation of 6-(fluoromethyl)-3-(phenylamino)-2-(pyridin-4-yl)-1,5,6,7-tetrahydro-4H-indol-4-one

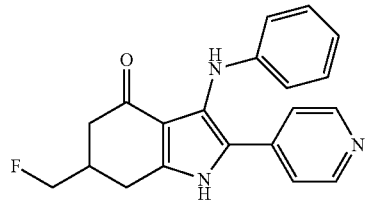 [SMILES: O=C1CC(CF)Cc2[nH]c(-c3ccncc3)c(Nc3ccccc3)c21]

Synthesis of Example 442

Intermediate 1-1-32

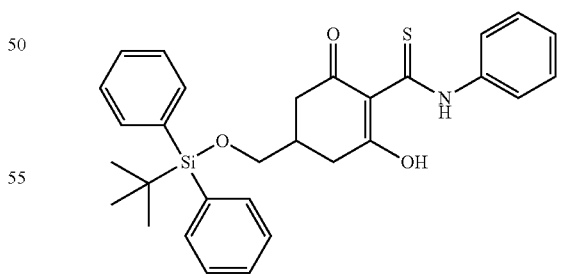

To a ice-cooled mixture of 5-({[tert-butyl(diphenyl)silyl]oxy}methyl)cyclohexane-1,3-dione (for analogous synthesis see the patent EP2617720 A1) (30 g, 78.8 mmol) and phenylisothiocyanate (10.66 g, 78.8 mmol) in MeCN (135 mL) was slowly added DBU (20 mL) and stirred for 16 h. Concentrated and purified by silica chromatography to give the Intermediate 1-1-32 (33.9 g, 83%).

395

Intermediate 1-2-80

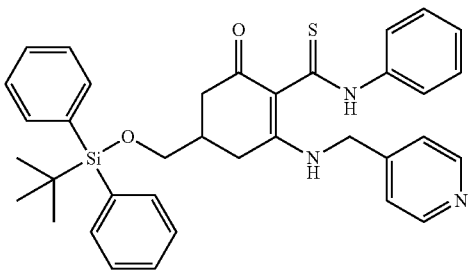 [SMILES: CC(C)(C)[Si](OCC1CC(=O)C(C(=S)Nc2ccccc2)=C(NCc2ccncc2)C1)(c1ccccc1)c1ccccc1]

A mixture of Intermediate 1-1-32 (20.1 g, 39 mmol) and 4-(aminomethyl)pyridine (8.43 g, 77.9 mmol) in DMA (110 mL) was heated at 100° C. for 2 h. Concentrated and purified by silica chromatography to give the Intermediate 1-2-80 (14.98 g, 63%).

3-anilino-6-({[tert-butyl(di phenyl)silyl]oxy}methyl)-2-(pyridin-4-yl)-1,5,6,7-tetrahydro-4H-indol-4-one

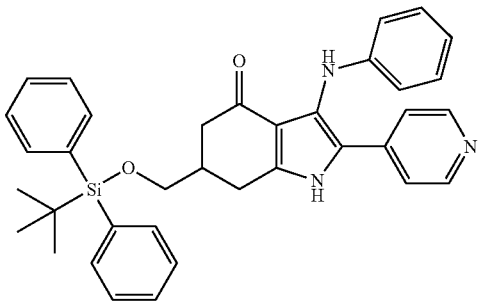 [SMILES: CC(C)(C)[Si](OCC1CC(=O)c2c([nH]c(-c3ccncc3)c2Nc2ccccc2)C1)(c1ccccc1)c1ccccc1]

To a solution of Intermediate 1-2-80 (14.97 g, 24.7 mmol) in EtOH (740 mL) was added SIBX (45%, 15.38 g, 24.7 mmol) and stirred at RT for 16 h. TEA (8 mL) added and concentrated. Purification by silica chromatography gave the 3-anilino-6-({[tert-butyl(diphenyl)silyl]oxy}methyl)-2-(pyridin-4-yl)-1,5,6,7-tetrahydro-4H-indol-4-one (11.2 g, 79%).

1H-NMR (400 MHz, DMSO-d6), Shift [ppm]=0.96-1.05 (11H), 2.23-2.42 (2H), 2.85 (1H), 3.06 (1H), 3.59-3.75 (2H), 6.56 (2H), 6.62 (1H), 7.03 (2H), 7.38-7.50 (8H), 7.57-7.66 (4H), 8.37-8.44 (2H), 11.95 (1H).

3-anilino-6-(hydroxymethyl)-2-(pyridin-4-yl)-1,5,6,7-tetrahydro-4H-indol-4-one

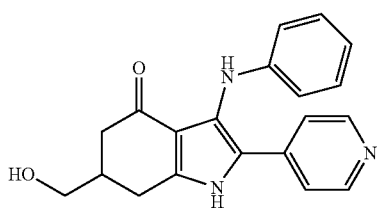 [SMILES: O=C1CC(CO)Cc2[nH]c(-c3ccncc3)c(Nc3ccccc3)c21]

396

To a solution of 3-anilino-6-({[tert-butyl(diphenyl)silyl]oxy}methyl)-2-(pyridin-4-yl)-1,5,6,7-tetrahydro-4H-indol-4-one (10 g, 17.5 mmol) in THF (250 mL) was added 1M TBAF in THF (19.24 mL, 19.24 mmol) and heated at 50° C. for 2 h. Additional solid TBAF (914 mg, 3.5 mmol) added and stirred at RT for 16 h. Reaction mixture diluted with EtOAc and washed with 2.5% NaOH(aq), sat. NaCl, dried over Na$_2$SO$_4$, filtered and concentrated. Purified by silica chromatography to give 3-anilino-6-(hydroxymethyl)-2-(pyridin-4-yl)-1,5,6,7-tetrahydro-4H-indol-4-one (4.31 g, 74%).

1H-NMR (400 MHz, DMSO-d6), Shift [ppm]=2.13-2.39 (3H), 2.62-2.76 (1H), 2.95 (1H), 3.43 (2H), 4.75 (1H), 6.52-6.71 (3H), 6.92-7.18 (2H), 7.33-7.57 (3H), 8.29-8.50 (2H), 11.90 (1H).

[3-anilino-4-oxo-2-(pyridin-4-yl)-4,5,6,7-tetrahydro-1H-indol-6-yl]methyl methanesulfonate

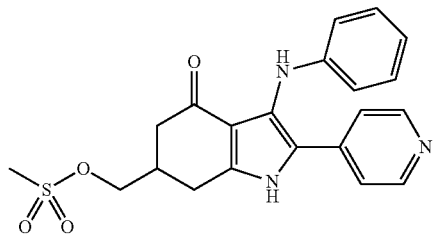 [SMILES: CS(=O)(=O)OCC1CC(=O)c2c([nH]c(-c3ccncc3)c2Nc2ccccc2)C1]

To a solution of 3-anilino-6-(hydroxymethyl)-2-(pyridin-4-yl)-1,5,6,7-tetrahydro-4H-indol-4-one (2 g, 6 mmol) in pyridine (32 mL) under Ar was added DMAP (73 mg, 0.6 mmol) followed by mesyl chloride (557 µL, 7.2 mmol) and stirred at RT for 4 h. MeOH added and concentrated. Purification by silica chromatography gave the [3-anilino-4-oxo-2-(pyridin-4-yl)-4,5,6,7-tetrahydro-1H-indol-6-yl]methyl methanesulfonate (2.16 g, 88%)

1H-NMR (400 MHz, DMSO-d6), Shift [ppm]=2.26-2.44 (2H), 2.61-2.72 (1H), 2.72-2.82 (1H), 3.04 (1H), 3.23 (3H), 4.20-4.34 (2H), 6.51-6.67 (3H), 7.04 (2H), 7.38-7.55 (3H), 8.37-8.49 (2H), 11.98 (1H).

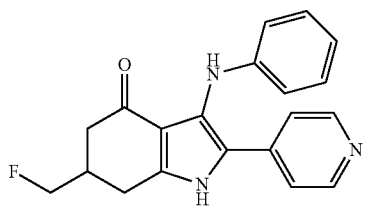 [SMILES: O=C1CC(CF)Cc2[nH]c(-c3ccncc3)c(Nc3ccccc3)c21]

To a solution of [3-anilino-4-oxo-2-(pyridin-4-yl)-4,5,6,7-tetrahydro-1H-indol-6-yl]methyl methanesulfonate (50 mg, 122 µmol) in THF (1 mL) was added 1M TBAF in THF (729 µL, 729 µmol) and heated at 80° C. for 2 h. Reaction mixture diluted with water and extracted with EtOAc. The EtOAc layers were combined and washed with 2.5% NaOH (aq), sat. NaCl, dried over Na$_2$SO$_4$, filtered and concentrated. Purified by preparative TLC to give the desired product (11 mg, 12%).

1H-NMR (400 MHz, DMSO-d6), Shift [ppm]=2.24-2.42 (2H), 2.57-2.71 (1H), 2.72-2.83 (1H), 3.01 (1H), 4.37-4.52

(1H), 4.52-4.61 (1H), 6.53-6.69 (3H), 6.98-7.15 (2H), 7.43-7.54 (3H), 8.34-8.46 (2H), 12.00 (1H).

Example 443 Preparation of 6-(chloromethyl)-3-(phenylamino)-2-(pyridin-4-yl)-1,5,6,7-tetrahydro-4H-indol-4-one

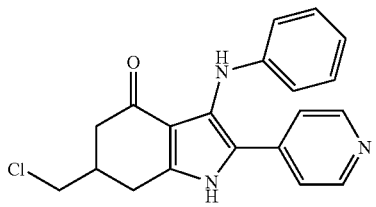 [SMILES: O=C1CC(CCl)Cc2[nH]c(-c3ccncc3)c(Nc3ccccc3)c21]

To a solution of 3-anilino-6-(hydroxymethyl)-2-(pyridin-4-yl)-1,5,6,7-tetrahydro-4H-indol-4-one (1 g, 3 mmol) in pyridine (16 mL) under Ar was added DMAP (36.6 mg, 0.3 mmol) followed by mesyl chloride (279 µL, 3.6 mmol) and stirred at RT for 19 h. MeOH added and concentrated. Purification by silica chromatography gave the desired product (91 mg, 8%).

1H-NMR (400 MHz, DMSO-d6), Shift [ppm]=2.30-2.46 (2H), 2.55-2.66 (1H), 2.69-2.83 (1H), 3.02-3.15 (1H), 3.70-3.83 (2H), 6.52-6.68 (3H), 6.99-7.09 (2H), 7.41-7.51 (3H), 8.38-8.45 (2H), 11.98 (1H).

Example 444 Preparation of N-{4-[6-(chloromethyl)-4-oxo-3-(phenylamino)-4,5,6,7-tetrahydro-1H-indol-2-yl]pyridin-2-yl}acetamide

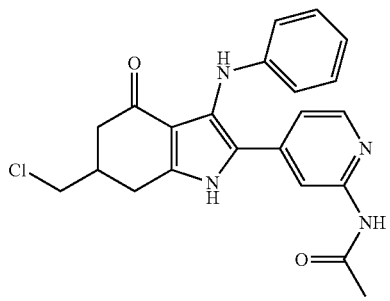 [SMILES: CC(=O)Nc1cc(-c2[nH]c3c(c2Nc2ccccc2)C(=O)CC(CCl)C3)ccn1]

Synthesis of Example 444

2-{[(2-aminopyridin-4-yl)methyl]amino}-4-({[tert-butyl(diphenyl)silyl]oxy}methyl)-6-oxo-N-phenyl-cyclohex-1-ene-1-carbothioamide

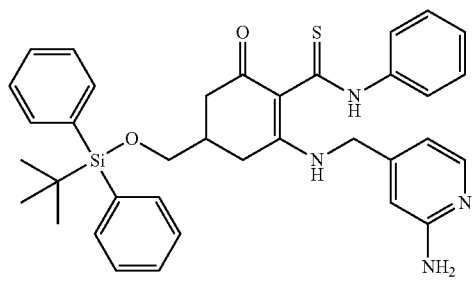 [SMILES: CC(C)(C)[Si](OCC1CC(=O)C(C(=S)Nc2ccccc2)=C(NCc2ccnc(N)c2)C1)(c1ccccc1)c1ccccc1]

A mixture of Intermediate 1-1-32 (33.9 g, 65.7 mmol) and 4-(aminomethyl)-pyridin-2-amine (16.19 g, 131.5 mmol) in DMA (250 mL) was heated at 120° C. for 2 h. Concentrated and purified by silica chromatography to give 2-{[(2-aminopyridin-4-yl)methyl]amino}-4-({[tert-butyl(diphenyl)silyl]oxy}methyl)-6-oxo-N-phenylcyclohex-1-ene-1-carbothioamide (24.6 g, 60%).

2-(2-aminopyridin-4-yl)-3-anilino-6-({[tert-butyl(diphenyl)silyl]oxy}methyl)-1,5,6,7-tetrahydro-4H-indol-4-one

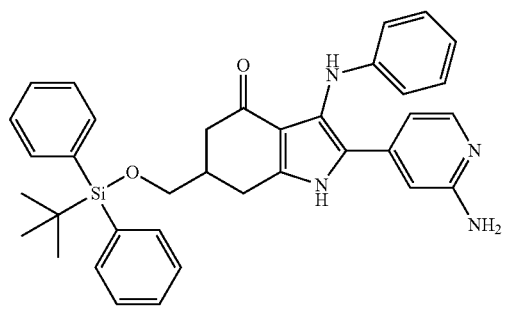 [SMILES: CC(C)(C)[Si](OCC1CC(=O)c2c([nH]c(-c3ccnc(N)c3)c2Nc2ccccc2)C1)(c1ccccc1)c1ccccc1]

Using method F1 2-{[(2-aminopyridin-4-yl)methyl]amino}-4-({[tert-butyl(diphenyl)silyl]oxy}methyl)-6-oxo-N-phenylcyclohex-1-ene-1-carbothioamide (5.28 g, 8.5 mmol) gave 2-(2-aminopyridin-4-yl)-3-anilino-6-({[tert-butyl(diphenyl)silyl]oxy}methyl)-1,5,6,7-tetrahydro-4H-indol-4-one (1.14 g, 23%) after silica chromatography.

1H-NMR (400 MHz, DMSO-d6), Shift [ppm]=1.02 (9H), 2.19-2.39 (2H), 2.81 (1H), 3.02 (1H), 3.58-3.76 (2H), 5.72 (2H), 6.50-6.64 (4H), 6.70 (1H), 7.00 (2H), 7.21 (1H), 7.37-7.50 (7H), 7.56-7.65 (4H), 7.76 (1H), 11.74 (1H).

N-{4-[3-anilino-6-({[tert-butyl(diphenyl)silyl]oxy}methyl)-4-oxo-4,5,6,7-tetrahydro-1H-indol-2-yl]pyridin-2-yl}acetamide

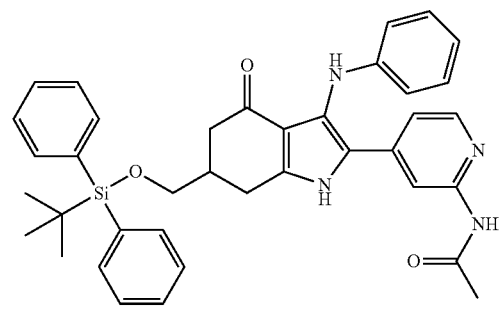 [SMILES: CC(=O)Nc1cc(-c2[nH]c3c(c2Nc2ccccc2)C(=O)CC(CO[Si](c2ccccc2)(c2ccccc2)C(C)(C)C)C3)ccn1]

To a solution of 2-(2-aminopyridin-4-yl)-3-anilino-6-({[tert-butyl(diphenyl)silyl]oxy}methyl)-1,5,6,7-tetrahydro-4H-indol-4-one (2.34 g, 4 mmol) in THF (100 mL) was added pyridine (2.02 g, 19.9 mmol) followed by acetyl chloride (45 µL, 6 mmol) and stirred at RT for 1 h. MeOH added and concentrated. Purification by silica chromatography gave N-{4-[3-anilino-6-({[tert-butyl(diphenyl)silyl]oxy}methyl)-4-oxo-4,5,6,7-tetrahydro-1H-indol-2-yl]pyridin-2-yl}acetamide (2.46 g, 98%).

1H-NMR (400 MHz, DMSO-d6), Shift [ppm]=1.02 (9H), 2.11 (3H), 2.24-2.43 (2H), 2.84 (1H), 3.10 (1H), 3.61-3.76

(2H), 6.52-6.70 (3H), 7.03 (2H), 7.31 (1H), 7.44 (7H), 7.61 (4H), 7.90 (1H), 8.13 (1H), 10.94 (1H), 12.16 (1H).

N-{4-[3-anilino-6-(hydroxymethyl)-4-oxo-4,5,6,7-tetrahydro-1H-indol-2-yl]pyridin-2-yl}acetamide

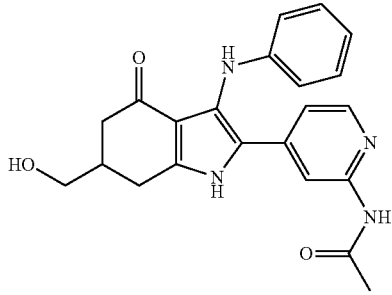 [SMILES: CC(=O)Nc1cc(-c2[nH]c3c(c2Nc2ccccc2)C(=O)CC(CO)C3)ccn1]

To a solution of N-{4-[3-anilino-6-({[tert-butyl(diphenyl)silyl]oxy}methyl)-4-oxo-4,5,6,7-tetrahydro-1H-indol-2-yl]pyridin-2-yl}acetamide (2.45 g, 3.9 mmol) in THF (65 mL) was added 1M TBAF in THF (4.68 mL, 4.68 mmol) and heated at 50° C. for 2 h and then stirred at RT for 16 h. Reaction mixture diluted with EtOAc and washed with 2.5% NaOH(aq), sat. NaCl, dried over Na$_2$SO$_4$, filtered and concentrated. Purified by silica chromatography to give N-{4-[3-anilino-6-(hydroxymethyl)-4-oxo-4,5,6,7-tetrahydro-1H-indol-2-yl]pyridin-2-yl}acetamide (1.174 g, 77%).

1H-NMR (400 MHz, DMSO-d6), Shift [ppm]=2.06 (3H), 2.18-2.35 (3H), 2.59-2.72 (1H), 2.95 (1H), 3.43 (2H), 4.74 (1H), 6.50-6.65 (3H), 7.01 (2H), 7.14 (1H), 7.35 (1H), 8.07 (1H), 8.21 (1H), 10.34 (1H), 11.90 (1H)

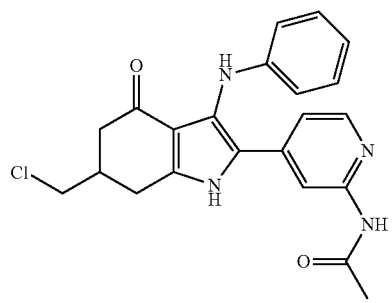 [SMILES: CC(=O)Nc1cc(-c2[nH]c3c(c2Nc2ccccc2)C(=O)CC(CCl)C3)ccn1]

To a solution of N-{4-[3-anilino-6-(hydroxymethyl)-4-oxo-4,5,6,7-tetrahydro-1H-indol-2-yl]pyridin-2-yl}acetamide (355 mg, 909 µmol) in pyridine (5 mL) under Ar was added DMAP (11 mg, 91 µmol) followed by mesyl chloride (84 µL, 1.09 mmol) and stirred at RT for 19 h. Additional mesyl chloride (84 µL, 1.09 mmol) added and stirred at RT for 3 h. MeOH added and concentrated. Purification by silica chromatography gave the desired product (20 mg, 5%).

1H-NMR (400 MHz, DMSO-d6), Shift [ppm]=2.06 (3H), 2.27-2.41 (2H), 2.53-2.65 (1H), 2.74 (1H), 3.09 (1H), 3.69-3.82 (2H), 6.52-6.66 (3H), 7.01 (2H), 7.15 (1H), 7.35 (1H), 8.08 (1H), 8.23 (1H), 10.35 (1H), 11.99 (1H).

Example 445 Preparation of 7-hydroxy-6,6-dimethyl-3-(phenylamino)-2-(pyridin-4-yl)-1,5,6,7-tetrahydro-4H-indol-4-one

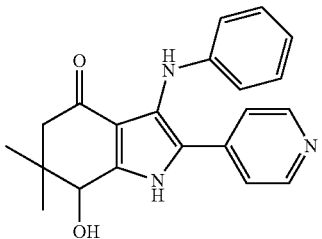 [SMILES: CC1(C)CC(=O)c2c([nH]c(-c3ccncc3)c2Nc2ccccc2)C1O]

To Example 1 (215 mg, 649 µmol) in 2M H$_2$SO$_4$(aq) (12 mL) and t-BuOH (10 mL) was added Ce(IV)(SO$_4$)$_2$.4H$_2$O (393 mg, 0.973 mmol) and stirred at RT for 20 h. Reaction poured into sat. NaHCO$_3$ and the pH adjusted pH 12 with 2M NaOH. The organices were extracted with DCM. The DCM layers were combined and dried over MgSO$_4$, filtered and concentrated. Purification by silica chromatography and crystallization from chlorofrom gave the desired product (36 mg, 16%).

1H-NMR (400 MHz, DMSO-d6), Shift [ppm]=0.97 (3H), 1.02 (3H), 2.21 (1H), 2.38 (1H), 4.52 (1H), 5.58 (1H), 6.55-6.63 (3H), 7.01-7.05 (2H), 7.40 (1H), 7.57 (2H), 8.40 (2H), 11.92 (1H).

Example 446 Preparation of 7-hydroxy-3-(phenylamino)-2-(pyridin-4-yl)-1,5,6,7-tetrahydro-4H-indol-4-one

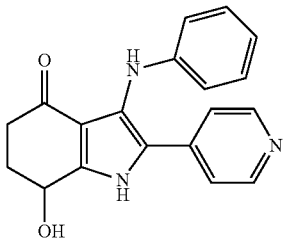 [SMILES: O=C1CCC(O)c2[nH]c(-c3ccncc3)c(Nc3ccccc3)c21]

To Example 9 (200 mg, 659 µmol) in 2M H$_2$SO$_4$(aq) (10 mL) and t-BuOH (10 mL) was added Ce(IV)(SO$_4$)$_2$.4H$_2$O (550 mg, 1.24 mmol) and stirred at RT for 2.5 h. The pH of the reaction mixture adjusted to pH 7 with 5M NaOH. The organices were extracted with EtOAc. The EtOAc layers were combined, washed with water, dried over MgSO$_4$, filtered and concentrated. Purification by silica chromatography and crystallization from chlorofrom gave the desired product (23 mg, 10%).

1H-NMR (400 MHz, DMSO-d6), Shift [ppm]=1.99-2.02 (2H), 2.31-2.33 (2H), 2.34-2.38 (2H), 4.91 (1H), 5.59 (1H), 6.57-6.65 (3H), 7.02-7.06 (2H), 7.45 (1H), 7.59 (2H), 8.41 (2H), 12.10 (1H).

Example 447 Preparation of 1-methyl-N-{4-[4-oxo-3-(phenylamino)-4,5,6,7-tetrahydro-1H-indol-2-yl]pyridin-2-yl}-1H-pyrazole-4-carboxamide

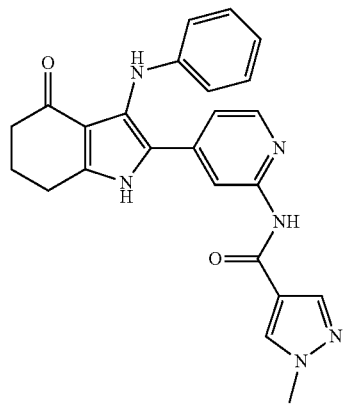 [SMILES: Cn1cc(C(=O)Nc2cc(-c3[nH]c4c(c3Nc3ccccc3)C(=O)CCC4)ccn2)cn1]

Using the Method G2: Example 139 (100 mg, 314 µmol) gave the desired product (30 mg, 22%) after preparative HPLC (basic method).

1H-NMR (400 MHz, DMSO-d6), Shift [ppm]=2.02-2.05 (2H), 2.31-2.35 (2H), 2.83-2.88 (2H), 6.55-6.60 (3H), 6.98-7.04 (2H), 7.17-7.29 (1H), 7.39 (1H), 8.11-8.13 (2H), 8.33 (1H), 8.42 (1H), 10.36 (1H), 11.96 (1H).

Example 448 Preparation of 1-tert-butyl-N-{4-[4-oxo-3-(phenylamino)-4,5,6,7-tetrahydro-1H-indol-2-yl]pyridin-2-yl}-1H-pyrazole-4-carboxamide

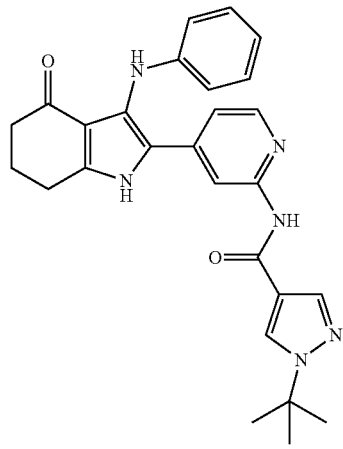 [SMILES: CC(C)(C)n1cc(C(=O)Nc2cc(-c3[nH]c4c(c3Nc3ccccc3)C(=O)CCC4)ccn2)cn1]

Using the Method G2: Example 139 (100 mg, 314 µmol) gave the desired product (40 mg, 27%) after preparative HPLC (basic method).

1H-NMR (400 MHz, DMSO-d6), Shift [ppm]=1.54 (9H), 2.05 (2H), 2.27-2.41 (2H), 2.80-2.92 (2H), 6.55-6.63 (3H), 7.02 (2H), 7.17-7.23 (1H), 7.39 (1H), 8.07 (1H), 8.13 (1H), 8.34 (1H), 8.63-8.71 (1H), 10.32 (1H), 11.96 (1H).

Example 449 Preparation of 1-benzyl-N-{4-[4-oxo-3-(phenylamino)-4,5,6,7-tetrahydro-1H-indol-2-yl]pyridin-2-yl}-1H-pyrazole-4-carboxamide

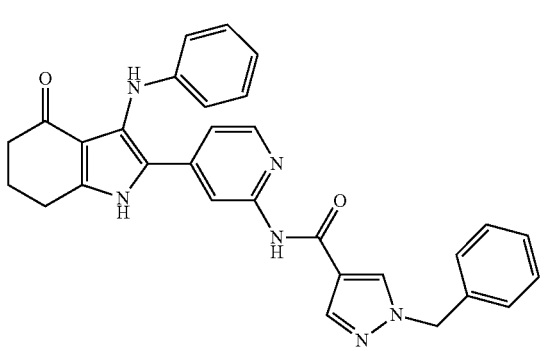 [SMILES: O=C(Nc1cc(-c2[nH]c3c(c2Nc2ccccc2)C(=O)CCC3)ccn1)c1cnn(Cc2ccccc2)c1]

Using the Method G2: Example 139 (100 mg, 314 µmol) gave the desired product (40 mg, 25%) after preparative HPLC (basic method).

1H-NMR (400 MHz, DMSO-d6), Shift [ppm]=1.98-2.10 (2H), 2.27-2.38 (2H), 2.86 (2H), 5.38 (2H), 6.52-6.65 (3H), 7.01 (2H), 7.18 (1H), 7.26-7.41 (6H), 8.12 (1H), 8.15 (1H), 8.32 (1H), 8.57 (1H), 10.41 (1H), 11.95 (1H).

Example 450 Preparation of 1-(4-methoxybenzyl)-N-{4-[4-oxo-3-(phenylamino)-4,5,6,7-tetrahydro-1H-indol-2-yl]pyridin-2-yl}-1H-pyrazole-4-carboxamide

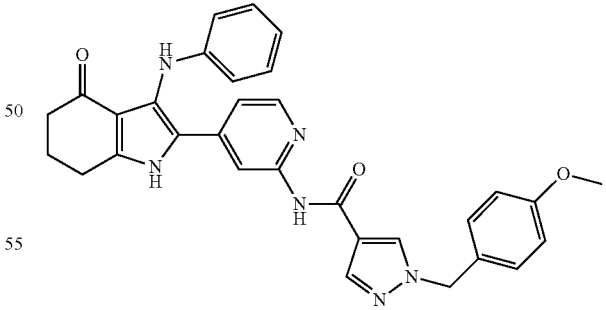

Using the Method G2: Example 139 (100 mg, 314 µmol) gave the desired product (40 mg, 24%) after preparative HPLC (basic method).

1H-NMR (400 MHz, DMSO-d6), Shift [ppm]=1.96-2.11 (2H), 2.33 (2H), 2.86 (2H), 3.74 (3H), 5.28 (2H), 6.52-6.63 (3H), 6.91-6.95 (2H), 7.01 (2H), 7.18 (1H), 7.24-7.30 (2H), 7.39 (1H), 8.09-8.17 (2H), 8.31 (1H), 8.51 (1H), 10.39 (1H), 11.95 (1H).

Example 451 Preparation of 3,4-difluoro-N-{4-[4-oxo-3-(phenylamino)-4,5,6,7-tetrahydro-1H-indol-2-yl]pyridin-2-yl}benzamide

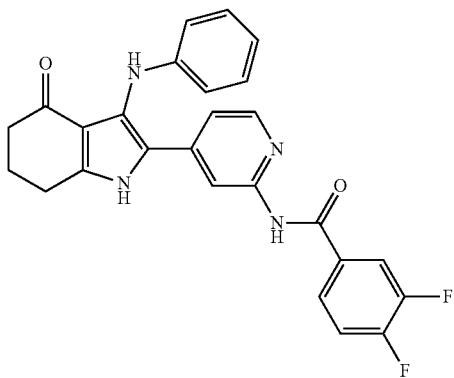 [SMILES: O=C(Nc1cc(-c2[nH]c3c(c2Nc2ccccc2)C(=O)CCC3)ccn1)c1ccc(F)c(F)c1]

Using the Method G2: Example 139 (100 mg, 314 µmol) gave the desired product (40 mg, 28%) after preparative HPLC (basic method).

1H-NMR (400 MHz, DMSO-d6), Shift [ppm]=1.99-2.14 (2H), 2.29-2.39 (2H), 2.87 (2H), 6.55-6.66 (3H), 7.02 (2H), 7.24 (1H), 7.40-7.45 (1H), 7.60 (1H), 7.92 (1H), 8.10 (1H), 8.18 (1H), 8.30-8.34 (1H), 10.82 (1H), 11.98 (1H).

Example 452 Preparation of 3,5-difluoro-N-{4-[4-oxo-3-(phenylamino)-4,5,6,7-tetrahydro-1H-indol-2-yl]pyridin-2-yl}benzamide

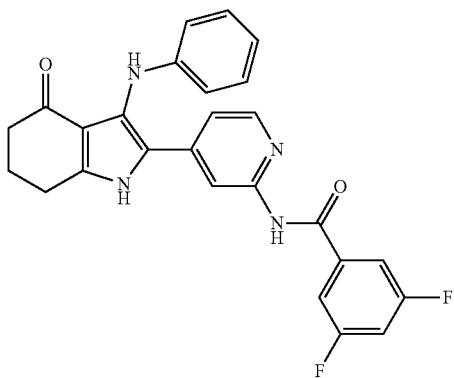 [SMILES: O=C(Nc1cc(-c2[nH]c3c(c2Nc2ccccc2)C(=O)CCC3)ccn1)c1cc(F)cc(F)c1]

Using the Method G2: Example 139 (100 mg, 314 µmol) gave the desired product (40 mg, 28%) after preparative HPLC (basic method).

1H-NMR (400 MHz, DMSO-d6), Shift [ppm]=1.99-2.10 (2H), 2.30-2.38 (2H), 2.87 (2H), 6.55-6.70 (3H), 7.02 (2H), 7.25 (1H), 7.43 (1H), 7.54 (1H), 7.70-7.77 (2H), 8.14-8.24 (1H), 8.32 (1H), 10.88 (1H), 11.99 (1H).

Example 453 Preparation of 4-fluoro-3-methoxy-N-{4-[4-oxo-3-(phenylamino)-4,5,6,7-tetrahydro-1H-indol-2-yl]pyridin-2-yl}benzamide

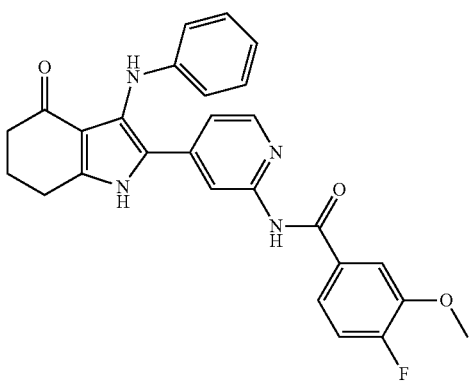 [SMILES: COc1cc(C(=O)Nc2cc(-c3[nH]c4c(c3Nc3ccccc3)C(=O)CCC4)ccn2)ccc1F]

Using the Method G2: Example 139 (100 mg, 314 µmol) gave the desired product (40 mg, 27%) after preparative HPLC (basic method).

1H-NMR (400 MHz, DMSO-d6), Shift [ppm]=2.00-2.11 (2H), 2.29-2.39 (2H), 2.87 (2H), 3.94 (3H), 6.55-6.65 (3H), 7.02 (2H), 7.24 (1H), 7.35 (1H), 7.42 (1H), 7.64 (1H), 7.85 (1H), 8.17 (1H), 8.32-8.37 (1H), 10.77 (1H), 11.97 (1H).

Example 454 Preparation of 1-methyl-N-{4-[4-oxo-3-(phenylamino)-4,5,6,7-tetrahydro-1H-indol-2-yl]pyridin-2-yl}-1H-pyrazole-3-carboxamide

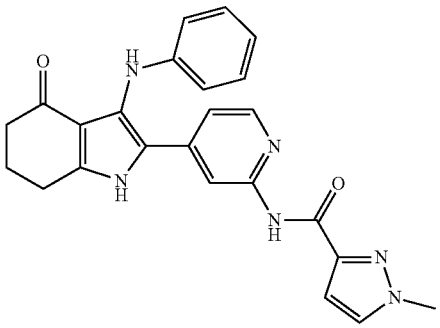 [SMILES: Cn1ccc(C(=O)Nc2cc(-c3[nH]c4c(c3Nc3ccccc3)C(=O)CCC4)ccn2)n1]

Using the Method G2: Example 139 (100 mg, 314 µmol) gave the desired product (20 mg, 15%) after preparative HPLC (basic method).

1H-NMR (400 MHz, DMSO-d6), Shift [ppm]=1.99-2.11 (2H), 2.30-2.39 (2H), 2.87 (2H), 3.96 (3H), 6.53-6.64 (3H), 6.83 (1H), 7.02 (2H), 7.21 (1H), 7.42 (1H), 7.88 (1H), 8.13 (1H), 8.34 (1H), 9.41 (1H), 11.99 (1H).

Example 455 Preparation of 2-[3-(cyclopropylmethoxy)pyridin-4-yl]-3-(phenylamino)-1,5,6,7-tetrahydro-4H-indol-4-one

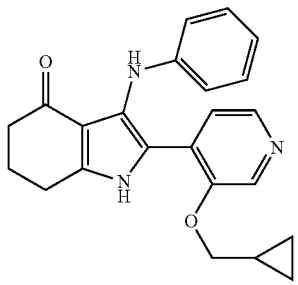 [SMILES: O=C1CCCc2[nH]c(-c3ccncc3OCC3CC3)c(Nc3ccccc3)c21]

Synthesis of Example 455

Intermediate 1-2-81

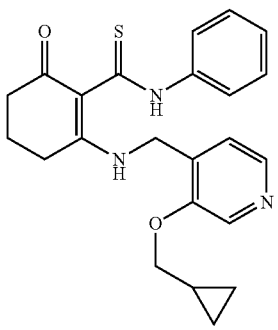 [SMILES: O=C1CCCC(NCc2ccncc2OCC2CC2)=C1C(=S)Nc1ccccc1]

A solution of Intermediate 1-1-5 (116 mg, 468 µmol) and [3-(cyclopropylmethoxy)pyridin-4-yl]methanamine (100 mg, 561 µmol) in DMA (3 mL) was heated at 130° C. for 3 h. Concentrated and purified by preparative HPLC (basic method) to give the Intermediate 1-2-81 (50 mg, 25%).

1H-NMR (400 MHz, DMSO-d6), Shift [ppm]=0.31-0.45 (2H), 0.50-0.67 (2H), 1.16-1.38 (1H), 1.82 (2H), 2.46 (2H), 2.82 (2H), 3.97-4.09 (2H), 4.72 (2H), 7.16-7.28 (1H), 7.32-7.48 (5H), 8.22 (1H), 8.36 (1H), 13.71 (1H), 14.59 (1H).

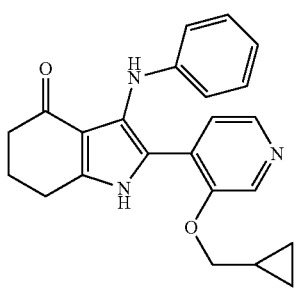 [SMILES: O=C1CCCc2[nH]c(-c3ccncc3OCC3CC3)c(Nc3ccccc3)c21]

Using method F1 Intermediate 1-2-81 (48 mg, 118 µmol) gave the desired product (11 mg, 24%) after preparative HPLC (basic method).

1H-NMR (400 MHz, DMSO-d6), Shift [ppm]=0.25-0.41 (2H), 0.48-0.61 (2H), 1.18-1.39 (1H), 1.99-2.15 (2H), 2.28-2.39 (2H), 2.85 (2H), 3.92 (2H), 6.48-6.60 (3H), 6.96 (2H), 7.26 (1H), 7.38 (1H), 8.02 (1H), 8.30 (1H), 11.25 (1H).

Example 456 Preparation of 3-(phenylamino)-2-(3-propoxypyridin-4-yl)-1,5,6,7-tetrahydro-4H-indol-4-one

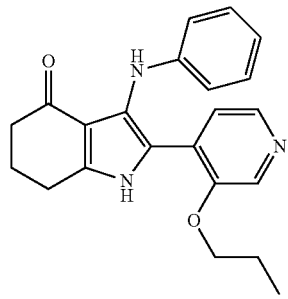 [SMILES: CCCOc1cnccc1-c1[nH]c2c(c1Nc1ccccc1)C(=O)CCC2]

Synthesis of Example 456

Intermediate 1-2-82

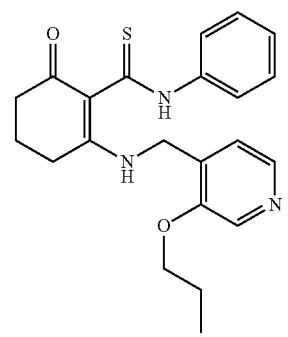 [SMILES: CCCOc1cnccc1CNC1=C(C(=S)Nc2ccccc2)C(=O)CCC1]

A solution of Intermediate (250 mg, 1 mmol) and (3-propoxy)pyridin-4-yl)methanamine (202 mg, 1.2 mmol) in DMA (3 mL) was heated at 130° C. for 3 h. Concentrated and purified by preparative HPLC (basic method) to give the desired product (105 mg, 25%).

1H-NMR (400 MHz, DMSO-d6), Shift [ppm]=1.00 (3H), 1.73-1.85 (4H), 2.45 (2H), 2.80 (2H), 4.12 (2H), 4.70 (2H), 7.17-7.26 (1H), 7.32-7.47 (5H), 8.23 (1H), 8.38 (1H), 13.69 (1H), 14.58 (1H).

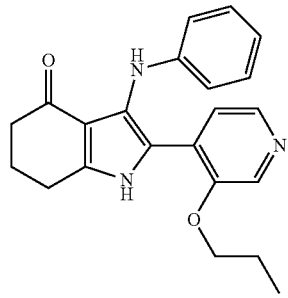 [SMILES: CCCOc1cnccc1-c1[nH]c2c(c1Nc1ccccc1)C(=O)CCC2]

Using method F1 intermediate (103 mg, 260 μmol) gave the desired product (32 mg, 32%) after preparative HPLC (basic method).

1H-NMR (400 MHz, DMSO-d6), Shift [ppm]=0.93 (3H), 1.75 (2H), 2.04 (2H), 2.30-2.38 (2H), 2.83 (2H), 3.99 (2H), 6.45-6.53 (2H), 6.55 (1H), 6.95 (2H), 7.25 (1H), 7.39 (1H), 8.02 (1H), 8.31 (1H), 11.23 (1H).

Example 457 Preparation of 2-[3-(2,2-difluoroethoxy)pyridin-4-yl]-3-(phenylamino)-1,5,6,7-tetrahydro-4H-indol-4-one

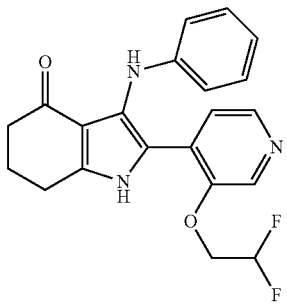 [SMILES: O=C1CCCc2[nH]c(-c3ccncc3OCC(F)F)c(Nc3ccccc3)c21]

Synthesis of Example 457

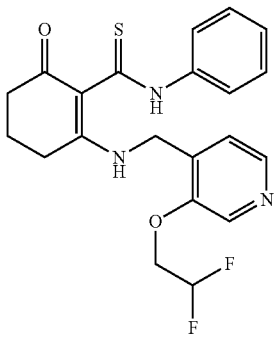 [SMILES: O=C1CCCC(NCc2ccncc2OCC(F)F)=C1C(=S)Nc1ccccc1]

A solution of Intermediate 1-1-5 (250 mg, 1 mmol) and [3-(2,2-difluoroethoxy)pyridin-4-yl]methanamine (228 mg, 1.2 mmol) in DMA (3 mL) was heated at 130° C. for 3 h. Concentrated and purified by preparative HPLC (basic method) to give the Intermediate 1-2-82 (119 mg, 27%)

1H-NMR (400 MHz, DMSO-d6), Shift [ppm]=1.80 (2H), 2.45 (2H), 2.77 (2H), 4.55 (2H), 4.73 (2H), 6.43 (1H), 7.17-7.27 (1H), 7.35-7.42 (3H), 7.42-7.48 (2H), 8.30 (1H), 8.47 (1H), 13.63 (1H), 14.54 (1H).

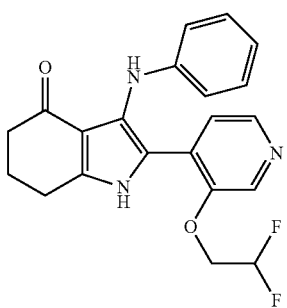 [SMILES: O=C1CCCc2[nH]c(-c3ccncc3OCC(F)F)c(Nc3ccccc3)c21]

Using method F1 Intermediate 1-2-82 (117 mg, 280 μmol) gave the desired product (39 mg, 34%) after preparative HPLC (basic method).

1H-NMR (400 MHz, DMSO-d6), Shift [ppm]=1.99-2.14 (2H), 2.28-2.41 (2H), 2.78-2.92 (2H), 4.31 (2H), 6.33 (1H), 6.49-6.61 (3H), 6.95 (2H), 7.24-7.33 (1H), 7.41-7.51 (1H), 8.11 (1H), 8.36 (1H), 11.29 (1H).

Example 458 Preparation of 3-(phenylamino)-2-[3-(2,2,2-trifluoroethoxy)pyridin-4-yl]-1,5,6,7-tetrahydro-4H-indol-4-one

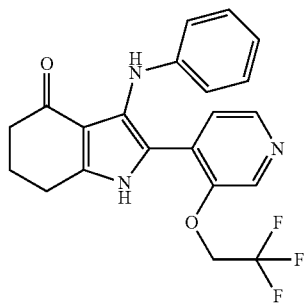 [SMILES: O=C1CCCc2[nH]c(-c3ccncc3OCC(F)(F)F)c(Nc3ccccc3)c21]

Synthesis of Example 458

Intermediate 1-2-83

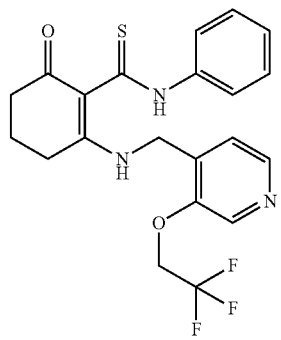 [SMILES: O=C1CCCC(NCc2ccncc2OCC(F)(F)F)=C1C(=S)Nc1ccccc1]

A solution of Intermediate 1-1-5 (250 mg, 1 mmol) and [3-(2,2,2-trifluoroethoxy)pyridin-4-yl]methanamine (250 mg, 1.2 mmol) in DMA (3 mL) was heated at 130° C. for 3 h. Concentrated and purified by preparative HPLC (acidic method) to give the Intermediate 1-2-83 (131 mg, 28%)

1H-NMR (400 MHz, DMSO-d6), Shift [ppm]=1.80 (2H), 2.45 (2H), 2.76 (2H), 4.74 (2H), 5.00 (2H), 7.19-7.26 (1H), 7.34-7.41 (3H), 7.43-7.47 (2H), 8.34 (1H), 8.51 (1H), 13.58 (1H), 14.50 (1H).

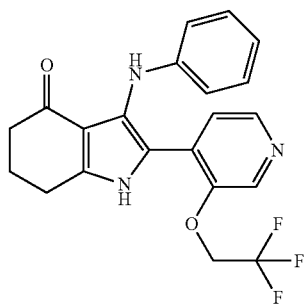 [SMILES: O=C1CCCc2[nH]c(-c3ccncc3OCC(F)(F)F)c(Nc3ccccc3)c21]

Using method F1 Intermediate 1-2-83 (129 mg, 296 µmol) gave the desired product (41 mg, 33%) after preparative HPLC (basic method).

1H-NMR (400 MHz, DMSO-d6), Shift [ppm]=2.01-2.12 (2H), 2.31-2.39 (2H), 2.83 (2H), 4.80 (2H), 6.49 (2H), 6.56 (1H), 6.90-6.99 (2H), 7.27 (1H), 7.37 (1H), 8.13 (1H), 8.44 (1H), 11.30 (1H).

Example 459 Preparation of 2-[3-(2-hydroxy-ethoxy)pyridin-4-yl]-3-(phenylamino)-1,5,6,7-tetra-hydro-4H-indol-4-one

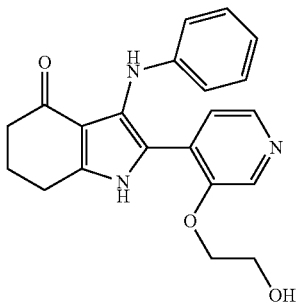 [SMILES: O=C1CCCc2[nH]c(-c3ccncc3OCCO)c(Nc3ccccc3)c21]

Synthesis of Example 459

Intermediate 1-2-84

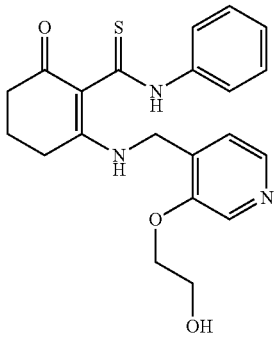 [SMILES: O=C1CCCC(NCc2ccncc2OCCO)=C1C(=S)Nc1ccccc1]

A solution of Intermediate 1-1-5 (250 mg, 1 mmol) and [3-(2,2-difluoroethoxy)pyridin-4-yl]methanamine (204 mg, 1.2 mmol) in DMA (3 mL) was heated at 130° C. for 3 h. Concentrated and purified by preparative HPLC (acidic method) to give the Intermediate 1-2-84 (28 mg, 6%).

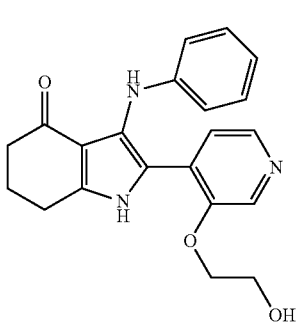 [SMILES: O=C1CCCc2[nH]c(-c3ccncc3OCCO)c(Nc3ccccc3)c21]

Using method F1 Intermediate 1-2-84 (27 mg, 68 µmol) gave the desired product (3.5 mg, 13%) after preparative HPLC (basic method).

1H-NMR (400 MHz, DMSO-d6), Shift [ppm]=2.01-2.09 (2H), 2.29-2.36 (2H), 2.83 (2H), 3.84 (2H), 4.21-4.29 (2H), 5.56 (1H), 6.52-6.62 (3H), 6.99 (2H), 7.30 (1H), 7.44 (1H), 8.00 (1H), 8.40 (1H), 11.49 (1H).

Example 460 Preparation of (4S)-2,2-dimethyl-N-{4-[4-oxo-3-(phenylamino)-4,5,6,7-tetrahydro-1H-indol-2-yl]pyridin-2-yl}-1,3-dioxolane-4-carboxamide

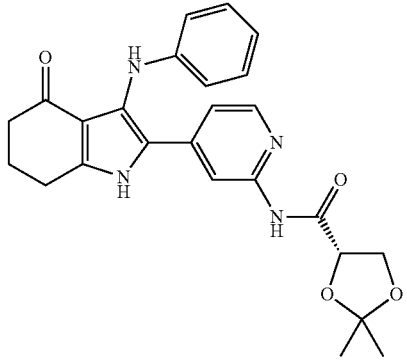 [SMILES: CC1(C)OC[C@@H](C(=O)Nc2cc(-c3[nH]c4c(c3Nc3ccccc3)C(=O)CCC4)ccn2)O1]

Using the Method G2: Example 139 (100 mg, 314 µmol) gave the desired product (30 mg, 21%) after preparative HPLC (basic method).

1H-NMR (400 MHz, DMSO-d6), Shift [ppm]=1.36 (3H), 1.46 (3H), 1.97-2.12 (2H), 2.28-2.38 (2H), 2.38-2.47 (1H), 2.86 (2H), 4.00 (1H), 4.25 (1H), 4.68 (1H), 6.52-6.66 (3H), 7.01 (2H), 7.20 (1H), 7.42 (1H), 8.10 (1H), 8.19-8.24 (1H), 9.73 (1H), 11.97 (1H).

Example 461 Preparation of N-{4-[6-(fluoromethyl)-4-oxo-3-(phenylamino)-4,5,6,7-tetrahydro-1H-indol-2-yl]pyridin-2-yl}acetamide

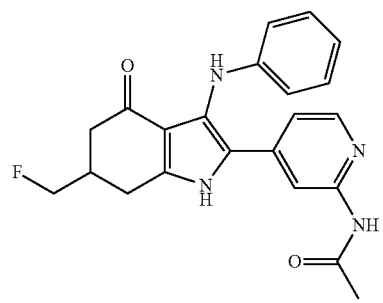 [SMILES: CC(=O)Nc1cc(-c2[nH]c3c(c2Nc2ccccc2)C(=O)CC(CF)C3)ccn1]

Synthesis of Example 461 [2-(2-acetamidopyridin-4-yl)-3-anilino-4-oxo-4,5,6,7-tetrahydro-1H-indol-6-yl]methyl methanesulfonate

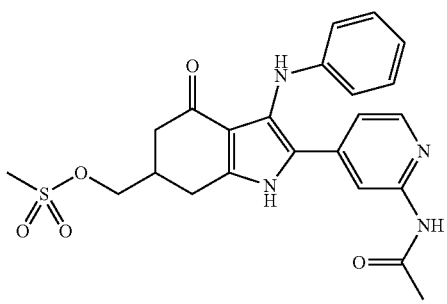 [SMILES: CC(=O)Nc1cc(-c2[nH]c3c(c2Nc2ccccc2)C(=O)CC(COS(C)(=O)=O)C3)ccn1]

To a solution of N-{4-[3-anilino-6-(hydroxymethyl)-4-oxo-4,5,6,7-tetrahydro-1H-indol-2-yl]pyridin-2-yl}acetamide (1.175 g, 3 mmol) in pyridine (16 mL) under Ar was added DMAP (37 mg, 301 µmol) followed by mesyl chloride (280 µL, 3.6 mmol) and stirred at RT for 5 h. MeOH added and concentrated. Purification by crystallzation (MeOH) and purification of the mother liquor by silica chromatography gave [2-(2-acetamidopyridin-4-yl)-3-anilino-4-oxo-4,5,6,7-tetrahydro-1H-indol-6-yl]methyl methanesulfonate (1.264 g, 90%).

1H-NMR (400 MHz, DMSO-d6), Shift [ppm]=2.06 (3H), 2.27-2.42 (2H), 2.59-2.70 (1H), 2.70-2.80 (1H), 3.04 (1H), 3.23 (3H), 4.22-4.33 (2H), 6.52-6.64 (3H), 7.01 (2H), 7.15 (1H), 7.36 (1H), 8.08 (1H), 8.23 (1H), 10.35 (1H), 11.99 (1H).

Example 462 Preparation of N-[4-(3-anilino-4-oxo-4,5,6,7-tetrahydro-1H-indol-2-yl)pyridin-2-yl]-2-(4-fluorophenoxy)acetamide

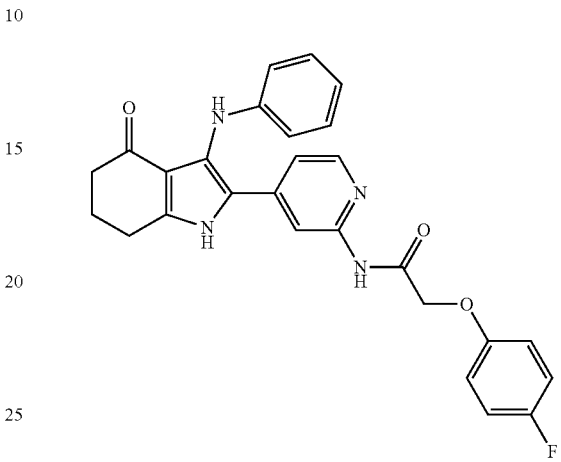

Using the Method G2: Example 139 (100 mg, 314 µmol) gave the desired product (40 mg, 27%) after preparative HPLC (basic method).

1H-NMR (400 MHz, DMSO-d6), Shift [ppm]=1.97-2.09 (2H), 2.27-2.39 (2H), 2.84 (2H), 4.76 (2H), 6.51-6.66 (3H), 6.93-7.06 (4H), 7.10-7.23 (3H), 7.39 (1H), 8.08-8.14 (1H), 8.23 (1H), 10.39 (1H), 11.94 (1H).

Example 463 Preparation of N-[4-(3-anilino-4-oxo-4,5,6,7-tetrahydro-1H-indol-2-yl)pyridin-2-yl]-2-(1-methyl-1H-imidazol-2-yl)acetamide

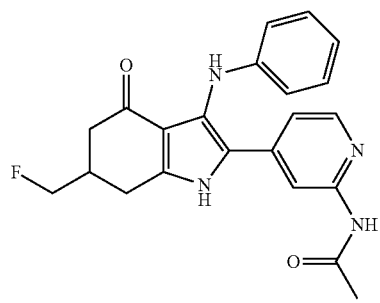 [SMILES: CC(=O)Nc1cc(-c2[nH]c3c(c2Nc2ccccc2)C(=O)CC(CF)C3)ccn1]

To a solution of [2-(2-acetamidopyridin-4-yl)-3-anilino-4-oxo-4,5,6,7-tetrahydro-1H-indol-6-yl]methyl methanesulfonate (50 mg, 107 µmol) in THF (1 mL) was added 1M TBAF in THF (640 µL, 640 µmol) and heated at 80° C. for 1 h. Concentrated and purified by preparative TLC to give the desired product (10 mg, 22%).

1H-NMR (400 MHz, DMSO-d6), Shift [ppm]=2.06 (3H), 2.25-2.41 (2H), 2.60-2.67 (1H), 2.68-2.79 (1H), 3.01 (1H), 4.42 (1H), 4.54 (1H), 6.51-6.63 (3H), 7.01 (2H), 7.15 (1H), 7.36 (1H), 8.08 (1H), 8.22 (1H), 10.35 (1H), 11.98 (1H).

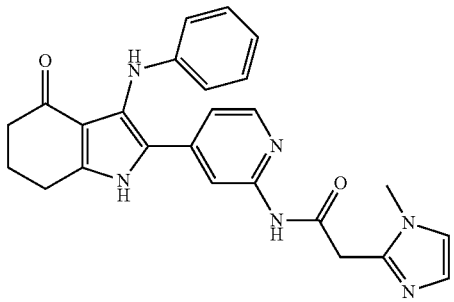 [SMILES: Cn1ccnc1CC(=O)Nc1cc(-c2[nH]c3c(c2Nc2ccccc2)C(=O)CCC3)ccn1]

Using the Method G2: Example 139 (100 mg, 314 µmol) gave the desired product (30 mg, 22%) after preparative HPLC (basic method).

1H-NMR (400 MHz, DMSO-d6), Shift [ppm]=1.96-2.12 (2H), 2.29-2.39 (2H), 2.84 (2H), 3.60 (3H), 3.89 (2H), 6.52-6.63 (3H), 6.79-7.03 (2H), 7.09 (1H), 7.16 (1H), 7.38 (1H), 8.09 (1H), 8.22 (1H), 10.78 (1H), 11.92 (1H).

Example 464 Preparation of 3-anilino-2-(3-hydroxypyridin-4-yl)-6,6-dimethyl-1,5,6,7-tetrahydro-4H-indol-4-one

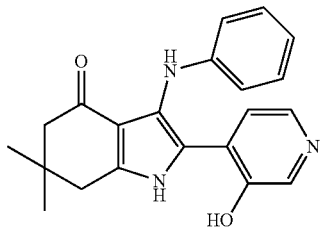

Synthesis of Example 464

Intermediate 1-2-85

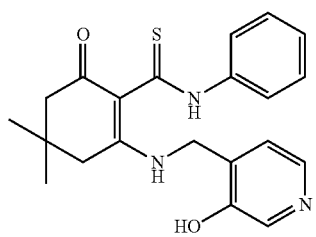 [SMILES: CC1(C)CC(=O)C(C(=S)Nc2ccccc2)=C(NCc2ccncc2O)C1]

A solution of intermediate 1-1-1 (624 mg, 2.3 mmol) and 4-(aminomethyl)pyridin-3-ol (synthesized according to Leroy et al., Synth. Commun., 1997, 27, 2905) (675 mg, 5.4 mmol) in DMA (10 mL) was heated at 130° C. for 60 mins using a microwave. Concentrated and purified by silica chromatography gave the Intermediate 1-2-85 (370 mg, 43%).

1H-NMR (400 MHz, DMSO-d6), Shift [ppm]=0.99 (6H), 2.39 (2H), 2.71 (2H), 4.69 (2H), 7.18-7.27 (2H), 7.33-7.41 (2H), 7.41-7.48 (2H), 8.06 (1H), 8.18 (1H), 10.37 (1H), 14.01 (1H), 14.69 (1H).

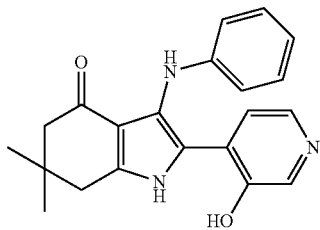

Using method F1 Intermediate 1-2-85 (370 mg, 970 µmol) gave the desired product (71 mg, 21%) after silica chromatography.

1H-NMR (400 MHz, DMSO-d6), Shift [ppm]=1.01-1.11 (6H), 2.22 (2H), 2.72-2.83 (2H), 6.56 (2H), 6.62 (1H), 7.01 (2H), 7.32 (1H), 7.46 (1H), 7.87 (1H), 8.16 (1H), 10.66 (1H), 11.40 (1H).

Example 465 Preparation of N-{4-[6,6-dimethyl-4-oxo-3-(phenylamino)-4,5,6,7-tetrahydro-1H-indol-2-yl]pyridin-2-yl}-1H-pyrazole-3-carboxamide

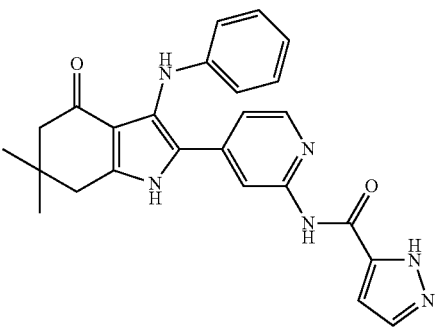 [SMILES: CC1(C)CC(=O)c2c([nH]c(-c3ccnc(NC(=O)c4ccn[nH]4)c3)c2Nc2ccccc2)C1]

Using the Method G2 at 50° C.: Example 122 (100 mg, 289 µmol) gave the desired product (34 mg, 25%) after preparative HPLC purification (basic method).

1H-NMR (600 MHz, DMSO-d6), Shift [ppm]=1.08 (6H), 2.24 (2H), 2.76 (2H), 6.56-6.63 (3H), 6.85 (1H), 7.00-7.06 (2H), 7.24 (1H), 7.39 (1H), 7.93 (1H), 8.14 (1H), 8.35 (1H), 9.47 (1H), 11.93 (1H), 13.51 (1H).

Example 466 Preparation of rel-(R,S)-2-fluoro-N-{4-[4'-oxo-3'-(phenylamino)-1',4',5',7'-tetrahydrospiro[cyclopropane-1,6'-indol]-2'-yl]pyridin-2-yl}cyclopropanecarboxamide

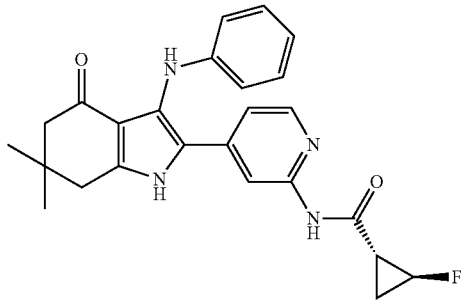

racemate

Using the Method G2 at 50° C.: Example 206 (35 mg, 102 µmol) gave the desired product (9 mg, 21%) after preparative HPLC purification (basic method).

1H-NMR (400 MHz, DMSO-d6), Shift [ppm]=0.35-0.54 (4H), 1.14-1.27 (1H), 1.44-1.59 (1H), 2.22 (2H), 2.52-2.61 (1H), 2.74 (2H), 4.72-4.98 (1H), 6.49-6.66 (3H), 7.01 (2H), 7.16 (1H), 7.40 (1H), 8.09 (1H), 8.16 (1H), 10.81 (1H), 11.91 (1H).

Example 467 Preparation of N-{4-[6,6-dimethyl-4-oxo-3-(phenylamino)-4,5,6,7-tetrahydro-1H-indol-2-yl]pyridin-2-yl}-3,5-difluorobenzamide

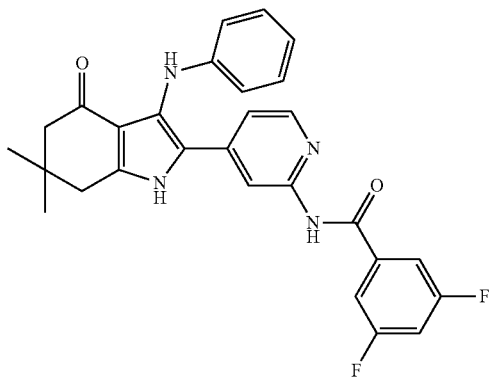 [SMILES: CC1(C)CC(=O)c2c([nH]c(-c3ccnc(NC(=O)c4cc(F)cc(F)c4)c3)c2Nc2ccccc2)C1]

Using the Method G2 at 50° C.: Example 122 (100 mg, 289 µmol) gave the desired product (25 mg, 18%) after preparative HPLC purification (basic method).

1H-NMR (400 MHz, DMSO-d6), Shift [ppm]=1.07 (6H), 2.24 (2H), 2.76 (2H), 6.55-6.63 (3H), 6.98-7.07 (2H), 7.27 (1H), 7.42 (1H), 7.51-7.58 (1H), 7.74 (2H), 8.19 (1H), 8.31 (1H), 10.88 (1H), 11.95 (1H)

Example 468 Preparation of 2-[2-(benzyloxy)pyridin-4-yl]-6,6-dimethyl-3-(phenylamino)-1,5,6,7-tetrahydro-4H-indol-4-one

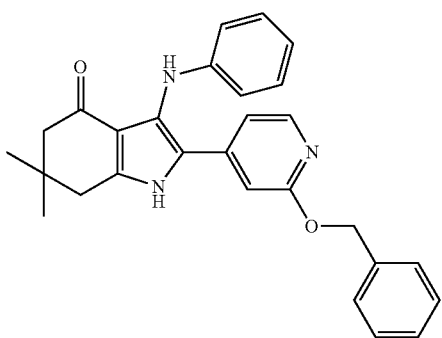 [SMILES: CC1(C)CC(=O)c2c([nH]c(-c3ccnc(OCc4ccccc4)c3)c2Nc2ccccc2)C1]

Synthesis of Example 468

Intermediate 1-2-86

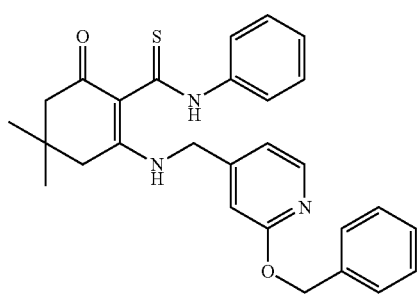 [SMILES: CC1(C)CC(=O)C(C(=S)Nc2ccccc2)=C(NCc2ccnc(OCc3ccccc3)c2)C1]

A solution of Intermediate 1-1-1 (250 mg, 908 µmol) and 1-[2-(benzyloxy)pyridin-4-yl]methanamine (389 mg, 1.8 mmol) in DMA (3 mL) was heated at 130° C. for 2 h. Concentrated and purified by preparative HPLC (basic method) to give the Intermediate 1-2-86 (180 mg, 40%).

1H-NMR (400 MHz, DMSO-d6), Shift [ppm]=0.97 (6H), 2.39 (2H), 2.63-2.69 (2H), 4.81 (2H), 5.35 (2H), 6.84 (1H), 6.99 (1H), 7.18-7.26 (1H), 7.27-7.52 (9H), 8.18 (1H), 14.01 (1H), 14.63 (1H).

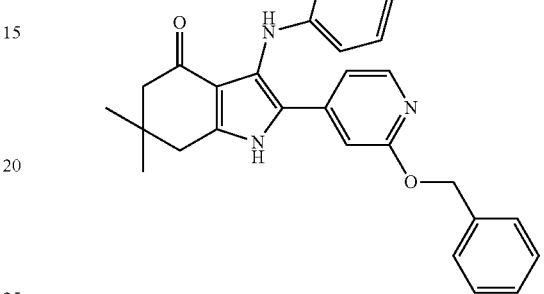

Using method F1 Intermediate 1-2-86 (185 mg, 392 µmol) gave the desired product (33 mg, 18%) after preparative HPLC (Column: XBridge C18 5µ 100×30 mm; Solvent A: Water+0.2 Vol-% NH4OH (32%), Solvent B: Acetonitrile; Gradient: 0.00-0.50 min 48% B (25→70 mL/min), 0.51-5.50 min 48-80% B (70 mL/min)).

1H-NMR (400 MHz, DMSO-d6), Shift [ppm]=1.06 (6H), 2.22 (2H), 2.73 (2H), 5.28 (2H), 6.56 (2H), 6.59-6.66 (1H), 6.97-7.10 (3H), 7.16 (1H), 7.27-7.39 (5H), 7.42 (1H), 8.00 (1H), 11.80 (1H).

Example 469 Preparation of 2-(2-hydroxypyridin-4-yl)-6,6-dimethyl-3-(phenylamino)-1,5,6,7-tetrahydro-4H-indol-4-one

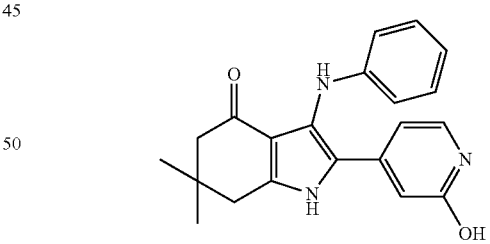

To a solution of Example 468 (25 mg, 57 µmol) in MeOH (4 mL), EtOAc (8 mL) was added two drops of 6M HCl. To this solution under Ar was added Pd/C (10%, 2 mg) and the reaction vessel was flushed with hydrogen (×3). The reaction was heated at 50° C. for 5 h. Filtered, concentrated and purified by silica chromatography to give the desired product (5.1 mg, 24%).

1H-NMR (400 MHz, DMSO-d6), Shift [ppm]=1.05 (6H), 2.21 (2H), 2.71 (2H), 6.44-6.50 (2H), 6.54-6.59 (2H), 6.62 (1H), 7.05 (2H), 7.21 (1H), 7.36 (1H), 11.23 (1H), 11.70 (1H).

Example 470 Preparation of N-{4-[4'-oxo-3'-(phenylamino)-1',4',5',7'-tetrahydrospiro[cyclopropane-1,6'-indol]-2'-yl]pyridin-2-yl}-1,3-oxazole-4-carboxamide

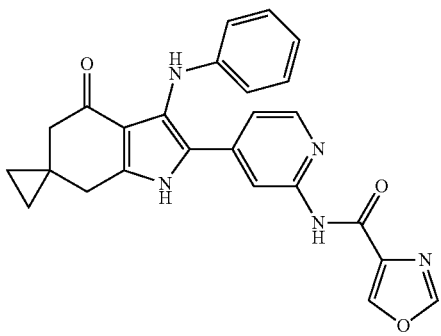 [SMILES: O=C(Nc1cc(-c2[nH]c3c(c2Nc2ccccc2)C(=O)CC2(CC2)C3)ccn1)c1cocn1]

Using the Method G2 at 50° C.: Example 206 (35 mg, 102 µmol) gave the desired product (9 mg, 21%) after preparative HPLC purification (basic method).

1H-NMR (400 MHz, DMSO-d6), Shift [ppm]=0.36-0.56 (4H), 2.24 (2H), 2.77 (2H), 6.56-6.64 (3H), 7.02 (2H), 7.26 (1H), 7.45 (1H), 8.17 (1H), 8.32 (1H), 8.62 (1H), 8.93 (1H), 9.73 (1H), 12.02 (1H).

Example 471 Preparation of 4-(methoxyimino)-6,6-dimethyl-N-phenyl-2-(pyridin-4-yl)-4,5,6,7-tetrahydro-1H-indol-3-amine

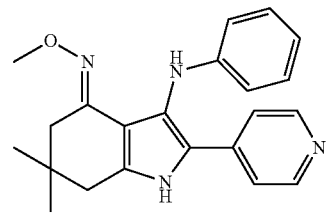 [SMILES: CO/N=C1\CC(C)(C)Cc2[nH]c(-c3ccncc3)c(Nc3ccccc3)c21]

A mixture of Example 1 (50 mg, 151 µmol), O-methylhydroxylamine hydrochloride (56.7 mg, 679 µmol) and DIPEA (97 mg, 754 µmol) in EtOH (2 mL) in a sealed tube was heated at 100° C. for 48 h. The reaction then heated at 150° C. for 6 h. Additional O-methylhydroxylamine hydrochloride (126 mg, 1.5 mmol), DIPEA (195 mg, 1.5 mmol) and DMAP (9 mg, 75 µmol) added and heated at 150° C. for 6 h. Concentrated and purified by preparative HPLC (basic method).

1H-NMR (400 MHz, DMSO-d6), Shift [ppm]=1.01 (6H), 2.41 (2H), 2.56 (2H), 3.70 (3H), 6.57 (2H), 6.64 (1H), 7.01-7.10 (2H), 7.14 (1H), 7.44-7.49 (2H), 8.31-8.40 (2H), 11.47 (1H).

Example 472 Preparation of 1-tert-butyl-N-{4-[6,6-dimethyl-4-oxo-3-(phenylamino)-4,5,6,7-tetrahydro-1H-indol-2-yl]pyridin-2-yl}-1H-pyrazole-4-carboxamide

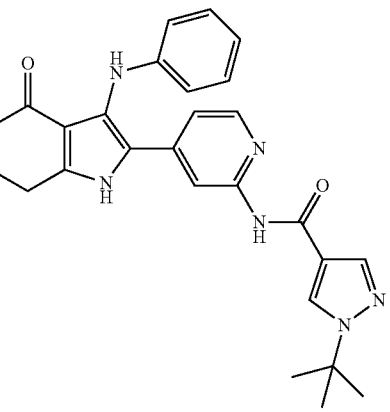

Using the Method G2 at 50° C.: Example 122 (100 mg, 289 µmol) gave the desired product (25 mg, 17%) after preparative HPLC purification (basic method).

1H-NMR (600 MHz, DMSO-d6), Shift [ppm]=1.07 (6H), 1.55 (9H), 2.23 (2H), 2.75 (2H), 6.55-6.63 (3H), 7.02 (2H), 7.20 (1H), 7.36 (1H), 8.07 (1H), 8.13 (1H), 8.33 (1H), 8.67 (1H), 10.29 (1H), 11.89 (1H).

Example 473 Preparation of N-{4-[6,6-dimethyl-4-oxo-3-(phenylamino)-4,5,6,7-tetrahydro-1H-indol-2-yl]pyridin-2-yl}-3,4-difluorobenzamide

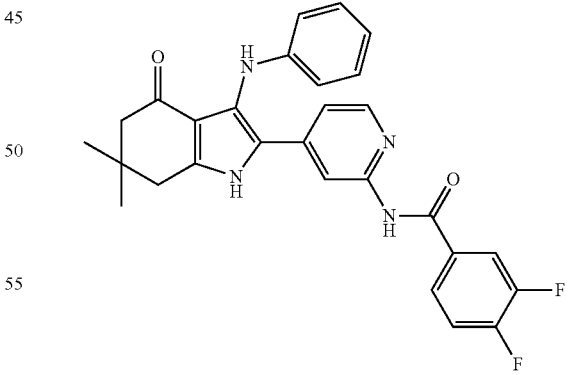

Using the Method G2 at 50° C.: Example 122 (100 mg, 289 µmol) gave the desired product (52 mg, 33%) after preparative HPLC purification (basic method).

1H-NMR (500 MHz, DMSO-d6), Shift [ppm]=1.07 (6H), 2.24 (2H), 2.76 (2H), 6.54-6.63 (3H), 7.02 (2H), 7.26 (1H), 7.41 (1H), 7.60 (1H), 7.92 (1H), 8.10 (1H), 8.18 (1H), 8.31 (1H), 10.82 (1H), 11.94 (1H).

Example 474 Preparation of N-{4-[6,6-dimethyl-4-oxo-3-(phenylamino)-4,5,6,7-tetrahydro-1H-indol-2-yl]pyridin-2-yl}-4-fluoro-3-methoxybenzamide

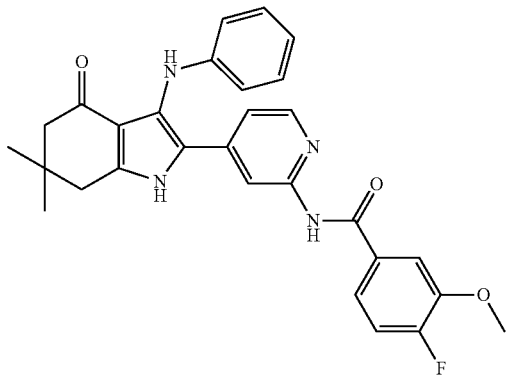

Using the Method G2 at 50° C.: Example 122 (100 mg, 289 μmol) gave the desired product (50 mg, 35%) after preparative HPLC purification (basic method).

1H-NMR (500 MHz, DMSO-d6), Shift [ppm]=1.07 (6H), 2.24 (2H), 2.76 (2H), 3.94 (3H), 6.56-6.63 (3H), 6.98-7.06 (2H), 7.25 (1H), 7.36 (1H), 7.41 (1H), 7.64 (1H), 7.85 (1H), 8.18 (1H), 8.34 (1H), 10.78 (1H), 11.93 (1H).

Example 475 Preparation of N-{4-[6,6-dimethyl-4-oxo-3-(phenylamino)-4,5,6,7-tetrahydro-1H-indol-2-yl]pyridin-2-yl}-2-fluoro-2-methylpropanamide

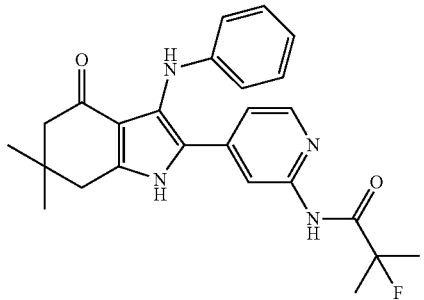 [SMILES: CC1(C)CC(=O)c2c([nH]c(-c3ccnc(NC(=O)C(C)(C)F)c3)c2Nc2ccccc2)C1]

Using the Method G2 at 50° C.: Example 122 (100 mg, 289 μmol) gave the desired product (54 mg, 41%) after preparative HPLC purification (basic method).

1H-NMR (500 MHz, DMSO-d6), Shift [ppm]=1.07 (6H), 1.55 (3H), 1.59 (3H), 2.24 (2H), 2.75 (2H), 6.50-6.69 (3H), 7.01 (2H), 7.19-7.30 (1H), 7.42 (1H), 8.07-8.20 (2H), 9.71 (1H), 11.92 (1H).

Example 476 Preparation of 2-(benzyloxy)-N-{4-[6,6-dimethyl-4-oxo-3-(phenylamino)-4,5,6,7-tetrahydro-1H-indol-2-yl]pyridin-2-yl}acetamide

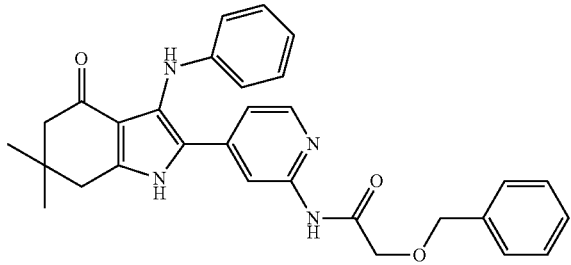 [SMILES: CC1(C)CC(=O)c2c([nH]c(-c3ccnc(NC(=O)COCc4ccccc4)c3)c2Nc2ccccc2)C1]

Using the Method G2 at 50° C.: Example 122 (100 mg, 289 μmol) gave the desired product (57 mg, 38%) after preparative HPLC purification (basic method).

1H-NMR (600 MHz, DMSO-d6), Shift [ppm]=1.03-1.13 (6H), 2.23 (2H), 2.75 (2H), 4.16 (2H), 4.60 (2H), 6.53-6.65 (3H), 7.01 (2H), 7.21 (1H), 7.32 (1H), 7.36-7.41 (5H), 8.09 (1H), 8.24 (1H), 9.85 (1H), 11.89 (1H).

Example 477 Preparation of N-{4-[6,6-dimethyl-4-oxo-3-(phenylamino)-4,5,6,7-tetrahydro-1H-indol-2-yl]pyridin-2-yl}-2,2-difluorocyclopropanecarboxamide

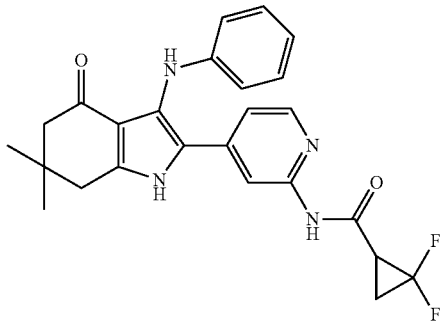 [SMILES: CC1(C)CC(=O)c2c([nH]c(-c3ccnc(NC(=O)C4CC4(F)F)c3)c2Nc2ccccc2)C1]

Using the Method G2 at 50° C.: Example 122 (100 mg, 289 μmol) gave the desired product (50 mg, 37%) after preparative HPLC purification (basic method).

1H-NMR (500 MHz, DMSO-d6), Shift [ppm]=1.06 (6H), 1.95-2.06 (2H), 2.23 (2H), 2.74 (2H), 2.92-3.04 (1H), 6.55 (2H), 6.57-6.63 (1H), 7.01 (2H), 7.18-7.23 (1H), 7.38 (1H), 8.08-8.12 (1H), 8.21 (1H), 10.87 (1H), 11.90 (1H).

Example 478 Preparation of 1-benzyl-N-{4-[6,6-dimethyl-4-oxo-3-(phenylamino)-4,5,6,7-tetrahydro-1H-indol-2-yl]pyridin-2-yl}-1H-pyrazole-4-carboxamide

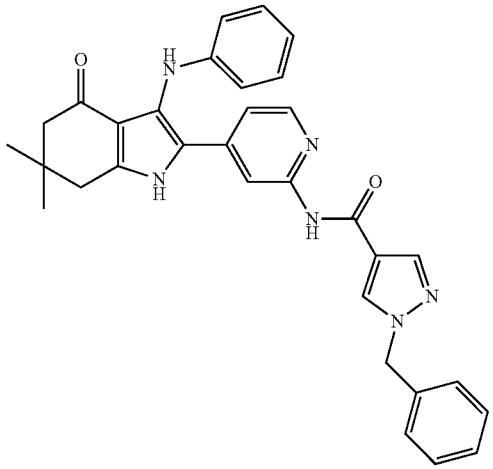 [SMILES: CC1(C)CC(=O)c2c([nH]c(-c3ccnc(NC(=O)c4cnn(Cc5ccccc5)c4)c3)c2Nc2ccccc2)C1]

Using the Method G2 at 50° C.: Example 122 (100 mg, 289 μmol) gave the desired product (40 mg, 25%) after preparative HPLC purification (basic method).

1H-NMR (600 MHz, DMSO-d6), Shift [ppm]=1.03-1.12 (6H), 2.23 (2H), 2.75 (2H), 5.38 (2H), 6.53-6.62 (3H), 7.01 (2H), 7.20 (1H), 7.26-7.43 (6H), 8.12 (1H), 8.15 (1H), 8.31 (1H), 8.56 (1H), 10.38 (1H), 11.88 (1H).

Example 479 Preparation of N-{4-[6,6-dimethyl-4-oxo-3-(phenylamino)-4,5,6,7-tetrahydro-1H-indol-2-yl]pyridin-2-yl}-1-(4-methoxybenzyl)-1H-pyrazole-4-carboxamide

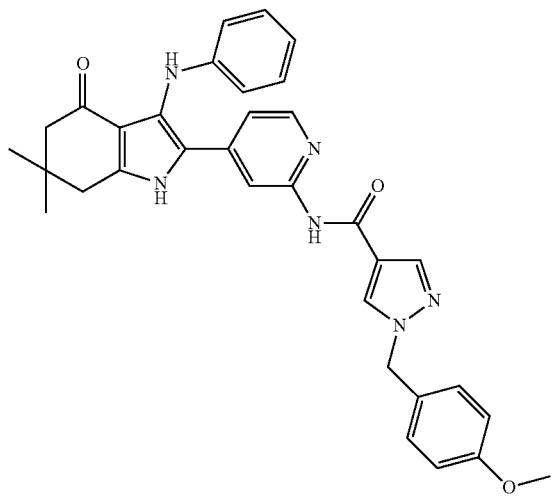

Using the Method G2 at 50° C.: Example 122 (100 mg, 289 µmol) gave the desired product (29 mg, 17%) after preparative HPLC purification (basic method).

1H-NMR (600 MHz, DMSO-d6), Shift [ppm]=1.03-1.10 (6H), 2.23 (2H), 2.75 (2H), 3.72-3.77 (3H), 5.28 (2H), 6.53-6.64 (3H), 6.90-6.96 (2H), 7.01 (2H), 7.19 (1H), 7.25-7.30 (2H), 7.36 (1H), 8.08-8.15 (2H), 8.30 (1H), 8.51 (1H), 10.36 (1H), 11.88 (1H).

Example 480 Preparation of N-{4-[6,6-dimethyl-4-oxo-3-(phenylamino)-4,5,6,7-tetrahydro-1H-indol-2-yl]pyridin-2-yl}-1,3-thiazole-5-carboxamide

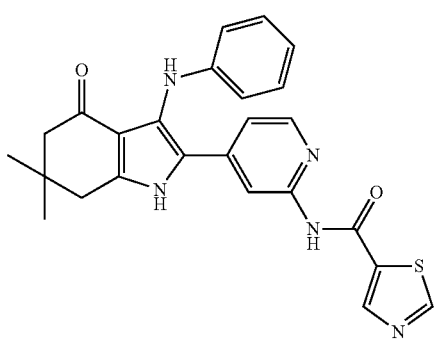 [SMILES: CC1(C)CC(=O)c2c([nH]c(-c3ccnc(NC(=O)c4cncs4)c3)c2Nc2ccccc2)C1]

Using the Method G2 at 50° C.: Example 122 (100 mg, 289 µmol) gave the desired product (54 mg, 39%) after preparative HPLC purification (basic method).

1H-NMR (600 MHz, DMSO-d6), Shift [ppm]=1.07 (6H), 2.24 (2H), 2.76 (2H), 6.55-6.64 (3H), 7.02 (2H), 7.26 (1H), 7.40 (1H), 8.18 (1H), 8.27 (1H), 8.87 (1H), 9.32 (1H), 11.06 (1H), 11.91 (1H).

Example 481 Preparation of 3-{[2-(hydroxymethyl)-5-methylphenyl]amino}-6,6-dimethyl-2-(pyridin-4-yl)-1,5,6,7-tetrahydro-4H-indol-4-one

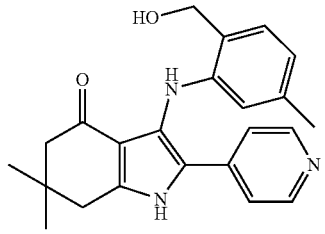

Synthesized according to Method F2. Intermediate 1-6-1 (100 mg) gave the desired product (3 mg, 2%) after preparative HPLC (acidic method).

1H-NMR (600 MHz, DMSO-d6), Shift [ppm]=1.08 (6H), 1.88 (3H), 2.25 (2H), 2.76 (2H), 4.56 (2H), 5.21 (1H), 6.10 (1H), 6.48 (1H), 7.06 (1H), 7.25-7.29 (2H), 7.59 (1H), 8.32 (2H), 11.78 (1H).

Example 482 Preparation of 3-{[2-(hydroxymethyl)-4-methylphenyl]amino}-6,6-dimethyl-2-(pyridin-4-yl)-1,5,6,7-tetrahydro-4H-indol-4-one

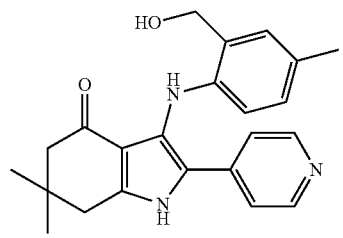

Synthesized according to Method F2. Intermediate 1-6-1 (100 mg) gave the desired product (16 mg, 14%) after preparative HPLC (acidic method).

1H-NMR (600 MHz, DMSO-d6), Shift [ppm]=1.06-1.11 (6H), 2.14 (3H), 2.25 (2H), 2.75 (2H), 4.58 (2H), 5.25 (1H), 6.21 (1H), 6.63-6.69 (1H), 7.01-7.04 (1H), 7.25-7.30 (2H), 7.49 (1H), 8.24-8.36 (2H), 11.77 (1H).

Example 483 Preparation of 3-{[2-(hydroxymethyl)-3-methylphenyl]amino}-6,6-dimethyl-2-(pyridin-4-yl)-1,5,6,7-tetrahydro-4H-indol-4-one

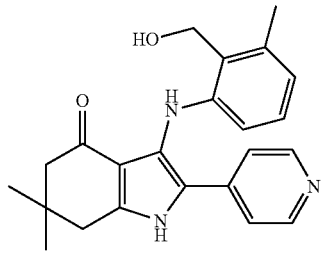 [SMILES: Cc1cccc(Nc2c(-c3ccncc3)[nH]c3c2C(=O)CC(C)(C)C3)c1CO]

Synthesized according to Method F2. Intermediate 1-6-1 (100 mg) gave the desired product (5 mg, 4%) after preparative HPLC (acidic method).

1H-NMR (600 MHz, DMSO-d6), Shift [ppm]=1.08 (6H), 2.25 (2H), 2.34 (3H), 2.75 (2H), 4.65 (2H), 5.08 (1H), 6.21 (1H), 6.54 (1H), 6.70-6.77 (1H), 7.25-7.31 (2H), 7.78 (1H), 8.24-8.38 (2H), 11.77 (1H).

Example 484 Preparation of 3-(phenylamino)-2-{2-[(4-phenylbutyl)amino]pyridin-4-yl}-1,5,6,7-tetrahydro-4H-indol-4-one

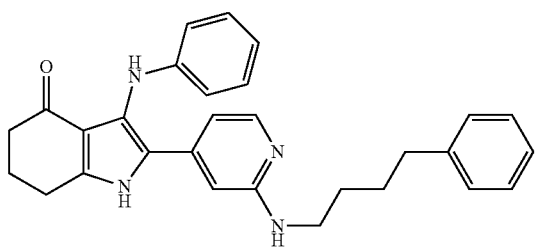 [SMILES: O=C1CCCc2[nH]c(-c3ccnc(NCCCCc4ccccc4)c3)c(Nc3ccccc3)c21]

To a solution of Example 139 (100 mg, 314 µmol) in MeOH (2.8 mL) was added 4-phenylbutanal (233 mg, 1.57 mmol) in AcOH (288 µL) and stirred at RT for 16 h. The reaction was cooled to 0° C. and NaBH₃CN (50 mg, 236 µmol) was added and stirred at RT for 16 h. Concentrated and purified by preparative HPLC (basic method) to give the desired product (30 mg, 21%).

1H-NMR (400 MHz, DMSO-d6), Shift [ppm]=1.40 (2H), 1.47-1.57 (2H), 1.95-2.09 (2H), 2.26-2.37 (3H), 2.52-2.58 (2H), 2.83 (2H), 2.99 (2H), 6.22 (1H), 6.46-6.53 (1H), 6.53-6.64 (3H), 6.69 (1H), 6.95-7.08 (2H), 7.12-7.20 (3H), 7.22-7.31 (3H), 7.81 (1H), 11.68 (1H).

Example 485 Preparation of 3-{[4-fluoro-2-(hydroxymethyl)phenyl]amino}-6,6-dimethyl-2-(pyridin-4-yl)-1,5,6,7-tetrahydro-4H-indol-4-one

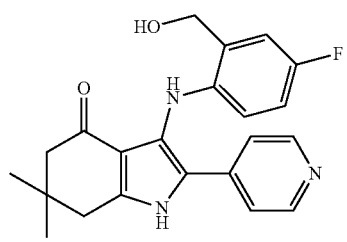 [SMILES: CC1(C)CC(=O)c2c([nH]c(-c3ccncc3)c2Nc2ccc(F)cc2CO)C1]

Synthesized according to Method F2. Intermediate 1-6-1 (100 mg) gave the desired product (12 mg, 10%) after preparative HPLC (basic method).

1H-NMR (500 MHz, DMSO-d6), Shift [ppm]=1.07 (6H), 2.25 (2H), 2.75 (2H), 4.60 (2H), 5.45 (1H), 6.26 (1H), 6.68 (1H), 7.09 (1H), 7.27-7.33 (2H), 7.38 (1H), 8.26-8.45 (2H), 11.85 (1H).

Example 486 Preparation of 3-{[3-fluoro-2-(hydroxymethyl)phenyl]amino}-6,6-dimethyl-2-(pyridin-4-yl)-1,5,6,7-tetrahydro-4H-indol-4-one

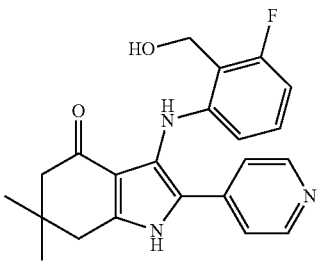 [SMILES: CC1(C)CC(=O)c2c([nH]c(-c3ccncc3)c2Nc2cccc(F)c2CO)C1]

Synthesized according to Method F2. Intermediate 1-6-1 (100 mg) gave the desired product (21 mg, 17%) after preparative HPLC (basic method).

1H-NMR (600 MHz, DMSO-d6), Shift [ppm]=1.08 (6H), 2.25 (2H), 2.76 (2H), 4.68 (2H), 5.34 (1H), 6.14 (1H), 6.48 (1H), 6.85 (1H), 7.34 (2H), 7.81 (1H), 8.35 (2H), 11.85 (1H).

Example 487 Preparation of 3-{[5-fluoro-2-(hydroxymethyl)phenyl]amino}-6,6-dimethyl-2-(pyridin-4-yl)-1,5,6,7-tetrahydro-4H-indol-4-one

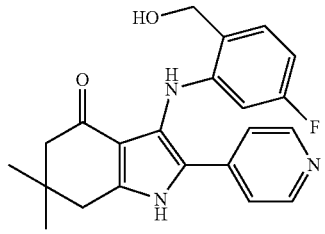

Synthesized according to Method F2. Intermediate 1-6-1 (100 mg) gave the desired product (9 mg, 7%) after preparative HPLC (basic method).

1H-NMR (600 MHz, DMSO-d6), Shift [ppm]=1.06-1.09 (6H), 2.25 (2H), 2.76 (2H), 4.58 (2H), 5.33 (1H), 5.96 (1H), 6.42 (1H), 7.19 (1H), 7.30-7.45 (2H), 7.66 (1H), 8.38 (2H), 11.90 (1H).

Example 488 Preparation of 3-{[2-(2-hydroxypropan-2-yl)phenyl]amino}-6,6-dimethyl-2-(pyridin-4-yl)-1,5,6,7-tetrahydro-4H-indol-4-one

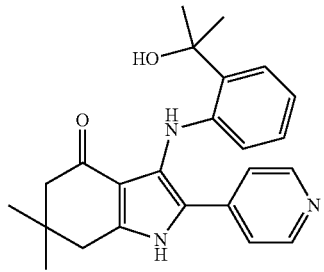 [SMILES: CC1(C)CC(=O)c2c([nH]c(-c3ccncc3)c2Nc2ccccc2C(C)(C)O)C1]

Synthesized according to Method F2. Intermediate 1-6-1 (100 mg) gave the desired product (8 mg, 6%) after preparative HPLC (basic method).

1H-NMR (600 MHz, DMSO-d6), Shift [ppm]=1.08 (6H), 1.62-1.67 (6H), 2.24 (2H), 2.73-2.77 (2H), 5.53 (1H), 6.36 (1H), 6.60 (1H), 6.73-6.80 (1H), 7.14-7.20 (1H), 7.31 (2H), 8.30 (2H), 8.84 (1H), 11.75 (1H).

Example 489 Preparation of 3-(phenylamino)-2-{2-[(2-phenylethyl)amino]pyridin-4-yl}-1,5,6,7-tetrahydro-4H-indol-4-one

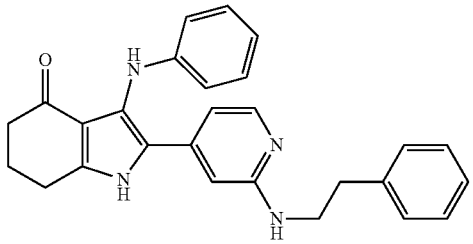 [SMILES: O=C1CCCc2[nH]c(-c3ccnc(NCCc4ccccc4)c3)c(Nc3ccccc3)c21]

To a solution of Example 139 (100 mg, 314 µmol) in MeOH (2.8 mL) was added phenylacetaldehyde (189 mg, 1.57 mmol) in AcOH (288 µL) and stirred at RT for 16 h. The reaction was cooled to 0° C. and NaBH₃CN (50 mg, 236 µmol) was added and stirred at RT for 16 h. Concentrated and purified by preparative HPLC (basic method) to give the desired product (20 mg, 15%).

1H-NMR (400 MHz, DMSO-d6), Shift [ppm]=1.99-2.10 (2H), 2.27-2.34 (2H), 2.72 (2H), 2.84 (2H), 3.17-3.27 (2H), 6.28 (1H), 6.51-6.64 (4H), 6.72 (1H), 7.01 (2H), 7.15-7.21 (3H), 7.26-7.32 (3H), 7.84 (1H), 11.70 (1H).

Example 490 Preparation of 3-(phenylamino)-2-{2-[(3-phenylpropyl)amino]pyridin-4-yl}-1,5,6,7-tetrahydro-4H-indol-4-one

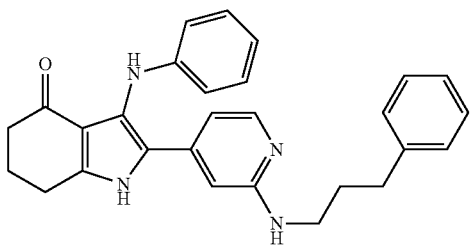 [SMILES: O=C1CCCc2[nH]c(-c3ccnc(NCCCc4ccccc4)c3)c(Nc3ccccc3)c21]

To a solution of Example 139 (100 mg, 314 µmol) in MeOH (2.8 mL) was added 3-phenylpropionaldehyde (211 mg, 1.57 mmol) in AcOH (288 µL) and stirred at RT for 16 h. The reaction was cooled to 0° C. and NaBH₃CN (50 mg, 236 µmol) was added and stirred at RT for 16 h. Concentrated and purified by preparative HPLC (basic method) to give the desired product (30 mg, 22%).

1H-NMR (400 MHz, DMSO-d6), Shift [ppm]=1.70 (2H), 1.97-2.11 (2H), 2.25-2.38 (2H), 2.52-2.59 (2H), 2.84 (2H), 3.00 (2H), 6.29 (1H), 6.52 (1H), 6.54-6.63 (3H), 6.70 (1H), 7.02 (2H), 7.14-7.21 (3H), 7.24-7.31 (3H), 7.82 (1H), 11.69 (1H).

Example 491 Preparation of 4-(ethoxyimino)-6,6-dimethyl-N-phenyl-2-(pyridin-4-yl)-4,5,6,7-tetrahydro-1H-indol-3-amine

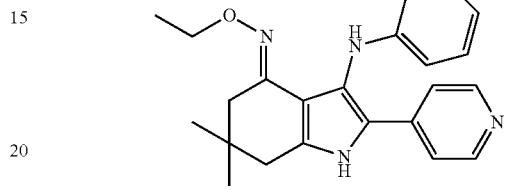

A mixture of Example 1 (50 mg, 151 µmol) and O-ethylhydroxylamine hydrochloride (41.5 mg, 679 µmol) in EtOH (2 mL) in a sealed tube was heated at 100° C. for 48 h. Additional O-ethylhydroxylamine hydrochloride (92 mg, 1.5 mmol) added and heated at 150° C. using a microwave for 6 h. Additional O-ethylhydroxylamine hydrochloride (184 mg, 3 mmol) and heated at 150° C. for 8 h using a microwave. Concentrated and purified by preparative HPLC (basic method), followed by purification by preparative TLC to give the desired product (7.1 mg, 12%).

1H-NMR (500 MHz, DMSO-d6), Shift [ppm]=1.01 (6H), 1.09 (3H), 2.41 (2H), 2.56 (2H), 3.94 (2H), 6.55 (2H), 6.61-6.66 (1H), 7.05 (2H), 7.14 (1H), 7.47-7.50 (2H), 8.30-8.46 (2H), 11.45 (1H).

Example 492 Preparation of N-{4-[4-oxo-3-(phenylamino)-4,5,6,7-tetrahydro-1H-indol-2-yl]pyridin-2-yl}-2-(pyridin-3-ylmethoxy)acetamide

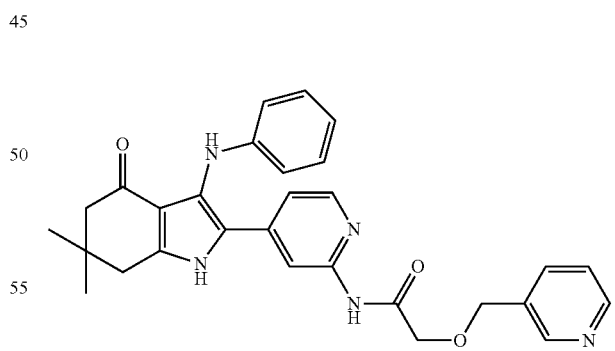

Using the Method G2 at 50° C.: Example 139 (100 mg, 314 µmol) gave the desired product (30 mg, 20%) after preparative HPLC (basic method).

1H-NMR (600 MHz, DMSO-d6), Shift [ppm]=2.05 (2H), 2.33 (2H), 2.83-2.91 (2H), 4.19 (2H), 4.64 (2H), 6.54-6.63 (3H), 6.98-7.07 (2H), 7.19 (1H), 7.36-7.39 (1H), 7.39-7.44 (1H), 7.80-7.86 (1H), 8.09 (1H), 8.24 (1H), 8.53 (1H), 8.60 (1H), 9.95 (1H), 11.93 (1H).

Example 493 Preparation of 2-[(1-methyl-1H-imidazol-2-yl)methoxy]-N-{4-[4-oxo-3-(phenylamino)-4,5,6,7-tetrahydro-1H-indol-2-yl]pyridin-2-yl}acetamide

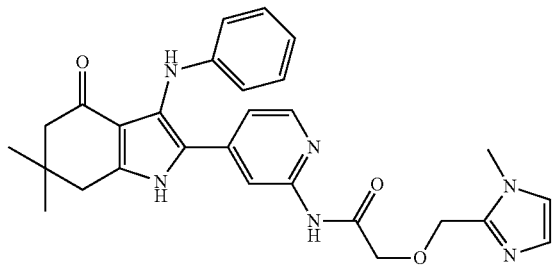 [SMILES: Cn1ccnc1COCC(=O)Nc1cc(-c2[nH]c3c(c2Nc2ccccc2)C(=O)CC(C)(C)C3)ccn1]

Using the Method G2 at 50° C.: Example 139 (100 mg, 314 μmol) gave the desired product (20 mg, 14%) after preparative HPLC (basic method).

1H-NMR (600 MHz, DMSO-d6), Shift [ppm]=2.05 (2H), 2.33 (2H), 2.86 (2H), 3.70 (3H), 4.13 (2H), 4.63 (2H), 6.53-6.63 (3H), 6.83 (1H), 6.98-7.03 (2H), 7.14-7.16 (1H), 7.18 (1H), 7.38 (1H), 8.09 (1H), 8.22 (1H), 9.99 (1H), 11.93 (1H).

Example 494 Preparation of 2-[(1-methyl-1H-1,2,4-triazol-5-yl)methoxy]-N-{4-[4-oxo-3-(phenylamino)-4,5,6,7-tetrahydro-1H-indol-2-yl]pyridin-2-yl}acetamide

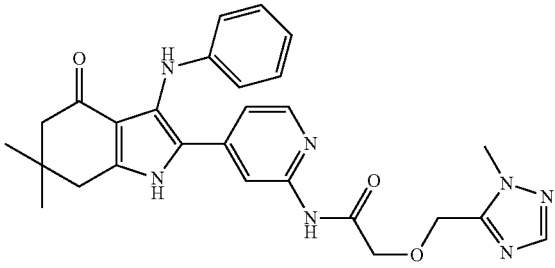 [SMILES: Cn1ncnc1COCC(=O)Nc1cc(-c2[nH]c3c(c2Nc2ccccc2)C(=O)CC(C)(C)C3)ccn1]

Using the Method G2 at 50° C.: Example 139 (100 mg, 314 μmol) gave the desired product (30 mg, 20%) after preparative HPLC (basic method).

1H-NMR (600 MHz, DMSO-d6), Shift [ppm]=2.05 (2H), 2.33 (2H), 2.87 (2H), 3.92 (3H), 4.21 (2H), 4.77 (2H), 6.53-6.62 (3H), 6.96-7.04 (2H), 7.19 (1H), 7.38 (1H), 7.90 (1H), 8.09 (1H), 8.22 (1H), 10.10 (1H), 11.92 (1H).

Example 495 Preparation of N-{4-[4-oxo-3-(phenylamino)-4,5,6,7-tetrahydro-1H-indol-2-yl]pyridin-2-yl}-2-(pyridin-2-ylmethoxy)acetamide

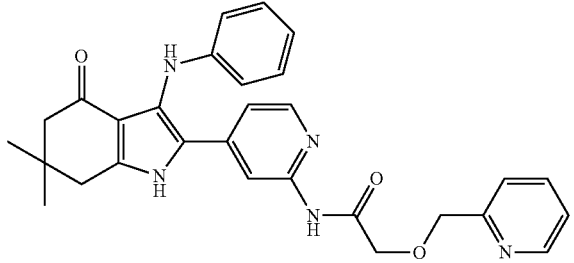 [SMILES: CC1(C)CC(=O)c2c([nH]c(-c3ccnc(NC(=O)COCc4ccccn4)c3)c2Nc2ccccc2)C1]

Using the Method G2 at 50° C.: Example 139 (100 mg, 314 μmol) gave the desired product (20 mg, 14%) after preparative HPLC (basic method).

1H-NMR (600 MHz, DMSO-d6), Shift [ppm]=2.05 (2H), 2.33 (2H), 2.86 (2H), 4.25 (2H), 4.72 (2H), 6.50-6.64 (3H), 7.01 (2H), 7.19 (1H), 7.33 (1H), 7.38 (1H), 7.51 (1H), 7.84 (1H), 8.10 (1H), 8.25 (1H), 8.56 (1H), 10.23 (1H), 11.93 (1H).

Example 496 Preparation of 2-[(4-methyl-1,3-thiazol-5-yl)methoxy]-N-{4-[4-oxo-3-(phenylamino)-4,5,6,7-tetrahydro-1H-indol-2-yl]pyridin-2-yl}acetamide

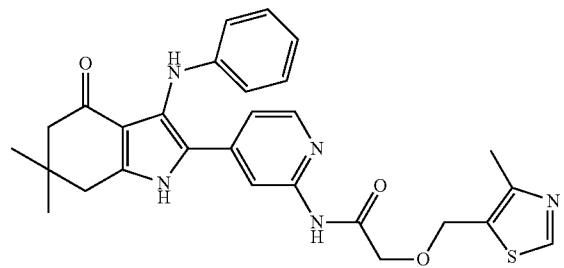 [SMILES: Cc1ncsc1COCC(=O)Nc1cc(-c2[nH]c3c(c2Nc2ccccc2)C(=O)CC(C)(C)C3)ccn1]

Using the Method G2 at 50° C.: Example 139 (100 mg, 314 μmol) gave the desired product (40 mg, 26%) after preparative HPLC (basic method).

1H-NMR (600 MHz, DMSO-d6), Shift [ppm]=2.05 (2H), 2.33 (2H), 2.38 (3H), 2.87 (2H), 4.16 (2H), 4.78 (2H), 6.51-6.67 (3H), 7.01 (2H), 7.19 (1H), 7.38 (1H), 8.09 (1H), 8.23 (1H), 8.98 (1H), 9.93 (1H), 11.93 (1H).

Example 497 Preparation of 6,6-dimethyl-3-(phenylamino)-2-{2-[(3-phenylpropyl)amino]pyridin-4-yl}-1,5,6,7-tetrahydro-4H-indol-4-one

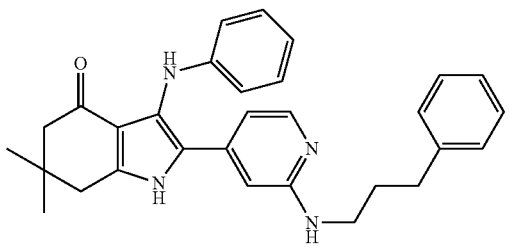 [SMILES: CC1(C)CC(=O)c2c([nH]c(-c3ccnc(NCCCc4ccccc4)c3)c2Nc2ccccc2)C1]

To a solution of Example 122 (100 mg, 289 μmol) in MeOH (2.6 mL) was added 3-phenylpropionaldehyde (194 mg, 1.44 mmol) in AcOH (264 μL) and stirred at RT for 16 h. The reaction was cooled to 0° C. and NaBH₃CN (181 mg, 2.9 mmol) was added and stirred at RT for 16 h. Concentrated and purified by preparative HPLC (basic method) to give the desired product (20 mg, 15%).

1H-NMR (600 MHz, DMSO-d6), Shift [ppm]=1.03-1.11 (6H), 1.71 (2H), 2.21 (2H), 2.53-2.58 (2H), 2.72 (2H), 3.01 (2H), 6.25 (1H), 6.53 (1H), 6.54-6.61 (3H), 6.70 (1H), 7.02 (2H), 7.14-7.22 (3H), 7.24-7.31 (3H), 7.82 (1H), 11.62 (1H).

Example 498 Preparation of 6,6-dimethyl-3-(phenylamino)-2-{2-[(2-phenylethyl)amino]pyridin-4-yl}-1,5,6,7-tetrahydro-4H-indol-4-one

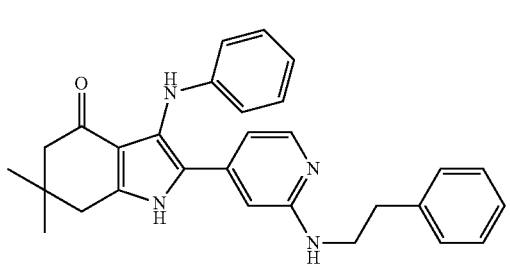 [SMILES: CC1(C)CC(=O)c2c([nH]c(-c3ccnc(NCCc4ccccc4)c3)c2Nc2ccccc2)C1]

To a solution of Example 122 (100 mg, 289 μmol) in MeOH (2.6 mL) was added phenylacetaldehyde (173 mg, 1.44 mmol) in AcOH (264 μL) and stirred at RT for 16 h. The reaction was cooled to 0° C. and NaBH$_3$CN (181 mg, 2.9 mmol) was added and stirred at RT for 16 h. Concentrated and purified by preparative HPLC (basic method) to give the desired product (5 mg, 4%).

1H-NMR (600 MHz, DMSO-d6), Shift [ppm]=1.06 (6H), 2.21 (2H), 2.69-2.76 (4H), 3.24 (2H), 6.22 (1H), 6.53-6.57 (3H), 6.59 (1H), 6.73 (1H), 6.97-7.04 (2H), 7.15-7.22 (3H), 7.24-7.31 (3H), 7.84 (1H), 11.64 (1H).

Example 499 Preparation of 2-{2-[(4-fluorobenzyl)amino]pyridin-4-yl}-3-(phenylamino)-1,5,6,7-tetrahydro-4H-indol-4-one

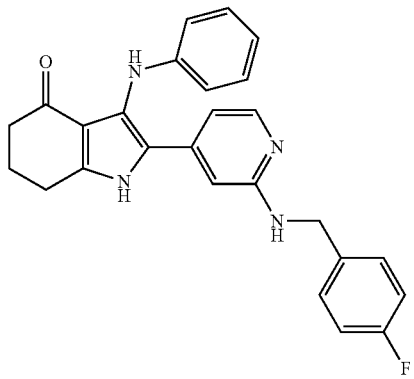 [SMILES: O=C1CCCc2[nH]c(-c3ccnc(NCc4ccc(F)cc4)c3)c(Nc3ccccc3)c21]

To a solution of Example 139 (100 mg, 314 μmol) in MeOH (2.8 mL) was added 4-fluorobenzaldehyde (195 mg, 1.57 mmol) in AcOH (288 μL) and stirred at RT for 16 h. The reaction was cooled to 0° C. and NaBH$_3$CN (50 mg, 236 μmol) was added and stirred at RT for 16 h. Concentrated and purified by preparative HPLC (basic method) to give the desired product (30 mg, 22%).

1H-NMR (600 MHz, DMSO-d6), Shift [ppm]=2.03 (2H), 2.31 (2H), 2.83 (2H), 4.24 (2H), 6.54-6.59 (3H), 6.61-6.65 (1H), 6.71 (1H), 6.82 (1H), 7.01-7.09 (4H), 7.22 (2H), 7.27 (1H), 7.82 (1H), 11.66 (1H).

Example 500 Preparation of 3-(phenylamino)-2-{2-[(1,3-thiazol-5-ylmethyl)amino]pyridin-4-yl}-1,5,6,7-tetrahydro-4H-indol-4-one

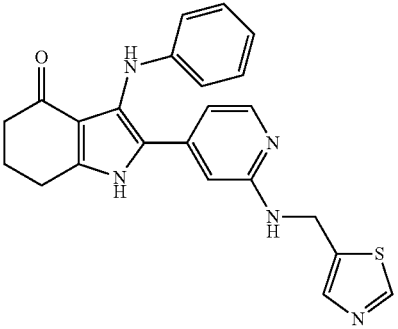 [SMILES: O=C1CCCc2[nH]c(-c3ccnc(NCc4cncs4)c3)c(Nc3ccccc3)c21]

To a solution of Example 139 (100 mg, 314 μmol) in MeOH (2.8 mL) was added 5-thiazolecarboxaldehyde (187 mg, 1.57 mmol) in AcOH (288 μL) and stirred at RT for 16 h. The reaction was cooled to 0° C. and NaBH$_3$CN (50 mg, 236 μmol) was added and stirred at RT for 16 h. Concentrated and purified by preparative HPLC (basic method) to give the desired product (20 mg, 15%).

1H-NMR (600 MHz, DMSO-d6), Shift [ppm]=2.03 (2H), 2.31 (2H), 2.83 (2H), 4.53 (2H), 6.56 (2H), 6.58-6.64 (2H), 6.76 (1H), 6.92 (1H), 7.02 (2H), 7.27 (1H), 7.66-7.73 (1H), 7.88 (1H), 8.79-8.90 (1H), 11.68 (1H).

Example 501 Preparation of 3-(phenylamino)-2-{2-[(1,3-thiazol-4-ylmethyl)amino]pyridin-4-yl}-1,5,6,7-tetrahydro-4H-indol-4-one

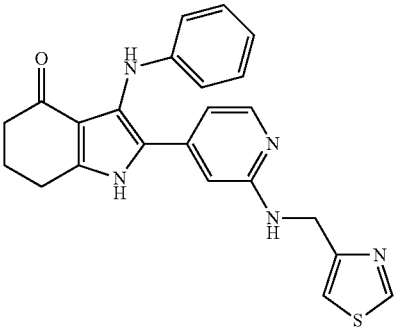 [SMILES: O=C1CCCc2[nH]c(-c3ccnc(NCc4cscn4)c3)c(Nc3ccccc3)c21]

To a solution of Example 139 (100 mg, 314 μmol) in MeOH (2.8 mL) was added 4-thiazolecarboxaldehyde (187 mg, 1.57 mmol) in AcOH (288 μL) and stirred at RT for 16 h. The reaction was cooled to 0° C. and NaBH$_3$CN (50 mg, 236 μmol) was added and stirred at RT for 16 h. Concentrated and purified by preparative HPLC (basic method) to give the desired product (20 mg, 15%).

1H-NMR (600 MHz, DMSO-d6), Shift [ppm]=2.04 (2H), 2.31 (2H), 2.83 (2H), 4.45 (2H), 6.56 (2H), 6.61 (1H), 6.66 (1H), 6.71-6.78 (2H), 7.00-7.06 (2H), 7.18-7.21 (1H), 7.27 (1H), 7.83 (1H), 9.01 (1H), 11.68 (1H).

Example 502 Preparation of N-{4-[4-oxo-3-(phenylamino)-4,5,6,7-tetrahydro-1H-indol-2-yl]pyridin-2-yl}-2-(2,2,2-trifluoroethoxy)acetamide

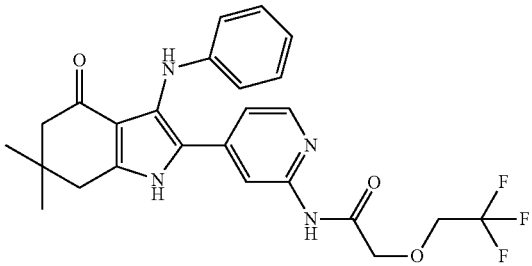 [SMILES: CC1(C)CC(=O)c2c([nH]c(-c3ccnc(NC(=O)COCC(F)(F)F)c3)c2Nc2ccccc2)C1]

Using the Method G2 at 50° C.: Example 139 (100 mg, 314 μmol) gave the desired product (20 mg, 14%) after preparative HPLC (basic method).
1H-NMR (400 MHz, DMSO-d6), Shift [ppm]=1.99-2.10 (2H), 2.33 (2H), 2.86 (2H), 4.21 (2H), 4.32 (2H), 6.51-6.66 (3H), 7.01 (2H), 7.18 (1H), 7.40 (1H), 8.09 (1H), 8.23 (1H), 10.17 (1H), 11.95 (1H).

Example 503 Preparation of 2-(pyridin-4-yl)-3-(pyridin-2-ylamino)-1,5,6,7-tetrahydro-4H-indol-4-one

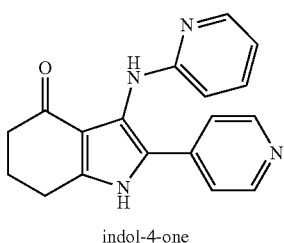 [SMILES: O=C1CCCc2[nH]c(-c3ccncc3)c(Nc3ccccn3)c21]

indol-4-one

Synthesis of Example 503

Intermediate 1-1-33

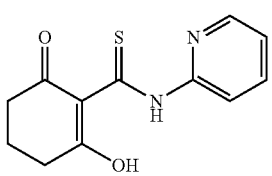 [SMILES: O=C1CCCC(O)=C1C(=S)Nc1ccccn1]

Synthesized according to Method A2. 1,3-cyclohexanedione (3.269 g) gave the desired Intermediate 1-1-33 (2.067 g, 27%) after silica chromatography.

Intermediate 1-2-87

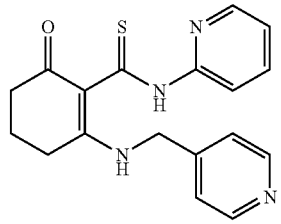 [SMILES: O=C1CCCC(NCc2ccncc2)=C1C(=S)Nc1ccccn1]

A solution of Intermediate 1-1-33 (2.06 g, 8.3 mmol) and 1-(pyridin-4-yl)methanamine (1.794 g, 1.698 mmol) in DMA (9.4 mL) was heated at 130° C. for 90 min. Concentrated and purified by preparative HPLC (basic method) to give the desired Intermediate 1-2-87 (700 mg, 25%).
1H-NMR (400 MHz, DMSO-d6), Shift [ppm]=1.80 (2H), 2.44-2.48 (2H), 2.78 (2H), 4.86 (2H), 7.21 (1H), 7.38-7.43 (2H), 7.77-7.85 (1H), 8.33-8.46 (2H), 8.57-8.64 (2H), 13.92 (1H), 15.11 (1H).

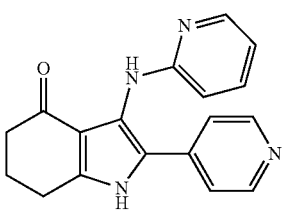 [SMILES: O=C1CCCc2[nH]c(-c3ccncc3)c(Nc3ccccn3)c21]

Using method F1 intermediate (695 mg, 2.1 mmol) gave the desired product (181 mg, 29%) after silica chromatography.
1H-NMR (400 MHz, DMSO-d6), Shift [ppm]=1.99-2.17 (2H), 2.25-2.36 (2H), 2.86 (2H), 6.36 (1H), 6.58 (1H), 7.37 (1H), 7.48-7.54 (2H), 7.93-7.96 (1H), 7.98 (1H), 8.40-8.48 (2H), 11.91 (1H).

Example 504 Preparation of N-{4-[6,6-dimethyl-4-oxo-3-(phenylamino)-4,5,6,7-tetrahydro-1H-indol-2-yl]pyridin-2-yl}-1-methyl-1H-pyrazole-3-carboxamide

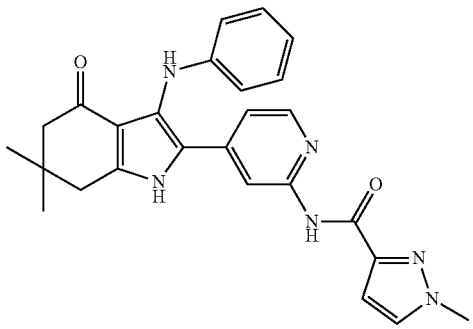

Using the Method G2 at 50° C.: Example 122 (100 mg, 314 μmol) gave the desired product (41 mg, 31%) after preparative HPLC (basic method).
1H-NMR (400 MHz, DMSO-d6), Shift [ppm]=1.07 (6H), 2.24 (2H), 2.76 (2H), 3.96 (3H), 6.54-6.64 (3H), 6.84 (1H), 6.96-7.07 (2H), 7.23 (1H), 7.41 (1H), 7.89 (1H), 8.13 (1H), 8.30-8.37 (1H), 9.41 (1H), 11.95 (1H).

Example 505 Preparation of N-{4-[6,6-dimethyl-4-oxo-3-(phenylamino)-4,5,6,7-tetrahydro-1H-indol-2-yl]pyridin-2-yl}-1,3-thiazole-2-carboxamide

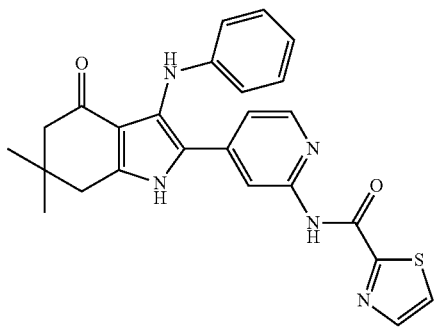 [SMILES: CC1(C)CC(=O)c2c([nH]c(-c3ccnc(NC(=O)c4nccs4)c3)c2Nc2ccccc2)C1]

Using the Method G2 at 50° C.: Example 122 (100 mg, 314 μmol) gave the desired product (55 mg, 42%) after preparative HPLC (basic method).

1H-NMR (400 MHz, DMSO-d6), Shift [ppm]=1.07 (6H), 2.25 (2H), 2.77 (2H), 6.55-6.66 (3H), 7.02 (2H), 7.30 (1H), 7.44 (1H), 8.13 (1H), 8.19 (2H), 8.27-8.31 (1H), 10.01 (1H), 11.98 (1H).

Example 506 Preparation of N-{4-[6,6-dimethyl-4-oxo-3-(phenylamino)-4,5,6,7-tetrahydro-1H-indol-2-yl]pyridin-2-yl}-1-methyl-1H-pyrazole-4-carboxamide

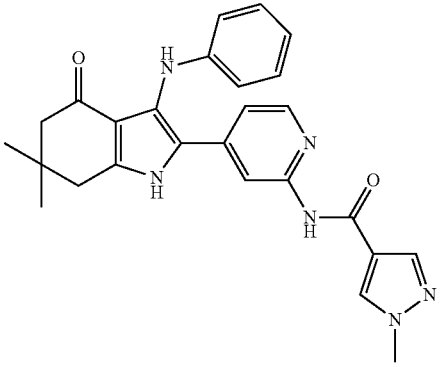 [SMILES: Cn1cc(C(=O)Nc2cc(-c3[nH]c4c(c3Nc3ccccc3)C(=O)CC(C)(C)C4)ccn2)cn1]

Using the Method G2 at 50° C.: Example 122 (100 mg, 314 μmol) gave the desired product (14 mg, 11%) after preparative HPLC (basic method) and silica chromatography.

1H-NMR (400 MHz, DMSO-d6), Shift [ppm]=1.07 (6H), 2.23 (2H), 2.75 (2H), 3.88 (3H), 6.54-6.64 (3H), 7.02 (2H), 7.20 (1H), 7.38 (1H), 8.09-8.17 (2H), 8.30-8.35 (1H), 8.42 (1H), 10.36 (1H), 11.92 (1H).

Example 507 Preparation of 6,6-dimethyl-3-(phenylamino)-2-{2-[(4-phenylbutyl)amino]pyridin-4-yl}-1,5,6,7-tetrahydro-4H-indol-4-one

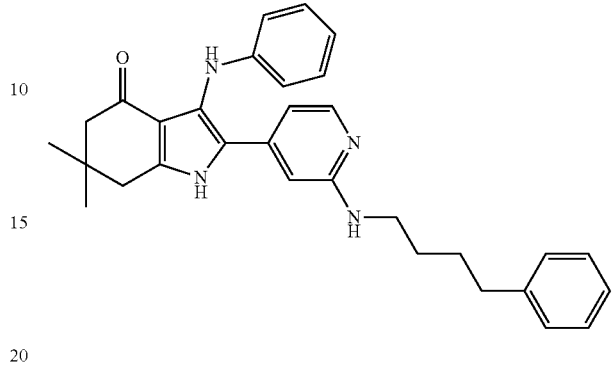

To a solution of Example 122 (100 mg, 289 μmol) in MeOH (2.6 mL) was added 4-phenylbutanal (214 mg, 1.44 mmol) in AcOH (264 μL) and stirred at RT for 16 h. The reaction was cooled to 0° C. and NaBH₃CN (181 mg, 2.9 mmol) was added and stirred at RT for 16 h. Concentrated and purified by preparative HPLC (basic method) to give the desired product (30 mg, 22%).

1H-NMR (500 MHz, DMSO-d6), Shift [ppm]=1.06 (6H), 1.33-1.46 (2H), 1.48-1.58 (2H), 2.21 (2H), 2.52-2.56 (2H), 2.72 (2H), 2.99 (2H), 6.22 (1H), 6.49-6.51 (1H), 6.55 (2H), 6.57-6.61 (1H), 6.69 (1H), 7.01 (2H), 7.13-7.20 (3H), 7.23-7.29 (3H), 7.81 (1H), 11.64 (1H).

Example 508 Preparation of 6,6-dimethyl-3-(phenylamino)-2-{2-[(1,3-thiazol-5-ylmethyl)amino]pyridin-4-yl}-1,5,6,7-tetrahydro-4H-indol-4-one

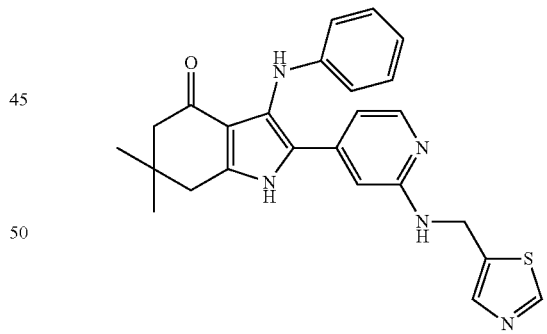

To a solution of Example 122 (100 mg, 289 μmol) in MeOH (2.6 mL) was added 5-thiazolecarboxaldehyde (172 mg, 1.44 mmol) in AcOH (264 μL) and stirred at RT for 16 h. The reaction was cooled to 0° C. and NaBH₃CN (181 mg, 2.9 mmol) was added and stirred at RT for 16 h. Concentrated and purified by preparative HPLC (basic method) to give the desired product (15 mg, 12%).

1H-NMR (500 MHz, DMSO-d6), Shift [ppm]=1.05 (6H), 2.21 (2H), 2.72 (2H), 4.53 (2H), 6.55 (2H), 6.58-6.62 (2H), 6.77 (1H), 6.95 (1H), 7.02 (2H), 7.29 (1H), 7.69 (1H), 7.88 (1H), 8.87 (1H), 11.66 (1H).

Example 509 Preparation of 2-{2-[(cyclopropylmethyl)amino]pyridin-4-yl}-6,6-dimethyl-3-(phenylamino)-1,5,6,7-tetrahydro-4H-indol-4-one

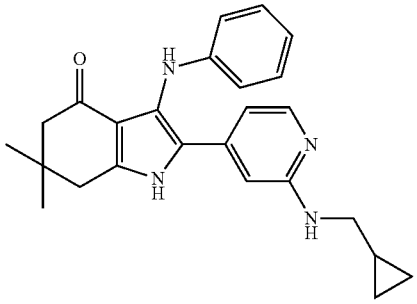 [SMILES: CC1(C)CC(=O)c2c([nH]c(-c3ccnc(NCC4CC4)c3)c2Nc2ccccc2)C1]

To a solution of Example 122 (100 mg, 289 μmol) in MeOH (2.6 mL) was added cyclopropanecarboxaldehyde (106 mg, 1.44 mmol) in AcOH (264 μL) and stirred at RT for 16 h. The reaction was cooled to 0° C. and NaBH$_3$CN (181 mg, 2.9 mmol) was added and stirred at RT for 16 h. Concentrated and purified by preparative HPLC (basic method) to give the desired product (6 mg, 5%).

1H-NMR (500 MHz, DMSO-d6), Shift [ppm]=0.06-0.13 (2H), 0.31-0.37 (2H), 0.83-0.95 (1H), 1.06 (6H), 2.21 (2H), 2.73 (2H), 2.86 (2H), 6.26 (1H), 6.52-6.57 (3H), 6.57-6.61 (1H), 6.70 (1H), 7.02 (2H), 7.27 (1H), 7.81 (1H), 11.64 (1H).

Example 510 Preparation of 3-{[4-(hydroxymethyl)pyridin-3-yl]amino}-6,6-dimethyl-2-(pyridin-4-yl)-1,5,6,7-tetrahydro-4H-indol-4-one

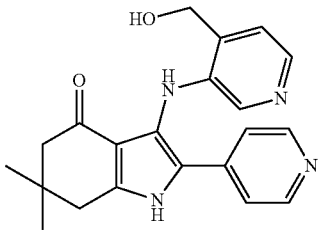 [SMILES: CC1(C)CC(=O)c2c([nH]c(-c3ccncc3)c2Nc2cnccc2CO)C1]

Synthesized according to Method F2. Intermediate 1-6-1 (100 mg) gave the desired product (23 mg, 19%) after preparative HPLC (basic method).

1H-NMR (400 MHz, DMSO-d6), Shift [ppm]=1.08 (6H), 2.24 (2H), 2.77 (2H), 4.61 (2H), 5.54 (1H), 7.24 (1H), 7.29 (1H), 7.39-7.43 (2H), 7.50 (1H), 7.88 (1H), 8.34-8.43 (2H), 11.93 (1H).

Example 511 Preparation of 3-{[3-(hydroxymethyl)pyridin-2-yl]amino}-6,6-dimethyl-2-(pyridin-4-yl)-1,5,6,7-tetrahydro-4H-indol-4-one

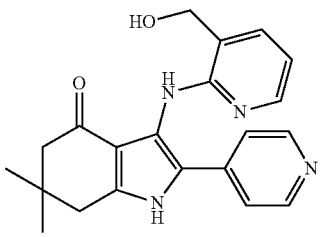 [SMILES: CC1(C)CC(=O)c2c([nH]c(-c3ccncc3)c2Nc2ncccc2CO)C1]

Synthesized according to Method F2. Intermediate 1-6-1 (100 mg) gave the desired product (4 mg, 3%) after preparative HPLC (basic method).

1H-NMR (400 MHz, DMSO-d6), Shift [ppm]=1.04-1.10 (6H), 2.21 (2H), 2.74 (2H), 4.57 (2H), 5.44 (1H), 6.60 (1H), 7.33-7.38 (2H), 7.49 (1H), 7.67 (1H), 7.89 (1H), 8.27-8.36 (2H), 11.75 (1H).

Example 513 Preparation of 3-[(4-benzylphenyl)amino]-6,6-dimethyl-2-(pyridin-4-yl)-1,5,6,7-tetrahydro-4H-indol-4-one

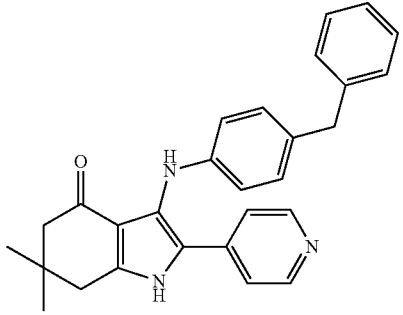 [SMILES: CC1(C)CC(=O)c2c([nH]c(-c3ccncc3)c2Nc2ccc(Cc3ccccc3)cc2)C1]

Synthesized according to Method F2. Intermediate 1-6-1 (100 mg) gave the desired product (16 mg, 12%) after preparative HPLC (acidic method) and silica chromatography.

1H-NMR (400 MHz, DMSO-d6), Shift [ppm]=1.06 (6H), 2.22 (2H), 2.74 (2H), 3.76 (2H), 6.46-6.54 (2H), 6.86-6.94 (2H), 7.10-7.18 (3H), 7.20-7.28 (2H), 7.33 (1H), 7.40-7.48 (2H), 8.36-8.43 (2H), 11.82 (1H).

Example 514 Preparation of 6,6-dimethyl-3-[(4-phenoxyphenyl)amino]-2-(pyridin-4-yl)-1,5,6,7-tetrahydro-4H-indol-4-one

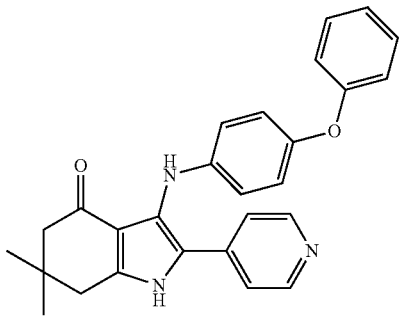 [SMILES: CC1(C)CC(=O)c2c([nH]c(-c3ccncc3)c2Nc2ccc(Oc3ccccc3)cc2)C1]

Synthesized according to Method F2. Intermediate 1-6-1 (100 mg) gave the desired product (27 mg, 20%) after preparative HPLC (acidic method) and silica chromatography.

1H-NMR (400 MHz, DMSO-d6), Shift [ppm]=1.08 (6H), 2.25 (2H), 2.75 (2H), 6.56-6.67 (2H), 6.72-6.82 (2H), 6.85 (2H), 7.01 (1H), 7.26-7.33 (2H), 7.43-7.50 (3H), 8.14 (1H), 8.40-8.44 (2H), 11.85 (1H).

Biological Investigations

The following assays can be used to illustrate the commercial utility of the compounds according to the present invention.

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

Biological Assay 1.0:
Bub1 Kinase Assay

Bub1-inhibitory activities of compounds described in the present invention were quantified using a time-resolved fluorescence energy transfer (TR-FRET) kinase assay which measures phosphorylation of the synthetic peptide Biotin-Ahx-VLLPKKSFAEPG (SEQ ID No. 1) (C-terminus in amide form), purchased from e.g. Biosyntan (Berlin, Germany) by the (recombinant) catalytic domain of human Bub1 (amino acids 704-1085), expressed in Hi5 insect cells with an N-terminal His6-tag and purified by affinity-(Ni-NTA) and size exclusion chromatography.

In a typical assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were tested in duplicate within the same microtiter plate. To this end, 100-fold concentrated compound solutions (in DMSO) were previously prepared by serial dilution (1:3.4) of 2 mM stocks in a clear low volume 384-well source microtiter plate (Greiner Bio-One, Frickenhausen, Germany), from which 50 nl of compounds were transferred into a black low volume test microtiter plate from the same supplier. Subsequently, 2 µL of Bub1 (the final concentration of Bub1 was adjusted depending on the activity of the enzyme lot in order to be within the linear dynamic range of the assay: typically ~200 ng/mL were used) in aqueous assay buffer [50 mM Tris/HCl pH 7.5, 10 mM magnesium chloride ($MgCl_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Triton X-100 (Sigma), 1× Complete EDTA-free protease inhibitor mixture (Roche)] were added to the compounds in the test plate and the mixture was incubated for 15 min at 22° C. to allow pre-equilibration of the putative enzyme-inhibitor complexes before the start of the kinase reaction, which was initiated by the addition of 3 µL 1.67-fold concentrated solution (in assay buffer) of adenosine-tri-phosphate (ATP, 10 µM final concentration) and peptide substrate (1 µM final concentration). The resulting mixture (5 µL final volume) was incubated at 22° C. during 60 min., and the reaction was stopped by the addition of 5 µL of an aqueous EDTA-solution (50 mM EDTA, in 100 mM HEPES pH 7.5 and 0.2% (w/v) bovine serum albumin) which also contained the TR-FRET detection reagents (0.2 µM streptavidin-XL665 [Cisbio Bioassays, Codolet, France] and 1 nM anti-phospho-Serine antibody [Merck Millipore, cat. #35-002] and 0.4 nM LANCE EU-W1024 labeled anti-mouse IgG antibody [Perkin-Elmer, product no. AD0077, alternatively a Terbium-cryptate-labeled anti-mouse IgG antibody from Cisbio Bioassays can be used]). The stopped reaction mixture was further incubated 1 h at 22° C. in order to allow the formation of complexes between peptides and detection reagents. Subsequently, the amount of product was evaluated by measurement of the resonance energy transfer from the Eu-chelate-antibody complex recognizing the Phospho-serine residue to the streptavidin-XL665 bound to the biotin moiety of the peptide. To this end, the fluorescence emissions at 620 nm and 665 nm after excitation at 330-350 nm were measured in a TR-FRET plate reader, e.g. a Rubystar or Pherastar (both from BMG Labtechnologies, Offenburg, Germany) or a Viewlux (Perkin-Elmer) and the ratio of the emissions (665 nm/622 nm) was taken as indicator for the amount of phosphorylated substrate. The data were normalised using two sets of control wells for high- (=enzyme reaction without inhibitor=0%=Minimum inhibition) and low- (=all assay components without enzyme=100%=Maximum inhibition) Bub1 activity. IC50 values were calculated by fitting the normalized inhibition data to a 4-parameter logistic equation (Minimum, Maximum, IC50, Hill; Y=Max+(Min−Max)/(1+(X/IC50)Hill)).

| Example Nr. | Biological Assay: Bub1 kinase assay median $IC_{50}$ [mol/l] |
|---|---|
| 1 | 6.25E−9 |
| 2 | 8.98E−9 |
| 3 | 3.78E−8 |
| 4 | 1.59E−8 |
| 5 | 2.52E−8 |
| 6 | 1.24E−8 |
| 7 | 5.57E−9 |
| 8 | 2.21E−8 |
| 9 | 1.21E−8 |
| 10 | 1.25E−8 |
| 11 | 1.65E−8 |
| 12 | 1.54E−8 |
| 13 | 6.55E−9 |
| 14 | 1.08E−8 |
| 15 | 2.36E−8 |
| 16 | 2.72E−8 |
| 17 | 4.04E−9 |
| 18 | 5.09E−9 |
| 19 | 1.95E−8 |
| 20 | 9.33E−9 |
| 21 | 1.32E−8 |
| 22 | 1.05E−8 |
| 24 | 2.04E−8 |
| 25 | 2.63E−8 |
| 26 | 3.27E−8 |
| 27 | 4.33E−8 |
| 28 | 5.93E−9 |
| 29 | 6.17E−9 |
| 30 | 5.69E−9 |
| 31 | 5.55E−9 |
| 32 | 1.57E−8 |
| 33 | 1.79E−8 |
| 34 | 3.1E−8 |
| 35 | 1.74E−8 |
| 36 | 2.64E−8 |
| 37 | 8.5E−9 |
| 38 | 7.97E−9 |
| 39 | 1.48E−8 |
| 40 | 1.52E−8 |
| 41 | 1.11E−8 |
| 42 | 2.3E−8 |
| 43 | 9.6E−9 |
| 44 | 1.7E−8 |
| 45 | 2.08E−8 |
| 46 | 2.91E−8 |
| 47 | 1.37E−8 |
| 48 | 1.35E−8 |
| 49 | 1.31E−8 |
| 50 | 3.63E−8 |
| 51 | 1.36E−7 |
| 52 | 9.98E−8 |
| 53 | 8.22E−8 |
| 54 | 1.48E−7 |
| 55 | 4.49E−7 |
| 56 | 6.54E−7 |
| 58 | 2.0E−5 |
| 59 | 4.22E−7 |
| 60 | 9.52E−8 |
| 61 | 6.85E−8 |

| Example Nr. | Biological Assay: Bub1 kinase assay median IC$_{50}$ [mol/l] |
|---|---|
| 62 | 1.67E−7 |
| 63 | 1.96E−7 |
| 64 | 1.82E−6 |
| 65 | 5.25E−7 |
| 66 | 2.26E−6 |
| 67 | 8.71E−8 |
| 68 | 8.42E−8 |
| 69 | 7.64E−8 |
| 70 | 8.17E−8 |
| 71 | 4.97E−8 |
| 72 | 4.71E−8 |
| 73 | 1.99E−5 |
| 74 | 8.23E−8 |
| 75 | 1.41E−5 |
| 76 | 4.27E−6 |
| 77 | 1.55E−6 |
| 78 | 6.95E−6 |
| 79 | 1.33E−7 |
| 80 | 1.88E−7 |
| 81 | 4.43E−8 |
| 82 | 5.1E−7 |
| 83 | 2.93E−7 |
| 84 | 1.27E−7 |
| 85 | 7.35E−8 |
| 86 | 5.46E−6 |
| 87 | 1.78E−6 |
| 88 | 2.61E−6 |
| 89 | 2.88E−7 |
| 90 | 5.09E−7 |
| 91 | 1.01E−7 |
| 92 | 2.96E−7 |
| 93 | 7.4E−6 |
| 94 | 1.14E−7 |
| 95 | 4.37E−8 |
| 96 | 8.55E−8 |
| 97 | 2.98E−6 |
| 98 | 1.54E−6 |
| 99 | 2.21E−6 |
| 100 | 9.52E−8 |
| 101 | 5.07E−7 |
| 102 | 9.54E−7 |
| 103 | 5.36E−8 |
| 104 | 5.24E−7 |
| 105 | 1.17E−6 |
| 106 | 5.35E−6 |
| 107 | 1.64E−7 |
| 108 | 1.04E−7 |
| 109 | 4.56E−6 |
| 110 | 2.35E−7 |
| 111 | 2.63E−6 |
| 112 | 3.48E−6 |
| 113 | 1.74E−7 |
| 114 | 8.64E−6 |
| 116 | >2.00E−5 |
| 117 | 1.75E−7 |
| 118 | 4.57E−7 |
| 119 | 2.34E−6 |
| 121 | 3.23E−7 |
| 122 | 5.8E−8 |
| 123 | 4.97E−7 |
| 124 | 1.54E−7 |
| 125 | 4.54E−7 |
| 126 | 1.45E−5 |
| 127 | 7.75E−6 |
| 128 | 5.76E−7 |
| 129 | 4.47E−7 |
| 130 | 5.81E−8 |
| 131 | 5.18E−8 |
| 132 | 5.02E−8 |
| 133 | 4.92E−8 |
| 134 | 4.97E−8 |
| 135 | 1.88E−7 |
| 136 | 9.24E−7 |
| 137 | 9.98E−8 |
| 138 | 9.24E−8 |
| 139 | 1.13E−7 |
| 140 | 2.04E−6 |
| 142 | 6.85E−8 |
| 143 | 5.58E−7 |
| 144 | 1.72E−6 |
| 145 | 1.48E−7 |
| 146 | 4.82E−8 |
| 147 | 2.58E−7 |
| 148 | 4.79E−7 |
| 149 | 9.41E−8 |
| 150 | 1.89E−6 |
| 151 | >4,.0E−5 |
| 152 | 2.39E−7 |
| 153 | 1.15E−5 |
| 154 | 3.0E−6 |
| 155 | 1.71E−6 |
| 156 | 7.43E−7 |
| 157 | 7.64E−7 |
| 158 | 9.56E−8 |
| 159 | 1.06E−6 |
| 160 | 2.04E−7 |
| 162 | 8.56E−8 |
| 163 | 1.26E−7 |
| 164 | 2.60E−7 |
| 165 | 7.33E−7 |
| 166 | 1.69E−6 |
| 167 | 5.31E−8 |
| 168 | 6.66E−6 |
| 169 | 1.25E−7 |
| 170 | 4.02E−8 |
| 171 | 1.44E−8 |
| 172 | 1.05E−6 |
| 173 | 4.74E−7 |
| 174 | 2.20E−7 |
| 175 | 2.17E−7 |
| 176 | 2.04E−6 |
| 177 | 5.67E−6 |
| 178 | 9.96E−8 |
| 179 | 1.62E−7 |
| 180 | 1.99E−7 |
| 181 | 3.27E−8 |
| 182 | 6.89E−8 |
| 183 | 7.09E−6 |
| 184 | 2.00E−7 |
| 185 | 1.30E−6 |
| 186 | 2.94E−6 |
| 187 | 5.23E−8 |
| 188 | 5.06E−8 |
| 189 | 2.59E−7 |
| 190 | 4.75E−7 |
| 191 | 3.26E−7 |
| 192 | 1.28E−6 |
| 193 | 9.21E−7 |
| 194 | 4.20E−8 |
| 195 | 1.02E−7 |
| 196 | 3.65E−8 |
| 197 | >2.00E−5 |
| 198 | 1.09E−5 |
| 199 | 1.20E−8 |
| 200 | 6.10E−7 |
| 201 | 4.74E−8 |
| 202 | 1.99E−6 |
| 203 | 1.15E−7 |
| 204 | 4.26E−8 |
| 205 | 2.29E−8 |
| 206 | 9.73E−9 |
| 207 | 7.32E−9 |
| 208 | 6.39E−9 |
| 209 | 3.12E−6 |
| 210 | 1.30E−7 |
| 211 | 1.14E−7 |
| 212 | 2.20E−7 |
| 213 | 1.22E−8 |
| 214 | 6.76E−8 |
| 215 | 9.68E−6 |

| Example Nr. | Biological Assay: Bub1 kinase assay median IC$_{50}$ [mol/l] |
|---|---|
| 216 | >2.00E−5 |
| 217 | >2.00E−5 |
| 218 | 9.06E−7 |
| 219 | 1.22E−8 |
| 220 | 1.40E−6 |
| 221 | 1.31E−8 |
| 222 | 2.85E−8 |
| 223 | 4.05E−8 |
| 224 | 2.48E−7 |
| 225 | 2.67E−8 |
| 226 | 2.04E−8 |
| 227 | 2.60E−7 |
| 228 | 5.67E−8 |
| 229 | 1.94E−8 |
| 230 | 2.00E−8 |
| 231 | 2.99E−8 |
| 232 | 3.47E−8 |
| 233 | 4.39E−8 |
| 234 | 1.94E−6 |
| 235 | 6.16E−8 |
| 236 | 8.26E−9 |
| 237 | 1.32E−8 |
| 238 | 1.77E−8 |
| 239 | 4.59E−8 |
| 240 | 6.74E−6 |
| 241 | 4.07E−8 |
| 242 | 1.82E−7 |
| 243 | 2.55E−7 |
| 244 | 3.10E−8 |
| 245 | 8.44E−8 |
| 246 | 6.02E−8 |
| 247 | 8.13E−8 |
| 248 | 2.82E−8 |
| 249 | 1.64E−8 |
| 249 | 7.55E−9 |
| 250 | 1.00E−8 |
| 251 | 1.05E−8 |
| 252 | 1.66E−8 |
| 253 | 2.33E−8 |
| 254 | 6.34E−9 |
| 255 | 5.35E−9 |
| 256 | 5.17E−9 |
| 257 | 5.97E−8 |
| 258 | 6.49E−9 |
| 259 | 1.01E−8 |
| 260 | 2.36E−8 |
| 261 | 4.17E−8 |
| 262 | 3.26E−8 |
| 263 | 1.40E−7 |
| 264 | 1.39E−8 |
| 265 | 1.91E−8 |
| 266 | 1.38E−8 |
| 267 | 9.55E−9 |
| 268 | 2.27E−8 |
| 269 | 2.94E−8 |
| 270 | 2.94E−8 |
| 271 | 7.64E−9 |
| 272 | 6.63E−9 |
| 273 | 7.66E−9 |
| 274 | 4.82E−8 |
| 275 | 1.27E−8 |
| 276 | 1.84E−8 |
| 277 | 8.52E−9 |
| 278 | 1.27E−8 |
| 279 | 1.26E−8 |
| 280 | 1.03E−8 |
| 281 | 1.12E−8 |
| 282 | 9.72E−9 |
| 283 | 1.89E−8 |
| 284 | 1.37E−8 |
| 285 | 3.08E−8 |
| 286 | 2.16E−8 |
| 287 | 4.84E−8 |
| 288 | 1.67E−8 |
| 289 | 1.59E−8 |
| 290 | 1.39E−8 |
| 291 | 2.87E−8 |
| 292 | 3.40E−7 |
| 293 | 1.12E−8 |
| 294 | 9.17E−9 |
| 295 | 3.80E−8 |
| 296 | 3.45E−6 |
| 297 | 2.71E−7 |
| 298 | |
| 299 | 7.43E−8 |
| 300 | 4.75E−7 |
| 301 | 7.38E−7 |
| 302 | 4.80E−7 |
| 303 | 1.41E−6 |
| 304 | 1.74E−7 |
| 305 | |
| 306 | 3.99E−6 |
| 307 | 2.08E−7 |
| 308 | 2.34E−7 |
| 309 | 2.38E−7 |
| 310 | 1.27E−7 |
| 311 | 4.06E−8 |
| 312 | 1.99E−8 |
| 313 | 5.89E−8 |
| 314 | 4.75E−8 |
| 315 | 1.01E−7 |
| 316 | 8.23E−8 |
| 317 | 1.09E−8 |
| 318 | 9.71E−9 |
| 319 | 8.69E−9 |
| 320 | 8.04E−9 |
| 321 | 1.12E−8 |
| 322 | 1.27E−8 |
| 323 | 2.16E−8 |
| 324 | 2.64E−8 |
| 325 | 1.98E−8 |
| 326 | 6.08E−7 |
| 327 | 2.80E−7 |
| 328 | 5.24E−7 |
| 329 | 6.54E−8 |
| 330 | 7.83E−9 |
| 331 | 1.30E−8 |
| 332 | 1.43E−8 |
| 333 | 7.33E−9 |
| 334 | 9.36E−9 |
| 335 | 9.90E−9 |
| 336 | 8.53E−9 |
| 337 | 2.29E−8 |
| 338 | 3.16E−8 |
| 339 | 3.94E−8 |
| 340 | 7.25E−9 |
| 341 | 7.89E−9 |
| 342 | 7.12E−9 |
| 343 | 8.45E−9 |
| 344 | 1.98E−8 |
| 345 | 7.25E−8 |
| 346 | 9.88E−9 |
| 347 | 1.01E−7 |
| 348 | 1.02E−8 |
| 349 | 8.19E−9 |
| 350 | 6.53E−9 |
| 351 | 6.22E−9 |
| 352 | 6.68E−9 |
| 353 | 1.44E−8 |
| 354 | 6.57E−9 |
| 355 | 6.45E−9 |
| 356 | 7.91E−9 |
| 357 | 3.08E−6 |
| 358 | 1.13E−6 |
| 359 | 2.08E−7 |
| 360 | 1.27E−5 |
| 361 | 6.00E−7 |
| 362 | 3.92E−7 |
| 363 | 2.07E−7 |
| 364 | 5.02E−7 |

| Example Nr. | Biological Assay: Bub1 kinase assay median IC$_{50}$ [mol/l] |
|---|---|
| 365 | 6.04E−7 |
| 366 | 1.66E−6 |
| 367 | 2.91E−7 |
| 368 | 6.22E−7 |
| 369 | 3.62E−7 |
| 370 | 1.30E−6 |
| 371 | 1.01E−6 |
| 372 | 9.53E−6 |
| 373 | 6.94E−7 |
| 374 | 1.88E−8 |
| 375 | 3.30E−7 |
| 376 | 2.51E−6 |
| 377 | 3.01E−8 |
| 378 | 6.45E−8 |
| 379 | 3.66E−8 |
| 380 | 4.37E−7 |
| 381 | 9.44E−8 |
| 382 | 8.40E−8 |
| 383 | 6.91E−8 |
| 384 | 1.13E−7 |
| 385 | 1.01E−8 |
| 386 | 2.03E−8 |
| 387 | 6.35E−8 |
| 388 | 4.34E−8 |
| 389 | 3.89E−8 |
| 390 | 3.96E−9 |
| 391 | 4.52E−9 |
| 392 | 8.75E−8 |
| 393 | 2.33E−7 |
| 394 | 1.15E−6 |
| 395 | 2.13E−7 |
| 396 | 2.46E−6 |
| 397 | 1.05E−6 |
| 398 | 5.52E−7 |
| 399 | 2.92E−7 |
| 400 | 1.57E−7 |
| 401 | 3.54E−7 |
| 402 | 3.12E−7 |
| 403 | 9.30E−9 |
| 404 | 1.17E−8 |
| 405 | 8.40E−9 |
| 406 | 5.37E−8 |
| 407 | 6.00E−7 |
| 408 | 6.42E−9 |
| 409 | 9.63E−9 |
| 410 | 3.55E−9 |
| 411 | 6.86E−9 |
| 412 | 2.84E−8 |
| 413 | 4.32E−8 |
| 414 | >2.00E−5 |
| 415 | 2.83E−7 |
| 416 | 6.89E−7 |
| 417 | 2.73E−7 |
| 418 | 2.66E−8 |
| 419 | 1.18E−8 |
| 420 | 2.49E−8 |
| 421 | 2.00E−7 |
| 422 | 3.30E−7 |
| 423 | 2.68E−8 |
| 426 | 2.58E−9 |
| 427 | 8.40E−9 |
| 428 | 5.09E−7 |
| 429 | 7.09E−8 |
| 432 | 2.36E−6 |
| 433 | 2.93E−6 |
| 435 | 1.38E−6 |
| 436 | 2.09E−8 |
| 437 | 5.79E−7 |
| 438 | 3.45E−7 |
| 439 | 6.49E−7 |
| 440 | 1.29E−8 |
| 441 | 5.72E−9 |
| 442 | 6.97E−9 |
| 443 | 5.05E−9 |
| 444 | 4.61E−9 |
| 445 | 1.00E−8 |
| 446 | 4.01E−8 |
| 447 | 1.12E−8 |
| 448 | 8.93E−9 |
| 449 | 4.38E−9 |
| 450 | 6.24E−9 |
| 451 | 8.82E−9 |
| 452 | 1.92E−8 |
| 453 | 1.00E−8 |
| 454 | 7.33E−9 |
| 455 | 2.44E−8 |
| 456 | 7.33E−8 |
| 457 | 5.35E−8 |
| 458 | 7.87E−8 |
| 459 | 5.88E−8 |
| 460 | 1.97E−8 |
| 461 | 6.88E−9 |
| 462 | 1.82E−8 |
| 463 | 1.42E−7 |
| 464 | 5.89E−8 |
| 465 | 7.19E−9 |
| 466 | 5.03E−9 |
| 467 | 2.33E−8 |
| 468 | >2.00E−5 |
| 469 | 2.16E−6 |
| 470 | 4.49E−9 |
| 471 | 4.43E−6 |
| 472 | 5.04E−9 |
| 473 | 1.03E−8 |
| 474 | 8.63E−9 |
| 475 | 3.87E−8 |
| 476 | 8.04E−9 |
| 477 | 6.62E−9 |
| 478 | 4.23E−9 |
| 479 | 5.09E−9 |
| 480 | 6.30E−9 |
| 481 | 7.86E−8 |
| 482 | 1.22E−8 |
| 483 | 9.48E−9 |
| 484 | 9.07E−7 |
| 485 | 5.84E−9 |
| 486 | 3.45E−9 |
| 487 | 3.35E−9 |
| 488 | 3.91E−8 |
| 489 | 3.32E−6 |
| 490 | 2.56E−6 |
| 491 | 1.24E−6 |
| 492 | 5.28E−9 |
| 493 | 8.63E−9 |
| 494 | 1.09E−8 |
| 495 | 1.06E−8 |
| 496 | 6.46E−9 |
| 497 | 1.44E−6 |
| 498 | 1.26E−6 |
| 499 | 8.30E−7 |
| 500 | 3.56E−7 |
| 501 | 9.67E−8 |
| 502 | 1.44E−8 |
| 503 | 3.61E−8 |
| 504 | 6.14E−9 |
| 505 | 1.11E−8 |
| 506 | 7.77E−9 |
| 507 | 9.59E−7 |
| 508 | 1.93E−7 |
| 509 | 2.21E−7 |
| 510 | 2.53E−8 |
| 511 | 6.52E−8 |
| 513 | >2.00E−5 |
| 514 | >2.00E−5 |

The invention claimed is:

1. A compound of formula (I)

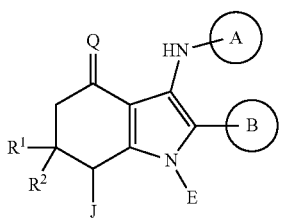

wherein:

$R^1$ is hydrogen, $C_1$-$C_4$-alkyl, $C_1$-$C_4$-haloalkyl, $C_3$-$C_6$-cycloalkyl, or phenyl, wherein said phenyl is optionally independently substituted, one or more times, with $R^3$, and wherein said $C_3$-$C_6$-cycloalkyl is optionally independently substituted, one or more times, with halogen;

$R^2$ is hydrogen, $C_1$-$C_4$-alkyl or $C_1$-$C_4$-haloalkyl;

or $R^1$ and $R^2$ are taken together with the carbon atom to which they are attached to form a 3- to 7-membered cycloalkyl ring;

ring A is a group selected from the group consisting of:

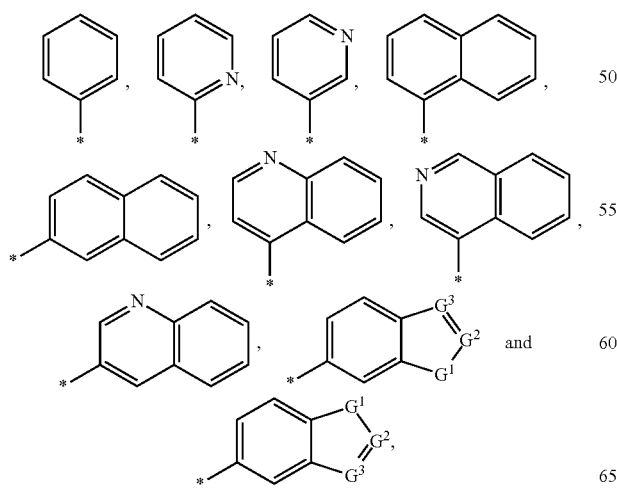

wherein * indicates the point of attachment of said group with the rest of the molecule and said group is optionally independently substituted, one or more times, with $R^3$;

$G^1$ is O, S, or $NR^{21}$;

$G^2$ and $G^3$ are independently $CR^{21}$ or N;

$R^3$ is hydrogen, halogen, hydroxy, amino, nitro, cyano, $C_3$-$C_6$-cycloalkyl, $C_2$-$C_4$-alkenyl, $C_2$-$C_4$-alkynyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $R^{18}$—O—C(O)—, $R^7R^8N$—C(O)—, $C_1$-$C_4$-alkyl-C(O)—NH—, $R^7R^8N$—, $R^7R^8N$—$SO_2$—, or a group selected from the group consisting of

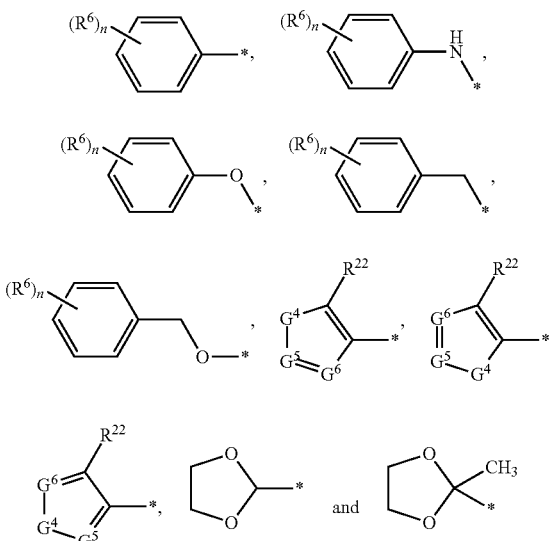

wherein * indicates the point of attachment of said group with the rest of the molecule, and wherein said $C_1$-$C_4$-alkyl, $C_1$-$C_4$-alkoxy, $C_1$-$C_4$-haloalkyl or $C_1$-$C_4$-haloalkoxy groups are optionally substituted with one or two hydroxy groups;

$G^4$ is O, S, or $NR^{21}$;

$G^5$ and $G^6$ are independently $CR^{21}$ or N;

each $R^6$ is independently halogen, hydroxy, amino, nitro, cyano, $C_1$-$C_4$-alkoxy, $C_1$-$C_4$-haloalkyl or $C_1$-$C_4$-haloalkoxy;

ring B is a group selected from the group consisting of:

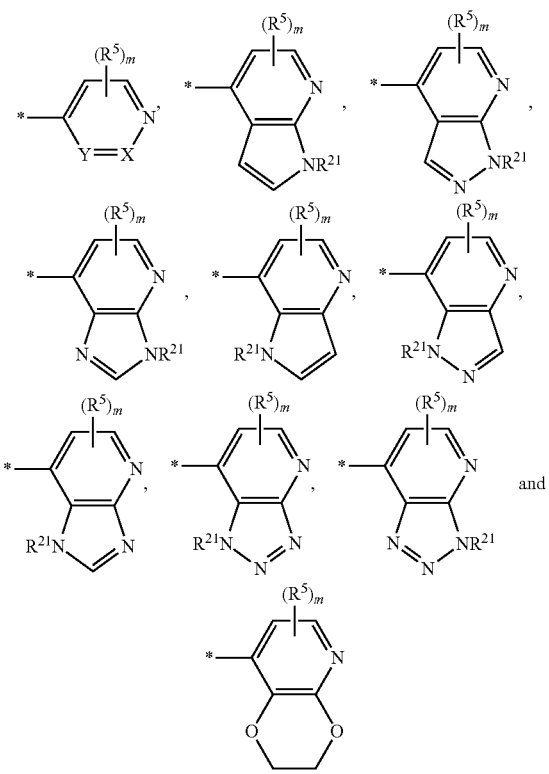

wherein * indicates the point of attachment of said group with the rest of the molecule;

X is $CR^4$ or N;
Y is $CR^4$ or N,
   wherein when one of X and Y is N, the other is $CR^4$;
each $R^4$ is independently hydrogen, halogen, hydroxy, cyano, $C_1$-$C_4$-alkyl, $C_3$-$C_4$-cycloalkyl, $C_1$-$C_4$-alkoxy, $C_1$-$C_4$-alkyl-S—, $C_1$-$C_4$-alkyl-SO—, $C_1$-$C_4$-alkyl-SO_2$—, $R^9R^{10}N$—, $R^{11}$—C(O)—($NR^7$)—, ($R^{11}$—C(O)—)($R^{12}$—C(O)—)N—, $R^9R^{10}N$—C(O)—($NR^7$)—, $R^9R^{10}N$—C(S)-($NR^7$)—, $R^{18}$—O—C(O)—($NR^7$)—, $R^9R^{10}N$—$SO_2$— or $C_1$-$C_4$-alkyl-$SO_2$—NH—,
   wherein said $C_1$-$C_4$-alkyl is optionally independently substituted, one or more times, with a substituent selected from hydroxy and halogen,
   wherein said $C_1$-$C_4$-alkoxy is optionally independently substituted, one or more times, with a substituent selected from hydroxy, halogen, $C_1$-$C_4$-alkoxy, $C_3$-$C_6$-cycloalkyl and phenyl,
      wherein said phenyl is optionally independently substituted, one or more times, with $R^3$, and
   wherein said $C_3$-$C_4$-cycloalkyl is optionally independently substituted, one or more times, with halogen;
each $R^5$ is independently halogen, hydroxy, amino, nitro, cyano, $C_1$-$C_4$-alkyl, $C_3$-$C_6$-cycloalkyl, $C_1$-$C_4$-alkoxy, $C_1$-$C_4$-haloalkyl, $C_1$-$C_4$-haloalkoxy or phenyl-$C_1$-$C_4$-alkyl,
   wherein said phenyl group is optionally independently substituted, one or more times, with a substituent selected from halogen, hydroxy, $C_1$-$C_3$-alkyl, $C_1$-$C_3$-haloalkyl and $C_1$-$C_3$-alkoxy, and
   wherein said $C_3$-$C_6$-cycloalkyl group is optionally independently substituted, one or more times, with halogen;

J is hydrogen or hydroxy;
E is hydrogen, $C_1$-$C_4$-alkyl, $C_1$-$C_4$-alkoxy-$C_2$-$C_4$-alkyl, $R^{17a}R^{17b}R^{17c}Si$—O—$C_2$-$C_4$-alkyl, $C_1$-$C_4$-alkyl-$SO_2$—$C_1$-$C_4$-alkyl, $R^{18}$—O—C(O)—$C_1$-$C_4$-alkyl, $R^7R^8N$—$C_2$-$C_4$-alkyl, $R^7R^8N$—C(O)—$C_1$-$C_4$-alkyl or phenyl-$C_1$-$C_4$-alkyl,
   wherein said $C_1$-$C_4$-alkyl is optionally independently substituted, one or more times, with a substituent selected from hydroxy and halogen, and
   wherein said phenyl group is optionally independently substituted, one or more times, with $R^5$;
Q is O or N—$OR^{16}$;
$R^7$ and $R^8$ are independently hydrogen, $C_1$-$C_1$-alkyl or tert-butyl-O—C(O)—;
$R^9$ and $R^{10}$ are independently hydrogen, $C_1$-$C_1$-alkyl, $C_3$-$C_6$-cyclo-alkyl-, $C_1$-$C_4$-haloalkyl-, phenyl or heteroaryl,
   wherein said phenyl or heteroaryl group is optionally independently substituted, one or more times, with $R^5$, and
   wherein said $C_1$-$C_4$-alkyl is optionally independently substituted, one or more times, with a substituent selected from the group consisting of hydroxy, $C_1$-$C_4$-alkoxy, $C_1$-$C_4$-alkyl-S—, $C_3$-$C_6$-cycloalkyl, 4- to 6-membered heterocycloalkyl, phenyl, heteroaryl and $R^{18}$—O—C(O)—,
      wherein said $C_3$-$C_6$-cycloalkyl or 4- to 6-membered heterocycloalkyl is optionally independently substituted, one or more times, with a substituent selected from the group consisting of halogen, $C_1$-$C_4$-alkyl and tert-butyl-O—C(O)—, and
      wherein said phenyl or heteroaryl group is optionally independently substituted, one or more times, with $R^5$;
or
$R^9$ and $R^{10}$ are taken together with the nitrogen atom to which they are attached to form a 3- to 7-membered nitrogen containing heterocyclic ring, optionally containing one additional heteroatom selected from the group consisting of O, NH and S, and which is optionally independently substituted, one or more times, with $R^5$;
$R^{11}$ and $R^{12}$ are independently $C_1$-$C_4$-alkyl, $C_2$-$C_4$-alkenyl, $C_2$-$C_4$-alkynyl, $C_3$-$C_6$-cycloalkyl, 4- to 6-membered heterocycloalkyl, phenyl, heteroaryl, or $R^{13}$—($C_1$-$C_4$-alkyl)-O—$CH_2$—,
   wherein said $C_1$-$C_4$-alkyl is optionally independently substituted, one or more times, with a substituent selected from the group consisting of halogen, hydroxy, cyano, $C_1$-$C_4$-alkoxy, $R^7R^8N$—, $R^{14}$, $R^{15}$, —O—, and phenyl optionally independently substituted, one or more times, with $R^5$,
   wherein said $C_3$-$C_6$-cycloalkyl is optionally independently substituted, one or more times, with a substituent selected from the group consisting of halogen, cyano, $C_1$-$C_4$-alkyl, $C_1$-$C_4$-haloalkyl and phenyl optionally independently substituted, one or more times, with $R^5$,
   wherein said 4- to 6-membered heterocycloalkyl is optionally independently substituted, one or more times, with a substituent selected from the group consisting of hydroxy, $C_1$-$C_4$-alkyl, $C_1$-$C_4$-alkoxy, $R^7R^8N$— and $R^{18}$—O—C(O)—, and
   wherein said phenyl or heteroaryl is optionally independently substituted, one or more times, with $R^5$;

449

$R^{13}$ is branched $C_3$-$C_4$-alkyl, $C_1$-$C_4$-haloalkyl, $C_2$-$C_4$-alkenyl, $C_2$-$C_4$-alkynyl, $C_3$-$C_6$-cycloalkyl, 4- to 6-membered heterocycloalkyl, phenyl or heteroaryl,
  wherein said phenyl or heteroaryl is optionally independently substituted, one or more times, with $R^5$;
$R^{14}$ is $C_1$-$C_4$-alkyl-S—, $C_1$-$C_4$-alkyl-$SO_2$—, $C_3$-$C_6$-cycloalkyl, 4- to 6-membered heterocycloalkyl, phenyl or heteroaryl,
  wherein said phenyl or heteroaryl is optionally independently substituted, one or more times, with $R^5$;
$R^{15}$ is phenyl or heteroaryl,
  wherein said phenyl or heteroaryl is optionally independently substituted, one or more times, with $R^5$;
$R^{16}$ is hydrogen, $C_1$-$C_6$-alkyl, phenyl or $C_1$-$C_4$-alkyl-C(O)—,
  wherein said phenyl group is optionally independently substituted, one or more times, with $R^5$;
$R^{17a}$, $R^{17b}$, and $R^{17c}$ are independently $C_1$-$C_4$-alkyl;
$R^{18}$ is hydrogen or $C_1$-$C_6$-alkyl;
$R^{21}$ is hydrogen, $C_1$-$C_4$-alkyl, $C_1$-$C_4$-haloalkyl, or $C_1$-$C_6$-cycloalkyl optionally independently substituted, one or more times, with halogen;
$R^{22}$ is hydrogen, halogen, $C_1$-$C_4$-alkyl, $C_1$-$C_4$-haloalkyl, or $C_1$-$C_6$-cycloalkyl optionally independently substituted, one or more times, with halogen;
m is 0, 1 or 2; and
n is 0, 1, 2 or 3,
or an N-oxide, a salt, a tautomer or a stereoisomer thereof, or a salt of said N-oxide, tautomer or stereoisomer.

2. The compound of formula (I) according to claim 1, wherein:
$R^1$ is hydrogen, $C_1$-$C_4$-alkyl, $C_1$-$C_4$-haloalkyl or phenyl, wherein said phenyl is optionally independently substituted, one or more times, with $R^3$;
$R^2$ is hydrogen, $C_1$-$C_4$-alkyl or $C_1$-$C_4$-haloalkyl;
or
$R^1$ and $R^2$ are taken together with the carbon atom to which they are attached to form a 3- to 7-membered cycloalkyl ring;
ring A is a group selected from the group consisting of:

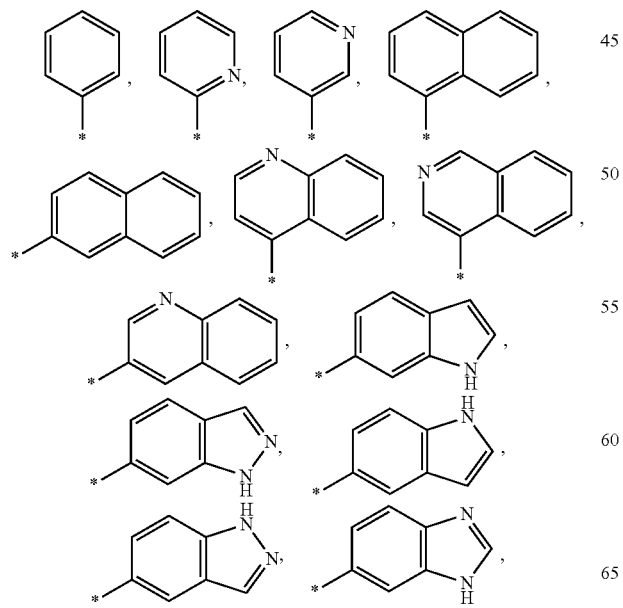

450

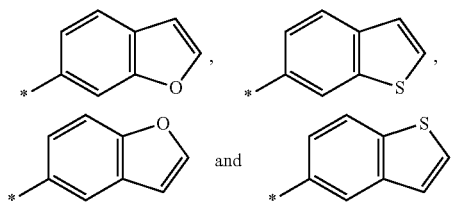

wherein * indicates the point of attachment of said group with the rest of the molecule and said group is optionally independently substituted, one or more times, with $R^3$;

$R^3$ is hydrogen, halogen, hydroxy, amino, nitro, cyano, $C_1$-$C_4$-alkyl, $C_2$-$C_4$-alkenyl, $C_2$-$C_4$-alkynyl, $C_1$-$C_4$-alkoxy, $C_1$-$C_4$-alkoxy-$C_1$-$C_4$-alkyl-, $C_1$-$C_4$-haloalkyl, $C_1$-$C_4$-haloalkoxy, $C_1$-$C_4$-alkyl-C(O)—, $R^{18}$—O—C(O)—, $R^7R^8N$—C(O)—, $C_1$-$C_4$-alkyl-C(O)—NH—, $R^7R^8N$—, $R^7R^8N$—$SO_2$—, or a group selected from the group consisting of

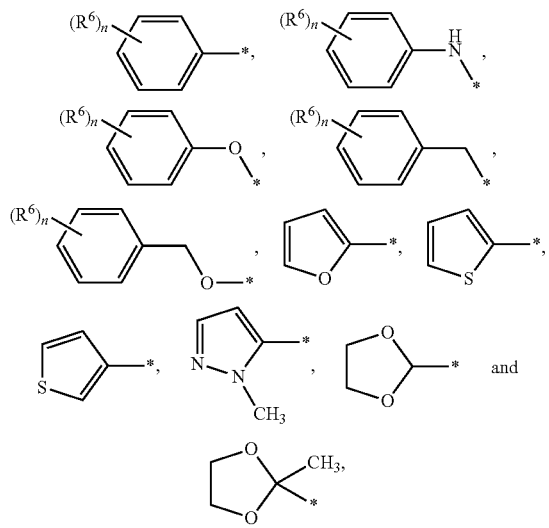

wherein * indicates the point of attachment of said group with the rest of the molecule, wherein said $C_1$-$C_4$-alkyl, $C_1$-$C_4$-alkoxy, $C_1$-$C_4$-haloalkyl or $C_1$-$C_4$-haloalkoxy groups are
optionally substituted with one or two hydroxy groups;
each $R^6$ is independently halogen, hydroxy, amino, nitro, cyano, $C_1$-$C_4$-alkyl, $C_1$-$C_4$-alkoxy, $C_1$-$C_4$-alkoxy-$C_1$-$C_4$-alkyl-, $C_1$-$C_4$-haloalkyl or $C_1$-$C_4$-haloalkoxy;
ring B is a group selected from the group consisting of:

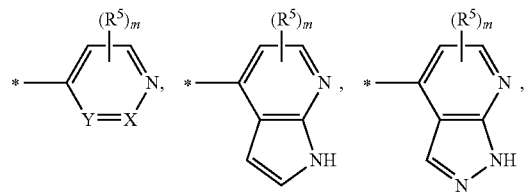

-continued

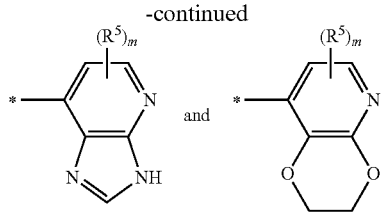

wherein * indicates the point of attachment of said group with the rest of the molecule;
X is CR$^4$ or N;
Y is CR$^4$ or N,
wherein when one of X and Y is N, the other is CR$^4$; and
each R$^4$ is independently hydrogen, halogen, hydroxy, cyano, C$_1$-C$_4$-alkyl, C$_1$-C$_4$-alkoxy, C$_1$-C$_4$-alkyl-S—, C$_1$-C$_4$-alkyl-SO—, C$_1$-C$_4$-alkyl-SO$_2$—,R$^9$R$^{10}$N—, R$^{11}$—C(O)—(NR$^{11}$)—, (R$^{11}$—C(O)—)(R$^{12}$—C(O)—)N—, R$^9$R$^{10}$N—C(O)—(NR$^7$)—, R$^9$R$^{10}$N—C(S)—(NR$^{11}$)—, R$^{18}$—O—C(O)—(NR$^7$)—, R$^9$R$^{10}$N—SO$_2$— or C$_1$-C$_4$-alkyl-SO$_2$—NH—,
  wherein said C$_1$-C$_4$-alkyl is optionally independently substituted, one or more times, with a substituent selected from the group consisting of hydroxy and halogen, and
  wherein said C$_1$-C$_4$-alkoxy is optionally independently substituted, one or more times, with a substituent selected from the group consisting of hydroxy, halogen, C$_1$-C$_4$-alkoxy, C$_3$-C$_6$-cycloalkyl and phenyl,
    wherein said phenyl is optionally independently substituted, one or more times, with R$^3$;
each R$^5$ is independently halogen, hydroxy, amino, nitro, cyano, C$_1$-C$_4$-alkyl, C$_1$-C$_4$-alkoxy, C$_1$-C$_4$-haloalkyl, C$_1$-C$_4$-haloalkoxy or phenyl-C$_1$-C$_4$-alkyl,
  wherein said phenyl group is optionally independently substituted, one or more times, with a substituent selected from the group consisting of halogen, hydroxy, C$_1$-C$_3$-alkyl, C$_1$-C$_3$-haloalkyl and C$_1$-C$_3$-alkoxy;
J is hydrogen or hydroxy;
E is hydrogen, C$_1$-C$_4$-alkyl, C$_1$-C$_4$-alkoxy-C$_2$-C$_4$-alkyl, R$^{17a}$R$^{17b}$R$^{17c}$Si—O—C$_2$-C$_4$-alkyl, C$_1$-C$_4$-alkyl-SO$_2$—C$_1$-C$_4$-alkyl, R$^{18}$—O—C(O)—C$_1$-C$_4$-alkyl, R$^7$R$^8$N—C$_2$-C$_4$-alkyl, R$^7$R$^8$N—C(O)—C$_1$-C$_4$-alkyl or phenyl-C$_1$-C$_4$-alkyl,
  wherein said C$_1$-C$_4$-alkyl is optionally independently substituted, one or more times, with a substituent selected from the group consisting of hydroxy and halogen, and
  wherein said phenyl group is optionally independently substituted, one or more times, with R$^5$;
Q is O or N—OR$^{16}$;
R$^7$ and R$^8$ are independently hydrogen, C$_1$-C$_4$-alkyl or tert-butyl-O—C(O)—;
R$^9$ and R$^{10}$ are independently hydrogen, C$_1$-C$_4$-alkyl, C$_3$-C$_6$-cyclo-alkyl-, phenyl or heteroaryl,
  wherein said phenyl or heteroaryl group is optionally independently substituted, one or more times, with R$^5$,
  wherein said C$_1$-C$_4$-alkyl is optionally independently substituted, one or more times, with hydroxy, C$_1$-C$_4$-alkoxy, C$_3$-C$_6$-cycloalkyl, 4- to 6-membered heterocycloalkyl, phenyl, heteroaryl or R$^{18}$—O—C(O)—,
  wherein said C$_3$-C$_6$-cycloalkyl or 4- to 6-membered heterocycloalkyl is optionally independently substituted, one or more times, with a substituent selected from the group consisting of halogen, C$_1$-C$_4$-alkyl and tert-butyl-O—C(O)—, and
  wherein said phenyl or heteroaryl group is optionally independently substituted, one or more times, with R$^5$;
or
R$^9$ and R$^{10}$ are taken together with the nitrogen atom to which they are attached to form a 3- to 7-membered nitrogen containing heterocyclic ring, optionally containing one additional heteroatom selected from the group consisting of O, NH and S, and which is optionally independently substituted, one or more times, with R$^5$;
R$^{11}$ and R$^{12}$ are independently C$_1$-C$_4$-alkyl, C$_2$-C$_4$-alkenyl, C$_2$-C$_4$-alkynyl, C$_3$-C$_6$-cycloalkyl, 4- to 6-membered heterocycloalkyl, phenyl, heteroaryl, or R$^{13}$—(C$_1$-C$_4$-alkyl)-O—CH$_2$—,
  wherein said C$_1$-C$_4$-alkyl is optionally independently substituted, one or more times, with a substituent selected from the group consisting of halogen, hydroxy, cyano, C$_1$-C$_4$-alkoxy, R$^7$R$^8$N—, R$^{14}$, R$^{15}$, —O—, and phenyl optionally independently substituted, one or more times, with R$^5$,
  wherein said C$_3$-C$_6$-cycloalkyl is optionally independently substituted, one or more times, with a substituent selected from the group consisting of halogen, cyano, C$_1$-C$_4$-alkyl, C$_1$-C$_4$-haloalkyl and phenyl optionally independently substituted, one or more times, with R$^5$,
  wherein said 4- to 6-membered heterocycloalkyl is optionally independently substituted, one or more times, with a substituent selected from the group consisting of hydroxy, C$_1$-C$_4$-alkyl, C$_1$-C$_4$-alkoxy, R$^7$R$^8$N— and R$^{1-8}$—O—C(O)—, and
  wherein said phenyl or heteroaryl is optionally independently substituted, one or more times, with R$^5$;
R$^{13}$ is branched C$_3$-C$_4$-alkyl, C$_1$-C$_4$-haloalkyl, C$_2$-C$_4$-alkenyl, C$_2$-C$_4$-alkynyl, C$_3$-C$_6$-cycloalkyl, 4- to 6-membered heterocycloalkyl, phenyl or heteroaryl,
  wherein said phenyl or heteroaryl is optionally independently substituted, one or more times, with R$^5$;
R$^{14}$ is C$_1$-C$_4$-alkyl-S—, C$_1$-C$_4$-alkyl-SO$_2$—, C$_3$-C$_6$-cycloalkyl, 4- to 6-membered heterocycloalkyl, phenyl or heteroaryl,
  wherein said phenyl or heteroaryl is optionally independently substituted, one or more times, with R$^5$;
R$^{15}$ is phenyl or heteroaryl,
  wherein said phenyl or heteroaryl is optionally independently substituted, one or more times, with R$^5$;
R$^{16}$ is hydrogen, C$_1$-C$_6$-alkyl, phenyl or C$_1$-C$_4$-alkyl-C(O)—,
  wherein said phenyl group is optionally independently substituted, one or more times, with R$^5$;
R$^{17a}$, R$^{17b}$, and R$^{17c}$ are independently C$_1$-C$_4$-alkyl;
R$^{18}$ is hydrogen or C$_1$-C$_6$-alkyl;
m is 0, 1 or 2; and
n is 0, 1, 2 or 3,
or an N-oxide, a salt, a tautomer or a stereoisomer thereof, or a salt of said N-oxide, tautomer or stereoisomer.
3. The compound of formula (I) according to claim 1, wherein:
R$^1$ is hydrogen, C$_1$-C$_4$-alkyl, C$_1$-C$_2$-haloalkyl or phenyl,
  wherein said phenyl is optionally independently substituted, one or more times, with R$^3$;
R$^2$ is hydrogen, C$_1$-C$_2$-alkyl or C$_1$-C$_2$-haloalkyl;
or
R$^1$ and R$^2$ are taken together with the carbon atom to which they are attached to form a 3- to 7-membered cycloalkyl ring;

ring A is a group selected from the group consisting of:

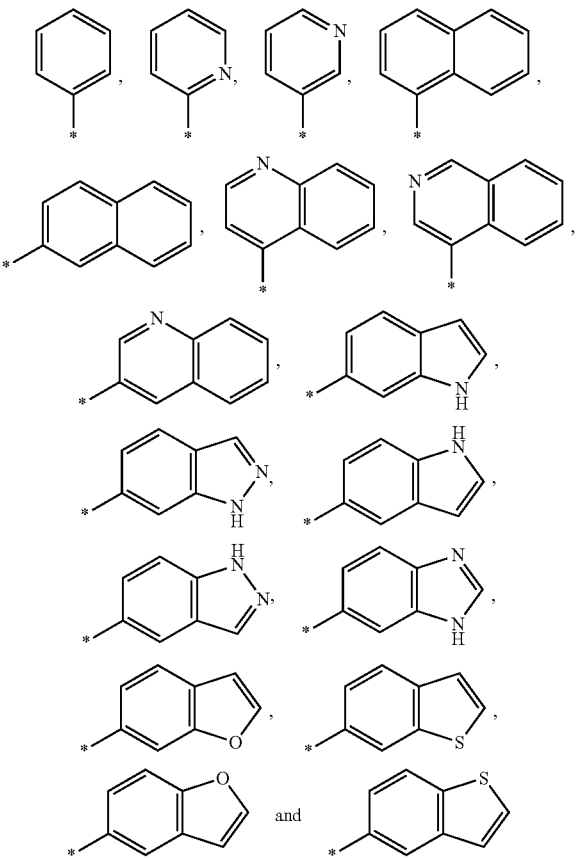

wherein * indicates the point of attachment of said group with the rest of the molecule and said group is optionally independently substituted, one or more times, with $R^3$;

$R^3$ is hydrogen, halogen, hydroxy, amino, nitro, cyano, $C_2$-$C_4$-alkynyl, $C_1$-$C_4$-alkoxy, $C_1$-$C_2$-alkoxy-$C_1$-$C_2$-alkyl-, $C_1$-$C_2$-haloalkyl, $C_1$-$C_2$-haloalkoxy, $C_1$-$C_2$-alkyl-C(O)—, $R^{18}$—O—C(O)—, $R^7R^8N$—C(O)—, $C_1$-$C_3$-alkyl-C(O)—NH—, $R^7R^8N$—, $R^7R^8N$—$SO_2$—, or a group selected from the group consisting of

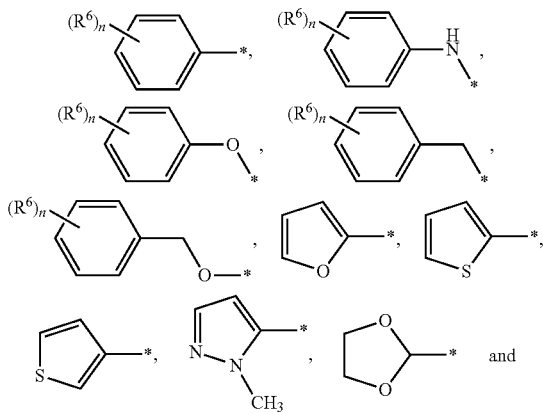

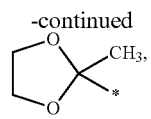

wherein * indicates the point of attachment of said group with the rest of the molecule, and
wherein said $C_1$-$C_4$-alkyl, $C_1$-$C_4$-alkoxy, $C_1$-$C_2$-haloalkyl or $C_1$-$C_2$-haloalkoxy groups are optionally substituted with one or two hydroxy groups;
each $R^6$ is independently halogen, hydroxy, amino, nitro, cyano, $C_1$-$C_2$-alkyl, $C_1$-$C_2$-alkoxy, $C_1$-$C_2$-alkoxy-$C_1$-$C_2$-alkyl-, $C_1$-$C_2$-haloalkyl or $C_1$-$C_2$-haloalkoxy;
ring B is a group selected from the group consisting of:

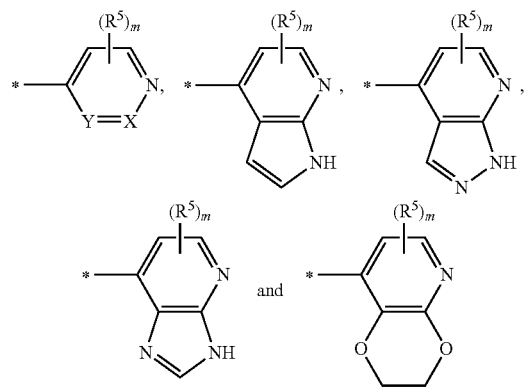

wherein * indicates the point of attachment of said group with the rest of the molecule;
X is $CR^4$ or N;
Y is $CR^4$ or N,
wherein when one of X and Y is N, the other is $CR^4$;
each $R^4$ is independently hydrogen, halogen, hydroxy, cyano, $C_1$-$C_3$-alkyl, $C_1$-$C_4$-alkoxy, $C_1$-$C_2$-alkyl-S—, $C_1$-$C_2$-alkyl-SO—, $C_1$-$C_2$-alkyl-$SO_2$—,$R^9R^{10}N$—, $R^{11}$—C(O)—($NR^7$)—, ($R^{11}$—C(O)—)($R^{12}$—C(O)—)N—, $R^9R^{10}N$—C(O)—($NR^7$)—, $R^9R^{10}N$—C(S)—($NR^7$)—, $R^{18}$—O—C(O)—($NR^7$)—, $R^9R^{10}N$—$SO_2$— or $C_1$-$C_2$-alkyl-$SO_2$—NH—,
wherein said $C_1$-$C_3$-alkyl is optionally independently substituted, one or more times, with a substituent selected from the group consisting of hydroxy and halogen, and
wherein said $C_1$-$C_4$-alkoxy is optionally independently substituted, one or more times, with hydroxy, halogen, $C_1$-$C_4$-alkoxy, $C_3$-$C_6$-cycloalkyl or phenyl,
wherein said phenyl is optionally independently substituted, one or more times, with $R^3$;
each $R^5$ is independently halogen, hydroxy, amino, nitro, cyano, $C_1$-$C_4$-alkyl, $C_1$-$C_3$-alkoxy, $C_1$-$C_3$-haloalkyl, $C_1$-$C_3$-haloalkoxy or phenyl-$C_1$-$C_4$-alkyl,
wherein said phenyl group is optionally independently substituted, one or more times, with $C_1$-$C_2$-alkoxy;
J is hydrogen or hydroxy;
E is hydrogen, $C_1$-$C_4$-alkyl, $R^{17a}R^{17b}R^{17c}Si$—O—$C_2$-alkyl, $R^{18}$—O—C(O)—$C_1$-$C_2$-alkyl, $R^7R^8N$—C(O)—$C_1$-$C_2$-alkyl or phenyl-$C_1$-$C_2$-alkyl,
wherein said $C_1$-$C_4$-alkyl is optionally independently substituted, one or more times, with a substituent selected from the group consisting of hydroxy and halogen; and wherein said phenyl group is optionally independently substituted, one or more times, with $R^5$;

Q is O or N—$OR^{16}$;

$R^7$ and $R^8$ are independently hydrogen, $C_1$-$C_4$-alkyl or tert-butyl-O—C(O)—;

$R^9$ and $R^{10}$ are independently hydrogen, $C_1$-$C_4$-alkyl, $C_3$-$C_6$-cyclo-alkyl-, phenyl or heteroaryl,
wherein said phenyl or heteroaryl group is optionally independently substituted, one or more times, with $R^5$,
wherein said $C_1$-$C_4$-alkyl is optionally independently substituted, one or more times, with a substituent selected from the group consisting of hydroxy, $C_1$-$C_2$-alkoxy, $C_1$-$C_2$-alkyl-S—, $C_3$-$C_6$-cycloalkyl, 4- to 6-membered heterocycloalkyl, phenyl, heteroaryl and $R^{18}$—O—C(O)—,
wherein said 4- to 6-membered heterocycloalkyl is optionally independently substituted, one or more times, with a substituent selected from the group consisting of $C_1$-$C_2$-alkyl and tert-butyl-O—C(O)—, and
wherein said phenyl or heteroaryl group is optionally independently substituted, one or more times, with $R^5$;

or $R^9$ and $R^{10}$ are taken together with the nitrogen atom to which they are attached to form a 3- to 7-membered nitrogen containing heterocyclic ring, optionally containing one additional heteroatom selected from the group consisting of O and NH, and which is optionally independently substituted, one or more times, with $R^5$;

$R^{11}$ and $R^{12}$ are independently $C_1$-$C_4$-alkyl, $C_3$-$C_6$-cycloalkyl, 4- to 6-membered heterocycloalkyl, phenyl, heteroaryl, $R^{13}$—$(CH_2)_o$—O—$CH_2$—, $R^{14}$—$(CH_2)_o$—, or $R^{15}$—O—$(CH_2)_o$—,
wherein said $C_1$-$C_4$-alkyl is optionally independently substituted, one or more times, with a substituent selected from the group consisting of halogen, hydroxy, cyano, $C_1$-$C_4$-alkoxy, $R^7R^8N$—, and phenyl optionally independently substituted, one or more times, with $R^5$,
wherein said $C_3$-$C_6$-cycloalkyl is optionally independently substituted, one or more times, with a substituent selected from the group consisting of halogen, cyano, $C_1$-$C_2$-alkyl, $C_1$-$C_2$-haloalkyl and phenyl optionally independently substituted, one or more times, with $R^5$,
wherein said 4- to 6-membered heterocycloalkyl is optionally independently substituted, one or more times, with a substituent selected from the group consisting of hydroxy, $C_1$-$C_2$-alkyl, $C_1$-$C_2$-alkoxy, $R^7R^8N$— and $R^{18}$—O—C(O)—, and
wherein said phenyl or heteroaryl is optionally independently substituted, one or more times, with $R^5$;

$R^{13}$ is branched $C_3$-$C_4$-alkyl, $C_1$-$C_2$-haloalkyl, $C_2$-$C_3$-alkenyl, $C_2$-$C_3$-alkynyl, $C_3$-$C_6$-cycloalkyl, 4- to 6-membered heterocycloalkyl, phenyl or heteroaryl,
wherein said phenyl or heteroaryl is optionally independently substituted, one or more times, with $R^5$;

$R^{14}$ is $C_1$-$C_2$-alkyl-S—, $C_1$-$C_2$-alkyl-$SO_2$—, $C_3$-$C_6$-cycloalkyl, 4- to 6-membered heterocycloalkyl, phenyl or heteroaryl,
wherein said phenyl or heteroaryl is optionally independently substituted, one or more times, with $R^5$;

$R^{15}$ is phenyl or heteroaryl,
wherein said phenyl or heteroaryl is optionally independently substituted, one or more times, with $R^5$;

$R^{16}$ is hydrogen, $C_1$-$C_2$-alkyl, or $C_1$-$C_2$-alkyl-C(O)—;

$R^{17a}$, $R^{17b}$, and $R^{17c}$ are independently $C_1$-$C_4$-alkyl;

$R^{18}$ is hydrogen or $C_1$-$C_4$-alkyl;

m is 0, 1 or 2;

n is 0, 1, or 2; and o is 1, 2, 3 or 4, or an N-oxide, a salt, a tautomer or a stereoisomer thereof, or a salt of said N-oxide, tautomer or stereoisomer.

4. The compound of formula (I) according to claim 1, wherein:

$R^1$ is hydrogen, $C_1$-$C_4$-alkyl, $C_1$-$C_2$-haloalkyl or phenyl, wherein said phenyl is optionally independently substituted, one or more times, with $R^3$;

$R^2$ is hydrogen or $C_1$-$C_2$-alkyl;

or $R^1$ and $R^2$ are taken together with the carbon atom to which they are attached to form a 3- to 6-membered cycloalkyl ring;

ring A is a group selected from the group consisting of:

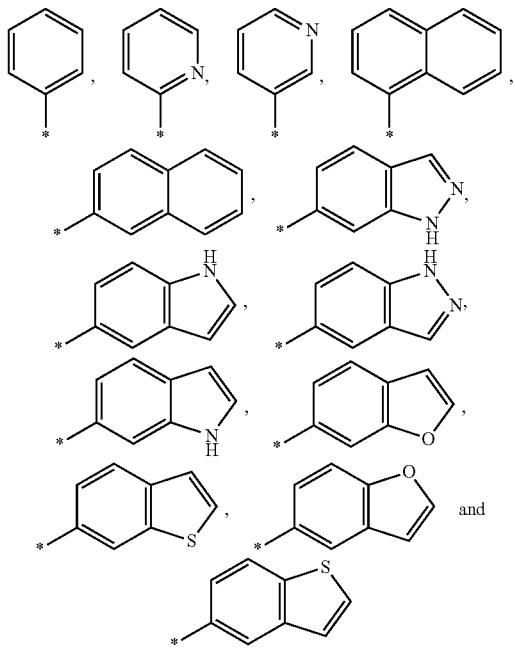

wherein * indicates the point of attachment of said group with the rest of the molecule and said group is optionally independently substituted, one or more times, with $R^3$;

$R^3$ is hydrogen, halogen, hydroxy, amino, nitro, cyano, $C_1$-$C_4$-alkyl, $C_2$-alkynyl, $C_1$-$C_3$-alkoxy, $C_1$-alkoxy-$C_2$-alkyl-, $C_1$-$C_2$-haloalkyl, $C_1$-$C_2$-haloalkoxy, $C_1$-$C_2$-alkyl-C(O)—, $R^{18}$—O—C(O)—, $R^7R^8N$—C(O)—, $C_1$-$C_3$-alkyl-C(O)—NH—, or a group selected from the group consisting of

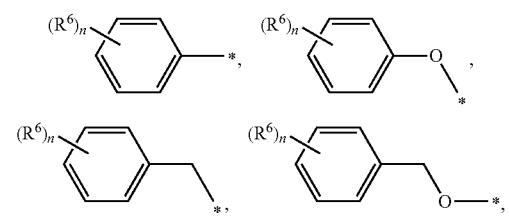

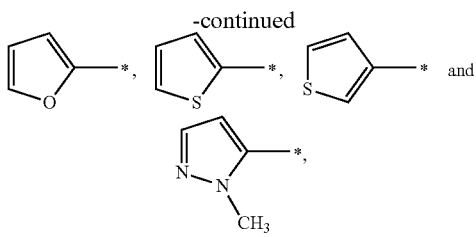

wherein * indicates the point of attachment of said group with the rest of the molecule, and
wherein said $C_1$-$C_4$-alkyl, $C_1$-$C_3$-alkoxy, $C_1$-$C_2$-haloalkyl or $C_1$-$C_2$-haloalkoxy groups are optionally substituted with one or two hydroxy groups;
$R^6$ is $C_1$-alkoxy;
ring B is a group selected from the group consisting of:

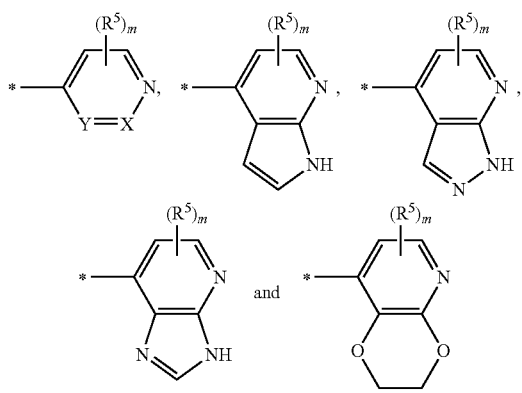

wherein * indicates the point of attachment of said group with the rest of the molecule;
X is $CR^4$ or N;
Y is $CR^4$ or N,
  wherein when one of X and Y is N, the other is $CR^4$;
each $R^4$ is independently hydrogen, halogen, hydroxy, cyano, $C_1$-$C_2$-alkyl, $C_1$-$C_4$-alkoxy, $C_1$-$C_2$-alkyl-S—, $R^9R^{10}N$—, $R^{11}$—C(O)—(NH)—, ($R^{11}$—C(O)—)($R^{12}$—C(O)—)N—, $R^9R^{10}N$—C(O)—($NR^7$)—, $R^9R^{10}N$—C(S)—($NR^7$)—, $R^{18}$—O—C(O)—($NR^7$)—, $R^9R^{10}N$—$SO_2$— or $C_1$-$C_2$-alkyl-$SO_2$—NH—,
  wherein said $C_1$-$C_2$-alkyl is optionally substituted, one time with hydroxy and/or one, two or three times, independently from each other, with halogen, and
  wherein said $C_1$-$C_4$-alkoxy is optionally independently substituted, one or more times, with a substituent selected from the group consisting of hydroxy, halogen, $C_1$-$C_2$-alkoxy, and $C_3$-$C_4$-cycloalkyl;
each $R^5$ is independently halogen, amino, $C_1$-$C_1$-alkyl, $C_1$-$C_2$-alkoxy, or phenyl-$C_1$-$C_2$-alkyl,
  wherein said phenyl group is optionally substituted, one or more times, with $C_1$-alkoxy;
J is hydrogen or hydroxy;
E is hydrogen, $C_1$-$C_4$-alkyl, $R^{18}$—O—C(O)—$C_1$-$C_2$-alkyl, or $R^7R^8N$—C(O)—$C_1$-$C_2$-alkyl,
  wherein said $C_1$-$C_4$-alkyl is optionally independently substituted, one or more times, with a substituent selected from the group consisting of hydroxy and halogen;
Q is O or N—$OR^{16}$;
$R^7$ and $R^8$ are independently hydrogen, $C_1$-$C_2$-alkyl or tert-butyl-O—C(O)—;
$R^9$ and $R^{10}$ are independently hydrogen, $C_1$-$C_4$-alkyl, $C_3$-$C_6$-cyclo-alkyl-, $C_1$-$C_4$-haloalkyl-, phenyl or heteroaryl,
  wherein said phenyl or heteroaryl group is optionally independently substituted, one or more times, with $R^5$, and
  wherein said $C_1$-$C_4$-alkyl is optionally independently substituted, one or more times, with a substituent selected from the group consisting of hydroxy, $C_1$-alkoxy, $C_1$-alkyl-S—, $C_3$-$C_6$-cycloalkyl, 4- to 6-membered heterocycloalkyl, phenyl, heteroaryl and $R^{18}$—O—C(O)—,
    wherein said 4- to 6-membered heterocycloalkyl is optionally substituted one time with tert-butyl-O—C(O)—, and
    wherein said phenyl or heteroaryl group is optionally independently substituted, one or more times, with $R^5$;
$R^{11}$ and $R^{12}$ are independently $C_1$-$C_4$-alkyl, $C_3$-$C_6$-cycloalkyl, 4- to 6-membered heterocycloalkyl, phenyl, heteroaryl, $R^{13}$—($CH_2$)$_o$—O—$CH_2$—, $R^{14}$—($CH_2$)$_o$—, or $R^{15}$—O—($CH_2$)$_o$—,
  wherein said $C_1$-$C_4$-alkyl is optionally independently substituted, one or more times, with a substituent selected from the group consisting of halogen, hydroxy, cyano, $C_1$-$C_4$-alkoxy, $R^7R^8N$—, and phenyl optionally independently substituted, one or more times, with $R^5$,
  wherein said $C_3$-$C_6$-cycloalkyl is optionally independently substituted, one or two times, with a substituent selected from the group consisting of halogen, cyano, $C_1$-$C_2$-alkyl, $C_1$-$C_2$-haloalkyl and phenyl optionally independently substituted, one or more times, with $R^5$,
  wherein said 4- to 6-membered heterocycloalkyl is optionally independently substituted, one or more times, with a substituent selected from the group consisting of $C_1$-$C_2$-alkyl, and $R^{18}$—O—C(O)—, and
  wherein said phenyl or heteroaryl is optionally independently substituted, one or more times, with $R^5$;
$R^{13}$ is branched $C_3$-$C_4$-alkyl, $C_1$-$C_2$-haloalkyl, $C_2$-$C_3$-alkenyl, $C_2$-$C_3$-alkynyl, 4- to 6-membered heterocycloalkyl, phenyl or heteroaryl,
  wherein said phenyl or heteroaryl is optionally independently substituted, one or more times, with $R^5$;
$R^{14}$ is $C_1$-$C_2$-alkyl-S—, $C_1$-$C_2$-alkyl-$SO_2$—, $C_3$-$C_6$-cycloalkyl, 4- to 6-membered heterocycloalkyl, phenyl or heteroaryl,
  wherein said phenyl or heteroaryl is optionally independently substituted, one or more times, with $R^5$;
$R^{15}$ is phenyl or heteroaryl,
  wherein said phenyl or heteroaryl is optionally independently substituted, one or more times, with $R^5$;
$R^{16}$ is hydrogen or $C_1$-$C_2$-alkyl-C(O)—;
$R^{18}$ is hydrogen or $C_1$-$C_4$-alkyl;
m is 0, 1 or 2;
n is 0, or 1; and
o is 1, 2, 3 or 4,
or an N-oxide, a salt, a tautomer or a stereoisomer thereof, or a salt of said N-oxide, tautomer or stereoisomer.

5. The compound of formula (I) according to claim 1, wherein:
$R^1$ is hydrogen, $C_1$-$C_3$-alkyl, $C_1$-$C_2$-haloalkyl or phenyl,
  wherein said phenyl is optionally independently substituted, one or more times, with $R^3$;
$R^2$ is hydrogen or $C_1$-$C_2$-alkyl;
or
$R^1$ and $R^2$ are taken together with the carbon atom to which they are attached to form a 3- to 4-membered cycloalkyl ring;

ring A is a group selected from the group consisting of:

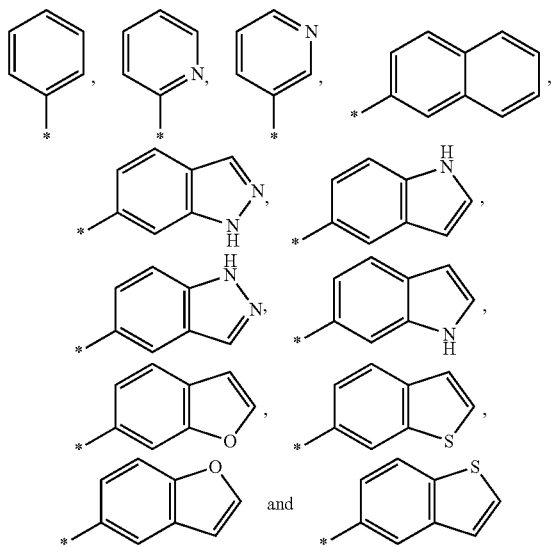

wherein * indicates the point of attachment of said group with the rest of the molecule and said group is optionally independently substituted, one or more times, with $R^3$;

$R^3$ is hydrogen, halogen, hydroxy, nitro, cyano, $C_1$-$C_3$-alkyl, $C_1$-$C_3$-alkoxy, $C_1$-haloalkyl, $C_1$-haloalkoxy, $C_1$-$C_2$-alkyl-C(O)—, $R^{18}$—O—C(O)—, $R^7R^8N$—C(O)—, or a group selected from the group consisting of

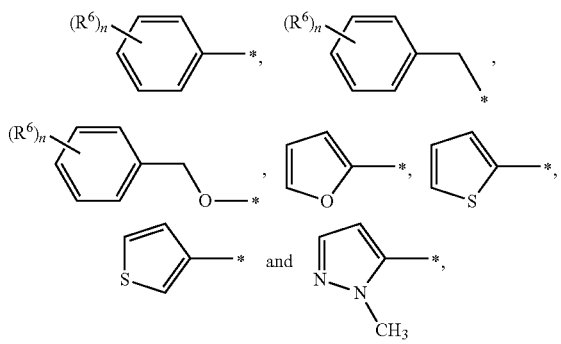

wherein * indicates the point of attachment of said group with the rest of the molecule, and wherein said $C_1$-$C_3$-alkyl, $C_1$-$C_3$-alkoxy, $C_1$-haloalkyl or $C_1$-haloalkoxy groups are optionally substituted with one hydroxy group;

$R^6$ is $C_1$-alkoxy;

ring B is a group selected from the group consisting of:

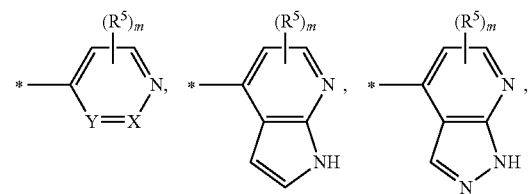

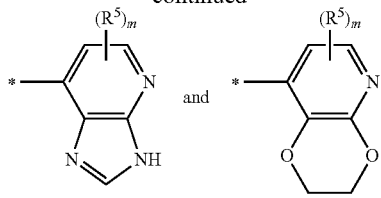

wherein * indicates the point of attachment of said group with the rest of the molecule;

X is $CR^4$ or N;

Y is $CR^4$ or N, wherein when one of X and Y is N, the other is $CR^4$;

each $R^4$ is independently hydrogen, halogen, hydroxy, cyano, $C_1$-alkyl, $C_1$-$C_3$-alkoxy, $C_1$-alkyl-S—, $R^9R^{10}N$—, $R^{11}$—C(O)—(NH)—, ($R^{11}$—C(O)—)($R^{12}$—C(O)—)N—, $R^9R^{10}N$—C(O)—($NR^7$)—, $R^9R^{10}N$—C(S)—($NR^7$)—, or $R^{18}$—O—C(O)—($NR^7$)—, wherein said $C_1$-alkyl is optionally independently substituted, one, two or three times, with halogen, and wherein said $C_1$-$C_3$-alkoxy is optionally independently substituted, one or more times, with a substituent selected from the group consisting of hydroxy, halogen, $C_1$-$C_2$-alkoxy, and $C_3$-$C_4$-cycloalkyl;

each $R^5$ is independently halogen, amino, $C_1$-$C_4$-alkyl, $C_1$-alkoxy, or phenyl-$C_1$-alkyl, wherein said phenyl group is optionally substituted one time with $C_1$-alkoxy;

J is hydrogen or hydroxy;

E is hydrogen, $C_1$-$C_3$-alkyl, $R^{18}$—O—C(O)—$C_1$-$C_2$-alkyl, or $R^7R^8N$—C(O)—$C_1$-$C_2$-alkyl, wherein said $C_1$-$C_3$-alkyl is optionally independently substituted, one or more times, with a substituent selected from the group consisting of hydroxy and halogen;

Q is O or N—$OR^{16}$;

$R^7$ and $R^8$ are independently hydrogen, $C_1$-alkyl or tert-butyl-O—C(O)—;

$R^9$ and $R^{10}$ are independently hydrogen, $C_1$-$C_4$-alkyl, $C_3$-$C_4$-cyclo-alkyl-, $C_1$-$C_3$-haloalkyl-, phenyl or heteroaryl, wherein said phenyl or heteroaryl group is optionally independently substituted, one or more times, with $R^5$, and wherein said $C_1$-$C_4$-alkyl is optionally independently substituted, one or more times, with a substituent selected from the group consisting of hydroxy, $C_1$-alkoxy, $C_1$-alkyl-S—, $C_3$-cycloalkyl, heteroaryl and $R^{18}$—O—C(O)—;

$R^{11}$ and $R^{12}$ are independently $C_1$-$C_4$-alkyl, $C_3$-$C_4$-cycloalkyl, 4- to 6-membered heterocycloalkyl, phenyl, heteroaryl, $R^{13}$—(CH$_2$)$_o$—O—CH$_2$—, $R^{14}$—(CH$_2$)$_o$—, or $R^{15}$—O—(CH$_2$)$_o$—, wherein said $C_1$-$C_4$-alkyl is optionally independently substituted, one or more times, with a substituent selected from the group consisting of halogen, hydroxy, cyano, $C_1$-$C_4$-alkoxy, $R^7R^8N$—, and phenyl optionally independently substituted, one or more times, with $R^5$, wherein said $C_3$-$C_4$-cycloalkyl is optionally independently substituted, one or two times, with halogen, cyano, $C_1$-alkyl, $C_1$-haloalkyl or phenyl optionally independently substituted, one or more times, with $R^5$, wherein said 4- to 6-membered heterocycloalkyl is optionally independently substituted, one or more times, with a substituent selected from the group consisting of $C_1$-alkyl and $R^{18}$—O—C(O)—, and
wherein said phenyl or heteroaryl is optionally independently substituted, one or two times, with $R^5$;
$R^{13}$ is branched $C_3$-alkyl, $C_1$-$C_2$-haloalkyl, $C_2$-alkenyl, $C_2$-alkynyl, 4- to 6-membered heterocycloalkyl, phenyl or heteroaryl,
wherein said phenyl or heteroaryl is optionally independently substituted, one or two times, with $R^5$;
$R^{14}$ is $C_1$-alkyl-S—, $C_1$-alkyl-$SO_2$—, $C_3$-$C_4$-cycloalkyl, 4- to 6-membered heterocycloalkyl, phenyl or heteroaryl,
wherein said phenyl or heteroaryl is optionally independently substituted, one or two times, with $R^5$;
$R^{15}$ is phenyl or heteroaryl,
wherein said phenyl or heteroaryl is optionally independently substituted, one or more times, with $R^5$;
$R^{16}$ is hydrogen or $C_1$-alkyl-C(O)—;
$R^{18}$ is hydrogen or $C_1$-$C_4$-alkyl;
m is 0, 1 or 2;
n is 0 or 1; and
o is 1, 2, 3 or 4,
or an N-oxide, a salt, a tautomer or a stereoisomer thereof, or a salt of said N-oxide, tautomer or stereoisomer.

6. The compound of formula (I) according to claim 1, wherein:
$R^1$ is hydrogen, $C_1$-$C_3$-alkyl, $C_1$-alkyl substituted one time with chlorine, $C_1$-alkyl substituted one, two or three times with fluorine, or phenyl,
wherein said phenyl is optionally independently substituted, one or more times, with $R^3$;
$R^2$ is hydrogen or $C_1$-alkyl;
or
$R^1$ and $R^2$ are taken together with the carbon atom to which they are attached to form a 3- to 4-membered cycloalkyl ring;
ring A is a group selected from the group consisting of:

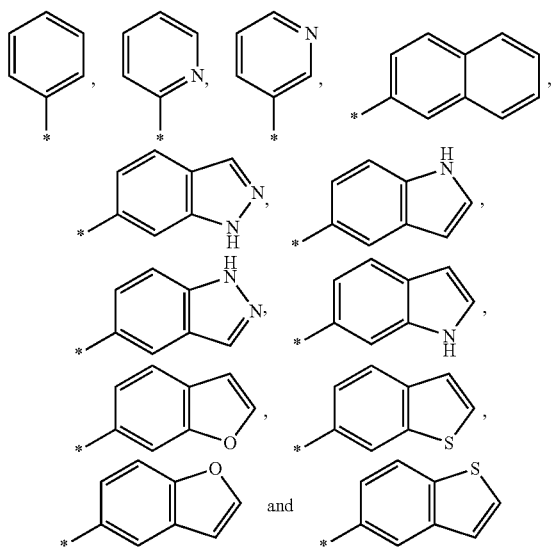

wherein * indicates the point of attachment of said group with the rest of the molecule and said group is optionally independently substituted, one or more times, with $R^3$;

$R^3$ is hydrogen, fluorine, chlorine, bromine, hydroxy, nitro, cyano, $C_1$-$C_3$-alkyl, $C_1$-$C_3$-alkoxy, —$CF_3$, —$OCF_3$, —$OCHF_2$, $C_1$— alkyl-C(O)—, $R^{18}$—O—C(O)—, $R^7R^8N$—C(O)—, or a group selected from the group consisting of

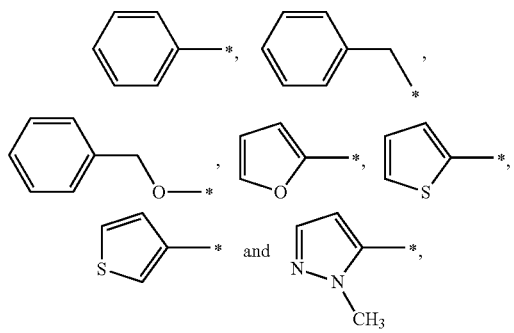

wherein * indicates the point of attachment of said group with the rest of the molecule, and
wherein said $C_1$-$C_3$-alkyl group is optionally substituted with one hydroxy group;
ring B is a group selected from the group consisting of:

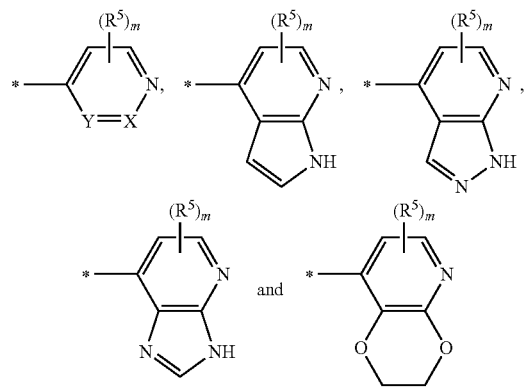

wherein * indicates the point of attachment of said group with the rest of the molecule;
X is $CR^4$;
Y is $CR^4$ or N,
wherein when one of X and Y is N, the other is $CR^4$;
each $R^4$ is independently hydrogen, halogen, hydroxy, cyano, $C_1$-alkyl, $C$—$C_3$-alkoxy, $C_1$-alkyl-S—, $R^9R^{10}N$—, $R^{11}$—C(O)—(NH)—, ($R^{11}$—C(O)—)($R^{12}$—C(O)—)N—, $R^9R^{10}N$—C(O)—($NR^7$)—, $R^9R^{10}N$—C(S)—($NR^7$)—, or $R^{18}$—O—C(O)—($NR^7$)—,
wherein said $C_1$-alkyl is optionally substituted, one or two times, with fluorine, and
wherein said $C_1$-$C_3$-alkoxy is optionally independently substituted, one or more times, with a substituent selected from the group consisting of hydroxy, fluorine, $C_1$-alkoxy, and $C_3$-cycloalkyl;
each $R^5$ is independently fluorine, chlorine, amino, $C_1$-$C_4$-alkyl, $C_1$-alkoxy, or phenyl-$C_1$-alkyl,
wherein said phenyl group is optionally substituted one time with $C_1$-alkoxy;
J is hydrogen or hydroxy;

E is hydrogen, $C_1$-$C_3$-alkyl, or $R^7R^8N$—C(O)—C—$C_2$-alkyl,
  wherein said $C_1$-$C_3$-alkyl is optionally substituted one time with hydroxy and/or optionally substituted one, two or three times with fluorine;
Q is O or N—$OR^{16}$;
$R^7$ and $R^8$ are independently hydrogen, $C_1$-alkyl or tert-butyl-O—C(O)—;
$R^9$ and $R^{10}$ are independently hydrogen, $C_1$-$C_3$-alkyl, $C_3$-$C_4$-cyclo-alkyl-, C—$C_3$-haloalkyl-, or heteroaryl,
  wherein said heteroaryl group is optionally substituted one time with $R^5$, and
  wherein said $C_1$-$C_3$-alkyl is optionally independently substituted, one or more times, with a substituent selected from the group consisting of hydroxy, $C_1$-alkoxy, $C_1$-alkyl-S—, $C_3$-cycloalkyl, and heteroaryl;
$R^{11}$ and $R^{12}$ are independently $C_1$-$C_4$-alkyl, $C_3$-$C_4$-cycloalkyl, 4- to 5-membered heterocycloalkyl, phenyl, heteroaryl, $R^{13}$—$(CH_2)_o$—O—$CH_2$—, $R^{14}$—$(CH_2)_o$—, or $R^{15}$—O—$(CH_2)_o$—,
  wherein said $C_1$-$C_4$-alkyl is optionally independently substituted, one or more times, with a substituent selected from the group consisting of halogen, hydroxy, cyano, $C_1$-$C_4$-alkoxy, $R^7R^8N$—, and phenyl optionally independently substituted, one or more times, with $R^5$,
  wherein said $C_3$-$C_4$-cycloalkyl is optionally independently substituted, one or two times, with a substituent selected from the group consisting of fluorine, cyano, —$CF_3$ and phenyl,
  wherein said 4- to 6-membered heterocycloalkyl is optionally independently substituted, one or more times, with $C_1$-alkyl or $R^{18}$—O—C(O)—, and
  wherein said phenyl or heteroaryl is optionally independently substituted, one or two times, with $R^5$;
$R^{13}$ is branched $C_3$-alkyl, $C_2$-alkenyl, $C_2$-alkynyl, 6-membered heterocycloalkyl, phenyl or heteroaryl,
  wherein said phenyl or heteroaryl is optionally substituted one time with $R^5$;
$R^{14}$ is $C_1$-alkyl-S—, $C_3$-cycloalkyl, 5-membered heterocycloalkyl, phenyl or heteroaryl,
  wherein said phenyl or heteroaryl is optionally substituted one time with $R^5$;
$R^{15}$ is phenyl or heteroaryl;
$R^{16}$ is hydrogen or $C_1$-alkyl-C(O)—;
$R^{18}$ is hydrogen or $C_1$-$C_4$-alkyl;
m is 0 or 1; and
o is 1, 2, 3 or 4,
or an N-oxide, a salt, a tautomer or a stereoisomer thereof, or a salt of said N-oxide, tautomer or stereoisomer.

7. The compound of formula (I) according to claim 1, which is selected from the group consisting of:
  6,6-dimethyl-3-(phenylamino)-2-(pyridin-4-yl)-1,5,6,7-tetrahydro-4H-indol-4-one;
  2-(3-chloropyridin-4-yl)-6,6-dimethyl-3-(phenylamino)-1,5,6,7-tetrahydro-4H-indol-4-one;
  6,6-dimethyl-3-[(3-methylphenyl)amino]-2-(pyridin-4-yl)-1,5,6,7-tetrahydro-4H-indol-4-one;
  3-[(3-chlorophenyl)amino]-6,6-dimethyl-2-(pyridin-4-yl)-1,5,6,7-tetrahydro-4H-indol-4-one;
  6,6-dimethyl-3-(phenylamino)-2-(pyrimidin-4-yl)-1,5,6,7-tetrahydro-4H-indol-4-one;
  3-[(3-fluorophenyl)amino]-6,6-dimethyl-2-(pyridin-4-yl)-1,5,6,7-tetrahydro-4H-indol-4-one;
  (6S)-3-(phenylamino)-6-(propan-2-yl)-2-(pyridin-4-yl)-1,5,6,7-tetrahydro-4H-indol-4-one;
  6-phenyl-3-(phenylamino)-2-(pyridin-4-yl)-1,5,6,7-tetrahydro-4H-indol-4-one;
  3-(phenylamino)-2-(pyridin-4-yl)-1,5,6,7-tetrahydro-4H-indol-4-one;
  3-[(4-chlorophenyl)amino]-6,6-dimethyl-2-(pyridin-4-yl)-1,5,6,7-tetrahydro-4H-indol-4-one;
  3-[(4-fluorophenyl)amino]-6,6-dimethyl-2-(pyridin-4-yl)-1,5,6,7-tetrahydro-4H-indol-4-one;
  3-[(3-bromophenyl)amino]-6,6-dimethyl-2-(pyridin-4-yl)-1,5,6,7-tetrahydro-4H-indol-4-one;
  3'-(phenylamino)-2'-(pyridin-4-yl)-1',7'-dihydrospiro[cyclobutane-1,6'-indol]-4'(5'H)-one;
  3-[(3-fluoro-5-methylphenyl)amino]-6,6-dimethyl-2-(pyridin-4-yl)-1,5,6,7-tetrahydro-4H-indol-4-one;
  3-[(3-ethylphenyl)amino]-6,6-dimethyl-2-(pyridin-4-yl)-1,5,6,7-tetrahydro-4H-indol-4-one;
  6,6-dimethyl-3-[(3-nitrophenyl)amino]-2-(pyridin-4-yl)-1,5,6,7-tetrahydro-4H-indol-4-one;
  (6R)-3-(phenylamino)-6-(propan-2-yl)-2-(pyridin-4-yl)-1,5,6,7-tetrahydro-4H-indol-4-one;
  (6S)-3-(phenylamino)-6-(propan-2-yl)-2-(pyridin-4-yl)-1,5,6,7-tetrahydro-4H-indol-4-one;
  3-[(3-chloro-5-fluorophenyl)amino]-6,6-dimethyl-2-(pyridin-4-yl)-1,5,6,7-tetrahydro-4H-indol-4-one;
  3-(phenylamino)-2-(pyridin-4-yl)-6-(trifluoromethyl)-1,5,6,7-tetrahydro-4H-indol-4-one;
  3-[(3,4-difluorophenyl)amino]-6,6-dimethyl-2-(pyridin-4-yl)-1,5,6,7-tetrahydro-4H-indol-4-one;
  6-methyl-3-(phenylamino)-2-(pyridin-4-yl)-1,5,6,7-tetrahydro-4H-indol-4-one;
  3-[(3-fluorophenyl)amino]-2-(2-fluoropyridin-4-yl)-6,6-dimethyl-1,5,6,7-tetrahydro-4H-indol-4-one;
  6,6-dimethyl-2-(pyridin-4-yl)-3-(pyridin-2-ylamino)-1,5,6,7-tetrahydro-4H-indol-4-one;
  3-(1-benzofuran-6-ylamino)-6,6-dimethyl-2-(pyridin-4-yl)-1,5,6,7-tetrahydro-4H-indol-4-one;
  6,6-dimethyl-3-(phenylamino)-2-(1H-pyrrolo[2,3-b]pyridin-4-yl)-1,5,6,7-tetrahydro-4H-indol-4-one;
  6-ethyl-3-(phenylamino)-2-(pyridin-4-yl)-1,5,6,7-tetrahydro-4H-indol-4-one;
  6-(2-methylpropyl)-3-(phenylamino)-2-(pyridin-4-yl)-1,5,6,7-tetrahydro-4H-indol-4-one;
  2-(3-fluoropyridin-4-yl)-6,6-dimethyl-3-(phenylamino)-1,5,6,7-tetrahydro-4H-indol-4-one;
  3-[(3,5-difluorophenyl)amino]-6,6-dimethyl-2-(pyridin-4-yl)-1,5,6,7-tetrahydro-4H-indol-4-one;
  6,6-dimethyl-2-(pyridin-4-yl)-3-[(3,4,5-trifluorophenyl)amino]-1,5,6,7-tetrahydro-4H-indol-4-one;
  2-(3-chloropyridin-4-yl)-3-(phenylamino)-1,5,6,7-tetrahydro-4H-indol-4-one;
  6,6-dimethyl-3-(phenylamino)-2-(1H-pyrazolo[3,4-b]pyridin-4-yl)-1,5,6,7-tetrahydro-4H-indol-4-one;
  N-4-[6,6-dimethyl-4-oxo-3-(phenylamino)-4,5,6,7-tetrahydro-1H-indol-2-yl]pyridin-2-ylpropanamide;
  N-4-[6,6-dimethyl-4-oxo-3-(phenylamino)-4,5,6,7-tetrahydro-1H-indol-2-yl]pyridin-2-ylacetamide;
  3'-(phenylamino)-2'-(pyridin-4-yl)-1',7'-dihydrospiro[cyclopropane-1,6'-indol]-4'(5'H)-one;
  N-4-[6,6-dimethyl-4-oxo-3-(phenylamino)-4,5,6,7-tetrahydro-1H-indol-2-yl]pyridin-2-ylcyclopropanecarboxamide;
  N-4-[4-oxo-3-(phenylamino)-4,5,6,7-tetrahydro-1H-indol-2-yl]pyridin-2-ylacetamide;
  N-(4-3-[(3-fluorophenyl)amino]-4-oxo-4,5,6,7-tetrahydro-1H-indol-2-ylpyridin-2-yl)acetamide;
  3-[(3-fluorophenyl)amino]-2-(pyridin-4-yl)-1,5,6,7-tetrahydro-4H-indol-4-one;

3-[(4-fluorophenyl)amino]-2-(pyridin-4-yl)-1,5,6,7-tetrahydro-4H-indol-4-one;
3-[(3-fluorophenyl)amino]-2-(pyridin-4-yl)-6-(trifluoromethyl)-1,5,6,7-tetrahydro-4H-indol-4-one;
2-(2-fluoropyridin-4-yl)-3-(phenylamino)-1,5,6,7-tetrahydro-4H-indol-4-one;
3-(biphenyl-3-ylamino)-6,6-dimethyl-2-(pyridin-4-yl)-1,5,6,7-tetrahydro-4H-indol-4-one;
4-[6,6-dimethyl-4-oxo-3-(phenylamino)-4,5,6,7-tetrahydro-1H-indol-2-yl]pyridine-2-carbonitrile;
N-(4-{3-[(3-fluorophenyl)amino]-4-oxo-4,5,6,7-tetrahydro-1H-indol-2-yl}pyridin-2-yl)cyclopropanecarboxamide;
N-4-[4-oxo-3-(phenylamino)-4,5,6,7-tetrahydro-1H-indol-2-yl]pyridin-2-ylcyclopropanecarboxamide;
2-(2-aminopyridin-4-yl)-3-(phenylamino)-6-(propan-2-yl)-1,5,6,7-tetrahydro-4H-indol-4-one;
2-(2-aminopyridin-4-yl)-3-[(3-fluorophenyl)amino]-6-(propan-2-yl)-1,5,6,7-tetrahydro-4H-indol-4-one;
6,6-dimethyl-2-(pyridin-4-yl)-3-[3-(trifluoromethyl)phenyl]amino-1,5,6,7-tetrahydro-4H-indol-4-one;
3-[(3-methoxyphenyl)amino]-6,6-dimethyl-2-(pyridin-4-yl)-1,5,6,7-tetrahydro-4H-indol-4-one;
6,6-dimethyl-3-[(2-methylphenyl)amino]-2-(pyridin-4-yl)-1,5,6,7-tetrahydro-4H-indol-4-one;
6,6-dimethyl-3-[(4-methylphenyl)amino]-2-(pyridin-4-yl)-1,5,6,7-tetrahydro-4H-indol-4-one;
6,6-dimethyl-3-(phenylamino)-2-(pyridazin-4-yl)-1,5,6,7-tetrahydro-4H-indol-4-one;
3-[(2,3-dimethoxyphenyl)amino]-6,6-dimethyl-2-(pyridin-4-yl)-1,5,6,7-tetrahydro-4H-indol-4-one;
3-[(3,4-dimethoxyphenyl)amino]-6,6-dimethyl-2-(pyridin-4-yl)-1,5,6,7-tetrahydro-4H-indol-4-one;
3-[(4-methoxyphenyl)amino]-6,6-dimethyl-2-(pyridin-4-yl)-1,5,6,7-tetrahydro-4H-indol-4-one;
3-[(2-fluorophenyl)amino]-6,6-dimethyl-2-(pyridin-4-yl)-1,5,6,7-tetrahydro-4H-indol-4-one;
3-[(2-chlorophenyl)amino]-6,6-dimethyl-2-(pyridin-4-yl)-1,5,6,7-tetrahydro-4H-indol-4-one;
3-[(2,4-dimethoxyphenyl)amino]-6,6-dimethyl-2-(pyridin-4-yl)-1,5,6,7-tetrahydro-4H-indol-4-one;
6,6-dimethyl-2-(pyridin-4-yl)-3-(pyridin-3-ylamino)-1,5,6,7-tetrahydro-4H-indol-4-one;
3-(isoquinolin-4-ylamino)-6,6-dimethyl-2-(pyridin-4-yl)-1,5,6,7-tetrahydro-4H-indol-4-one;
3-[(3-aminophenyl)amino]-6,6-dimethyl-2-(pyridin-4-yl)-1,5,6,7-tetrahydro-4H-indol-4-one;
6,6-dimethyl-2-(pyridin-4-yl)-3-(quinolin-3-ylamino)-1,5,6,7-tetrahydro-4H-indol-4-one;
3-(1-benzofuran-5-ylamino)-6,6-dimethyl-2-(pyridin-4-yl)-1,5,6,7-tetrahydro-4H-indol-4-one;
3-(1H-indol-6-ylamino)-6,6-dimethyl-2-(pyridin-4-yl)-1,5,6,7-tetrahydro-4H-indol-4-one;
3-(1-benzothiophen-5-ylamino)-6,6-dimethyl-2-(pyridin-4-yl)-1,5,6,7-tetrahydro-4H-indol-4-one;
3-(1H-indol-5-ylamino)-6,6-dimethyl-2-(pyridin-4-yl)-1,5,6,7-tetrahydro-4H-indol-4-one;
3-[(2-bromophenyl)amino]-6,6-dimethyl-2-(pyridin-4-yl)-1,5,6,7-tetrahydro-4H-indol-4-one;
3-[(4-bromophenyl)amino]-6,6-dimethyl-2-(pyridin-4-yl)-1,5,6,7-tetrahydro-4H-indol-4-one;
3-(1H-benzimidazol-6-ylamino)-6,6-dimethyl-2-(pyridin-4-yl)-1,5,6,7-tetrahydro-4H-indol-4-one;
3-(1H-indazol-6-ylamino)-6,6-dimethyl-2-(pyridin-4-yl)-1,5,6,7-tetrahydro-4H-indol-4-one;
6,6-dimethyl-2-(pyridin-4-yl)-3-(quinolin-4-ylamino)-1,5,6,7-tetrahydro-4H-indol-4-one;
3-[(2,5-dimethoxyphenyl)amino]-6,6-dimethyl-2-(pyridin-4-yl)-1,5,6,7-tetrahydro-4H-indol-4-one;
3-[(3,5-dichlorophenyl)amino]-6,6-dimethyl-2-(pyridin-4-yl)-1,5,6,7-tetrahydro-4H-indol-4-one;
3-[(2,5-dichlorophenyl)amino]-6,6-dimethyl-2-(pyridin-4-yl)-1,5,6,7-tetrahydro-4H-indol-4-one;
3-[6,6-dimethyl-4-oxo-2-(pyridin-4-yl)-4,5,6,7-tetrahydro-1H-indol-3-yl]aminobenzonitrile;
3-[3-(benzyloxy)phenyl]amino-6,6-dimethyl-2-(pyridin-4-yl)-1,5,6,7-tetrahydro-4H-indol-4-one;
3-[(4-fluoro-3-methylphenyl)amino]-6,6-dimethyl-2-(pyridin-4-yl)-1,5,6,7-tetrahydro-4H-indol-4-one;
3-[(2-fluoro-5-methylphenyl)amino]-6,6-dimethyl-2-(pyridin-4-yl)-1,5,6,7-tetrahydro-4H-indol-4-one;
3-[(4-ethylphenyl)amino]-6,6-dimethyl-2-(pyridin-4-yl)-1,5,6,7-tetrahydro-4H-indol-4-one;
3-[(2-ethylphenyl)amino]-6,6-dimethyl-2-(pyridin-4-yl)-1,5,6,7-tetrahydro-4H-indol-4-one;
6,6-dimethyl-3-[3-(propan-2-yl)phenyl]amino-2-(pyridin-4-yl)-1,5,6,7-tetrahydro-4H-indol-4-one;
6,6-dimethyl-3-[4-(propan-2-yl)phenyl]amino-2-(pyridin-4-yl)-1,5,6,7-tetrahydro-4H-indol-4-one;
3-[(5-chloro-2-fluorophenyl)amino]-6,6-dimethyl-2-(pyridin-4-yl)-1,5,6,7-tetrahydro-4H-indol-4-one;
6,6-dimethyl-3-[2-(propan-2-yl)phenyl]amino-2-(pyridin-4-yl)-1,5,6,7-tetrahydro-4H-indol-4-one;
3-[(3-hydroxyphenyl)amino]-6,6-dimethyl-2-(pyridin-4-yl)-1,5,6,7-tetrahydro-4H-indol-4-one;
6,6-dimethyl-3-[(4-nitrophenyl)amino]-2-(pyridin-4-yl)-1,5,6,7-tetrahydro-4H-indol-4-one;
3-[(3-chloro-2-methylphenyl)amino]-6,6-dimethyl-2-(pyridin-4-yl)-1,5,6,7-tetrahydro-4H-indol-4-one;
3-[(3-chloro-4-methylphenyl)amino]-6,6-dimethyl-2-(pyridin-4-yl)-1,5,6,7-tetrahydro-4H-indol-4-one;
3-[(5-chloro-2-methylphenyl)amino]-6,6-dimethyl-2-(pyridin-4-yl)-1,5,6,7-tetrahydro-4H-indol-4-one;
3-[(3-chloro-2-fluorophenyl)amino]-6,6-dimethyl-2-(pyridin-4-yl)-1,5,6,7-tetrahydro-4H-indol-4-one;
3-[(3-chloro-4-fluorophenyl)amino]-6,6-dimethyl-2-(pyridin-4-yl)-1,5,6,7-tetrahydro-4H-indol-4-one;
3-[(2-fluoro-3-methylphenyl)amino]-6,6-dimethyl-2-(pyridin-4-yl)-1,5,6,7-tetrahydro-4H-indol-4-one;
N-(3-[6,6-dimethyl-4-oxo-2-(pyridin-4-yl)-4,5,6,7-tetrahydro-1H-indol-3-yl]aminophenyl)-2-methylpropanamide;
N-(3-[6,6-dimethyl-4-oxo-2-(pyridin-4-yl)-4,5,6,7-tetrahydro-1H-indol-3-yl]aminophenyl)propanamide;
3-[6,6-dimethyl-4-oxo-2-(pyridin-4-yl)-4,5,6,7-tetrahydro-1H-indol-3-yl]amino-N-methylbenzamide;
3-(1H-indazol-5-ylamino)-6,6-dimethyl-2-(pyridin-4-yl)-1,5,6,7-tetrahydro-4H-indol-4-one;
3-[6,6-dimethyl-4-oxo-2-(pyridin-4-yl)-4,5,6,7-tetrahydro-1H-indol-3-yl]aminobenzamide;
N-(3-[6,6-dimethyl-4-oxo-2-(pyridin-4-yl)-4,5,6,7-tetrahydro-1H-indol-3-yl]aminophenyl)butanamide;
2-(2-chloropyridin-4-yl)-6,6-dimethyl-3-(phenylamino)-1,5,6,7-tetrahydro-4H-indol-4-one;
3-[(3-ethoxyphenyl)amino]-6,6-dimethyl-2-(pyridin-4-yl)-1,5,6,7-tetrahydro-4H-indol-4-one;
6,6-dimethyl-3-[3-(propan-2-yloxy)phenyl]amino-2-(pyridin-4-yl)-1,5,6,7-tetrahydro-4H-indol-4-one;
3-[3-(2-hydroxyethoxy)phenyl]amino-6,6-dimethyl-2-(pyridin-4-yl)-1,5,6,7-tetrahydro-4H-indol-4-one;
6,6-dimethyl-2-(pyridin-4-yl)-3-[3-(trifluoromethoxy)phenyl]amino-1,5,6,7-tetrahydro-4H-indol-4-one;
6,6-dimethyl-3-[(3-propoxyphenyl)amino]-2-(pyridin-4-yl)-1,5,6,7-tetrahydro-4H-indol-4-one;

N-(3-[6,6-dimethyl-4-oxo-2-(pyridin-4-yl)-4,5,6,7-tetrahydro-1H-indol-3-yl]aminophenyl)acetamide;
3-[(4-fluoro-3-methoxyphenyl)amino-6,6-dimethyl-2-(pyridin-4-yl)-1,5,6,7-tetrahydro-4H-indol-4-one;
3-[4-fluoro-3-(hydroxymethyl)phenyl]amino-6,6-dimethyl-2-(pyridin-4-yl)-1,5,6,7-tetrahydro-4H-indol-4-one;
3-[3-(1-hydroxyethyl)phenyl]amino-6,6-dimethyl-2-(pyridin-4-yl)-1,5,6,7-tetrahydro-4H-indol-4-one;
3-[(3-acetylphenyl)amino]-6,6-dimethyl-2-(pyridin-4-yl)-1,5,6,7-tetrahydro-4H-indol-4-one;
3-[(3-tert-butylphenyl)amino]-6,6-dimethyl-2-(pyridin-4-yl)-1,5,6,7-tetrahydro-4H-indol-4-one;
3-[6,6-dimethyl-4-oxo-2-(pyridin-4-yl)-4,5,6,7-tetrahydro-1H-indol-3-yl]amino-N,N-dimethylbenzamide;
3-[3-(difluoromethoxy)phenyl]amino-6,6-dimethyl-2-(pyridin-4-yl)-1,5,6,7-tetrahydro-4H-indol-4-one;
tert-butyl 3-[6,6-dimethyl-4-oxo-2-(pyridin-4-yl)-4,5,6,7-tetrahydro-1H-indol-3-yl]aminobenzoate;
3-[3-(1,3-dioxolan-2-yl)phenyl]amino-6,6-dimethyl-2-(pyridin-4-yl)-1,5,6,7-tetrahydro-4H-indol-4-one;
3-[(4-fluoro-2-methoxyphenyl)amino-6,6-dimethyl-2-(pyridin-4-yl)-1,5,6,7-tetrahydro-4H-indol-4-one;
2-(2-aminopyridin-4-yl)-6,6-dimethyl-3-(phenylamino)-1,5,6,7-tetrahydro-4H-indol-4-one;
3-[(3-fluorophenyl)amino]-2-{2-[(3-fluorophenyl)amino]pyridin-4-yl}-6,6-dimethyl-1,5,6,7-tetrahydro-4H-indol-4-one;
3-[(2-methoxyphenyl)amino]-6,6-dimethyl-2-(pyridin-4-yl)-1,5,6,7-tetrahydro-4H-indol-4-one;
3-[(2-ethoxy-4-fluorophenyl)amino]-6,6-dimethyl-2-(pyridin-4-yl)-1,5,6,7-tetrahydro-4H-indol-4-one;
6,6-dimethyl-3-(phenylamino)-2-[2-(pyrrolidin-1-yl)pyridin-4-yl]-1,5,6,7-tetrahydro-4H-indol-4-one;
6,6-dimethyl-242-(morpholin-4-yl)pyridin-4-yl]-3-(phenylamino)-1,5,6,7-tetrahydro-4H-indol-4-one;
3-[(2-ethoxyphenyl)amino]-6,6-dimethyl-2-(pyridin-4-yl)-1,5,6,7-tetrahydro-4H-indol-4-one;
3-[4-fluoro-3-(trifluoromethyl)phenyl]amino-6,6-dimethyl-2-(pyridin-4-yl)-1,5,6,7-tetrahydro-4H-indol-4-one;
3-(1-benzothiophen-6-ylamino)-6,6-dimethyl-2-(pyridin-4-yl)-1,5,6,7-tetrahydro-4H-indol-4-one;
6,6-dimethyl-2-(3-methylpyridin-4-yl)-3-(phenylamino)-1,5,6,7-tetrahydro-4H-indol-4-one;
N-4-[6,6-dimethyl-4-oxo-3-(phenylamino)-4,5,6,7-tetrahydro-1H-indol-2-yl]pyridin-2-yl-2-methylpropanamide;
N-acetyl-N-4-[6,6-dimethyl-4-oxo-3-(phenylamino)-4,5,6,7-tetrahydro-1H-indol-2-yl]pyridin-2-ylacetamide;
3-[(3,4-difluorophenyl)amino]-2-(pyridin-4-yl)-1,5,6,7-tetrahydro-4H-indol-4-one;
2-(3,5-difluoropyridin-4-yl)-6,6-dimethyl-3-(phenylamino)-1,5,6,7-tetrahydro-4H-indol-4-one;
2-(3,5-difluoropyridin-4-yl)-3-[(3-fluorophenyl)amino]-1,5,6,7-tetrahydro-4H-indol-4-one;
2-(2-bromopyridin-4-yl)-6,6-dimethyl-3-(phenylamino)-1,5,6,7-tetrahydro-4H-indol-4-one;
2-(2-aminopyridin-4-yl)-3-[(3-fluorophenyl)amino]-1,5,6,7-tetrahydro-4H-indol-4-one;
2-(2-aminopyridin-4-yl)-3-(phenylamino)-1,5,6,7-tetrahydro-4H-indol-4-one;
6,6-dimethyl-3-(phenylamino)-2-[2-(trifluoromethyl)pyridin-4-yl]-1,5,6,7-tetrahydro-4H-indol-4-one;
2-(3-chloropyridin-4-yl)-3-[(4-fluorophenyl)amino]-1,5,6,7-tetrahydro-4H-indol-4-one;
2-(2-methylpyridin-4-yl)-3-(phenylamino)-1,5,6,7-tetrahydro-4H-indol-4-one;
3-[6,6-dimethyl-4-oxo-2-(pyridin-4-yl)-4,5,6,7-tetrahydro-1H-indol-3-yl]amino-N-ethylbenzamide;
6,6-dimethyl-2-[2-(methylamino)pyridin-4-yl]-3-(phenylamino)-1,5,6,7-tetrahydro-4H-indol-4-one;
2-[6,6-dimethyl-4-oxo-2-(pyridin-4-yl)-4,5,6,7-tetrahydro-1H-indol-3-yl]aminobenzonitrile;
5-[6,6-dimethyl-4-oxo-2-(pyridin-4-yl)-4,5,6,7-tetrahydro-1H-indol-3-yl]amino-2-fluorobenzonitrile;
3-[4-fluoro-3-(trifluoromethoxy)phenyl]amino-6,6-dimethyl-2-(pyridin-4-yl)-1,5,6,7-tetrahydro-4H-indol-4-one;
6,6-dimethyl-2-(2-methylpyridin-4-yl)-3-(phenylamino)-1,5,6,7-tetrahydro-4H-indol-4-one;
2-(2-methoxypyridin-4-yl)-3-(phenylamino)-1,5,6,7-tetrahydro-4H-indol-4-one;
3-[6,6-dimethyl-4-oxo-2-(pyridin-4-yl)-4,5,6,7-tetrahydro-1H-indol-3-yl]aminobenzoic acid;
2-(2-bromopyridin-4-yl)-3-(phenylamino)-1,5,6,7-tetrahydro-4H-indol-4-one;
6,6-dimethyl-3-(2-methyl-1,3-dioxolan-2-yl)phenyl]amino-2-(pyridin-4-yl)-1,5,6,7-tetrahydro-4H-indol-4-one;
3-[3-(1-hydroxypropyl)phenyl]amino-6,6-dimethyl-2-(pyridin-4-yl)-1,5,6,7-tetrahydro-4H-indol-4-one;
6,6-dimethyl-2-(pyridin-4-yl)-3-(2,2,2-trifluoro-1-hydroxyethyl)phenyl]amino-1,5,6,7-tetrahydro-4H-indol-4-one;
3-[3-(1-methoxyethyl)phenyl]amino-6,6-dimethyl-2-(pyridin-4-yl)-1,5,6,7-tetrahydro-4H-indol-4-one;
6,6-dimethyl-3-(naphthalen-1-ylamino)-2-(pyridin-4-yl)-1,5,6,7-tetrahydro-4H-indol-4-one;
6,6-dimethyl-3-(naphthalen-2-ylamino)-2-(pyridin-4-yl)-1,5,6,7-tetrahydro-4H-indol-4-one;
6,6-dimethyl-3-[(2-phenoxyphenyl)amino]-2-(pyridin-4-yl)-1,5,6,7-tetrahydro-4H-indol-4-one;
3-(biphenyl-2-ylamino)-6,6-dimethyl-2-(pyridin-4-yl)-1,5,6,7-tetrahydro-4H-indol-4-one;
6,6-dimethyl-2-(1-oxidopyridin-4-yl)-3-(phenylamino)-1,5,6,7-tetrahydro-4H-indol-4-one;
N-(cyclopropylcarbonyl)-N-(4-{3-[(3-fluorophenyl)amino]-4-oxo-4,5,6,7-tetrahydro-1H-indol-2-yl}pyridin-2-yl)cyclopropanecarboxamide;
N-(cyclopropylcarbonyl)-N-4-[4-oxo-3-(phenylamino)-4,5,6,7-tetrahydro-1H-indol-2-yl]pyridin-2-ylcyclopropanecarboxamide;
2-[2-(dimethylamino)pyridin-4-yl]-6,6-dimethyl-3-(phenylamino)-1,5,6,7-tetrahydro-4H-indol-4-one;
N-4-[6,6-dimethyl-4-oxo-3-(phenylamino)-4,5,6,7-tetrahydro-1H-indol-2-yl]pyridin-2-ylmethanesulfonamide;
N-4-[6,6-dimethyl-4-oxo-3-(phenylamino)-4,5,6,7-tetrahydro-1H-indol-2-yl]pyridin-2-yl-2,2-difluoroacetamide;
2-(2-aminopyridin-4-yl)-3-[(4-fluorophenyl)amino]-6-(propan-2-yl)-1,5,6,7-tetrahydro-4H-indol-4-one;
N-4-[4-oxo-3-(phenylamino)-4,5,6,7-tetrahydro-1H-indol-2-yl]pyridin-2-ylmethanesulfonamide;
1-methyl-3-(phenylamino)-2-(pyridin-4-yl)-1,5,6,7-tetrahydro-4H-indol-4-one;
1-ethyl-3-(phenylamino)-2-(pyridin-4-yl)-1,5,6,7-tetrahydro-4H-indol-4-one;
3-(phenylamino)-1-propyl-2-(pyridin-4-yl)-1,5,6,7-tetrahydro-4H-indol-4-one;
methyl 3-[4-oxo-3-(phenylamino)-2-(pyridin-4-yl)-4,5,6,7-tetrahydro-1H-indol-1-yl]propanoate;

3-[4-oxo-3-(phenylamino)-2-(pyridin-4-yl)-4,5,6,7-tetrahydro-1H-indol-1-yl]propanoic acid;
3-[4-oxo-3-(phenylamino)-2-(pyridin-4-yl)-4,5,6,7-tetrahydro-1H-indol-1-yl]propanamide;
1-(3-hydroxypropyl)-3-(phenylamino)-2-(pyridin-4-yl)-1,5,6,7-tetrahydro-4H-indol-4-one;
1-[2-(methylsulfonyl)ethyl]-3-(phenylamino)-2-(pyridin-4-yl)-1,5,6,7-tetrahydro-4H-indol-4-one;
2-(3-chloropyridin-4-yl)-1-ethyl-3-(phenylamino)-1,5,6,7-tetrahydro-4H-indol-4-one;
1,6-dimethyl-3-(phenylamino)-2-(pyridin-4-yl)-1,5,6,7-tetrahydro-4H-indol-4-one;
1,6,6-trimethyl-3-(phenylamino)-2-(pyridin-4-yl)-1,5,6,7-tetrahydro-4H-indol-4-one;
6,6-dimethyl-3-(phenylamino)-2-(pyridin-4-yl)-1-(2,2,2-trifluoroethyl)-1,5,6,7-tetrahydro-4H-indol-4-one;
1-ethyl-6,6-dimethyl-3-(phenylamino)-2-(pyridin-4-yl)-1,5,6,7-tetrahydro-4H-indol-4-one;
6,6-dimethyl-3-(phenylamino)-1-propyl-2-(pyridin-4-yl)-1,5,6,7-tetrahydro-4H-indol-4-one;
1-(24tert-butyl(dimethyl)silyl]oxyethyl)-6,6-dimethyl-3-(phenylamino)-2-(pyridin-4-yl)-1,5,6,7-tetrahydro-4H-indol-4-one;
1-(2-hydroxyethyl)-6,6-dimethyl-3-(phenylamino)-2-(pyridin-4-yl)-1,5,6,7-tetrahydro-4H-indol-4-one;
4-[1-(2-amino-2-oxoethyl)-6,6-dimethyl-4-oxo-3-(phenylamino)-4,5,6,7-tetrahydro-1H-indol-2-yl]pyridinium formate;
1-benzyl-6,6-dimethyl-3-(phenylamino)-2-(pyridin-4-yl)-1,5,6,7-tetrahydro-4H-indol-4-one;
N-4-[1-ethyl-6,6-dimethyl-4-oxo-3-(phenylamino)-4,5,6,7-tetrahydro-1H-indol-2-yl]pyridin-2-ylacetamide;
1-(2,2-difluoroethyl)-6,6-dimethyl-3-(phenylamino)-2-(pyridin-4-yl)-1,5,6,7-tetrahydro-4H-indol-4-one;
4-(hydroxyimino)-6,6-dimethyl-N-phenyl-2-(pyridin-4-yl)-4,5,6,7-tetrahydro-1H-indol-3-amine;
1-([6,6-dimethyl-3-(phenylamino)-2-(pyridin-4-yl)-1,5,6,7-tetrahydro-4H-indol-4-ylidene]aminooxy)ethanone;
2-(3-bromopyridin-4-yl)-3-(phenylamino)-1,5,6,7-tetrahydro-4H-indol-4-one;
4-[4-oxo-3-(phenylamino)-4,5,6,7-tetrahydro-1H-indol-2-yl]pyridine-3-carbonitrile;
4-{3-[(3-fluorophenyl)amino]-6,6-dimethyl-4-oxo-4,5,6,7-tetrahydro-1H-indol-2-yl}pyridine-3-carbonitrile;
2-(3-bromopyridin-4-yl)-6,6-dimethyl-3-(phenylamino)-1,5,6,7-tetrahydro-4H-indol-4-one;
6,6-dimethyl-2-[2-(methyl sulfanyl)pyridin-4-yl]-3-(phenylamino)-1,5,6,7-tetrahydro-4H-indol-4-one;
6,6-dimethyl-2-[3-(methyl sulfanyl)pyridin-4-yl]-3-(phenylamino)-1,5,6,7-tetrahydro-4H-indol-4-one;
4-[6,6-dimethyl-4-oxo-3-(phenylamino)-4,5,6,7-tetrahydro-1H-indol-2-yl]pyridin-3-yl(methyl)sulfoniumolate;
2-(2-aminopyridin-4-yl)-3-[(3-bromophenyl)amino]-6,6-dimethyl-1,5,6,7-tetrahydro-4H-indol-4-one;
2-{2-[(1-benzyl-1H-pyrazol-4-yl)amino]pyridin-4-yl}-6,6-dimethyl-3-(phenylamino)-1,5,6,7-tetrahydro-4H-indol-4-one;
6,6-dimethyl-2-{24(1-methyl-1H-pyrazol-4-yl)amino]pyridin-4-yl}-3-(phenylamino)-1,5,6,7-tetrahydro-4H-indol-4-one;
2'-(2-aminopyridin-4-yl)-3'-(phenylamino)-1',7'-dihydrospiro[cyclopropane-1,6'-indol]-4'(5'H)-one;
2'-(2-fluoropyridin-4-yl)-3'-(phenylamino)-1',7'-dihydrospiro[cyclopropane-1,6'-indol]-4'(5'H)-one;
2'-(3-fluoropyridin-4-yl)-3'-(phenylamino)-1',7'-dihydrospiro[cyclopropane-1,6'-indol]-4'(5'H)-one;
2-(2,6-dimethylpyridin-4-yl)-6,6-dimethyl-3-(phenylamino)-1,5,6,7-tetrahydro-4H-indol-4-one;
2-(2,3-dihydro[1,4]dioxino[2,3-b]pyridin-8-yl)-6,6-dimethyl-3-(phenylamino)-1,5,6,7-tetrahydro-4H-indol-4-one;
2-(2-aminopyridin-4-yl)-3-[(4-fluorophenyl)amino]-1,5,6,7-tetrahydro-4H-indol-4-one;
2-(2-aminopyridin-4-yl)-3-[(3,4-difluorophenyl)amino]-1,5,6,7-tetrahydro-4H-indol-4-one;
2-(2-fluoropyridin-4-yl)-6,6-dimethyl-3-(phenylamino)-1,5,6,7-tetrahydro-4H-indol-4-one;
2-(2,3-dichloropyridin-4-yl)-6,6-dimethyl-3-(phenylamino)-1,5,6,7-tetrahydro-4H-indol-4-one;
2-(2,5-dichloropyridin-4-yl)-6,6-dimethyl-3-(phenylamino)-1,5,6,7-tetrahydro-4H-indol-4-one;
2-(2,6-dichloropyridin-4-yl)-6,6-dimethyl-3-(phenylamino)-1,5,6,7-tetrahydro-4H-indol-4-one;
2-(2,6-dichloropyridin-4-yl)-3-(phenylamino)-1,5,6,7-tetrahydro-4H-indol-4-one;
2-(2,5-difluoropyridin-4-yl)-3-(phenylamino)-1,5,6,7-tetrahydro-4H-indol-4-one;
2-(2-chloro-3-fluoropyridin-4-yl)-6,6-dimethyl-3-(phenylamino)-1,5,6,7-tetrahydro-4H-indol-4-one;
2-(2-chloro-5-fluoropyridin-4-yl)-6,6-dimethyl-3-(phenylamino)-1,5,6,7-tetrahydro-4H-indol-4-one;
2-(3H-imidazo[4,5-b]pyridin-7-yl)-6,6-dimethyl-3-(phenylamino)-1,5,6,7-tetrahydro-4H-indol-4-one;
2-(2-aminopyridin-4-yl)-3-[(3,4-difluorophenyl)amino]-6-(propan-2-yl)-1,5,6,7-tetrahydro-4H-indol-4-one;
2-(2-aminopyrimidin-4-yl)-6,6-dimethyl-3-(phenylamino)-1,5,6,7-tetrahydro-4H-indol-4-one;
2-(6-aminopyrimidin-4-yl)-6,6-dimethyl-3-(phenylamino)-1,5,6,7-tetrahydro-4H-indol-4-one;
N-4-[4-oxo-3-(phenylamino)-4,5,6,7-tetrahydro-1H-indol-2-yl]pyridin-2-ylpropanamide;
N-4-[4-oxo-3-(phenylamino)-4,5,6,7-tetrahydro-1H-indol-2-yl]pyridin-2-ylbutanamide;
2,2-dimethyl-N-4-[4-oxo-3-(phenylamino)-4,5,6,7-tetrahydro-1H-indol-2-yl]pyridin-2-ylpropanamide;
1-methyl-N-4-[4-oxo-3-(phenylamino)-4,5,6,7-tetrahydro-1H-indol-2-yl]pyridin-2-ylcyclopropanecarboxamide;
N-4-[4-oxo-3-(phenylamino)-4,5,6,7-tetrahydro-1H-indol-2-yl]pyridin-2-ylcyclobutanecarboxamide;
2-methyl-N-4-[4-oxo-3-(phenylamino)-4,5,6,7-tetrahydro-1H-indol-2-yl]pyridin-2-ylpropanamide;
2-cyclopropyl-N-4-[4-oxo-3-(phenylamino)-4,5,6,7-tetrahydro-1H-indol-2-yl]pyridin-2-ylacetamide;
2,2-dimethyl-N-4-[4-oxo-3-(phenylamino)-4,5,6,7-tetrahydro-1H-indol-2-yl]pyridin-2-ylcyclopropanecarboxamide;
N-4-[4-oxo-3-(phenylamino)-4,5,6,7-tetrahydro-1H-indol-2-yl]pyridin-2-yl-2-phenylacetamide;
N-4-[4-oxo-3-(phenylamino)-4,5,6,7-tetrahydro-1H-indol-2-yl]pyridin-2-ylbut-3-ynamide;
N-4-[4-oxo-3-(phenylamino)-4,5,6,7-tetrahydro-1H-indol-2-yl]pyridin-2-yl-3-phenylpropanamide;
N-4-[4-oxo-3-(phenylamino)-4,5,6,7-tetrahydro-1H-indol-2-yl]pyridin-2-yl-4-phenylbutanamide;
2-methyl-N-4-[4-oxo-3-(phenylamino)-4,5,6,7-tetrahydro-1H-indol-2-yl]pyridin-2-ylcyclopropanecarboxamide;
N-4-[4-oxo-3-(phenylamino)-4,5,6,7-tetrahydro-1H-indol-2-yl]pyridin-2-ylbenzamide;
rel-(1 S,2S)—N-4-[4-oxo-3-(phenylamino)-4,5,6,7-tetrahydro-1H-indol-2-yl]pyridin-2-yl-2-phenylcyclopropanecarboxamide;

N-4-[6,6-dimethyl-4-oxo-3-(phenylamino)-4,5,6,7-tetrahydro-1H-indol-2-yl]pyridin-2-yl-N-methylacetamide;
2-fluoro-N-4-[4-oxo-3-(phenylamino)-4,5,6,7-tetrahydro-1H-indol-2-yl]pyridin-2-ylpropanamide;
2-fluoro-2-methyl-N-4-[4-oxo-3-(phenylamino)-4,5,6,7-tetrahydro-1H-indol-2-yl]pyridin-2-ylpropanamide;
3-hydroxy-2,2-dimethyl-N-4-[4-oxo-3-(phenylamino)-4,5,6,7-tetrahydro-1H-indol-2-yl]pyridin-2-ylpropanamide;
2-(methylsulfanyl)-N-4-[4-oxo-3-(phenylamino)-4,5,6,7-tetrahydro-1H-indol-2-yl]pyridin-2-ylacetamide;
2-cyano-2-methyl-N-4-[4-oxo-3-(phenylamino)-4,5,6,7-tetrahydro-1H-indol-2-yl]pyridin-2-ylpropanamide;
1-cyano-N-4-[4-oxo-3-(phenylamino)-4,5,6,7-tetrahydro-1H-indol-2-yl]pyridin-2-ylcyclopropanecarboxamide;
3,3,3-trifluoro-2-methyl-N-4-[4-oxo-3-(phenylamino)-4,5,6,7-tetrahydro-1H-indol-2-yl]pyridin-2-ylpropanamide;
2-(methylsulfonyl)-N-4-[4-oxo-3-(phenylamino)-4,5,6,7-tetrahydro-1H-indol-2-yl]pyridin-2-ylacetamide;
rel-(1R,2S)-2-fluoro-N-4-[4-oxo-3-(phenylamino)-4,5,6,7-tetrahydro-1H-indol-2-yl]pyridin-2-ylcyclopropanecarboxamide;
(1S,2R)-2-fluoro-N-4-[4-oxo-3-(phenylamino)-4,5,6,7-tetrahydro-1H-indol-2-yl]pyridin-2-ylcyclopropanecarboxamide;
(1R,2S)-2-fluoro-N-4-[4-oxo-3-(phenylamino)-4,5,6,7-tetrahydro-1H-indol-2-yl]pyridin-2-ylcyclopropanecarboxamide;
rel-(1S,2S)-2-fluoro-N-4-[4-oxo-3-(phenylamino)-4,5,6,7-tetrahydro-1H-indol-2-yl]pyridin-2-ylcyclopropanecarboxamide;
(1R,2R)-2-fluoro-N-4-[4-oxo-3-(phenylamino)-4,5,6,7-tetrahydro-1H-indol-2-yl]pyridin-2-ylcyclopropanecarboxamide;
rel-(1S,2R)—N-4-[6,6-dimethyl-4-oxo-3-(phenylamino)-4,5,6,7-tetrahydro-1H-indol-2-yl]pyridin-2-yl-2-fluorocyclopropanecarboxamide;
(1S,2R)—N-[4-(3-anilino-6,6-dimethyl-4-oxo-4,5,6,7-tetrahydro-1H-indol-2-yl)pyridin-2-yl]-2-fluorocyclopropanecarboxamide;
(1R,2S)—N-[4-(3-anilino-6,6-dimethyl-4-oxo-4,5,6,7-tetrahydro-1H-indol-2-yl)pyridin-2-yl]-2-fluorocyclopropanecarboxamide;
rel-(1R,2R)—N-4-[6,6-dimethyl-4-oxo-3-(phenylamino)-4,5,6,7-tetrahydro-1H-indol-2-yl]pyridin-2-yl-2-fluorocyclopropanecarboxamide;
(1S,2S)—N-[4-(3-anilino-6,6-dimethyl-4-oxo-4,5,6,7-tetrahydro-1H-indol-2-yl)pyridin-2-yl]-2-fluorocyclopropanecarboxamide;
(1R,2R)—N-4-[6,6-dimethyl-4-oxo-3-(phenylamino)-4,5,6,7-tetrahydro-1H-indol-2-yl]pyridin-2-yl-2-fluorocyclopropanecarboxamide;
2,2-difluoro-N-4-[4-oxo-3-(phenylamino)-4,5,6,7-tetrahydro-1H-indol-2-yl]pyridin-2-ylcyclopropanecarboxamide;
1-fluoro-N-4-[4-oxo-3-(phenylamino)-4,5,6,7-tetrahydro-1H-indol-2-yl]pyridin-2-ylcyclopropanecarboxamide;
rel-(1S,2R)—N-4-[4-oxo-3-(phenylamino)-4,5,6,7-tetrahydro-1H-indol-2-yl]pyridin-2-yl-2-(trifluoromethyl)cyclopropanecarboxamide;
3-fluoro-2,2-dimethyl-N-4-[4-oxo-3-(phenylamino)-4,5,6,7-tetrahydro-1H-indol-2-yl]pyridin-2-ylpropanamide;
2-fluoro-N-4-[4-oxo-3-(phenylamino)-4,5,6,7-tetrahydro-1H-indol-2-yl]pyridin-2-ylbenzamide;
3-fluoro-N-4-[4-oxo-3-(phenylamino)-4,5,6,7-tetrahydro-1H-indol-2-yl]pyridin-2-ylbenzamide;
4-fluoro-N-4-[4-oxo-3-(phenylamino)-4,5,6,7-tetrahydro-1H-indol-2-yl]pyridin-2-ylbenzamide;
N-4-[6,6-dimethyl-4-oxo-3-(phenylamino)-4,5,6,7-tetrahydro-1H-indol-2-yl]pyridin-2-yl-4-fluorobenzamide;
N-4-[4-oxo-3-(phenylamino)-4,5,6,7-tetrahydro-1H-indol-2-yl]pyridin-2-ylpyridine-4-carboxamide;
N-4-[4-oxo-3-(phenylamino)-4,5,6,7-tetrahydro-1H-indol-2-yl]pyridin-2-ylpyridine-2-carboxamide;
N-4-[4-oxo-3-(phenylamino)-4,5,6,7-tetrahydro-1H-indol-2-yl]pyridin-2-yl-1,3-thiazole-2-carboxamide;
N-4-[4-oxo-3-(phenylamino)-4,5,6,7-tetrahydro-1H-indol-2-yl]pyridin-2-yl-1,3-thiazole-4-carboxamide;
N-4-[6,6-dimethyl-4-oxo-3-(phenylamino)-4,5,6,7-tetrahydro-1H-indol-2-yl]pyridin-2-yl-1,3-thiazole-4-carboxamide;
N-4-[4-oxo-3-(phenylamino)-4,5,6,7-tetrahydro-1H-indol-2-yl]pyridin-2-yl-1,3-thiazole-5-carboxamide;
N-4-[4-oxo-3-(phenylamino)-4,5,6,7-tetrahydro-1H-indol-2-yl]pyridin-2-yl-1H-imidazole-2-carboxamide;
N-4-[4-oxo-3-(phenylamino)-4,5,6,7-tetrahydro-1H-indol-2-yl]pyridin-2-yl-1H-pyrazole-5-carboxamide;
N-4-[4-oxo-3-(phenylamino)-4,5,6,7-tetrahydro-1H-indol-2-yl]pyridin-2-yl-1,2-thiazole-3-carboxamide;
N-4-[4-oxo-3-(phenylamino)-4,5,6,7-tetrahydro-1H-indol-2-yl]pyridin-2-yl-1,2-thiazole-4-carboxamide;
N-4-[4-oxo-3-(phenylamino)-4,5,6,7-tetrahydro-1H-indol-2-yl]pyridin-2-yl-1,3-oxazole-4-carboxamide;
N-4-[4-oxo-3-(phenylamino)-4,5,6,7-tetrahydro-1H-indol-2-yl]pyridin-2-ylpyridine-3-carboxamide;
N-4-[4-oxo-3-(phenylamino)-4,5,6,7-tetrahydro-1H-indol-2-yl]pyridin-2-yl-1,2-thiazole-5-carboxamide;
N-4-[4-oxo-3-(phenylamino)-4,5,6,7-tetrahydro-1H-indol-2-yl]pyridin-2-yl-1H-1,2,3-triazole-5-carboxamide;
N-4-[4-oxo-3-(phenylamino)-4,5,6,7-tetrahydro-1H-indol-2-yl]pyridin-2-yl-1,3-oxazole-5-carboxamide;
N-4-[4-oxo-3-(phenylamino)-4,5,6,7-tetrahydro-1H-indol-2-yl]pyridin-2-yl-1H-tetrazole-5-carboxamide;
N-4-[4-oxo-3-(phenylamino)-4,5,6,7-tetrahydro-1H-indol-2-yl]pyridin-2-yl-2-(1H-pyrrol-2-yl)acetamide;
N-4-[4-oxo-3-(phenylamino)-4,5,6,7-tetrahydro-1H-indol-2-yl]pyridin-2-yl-2-(1,3-thiazol-2-yl)acetamide;
N-4-[4-oxo-3-(phenylamino)-4,5,6,7-tetrahydro-1H-indol-2-yl]pyridin-2-yl-2-(1H-pyrrol-3-yl)acetamide;
N-4-[4-oxo-3-(phenylamino)-4,5,6,7-tetrahydro-1H-indol-2-yl]pyridin-2-yl-2-(1,3-thiazol-4-yl)acetamide;
2-(furan-2-yl)-N-4-[4-oxo-3-(phenylamino)-4,5,6,7-tetrahydro-1H-indol-2-yl]pyridin-2-ylacetamide;
2-(3-methyl-1,2-oxazol-5-yl)-N-4-[4-oxo-3-(phenylamino)-4,5,6,7-tetrahydro-1H-indol-2-yl]pyridin-2-ylacetamide;
N-4-[4-oxo-3-(phenylamino)-4,5,6,7-tetrahydro-1H-indol-2-yl]pyridin-2-yl-2-(thiophen-2-yl)acetamide;
N-4-[4-oxo-3-(phenylamino)-4,5,6,7-tetrahydro-1H-indol-2-yl]pyridin-2-yl-2-(thiophen-3-yl)acetamide;
2-(1-methyl-1H-pyrazol-5-yl)-N-4-[4-oxo-3-(phenylamino)-4,5,6,7-tetrahydro-1H-indol-2-yl]pyridin-2-ylacetamide;
N-4-[4'-oxo-3'-(phenylamino)-1',4',5',7'-tetrahydrospiro[cyclopropane-1,6'-indol]-2'-yl]pyridin-2-ylacetamide;
N-4-[4'-oxo-3'-(phenylamino)-1',4',5',7'-tetrahydrospiro[cyclopropane-1,6'-indol]-2'-yl]pyridin-2-ylcyclopropanecarboxamide;

tert-butyl 3-(4-[4-oxo-3-(phenylamino)-4,5,6,7-tetrahydro-1H-indol-2-yl]pyridin-2-ylcarbamoyl)azetidine-1-carboxylate;
N-4-[4-oxo-3-(phenylamino)-4,5,6,7-tetrahydro-1H-indol-2-yl]pyridin-2-ylazetidine-3-carboxamide;
tert-butyl methyl [2-oxo-2-(4-[4-oxo-3-(phenylamino)-4,5,6,7-tetrahydro-1H-indol-2-yl]pyridin-2-ylamino)ethyl]carbamate;
N-[4-(3-anilino-4-oxo-4,5,6,7-tetrahydro-1H-indol-2-yl)pyridin-2-yl]-N$^2$-methylglycinamide;
tert-butyl methyl [3-oxo-3-(4-[4-oxo-3-(phenylamino)-4,5,6,7-tetrahydro-1H-indol-2-yl]pyridin-2-ylamino)propyl]carbamate;
N-[4-(3-anilino-4-oxo-4,5,6,7-tetrahydro-1H-indol-2-yl)pyridin-2-yl]-N$^3$-methyl-beta-alaninamide;
tert-butyl methyl[(2R)-1-oxo-1-(4-[4-oxo-3-(phenylamino)-4,5,6,7-tetrahydro-1H-indol-2-yl]pyridin-2-ylamino)propan-2-yl]carbamate;
N-[4-(3-anilino-4-oxo-4,5,6,7-tetrahydro-1H-indol-2-yl)pyridin-2-yl]-N$^2$-methyl-D-alaninamide;
tert-butyl methyl[(2S)-1-oxo-1-(4-[4-oxo-3-(phenylamino)-4,5,6,7-tetrahydro-1H-indol-2-yl]pyridin-2-ylamino)propan-2-yl]carbamate;
N-[4-(3-anilino-4-oxo-4,5,6,7-tetrahydro-1H-indol-2-yl)pyridin-2-yl]-N$^2$-methyl-L-alaninamide;
N-[4-(3-anilino-4-oxo-4,5,6,7-tetrahydro-1H-indol-2-yl)pyridin-2-yl]-N$^2$,N$^2$-dimethyl-D-alaninamide;
N-[4-(3-anilino-4-oxo-4,5,6,7-tetrahydro-1H-indol-2-yl)pyridin-2-yl]-N$^2$,2-dimethylalaninamide;
N-[4-(3-anilino-4-oxo-4,5,6,7-tetrahydro-1H-indol-2-yl)pyridin-2-yl]-N$^2$,N$^2$-dimethylglycinamide;
N-4-[4-oxo-3-(phenylamino)-4,5,6,7-tetrahydro-1H-indol-2-yl]pyridin-2-yl-2-(pyrrolidin-1-yl)acetamide;
1-methyl-N-4-[4-oxo-3-(phenylamino)-4,5,6,7-tetrahydro-1H-indol-2-yl]pyridin-2-yl-D-prolinamide;
1-methyl-5-oxo-N-4-[4-oxo-3-(phenylamino)-4,5,6,7-tetrahydro-1H-indol-2-yl]pyridin-2-yl-D-prolinamide;
5-oxo-N-4-[4-oxo-3-(phenylamino)-4,5,6,7-tetrahydro-1H-indol-2-yl]pyridin-2-yl-D-prolinamide;
methyl (4-{3-[(3-fluorophenyl)amino]-4-oxo-4,5,6,7-tetrahydro-1H-indol-2-yl}pyridin-2-yl)carbamate;
N-(4-{3-[(4-fluorophenyl)amino]-4-oxo-4,5,6,7-tetrahydro-1H-indol-2-yl}pyridin-2-yl)acetamide;
N-(4-{3-[(4-fluorophenyl)amino]-4-oxo-4,5,6,7-tetrahydro-1H-indol-2-yl}pyridin-2-yl)cyclopropanecarboxamide;
N-(4-{3-[(3,4-difluorophenyl)amino]-4-oxo-4,5,6,7-tetrahydro-1H-indol-2-yl}pyridin-2-yl)acetamide;
N-(4-{3-[(3,4-difluorophenyl)amino]-4-oxo-4,5,6,7-tetrahydro-1H-indol-2-yl}pyridin-2-yl)cyclopropanecarboxamide;
N-4-[4-oxo-3-(phenylamino)-6-(propan-2-yl)-4,5,6,7-tetrahydro-1H-indol-2-yl]pyridin-2-ylacetamide;
N-4-[4-oxo-3-(phenylamino)-6-(propan-2-yl)-4,5,6,7-tetrahydro-1H-indol-2-yl]pyridin-2-ylcyclopropanecarboxamide;
N-4-[3-[(3-fluorophenyl)amino]-4-oxo-6-(propan-2-yl)-4,5,6,7-tetrahydro-1H-indol-2-yl]pyridin-2-ylacetamide;
N-4-[3-[(3-fluorophenyl)amino]-4-oxo-6-(propan-2-yl)-4,5,6,7-tetrahydro-1H-indol-2-yl]pyridin-2-ylcyclopropanecarboxamide;
N-4-[3-[(4-fluorophenyl)amino]-4-oxo-6-(propan-2-yl)-4,5,6,7-tetrahydro-1H-indol-2-yl]pyridin-2-ylacetamide;
N-4-[3-[(4-fluorophenyl)amino]-4-oxo-6-(propan-2-yl)-4,5,6,7-tetrahydro-1H-indol-2-yl]pyridin-2-ylcyclopropanecarboxamide;
N-4-[3-[(3,4-difluorophenyl)amino]-4-oxo-6-(propan-2-yl)-4,5,6,7-tetrahydro-1H-indol-2-yl]pyridin-2-ylacetamide;
N-4-[3-[(3,4-difluorophenyl)amino]-4-oxo-6-(propan-2-yl)-4,5,6,7-tetrahydro-1H-indol-2-yl]pyridin-2-ylcyclopropanecarboxamide;
2-methoxy-N-4-[4-oxo-3-(phenylamino)-4,5,6,7-tetrahydro-1H-indol-2-yl]pyridin-2-ylacetamide;
2-methoxy-2-methyl-N-4-[4-oxo-3-(phenylamino)-4,5,6,7-tetrahydro-1H-indol-2-yl]pyridin-2-ylpropanamide;
2-hydroxy-2-methyl-N-4-[4-oxo-3-(phenylamino)-4,5,6,7-tetrahydro-1H-indol-2-yl]pyridin-2-ylpropanamide;
2-ethoxy-2-methyl-N-4-[4-oxo-3-(phenylamino)-4,5,6,7-tetrahydro-1H-indol-2-yl]pyridin-2-ylpropanamide;
2-methoxy-N-4-[4-oxo-3-(phenylamino)-4,5,6,7-tetrahydro-1H-indol-2-yl]pyridin-2-ylpropanamide;
N-4-[4-oxo-3-(phenylamino)-4,5,6,7-tetrahydro-1H-indol-2-yl]pyridin-2-yl-2-propoxyacetamide;
2-(2-methylpropoxy)-N-4-[4-oxo-3-(phenylamino)-4,5,6,7-tetrahydro-1H-indol-2-yl]pyridin-2-ylacetamide;
N-4-[4-oxo-3-(phenylamino)-4,5,6,7-tetrahydro-1H-indol-2-yl]pyridin-2-yl-2-(2,2,3, 3-tetrafluoropropoxy)acetamide;
2-butoxy-N-4-[4-oxo-3-(phenylamino)-4,5,6,7-tetrahydro-1H-indol-2-yl]pyridin-2-ylacetamide;
2-ethoxy-N-4-[4-oxo-3-(phenylamino)-4,5,6,7-tetrahydro-1H-indol-2-yl]pyridin-2-ylacetamide;
N-4-[4-oxo-3-(phenylamino)-4,5,6,7-tetrahydro-1H-indol-2-yl]pyridin-2-yl-2-(prop-2-en-1-yloxy)acetamide;
N-4-[4-oxo-3-(phenylamino)-4,5,6,7-tetrahydro-1H-indol-2-yl]pyridin-2-yl-2-(prop-2-yn-1-yloxy)acetamide;
N-4-[4-oxo-3-(phenylamino)-4,5,6,7-tetrahydro-1H-indol-2-yl]pyridin-2-yl-2-phenoxyacetamide;
2-(3-fluorophenoxy)-N-4-[4-oxo-3-(phenylamino)-4,5,6,7-tetrahydro-1H-indol-2-yl]pyridin-2-ylacetamide;
2-(2-fluorophenoxy)-N-4-[4-oxo-3-(phenylamino)-4,5,6,7-tetrahydro-1H-indol-2-yl]pyridin-2-ylacetamide;
2-(benzyloxy)-N-4-[4-oxo-3-(phenylamino)-4,5,6,7-tetrahydro-1H-indol-2-yl]pyridin-2-ylacetamide;
2-[(4-fluorobenzyl)oxy]-N-4-[4-oxo-3-(phenylamino)-4,5,6,7-tetrahydro-1H-indol-2-yl]pyridin-2-ylacetamide;
2-[(4-methoxybenzyl)oxy]-N-4-[4-oxo-3-(phenylamino)-4,5,6,7-tetrahydro-1H-indol-2-yl]pyridin-2-ylacetamide;
N-4-[4-oxo-3-(phenylamino)-4,5,6,7-tetrahydro-1H-indol-2-yl]pyridin-2-yl-2-[tetrahydro-2H-pyran-2-ylmethoxy]acetamide;
N-4-[4-oxo-3-(phenylamino)-4,5,6,7-tetrahydro-1H-indol-2-yl]pyridin-2-yl-2-(thiophen-3-yloxy)acetamide;
2-[(2-chlorothiophen-3-yl)oxy]-N-4-[4-oxo-3-(phenylamino)-4,5,6,7-tetrahydro-1H-indol-2-ylacetamide;
2-[(5-methyl-1,2-oxazol-3-yl)oxy]-N-4-[4-oxo-3-(phenylamino)-4,5,6,7-tetrahydro-1H-indol-2-yl]pyridin-2-ylacetamide;
N-4-[4-oxo-3-(phenylamino)-4,5,6,7-tetrahydro-1H-indol-2-yl]pyridin-2-yl-2-(pyridin-2-yloxy)acetamide;
2-(1,2-oxazol-3-yloxy)-N-4-[4-oxo-3-(phenylamino)-4,5,6,7-tetrahydro-1H-indol-2-yl]pyridin-2-ylacetamide;
2-[(3-methyl-1,2,4-oxadiazol-5-yl)methoxy]-N-4-[4-oxo-3-(phenylamino)-4,5,6,7-tetrahydro-1H-indol-2-yl]pyridin-2-ylacetamide;

2-[(3-methyl-1,2-oxazol-5-yl)methoxy]-N-4-[4-oxo-3-(phenylamino)-4,5,6,7-tetrahydro-1H-indol-2-yl]pyridin-2-ylacetamide;
2-[(1-methyl-1H-pyrazol-5-yl)methoxy]-N-4-[4-oxo-3-(phenylamino)-4,5,6,7-tetrahydro-1H-indol-2-yl]pyridin-2-ylacetamide;
2-(furan-2-ylmethoxy)-N-4-[4-oxo-3-(phenylamino)-4,5,6,7-tetrahydro-1H-indol-2-yl]pyridin-2-ylacetamide;
2-[(5-methyl-1,3,4-oxadiazol-2-yl)methoxy]-N-4-[4-oxo-3-(phenylamino)-4,5,6,7-tetrahydro-1H-indol-2-yl]pyridin-2-ylacetamide;
2-[(5-methyl-1,2-oxazol-3-yl)methoxy]-N-4-[4-oxo-3-(phenylamino)-4,5,6,7-tetrahydro-1H-indol-2-yl]pyridin-2-ylacetamide;
2-[(5-methyl-1,3-oxazol-2-yl)methoxy]-N-4-[4-oxo-3-(phenylamino)-4,5,6,7-tetrahydro-1H-indol-2-yl]pyridin-2-ylacetamide;
2-[(5-methyl-1,3,4-thiadiazol-2-yl)methoxy]-N-4-[4-oxo-3-(phenylamino)-4,5,6,7-tetrahydro-1H-indol-2-yl]pyridin-2-ylacetamide;
N-6-[6,6-dimethyl-4-oxo-3-(phenylamino)-4,5,6,7-tetrahydro-1H-indol-2-yl]pyrimidin-4-ylacetamide;
2-[2-(methylamino)pyridin-4-yl]-3-(phenylamino)-1,5,6,7-tetrahydro-4H-indol-4-one;
2-[2-(cyclobutylamino)pyridin-4-yl]-6,6-dimethyl-3-(phenylamino)-1,5,6,7-tetrahydro-4H-indol-4-one;
2-[2-(azetidin-1-yl)pyridin-4-yl]-6,6-dimethyl-3-(phenylamino)-1,5,6,7-tetrahydro-4H-indol-4-one;
6,6-dimethyl-3-(phenylamino)-2-{2-[(2,2,2-trifluoroethyl)amino]pyridin-4-yl}-1,5,6,7-tetrahydro-4H-indol-4-one;
6,6-dimethyl-3-(phenylamino)-2-{2-[(3,3,3-trifluoropropyl)amino]pyridin-4-yl}-1,5,6,7-tetrahydro-4H-indol-4-one;
2-(2-[1,1-difluoropropan-2-yl]aminopyridin-4-yl)-6,6-dimethyl-3-(phenylamino)-1,5,6,7-tetrahydro-4H-indol-4-one;
3-(phenylamino)-2-[2-(propan-2-ylamino)pyridin-4-yl]-1,5,6,7-tetrahydro-4H-indol-4-one;
3-(phenylamino)-2-{2-[(3,3,3-trifluoropropyl)amino]pyridin-4-yl}-1,5,6,7-tetrahydro-4H-indol-4-one;
2-[2-(benzylamino)pyridin-4-yl]-3-(phenylamino)-1,5,6,7-tetrahydro-4H-indol-4-one;
3-(phenylamino)-2-{2-[(pyridin-4-ylmethyl)amino]pyridin-4-yl}-1,5,6,7-tetrahydro-4H-indol-4-one;
2-{2-[(cyclopropylmethyl)amino]pyridin-4-yl}-3-(phenylamino)-1,5,6,7-tetrahydro-4H-indol-4-one;
N-4-[4-oxo-3-(phenylamino)-4,5,6,7-tetrahydro-1H-indol-2-yl]pyridin-2-ylglycine;
2-[2-({(4S)-2,2-dimethyl-1,3-dioxolan-4-yl]methylamino)pyridin-4-yl]-3-(phenylamino)-1,5,6,7-tetrahydro-4H-indol-4-one;
2-(2-[(2 S)-2,3-dihydroxypropyl]aminopyridin-4-yl)-3-(phenylamino)-1,5,6,7-tetrahydro-4H-indol-4-one;
3-(phenylamino)-2-{2-[(pyridin-3-ylmethyl)amino]pyridin-4-yl}-1,5,6,7-tetrahydro-4H-indol-4-one;
tert-butyl 3-[(4-[4-oxo-3-(phenylamino)-4,5,6,7-tetrahydro-1H-indol-2-yl]pyridin-2-ylamino)methyl]azetidine-1-carboxylate;
2-{2-[(1-methyl-1H-tetrazol-5-yl)amino]pyridin-4-yl}-3-(phenylamino)-1,5,6,7-tetrahydro-4H-indol-4-one;
2-{2-[(3-fluorophenyl)amino]pyridin-4-yl}-3-(phenylamino)-1,5,6,7-tetrahydro-4H-indol-4-one;
3-(phenylamino)-2-[3-(propan-2-ylamino)pyridin-4-yl]-1,5,6,7-tetrahydro-4H-indol-4-one;
1-ethyl-3-{4-[4-oxo-3-(phenylamino)-4,5,6,7-tetrahydro-1H-indol-2-yl]pyridin-2-yl}urea;
1-{4-[4-oxo-3-(phenylamino)-4,5,6,7-tetrahydro-1H-indol-2-yl]pyridin-2-yl}-3-propan-2-ylurea;
1-cyclopropyl-3-{4-[4-oxo-3-(phenylamino)-4,5,6,7-tetrahydro-1H-indol-2-yl]pyridin-2-yl}urea;
1-tert-butyl-3-{4-[4-oxo-3-(phenylamino)-4,5,6,7-tetrahydro-1H-indol-2-yl]pyridin-2-yl}urea;
1-(2-methylpropyl)-3-{4-[4-oxo-3-(phenylamino)-4,5,6,7-tetrahydro-1H-indol-2-yl]pyridin-2-yl}urea;
1-{4-[4-oxo-3-(phenylamino)-4,5,6,7-tetrahydro-1H-indol-2-yl]pyridin-2-yl}-3-(2,2,2-trifluoroethyl)urea;
1-(2-methoxyethyl)-3-{4-[4-oxo-3-(phenylamino)-4,5,6,7-tetrahydro-1H-indol-2-yl]pyridin-2-yl}urea;
1-(furan-2-ylmethyl)-3-{4-[4-oxo-3-(phenylamino)-4,5,6,7-tetrahydro-1H-indol-2-yl]pyridin-2-yl}urea;
1-{4-[4-oxo-3-(phenylamino)-4,5,6,7-tetrahydro-1H-indol-2-yl]pyridin-2-yl}-3-pyridin-4-ylurea;
1-{4-[4-oxo-3-(phenylamino)-4,5,6,7-tetrahydro-1H-indol-2-yl]pyridin-2-yl}-3-pyridin-2-ylurea;
1-(2,2-difluoroethyl)-3-{4-[4-oxo-3-(phenylamino)-4,5,6,7-tetrahydro-1H-indol-2-yl]pyridin-2-yl}urea;
1-(2-chloroethyl)-3-{4-[4-oxo-3-(phenylamino)-4,5,6,7-tetrahydro-1H-indol-2-yl]pyridin-2-yl}urea;
1-[2-(methyl sulfanyl)ethyl]-3-{4-[4-oxo-3-(phenylamino)-4,5,6,7-tetrahydro-1H-indol-2-yl]pyridin-2-yl}urea;
1-(1-methyl-1H-pyrazol-4-yl)-3-{4-[4-oxo-3-(phenylamino)-4,5,6,7-tetrahydro-1H-indol-2-yl]pyridin-2-yl}urea;
1-{4-[6,6-dimethyl-4-oxo-3-(phenylamino)-4,5,6,7-tetrahydro-1H-indol-2-yl]pyridin-2-yl}-3-(1-methyl-1H-pyrazol-4-yl)urea;
1-methyl-3-{4-[4-oxo-3-(phenylamino)-4,5,6,7-tetrahydro-1H-indol-2-yl]pyridin-2-yl}thiourea;
1-ethyl-3-{4-[4-oxo-3-(phenylamino)-4,5,6,7-tetrahydro-1H-indol-2-yl]pyridin-2-yl}thiourea;
1-{4-[4-oxo-3-(phenylamino)-4,5,6,7-tetrahydro-1H-indol-2-yl]pyridin-2-yl}-3-(2,2,2-trifluoroethyl)thiourea;
1-cyclopropyl-3-{4-[4-oxo-3-(phenylamino)-4,5,6,7-tetrahydro-1H-indol-2-yl]pyridin-2-yl}thiourea;
1-tert-butyl-3-{4-[4-oxo-3-(phenylamino)-4,5,6,7-tetrahydro-1H-indol-2-yl]pyridin-2-yl}thiourea;
1-cyclopentyl-3-{4-[4-oxo-3-(phenylamino)-4,5,6,7-tetrahydro-1H-indol-2-yl]pyridin-2-yl}thiourea;
1-(cyclopropylmethyl)-3-{4-[4-oxo-3-(phenylamino)-4,5,6,7-tetrahydro-1H-indol-2-yl]pyridin-2-yl}thiourea;
1-{4-[4-oxo-3-(phenylamino)-4,5,6,7-tetrahydro-1H-indol-2-yl]pyridin-2-yl}-3-propylthiourea;
2-[2-(difluoromethyl)pyridin-4-yl]-6,6-dimethyl-3-(phenylamino)-1,5,6,7-tetrahydro-4H-indol-4-one;
2-[2-(difluoromethyl)pyridin-4-yl]-3-(phenylamino)-1,5,6,7-tetrahydro-4H-indol-4-one;
2-[2-(difluoromethyl)pyridin-4-yl]-3-[(3-fluorophenyl)amino]-6,6-dimethyl-1,5,6,7-tetrahydro-4H-indol-4-one;
2-(3-methoxypyridin-4-yl)-6,6-dimethyl-3-(phenylamino)-1,5,6,7-tetrahydro-4H-indol-4-one;
2-(3-ethoxypyridin-4-yl)-6,6-dimethyl-3-(phenylamino)-1,5,6,7-tetrahydro-4H-indol-4-one;
6,6-dimethyl-3-(phenylamino)-2-(3-propoxypyridin-4-yl)-1,5,6,7-tetrahydro-4H-indol-4-one;
6,6-dimethyl-3-(phenylamino)-2-[3-(propan-2-yloxy)pyridin-4-yl]-1,5,6,7-tetrahydro-4H-indol-4-one;
2-(3-tert-butoxypyridin-4-yl)-6,6-dimethyl-3-(phenylamino)-1,5,6,7-tetrahydro-4H-indol-4-one;
2-[3-(2,2-difluoroethoxy)pyridin-4-yl]-6,6-dimethyl-3-(phenylamino)-1,5,6,7-tetrahydro-4H-indol-4-one;

2-[3-(2-hydroxyethoxy)pyridin-4-yl]-6,6-dimethyl-3-(phenylamino)-1,5,6,7-tetrahydro-4H-indol-4-one;
2-[3-(2-methoxyethoxy)pyridin-4-yl]-6,6-dimethyl-3-(phenylamino)-1,5,6,7-tetrahydro-4H-indol-4-one;
2-[3-(cyclopropylmethoxy)pyridin-4-yl]-6,6-dimethyl-3-(phenylamino)-1,5,6,7-tetrahydro-4H-indol-4-one;
6,6-dimethyl-3-(phenylamino)-2-[3-(2,2,2-trifluoroethoxy)pyridin-4-yl]-1,5,6,7-tetrahydro-4H-indol-4-one;
2-(3-methoxypyridin-4-yl)-3-(phenylamino)-1,5,6,7-tetrahydro-4H-indol-4-one;
3-(biphenyl-4-ylamino)-6,6-dimethyl-2-(pyridin-4-yl)-1,5,6,7-tetrahydro-4H-indol-4-one;
3-[(3-benzylphenyl)amino]-6,6-dimethyl-2-(pyridin-4-yl)-1,5,6,7-tetrahydro-4H-indol-4-one;
3-[(2-benzylphenyl)amino]-6,6-dimethyl-2-(pyridin-4-yl)-1,5,6,7-tetrahydro-4H-indol-4-one;
6,6-dimethyl-3-[3-(1-methyl-1H-pyrazol-5-yl)phenyl]amino-2-(pyridin-4-yl)-1,5,6,7-tetrahydro-4H-indol-4-one;
6,6-dimethyl-2-(pyridin-4-yl)-3-[3-(thiophen-3-yl)phenyl]amino-1,5,6,7-tetrahydro-4H-indol-4-one;
3-[(furan-2-yl)phenyl]amino-6,6-dimethyl-2-(pyridin-4-yl)-1,5,6,7-tetrahydro-4H-indol-4-one;
6,6-dimethyl-2-(pyridin-4-yl)-3-[3-(thiophen-2-yl)phenyl]amino-1,5,6,7-tetrahydro-4H-indol-4-one;
6,6-dimethyl-3-[(3-phenoxyphenyl)amino]-2-(pyridin-4-yl)-1,5,6,7-tetrahydro-4H-indol-4-one;
6,6-dimethyl-3-[(4-phenylpyridin-2-yl)amino]-2-(pyridin-4-yl)-1,5,6,7-tetrahydro-4H-indol-4-one;
6,6-dimethyl-3-[(6-phenylpyridin-2-yl)amino]-2-(pyridin-4-yl)-1,5,6,7-tetrahydro-4H-indol-4-one;
3-[2-(hydroxymethyl)phenyl]amino-6,6-dimethyl-2-(pyridin-4-yl)-1,5,6,7-tetrahydro-4H-indol-4-one;
3-[2-(2-hydroxyethyl)phenyl]amino-6,6-dimethyl-2-(pyridin-4-yl)-1,5,6,7-tetrahydro-4H-indol-4-one;
3-[(3-ethynylphenyl)amino]-6,6-dimethyl-2-(pyridin-4-yl)-1,5,6,7-tetrahydro-4H-indol-4-one;
2-[6,6-dimethyl-4-oxo-2-(pyridin-4-yl)-4,5,6,7-tetrahydro-1H-indol-3-yl]aminobenzamide;
methyl 3-[6,6-dimethyl-4-oxo-2-(pyridin-4-yl)-4,5,6,7-tetrahydro-1H-indol-3-yl]aminothiophene-2-carboxylate;
3-[6,6-dimethyl-4-oxo-2-(pyridin-4-yl)-4,5,6,7-tetrahydro-1H-indol-3-yl]aminothiophene-2-carboxylic acid;
4-[6,6-dimethyl-4-oxo-2-(pyridin-4-yl)-4,5,6,7-tetrahydro-1H-indol-3-yl]aminobenzenesulfonamide;
4-[6,6-dimethyl-4-oxo-2-(pyridin-4-yl)-4,5,6,7-tetrahydro-1H-indol-3-yl]aminobenzonitrile;
3-[4-(dimethylamino)phenyl]amino-6,6-dimethyl-2-(pyridin-4-yl)-1,5,6,7-tetrahydro-4H-indol-4-one;
2-(3-chloropyridin-4-yl)-3-[(3-fluorophenyl)amino]-6-(trifluoromethyl)-1,5,6,7-tetrahydro-4H-indol-4-one;
2-[2-(hydroxymethyl)pyridin-4-yl]-6,6-dimethyl-3-(phenylamino)-1,5,6,7-tetrahydro-4H-indol-4-one;
6,6-dimethyl-3-(phenylamino)-2-[3-(trifluoromethyl)pyridin-4-yl]-1,5,6,7-tetrahydro-4H-indol-4-one;
4-[6,6-dimethyl-4-oxo-3-(phenylamino)-4,5,6,7-tetrahydro-1H-indol-2-yl]pyridine-2-sulfonamide;
(6R)-3-(phenylamino)-2-(pyridin-4-yl)-6-(trifluoromethyl)-1,5,6,7-tetrahydro-4H-indol-4-one;
(6S)-3-(phenylamino)-2-(pyridin-4-yl)-6-(trifluoromethyl)-1,5,6,7-tetrahydro-4H-indol-4-one;
6-(fluoromethyl)-3-(phenylamino)-2-(pyridin-4-yl)-1,5,6,7-tetrahydro-4H-indol-4-one;
6-(chloromethyl)-3-(phenylamino)-2-(pyridin-4-yl)-1,5,6,7-tetrahydro-4H-indol-4-one;
N-4-[6-(chloromethyl)-4-oxo-3-(phenylamino)-4,5,6,7-tetrahydro-1H-indol-2-yl]pyridin-2-ylacetamide;
7-hydroxy-6,6-dimethyl-3-(phenylamino)-2-(pyridin-4-yl)-1,5,6,7-tetrahydro-4H-indol-4-one;
7-hydroxy-3-(phenylamino)-2-(pyridin-4-yl)-1,5,6,7-tetrahydro-4H-indol-4-one;
1-methyl-N-4-[4-oxo-3-(phenylamino)-4,5,6,7-tetrahydro-1H-indol-2-yl]pyridin-2-yl-1H-pyrazole-4-carboxamide;
1-tert-butyl-N-4-[4-oxo-3-(phenylamino)-4,5,6,7-tetrahydro-1H-indol-2-yl]pyridin-2-yl-1H-pyrazole-4-carboxamide;
1-benzyl-N-4-[4-oxo-3-(phenylamino)-4,5,6,7-tetrahydro-1H-indol-2-yl]pyridin-2-yl-1H-pyrazole-4-carboxamide;
1-(4-methoxybenzyl)-N-4-[4-oxo-3-(phenylamino)-4,5,6,7-tetrahydro-1H-indol-2-yl]pyridin-2-yl-1H-pyrazole-4-carboxamide;
3,4-difluoro-N-4-[4-oxo-3-(phenylamino)-4,5,6,7-tetrahydro-1H-indol-2-yl]pyridin-2-ylbenzamide;
3,5-difluoro-N-4-[4-oxo-3-(phenylamino)-4,5,6,7-tetrahydro-1H-indol-2-yl]pyridin-2-ylbenzamide;
4-fluoro-3-methoxy-N-4-[4-oxo-3-(phenylamino)-4,5,6,7-tetrahydro-1H-indol-2-yl]pyridin-2-ylbenzamide;
1-methyl-N-4-[4-oxo-3-(phenylamino)-4,5,6,7-tetrahydro-1H-indol-2-yl]pyridin-2-yl-1H-pyrazole-3-carboxamide;
2-[3-(cyclopropylmethoxy)pyridin-4-yl]-3-(phenylamino)-1,5,6,7-tetrahydro-4H-indol-4-one;
3-(phenylamino)-2-(3-propoxypyridin-4-yl)-1,5,6,7-tetrahydro-4H-indol-4-one;
2-[3-(2,2-difluoroethoxy)pyridin-4-yl]-3-(phenylamino)-1,5,6,7-tetrahydro-4H-indol-4-one;
3-(phenylamino)-2-[3-(2,2,2-trifluoroethoxy)pyridin-4-yl]-1,5,6,7-tetrahydro-4H-indol-4-one;
2-[3-(2-hydroxyethoxy)pyridin-4-yl]-3-(phenylamino)-1,5,6,7-tetrahydro-4H-indol-4-one;
(4S)-2,2-dimethyl-N-4-[4-oxo-3-(phenylamino)-4,5,6,7-tetrahydro-1H-indol-2-yl]pyridin-2-yl-1,3-dioxolane-4-carboxamide;
N-4-[6-(fluoromethyl)-4-oxo-3-(phenylamino)-4,5,6,7-tetrahydro-1H-indol-2-yl]pyridin-2-ylacetamide;
N-[4-(3-anilino-4-oxo-4,5,6,7-tetrahydro-1H-indol-2-yl)pyridin-2-yl]-2-(4-fluorophenoxy)acetamide;
N-[4-(3-anilino-4-oxo-4,5,6,7-tetrahydro-1H-indol-2-yl)pyridin-2-yl]-2-(1-methyl-1H-imidazol-2-yl)acetamide;
3-anilino-2-(3-hydroxypyridin-4-yl)-6,6-dimethyl-1,5,6,7-tetrahydro-4H-indol-4-one;
N-4-[6,6-dimethyl-4-oxo-3-(phenylamino)-4,5,6,7-tetrahydro-1H-indol-2-yl]pyridin-2-yl-1H-pyrazole-3-carboxamide;
rel-(1R,2S)-2-fluoro-N-4-[4'-oxo-3'-(phenylamino)-1',4',5',7'-tetrahydrospiro[cyclopropane-1,6'-indol]-2'-yl]pyridin-2-ylcyclopropanecarboxamide;
N-4-[6,6-dimethyl-4-oxo-3-(phenylamino)-4,5,6,7-tetrahydro-1H-indol-2-yl]pyridin-2-yl-3,5-difluorobenzamide;
2-[2-(benzyloxy)pyridin-4-yl]-6,6-dimethyl-3-(phenylamino)-1,5,6,7-tetrahydro-4H-indol-4-one;
2-(2-hydroxypyridin-4-yl)-6,6-dimethyl-3-(phenylamino)-1,5,6,7-tetrahydro-4H-indol-4-one;
N-4-[4'-oxo-3'-(phenylamino)-1',4',5',7'-tetrahydrospiro[cyclopropane-1,6'-indol]-2'-yl]pyridin-2-yl-1,3-oxazole-4-carboxamide;
4-(methoxyimino)-6,6-dimethyl-N-phenyl-2-(pyridin-4-yl)-4,5,6,7-tetrahydro-1H-indol-3-amine;

1-tert-butyl-N-4-[6,6-dimethyl-4-oxo-3-(phenylamino)-4,5,6,7-tetrahydro-1H-indol-2-yl]pyridin-2-yl-1H-pyrazole-4-carboxamide;
N-4-[6,6-dimethyl-4-oxo-3-(phenylamino)-4,5,6,7-tetrahydro-1H-indol-2-yl]pyridin-2-yl-3,4-difluorobenzamide;
N-4-[6,6-dimethyl-4-oxo-3-(phenylamino)-4,5,6,7-tetrahydro-1H-indol-2-yl]pyridin-2-yl-4-fluoro-3-methoxybenzamide;
N-4-[6,6-dimethyl-4-oxo-3-(phenylamino)-4,5,6,7-tetrahydro-1H-indol-2-yl]pyridin-2-yl-2-fluoro-2-methylpropanamide;
2-(benzyloxy)-N-4-[6,6-dimethyl-4-oxo-3-(phenylamino)-4,5,6,7-tetrahydro-1H-indol-2-yl]pyridin-2-ylacetamide;
N-4-[6,6-dimethyl-4-oxo-3-(phenylamino)-4,5,6,7-tetrahydro-1H-indol-2-yl]pyridin-2-yl-2,2-difluorocyclopropanecarboxamide;
1-benzyl-N-4-[6,6-dimethyl-4-oxo-3-(phenylamino)-4,5,6,7-tetrahydro-1H-indol-2-yl]pyridin-2-yl-1H-pyrazole-4-carboxamide;
N-4-[6,6-dimethyl-4-oxo-3-(phenylamino)-4,5,6,7-tetrahydro-1H-indol-2-yl]pyridin-2-yl-1-(4-methoxybenzyl)-1H-pyrazole-4-carboxamide;
N-4-[6,6-dimethyl-4-oxo-3-(phenylamino)-4,5,6,7-tetrahydro-1H-indol-2-yl]pyridin-2-yl-1,3-thiazole-5-carboxamide;
3-[2-(hydroxymethyl)-5-methylphenyl]amino-6,6-dimethyl-2-(pyridin-4-yl)-1,5,6,7-tetrahydro-4H-indol-4-one;
3-[2-(hydroxymethyl)-4-methylphenyl]amino-6,6-dimethyl-2-(pyridin-4-yl)-1,5,6,7-tetrahydro-4H-indol-4-one;
3-[2-(hydroxymethyl)-3-methylphenyl]amino-6,6-dimethyl-2-(pyridin-4-yl)-1,5,6,7-tetrahydro-4H-indol-4-one;
3-(phenylamino)-2-{2-[(4-phenylbutyl)amino]pyridin-4-yl}-1,5,6,7-tetrahydro-4H-indol-4-one;
3-[4-fluoro-2-(hydroxymethyl)phenyl]amino-6,6-dimethyl-2-(pyridin-4-yl)-1,5,6,7-tetrahydro-4H-indol-4-one;
3-[3-fluoro-2-(hydroxymethyl)phenyl]amino-6,6-dimethyl-2-(pyridin-4-yl)-1,5,6,7-tetrahydro-4H-indol-4-one;
3-[5-fluoro-2-(hydroxymethyl)phenyl]amino-6,6-dimethyl-2-(pyridin-4-yl)-1,5,6,7-tetrahydro-4H-indol-4-one;
3-[2-(2-hydroxypropan-2-yl)phenyl]amino-6,6-dimethyl-2-(pyridin-4-yl)-1,5,6,7-tetrahydro-4H-indol-4-one;
3-(phenylamino)-2-{2-[(2-phenylethyl)amino]pyridin-4-yl}-1,5,6,7-tetrahydro-4H-indol-4-one;
3-(phenylamino)-2-{2-[(3-phenylpropyl)amino]pyridin-4-yl}-1,5,6,7-tetrahydro-4H-indol-4-one;
4-(ethoxyimino)-6,6-dimethyl-N-phenyl-2-(pyridin-4-yl)-4,5,6,7-tetrahydro-1H-indol-3-amine;
N-4-[4-oxo-3-(phenylamino)-4,5,6,7-tetrahydro-1H-indol-2-yl]pyridin-2-yl-2-(pyridin-3-ylmethoxy)acetamide;
2-[(1-methyl-1H-imidazol-2-yl)methoxy]-N-4-[4-oxo-3-(phenylamino)-4,5,6,7-tetrahydro-1H-indol-2-yl]pyridin-2-ylacetamide;
2-[(1-methyl-1H-1,2,4-triazol-5-yl)methoxy]-N-4-[4-oxo-3-(phenylamino)-4,5,6,7-tetrahydro-1H-indol-2-yl]pyridin-2-ylacetamide;
N-4-[4-oxo-3-(phenylamino)-4,5,6,7-tetrahydro-1H-indol-2-yl]pyridin-2-yl-2-(pyridin-2-ylmethoxy)acetamide;
2-[(4-methyl-1,3-thiazol-5-yl)methoxy]-N-4-[4-oxo-3-(phenylamino)-4,5,6,7-tetrahydro-1H-indol-2-yl]pyridin-2-ylacetamide;
6,6-dimethyl-3-(phenylamino)-2-{2-[(3-phenylpropyl)amino]pyridin-4-yl}-1,5,6,7-tetrahydro-4H-indol-4-one;
6,6-dimethyl-3-(phenylamino)-2-{2-[(2-phenylethyl)amino]pyridin-4-yl}-1,5,6,7-tetrahydro-4H-indol-4-one;
2-{2-[(4-fluorobenzyl)amino]pyridin-4-yl}-3-(phenylamino)-1,5,6,7-tetrahydro-4H-indol-4-one;
3-(phenylamino)-2-{2-[(1,3-thiazol-5-ylmethyl)amino]pyridin-4-yl}-1,5,6,7-tetrahydro-4H-indol-4-one;
3-(phenylamino)-2-{2-[(1,3-thiazol-4-ylmethyl)amino]pyridin-4-yl}-1,5,6,7-tetrahydro-4H-indol-4-one;
N-4-[4-oxo-3-(phenylamino)-4,5,6,7-tetrahydro-1H-indol-2-yl]pyridin-2-yl-2-(2,2,2-trifluoroethoxy)acetamide;
2-(pyridin-4-yl)-3-(pyridin-2-ylamino)-1,5,6,7-tetrahydro-4H-indol-4-one;
N-4-[6,6-dimethyl-4-oxo-3-(phenylamino)-4,5,6,7-tetrahydro-1H-indol-2-yl]pyridin-2-yl-1-methyl-1H-pyrazole-3-carboxamide;
N-4-[6,6-dimethyl-4-oxo-3-(phenylamino)-4,5,6,7-tetrahydro-1H-indol-2-yl]pyridin-2-yl-1,3-thiazole-2-carboxamide;
N-4-[6,6-dimethyl-4-oxo-3-(phenylamino)-4,5,6,7-tetrahydro-1H-indol-2-yl]pyridin-2-yl-1-methyl-1H-pyrazole-4-carboxamide;
6,6-dimethyl-3-(phenylamino)-2-{2-[(4-phenylbutyl)amino]pyridin-4-yl}-1,5,6,7-tetrahydro-4H-indol-4-one;
6,6-dimethyl-3-(phenylamino)-2-{2-[(1,3-thiazol-5-ylmethyl)amino]pyridin-4-yl}-1,5,6,7-tetrahydro-4H-indol-4-one;
2-{2-[(cyclopropylmethyl)amino]pyridin-4-yl}-6,6-dimethyl-3-(phenylamino)-1,5,6,7-tetrahydro-4H-indol-4-one;
3-[4-(hydroxymethyl)pyridin-3-yl]amino-6,6-dimethyl-2-(pyridin-4-yl)-1,5,6,7-tetrahydro-4H-indol-4-one;
3-[3-(hydroxymethyl)pyridin-2-yl]amino-6,6-dimethyl-2-(pyridin-4-yl)-1,5,6,7-tetrahydro-4H-indol-4-one;
3-[(4-benzylphenyl)amino]-6,6-dimethyl-2-(pyridin-4-yl)-1,5,6,7-tetrahydro-4H-indol-4-one; and
6,6-dimethyl-3-[(4-phenoxyphenyl)amino]-2-(pyridin-4-yl)-1,5,6,7-tetrahydro-4H-indol-4-one,
or an N-oxide, a salt, a tautomer or a stereoisomer thereof, or a salt of said N-oxide, tautomer or stereoisomer.

8. The compound of claim 1 or a salt thereof.

9. The compound of claim 7 or a salt thereof.

10. A pharmaceutical composition comprising at least one compound of formula (I) according to claim 1, or an N-oxide, a salt, a tautomer or a stereoisomer thereof, or a salt of said N-oxide, tautomer or stereoisomer, together with at least one pharmaceutically acceptable auxiliary.

11. A combination comprising one or more first active ingredients selected from the compound of formula (I) according to claim 1, or an N-oxide, a salt, a tautomer or a stereoisomer thereof, or a salt of said N-oxide, tautomer or stereoisomer, and one or more second active ingredients selected from the group consisting of chemotherapeutic anti-cancer agents and target-specific anti-cancer agents.

12. A method of preparing the compound of formula (I) according to claim 1, or an N-oxide, a salt, a tautomer or a stereoisomer thereof, or a salt of said N-oxide, tautomer or stereoisomer, wherein the compound of formula (I) has a structure of formula (Ia), comprising reacting a compound of formula (1-2):

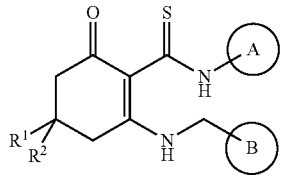

(1-2)

wherein $R^1$, $R^2$, ring A, and ring B have the meaning according to claim 1,
with a base and/or oxidizing reagent,
to give the compound of formula (Ia):

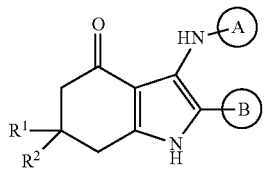

(Ia)

wherein $R^1$, $R^2$, ring A, and ring B have the meaning according to claim 1.

13. A method of preparing the compound of formula (I) according to claim 1, or an N-oxide, a salt, a tautomer or a stereoisomer thereof, or a salt of said N-oxide, tautomer or stereoisomer, wherein the compound of formula (I) has a structure of formula (Ia), comprising reacting a compound of formula (1-6):

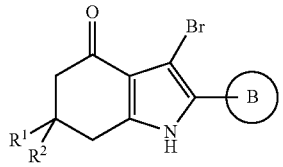

(1-6)

wherein $R^1$, $R^2$, and ring B have the meaning according to claim 1,
with an amine of formula:

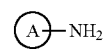

wherein ring A has the meaning according to claim 1,
to give the compound of formula (Ia):

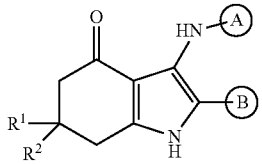

(Ia)

wherein $R^1$, $R^2$, ring A, and ring B have the meaning according to claim 1.

* * * * *